US007553854B2

(12) United States Patent
Sutton et al.

(10) Patent No.: US 7,553,854 B2
(45) Date of Patent: Jun. 30, 2009

(54) 6-O-SUBSTITUTED BENZOXAZOLE AND BENZOTHIAZOLE COMPOUNDS AND METHODS OF INHIBITING CSF-1R SIGNALING

(75) Inventors: James C Sutton, Pleasanton, CA (US); Marion Wiesmann, Brisbane, CA (US); Weibo Wang, Moraga, CA (US); Mika Lindvall, Oakland, CA (US); Jiong Lan, Moraga, CA (US); Savithri Ramurthy, Walnut Creek, CA (US); Anu Sharma, El Cerrito, CA (US); Elizabeth J. Mieuli, Stanford, CA (US); Liana M. Klivansky, Oakland, CA (US); William Lenahan, San Leandro, CA (US); Susan Kaufman, Lafayette, CA (US); Hong Yang, Foster City, CA (US); Simon C. Ng, Walnut Creek, CA (US); Keith Pfister, San Ramon, CA (US); Allan S. Wagman, Belmont, CA (US); Victoria Sung, San Francisco, CA (US); Martin Sendzik, San Mateo, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 11/737,069

(22) Filed: Apr. 18, 2007

(65) Prior Publication Data
US 2008/0045528 A1 Feb. 21, 2008

Related U.S. Application Data

(60) Provisional application No. 60/793,517, filed on Apr. 19, 2006, provisional application No. 60/893,857, filed on Mar. 8, 2007.

(51) Int. Cl.
*C07D 215/00* (2006.01)
*A61K 31/44* (2006.01)
(52) U.S. Cl. .................. 514/312; 514/338; 546/153; 546/270.1; 546/271.7
(58) Field of Classification Search ............... 546/153, 546/270.1, 271.7; 514/312, 338
See application file for complete search history.

(56) References Cited

U.S. PATENT DOCUMENTS

| 4,107,288 A | 8/1978 | Oppenheim et al. |
|---|---|---|
| 4,231,938 A | 11/1980 | Monaghan et al. |
| 4,294,926 A | 10/1981 | Monaghan et al. |
| 4,319,039 A | 3/1982 | Albers-Schonberg |
| 4,346,227 A | 8/1982 | Terahara et al. |
| 4,410,629 A | 10/1983 | Terahara et al. |
| 4,444,784 A | 4/1984 | Hoffman et al. |
| 4,537,859 A | 8/1985 | Terahara et al. |
| 4,681,893 A | 7/1987 | Roth |
| 4,782,084 A | 11/1988 | Vyas et al. |
| 4,820,850 A | 4/1989 | Verhoeven et al. |
| 4,873,346 A | 10/1989 | Anderson |
| 4,885,314 A | 12/1989 | Vyas et al. |
| 4,911,165 A | 3/1990 | Lennard et al. |
| 4,916,239 A | 4/1990 | Treiber |
| 4,929,437 A | 5/1990 | Tobert |
| 5,030,447 A | 7/1991 | Joshi et al. |
| 5,118,853 A | 6/1992 | Lee et al. |
| 5,134,142 A | 7/1992 | Matsuo et al. |
| 5,145,684 A | 9/1992 | Liversidge et al. |
| 5,180,589 A | 1/1993 | Joshi et al. |
| 5,189,164 A | 2/1993 | Kapa et al. |
| 5,273,995 A | 12/1993 | Roth |
| 5,290,946 A | 3/1994 | Lee et al. |
| 5,342,952 A | 8/1994 | Butler et al. |
| 5,344,991 A | 9/1994 | Reitz et al. |
| 5,354,772 A | 10/1994 | Kathawala |
| 5,356,896 A | 10/1994 | Kabadi et al. |
| 5,380,738 A | 1/1995 | Norman et al. |
| 5,393,790 A | 2/1995 | Reitz et al. |

(Continued)

FOREIGN PATENT DOCUMENTS

| EP | 0 261 459 A2 | 3/1988 |
|---|---|---|
| EP | 0604181 | 6/1994 |
| EP | 0618221 | 10/1994 |

(Continued)

OTHER PUBLICATIONS

Abu-Duhier et al., "Mutational analysis of class III receptor tyrosine kinases (C-KIT, C-FMS, FLT3) in idiopathic myelofibrosis." Br J Haematol, 2003. 120(3): p. 464-70.
Alvarez et al., "Properties of Bisphosphonates in the 13762 Rat Mammary Carcinoma Model of Tumor-Induced Bone Resorption." 2003, *Clin. Canc. Res.*, 9: 5705.
Baker et al., "Expression of the colony-stimulating factor 1 receptor in B lymphocytes." Oncogene, 1993. 8(2): p. 371-8.
Balkwill "TNF-alpha in promotion and progression of cancer." Cancer Metastasis Rev, 2006. 25(3): p. 409-16.
Balkwill et al., "Smoldering and polarized inflammation in the initiation and promotion of malignant disease." Cancer Cell, 2005. 7(3): p. 211-7.

(Continued)

*Primary Examiner*—D. Margaret Seaman
*Assistant Examiner*—Niloofar Rahmani
(74) *Attorney, Agent, or Firm*—Vinit Kathardekar; Hugo Eng

(57) ABSTRACT

Benzoxazole and benzothiazole compounds and the stereoisomers, tautomers, solvates, oxides, esters, and prodrugs thereof and pharmaceutically acceptable salts thereof are disclosed. Compositions of the compounds, either alone or in combination with at least one additional therapeutic agent, with a pharmaceutically acceptable carrier, and uses of the compounds, either alone or in combination with at least one additional therapeutic agent are also disclosed. The embodiments are useful for inhibiting cellular proliferation, inhibiting the growth and/or metathesis of tumors, treating or preventing cancer, treating or preventing degenerating bone diseases such as rheumatoid arthritis, and/or inhibiting molecules such as CSF-1R.

78 Claims, No Drawings

U.S. PATENT DOCUMENTS

| | | |
|---|---|---|
| 5,409,944 A | 4/1995 | Black et al. |
| 5,420,245 A | 5/1995 | Brown et al. |
| 5,436,265 A | 7/1995 | Black et al. |
| 5,466,823 A | 11/1995 | Talley et al. |
| 5,474,995 A | 12/1995 | Ducharme et al. |
| 5,489,691 A | 2/1996 | Butler et al. |
| 5,510,510 A | 4/1996 | Patel et al. |
| 5,523,430 A | 6/1996 | Patel et al. |
| 5,532,359 A | 7/1996 | Marsters, Jr. et al. |
| 5,536,752 A | 7/1996 | Ducharme et al. |
| 5,550,142 A | 8/1996 | Ducharme et al. |
| 5,571,792 A | 11/1996 | Bolton et al. |
| 5,589,485 A | 12/1996 | Hochlowski et al. |
| 5,602,098 A | 2/1997 | Sebti et al. |
| 5,604,260 A | 2/1997 | Guay et al. |
| 5,607,915 A | 3/1997 | Patton |
| 5,633,272 A | 5/1997 | Talley et al. |
| 5,661,152 A | 8/1997 | Bishop et al. |
| 5,698,584 A | 12/1997 | Black et al. |
| 5,710,140 A | 1/1998 | Ducharme et al. |
| 5,861,419 A | 1/1999 | Dube et al. |
| 5,932,598 A | 8/1999 | Talley et al. |
| 6,001,843 A | 12/1999 | Dube et al. |
| 6,020,343 A | 2/2000 | Belley et al. |
| 6,284,781 B1 | 9/2001 | Danishefsky et al. |
| 6,288,237 B1 | 9/2001 | Hoefle et al. |
| 6,706,738 B2 | 3/2004 | Clark et al. |
| 7,071,216 B2 | 7/2006 | Renhowe et al. |
| 7,144,888 B2 | 12/2006 | Doherty et al. |
| 2003/0078274 A1 | 4/2003 | Lipton |
| 2004/0077633 A1 | 4/2004 | Watson et al. |
| 2004/0082583 A1 | 4/2004 | Cheung et al. |
| 2004/0122237 A1 | 6/2004 | Payman et al. |
| 2004/0127527 A1 | 7/2004 | Hongu et al. |
| 2004/0209892 A1 | 10/2004 | DiPietro et al. |
| 2005/0192287 A1 | 9/2005 | Costales et al. |
| 2005/0245547 A1* | 11/2005 | Kim et al. ................ 514/264.1 |
| 2006/0079564 A1 | 4/2006 | Jansen et al. |

FOREIGN PATENT DOCUMENTS

| | | |
|---|---|---|
| EP | 0675112 | 10/1995 |
| EP | 0696593 | 2/1996 |
| EP | 1535910 | 6/2005 |
| JP | 2000351769 A2 | 12/2000 |
| WO | WO 84/02131 | 6/1984 |
| WO | WO 94/15932 | 7/1994 |
| WO | WO 94/19357 | 9/1994 |
| WO | WO 95/08542 | 3/1995 |
| WO | WO 95/10514 | 4/1995 |
| WO | WO 95/10515 | 4/1995 |
| WO | WO 95/10516 | 4/1995 |
| WO | WO 95/11917 | 5/1995 |
| WO | WO 95/12572 | 5/1995 |
| WO | WO 95/12612 | 5/1995 |
| WO | WO 95/24612 | 9/1995 |
| WO | WO 95/25086 | 9/1995 |
| WO | WO 95/32987 | 12/1995 |
| WO | WO 95/34535 | 12/1995 |
| WO | WO 96/00736 | 1/1996 |
| WO | WO 96/05168 | 2/1996 |
| WO | WO 96/05169 | 2/1996 |
| WO | WO 96/05529 | 2/1996 |
| WO | WO 96/06138 | 2/1996 |
| WO | WO 96/06193 | 2/1996 |
| WO | WO 96/16443 | 5/1996 |
| WO | WO 96/17861 | 6/1996 |
| WO | WO 96/21456 | 7/1996 |
| WO | WO 96/21701 | 7/1996 |
| WO | WO 96/22278 | 7/1996 |
| WO | WO 96/24611 | 8/1996 |
| WO | WO 96/24612 | 8/1996 |
| WO | WO 96/30017 | 10/1996 |
| WO | WO 96/30018 | 10/1996 |
| WO | WO 96/30343 | 10/1996 |
| WO | WO 96/30362 | 10/1996 |
| WO | WO 96/30363 | 10/1996 |
| WO | WO 96/31111 | 10/1996 |
| WO | WO 96/31477 | 10/1996 |
| WO | WO 96/31478 | 10/1996 |
| WO | WO 96/31501 | 10/1996 |
| WO | WO 96/33159 | 10/1996 |
| WO | WO 96/34850 | 11/1996 |
| WO | WO 96/34851 | 11/1996 |
| WO | WO 97/00252 | 1/1997 |
| WO | WO 97/02920 | 1/1997 |
| WO | WO 97/03047 | 1/1997 |
| WO | WO 97/03050 | 1/1997 |
| WO | WO 97/04785 | 2/1997 |
| WO | WO 97/17070 | 5/1997 |
| WO | WO 97/18813 | 5/1997 |
| WO | WO 97/21701 | 6/1997 |
| WO | WO 97/23478 | 7/1997 |
| WO | WO 97/26246 | 7/1997 |
| WO | WO 97/30053 | 8/1997 |
| WO | WO 97/38665 | 10/1997 |
| WO | WO 97/44350 | 11/1997 |
| WO | WO 98/02436 | 1/1998 |
| WO | WO 98/28980 | 7/1998 |
| WO | WO 98/29119 | 7/1998 |
| WO | WO 99/18081 A1 | 4/1999 |
| WO | WO 99/32106 A1 | 7/1999 |
| WO | WO 00/44777 | 8/2000 |
| WO | WO 00/50032 | 8/2000 |
| WO | WO 00/61186 | 10/2000 |
| WO | WO 00/61580 A1 | 10/2000 |
| WO | WO 01/01986 A1 | 1/2001 |
| WO | WO 01/30768 | 5/2001 |
| WO | WO 01/98278 | 12/2001 |
| WO | WO 02/44156 A2 | 6/2002 |
| WO | WO 02/50045 A1 | 6/2002 |
| WO | WO 02/083064 | 10/2002 |
| WO | WO 02/083111 A2 | 10/2002 |
| WO | WO 02/083138 | 10/2002 |
| WO | WO 02/083139 | 10/2002 |
| WO | WO 02/083140 | 10/2002 |
| WO | WO 03/013526 | 2/2003 |
| WO | WO 03/039460 | 5/2003 |
| WO | WO 03/049527 | 6/2003 |
| WO | WO 03/049678 | 6/2003 |
| WO | WO 03/049679 | 6/2003 |
| WO | WO 03/050064 | 6/2003 |
| WO | WO 03/050122 | 6/2003 |
| WO | WO 03/079973 | 10/2003 |
| WO | WO 03/082272 A1 | 10/2003 |
| WO | WO 03/099211 | 12/2003 |
| WO | WO 03/105855 | 12/2003 |
| WO | WO 03/106417 | 12/2003 |
| WO | WO 2004/014871 A1 | 2/2004 |
| WO | WO 2004/039774 | 5/2004 |
| WO | WO 2004/043925 A2 | 5/2004 |
| WO | WO 2004/072025 A2 | 8/2004 |
| WO | WO 2004/085425 A1 | 10/2004 |
| WO | WO 2005/030140 A2 | 4/2005 |
| WO | WO 2005/037273 A1 | 4/2005 |
| WO | WO 2005/063738 A1 | 7/2005 |
| WO | WO 2005/073224 | 8/2005 |
| WO | WO 2005/110410 A2 | 11/2005 |
| WO | WO 2005/110994 A2 | 11/2005 |
| WO | WO 2005/118572 A1 | 12/2005 |

WO  WO 2006/002236 A1  1/2006

OTHER PUBLICATIONS

Bankston et al., A Scaleable Synthesis of BAY 43-9006: A Potent Raf Kinase Inhibitor for the treatment of cancer.; Bayer Research Center, Pharmaceutical Division. Organic Process Research and Development 2002 (6) 777-781.
Ben-Av et al., "Induction of vascular endothelial growth factor expression in synovial fibroblasts by prostaglandin E and interleukin-1: a potential mechanism of inflammatory angiogenesis." *FEBS Letters* 372:83-87 (1995).
Benezra et al., "In Vivo Angiogenic Activity of Interleukins." *Arch. Ophthalmol.* 108:573-576 (1990).
Bingle et al., "The role of tumour-associated macrophages in tumour progression: implications for new anticancer therapies." J Pathol, 2002. 196(3): p. 254-65.
Bouma et al., "Thrombin-activatable fibrinolysis inhibitor (TAFI, plasma procarboxypeptidase B, Procarboxypeptidase R, procarboxypeptidase U)." *Thrombosis Res.* 101:329-354 (2001).
Bourette et al., "Early events in M-CSF receptor signaling." Growth Factors, 2000. 17(3): p. 155-66.
Brower "Tumor angiogenesis—new drugs on the block." *Nature Biotechnology*, 17:963-968 (Oct. 1999).
Campbell et al., "The colony-stimulating factors and collagen-induced arthritis: exacerbation of disease by M-CSF and G-CSF and requirement for endogenous M-CSF." J Leukoc Biol, 2000. 68(1): p. 144-50.
Cenci et al., "M-CSF neutralization and egr-1 deficiency prevent ovariectomy-induced bone loss." *J. Clin Invest*, 2000. 105(9): p. 1279-87.
Chakraborty "Developmental expression of the cyclo-oxygenase-1 and cyclo-oxygenase-2 genes in the peri-implantation mouse uterus and their differential regulation by the blastocyst and ovarian steroids." *J. Mol. Endocrinol.* 16:107-122 (1996).
Chiarugi et al., "Cox-2, iNOS and p53 as play-makers of tumor angiogenesis (Review)." *Intl. J. Mol. Med.* 2:715-719 (1998).
Choueiri et al., "The central role of osteoblasts in the metastasis of prostate cancer." Cancer Metastasis Rev, 2006. 25(4): p. 601-9.
Cohen et al., "Structural bioinformatics-based design of selective, irreversible kinase inhibitors." *Science*, 2005. 308(5726): p. 1318-21.
Corey et al., "Zoledronic Acid Exhibits Inhibitory Effects on Osteoblastic and Osteolytic Metastases of Prostate Cancer", *Clin. Canc. Res.* 2003, 9:295.
Da Costa et al., "Presence of osteoclast-like multinucleated giant cells in the bone and nonstotic lesions of Langerhans cell histiocytosis." *J Exp Med*, 2005. 201(5): p. 687-93.
Dai et al. "Targeted disruption of the mouse colony-stimulating factor 1 receptor gene results in osteopetrosis, mononuclear phagocyte deficiency, increased primitive progenitor cell frequencies, and reproductive defects." *Blood*, 2002. 99(1): p. 111-20.
Daroszewska et al., "Mechanisms of disease: genetics of Pagets's disease of bone and related disorders." *Nat Clin Pract Rheumatol*, 2006. 2(5): p. 270-7.
Diaz-Flores, "Intense Vascular Sprouting From Rat Femoral Vein Induced by Prostaglandins E1 and E2." *Anat. Rec.*, (238):68-76 (1994).
Drees, P., et al., "Mechanisms of disease: Molecular insights into aseptic loosening of orthopedic implants." *Nat Clin Pract Rheumatol*, 2007. 3(3): p. 165-71.
Feldstein et al., "Practice patterns in patients at risk for glucocorticold-induced osteoporosis." *Osteoporos Int*, 2005. 16(12): p. 2168-74.
Fernandez et al., "Neovascularization produced by angiotensin II." *J. Lab. Clin. Med.* 105:141-145 (1985).
Gu et al., "Effect of Novel CAAX Peptidomimetic Farnesyltransferase Inhibitor on Angiogenesis In Vitro and In Vivo." *European J. of Cancer* 35(9):1394-1401 (1999).
Guzman-Clark et al., "Barriers in the management of glucocorticoid-induced osteoporosis." *Arthritis Rheum*, 2007. 57(1): p. 140-6.
Hao et al., "Expression of macrophage colony-stimulating factor and its receptor in microglia activation is linked to teratogen-induced neuronal damage." *Neuroscience*, 2002. 112(4): p. 889-900.

Harada et al., "Expression and Regulation of Vascular Endothelial Growth Factor in Osteoblasts." *Clin, Orthop.* 313, 76-80 (1995).
HLA et al. "Human cyclooxygenase-2 cDNA." *PNAS* 89:7384-7399 (1992).
Ikonomidis et al., "Increased circulating C-reactive protein and macrophage-colony stimulating factor are complementary predictors of long-term outcome in patients with chronic coronary artery disease." *Eur Heart J*, 2005. 26(16): p. 1618-24.
Inaba et al. "Expression of M-CSF receptor encoded by c-fms on smooth muscle cells derived from arteriosclerotic lesion." *J Biol Chem*, 1992. 267(8): p. 5693-9.
Kacinski, "CSF-1 and its receptor in breast carcinomas and neoplasms of the female reproductive tract." *Mol Reprod Dev*, 1997. 46(1): p. 71-4.
Kaku et al., "Amyloid beta protein deposition and neuron loss in osteopetrotic (op/op) mice." *Brain Res Brain Res Protoc*, 2003. 12(2): p. 104-8.
Kim et al., "Modulation of Bone Microenvironment with Zoledronate Enhances the Therapeutic Effects of STI571 and Paclitaxel against Experimental Bone Metastasis of Human Prostate Cancer." 2005, *Canc. Res.*, 65(9): 3707.
Kim et al., Inhibition of vascular endothelial growth factor-induced angiogenesis suppresses tumor growth in vivo.*Nature*, 362:841-844 (1993).
Kirma et al., "Elevated expression of the oncogene c-fms and its ligand, the macrophage colony-stimulating factor-1, in cervical cancer and the role of transforming growth factor-beta1 in inducing c-fms expression." *Cancer Res*, 2007. 67(5): p. 1918-26.
Kitaura et al., "M-CSF mediates TNF-induced inflammatory osteolysis." *J Clin Invest*, 2005. 115(12): p. 3418-27.
Korte, "Changes of the Coagulation and Fibrinolysis System in Malignancy: Their possible Impact on Future Diagnostic and Therapeutic Procedures." *Clin. Chem. La. Med.* 38 (8):679-692 (2000).
Lee et al., "The Cbl protooncoprotein stimulates CSF-1 receptor multiubiquitination and endocytosis, and attenuates macrophage proliferation" *Embo J*, 1999. 18(13): p. 3616-28.
Lester et al., "The causes and treatment of bone loss associated with carcinoma of the breast." Cancer Treat Rev, 2005. 31(2): p. 115-42.
Lester et al., "Current management of treatment-induced bone loss in women with breast cancer treated in the United Kingdom." *Br J Cancer*, 2006. 94(1): p. 30-5.
Majima, "Significant roles of inducible cyclooxygenase (COX)-2 in angiogenesis in rat sponge implants." *Jpn. J. Pharmacol.* 75:105-114 (1997).
Mantovani et al., "The chemokine system in diverse forms of macrophage activation and polarization." *Trends Immunol*, 2004. 25(12): p. 677-86.
Murayama et al., "Intraperitoneal administration of anti-c-fms monoclonal antibody prevents initial events of atherogenesis but does not reduce the size of advanced lesions in apolipoprotein E-deficient mice." *Circulation*, 1999. 99(13): p. 1740-6.
Murphy, Jr., et al., "Expression of macrophage colony-stimulating factor receptor is increased in the AbetaPP(V717F) transgenic mouse model of Alzheimer's disease." *Am J Pathol*, 2000. 157(3): p. 895-904.
Murphy, Jr., et al., "Macrophage colony-stimulating factor augments beta-amyloid-induced interleukin-1, interleukin-6, and nitric oxide production by microglial cells." *J Biol Chem*, 1998. 273(33): p. 20967-71.
Ngan et al., "Proto-oncogenes and p53 protein expression in normal cervical stratified squamous epithelium and cervical intra-epithelial neoplasia." *Eur J Cancer*, 1999. 35(10): p. 1546-50.
Pattan et al., "Synthesis and biological activity of α-[(6-chloro-5-fluoro-2benzothiazolyl)amino]acetanilides"., J. S. Dept. of Mechanical Chemistry, K.L.E.S's College of Pharmacy, Belg. Indian Drugs (2002), 39(10), 515-517.
Paulus et al., "Colony-Stimulating Factor-1 Antibody Reverses Chemoresistance in Human MCF-7 Breast Cancer Xenografts." *Cancer Res*, 2006. 66(8): p. 4349-4356.
Pollard, "Role of colony-stimulating factor-1 in reproduction and development." *Mol Reprod Dev*, 1997. 46(1): p. 54-60; discussion 60-1.

Pollard, "Tumour-educated macrophages promote tumour progression and metastasis." *Nat Rev Cancer*, 2004. 4(1): p. 71-8.

Rabello et al., "CSF1 gene associated with aggressive periodontitis in the Japanese poplulation." *Biochem Biophys Res Commun*, 2006. 347(3): p. 791-6.

Ridge et al., "FMS mutations in myelodysplastic, leukemic, and normal subjects." *Proc Natl Acad Sci U S A*, 1990. 87(4): p. 1377-80.

Ritchlin et al., "Mechanisms of TNF-alpha- and RANKL-mediated osteoclastogenesis and bone resorption in psoriatic arthritis." *J Clin Invest*, 2003. 111(6): p. 821-31.

Roggia et al., "Role of TNF-alpha producing T-cells in bone loss induced by estrogen deficiency." *Minerva Med*, 2004. 95(2): p. 125-32.

Roussel et al., "Transforming potential of the c-fms proto-oncogene (CSF-1 receptor)" *Nature* 1987. 325(6104): p. 549-552.

Saitoh et al., "Clinical significance of increased plasma concentration of macrophage colony-stimulating factor in patients with angina pectoris." *J Am Coll Cardiol*, 2000. 35(3): p. 655-65.

Sawada et al., "Activation and proliferation of the isolated microglia by colony stimulating factor-1 and possible involvement of protein kinase C." *Brain Res*, 1990. 509(1): p. 119-24.

Scholl et al., "Anti-colony-stimulating factor-1 antibody staining in primary breast adenocarcinomas correlates with marked inflammatory cell infiltrates and prognosis." *J Natl Cancer Inst*, 1994. 86(2): p. 120-6.

Seed et al., "The Inhibition of colon-26 Adenocarcinoma Development and Angiogenesis by Topical Diclofenac in 2.5% Hyaluronan." *Cancer Res.* 57:1625 (1997).

Sherr et al., "The c-fms proto-oncogene product is related to the receptor for the mononuclear phagocyte growth factor, CSF 1" *Cell*, 1985. 41(3): p. 665-676.

Stanley et al., "Biology and action of colony—stimulating factor-1." *Mol Reprod Dev*, 1997. 46(1): p. 4-10.

Stoch et al., "Bone loss in men with prostate cancer treated with gonadotropin-releasing hormone agonists." *J Clin Endocrinol Metab*, 2001. 86(6): p. 2787-91.

Tanaka et al., "Macrophage colony-stimulating factor is indispensable for both proliferation and differentiation of osteoclast progenitors." *J Clin Invest*, 1993. 91(1): p. 257-63.

Terato, et al., *Journal of Immunology* 148:2103-2108; 1992.

Tsujii et al., "Cyclooxygenase Regulates Angiogenesis Induced by Colon Cancer Cells." *Cells* 93:705 (1998).

Vessella, "Targeting factors involved in bone remodeling as treatment strategies in prostate cancer bone metastasis." *Clin Cancer Res*, 2006. 12(20 Pt 2): p. 6285s-6290s.

West et al., "A landscape effect in tenosynovial giant-cell tumor from activation of CSF1 expression by a translocation in a minority of tumor cells." *Proc Natl Acad Sci U S A*, 2006. 103(3): p. 690-5.

Xin et al., Peroxisome Proliferator-activated Receptor g Ligands Are Potent Inhibitors of Angiogenesis in Vitro and in Vivo* *J. Biol. Chem.* 274:9116 (1999).

Yalpani, "Cholesterol Lowering Drugs", *Chemistry & Industry*, pp. 85-89 (Feb. 5, 1996).

Yang et al., "The relationship between point mutation and abnormal expression of c-fms oncogene in hepatocellular carcinoma." *Hepatobiliary Pancreat Dis Int*, 2004. 3(1): p. 86-9.

Zacharski et al., "Heparin and Cancer." *Thromb. Haemost.* 80:10-23 (1998).

Ziche et al., "Role of Prostaglandin $E_1$ and Copper in Angiogenesis" *JNCI* 69:475 (1982).

Zins et al., "Colon Cancer Cell-Derived Tumor Necrosis Factor-{alpha} Mediates the Tumor Growth-Promoting Response in Macrophages by Up-regulating the Colony-Stimulating Factor-1 Pathway" *Cancer Res*, 2007. 67(3): p. 1038-1045.

* cited by examiner

US 7,553,854 B2

6-O-SUBSTITUTED BENZOXAZOLE AND BENZOTHIAZOLE COMPOUNDS AND METHODS OF INHIBITING CSF-1R SIGNALING

CROSS REFERENCE TO RELATED APPLICATIONS

This application claims the benefit under 35 U.S.C. §119 (e) of U.S. Provisional Application Ser. No. 60/793,517, filed Apr. 19, 2006, and No. 60/893,857, filed Mar. 8, 2007, both of which are hereby incorporated by reference into this application in their entirety.

BACKGROUND OF THE INVENTION

1. Field of the Invention

The present invention relates to 6-O-substituted benzoxazole and benzothiazole compounds, their tautomers, stereoisomers, solvates, oxides, esters, metabolites, and prodrugs, and to the pharmaceutically acceptable salts thereof. This invention also relates to compositions of the compounds together with pharmaceutically acceptable carriers. In another aspect, this invention relates to uses of the compounds, either alone or in combination with at least one additional therapeutic agent, in the prophylaxis or treatment of cancer.

2. State of the Art

CSF-1R is the receptor for M-CSF (macrophage colony stimulating factor, also called CSF-1) and mediates the biological effects of this cytokine (Sherr 1985). The cloning of the colony stimulating factor-1 receptor (also called c-fms) was described for the first time in Roussel et al., Nature 325:549-552 (1987). In that publication, it was shown that CSF-1R had transforming potential dependent on changes in the C-terminal tail of the protein including the loss of the inhibitory tyrosine 969 phosphorylation which binds Cbl and thereby regulates receptor down regulation (Lee 1999).

CSF-1R is a single chain, transmembrane receptor tyrosine kinase (RTK) and a member of the family of immunoglobulin (Ig) motif containing RTKs characterized by repeated Ig domains in the extracellular portion of the receptor. The intracellular protein tyrosine kinase domain is interrupted by a unique insert domain that is also present in the other related RTK class III family members that include the platelet derived growth factor receptors (PDGFR), stem cell growth factor receptor (c-Kit) and fms-like cytokine receptor (FLT3). In spite of the structural homology among this family of growth factor receptors, they have distinct tissue-specific functions. CSF-1R is mainly expressed on cells of the monocytic lineage and in the female reproductive tract and placenta. In addition, expression of CSF-1R has been reported in Langerhans cells in skin, a subset of smooth muscle cells (Inaba 1992), B cells (Baker 1993) and microglia (Sawada 1990).

The main biological effects of CSF-1R signaling are the differentiation, proliferation, migration, and survival of the precursor macrophages and osteoclasts from the monocytic lineage. Activation of CSF-1R is mediated by its only ligand, M-CSF. Binding of M-CSF to CSF-1R induces the formation of homodimers and activation of the kinase by tyrosine phosphorylation (Stanley 1997). Further signaling is mediated by the p85 subunit of PI3K and Grb2 connecting to the PI3K/AKT and Ras/MAPK pathways, respectively. These two important signaling pathways can regulate proliferation, survival and apoptosis. Other signaling molecules that bind the phosphorylated intracellular domain of CSF-1R include STAT1, STAT3, PLCγ, and Cbl (Bourette 2000).

CSF-1R signaling has a physiological role in immune responses, in bone remodeling and in the reproductive system. The knockout animals for either M-CSF-1 (op/op mouse; Pollard 1996) or CSF-1R (Dai 2002) have been shown to have osteopetrotic, hematopoietic, tissue macrophage, and reproductive phenotypes consistent with a role for CSF-1R in the respective cell types.

The recent success of targeted therapeutics, such as Herceptin® and Avastin®, has underscored the importance in developing "cleaner" less promiscuous drugs with a more specific mechanism of action. These drugs can minimize adverse events, have greater predictability, give physicians greater flexibility in their treatments, and provide researchers with a better understanding of a particular target. Additionally, targeted therapy may allow treatment of multiple indications affected by the same signaling pathway with fewer and potentially easier to manage toxicities. (*BioCentury*, V. 14(10) February, 2006) Inhibition of an individual kinase, such as CSF-1R, which is integrated within a pathway associated with cancer or other diseases, can effectively modulate downstream kinases as well, thereby affecting the entire pathway. However, the active sites of 491 human protein kinase domains are highly conserved, which makes the design of selective inhibitors a formidable challenge (Cohen 2005). Accordingly, there is a need for selective kinase inhibitors, such as selective CSF-1R inhibitors.

SUMMARY OF THE INVENTION

A continuing need exists for compounds that inhibit cellular proliferation, inhibit the growth of tumors, treat cancer, modulate cell cycle arrest, and/or specifically inhibit molecules such as CSF-1R, and for pharmaceutical formulations and medicaments that contain such compounds. A need also exists for selective CSF-1R inhibitory compounds. A need also exists for methods of administering such compounds, pharmaceutical formulations, and medicaments to patients or subjects in need thereof.

One embodiment is directed to compounds, stereoisomers, tautomers, solvates, oxides, esters, and prodrugs of Formula (I), the pharmaceutically acceptable salts thereof, and the related compositions and methods wherein Formula (I) is:

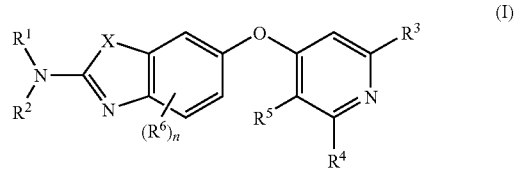

(I)

and wherein X is O, S, or S(O);

$R^1$ and $R^2$ are independently selected from the group consisting of hydrogen, alkyl, substituted alkyl, acyl, cycloalkyl, substituted cycloalkyl, cycloalkenyl, substituted cycloalkenyl, aryl, substituted aryl, heterocyclyl, substituted heterocyclyl, heteroaryl, and substituted heteroaryl; or $R^1$ and $R^2$ are taken together to form a group selected from heterocyclyl, substituted heterocyclyl, heteroaryl, or substituted heteroaryl;

$R^3$ is selected from the group consisting of hydrogen, halo, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclyl, substituted heterocyclyl, amino, substituted amino, acyl, acylamino, alkoxy, substituted alkoxy, carboxyl, carboxyl ester, substituted sulfonyl, aminosulfonyl, and aminocarbonyl;

each $R^6$ is independently alkyl, substituted alkyl, alkoxy, substituted alkoxy, amino, substituted amino, or halo;

n is 0, 1, or 2; and when X is O, $R^4$ is hydrogen, substituted alkyl, alkenyl, substituted alkenyl, alkynyl, or substituted alkynyl, and $R^5$ is hydrogen, alkyl, substituted alkyl, alkenyl, substituted alkenyl, alkynyl, substituted alkynyl, aminocarbonyl, halo, heteroaryl, substituted heteroaryl, cycloalkyl, or substituted cycloalkyl, or $R^4$ and $R^5$ are taken together to form a group selected from heterocyclyl, substituted heterocyclyl, cycloalkyl, substituted cycloalkyl, aryl, substituted aryl, heteroaryl, and substituted heteroaryl; and when X is S or S(O), $R^4$ is hydrogen, substituted alkyl, alkenyl, substituted alkenyl, alkynyl, or substituted alkynyl, and $R^5$ is hydrogen, alkyl, substituted alkyl, alkenyl, substituted alkenyl, alkynyl, substituted alkynyl, aminocarbonyl, halo, heteroaryl, substituted heteroaryl, cycloalkyl, or substituted cycloalkyl.

Another embodiment is directed to compounds, stereoisomers, tautomers, and solvates of Formula (IIa) or (IIb), the pharmaceutically acceptable salts thereof, and the related compositions and methods wherein Formula (IIa) and (IIb) are

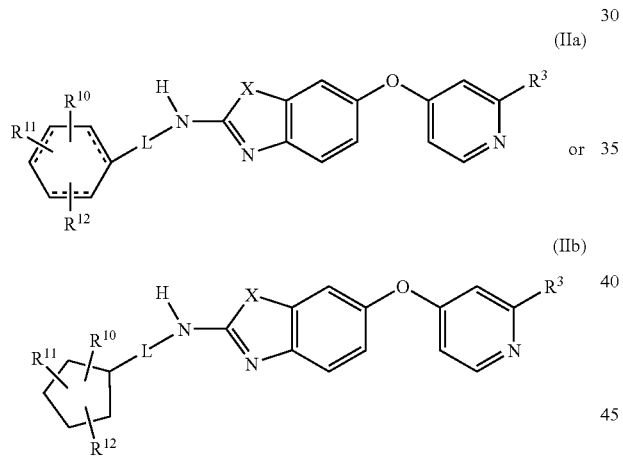

and wherein X is O or S;

the dashed lines are saturated bonds or unsaturated bonds;

L is a covalent bond or is alkylidene or substituted alkylidene;

$R^{10}$, $R^{11}$ and $R^{12}$ are independently selected from the group consisting of hydrogen, halo, hydroxy, alkyl, substituted alkyl, alkoxy, substituted alkoxy, amino, substituted amino, cycloalkyl, substituted cycloalkyl, heterocyclyl, substituted heterocyclyl, aryl, substituted aryl, heteroaryl, and substituted heteroaryl; or $R^{11}$ is taken together with $R^{12}$ to form a group selected from the group consisting of aryl, substituted aryl, heterocyclyl, substituted heterocyclyl, heteroaryl, and substituted heteroaryl; and $R^3$ is selected from the group consisting of hydrogen, halogen, substituted alkyl, carbonitrile, aryl, substituted aryl, heteroaryl, substituted heteroaryl, heterocyclyl, substituted heterocyclyl, amino, substituted amino, acyl, acylamino, alkoxy, substituted alkoxy, carboxyl, carboxyl ester, substituted sulfonyl, aminosulfonyl, and aminocarbonyl.

Another embodiment is directed to compounds, stereoisomers, tautomers, and solvates of Formula (IIIa), the pharmaceutically acceptable salts thereof, and the related compositions and methods wherein Formula (IIIa) is

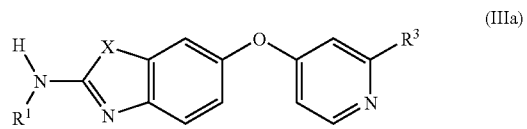

and wherein X is O or S;

$R^1$ is alkyl or alkyl substituted with a substituent selected from the group consisting of aryl, cycloalkyl, heterocyclyl, substituted heterocyclyl, heteroaryl, and substituted heteroaryl; and $R^3$ is selected from the group consisting of hydrogen, halogen, substituted alkyl, carbonitrile, aryl, substituted aryl, heteroaryl, substituted heteroaryl, heterocyclyl, substituted heterocyclyl, amino, substituted amino, acyl, acylamino, alkoxy, substituted alkoxy, carboxyl, carboxyl ester, substituted sulfonyl, aminosulfonyl, and aminocarbonyl.

Another embodiment is directed to compounds, stereoisomers, tautomers, and solvates of Formula (IIIb), the pharmaceutically acceptable salts thereof, and the related compositions and methods wherein Formula (IIIb) is

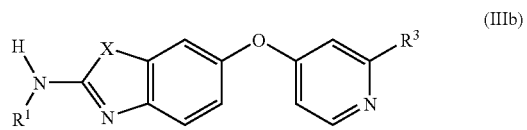

and wherein X is O or S;

$R^1$ is selected from the group consisting of acyl, cycloalkyl, substituted cycloalkyl, cycloalkenyl, substituted cycloalkenyl, heterocyclyl, substituted heterocyclyl, heteroaryl, and substituted heteroaryl; and $R^3$ is selected from the group consisting of hydrogen, halogen, substituted alkyl, carbonitrile, aryl, substituted aryl, heteroaryl, substituted heteroaryl, heterocyclyl, substituted heterocyclyl, amino, substituted amino, acyl, acylamino, alkoxy, substituted alkoxy, carboxyl, carboxyl ester, substituted sulfonyl, aminosulfonyl, and aminocarbonyl.

Another embodiment is directed to compounds, stereoisomers, tautomers, and solvates of Formula (IV), the pharmaceutically acceptable salts thereof, and the related compositions and methods wherein Formula (IV) is

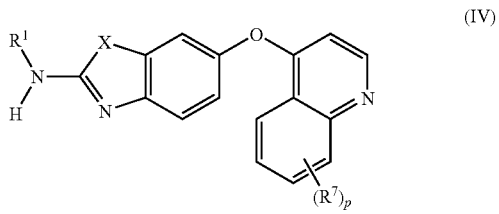

and wherein X is O or S;

$R^7$ is independently selected from the group consisting of alkoxy, haloalkoxy, halo, and carbonitrile;

p is 0, 1, or 2;

R[1] is -LR[8] or alkyl substituted with 0, 1, 2, or 3 substituents independently selected from halo, hydroxy, haloalkyl, alkoxy, haloalkoxy, aryloxy, aminocarbonyl, carboxyl ester, carboxy, and substituted sulfonyl;

L is a covalent bond, alkylidene, or substituted alkylidene; and

R[8] is selected from the group consisting of cycloalkyl, substituted cycloalkyl, tetrahydropyranyl, morpholino, pyridyl, and when p is 0, R[8] is optionally 2-methoxyphenyl.

Another embodiment is directed to compounds, stereoisomers, tautomers, and solvates of Formula (V), the pharmaceutically acceptable salts thereof, and the related compositions and methods wherein Formula (V) is

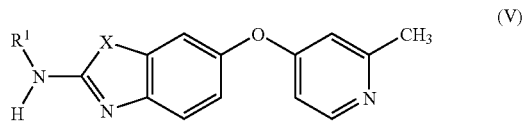

(V)

and wherein X is O or S;

R[1] is -LR[9] or alkyl substituted with 0, 1, 2, or 3 substituents independently selected from halo, hydroxy, haloalkyl, alkoxy, haloalkoxy, aryloxy, aminocarbonyl, carboxyl ester, carboxy, and substituted sulfonyl;

L is a covalent bond, alkylidene, or substituted alkylidene; and

R[9] is selected from the group consisting of cycloalkyl, substituted cycloalkyl, tetrahydropyranyl, morpholino, and pyridyl.

Another embodiment is directed to a method of treating a CSF-1R mediated disorder with a CSR-1R inhibitory compound of Formula (I), (IIa), (IIb), (IIIa), (IIIb), (IV), or (V).

In a more particular embodiment said compound does not substantially inhibit Raf kinase. In a more particular embodiment said compound preferentially inhibits CSF-1R over Raf kinase. In a more particular embodiment said compound inhibits Raf kinase at an IC$_{50}$ of greater than about 1 µM. In a more particular embodiment said compound inhibits CSF-1R at an IC$_{50}$ of at less than about 1 µM. More particular still, said compound inhibits CSF-1R at an IC$_{50}$ of at less than about 0.1 µM.

DETAILED DESCRIPTION

Throughout this application, the text refers to various embodiments of the present compounds, compositions, and methods. The various embodiments described are meant to provide a variety illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

DEFINITIONS

Unless specifically defined otherwise, the terms used herein are defined below.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, spirocycloalkylidene, SO$_3$H, substituted sulfonyl, sulfonyloxy, thioacyl, thiocyanate, thiol, alkylthio, and substituted alkylthio, wherein said substituents are defined herein.

"Alkylidene" or "alkylene" refers to divalent saturated aliphatic hydrocarbyl groups having from 1 to 10 carbon atoms and preferably 1 to 6 carbon atoms. The alkylidene and alkylene groups include branched and straight chain hydrocarbyl groups.

"Substituted alkylidene" or "substituted alkylene" refers to an alkylidene group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, oxo, thione, spirocycloalkylidene, SO$_3$H, substituted sulfonyl, sulfonyloxy, thioacyl, thiocyanate, thiol, alkylthio, and substituted alkylthio, wherein said substituents are defined herein.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, substituted hydrazino-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, substituted hydrazino, heteroaryl, substituted heteroaryl, heterocyclic and substituted heterocyclic are as defined herein. Acyl includes the "acetyl" group $CH_3C(O)$—.

"Acylamino" refers to the groups —$NR^{20}C(O)$alkyl, —$NR^{20}C(O)$substituted alkyl, —$NR^{20}C(O)$cycloalkyl, —$NR^{20}C(O)$substituted cycloalkyl, —$NR^{20}C(O)$cycloalkenyl, —$NR^{20}C(O)$substituted cycloalkenyl, —$NR^{20}C(O)$alkenyl, —$NR^{20}C(O)$substituted alkenyl, —$NR^{20}C(O)$alkynyl, —$NR^{20}C(O)$substituted alkynyl, —$NR^{20}C(O)$aryl, —$NR^{20}C(O)$substituted aryl, —$NR^{20}C(O)$heteroaryl, —$NR^{20}C(O)$substituted heteroaryl, —$NR^{20}C(O)$heterocyclic, and —$NR^{20}C(O)$substituted heterocyclic wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Amino" refers to the group —$NH_2$.

"Substituted amino" refers to the group —$NR^{21}R^{22}$ where $R^{21}$ and $R^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cylcoalkyl, —$SO_2$-cycloalkenyl, —$SO_2$-substituted cycloalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein $R^{21}$ and $R^{22}$ are optionally joined, together with the nitrogen bound thereto to form a heterocyclic or substituted heterocyclic group, provided that $R^{21}$ and $R^{22}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein. When $R^{21}$ is hydrogen and $R^{22}$ is alkyl, the substituted amino group is sometimes referred to herein as alkylamino. When $R^{21}$ and $R^{22}$ are alkyl, the substituted amino group is sometimes referred to herein as dialkylamino. When referring to a monosubstituted amino, it is meant that either $R^{21}$ or $R^{22}$ is hydrogen but not both. When referring to a disubstituted amino, it is meant that neither $R^{21}$ nor $R^{22}$ are hydrogen.

"Hydroxyamino" refers to the group —NHOH.

"Alkoxyamino" refers to the group —NHO-alkyl wherein alkyl is defined herein.

"Aminocarbonyl" refers to the group —$C(O)NR^{23}R^{24}$ where $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, substituted heterocyclyl, hydroxy, alkoxy, substituted alkoxy, amino, substituted amino, and acylamino, and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —$C(S)NR^{23}R^{24}$ where $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonylamino" refers to the group —$NR^{20}C(O)NR^{23}R^{24}$ where $R^{20}$ is hydrogen or alkyl and $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —$NR^{20}C(S)NR^{23}R^{24}$ where $R^{20}$ is hydrogen or alkyl and $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—$C(O)NR^{23}R^{24}$ where $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —$SO_2NR^{23}R^{24}$ where $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—$SO_2NR^{23}R^{24}$ where $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylamino" refers to the group —$NR^{20}$—$SO_2NR^{23}R^{24}$ where $R^{20}$ is hydrogen or alkyl and $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

"Amidino" refers to the group —$C(=NR^{25})NR^{23}R^{24}$ where $R^{25}$, $R^{23}$, and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiocyanate, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Alkenyl" refers to alkenyl groups having from 2 to 6 carbon atoms and preferably 2 to 4 carbon atoms and having at least 1 and preferably from 1 to 2 sites of vinyl unsaturation (>C=C<). Such groups are exemplified, for example, by vinyl, allyl, and but-3-en-yl.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO₃H, substituted sulfonyl, sulfonyloxy, thioacyl, thiol, alkylthio, and substituted alkylthio, wherein said substituents are defined herein and with the proviso that any hydroxy or thiol substitution is not attached to a vinyl (unsaturated) carbon atom.

"Alkynyl" refers to hydrocarbyl groups having from 2 to 6 carbon atoms and preferably 2 to 3 carbon atoms and having at least 1 and preferably from 1 to 2 sites of acetylenic unsaturation (—C≡C—).

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO₃H, substituted sulfonyl, sulfonyloxy, thioacyl, thiol, alkylthio, and substituted alkylthio, wherein said substituents are defined herein and with the proviso that any hydroxy or thiol substitution is not attached to an acetylenic carbon atom.

"Azido" refers to the group —N₃.

"Hydrazino" refers to the group —NHNH₂.

"Substituted hydrazino" refers to the group —NR²⁶NR²⁷R²⁸ where R²⁶, R²⁷, and R²⁸ are independently selected from the group consisting of hydrogen, alkyl, substituted alkyl, alkenyl, substituted alkenyl, alkynyl, substituted alkynyl, aryl, substituted aryl, carboxyl ester, cycloalkyl, substituted cycloalkyl, cycloalkenyl, substituted cycloalkenyl, heteroaryl, substituted heteroaryl, heterocyclic, substituted heterocyclic, —SO₂-alkyl, —SO₂-substituted alkyl, —SO₂-alkenyl, —SO₂-substituted alkenyl, —SO₂-cycloalkyl, —SO₂-substituted cylcoalkyl, —SO₂-cycloalkenyl, —SO₂-substituted cycloalkenyl, —SO₂-aryl, —SO₂-substituted aryl, —SO₂-heteroaryl, —SO₂-substituted heteroaryl, —SO₂-heterocyclic, and —SO₂-substituted heterocyclic and wherein R²⁷ and R²⁸ are optionally joined, together with the nitrogen bound thereto to form a heterocyclic or substituted heterocyclic group, provided that R²⁷ and R²⁸ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Cyano" or "carbonitrile" refers to the group —CN.

"Cyanate" refers to the group —OCN.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"(Carboxyl ester)amino" refers to the group —NR²⁰—C(O)O-alkyl, —NR²⁰—C(O)O-substituted alkyl, —NR²⁰—C(O)O-alkenyl, —NR²⁰—C(O)O-substituted alkenyl, —NR²⁰—C(O)O-alkynyl, —NR²⁰—C(O)O-substituted alkynyl, —NR²⁰—C(O)O-aryl, —NR²⁰—C(O)O-substituted aryl, —NR²⁰—C(O)O-cycloalkyl, —NR²⁰—C(O)O-substituted cycloalkyl, —NR²⁰—C(O)O-cycloalkenyl, —NR²⁰—C(O)O-substituted cycloalkenyl, —NR²⁰—C(O)O-heteroaryl, —NR²⁰—C(O)O-substituted heteroaryl, —NR²⁰—C(O)O-heterocyclic, and —NR²⁰—C(O)O-substituted heterocyclic wherein R²⁰ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Cycloalkyl" refers to cyclic alkyl groups of from 3 to 10 carbon atoms having single or multiple cyclic rings including fused, bridged, and spiro ring systems. In fused ring systems, one or more the rings can be cycloalkyl, heterocyclic, aryl, or heteroaryl provided that the point of attachment is through the cycloalkyl ring. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 4 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiocyanate, thiol, alkylthio, and substituted alkylthio, wherein said substituents are defined herein.

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)$NH_2$.

"Substituted guanidino" refers to —$NR^{29}$C(=$NR^{29}$)N($R^{29}$)$_2$ where each $R^{29}$ is independently selected from the group consisting of hydrogen, alkyl, substituted alkyl, aryl, substituted aryl, heteroaryl, substituted heteroaryl, heterocyclyl, and substituted heterocyclyl and two $R^{29}$ groups attached to a common guanidino nitrogen atom are optionally joined together with the nitrogen bound thereto to form a heterocyclic or substituted heterocyclic group, provided that at least one $R^{29}$ is not hydrogen, and wherein said substituents are as defined herein.

"Halo" or "halogen" refers to fluoro, chloro, bromo and iodo.

"Haloalkyl" refers to substitution of alkyl groups with 1 to 5 or preferably 1 to 3 halo groups.

"Haloalkoxy" refers to substitution of alkoxy groups with 1 to 5 or preferably 1 to 3 halo groups.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated, partially saturated, or unsaturated group (but not aromatic) having a single ring or multiple condensed rings, including fused bridged and spirocycyl ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —$NO_2$.

"Oxo" refers to the atom (=O).

"Oxide" refers to products resulting from the oxidation of one or more heteroatoms. Examples include N-oxides, sulfoxides, and sulfones.

"Spirocyclyl" refers to divalent cyclic groups from 3 to 10 carbon atoms having a cycloalkyl or heterocyclyl ring with a spiro union (the union formed by a single atom which is the only common member of the rings) as exemplified by the following structure:

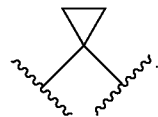

"Spirocycloalkyl" or "spirocycloalkylidene" refers to divalent cyclic groups having a cycloalkyl ring with a spiro union, as described for spirocyclyl.

"Sulfonyl" refers to the divalent group —S(O)$_2$—.

"Substituted sulfonyl" refers to the group —$SO_2$-alkyl, —$SO_2$-substituted alkyl, —$SO_2$-alkenyl, —$SO_2$-substituted alkenyl, —$SO_2$-cycloalkyl, —$SO_2$-substituted cylcoalkyl, —$SO_2$-cycloalkenyl, —$SO_2$-substituted cycloalkenyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cylcoalkyl, —OSO$_2$-cycloalkenyl, —OSO$_2$-substituted cycloalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thiol" refers to the group —SH.

"Alkylthio" refers to the group —S-alkyl wherein alkyl is as defined herein.

"Substituted alkylthio" refers to the group —S-(substituted alkyl) wherein substituted alkyl is as defined herein.

"Thiocarbonyl" refers to the divalent group —C(S)— which is equivalent to —C(=S)—.

"Thione" refers to the atom (=S).

"Thiocyanate" refers to the group —SCN.

"Solvate" or "solvates" refer compounds or a salt thereof that are bound to a stoichiometric or non-stoichiometric amount of a solvent. Preferred solvents are volatile, non-toxic, and/or acceptable for administration to humans in trace amounts. Suitable solvates include water.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Prodrug" refers to any derivative of a compound of the embodiments that is capable of directly or indirectly providing a compound of the embodiments or an active metabolite or residue thereof when administered to a subject. Particularly favored derivatives and prodrugs are those that increase the bioavailability of the compounds of the embodiments when such compounds are administered to a subject (e.g., by allowing an orally administered compound to be more readily absorbed into the blood) or which enhance delivery of the parent compound to a biological compartment (e.g., the brain or lymphatic system) relative to the parent species. Prodrugs include ester forms of the compounds of the invention. Examples of ester prodrugs include formate, acetate, propionate, butyrate, acrylate, and ethylsuccinate derivatives. An general overview of prodrugs is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate. The term also includes pharmaceutically acceptable salts of stereoisomers, tautomers, esters, and prodrugs of the compound.

"Patient" refers to mammals and includes humans and non-human mammals.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Reference to "selective" inhibition, refers to a compound, composition, or chemotype that preferentially inhibits a particular target or class of targets. Reference to "selective inhibition of CSF-1R" indicates the preferential inhibition of CSF-1R and optionally like kinase receptors such as PDGFR. In some embodiments, selective inhibition of CSF-1R refers to preferential inhibition of CSF-1R over Raf kinase. "Selective," "targeted," "specific," or "preferential" inhibition is not intended to mean complete absence of inhibitory activity with respect to all other kinases or receptors.

"CSF-1R inhibitor" refers to a compound that can inhibit CSF-1R. Preferably, a CSF-1R inhibitor is selective of CSF-1R over other targets. In an embodiment, a CSF-1R inhibitor has selective inhibition of CSF-1R over Raf kinase. In a preferred embodiment, such selective inhibition refers to at least a 2:1 binding preference of a compound of this invention to CSF-1R relative to Raf kinase, more preferably at least 5:1, and even more preferably at least 10:1.

Unless indicated otherwise, the nomenclature of substituents that are not explicitly defined herein are arrived at by naming the terminal portion of the functionality followed by the adjacent functionality toward the point of attachment. For example, the substituent "arylalkyloxycabonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

One embodiment is directed to compounds, stereoisomers, tautomers, solvates, oxides, esters, and prodrugs of Formula (I), the pharmaceutically acceptable salts thereof, and the related compositions and methods wherein Formula (I) is:

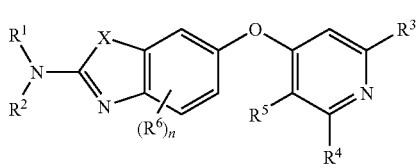

and wherein X is O, S, or S(O);

$R^1$ and $R^2$ are independently selected from the group consisting of hydrogen, alkyl, substituted alkyl, acyl, cycloalkyl, substituted cycloalkyl, cycloalkenyl, substituted cycloalkenyl, aryl, substituted aryl, heterocyclyl, substituted heterocyclyl, heteroaryl, and substituted heteroaryl; or $R^1$ and $R^2$ are taken together to form a group selected from heterocyclyl, substituted heterocyclyl, heteroaryl, or substituted heteroaryl;

$R^3$ is selected from the group consisting of hydrogen, halo, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclyl, substituted heterocyclyl, amino, substituted amino, acyl, acylamino, alkoxy, substituted alkoxy, carboxyl, carboxyl ester, substituted sulfonyl, aminosulfonyl, and aminocarbonyl;

each $R^6$ is independently alkyl, substituted alkyl, alkoxy, substituted alkoxy, amino, substituted amino, or halo;

n is 0, 1, or 2; and when X is O, $R^4$ is hydrogen, substituted alkyl, alkenyl, substituted alkenyl, alkynyl, or substituted alkynyl, and $R^5$ is hydrogen, alkyl, substituted alkyl, alkenyl, substituted alkenyl, alkynyl, substituted alkynyl, aminocarbonyl, halo, heteroaryl, substituted heteroaryl, cycloalkyl, or substituted cycloalkyl, or $R^4$ and $R^5$ are taken together to form a group selected from heterocyclyl, substituted heterocyclyl, cycloalkyl, substituted cycloalkyl, aryl, substituted aryl, heteroaryl, and substituted heteroaryl; and when X is S or S(O), $R^4$ is hydrogen, substituted alkyl, alkenyl, substituted alkenyl, alkynyl, or substituted alkynyl, and $R^5$ is hydrogen, alkyl, substituted alkyl, alkenyl, substituted alkenyl, alkynyl, substituted alkynyl, aminocarbonyl, halo, heteroaryl, substituted heteroaryl, cycloalkyl, or substituted cycloalkyl.

In some embodiments, X is O.

In some embodiments, X is S.

In some embodiments, X is S(O).

In some embodiments, the oxide of Formula (I) is an oxide wherein X is $S(O)_2$.

In some embodiments, $R^2$ is hydrogen or methyl.

In some embodiments, $R^1$ is alkyl substituted with 0, 1, 2, or 3 substituents independently selected from halo, hydroxy, haloalkyl, alkoxy, haloalkoxy, aryloxy, aminocarbonyl, carboxyl ester, carboxyl, and substituted sulfonyl. Substituted and unsubstituted $R^1$ alkyl groups include branched hydrocarbyl groups such as pent-2-yl.

In some embodiments, $R^1$ is $-LR^{1a}$ wherein L is a covalent bond, alkylidene, or substituted alkylidene, and $R^{1a}$ selected from cycloalkyl, cycloalkenyl, aryl, heterocyclyl, and heteroaryl, wherein each $R^{1a}$ is substituted or unsubstituted.

In some aspects, $R^{1a}$ is selected from phenyl, furan-2-yl, furan-3-yl, tetrahydropyran-2-yl, tetrahydropyran-3-yl, tetrahydropyran-4-yl, cyclopropyl, cyclobutyl, cyclopentyl, cyclohexyl, cycloheptyl, cyclooctyl, cyclohexenyl, pyrid-2-yl, pyrid-3-yl, pyrid-4-yl, 2,3-dihydrobenzofuran, 2,3-dihydrobenzo[b][1,4]dioxine, 3,4-dihydro-2H-benzo[b][1,4]dioxepine, pyrazinyl, pyrrolidinyl, piperidinyl, piperidinone, pyrrolidinone, pyridin-2(1H)-one, morpholino, napthyl, bicyclo[3.1.1]heptane, bicyclo[2.2.1]heptane, 1,2,3,4-tetrahydronaphthalene, 2,3-dihydro-1H-indene, and azepan-2-one, wherein each $R^{1a}$ is substituted or unsubstituted. In some such aspects L is a covalent bond.

In some embodiments, L is a covalent bond.

In some embodiments of the compound of Formula (I), L is alkylidene substituted with 0, 1, 2, or 3 substituents independently selected from alkyl, substituted alkyl, hydroxy, alkoxy, haloalkoxy, aminocarbonyl, carboxyl ester, and carboxyl.

In some embodiments of the compound of Formula (I), $R^1$ is

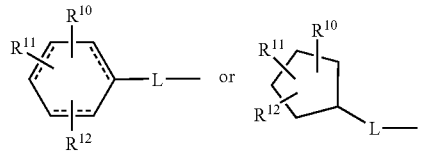

wherein the dashed lines are saturated bonds or unsaturated bonds;

wherein L is a covalent bond or is alkylidene or substituted alkylidene; and $R^{10}$, $R^{11}$ and $R^{12}$ are independently selected from the group consisting of hydrogen, halo, hydroxy, alkyl, substituted alkyl, alkoxy, substituted alkoxy, amino, substituted amino, cycloalkyl, substituted cycloalkyl, heterocyclyl, substituted heterocyclyl, aryl, substituted aryl, heteroaryl, and substituted heteroaryl; or $R^{11}$ is taken together with $R^{12}$ to form a group selected from the group consisting of aryl, substituted aryl, heterocyclyl, substituted heterocyclyl, heteroaryl, and substituted heteroaryl. In some aspects, $R^{10}$ is hydrogen.

In some embodiments, the dashed lines are saturated bonds, thereby forming a cyclohexyl group.

In some embodiments of the compound of Formula (I), L is a covalent bond.

In some embodiments of the compound of Formula (I), L is methylene or substituted methylene.

In some embodiments of the compound of Formula (I) when L is not a covalent bond, L is substituted with alkyl, substituted alkyl, carboxyl, aminocarbonyl, and carboxyl ester.

In some embodiments of the compound of Formula (I), $R^{10}$, $R^{11}$, and $R^{12}$ are independently selected from the group consisting of hydrogen, halo, hydroxyl, alkyl, substituted alkyl, and alkoxy.

In some embodiments of the compound of Formula (I), at least one of $R^{10}$, $R^{11}$, and $R^{12}$ is hydroxyl.

In some embodiments, $R^{11}$ and $R^{12}$ are independently selected from the group consisting of hydrogen, halo, alkyl, substituted alkyl, and alkoxy.

In some embodiments, $R^{11}$ is taken together with $R^{12}$ to form aryl or substituted aryl.

In some embodiments, $R^1$ is alkyl or substituted alkyl.

In some embodiments, $R^1$ is substituted alkyl, wherein the substituent of $R^1$ is selected from the group consisting of alkyl, aryl, substituted aryl, cycloalkyl, substituted cycloalkyl, heterocyclyl, substituted heterocyclyl, heteroaryl, and substituted heteroaryl.

In some embodiments, $R^1$ is substituted alkyl, wherein the substituent of $R^1$ is selected from the group consisting of alkyl, aryl, cycloalkyl, heterocyclyl, substituted heterocyclyl, heteroaryl, and substituted heteroaryl.

In some embodiments, $R^1$ is substituted alkyl, wherein the substituent of $R^1$ is cycloalkyl or substituted cycloalkyl.

In some embodiments, $R^1$ is substituted alkyl, wherein the substituent of $R^1$ is cycloalkyl or substituted cycloalkyl.

In some embodiments, $R^1$ is selected from the group consisting of cycloalkyl, substituted cycloalkyl, cycloalkenyl, substituted cycloalkenyl, heterocyclyl, substituted heterocyclyl, heteroaryl, and substituted heteroaryl.

In some embodiments, $R^1$ is selected from the group consisting of cycloalkyl, substituted cycloalkyl, heterocyclyl, and substituted heterocyclyl.

In some embodiments, $R^3$ is acylamino or aminocarbonyl.

In some embodiments, $R^3$ is —C(O)NH-L$R^{3a}$ wherein L is a covalent bond, alkylidene, or substituted alkylidene, and $R^{3a}$ is selected from the group consisting of alkyl, haloalkyl, amino, acylamino, (carboxyl ester)amino, hydroxy, alkoxy, substituted alkoxy, cycloalkyl, substituted cycloalkyl, heterocyclyl, and substituted heterocyclyl.

In some embodiments, $R^3$ is —C(O)NHCH$_3$.

In some embodiments, $R^3$ is hydrogen, carboxyl, substituted alkyl, carbonitrile, heteroaryl, or substituted heteroaryl.

In some embodiments, $R^3$ is selected from the group consisting of pyrazol-1-yl, pyrazol-3-yl, pyrazol-4-yl, pyridine-2-yl, pyridine-3-yl, pyridine-4-yl, pyrimidin-4-yl, pyrimidin-3-yl, pyrimidin-2-yl, thiazoyl, tetrazolyl, imidazol-1-yl, imidazol-2-yl, imidazol-3-yl, pyrazinyl, phenyl, tetrahydropyridine, 1H-pyrrolo[2,3-b]pyridine, furanyl, oxazole, oxadiazole, cyclopropyl, cyclohexyl, cyclohexenyl, piperidinyl, morpholino, tetrahydro-1H-benzo[d]imidazole, pyrrolidinyl, piperazinyl, and piperazin-2-one, wherein each $R^3$ is substituted or unsubstituted.

In some embodiments, $R^4$ is hydrogen.

In some embodiments, $R^5$ is hydrogen.

In some embodiments and in combination with any of the aforementioned embodiments, n is 0, $R^4$ and $R^5$ are hydrogen, and $R^3$ is selected from the group consisting of hydrogen, halo, substituted alkyl, carbonitrile, aryl, substituted aryl, heteroaryl, substituted heteroaryl, heterocyclyl, substituted heterocyclyl, amino, substituted amino, acyl, acylamino, alkoxy, substituted alkoxy, carboxyl, carboxyl ester, substituted sulfonyl, aminosulfonyl, and aminocarbonyl.

In some embodiments, $R^4$ and $R^5$ are taken together to form an aryl or substituted aryl group.

Another embodiment is directed to compounds, stereoisomers, tautomers, and solvates of Formula (IIa) or (IIb), the pharmaceutically acceptable salts thereof, and the related compositions and methods

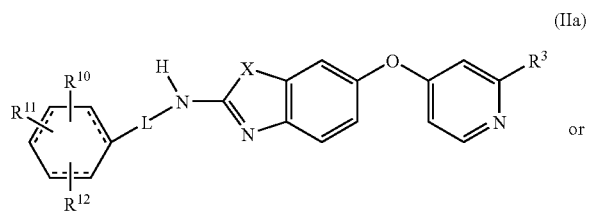

(IIa)

or

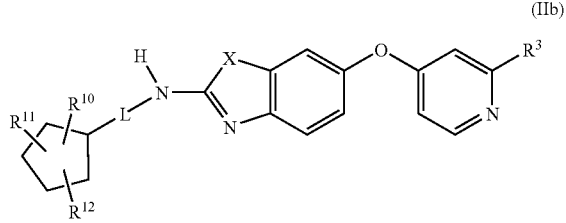

-continued (IIb)

wherein X is O or S;

wherein the dashed lines are saturated bonds or unsaturated bonds;

wherein L is a covalent bond or is alkylidene or substituted alkylidene;

$R^{10}$, $R^{11}$ and $R^{12}$ are independently selected from the group consisting of hydrogen, halo, hydroxy, alkyl, substituted alkyl, alkoxy, substituted alkoxy, amino, substituted amino, cycloalkyl, substituted cycloalkyl, heterocyclyl, substituted heterocyclyl, aryl, substituted aryl, heteroaryl, and substituted heteroaryl; or $R^{11}$ is taken together with $R^{12}$ to form a group selected from the group consisting of aryl, substituted aryl, heterocyclyl, substituted heterocyclyl, heteroaryl, and substituted heteroaryl; and $R^3$ is selected from the group consisting of hydrogen, halogen, substituted alkyl, carbonitrile, aryl, substituted aryl, heteroaryl, substituted heteroaryl, heterocyclyl, substituted heterocyclyl, amino, substituted amino, acyl, acylamino, alkoxy, substituted alkoxy, carboxyl, carboxyl ester, substituted sulfonyl, aminosulfonyl, and aminocarbonyl.

In some embodiments of the compound of Formula (IIa) or (IIb), X is O.

In some embodiments of the compound of Formula (IIa) or (IIb), X is S.

In some embodiments, the dashed lines are saturated bonds, thereby forming a cyclohexyl group.

In some embodiments of the compound of Formula (IIa) or (IIb), L is a covalent bond.

In some embodiments of the compound of Formula (IIa) or (IIb), L is methylene or substituted methylene.

In some embodiments of the compound of Formula (IIa) or (IIb), L is substituted with alkyl, substituted alkyl, carboxyl, aminocarbonyl, or carboxyl ester.

In some embodiments of the compound of Formula (IIa) or (IIb), $R^{10}$, $R^{11}$, and $R^{12}$ are independently selected from the group consisting of hydrogen, halo, hydroxyl, alkyl, substituted alkyl, and alkoxy.

In some embodiments of the compound of Formula (IIa) or (IIb), at least one of $R^{10}$, $R^{11}$, and $R^{12}$ is hydroxyl.

In some embodiments of the compound of Formula (IIa) or (IIb), $R^{11}$ and $R^{12}$ are independently selected from the group consisting of hydrogen, halo, alkyl, substituted alkyl, and alkoxy.

In some embodiments of the compound of Formula (IIa) or (IIb), $R^{11}$ is taken together with $R^{12}$ to form aryl or substituted aryl.

In some embodiments of the compound of Formula (IIa) or (IIb), $R^3$ is acylamino or aminocarbonyl.

In some embodiments of the compound of Formula (IIa) or (IIb), $R^3$ is —C(O)NHCH$_3$.

In some embodiments of the compound of Formula (IIa) or (IIb), $R^3$ is hydrogen, carboxyl, substituted alkyl, carbonitrile, heteroaryl, or substituted heteroaryl.

Another embodiment is directed to compounds, stereoisomers, tautomers, and solvates of Formula (IIIa), the pharmaceutically acceptable salts thereof, and the related compositions and methods wherein Formula (IIIa) is

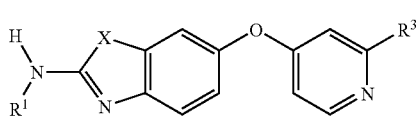

and wherein X is O or S;

R¹ is alkyl or alkyl substituted with a substituent selected from the group consisting of aryl, cycloalkyl, heterocyclyl, substituted heterocyclyl, heteroaryl, and substituted heteroaryl; and R³ is selected from the group consisting of hydrogen, halogen, substituted alkyl, carbonitrile, aryl, substituted aryl, heteroaryl, substituted heteroaryl, heterocyclyl, substituted heterocyclyl, amino, substituted amino, acyl, acylamino, alkoxy, substituted alkoxy, carboxyl, carboxyl ester, substituted sulfonyl, aminosulfonyl, and aminocarbonyl.

In some embodiments of the compound of Formula (IIIa), X is O.

In some embodiments of the compound of Formula (IIIa), X is S.

In some embodiments of the compound of Formula (IIIa), R¹ is alkyl substituted with cycloalkyl.

In some embodiments of the compound of Formula (IIIa), R³ is acylamino or aminocarbonyl.

In some embodiments of the compound of Formula (IIIa), R³ is —C(O)NHCH₃.

In some embodiments of the compound of Formula (IIIa), R³ is hydrogen, carboxyl, substituted alkyl, carbonitrile, heteroaryl, or substituted heteroaryl.

Another embodiment is directed to compounds, stereoisomers, tautomers, and solvates of Formula (IIIb), the pharmaceutically acceptable salts thereof, and the related compositions and methods wherein Formula (IIIb) is

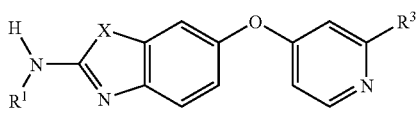

and wherein X is O or S;

R¹ is selected from the group consisting of acyl, cycloalkyl, substituted cycloalkyl, cycloalkenyl, substituted cycloalkenyl, heterocyclyl, substituted heterocyclyl, heteroaryl, and substituted heteroaryl; and R³ is selected from the group consisting of hydrogen, halogen, substituted alkyl, carbonitrile, aryl, substituted aryl, heteroaryl, substituted heteroaryl, heterocyclyl, substituted heterocyclyl, amino, substituted amino, acyl, acylamino, alkoxy, substituted alkoxy, carboxyl, carboxyl ester, substituted sulfonyl, aminosulfonyl, and aminocarbonyl.

In some embodiments of the compound of Formula (IIIb), X is O.

In some embodiments of the compound of Formula (IIIb), X is S.

In some embodiments of the compound of Formula (IIIb), R¹ is selected from the group consisting of cycloalkyl, substituted cycloalkyl, heterocyclyl, and substituted heterocyclyl.

In some embodiments of the compound of Formula (IIIb), R³ is acylamino or aminocarbonyl.

In some embodiments of the compound of Formula (IIIb), R³ is —C(O)NHCH₃.

In some embodiments of the compound of Formula (IIIb), R³ is hydrogen, carboxyl, substituted alkyl, carbonitrile, heteroaryl, or substituted heteroaryl.

In some embodiments of the compound of Formula (IIIb), R³ is —C(O)NH-LR³ᵃ, wherein L is a covalent bond, alkylidene, or substituted alkylidene, and R³ᵃ is selected from the group consisting of alkyl, haloalkyl, amino, acylamino, (carboxyl ester)amino, hydroxy, alkoxy, substituted alkoxy, cycloalkyl, substituted cycloalkyl, heterocyclyl, and substituted heterocyclyl.

In some embodiments of the compound of Formula (IIIb), R³ is selected from the group consisting of pyrazol-1-yl, pyrazol-3-yl, pyrazol-4-yl, pyridine-2-yl, pyridine-3-yl, pyridine-4-yl, pyrimidin-4-yl, pyrimidin-3-yl, pyrimidin-2-yl, thiazoyl, tetrazolyl, imidazol-1-yl, imidazol-2-yl, imidazol-3-yl, pyrazinyl, phenyl, tetrahydropyridine, 1H-pyrrolo[2,3-b]pyridine, furanyl, oxazole, oxadiazole, cyclopropyl, cyclohexyl, cyclohexenyl, piperidinyl, morpholino, tetrahydro-1H-benzo[d]imidazole, pyrrolidinyl, piperazinyl, and piperazin-2-one, wherein each R³ is substituted or unsubstituted.

Another embodiment is directed to a compound, stereoisomer, tautomer, solvate, oxide, ester, and prodrug of Formula (IV), a pharmaceutically acceptable salt thereof, and the related compositions and methods wherein Formula (IV) is

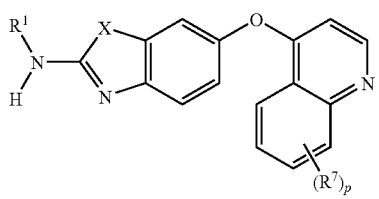

and wherein X is O or S;

R⁷ is independently selected from the group consisting of alkoxy, haloalkoxy, halo, and carbonitrile;

p is 0, 1, or 2;

R¹ is -LR⁸ or alkyl substituted with 0, 1, 2, or 3 substituents independently selected from halo, hydroxy, haloalkyl, alkoxy, haloalkoxy, aryloxy, aminocarbonyl, carboxyl ester, carboxy, and substituted sulfonyl;

L is a covalent bond, alkylidene, or substituted alkylidene; and

R⁸ is selected from the group consisting of cycloalkyl, substituted cycloalkyl, tetrahydropyranyl, morpholino, pyridyl, and when p is 0, R¹ᵃ is optionally 2-methoxyphenyl.

In some embodiments, X is S.

In some embodiments, p is 0.

Another embodiment is directed to a compound, stereoisomer, tautomer, solvate, oxide, ester, and prodrug of Formula (V), the pharmaceutically acceptable salt thereof, and the related compositions and methods wherein Formula (V) is

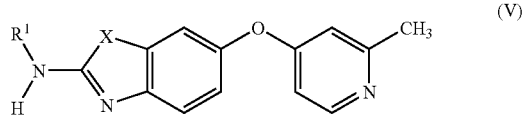

(V)

wherein X is O or S;

R¹ is -LR⁹ or alkyl substituted with 0, 1, 2, or 3 substituents independently selected from halo, hydroxy, haloalkyl, alkoxy, haloalkoxy, aryloxy, aminocarbonyl, carboxyl ester, carboxy, and substituted sulfonyl;

L is a covalent bond, alkylidene, or substituted alkylidene; and

R⁹ is selected from the group consisting of cycloalkyl, substituted cycloalkyl, tetrahydropyranyl, morpholino, and pyridyl.

In some embodiments, X is S.

In some embodiments, L is a covalent bond or is alkylidene.

In some embodiments, R⁹ is cyclohexyl or substituted cyclohexyl.

Representative compounds are presented in Table 1.

TABLE 1

| Cmpd. No. | X | R¹ | R² | R⁴ | R⁵ | R³ |
|---|---|---|---|---|---|---|
| 1 | O | 4-bromophenyl | H | H | H | —C(O)NHCH₃ |
| 2 | O | 2-(R)-1-phenylethyl | H | H | H | —C(O)NHCH₃ |
| 3 | O | 2-morpholin-4-ylphenyl | H | H | H | —C(O)NHCH₃ |
| 4 | O | 2,3-dihydrobenzo[1,4]-dioxin-6-yl | H | (3,4-dimethoxyphenyl) | | H |
| 5 | O | (2,3-dihydrobenzo[1,4]dioxin-6-yl | H | H | H | —C(O)NHCH₃ |
| 6 | O | (1-thiazol-2-yl-ethyl) | H | H | H | —C(O)NHCH₃ |
| 7 | O | 2-(S)-phenylethyl | H | H | H | —C(O)NHCH₃ |
| 8 | O | 2-chlorobenzyl | H | H | H | —C(O)NHCH₃ |
| 9 | O | 2,4-dichlorobenzyl | H | H | H | —C(O)NHCH₃ |
| 10 | O | 3-methylcyclohexyl | H | H | H | —C(O)NHCH₃ |
| 11 | O | 2-methoxyphenyl | H | H | H | —C(O)NHCH₃ |
| 12 | O | 2-ethoxyphenyl | H | H | H | —C(O)NHCH₃ |
| 13 | O | (1S,2S,3S,5R)-2,6,6-trimethylbicyclo-[3.1.1]hept-3-yl | H | H | H | —C(O)NHCH₃ |
| 14 | O | 1-(R)-phenylethyl | H | (3,4-dimethoxyphenyl) | | H |
| 15 | O | (1S,2R,4R)-7,7-dimethylbicyclo-[2.1.1]hept-2-ylmethyl | H | H | H | —C(O)NHCH₃ |
| 16 | O | 2-fluorobenzyl | H | H | H | —C(O)NHCH₃ |
| 17 | O | 2-methoxybenzyl | H | H | H | —C(O)NHCH₃ |
| 18 | O | 2-(R)-1-naphthalenylethyl | H | H | H | —C(O)NHCH₃ |
| 19 | O | 2-(R)-1-phenylpropyl | H | H | H | —C(O)NHCH₃ |
| 20 | O | 2-(S)-1-naphthalen-2-ylethyl | H | H | H | —C(O)NHCH₃ |
| 21 | O | cyclohexylmethyl | H | H | H | —C(O)NHCH₃ |
| 22 | O | cyclobutyl | H | H | H | —C(O)NHCH₃ |
| 23 | O | cyclopentyl | H | H | H | —C(O)NHCH₃ |
| 24 | O | cyclohexyl | H | H | H | —C(O)NHCH₃ |
| 25 | O | (2-morpholin-4-ylmethyl) | H | H | H | —C(O)NHCH₃ |
| 26 | O | phenyl | H | H | H | —C(O)NHCH₃ |
| 27 | O | (4-chlorobenzyl) | H | H | H | —C(O)NHCH₃ |

TABLE 1-continued

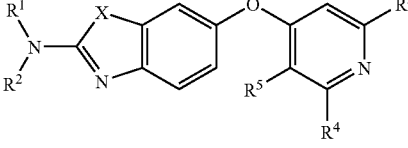

| Cmpd. No. | X | R¹ | R² | R⁴ | R⁵ | R³ |
|---|---|---|---|---|---|---|
| 28 | O | 2,4-dimethoxyphenyl | H | H | H | —C(O)NHCH₃ |
| 29 | O | cyclohexyl | H | H | H | —NHC(O)CH₃ |
| 30 | O | tetrahydropyran-4-yl | H | H | H | —C(O)NHCH₃ |
| 31 | O | 2-(R)-1-(2-methoxyphenyl) | H | H | H | —C(O)NHCH₃ |
| 32 | O | 2-chlorobenzyl | H | H | H | —C(O)NHCH₃ |
| 33 | O | 2,5-difluorobenzyl | H | H | H | —NHC(O)CH₃ |
| 34 | O | cyclohexylmethyl | H | H | H | —NHC(O)CH₃ |
| 35 | O | 2-(R)-phenylacetic acid | H | H | H | —C(O)NHCH₃ |
| 36 | O | 2-(R)-carboxylic acid methylamide | H | H | H | —C(O)NHCH₃ |
| 37 | O | 2-(R)-hydroxy-1-phenyl-ethyl | H | H | H | —C(O)NHCH₃ |
| 38 | O | 2-(S)-phenylacetic acid | H | H | H | —C(O)NHCH₃ |
| 39 | O | 2-(S)-carboxylic acid methylamide | H | H | H | —C(O)NHCH₃ |
| 40 | O | Pyridine-2-ylmethyl | H | H | H | —C(O)NHCH₃ |
| 41 | O | benzyl | H | H | H | —C(O)NHCH₃ |
| 42 | O | 3-chlorobenzyl | H | H | H | —C(O)NHCH₃ |
| 43 | O | 2-(2-pyrrolidin-1-ylethyl)phenyl | H | H | H | —C(O)NHCH₃ |
| 44 | O | 2-(2-piperidin-1-ylethyl)phenyl | H | H | H | —C(O)NHCH₃ |
| 45 | O | 2-(4-methyl-imidazol-1-yl)phenyl | H | H | H | —C(O)NHCH₃ |
| 46 | O | 2-oxazol-5-ylphenyl | H | H | H | —C(O)NHCH₃ |
| 47 | O | 2-(2-methylimidazol-1-yl)phenyl | H | H | H | —C(O)NHCH₃ |
| 48 | O | 2-morpholin-4-yl-ethyl | H | H | H | —C(O)NHCH₃ |
| 49 | O | (1S,2R)-2-hydroxy-indan-1-yl | H | H | H | —C(O)NHCH₃ |
| 50 | O | (1R,2S)-2-hydroxy-indan-1-yl | H | H | H | —C(O)NHCH₃ |
| 51 | O | 2-(R)-3-hydroxy-1-phenylpropyl | H | H | H | —C(O)NHCH₃ |
| 52 | O | (1S,2S)-2-hydroxycyclohexyl | H | H | H | —C(O)NHCH₃ |
| 53 | O | 2-(R)-phenylacetic acid methyl ester | H | H | H | —C(O)NHCH₃ |
| 54 | O | 2-(R)-cyclohexylethyl | H | H | H | —C(O)NHCH₃ |
| 55 | O | 2-(S)-phenylacetic acid methyl ester | H | H | H | —C(O)NHCH₃ |
| 56 | O | 2-(S)-hydroxy-1-phenylethyl | H | H | H | —C(O)NHCH₃ |
| 57 | O | Pyridine-4-ylmethyl | H | H | H | —C(O)NHCH₃ |
| 58 | O | 2-piperidin-1-ylethyl | H | H | H | —C(O)NHCH₃ |
| 59 | O | Pyrindin-3-ylmethyl | H | H | H | —C(O)NHCH₃ |
| 60 | O | cyclohexylmethyl | H | H | H | —C(O)OH |
| 61 | O | phenethyl | H | H | H | —C(O)NHCH₃ |
| 62 | O | 2-(R)-cyclohexylmethyl-carbamoylmethyl | H | H | H | —C(O)NHCH₃ |
| 63 | O | 2-pyrrolidin-1-ylethyl | H | H | H | —C(O)NHCH₃ |
| 64 | O | 2-piperidin-1-ylethyl | H | H | H | —C(O)NHCH₃ |
| 65 | O | 2,3-dihydrobenzo-[1,4]dioxin-5-ylmethyl | H | H | H | —C(O)NHCH₃ |
| 66 | O | 2-(S)-1-cyclohexyl-2-hydroxyethyl | H | H | H | —C(O)NHCH₃ |
| 67 | O | 2-(R)-1-cyclohexyl-2-hydroxyethyl | H | H | H | —C(O)NHCH₃ |
| 68 | O | cyclohexylmethyl | H | H | H | —C(O)NHNHC(O)OC(CH₃)₃ |
| 69 | O | cyclohexylmethyl | H | H | H | —C(O)NH₂ |
| 70 | O | Cyclohex-3-enyl | H | H | H | —C(O)NHCH₃ |
| 71 | O | 2,4-difluorobenzyl | H | H | H | —C(O)NHCH₃ |
| 72 | O | 2-bromobenzyl | H | H | H | —C(O)NHCH₃ |
| 73 | O | 2-fluoro-5-methoxybenzyl | H | H | H | —C(O)NHCH₃ |
| 74 | O | 3-(2-morpholin-4-ylethyl)phenyl | H | H | H | —C(O)NHCH₃ |
| 75 | O | Cyclohexanecarboxylic acid ethyl ester | H | H | H | —C(O)NHCH₃ |
| 76 | O | 2,6-dichlorobenzyl | H | H | H | —C(O)NHCH₃ |

TABLE 1-continued

| Cmpd. No. | X | R¹ | R² | R⁴ | R⁵ | R³ |
|---|---|---|---|---|---|---|
| 77 | O | 2,3-dichlorobenzyl | H | H | H | —C(O)NHCH₃ |
| 78 | O | 2-chloro-6-fluorobenzyl | H | H | H | —C(O)NHCH₃ |
| 79 | O | 2,3,-difluorobenzyl | H | H | H | —C(O)NHCH₃ |
| 80 | O | cyclohexylmethyl | H | H | H | —CH₂OH |
| 81 | O | cyclohexylmethyl | H | H | H | oxadiazolyl |
| 82 | O | cyclohexylmethyl | H | H | H | —CN |
| 83 | O | 2,5-dimethoxybenzyl | H | H | H | —C(O)NHCH₃ |
| 84 | O | 2,6-dimethoxybenzyl | H | H | H | —C(O)NHCH₃ |
| 85 | O | 2-dimethyaminobenzyl | H | H | H | —C(O)NHCH₃ |
| 86 | O | 2-aminobenzyl | H | H | H | —C(O)NHCH₃ |
| 87 | O | 2,6-difluorobenzyl | H | H | H | —C(O)NHCH₃ |
| 88 | O | 2-morpholin-4-ylbenzyl | H | H | H | —C(O)NHCH₃ |
| 89 | O | 2-methylbenzyl | H | H | H | —C(O)NHCH₃ |
| 90 | O | 3,4-dimethoxybenzyl | H | H | H | —C(O)NHCH₃ |
| 91 | O | 2,3-dimethoxybenzyl | H | H | H | —C(O)NHCH₃ |
| 92 | O | 2,4-dimethoxybenzyl | H | H | H | —C(O)NHCH₃ |
| 93 | O | Cyclohexanecarboxylic acid-methyl | H | H | H | —C(O)NHCH₃ |
| 94 | O | 2,3-dihydrobenzo-[1,4]dioxin-5-yl | H | H | H | —C(O)NHCH₃ |
| 95 | O | Benzo[1,3]dioxol-5-yl | H | H | H | —C(O)NHCH₃ |
| 96 | O | 2-ethoxybenzyl | H | H | H | —C(O)NHCH₃ |
| 97 | O | 2-trifluoromethylbenzyl | H | H | H | —C(O)NHCH₃ |
| 98 | O | isopropyl | H | H | H | —C(O)NHCH₃ |
| 99 | O | isobutyl | H | H | H | —C(O)NHCH₃ |
| 100 | O | Tert-butyl | H | H | H | —C(O)NHCH₃ |
| 101 | O | cycloheptylmethyl | H | H | H | —C(O)NHCH₃ |
| 102 | O | Tetrahydrofuran-2-ylmethyl | H | H | H | —C(O)NHCH₃ |
| 103 | O | Benzyl-piperidin-4-yl | H | H | H | —C(O)NHCH₃ |
| 104 | O | 1,2,3,4-tetrahydronaphthalen-1-yl | H | H | H | —C(O)NHCH₃ |
| 105 | O | 2-pyrazol-1-ylbenzyl | H | H | H | —C(O)NHCH₃ |
| 106 | O | benzyl | CH₃ | H | H | —C(O)NHCH₃ |
| 107 | O | 1-phenyl-piperidin-4-yl | H | H | H | —C(O)NHCH₃ |
| 108 | O | 3,4-dihydro-2H-benzo-[b][1,4]dioxepin-6ylmethyl | H | H | H | —C(O)NHCH₃ |
| 109 | O | cyclohexylmethyl | H | H | H | 5-methyl-1H-imidazol-2-yl |
| 110 | O | 2,3-dihydrobenzo-[1,4]dioxine-5-carbonyl | H | H | H | —C(O)NHCH₃ |
| 111 | O | cyclohexylmethyl | H | H | H | —CH₂NH₂ |
| 112 | O | Carboxylic acid methylamide | H | H | H | —C(O)NHCH₃ |
| 113 | O | 2,4,6-trimethoxybenzyl | H | H | H | —C(O)NHCH₃ |
| 114 | O | 5-chloro-2-methoxybenzyl | H | H | H | —C(O)NHCH₃ |
| 115 | O | 5-fluoro-2-methoxybenzyl | H | H | H | —C(O)NHCH₃ |
| 116 | O | 2-fluoro-6-methoxybenzyl | H | H | H | —C(O)NHCH₃ |
| 117 | O | 2-chloro-3,4-dimethoxybenzyl | H | H | H | —C(O)NHCH₃ |
| 118 | O | 2-piperidin-1-ylbenzyl | H | H | H | —C(O)NHCH₃ |
| 119 | O | 2,3-dihydro-benzo-[1,4]dioxin-2-ylmethyl | H | H | H | —C(O)NHCH₃ |
| 120 | O | 4-benzyl-morpholin-2-ylmethyl | H | H | H | —C(O)NHCH₃ |
| 121 | O | 2-chloro-6-methoxybenzyl | H | H | H | —C(O)NHCH₃ |
| 122 | O | 2,3-dihydrobenzo-[1,4]dioxin-6-ylmethyl | H | H | H | —C(O)NHCH₃ |
| 123 | O | 2-(2,3-dihydrobenzo-[1,4]dioxin-5-yl)ethyl | H | H | H | —C(O)NHCH₃ |
| 124 | O | 2,3-dihydrobenzofuran-5-ylmethyl | H | H | H | —C(O)NHCH₃ |
| 125 | O | 2-(2,3-dihydrobenzo-[1,4]dioxin-5-yl)ethyl | H | H | H | —C(O)NHCH₃ |
| 126 | S | 4-chloro-3-trifluoromethylphenyl | H | H | H | —C(O)NHCH₃ |
| 127 | S | 2-chlorobenzyl | H | H | H | —C(O)NHCH₃ |
| 128 | S | cyclohexylmethyl | H | H | H | —C(O)NHCH₃ |

TABLE 1-continued

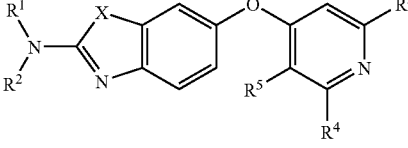

| Cmpd. No. | X | R¹ | R² | R⁴ | R⁵ | R³ |
|---|---|---|---|---|---|---|
| 129 | S | 2-(R)-1-(2-methoxyphenyl)ethyl | H | H | H | —C(O)NHCH₃ |
| 130 | S | 2,4-dichlorobenzyl | H | H | H | —C(O)NHCH₃ |
| 131 | S | 2-(R)-1-phenylethyl | H | H | H | —C(O)NHCH₃ |
| 132 | S | 2-methoxylbenzyl | H | H | H | —C(O)NHCH₃ |
| 133 | S | 2-phenethyl | H | H | H | —C(O)NHCH₃ |
| 134 | S | 2,3-dichlorobenzyl | H | H | H | —C(O)NHCH₃ |
| 135 | S | cyclohexyl | H | H | H | —C(O)NHCH₃ |
| 136 | S | 3-methylcyclohexyl | H | H | H | —C(O)NHCH₃ |
| 137 | S | (1S,2S)-2-hydroxycyclohexyl | H | H | H | —C(O)NHCH₃ |
| 138 | S | 2-(R)-cyclohexylethyl | H | H | H | —C(O)NHCH₃ |
| 139 | S | 2,5-difluorobenzyl | H | H | H | —C(O)NHCH₃ |
| 140 | S | 2-fluorobenzyl | H | H | H | —C(O)NHCH₃ |
| 141 | S | Tetrahydropyran-4-ylmethyl | H | H | H | —C(O)NHCH₃ |
| 142 | S | 2-morpholin-4-ylbenzyl | H | H | H | —C(O)NHCH₃ |
| 143 | S | 2-pyrazol-1-yl-benzyl | H | H | H | —C(O)NHCH₃ |
| 144 | S | 2-dimethylaminobenzyl | H | H | H | —C(O)NHCH₃ |
| 145 | S | 2,6-dimethoxybenzyl | H | H | H | —C(O)NHCH₃ |
| 146 | S | 2,5-dimethoxybenzyl | H | H | H | —C(O)NHCH₃ |
| 147 | S | 2,3-difluorobenzyl | H | H | H | —C(O)NHCH₃ |
| 148 | S | cycloheptylmethyl | H | H | H | —C(O)NHCH₃ |
| 149 | S | 2,6-difluorobenzyl | H | H | H | —C(O)NHCH₃ |
| 150 | S | Pyridin-2-ylmethyl | H | H | H | —C(O)NHCH₃ |
| 151 | S | 3,4-dimethoxybenzyl | H | H | H | —C(O)NHCH₃ |
| 152 | S | 2,3-dihydrobenzo-[1,4]dioxin-5-ylmethyl | H | H | H | —C(O)NHCH₃ |
| 153 | S | 2-piperidin-1-yl-benzyl | H | H | H | —C(O)NHCH₃ |
| 154 | S | Pyridin-3-ylmethyl | H | H | H | —C(O)NHCH₃ |
| 155 | S | (1R,2R)-2-benzyloxycyclohexyl | H | H | H | —C(O)NHCH₃ |
| 156 | S | (1S,2S)-2-benzyloxycyclohexyl | H | H | H | —C(O)NHCH₃ |
| 157 | S | (1R,2R)-2-hydroxycyclohexyl | H | H | H | —C(O)NHCH₃ |
| 158 | S | 2,6-dichlorobenzyl | H | H | H | —C(O)NHCH₃ |
| 159 | S | cyclohexylmethyl | H | H | H | —C(O)NH(CH₂)₂OCH₃ |
| 160 | S | cyclohexylmethyl | H | H | H | —C(O)NH(CH₂)₂N(CH₃)₂ |
| 161 | S | 4-sulfonamido-benzyl | H | H | H | —C(O)NHCH₃ |

Representative compounds of Formula (I) include, for example,

4-[2-(4-Bromo-phenylamino)-benzooxazol-6-yloxy]-pyridine-2-carboxylic acid methylamide, 4-[2-((R)-1-Phenyl-ethylamino)-benzooxazol-6-yloxy]-pyridine-2-carboxylic acid methylamide, 4-[2-(2-Morpholin-4-yl-phenylamino)-benzooxazol-6-yloxy]-pyridine-2-carboxylic acid methylamide, (2,3-Dihydro-benzo[1,4]dioxin-6-yl)-[6-(6,7-dimethoxy-quinolin-4-yloxy)-benzooxazol-2-yl]-amine, 4-[2-(2,3-Dihydro-benzo[1,4]dioxin-6-ylamino)-benzooxazol-6-yloxy]-pyridine-2-carboxylic acid methylamide, 4-[2-(1-Thiazol-2-yl-ethylamino)-benzooxazol-6-yloxy]-pyridine-2-carboxylic acid methylamide, 4-[2-((S)-1-Phenyl-ethylamino)-benzooxazol-6-yloxy]-pyridine-2-carboxylic acid methylamide, 4-[2-(2-Chloro-benzylamino)-benzooxazol-6-yloxy]-pyridine-2-carboxylic acid methylamide, 4-[2-(2,4-Dichloro-benzylamino)-benzooxazol-6-yloxy]-pyridine-2-carboxylic acid methylamide, 4-[2-(3-Methyl-cyclohexylamino)-benzooxazol-6-yloxy]-pyridine-2-carboxylic acid methylamide, 4-[2-(2-Methoxy-phenylamino)-benzooxazol-6-yloxy]-pyridine-2-carboxylic acid methylamide, 4-[2-(2-Ethoxy-phenylamino)-benzooxazol-6-yloxy]-pyridine-2-carboxylic acid methylamide, 4-[2-((1S,2S,3S,5R)-2,6,6-Trimethyl-bicyclo[3.1.1]hept-3-ylamino)-benzooxazol-6-yloxy]-pyridine-2-carboxylic acid methylamide,

[6-(6,7-Dimethoxy-quinolin-4-yloxy)-benzooxazol-2-yl]-((R)-1-phenyl-ethyl)-amine, 4-{2-[((1S,2R,4R)-7,7-Dimethyl-bicyclo[2.2.1]hept-2-yl-methyl)-amino]-benzooxazol-6-yloxy}-pyridine-2-carboxylic acid methylamide, 4-[2-(2-Fluoro-benzylamino)-benzooxazol-6-yloxy]-pyridine-2-carboxylic acid methylamide, 4-[2-(2-Methoxy-benzylamino)-benzooxazol-6-yloxy]-pyridine-2-carboxylic acid methylamide, 4-[2-((R)-1-Naphthalen-1-yl-ethylamino)-benzooxazol-6-yloxy]-pyridine-2-carboxylic acid methylamide, 4-[2-((R)-1-Phenyl-propylamino)-benzooxazol-6-yloxy]-pyridine-2-carboxylic acid methylamide, 4-[2-((S)-1-Naphthalen-2-yl-ethylamino)-benzooxazol-6-yloxy]-pyridine-2-carboxylic acid methylamide, 4-[2-(Cyclohexylmethyl-amino)-benzooxazol-6-yloxy]-pyridine-2-carboxylic acid methylamide,
4-(2-Cyclobutylamino-benzooxazol-6-yloxy)-pyridine-2-carboxylic acid methylamide,
4-(2-Cyclopentylamino-benzooxazol-6-yloxy)-pyridine-2-carboxylic acid methylamide,
4-(2-Cyclohexylamino-benzooxazol-6-yloxy)-pyridine-2-carboxylic acid methylamide,
4-[2-(2-Morpholin-4-ylmethyl-phenylamino)-benzooxazol-6-yloxy]-pyridine-2-carboxylic acid methylamide,
4-(2-Phenylamino-benzooxazol-6-yloxy)-pyridine-2-carboxylic acid methylamide,
4-[2-(4-Chloro-benzylamino)-benzooxazol-6-yloxy]-pyridine-2-carboxylic acid methylamide,
4-[2-(2,4-Dimethoxy-phenylamino)-benzooxazol-6-yloxy]-pyridine-2-carboxylic acid methyl amide,
N-[4-(2-Cyclohexylamino-benzooxazol-6-yloxy)-pyridin-2-yl]-acetamide,
4-[2-(Tetrahydro-pyran-4-ylamino)-benzooxazol-6-yloxy]-pyridine-2-carboxylic acid methylamide,
4-{2-[(R)-1-(2-Methoxy-phenyl)-ethylamino]-benzooxazol-6-yloxy}-pyridine-2-carboxylic acid methylamide,
N-{4-[2-(2-Chloro-benzylamino)-benzooxazol-6-yloxy]-pyridin-2-yl}-acetamide,
4-[2-(2,5-Difluoro-benzylamino)-benzooxazol-6-yloxy]-pyridine-2-carboxylic acid methylamide,
N-{4-[2-(Cyclohexylmethyl-amino)-benzooxazol-6-yloxy]-pyridin-2-yl}-acetamide,
(R)-[6-(2-Methylcarbamoyl-pyridin-4-yloxy)-benzooxazol-2-ylamino]-phenyl-acetic acid,
4-{2-[((R)-Methylcarbamoyl-phenyl-methyl)-amino]-benzooxazol-6-yloxy}-pyridine-2-carboxylic acid methylamide,
4-[2-((R)-2-Hydroxy-1-phenyl-ethylamino)-benzooxazol-6-yloxy]-pyridine-2-carboxylic acid methylamide,
(S)-[6-(2-Methylcarbamoyl-pyridin-4-yloxy)-benzooxazol-2-ylamino]-phenyl-acetic acid,
4-{2-[((S)-Methylcarbamoyl-phenyl-methyl)-amino]-benzooxazol-6-yloxy}-pyridine-2-carboxylic acid methylamide,
4-{2-[(Pyridin-2-ylmethyl)-amino]-benzooxazol-6-yloxy}-pyridine-2-carboxylic acid methylamide,
4-(2-Benzylamino-benzooxazol-6-yloxy)-pyridine-2-carboxylic acid methylamide,
4-[2-(3-Chloro-benzylamino)-benzooxazol-6-yloxy]-pyridine-2-carboxylic acid methylamide,
4-{2-[2-(2-Pyrrolidin-1-yl-ethyl)-phenylamino]-benzooxazol-6-yloxy}-pyridine-2-carboxylic acid methylamide,
4-{2-[2-(2-Piperidin-1-yl-ethyl)-phenylamino]-benzooxazol-6-yloxy}-pyridine-2-carboxylic acid methylamide,
4-{2-[2-(4-Methyl-imidazol-1-yl)-phenylamino]-benzooxazol-6-yloxy}-pyridine-2-carboxylic acid methylamide,
4-[2-(2-Oxazol-5-yl-phenylamino)-benzooxazol-6-yloxy]-pyridine-2-carboxylic acid methylamide,
4-{2-[2-(2-Methyl-imidazol-1-yl)-phenylamino]-benzooxazol-6-yloxy}-pyridine-2-carboxylic acid methylamide,
4-(2-Amino-benzooxazol-6-yloxy)-pyridine-2-carboxylic acid methylamide,
4-(2-Hydroxy-benzooxazol-6-yloxy)-pyridine-2-carboxylic acid methylamide,
4-{2-[2-(2-Morpholin-4-yl-ethyl)-phenylamino]-benzooxazol-6-yloxy}-pyridine-2-carboxylic acid methylamide,
4-[2-((1S,2R)-2-Hydroxy-indan-1-ylamino)-benzooxazol-6-yloxy]-pyridine-2-carboxylic acid methylamide,
4-[2-((1R,2S)-2-Hydroxy-indan-1-ylamino)-benzooxazol-6-yloxy]-pyridine-2-carboxylic acid methylamide,
4-[2-((R)-3-Hydroxy-1-phenyl-propylamino)-benzooxazol-6-yloxy]-pyridine-2-carboxylic acid methylamide,
4-[2-((1S,2S)-2-Hydroxy-cyclohexylamino)-benzooxazol-6-yloxy]-pyridine-2-carboxylic acid methylamide,
(R)-[6-(2-Methylcarbamoyl-pyridin-4-yloxy)-benzooxazol-2-ylamino]-phenyl-acetic acid methyl ester,
4-[2-((R)-1-Cyclohexyl-ethylamino)-benzooxazol-6-yloxy]-pyridine-2-carboxylic acid methylamide,
(S)-[6-(2-Methylcarbamoyl-pyridin-4-yloxy)-benzooxazol-2-ylamino]-phenyl-acetic acid methyl ester,
4-[2-((S)-2-Hydroxy-1-phenyl-ethylamino)-benzooxazol-6-yloxy]-pyridine-2-carboxylic acid methylamide,
4-{2-[(Pyridin-4-ylmethyl)-amino]-benzooxazol-6-yloxy}-pyridine-2-carboxylic acid methylamide,
4-{2-[3-(2-Piperidin-1-yl-ethyl)-phenylamino]-benzooxazol-6-yloxy}-pyridine-2-carboxylic acid methylamide,
4-{2-[(Pyridin-3-ylmethyl)-amino]-benzooxazol-6-yloxy}-pyridine-2-carboxylic acid methylamide,
4-[2-(Cyclohexylmethyl-amino)-benzooxazol-6-yloxy]-pyridine-2-carboxylic acid,
4-(2-Phenethylamino-benzooxazol-6-yloxy)-pyridine-2-carboxylic acid methylamide,
4-{2-[((R)-Cyclohexyl-methylcarbamoyl-methyl)-amino]-benzooxazol-6-yloxy}-pyridine-2-carboxylic acid methylamide,
4-[2-(2-Pyrrolidin-1-yl-ethylamino)-benzooxazol-6-yloxy]-pyridine-2-carboxylic acid methylamide,
4-[2-(2-Piperidin-1-yl-ethylamino)-benzooxazol-6-yloxy]-pyridine-2-carboxylic acid methyl-amide,
4-{2-[(2,3-Dihydro-benzo[1,4]dioxin-5-ylmethyl)-amino]-benzooxazol-6-yloxy}-pyridine-2-carboxylic acid methylamide,
4-[2-((S)-1-Cyclohexyl-2-hydroxy-ethylamino)-benzooxazol-6-yloxy]-pyridine-2-carboxylic acid methylamide,
4-[2-((R)-1-Cyclohexyl-2-hydroxy-ethylamino)-benzooxazol-6-yloxy]-pyridine-2-carboxylic acid methylamide,
N'-{4-[2-(Cyclohexylmethyl-amino)-benzooxazol-6-yloxy]-pyridine-2-carbonyl}-hydrazine-carboxylic acid tert-butyl ester,
4-(Cyclohexylmethyl-amino)-benzooxazol-6-yloxy]-pyridine-2-carboxylic acid amide,
4-[2-(Cyclohex-3-enylamino)-benzooxazol-6-yloxy]-pyridine-2-carboxylic acid methylamide,
4-[2-(2,4-Difluoro-benzylamino)-benzooxazol-6-yloxy]-pyridine-2-carboxylic acid methylamide,
4-[2-(2-Bromo-benzylamino)-benzooxazol-6-yloxy]-pyridine-2-carboxylic acid methylamide,
4-[2-(2-Fluoro-5-methoxy-benzylamino)-benzooxazol-6-yloxy]-pyridine-2-carboxylic acid methylamide,
4-{2-[3-(2-Morpholin-4-yl-ethyl)-phenylamino]-benzooxazol-6-yloxy}-pyridine-2-carboxylic acid methylamide,
1-{[6-(2-Methylcarbamoyl-pyridin-4-yloxy)-benzooxazol-2-ylamino]-methyl}-cyclohexane-carboxylic acid ethyl ester,
4-[2-(2,6-Dichloro-benzylamino)-benzooxazol-6-yloxy]-pyridine-2-carboxylic acid methylamide,
4-[2-(2,3-Dichloro-benzylamino)-benzooxazol-6-yloxy]-pyridine-2-carboxylic acid methylamide,
4-[2-(2-Chloro-6-fluoro-benzylamino)-benzooxazol-6-yloxy]-pyridine-2-carboxylic acid methylamide,
4-[2-(2,3-Difluoro-benzylamino)-benzooxazol-6-yloxy]-pyridine-2-carboxylic acid methylamide, {4-[2-(Cyclohexylmethyl-amino)-benzooxazol-6-yloxy]-pyridin-2-yl}-methanol,
Cyclohexylmethyl-[6-(2-[1,3,4]oxadiazol-2-yl-pyridin-4-yloxy)-benzooxazol-2-yl]-amine,
4-[2-(Cyclohexylmethyl-amino)-benzooxazol-6-yloxy]-pyridine-2-carbonitrile,
4-[2-(2,5-Dimethoxy-benzylamino)-benzooxazol-6-yloxy]-pyridine-2-carboxylic acid methyl amide,
4-[2-(2,6-Dimethoxy-benzylamino)-benzooxazol-6-yloxy]-pyridine-2-carboxylic acid methylamide,
4-[2-(2-Dimethylamino-benzylamino)-benzooxazol-6-yloxy]-pyridine-2-carboxylic acid methylamide,
4-[2-(2-Amino-benzylamino)-benzooxazol-6-yloxy]-pyridine-2-carboxylic acid methylamide,
4-[2-(2,6-Difluoro-benzylamino)-benzooxazol-6-yloxy]-pyridine-2-carboxylic acid methylamide,
4-[2-(2-Morpholin-4-yl-benzylamino)-benzooxazol-6-yloxy]-pyridine-2-carboxylic acid methylamide,
4-[2-(2-Methyl-benzylamino)-benzooxazol-6-yloxy]-pyridine-2-carboxylic acid methylamide,
4-[2-(3,4-Dimethoxy-benzylamino)-benzooxazol-6-yloxy]-pyridine-2-carboxylic acid methyl amide,
4-[2-(2,3-Dimethoxy-benzylamino)-benzooxazol-6-yloxy]-pyridine-2-carboxylic acid methylamide,
4-[2-(2,4-Dimethoxy-benzylamino)-benzooxazol-6-yloxy]-pyridine-2-carboxylic acid methylamide,
1-{[6-(2-Methylcarbamoyl-pyridin-4-yloxy)-benzooxazol-2-ylamino]-methyl}-cyclohexane-carboxylic acid,
4-[2-(2,3-Dihydro-benzo[1,4]dioxin-5-ylamino)-benzooxazol-6-yloxy]-pyridine-2-carboxylic acid methylamide,
4-[2-(Benzo[1,3]dioxol-5-ylamino)-benzooxazol-6-yloxy]-pyridine-2-carboxylic acid methylamide,
4-[2-(2-Ethoxy-benzylamino)-benzooxazol-6-yloxy]-pyridine-2-carboxylic acid methylamide,
4-[2-(2-Trifluoromethyl-benzylamino)-benzooxazol-6-yloxy]-pyridine-2-carboxylic acid methyl amide,
4-(2-Isopropylamino-benzooxazol-6-yloxy)-pyridine-2-carboxylic acid methylamide,
4-(2-Isobutylamino-benzooxazol-6-yloxy)-pyridine-2-carboxylic acid methylamide,
4-(2-tert-Butylamino-benzooxazol-6-yloxy)-pyridine-2-carboxylic acid methylamide,
4-[2-(Cycloheptylmethyl-amino)-benzooxazol-6-yloxy]-pyridine-2-carboxylic acid methylamide,
4-{2-[(Tetrahydro-furan-2-ylmethyl)-amino]-benzooxazol-6-yloxy}-pyridine-2-carboxylic acid methylamide,
4-[2-(1-Benzyl-piperidin-4-ylamino)-benzooxazol-6-yloxy]-pyridine-2-carboxylic acid methylamide,
4-[2-(1,2,3,4-Tetrahydro-naphthalen-1-ylamino)-benzooxazol-6-yloxy]-pyridine-2-carboxylic acid methylamide,
4-[2-(2-Pyrazol-1-yl-benzylamino)-benzooxazol-6-yloxy]-pyridine-2-carboxylic acid methylamide,
4-[2-(Benzyl-methyl-amino)-benzooxazol-6-yloxy]-pyridine-2-carboxylic acid methylamide,
4-[2-(1-Phenyl-piperidin-4-ylamino)-benzooxazol-6-yloxy]-pyridine-2-carboxylic acid methylamide,
4-{2-[(3,4-Dihydro-2H-benzo[b][1,4]dioxepin-6-ylmethyl)-amino]-benzooxazol-6-yloxy}-pyridine-2-carboxylic acid methylamide,
Cyclohexylmethyl-{6-[2-(5-methyl-1H-imidazol-2-yl)-pyridin-4-yloxy]-benzooxazol-2-yl}-amine,
4-{2-[(2,3-Dihydro-benzo[1,4]dioxine-5-carbonyl)-amino]-benzooxazol-6-yloxy}-pyridine-2-carboxylic acid methylamide,
[6-(2-Aminomethyl-pyridin-4-yloxy)-benzooxazol-2-yl]-cyclohexylmethyl-amine,
4-{2-[(1-Methylcarbamoyl-cyclohexylmethyl)-amino]-benzooxazol-6-yloxy}-pyridine-2-carboxylic acid methylamide,
4-[2-(2,4,6-Trimethoxy-benzylamino)-benzooxazol-6-yloxy]-pyridine-2-carboxylic acid methylamide,
4-[2-(5-Chloro-2-methoxy-benzylamino)-benzooxazol-6-yloxy]-pyridine-2-carboxylic acid methylamide,
4-[2-(5-Fluoro-2-methoxy-benzylamino)-benzooxazol-6-yloxy]-pyridine-2-carboxylic acid methylamide,
4-[2-(2-Fluoro-6-methoxy-benzylamino)-benzooxazol-6-yloxy]-pyridine-2-carboxylic acid methylamide,
4-[2-(2-Chloro-3,4-dimethoxy-benzylamino)-benzooxazol-6-yloxy]-pyridine-2-carboxylic acid methylamide,
4-[2-(2-Piperidin-1-yl-benzylamino)-benzooxazol-6-yloxy]-pyridine-2-carboxylic acid methylamide,
4-{2-[(2,3-Dihydro-benzo[1,4]dioxin-2-ylmethyl)-amino]-benzooxazol-6-yloxy}-pyridine-2-carboxylic acid methylamide,
4-{2-[(4-Benzyl-morpholin-2-ylmethyl)-amino]-benzooxazol-6-yloxy}-pyridine-2-carboxylic acid methylamide,
4-[2-(2-Chloro-6-methoxy-benzylamino)-benzooxazol-6-yloxy]-pyridine-2-carboxylic acid methylamide,
4-{2-[(2,3-Dihydro-benzo[1,4]dioxin-6-ylmethyl)-amino]-benzooxazol-6-yloxy}-pyridine-2-carboxylic acid methylamide,
4-{2-[2-(2,3-Dihydro-benzo[1,4]dioxin-5-yl)-ethylamino]-benzooxazol-6-yloxy}-pyridine-2-carboxylic acid methylamide,
4-{2-[(2,3-Dihydro-benzofuran-5-ylmethyl)-amino]-benzooxazol-6-yloxy}-pyridine-2-carboxylic acid methylamide, and
4-{2-[1-(2,3-Dihydro-benzo[1,4]dioxin-5-yl)-ethylamino]-benzooxazol-6-yloxy}-pyridine-2-carboxylic acid methylamide.

Representative compounds of Formula (I) include, for example,
4-[2-(4-Chloro-3-trifluoromethyl-phenylamino)-benzothiazol-6-yloxy]-pyridine-2-carboxylic acid methylamide,
4-[2-(2-Chloro-benzylamino)-benzothiazol-6-yloxy]-pyridine-2-carboxylic acid methylamide,
4-[2-(Cyclohexylmethyl-amino)-benzothiazol-6-yloxy]-pyridine-2-carboxylic acid methylamide,
4-{2-[(R)-1-(2-Methoxy-phenyl)-ethylamino]-benzothiazol-6-yloxy}-pyridine-2-carboxylic acid methylamide,
4-[2-(2,4-Dichloro-benzylamino)-benzothiazol-6-yloxy]-pyridine-2-carboxylic acid methylamide,
4-[2-((R)-1-Phenyl-ethylamino)-benzothiazol-6-yloxy]-pyridine-2-carboxylic acid methylamide,
4-[2-(2-Methoxy-benzylamino)-benzothiazol-6-yloxy]-pyridine-2-carboxylic acid methylamide,
4-(2-Phenethylamino-benzothiazol-6-yloxy)-pyridine-2-carboxylic acid methylamide,
4-[2-(2,3-Dichloro-benzylamino)-benzothiazol-6-yloxy]-pyridine-2-carboxylic acid methylamide,
4-(2-Cyclohexylamino-benzothiazol-6-yloxy)-pyridine-2-carboxylic acid methylamide,
4-[2-(3-Methyl-cyclohexylamino)-benzothiazol-6-yloxy]-pyridine-2-carboxylic acid methylamide,
4-[2-((1S,2S)-2-Hydroxy-cyclohexylamino)-benzothiazol-6-yloxy]-pyridine-2-carboxylic acid methylamide,
4-[2-((R)-1-Cyclohexyl-ethylamino)-benzothiazol-6-yloxy]-pyridine-2-carboxylic acid methylamide,
4-[2-(2,5-Difluoro-benzylamino)-benzothiazol-6-yloxy]-pyridine-2-carboxylic acid methylamide,
4-[2-(2-Fluoro-benzylamino)-benzothiazol-6-yloxy]-pyridine-2-carboxylic acid methylamide, 4-{2-[(Tetrahydro-pyran-4-ylmethyl)-amino]-benzothiazol-6-yloxy}-pyridine-2-carboxylic acid methylamide, 4-[2-(2-Morpholin-4-yl-benzylamino)-benzothiazol-6-yloxy]-pyridine-2-carboxylic acid methyl amide, 4-[2-(2-Pyrazol-1-yl-benzylamino)-benzothiazol-6-yloxy]-pyridine-2-carboxylic acid methylamide, 4-[2-(2-Dimethylamino-benzylamino)-benzothiazol-6-yloxy]-pyridine-2-carboxylic acid methylamide, 4-[2-(2,6-Dimethoxy-benzylamino)-benzothiazol-6-yloxy]-pyridine-2-carboxylic acid methylamide, 4-[2-(2,5-Dimethoxy-benzylamino)-benzothiazol-6-yloxy]-pyridine-2-carboxylic acid methylamide, 4-[2-(2,3-Difluoro-benzylamino)-benzothiazol-6-yloxy]-pyridine-2-carboxylic acid methylamide, 4-[2-(Cycloheptylmethyl-amino)-benzothiazol-6-yloxy]-pyridine-2-carboxylic acid methylamide, 4-[2-(2,6-Difluoro-benzylamino)-benzothiazol-6-yloxy]-pyridine-2-carboxylic acid methylamide, 4-{2-[(Pyridin-2-ylmethyl)-amino]-benzothiazol-6-yloxy}-pyridine-2-carboxylic acid methylamide, 4-[2-(3,4-Dimethoxy-benzylamino)-benzothiazol-6-yloxy]-pyridine-2-carboxylic acid methyl amide, 4-{2-[(2,3-Dihydro-benzo[1,4]dioxin-5-ylmethyl)-amino]-benzothiazol-6-yloxy}-pyridine-2-carboxylic acid methylamide, 4-[2-(2-Piperidin-1-yl-benzylamino)-benzothiazol-6-yloxy]-pyridine-2-carboxylic acid methylamide, 4-{2-[(Pyridin-3-ylmethyl)-amino]-benzothiazol-6-yloxy}-pyridine-2-carboxylic acid methylamide, 4-[2-((1R,2R)-2-Benzyloxy-cyclohexylamino)-benzothiazol-6-yloxy]-pyridine-2-carboxylic acid methylamide, 4-[2-((1S,2S)-2-Benzyloxy-cyclohexylamino)-benzothiazol-6-yloxy]-pyridine-2-carboxylic acid methylamide, 4-[2-((1R,2R)-2-Hydroxy-cyclohexylamino)-benzothiazol-6-yloxy]-pyridine-2-carboxylic acid methylamide, 4-[2-(2,6-Dichloro-benzylamino)-benzothiazol-6-yloxy]-pyridine-2-carboxylic acid methylamide, and 4-[2-(4-Sulfonamido-benzylamino)-benzothiazol-6-yloxy]-pyridine-2-carboxylic acid methylamide or a pharmaceutically acceptable salt, tautomer, solvate, or stereoisomer thereof.

In other embodiments, provided is a compound of Table 2, 3, or 4 or a stereoisomer, tautomer, solvate, oxide, ester, prodrug, or pharmaceutically acceptable salt thereof.

It will also be apparent to those skilled in the art that the compounds of the invention, including the compounds of compounds of Formulas (I), (IIa), (IIb), (IIIa), (IIIb), (IV), or (V) or their stereoisomers, as well as the pharmaceutically acceptable salts, esters, metabolites and prodrugs of any of them, may be subject to tautomerization and may therefore exist in various tautomeric forms wherein a proton of one atom of a molecule shifts to another atom and the chemical bonds between the atoms of the molecules are consequently rearranged. See, e.g., March, *Advanced Organic Chemistry Reactions, Mechanisms and Structures*, Fourth Edition, John Wiley & Sons, pages 69-74 (1992).

Preferred embodiments, including the compounds of Formulas (I), (IIa), (IIb), (IIIa), (IIIb), (IV), or (V) or their tautomers, as well as the pharmaceutically acceptable salts, esters, metabolites and prodrugs of any of them, may comprise asymmetrically substituted carbon atoms. Such asymmetrically substituted carbon atoms can result in the compounds of preferred embodiments existing in enantiomers, diastereomers, and other stereoisomeric forms that may be defined, in terms of absolute stereochemistry, such as in (R)- or (S)-forms. As a result, all such possible isomers, individual stereoisomers in their optically pure forms, mixtures thereof, racemic mixtures (or "racemates"), mixtures of diastereomers, as well as single diastereomers of the compounds of the preferred embodiments are contemplated. The terms "S" and "R" configuration, as used herein, are as defined by the IUPAC 1974 RECOMMENDATIONS FOR SECTION E, FUNDAMENTAL STEREOCHEMISTRY, *Pure Appl. Chem.* 45:13-30 (1976). The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the CHEMICAL ABSTRACTS INDEX GUIDE-APPENDIX IV (1987) paragraph 203.

Methods for Treating CSF-1R Mediated Diseases

There are 3 distinct mechanisms by which CSF-1R signaling is likely involved in tumor growth and metastasis. The first is that expression of CSF-ligand and receptor has been found in tumor cells originating in the female reproductive system (breast, ovarian, endometrium, cervical) (Scholl 1994; Kacinski 1997; Nagan 199; Kirma 2007) and the expression has been associated with breast cancer xenograft growth as well as poor prognosis in breast cancer patients. Two point mutations were seen in CSF-1R in about 10-20% of acute myelocytic leukemia, chronic myelocytic leukemia and myelodysplasia patients tested in one study, and one of the mutations was found to disrupt receptor turnover (Ridge 1990). However the incidence of the mutations could not be confirmed in later studies (Abu-Duhier 2003). Mutations were also found in some cases of hepatocellular cancer (Yang 2004) and idiopathic myelofibrosis (Abu-Duhier 2003).

Pigmented villonodular synovitis (PVNS) and Tenosynovial Giant cell tumors (TGCT) can occur as a result of a translocation that fuses the M-CSF gene to a collagen gene COL6A3 and results in overexpression of M-CSF (West 2006). A landscape effect is proposed to be responsible for the resulting tumor mass that consists of monocytic cells attracted by cells that express M-CSF. TGCTs are smaller tumors that can be relatively easily removed from fingers where they mostly occur. PVNS is more aggressive as it can recur in large joints and is not as easily controlled surgically.

The second mechanism is based on blocking signaling through M-CSF/CSF-1R at metastatic sites in bone which induces osteoclastogenesis, bone resorption and osteolytic bone lesions. Breast, kidney, and lung cancers are examples of cancers that have been found to metastasize to the bone and cause osteolytic bone disease resulting in skeletal complications. M-CSF released by tumor cells and stroma induces the differentiation of hematopoietic myeloid monocyte progenitors to mature osteoclasts in collaboration with the receptor activator of nuclear factor kappa-B ligand—RANKL. During this process, M-CSF acts as a permissive factor by giving the survival signal to osteoclasts (Tanaka 1993). Inhibition of CSF-1R kinase activity during osteoclast differentiation and maturation with a small molecule inhibitor is likely to prevent unbalanced activity of osteoclasts that cause osteolytic disease and the associated skeletal related events in metastatic disease. Whereas breast, lung cancer and multiple myeloma typically result in osteolytic lesions, metastasis to the bone in prostate cancer initially has an osteoblastic appearance in which increased bone forming activity results in 'woven bone' which is different from typical lamellar structure of normal bone. During disease progression bone lesions display a significant osteolytic component as well as high serum levels of bone resorption and suggests that anti-resorptive therapy may be useful. Bisphosphonates have been shown to inhibit the formation of osteolytic lesions and reduced the number of skeletal-related events only in men with hormone-refractory metastatic prostate cancer but at this point their effect on osteoblastic lesions is controversial and bisphosphonates have not been beneficial in preventing bone metastasis or hormone responsive prostate cancer to date. The effect of anti-resorptive agents in mixed osteolytic/osteoblastic prostate cancer is still being studied in the clinic (Choueiri 2006; Vessella 2006).

The third mechanism is based on the recent observation that tumor associated macrophages (TAM) found in solid tumors of the breast, prostate, ovarian and cervical cancers correlated with poor prognosis (Bingle 2002; Pollard 2004). Macrophages are recruited to the tumor by M-CSF and other chemokines. The macrophages can then contribute to tumor progression through the secretion of angiogenic factors, proteases and other growth factors and cytokines and may be blocked by inhibition of CSF-1R signaling. Recently it was shown by Zins et al (Zins 2007) that expression of siRNA of Tumor necrosis factor alpha (TNFα), M-CSF or the combination of both would reduce tumor growth in a mouse xenograft model between 34% and 50% after intratumoral injection of the respective siRNA into the xenograft. siRNA targeting the TNFα secreted by the human SW620 cells reduced the mouse M-CSF and led to reduction of macrophages in the tumor. In addition, treatment of MCF-7 tumor xenografts with an antigen binding fragment directed against M-CSF antibody did result in 40% tumor growth inhibition, reversed the resistance to chemotherapeutics and improved survival of the mice when given in combination with chemotherapeutics (Paulus 2006).

TAMs are only one example of an emerging link between chronic inflammation and cancer. There is additional evidence for a link between inflammation and cancer as many chronic diseases are associated with an increased risk of cancer; cancers arise at sites of chronic inflammation and chemical mediators of inflammation are found in many cancers; deletion of the cellular or chemical mediators of inflammation inhibits development of experimental cancers and long-term use of anti-inflammatory agents reduce the risk of some cancers. A link to cancer exists for a number of inflammatory conditions among those H. pylori induced gastritis for gastric cancer, Schistosomiasis for bladder cancer, HHV8 for Kaposi's sarcoma, endometriosis for ovarian cancer and prostatitis for prostate cancer (Balkwill 2005). Macrophages are key cells in chronic inflammation and respond differentially to their microenvironment. There are two types of macrophages that are considered extremes in a continuum of functional states: M1 macrophages are involved in Type 1 reactions. These reactions involve the activation by microbial products and consequent killing of pathogenic microorganisms that result in reactive oxygen intermediates. On the other end of the extreme are M2 macrophages involved in Type 2 reactions that promote cell proliferation, tune inflammation and adaptive immunity and promote tissue remodeling, angiogenesis and repair (Mantovani 2004). Chronic inflammation resulting in established neoplasia is usually associated with M2 macrophages. A pivotal cytokine that mediates inflammatory reactions is TNFα that true to its name can stimulate anti-tumor immunity and hemorrhagic necrosis at high doses but has also recently been found to be expressed by tumor cells and acting as a tumor promoter (Zins 2007; Balkwill 2006). The specific role of macrophages with respect to the tumor still needs to be better understood including the potential spatial and temporal dependence on their function and the relevance to specific tumor types.

In another embodiment, a method for treating periodontitis, histiocytosis X, osteoporosis, Paget's disease of bone (PDB), bone loss due to cancer therapy, periprosthetic osteolysis, glucocorticoid-induced osteoporosis, rheumatoid arthritis, psiratic arthritis, osteoarthritis, inflammatory arthridities, and inflammation is provided.

Rabello 2006 has demonstrated that SNPs in the CSF1 gene exhibited a positive association with aggressive periodontitis: an inflammatory disease of the periodontal tissues that causes tooth loss due to resorption of the alveolar bone.

Histiocytosis X (also called Langerhans cell histiocytosis, LCH) is a proliferative disease of Langerhans dendritic cells that appear to differentiate into osteoclasts in bone and extraosseous LCH lesions. Langerhans cells are derived from circulating monocytes (Ginoux 2006). Increased levels of M-CSF that have been measured in sera and lesions where found to correlate with disease severity (da Costa 2005). The disease occurs primarily in a pediatric patient population and has to be treated with chemotherapy when the disease becomes systemic or is recurrent.

The pathophysiology of osteoporosis is mediated by loss of bone forming osteoblasts and increased osteoclast dependent bone resorption. Supporting data has been described by Cenci et al showing that an anti-M-CSF antibody injection preserves bone density and inhibits bone resorption in ovarectomized mice (Cenci 2000). Recently a potential link between postmenopausal bone loss due to estrogen deficiency was identified and found that the presence of TNFα-producing T-cell affected bone metabolism (Roggia 2004). A possible mechanism could be the induction of M-CSF by TNF alpha in vivo. An important role for M-CSF in TNFα-induced osteoclastogenesis was confirmed by the effect of an antibody directed against the M-CSF-inhibitor that blocked the TNFα-induced osteolysis in mice and thereby making inhibitors of CSF-1R signaling potential targets for inflammatory arthritis (Kitaura 2005).

Paget's disease of bone (PDB) is the $2^{nd}$ most common bone metabolism disorder after osteoporosis in which focal abnormalities of increased bone turnover lead to complications such as bone pain, deformity, pathological fractures, and deafness. Mutations in four genes have been identified that regulate normal osteoclast function and predispose individuals to PDB and related disorders: insertion mutations in TNFRSF11A, which encodes receptor activator of nuclear factor (NF) kappaB (RANK)—a critical regulator of osteoclast function, inactivating mutations of TNFRSF11B which encodes osteoprotegerin (a decoy receptor for RANK ligand), mutations of the sequestosome 1 gene (SQSTM1), which encodes an important scaffold protein in the NFkappaB pathway and mutations in the valosin-containing protein (VCP) gene. This gene encodes VCP, which has a role in targeting the inhibitor of NFkappaB for degradation by the proteasome (Daroszewska, 2006). Targeted CSF-1R inhibitors provide an opportunity to block the deregulation of the RANKL signaling indirectly and add an additional treatment option to the currently used bisphosphonates.

Cancer therapy induced bone loss especially in breast and prostate cancer patients is an additional indication where a targeted CSF-1R inhibitor could prevent bone loss (Lester 2006). With the improved prognosis for early breast cancer the long-term consequences of the adjuvant therapies become more important as some of the therapies including chemotherapy, irradiation, aromatase inhibitors and ovary ablation affect bone metabolism by decreasing the bone mineral density, resulting in increased risk for osteoporosis and associated fractures (Lester 2006). The equivalent to adjuvant aromatase inhibitor therapy in breast cancer is androgen ablation therapy in prostate cancer which leads to loss of bone mineral density and significantly increases the risk of osteoporosis-related fractures (Stoch 2001).

Targeted inhibition of CSF-1R signaling is likely to be beneficial in other indications as well when targeted cell types include osteoclasts and macrophages e.g. treatment of specific complications in response to joint replacement as a consequence of rheumatoid arthritis. Implant failure due to periprosthetic bone loss and consequent loosing of prostheses is a major complication of joint replacement and requires repeated surgery with high socioeconomic burdens for the individual patient and the health-care system. To date, there is no approved drug therapy to prevent or inhibit periprosthetic osteolysis (Drees 2007).

Glucocorticoid-induced osteoporosis (GIOP) is another indication in which a CSF-1R inhibitor could prevent bone loss after longterm glucocorticocosteroid use that is given as a result of various conditions among those chronic obstructive pulmonary disease, asthma and rheumatoid arthritis (Guzman-Clark 2007; Feldstein 2005).

Rheumatoid arthritis, psoriatic arthritis and inflammatory arthridities are in themselves potential indications for CSF-1R signaling inhibitors in that they consist of a macrophage component, and to a varying degree, bone destruction (Ritchlin 2003). Osteoarthritis and rheumatoid arthritis are inflammatory autoimmune diseases caused by the accumulation of macrophages in the connective tissue and infiltration of macrophages into the synovial fluid, which is at least partially mediated by M-CSF. Campbell et al. (2000) demonstrated that M-CSF is produced by human-joint tissue cells (chondrocytes, synovial fibroblasts) in vitro and is found in synovial fluid of patients with rheumatoid arthritis, suggesting that it contributes to the synovial tissue proliferation and macrophage infiltration which is associated with the pathogenesis of the disease. Inhibition of CSF-1R signaling is likely to control the number of macrophages in the joint and alleviate pain from the associated bone destruction. In order to minimize adverse affects and to further understand the impact of the CSF-1R signaling in these indications, one method is to specifically inhibit CSF-1R without targeting a myriad other kinases, such as Raf kinase.

Recent literature reports correlate increased circulating M-CSF with poor prognosis and atherosclerotic progression in chronic coronary artery disease (Saitoh 2000; Ikonomidis 2005); M-CSF influences the atherosclerotic process by aiding the formation of foam cells (macrophages with ingested oxidized LDL) that express CSF-1R and represent the initial plaque (Murayama 1999).

Expression and signaling of M-CSF and CSF-1R is found in activated microglia. Microglia, which are resident macrophages of the central nervous system, can be activated by various insults, including infection and traumatic injury. M-CSF is considered a key regulator of inflammatory responses in the brain and M-CSF levels increase in HIV-1 encephalitis, Alzheimer's disease (AD) and brain tumors. Microgliosis as a consequence of autocrine signaling by M-CSF/CSF-1R results in induction of inflammatory cytokines and nitric oxides being released as demonstrated by e.g. using an experimental neuronal damage model (Hao 2002; Murphy 1998). Microglia that have increased expression of CSF-1R are found to surround plaques in AD and in the amyloid precursor protein V717F transgenic mouse model of AD (Murphy 2000). On the other hand op/op mice with fewer microglia in the brain resulted in fibrilar deposition of Aβ and neuronal loss compared to normal control suggesting that microglia do have a neuroprotective function in the development of AD lacking in the op/op mice (Kaku 2003).

In one aspect, the preferred embodiments provide methods for treating CSF-1R related disorders in a human or animal subject in need of such treatment comprising administering to said subject an amount of a compound of Formula (I), (IIa), (IIb), (IIIa), (IIIb), (IV), or (V) effective to reduce or prevent the disorder. In a preferred embodiment, the disorder is tumor growth and/or metathesis in the subject.

In other aspects, the preferred embodiments provide methods for treating CSF-1R related disorders in a human or animal subject in need of such treatment comprising administering to said subject an amount of a compound of Formula (I), (IIa), (IIb), (IIIa), (IIIb), (IV), or (V) effective to reduce or prevent osteoclastogenesis, bone resorption and/or bone lesions in the subject.

In yet other aspects, the preferred embodiments provide methods for treating CSF-1R related disorders in a human or animal subject in need of such treatment comprising administering to said subject an amount of a compound of Formula (I), (IIa), (IIb), (IIIa), (IIIb), (IV), or (V) effective to treat the disorder in the subject in combination with at least one additional agent. In a more particular embodiment the additional agent is a bisphosphonate. In one embodiment the disorder is tumor growth and/or metastasis, osteoclastogenesis, bone resorption and/or bone lesions In yet other aspects, the preferred embodiments provide compounds of Formula (I), (IIa), (IIb), (IIIa), (IIIb), (IV), or (V) that are capable of selectively or preferentially inhibiting CSF-1R. In preferred embodiments the selective inhibitors of CSF-1R are capable of inhibiting CSF-1R at greater than about 5-fold, or about 10 fold, or about 20 fold, or about 30 fold, or about 50 fold, or about 100 fold, or about 250 fold, or about 500 fold, or about 750 fold, or about 1,000 fold, or about 2,000 the inhibitory activity (with respect to $IC_{50}$ values, for example) in Raf kinase.

In other aspects provided is a method of inhibiting CSF-1R comprising contacting a cell with a compound of Formula (I), (IIa), (IIb), (IIIa), (IIIb), (IV), or (V). In some aspects said compound is 4-{2-[(2,3-Dihydro-benzofuran-5-ylmethyl)-amino]-benzooxazol-6-yloxy}-pyridine-2-carboxylic acid methylamide or 4-[2-((1R,2R)-2-Benzyloxy-cyclohexylamino)-benzothiazol-6-yloxy]-pyridine-2-carboxylic acid methylamide.

In one aspect, the inhibitory effect of compounds on Raf is determined using the following biotinylated assay. The Raf kinase activity is measured by providing ATP, a recombinant kinase inactive MEK substrate and assaying the transfer of phosphate moiety to the MEK residue. Recombinant full length MEK with an inactivating K97R ATP binding site mutation (rendering kinase inactive) is expressed in *E. coli* and labelled with biotin post purification. The MEK cDNA is subcloned with an N-terminal $(His)_6$ tag and expressed in *E. coli* and the recombinant MEK substrate is purified from *E. coli* lysate by nickel affinity chromatography followed by anion exchange. The final MEK substrate preparation is biotinylated (Pierce EZ-Link Sulfo-NHS-LC-Biotin) and concentrated to about 11.25 μM. Recombinant Raf (including c-Raf and mutant B-Raf isoforms) is obtained by purification from sf9 insect cells infected with the corresponding human Raf recombinant expression vectors. The recombinant Raf isoforms are purified via a Glu antibody interaction or by Metal Ion Chromatography.

For each assay, the compound is serially diluted, for instance, starting at 25 μM with 3-fold dilutions, in DMSO and then mixed with various Raf isoforms (about 0.50 nM each). The kinase inactive biotin-MEK substrate (50 nM) is added in reaction buffer plus ATP (1 μM). The reaction buffer contains 30 mM Tris-HCl$_2$ pH 7.5, 10 mM MgCl$_2$, 2 mM DTT, 4 mM EDTA, 25 mM beta-glycerophosphate, 5 mM MnCl$_2$, and 0.01% BSA/PBS. Reactions are subsequently incubated for about 2 hours at room temperature and stopped by the addition of 0.5 M EDTA. Stopped reaction mixture is transferred to a neutradavin-coated plate and incubated for about 1 hour. Phosphorylated product is measured with the DELFIA time-resolved fluorescence system, using a rabbit anti-p-MEK (Cell Signaling) as the primary antibody and europium labeled anti-rabbit as the secondary antibody. Time resolved fluorescence can be read on a Wallac 1232 DELFIA fluorometer. The concentration of the compound for 50% inhibition (IC$_{50}$) is calculated by non-linear regression using XL Fit data analysis software.

In yet other aspects, the preferred embodiments provide methods for treating CSF-1R related disorders in a human or animal subject in need of such treatment comprising administering to said subject an amount of a compound of Formula (I), (IIa), (IIb), (IIIa), (IIIb), (IV), or (V) effective to reduce or prevent tumor growth in the subject in combination with at least one additional agent for the treatment of cancer. In a more particular embodiment the additional agent is a bisphosphonate.

A number of suitable anticancer agents to be used as combination therapeutics are contemplated for use in the methods of the preferred embodiments. Indeed, the preferred embodiments include administration of numerous additional anticancer agents such as, but not limited to, agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons [e.g. IFN-α, etc.] and interleukins [e.g. IL-2, etc.], etc.); adoptive immunotherapy agents; hematopoietic growth factors; agents that induce tumor cell differentiation (e.g. all-trans-retinoic acid, etc.); gene therapy reagents; antisense therapy reagents and nucleotides; tumor vaccines; inhibitors of angiogenesis, and the like. Numerous other examples of chemotherapeutic compounds and anticancer therapies suitable for coadministration with the disclosed compounds of Formula (I), (IIa), (IIb), (IIIa), (IIIb), (IV), or (V) are known to those skilled in the art.

In preferred embodiments, additional anticancer agents to be used in combination with compounds of the preferred embodiments comprise agents that induce or stimulate apoptosis. Agents that induce apoptosis include, but are not limited to, radiation (e.g., ω); kinase inhibitors (e.g., Epidermal Growth Factor Receptor [EGFR] kinase inhibitor, Vascular Endothelial Growth Factor Receptor [VEGFR] kinase inhibitor, Fibroblast Growth Factor Receptor [FGFR] kinase inhibitor, Platelet-derived Growth Factor Receptor [PDGFR] I kinase inhibitor, and Bcr-Abl kinase inhibitors such as STI-571, Gleevec, and Glivec]); antisense molecules; antibodies [e.g., Herceptin and Rituxan]; anti-estrogens [e.g., raloxifene and tamoxifen]; anti-androgens [e.g., flutamide, bicalutamide, finasteride, aminoglutethamide, ketoconazole, and corticosteroids]; cyclooxygenase 2 (COX-2) inhibitors [e.g., Celecoxib, meloxicam, NS-398, and non-steroidal antiinflammatory drugs (NSAIDs)]; and cancer chemotherapeutic drugs [e.g., irinotecan (Camptosar), CPT-11, fludarabine (Fludara), dacarbazine (DTIC), dexamethasone, mitoxantrone, Mylotarg, VP-16, cisplatinum, 5-FU, Doxrubicin, Taxotere or taxol; cellular signaling molecules; ceramides and cytokines; and staurosprine, and the like.

The compounds of the preferred embodiments are useful in vitro or in vivo in inhibiting the growth of cancer cells. The compounds may be used alone or in compositions together with a pharmaceutically acceptable carrier or excipient.

In other aspects, the preferred embodiments provide pharmaceutical compositions comprising at least one compound of Formula (I), (IIa), (IIb), (IIIa), (IIIb), (IV), or (V) together with a pharmaceutically acceptable carrier suitable for administration to a human or animal subject, either alone or together with other anticancer agents.

In other aspects, the preferred embodiments provide methods of manufacture of compounds of Formula (I), (IIa), (IIb), (IIIa), (IIIb), (IV), or (V) as described herein.

In other aspects provided is a pharmaceutical composition comprising an effective amount of a compound, stereoisomer, tautomer, solvate, oxide, ester, or prodrug of Formula (I), (IIa), (IIb), (IIIa), (IIIb), (IV), or (V) or a pharmaceutically acceptable salt thereof and a pharmaceutically acceptable carrier. In some aspects the compound preferentially inhibits CSF-1R over Raf kinase. More particularly said compound inhibits Raf kinase at greater than about 1 μM.

Other aspects further comprise an additional agent. More particularly, said additional agent is a bisphosphonate.

Other aspects provide compounds of Formula (I), (IIa), (IIb), (IIIa), (IIIb), (IV), or (V) effective to inhibit CSF-1R activity in a human or animal subject when administered thereto. More particularly, said compound exhibits an IC$_{50}$ value with respect to CSF-1R inhibition of less than about 1 μM. More particularly, said compound exhibits an IC$_{50}$ value with respect to Raf inhibition of greater than about 1 μM.

Another embodiment provides a method of inhibiting CSF-1R, wherein said compound selectively inhibits CSF-1R.

The compounds of the embodiments are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

Administration and Pharmaceutical Composition

In general, the compounds of preferred embodiments will be administered in a therapeutically effective amount by any of the accepted modes of administration for agents that serve similar utilities. The actual amount of the compound of preferred embodiments, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day. All of these factors are within the skill of the attending clinician.

Effective amounts of the compounds of the preferred embodiments generally include any amount sufficient to detectably inhibit CSF-1R activity by any of the assays described herein, by other CSF-1R kinase activity assays known to those having ordinary skill in the art or by detecting an inhibition or alleviation of symptoms of cancer.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the preferred embodiments, a therapeutically effective dose generally can be a total daily dose administered to a host in single or divided doses may be in amounts, for example, of from about 0.001 to about 1000 mg/kg body weight daily and more preferred from about 1.0 to about 30 mg/kg body weight daily. Dosage unit compositions may contain such amounts of submultiples thereof to make up the daily dose.

The choice of formulation depends on various factors such as the mode of drug administration and bioavailability of the drug substance. In general, compounds of preferred embodiments can be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of preferred embodiments is inhalation. This is an effective method for delivering a therapeutic agent directly to the respiratory tract (see U.S. Pat. No. 5,607,915).

Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinyl-pyrrolidinone, low melting waxes, ion exchange resins, and the like, as well as combinations of any two or more thereof. Liquid and semisolid excipients can be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable pharmaceutically acceptable excipients are described in "Remington's Pharmaceutical Sciences," Mack Pub. Co., New Jersey (1991), incorporated herein by reference.

As used herein, the term "pharmaceutically acceptable salts" refers to the nontoxic acid or alkaline earth metal salts of the compounds of Formulas (I), (IIa), (IIb), (IIIa), (IIIb), (IV), or (V). These salts can be prepared in situ during the final isolation and purification of the compounds of Formulas (I), (IIa), (IIb), (IIIa), (IIIb), (IV), or (V), or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with agents such as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of Formulas (I), (IIa), (IIb), (IIa), (IIIb), (IV), or (V), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the preferred embodiments which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the embodiments. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

It will be apparent to those skilled in the art that the compounds of the preferred embodiments, including the compounds of Formulas (I), (IIa), (IIb), (IIIa), (IIIb), (IV), or (V) or their tautomers, prodrugs, and stereoisomers, as well as the pharmaceutically acceptable salts, esters and prodrugs of any of them, may be processed in vivo through metabolism in a human or animal body or cell to produce metabolites. The term "metabolite" as used herein refers to the formula of any derivative produced in a subject after administration of a parent compound. The derivatives may be produced from the parent compound by various biochemical transformations in the subject such as, for example, oxidation, reduction, hydrolysis, or conjugation and include, for example, oxides and demethylated derivatives. The metabolites of a compound of the embodiments may be identified using routine techniques known in the art. See, e.g., Bertolini, G. et al., *J. Med. Chem.* 40:2011-2016 (1997); Shan, D. et al., *J. Pharm. Sci.* 86(7):765-767; Bagshawe K., *Drug Dev. Res.* 34:220-230 (1995); Bodor, N., *Advances in Drug Res.* 13:224-331 (1984); Bundgaard, H., *Design of Prodrugs* (Elsevier Press 1985); and Larsen, I. K., *Design and Application of Prodrugs, Drug Design and Development* (Krogsgaard-Larsen et al., eds., Harwood Academic Publishers, 1991). It should be understood that individual chemical compounds that are metabolites of the compounds of Formulas (I), (IIa), (IIb), or (III) or their tautomers, prodrugs, and stereoisomers, as well as the pharmaceutically acceptable salts, esters and prodrugs of any of them, are included within the preferred embodiments.

The compounds of the preferred embodiments may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intrathecal, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the preferred embodiments can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the preferred embodiments, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq. (1976).

Compressed gases may be used to disperse a compound of preferred embodiments in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from about 10 to about 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of about 400 nm) in the presence of a surface modifier and then dispersed in a liquid medium to give a pharmaceutical formulation that exhibits remarkably high bioavailability.

Combination Therapies

While the compounds of the preferred embodiments can be administered as the sole active pharmaceutical agent, they can also be used in combination with one or more other agents used in the treatment of cancer. The compounds of the preferred embodiments are also useful in combination with known therapeutic agents and anti-cancer agents, and combinations of the presently disclosed compounds with other anti-cancer or chemotherapeutic agents are within the scope of the preferred embodiments. Examples of such agents can be found in *Cancer Principles and Practice of Oncology*, V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anticancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The compounds of the preferred embodiments are also useful when co-administered with radiation therapy.

Therefore, in one embodiment, the compounds are also used in combination with known anticancer agents including, for example, estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

Estrogen receptor modulators are compounds that can interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

Androgen receptor modulators are compounds which can interfere with or inhibit the binding of androgens to an androgen receptor. Representative examples of androgen receptor modulators include finasteride and other 5α-reductase inhibitors, nilutamide, flutamide, bicalutamide, liarozole, and abiraterone acetate. Retinoid receptor modulators are compounds which interfere or inhibit the binding of retinoids to a retinoid receptor. Examples of retinoid receptor modulators include bexarotene, tretinoin, 13-cis-retinoic acid, 9-cis-retinoic acid, α-difluoromethylornithine, LX23-7553, trans-N-(4'-hydroxyphenyl) retinamide, and N4-carboxyphenyl retinamide.

Cytotoxic and/or cytostatic agents are compounds which can cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors. Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine (chloro)platinum(II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxy-caminomycin, annamycin, galarubicin, elinafide, MEN10755, and 4-demethoxy-3-deamino-3-aziridinyl-4-methylsulphonyl-daunorubicin (see WO 00/50032).

A representative example of a hypoxia activatable compound is tirapazamine. Proteasome inhibitors include, but are not limited to, lactacystin and bortezomib. Examples of microtubule inhibitors/microtubule-stabilizing agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butyl-amide, TDX258, the epothilones (see for example U.S. Pat. Nos. 6,284,781 and 6,288,237) and BMS188797. Representative examples of topoisomerase inhibitors include topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13 (9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa, 9b)-9-[2-[N-[2-(dimethylamino)ethyl]-N-methylamino]ethyl]-5-[4-hydrOxy-3,5-dimethoxyphenyl]-5,5a,6,8,8a,9-hexahydrofuro(3',4':6,7)naphtho(2,3-d)-1,3-dioxol-6-one, 2,3-(methylenedioxy)-5-methyl-7-hydroxy-8-methoxybenzo [c]-phenanthridinium, 6,9-bis[(2-aminoethyl)amino]benzo [g]isoquinoline-5,10-dione, 5-(3-aminopropylamino)-7,10-dihydroxy-2-(2-hydroxyethylaminomethyl)-6H-pyrazolo[4, 5,1'-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna. Examples of inhibitors of mitotic kinesins, such as the human mitotic kinesin KSP, are described in PCT Publications WO 01/30768 and WO 01/98278, WO 03/050,064 (Jun. 19, 2003), WO 03/050,122 (Jun. 19, 2003), WO 03/049,527 (Jun. 19, 2003), WO 03/049, 679 (Jun. 19, 2003), WO 03/049,678 (Jun. 19, 2003) and WO 03/39460 (May 15, 2003) and pending PCT Appl. Nos. US03/ 06403 (filed Mar. 4, 2003), US03/15861 (filed May 19, 2003), US03/15810 (filed May 19, 2003), US03/18482 (filed Jun. 12, 2003) and US03/18694 (filed Jun. 12, 2003). In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Inhibitors of kinases involved in mitotic progression include, but are not limited to, inhibitors of aurora kinase, inhibitors of Polo-like kinases (PLK) (e.g., inhibitors of PLK-1), inhibitors of bub-1 and inhibitors of bub-1R. Antiproliferative agents include antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl] adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1-diazatetracyclo (7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone. Examples of monoclonal antibody targeted therapeutic agents include those therapeutic agents which have cytotoxic agents or radioisotopes attached to a cancer cell specific or target cell specific monoclonal antibody. Examples include, for example, Bexxar. HMG-CoA reductase inhibitors are inhibitors of 3-hydroxy-3-methylglutaryl-CoA reductase. Compounds which have inhibitory activity for HMG-CoA reductase can be readily identified by using assays well-known in the art such as those described or cited in U.S. Pat. No. 4,231,938 and WO 84/02131. Examples of HMG-CoA reductase inhibitors that may be used include, but are not limited to, lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. In an embodiment, the HMG-CoA reductase inhibitor is selected from lovastatin or simvastatin.

Prenyl-protein transferase inhibitors are compounds which inhibit any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2(1H)quinolinone, (−)-6-[amino(4-chlorophenyl)(1-methyl-1H-imidazol-5-yl) methyl]-4-(3-chlorophenyl)-1-methyl-2(1H)-quinolinone, (+)-6-[amino(4-chlorophenyl)(1-methyl-1H-imidazol-5-yl) methyl]-4-(3-chlorophenyl)-1-methyl-2(1H)-quinolinone, 5 (S)-n-butyl-1-(2,3-dimethylphenyl)-4-[1-(4-cyanobenzyl)-5-imidazolylmethyl-2-piperazinone, (S)-1-(3-chlorophenyl)-4-[1-(4-cyanobenzyl)-5-imidazolylmethyl]-5-[2-(ethanesulfonyl)methyl)-2-piperazinone, 5 (S)-n-butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{-[4-hydroxymethyl-4-(4-chloropyridin-2-ylmethyl)-piperidine-1-ylmethyl]-2-methylimidazol-1-ylmethyl}benzonitrile, 4-{-5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2'] bipyridin-5'-ylmethyl]-3H-imidazol-4-ylmethyl}benzonitrile, 4-{3-[4-(2-oxo-2H-[1,2']bipyridin-5'-ylmethyl]-3H-imidazol-4-ylmethyl}benzonitrile, 4-[3-(2-oxo-1-phenyl-1,2-dihydropyridin-4-ylmethyl)-3H-imidazol-4-ylmethyl}benzonitrile, 18,19-dihydro-19-oxo-5H,17H-6,10:12,16-dimetheno-1H-imidazo[4,3-c][1,11,4] dioxaazacyclo-nonadecine-9-carbonitrile, (±)-19,20-dihydro-19-oxo-5H-18,21-ethano-12,14-etheno-6,10-metheno-22H-benzo[d]imidazo[4,3-k][1,6,9,12]oxatriazacyclooctadecine-9-carbonitrile, 19,20-dihydro-19-oxo-5H, 17H-18,21-ethano-6,10:12,16-dimetheno-22H-imidazo[3,4-h][1,8,11,14]oxatriazacycloeicosine-9-carbonitrile, and (.+−.)-19,20-dihydro-3-methyl-19-oxo-5H-18,21-ethano-12,14-etheno-6,10-metheno-22H-benzo[d]imidazo[4,3-k][1,6,9, 12]oxa-triazacyclooctadecine-9-carbonitrile. Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer* 35(9): 1394-1401 (1999).

Angiogenesis inhibitors refers to compounds that can inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-.alpha., interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS* 89:7384 (1992); *JNCI* 69:475 (1982); *Arch. Opthalmol.* 108:573 (1990); *Anat. Rec.*, (238):68 (1994);

*FEBS Letters* 372:83 (1995); *Clin, Orthop.* 313:76 (1995); *J. Mol. Endocrinol.* 16:107 (1996); *Jpn. J. Pharmacol.* 75:105 (1997); *Cancer Res.* 57:1625 (1997); *Cell* 93:705 (1998); *Intl. J. Mol. Med.* 2:715 (1998); *J. Biol. Chem.* 274:9116 (1999)), steroidal anti-inflammatories (such as corticosteroids, mineralocorticoids, dexamethasone, prednisone, prednisolone, methylpred, betamethasone), carboxyamidotriazole, combretastatin A4, squalamine, 6-O-chloroacetylcarbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology,* 17:963-968 (October 1999); Kim et al., *Nature,* 362:841-844 (1993); WO 00/44777; and WO 00/61186). Other therapeutic agents that modulate or inhibit angiogenesis and may also be used in combination with the compounds of the preferred embodiments include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002). The preferred embodiments also encompass combinations of the compounds of the preferred embodiments with NSAIDs which are selective COX-2 inhibitors (generally defined as those which possess a specificity for inhibiting COX-2 over COX-1 of at least about 100 fold as measured by the ratio of $IC_{50}$ for COX-2 over $IC_{50}$ for COX-1 evaluated by cell or microsomal assays). Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference. Representative inhibitors of COX-2 that are useful in the methods of the preferred embodiments include 3-phenyl-4-(4-(methylsulfonyl)phenyl)-2-(5H)-furanone; and 5-chloro-3-(4-methylsulfonyl)phenyl-2-(2-methyl-5-pyridinyl)pyridine. Compounds which are described as specific inhibitors of COX-2 and are therefore useful in the preferred embodiments, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, U.S. Pat. No. 5,932,598, issued Aug. 3, 1999, U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998. Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPT4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

Agents that interfere with cell cycle checkpoints are compounds that can inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

Inhibitors of cell proliferation and survival signaling pathway can be pharmaceutical agents that can inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of cytokine receptors, inhibitors of MET, inhibitors of PI3K (for example LY294002), serine/threonine kinases (including but not limited to inhibitors of Akt such as described in WO 02/083064, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779). Such agents include small molecule inhibitor compounds and antibody antagonists.

Apoptosis inducing agents include activators of TNF receptor family members (including the TRAIL receptors).

In certain presently preferred embodiments, representative agents useful in combination with the compounds of the preferred embodiments for the treatment of cancer include, for example, irinotecan, topotecan, gemcitabine, 5-fluorouracil, leucovorin carboplatin, cisplatin, taxanes, tezacitabine, cyclophosphamide, vinca alkaloids, imatinib (Gleevec), anthracyclines, rituximab, trastuzumab, as well as other cancer chemotherapeutic agents.

The above compounds to be employed in combination with the compounds of the preferred embodiments can be used in therapeutic amounts as indicated in the *Physicians' Desk Reference* (PDR) 47th Edition (1993), which is incorporated herein by reference, or such therapeutically useful amounts as would be known to one of ordinary skill in the art.

The compounds of the preferred embodiments and the other anticancer agents can be administered at the recommended maximum clinical dosage or at lower doses. Dosage levels of the active compounds in the compositions of the preferred embodiments may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

General Synthetic Methods

The compounds of preferred embodiments can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of preferred embodiments contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of the embodiments, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4th Edition), and Larock's *Comprehensive Organic Transformations* (VCH Publishers Inc., 1989).

The various starting materials, intermediates, and compounds of the preferred embodiments may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

Compounds of the embodiments may generally be prepared using a number of methods familiar to one of skill in the art, such as, for example, the methods disclosed in U.S. patent application Publication Nos. US20040087626 A1 and US20040122237 A1, the disclosures of which are incorporated herein in their entirety, in connection with the following description and examples. The compounds of the embodiments may be generally made in accordance with the following reaction Schemes 1-8, which are described in detail in the Examples, below.

Schemes 1-8 illustrate general methods for the preparation of intermediates and compounds of the embodiments. These compounds are prepared from starting materials either known in the art or are commercially available. The specific compounds are for illustrative purposes only.

Scheme 1

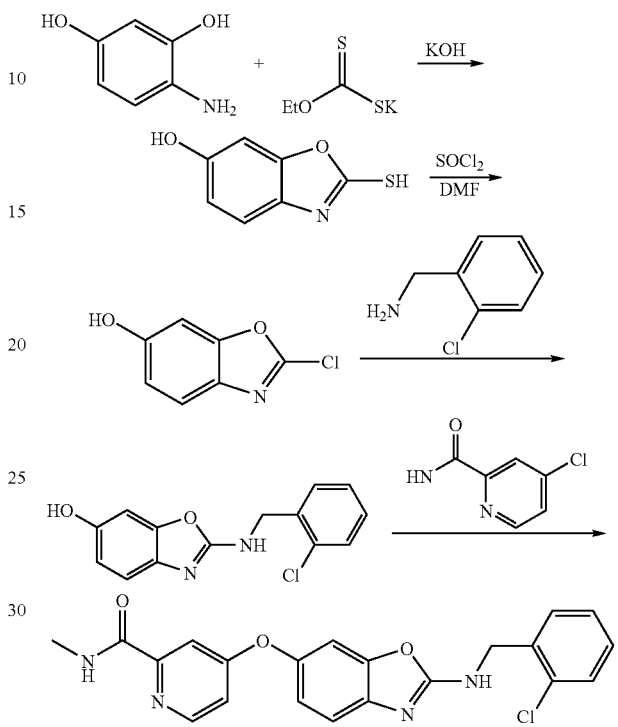

In Scheme 1, 2-hydroxyaniline or a derivative thereof reacts with ethylxanthic acid to give a thiol-benzoxazole. The thiol-benzoxazole is converted to a chloro-benzoxazole with reaction with thionyl chloride. Alternatively, the thiol benzoxazole can be converted to halogenated benzoxazole with a array of halogenating agents, such as, but not limited to phosphorus trichloride, phosphorus tribromide, phosgene, or oxalyl chloride. The chloro-benzoxazole is then reacted with a benzylamine such as 2-chlorobenzylamine to give a benzylamino-benzoxazole. The benzylamino-benzoxazole is coupled with chloro-pyridine in the presence of a base such as, cesium carbonate to give a compound of the invention. Alternatively, a halogenated pyridine can be used for the coupling.

Scheme 2

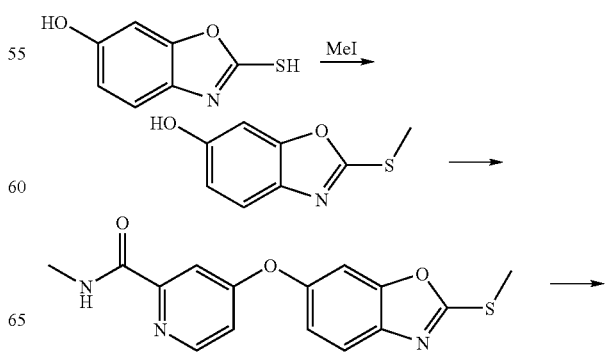

-continued

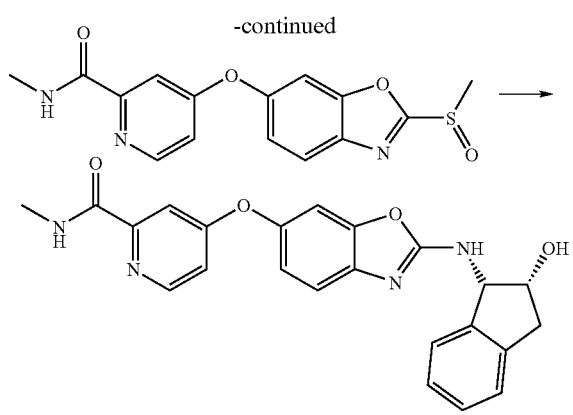

In Scheme 2, a thiol-benzoxazole or derivative thereof is alkylated at the thiol moiety. The alkylated thiol-benzoxazole is coupled with the corresponding halo pyridine such as chloro-pyridine in the presence of a base such as cesium carbonate to give a compound of the invention. The resulting benzoxazolyloxy-pyridine is oxidized, for instance, with mCPBA. Other oxidizing agents can be used to oxidize the thiol to a sulfoxide. Other oxidizing agents include, but are not limited to, hydrogen peroxide, sodium periodate, pyridinium chlorochromate or chromium trioxide. The sulfoxide of the benzoxazolyloxy-pyridine is subjected to nucleophilic attack with an amine to give a compound of the invention.

Scheme 3

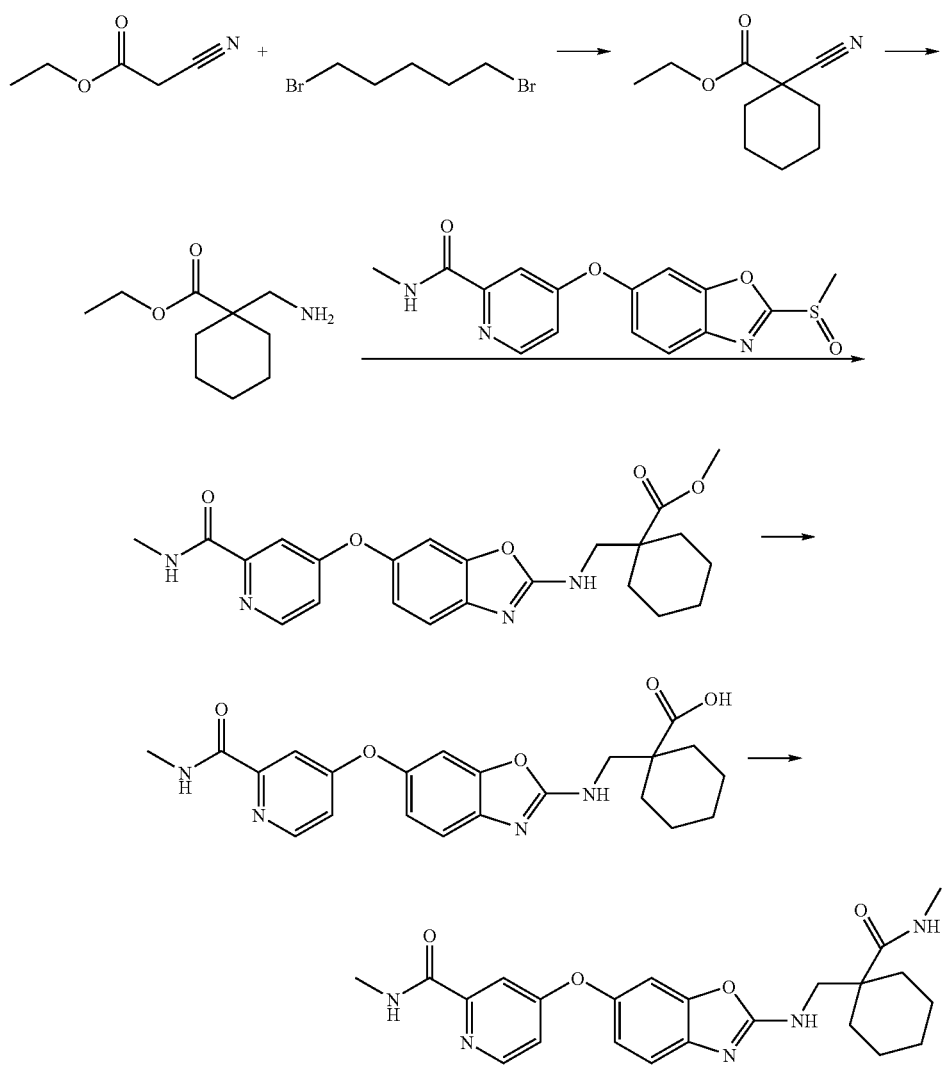

In Scheme 3, cyanoacetate and 1,5-dibromopentane are coupled to form 1-cyano-cyclohexanecarboxylic acid ethyl ester after cyclization. This product is reduced with hydrogen and Raney nickel. Other reducing agents can be used to reduce the nitrile group to an amine. Other reducing agents include, but are not limited to, catalytic hydrogenation using platinum oxide or Raney nickel or lithium aluminum hydride, diisobutyl aluminum hydride, sodium borohydride, or lithium triethylborohydride. The reduced product is coupled with sulfoxo-benzoxazolyloxy-pyridine. The resulting product from the coupling reaction can be further functionalized or derivatized. For example, in Scheme 3, an ester group can be converted to a carboxylic acid group from hydrolysis and then converted to an amide from reaction with an amine. These reactions are well-known conversions to one skilled in the art.

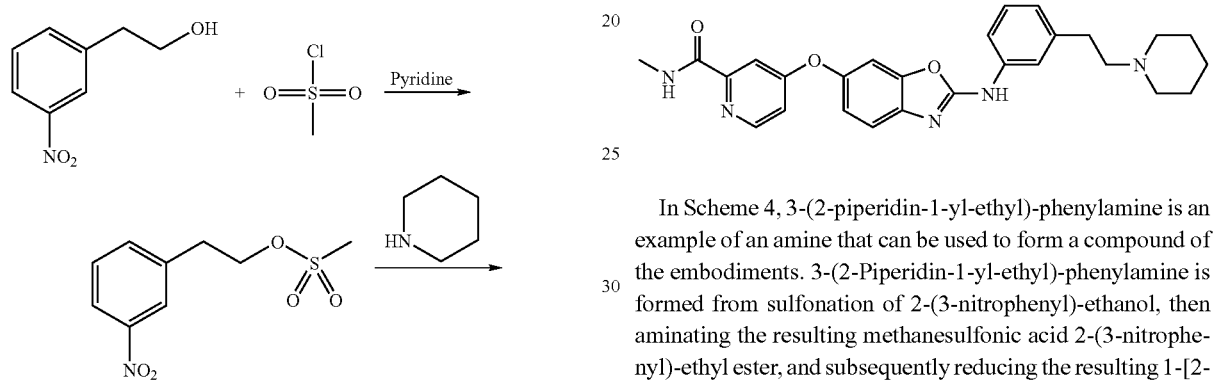

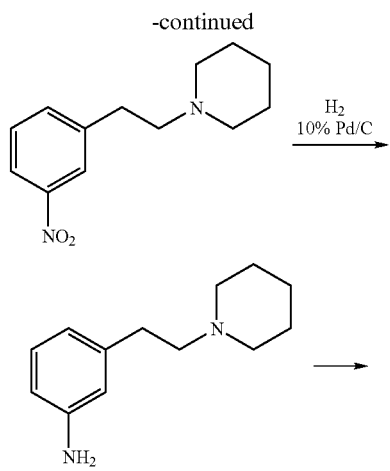

In Scheme 4, 3-(2-piperidin-1-yl-ethyl)-phenylamine is an example of an amine that can be used to form a compound of the embodiments. 3-(2-Piperidin-1-yl-ethyl)-phenylamine is formed from sulfonation of 2-(3-nitrophenyl)-ethanol, then aminating the resulting methanesulfonic acid 2-(3-nitrophenyl)-ethyl ester, and subsequently reducing the resulting 1-[2-(3-nitrophenyl)-ethyl]-piperidine.

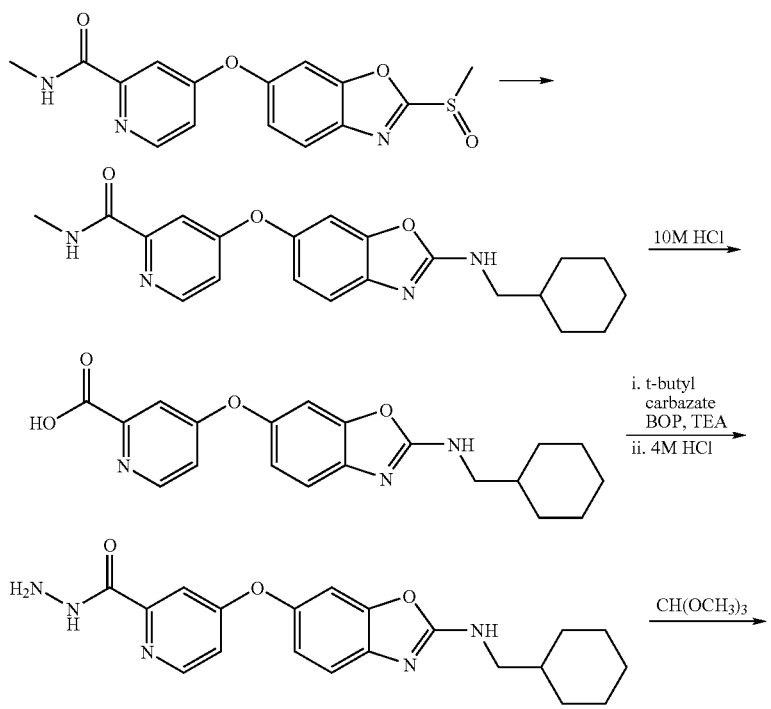

-continued

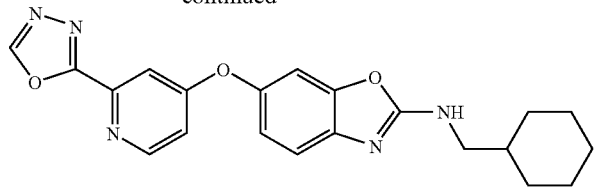

In Scheme 5, 4-(2-(methylsulfinyl)benzo[d]oxazol-6-yloxy)-N-methylpyridine-2-carboxamide is aminated with cyclohexylmethanamine. The resulting 4-(2-(cyclohexylmethylamino)benzo[d]oxazol-6-yloxy)-N-methylpyridine-2-carboxamide is then hydrolyzed to form 4-[2-(cyclohexylmethyl-amino)-benzooxazol-6-yloxy]-pyridine-2-carboxylic acid. 4-[2-(Cyclohexylmethyl-amino)-benzooxazol-6-yloxy]-pyridine-2-carboxylic acid then reacts with benzotriazol-1-yloxytris(dimethylamino)-phosphonium hexafluorophosphate, tert-butyl carbazate, and triethyl amine to form 4-(2-(cyclohexylmethylamino)benzo[d]oxazol-6-yloxy)pyridine-2-carbohydrazide. 4-(2-(Cyclohexylmethylamino)benzo[d]oxazol-6-yloxy)pyridine-2-carbohydrazide then reacts with trimethyl orthoformate to form a compound of the embodiments.

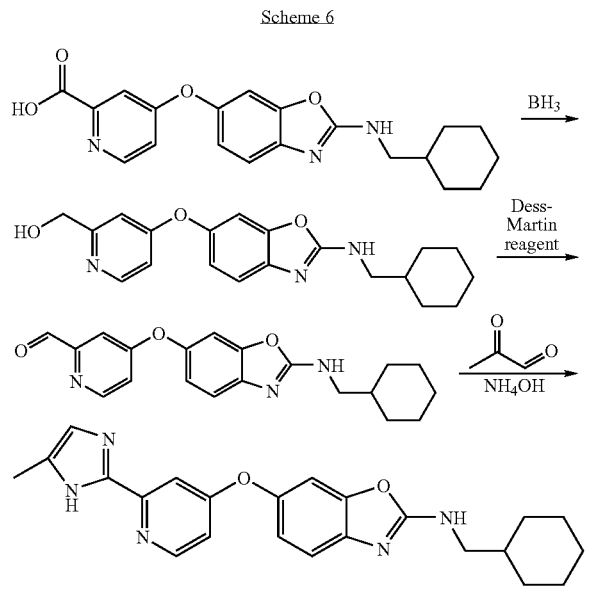

In Scheme 6, a compound of the embodiment can be further functionalized. For instance, 4-(2-(cyclohexylmethylamino)benzo[d]oxazol-6-yloxy)pyridine-2-carboxylic acid is reduced to {4-(2-(cyclohexylmethylamino)benzo[d]oxazol-6-yloxy)pyridine-2-yl}-methanol with borane. Other suitable reducing agents include, but are not limited to, lithium aluminum hydride, aluminum hydride, diisobultyl aluminum hydride, sodium borohydride, or lithium triethylborohydride. {4-(2-(Cyclohexylmethylamino)benzo[d]oxazol-6-yloxy)pyridine-2-yl}-methanol is then oxidized to 4-(2-(cyclohexylmethylamino)benzo[d]oxazol-6-yloxy)pyridine-2-carbaldehyde with Dess-Martin reagent. Other suitable oxidizing agents include, but are not limited to, pyridinium chlorochromate, $SO_3$ pyridine in DMSO, or conditions commonly referred to as a Swern or Moffet oxidation. 4-(2-(Cyclohexylmethylamino)benzo[d]oxazol-6-yloxy)pyridine-2-carbaldehyde is then converted to cyclohexylmethyl-{6-[2-(5-methyl-1H-imidazol-2-yl)-pyridin-4-yloxy]-benzooxazol-2-yl}-amine by reaction with pyruvic aldehyde.

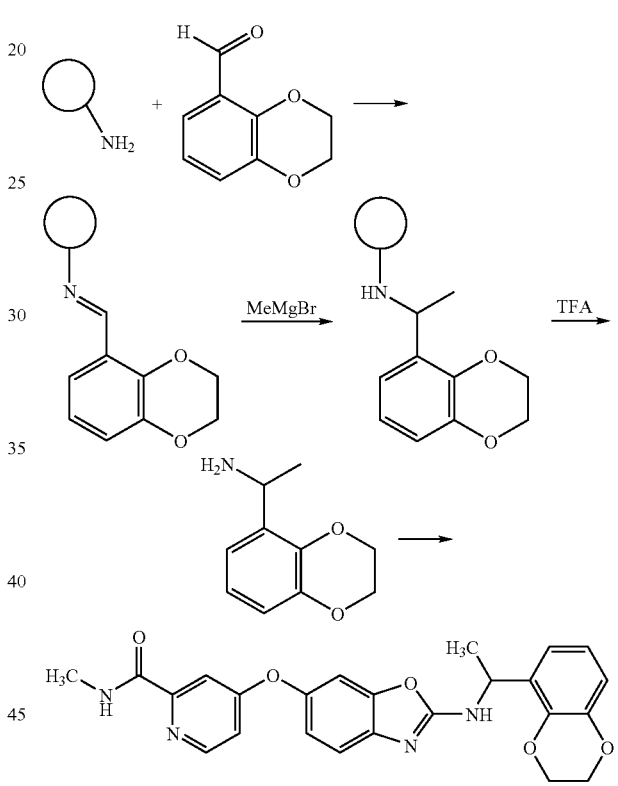

In Scheme 7, a compound of the embodiments is synthesized from reaction of 4-(2-methanesulfinyl-benzooxazol-6-yloxy)-pyridine-2-carboxylic acid methylamide (from Example 2) with 1-(2,3-dihydro-benzo[1,4]dioxin-5-yl)-ethylamine. In one instance, 1-(2,3-dihydro-benzo[1,4]dioxin-5-yl)-ethylamine is synthesized via a resin.

An amine linked to a resin is reacted with 2,3-dihydro-benzo[1,4]dioxine-5-carbaldehyde, thus giving C-(2,3-dihydro-benzo[1,4]dioxin-5-yl)-methyleneamine. C-(2,3-dihydro-benzo[1,4]dioxin-5-yl)-methyleneamine is derivatized with alkylation at the imino site, such as with methyl magnesium bromide. Other alkylating agents can be used according to the desired molecule. The resulting 1-(2,3-dihydro-benzo[1,4]dioxin-5-yl)-ethylamine is cleaved from the resin. An example of a resin-cleaving agent is trifluoroacetic acid (TFA). The resulting 1-(2,3-dihydro-benzo[1,4]dioxin-5-yl)-ethylamine can be used for synthesis of a compound of the embodiments. For instance, 1-(2,3-dihydro-benzo[1,4]dioxin-5-yl)-ethylamine can be used to react with 4-(2-methanesulfinyl-benzooxazol-6-yloxy)-pyridine-2-carboxylic acid methylamide to form 4-{2-[1-(2,3-dihydro-benzo[1,4]dioxin-5-yl)-ethylamino]-benzooxazol-6-yloxy}-pyridine-2-carboxylic acid methylamide.

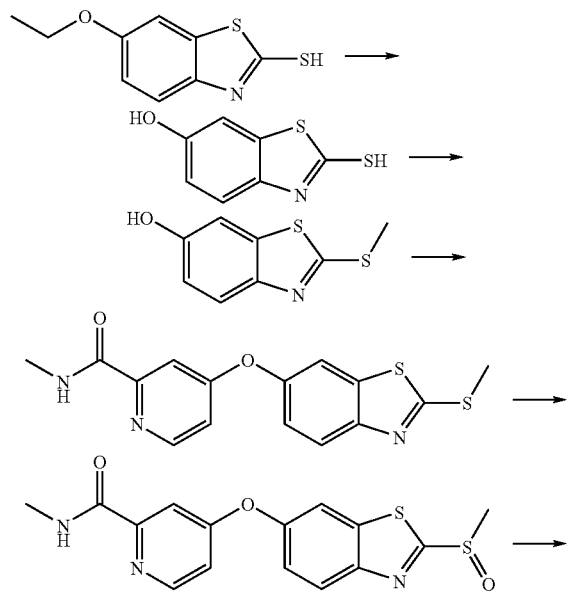

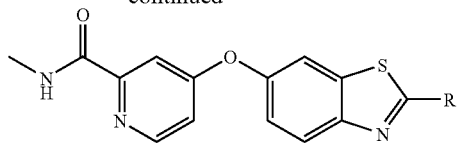

R = various amines

In Scheme 8, 2-mercapto-benzothiazol-6-ol was prepared as per U.S. Pat. No. 4,873,346. 2-Mercapto-benzothiazol-6-ol is then converted to 2-methylsulfanyl-benzothiazol-6-ol via conventional procedures to remove an ethereal protecting group. Reaction of 2-methylsulfanyl-benzothiazol-6-ol with methyl iodide provides alkylation at the thiol position. Reaction of 2-methylsulfanyl-benzothiazol-6-ol with 4-chloro-pyridine-2-carboxylic acid methylamide gives 4-(2-methylsulfanyl-benzothiazol-6-yloxy)-pyridine-2-carboxylic acid methylamide. Subsequent oxidation of 4-(2-methylsulfanyl-benzothiazol-6-yloxy)-pyridine-2-carboxylic acid methylamide gives 4-(2-methanesulfinyl-benzothiazol-6-yloxy)-pyridine-2-carboxylic acid methylamide. 4-(2-Methanesulfinyl-benzothiazol-6-yloxy)-pyridine-2-carboxylic acid methylamide can be a substrate for reaction with various amines. For instance, 4-(2-methanesulfinyl-benzothiazol-6-yloxy)-pyridine-2-carboxylic acid methylamide can react with cyclohexylmethylamine to give 4-[2-(cyclohexylmethyl-amino)-benzothiazol-6-yloxy]-pyridine-2-carboxylic acid methylamide.

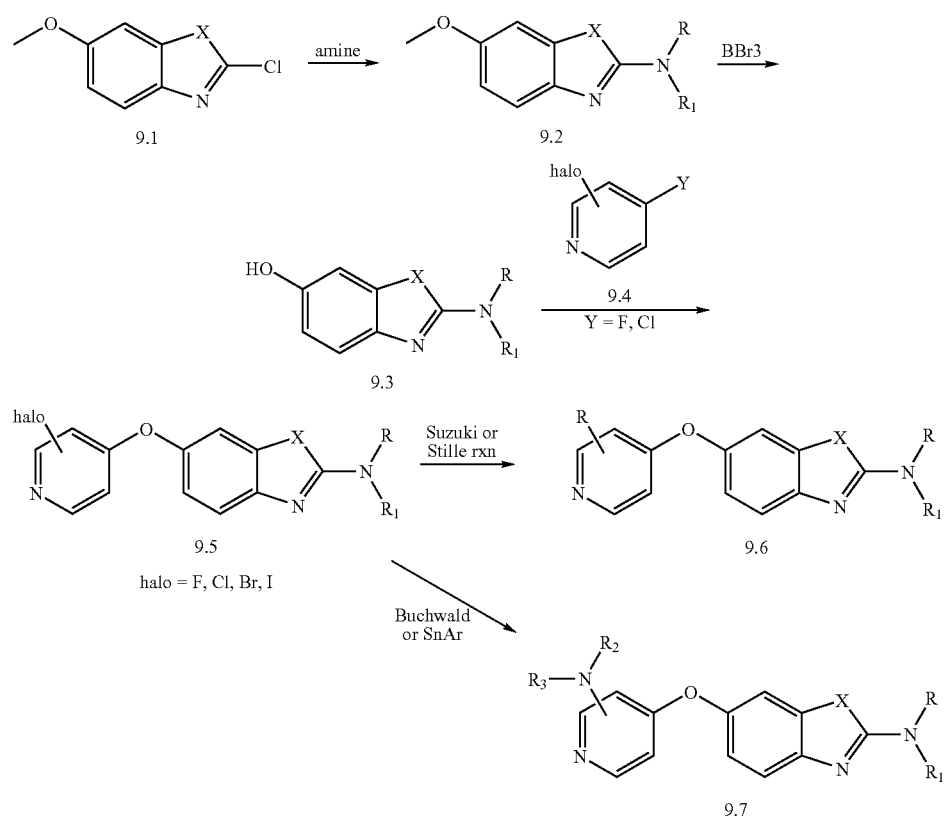

In Scheme 9 benzoxazoles or benzothiazoles of formula 9.1 can be reacted with a substituted amine to provide intermediates of the formula 9.2. Treatment of intermediates of formula 9.2 with a reagent such as, for example, BBr$_3$ provides phenols of the formula 9.3. Subsequent treatment of intermediates of formula 9.3 with 4-halo pyridines of formula 9.4 at temperatures generally ranging from, but not limited to, room temperature to 130° C. provides in the presence of a base such as, for example, potassium or cesium carbonate provides compounds for formula 9.5. Further treatment with boronic acids or stannanes under conditions known to those practiced in the art as Suzuki or Stille reactions provides compounds of formula 9.6. In addition, treatment of a compound of formula 9.5 with a substituted amine under conditions known to those practiced in the art for a Buchwald reaction or SnAr reaction provides compounds of formula 9.7.

minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.).

In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LCMS instruments: a Waters System (Alliance HT HPLC and a Micromass ZQ mass spectrometer; Column: Eclipse XDB-C18, 2.1×50 mm; gradient: 5-95% (or 35-95%, or 65-95% or 95-95%) acetonitrile in water with 0.05% TFA over a 4 min period; flow rate 0.8 mL/min; molecular weight Scheme 10

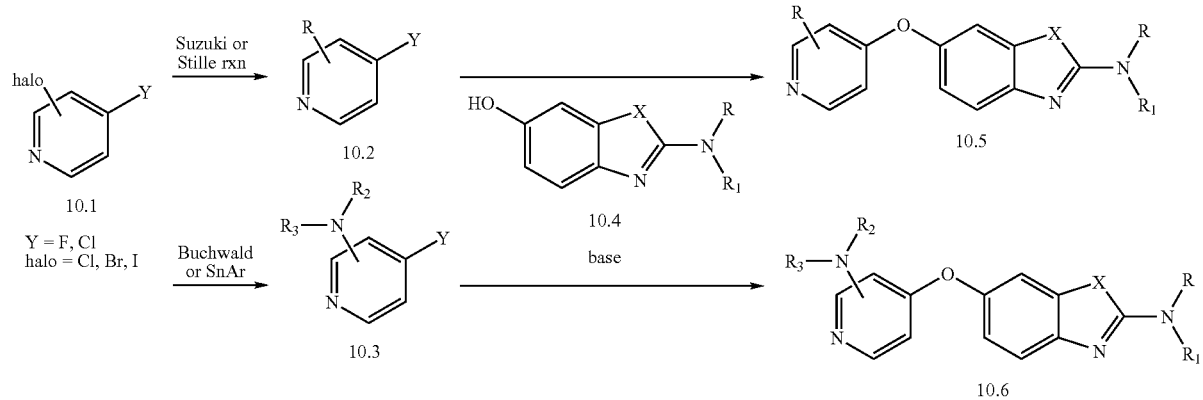

In Scheme 10 benzoxazoles or benzothiazoles of formula 10.5 and 10.6 can be prepared starting with a 4-halopyridine for formula 10.1 which can be (1) treated with boronic acids or stannanes under conditions known to those practiced in the art as Suzuki or Stille reactions provides intermediates of formula 10.2 or (2) reacted with a substituted amine under conditions known to those practiced in the art for a Buchwald reaction or SnAr reaction to provide intermediates of formula 10.3. Subsequent reaction of intermediates of formula 10.2 or 10.3 with a phenolic intermediate of formula 10.4 in the presence of a base such as, for example, potassium or cesium carbonate in a solvent such as, for example, dimethyl formamide, acetonitrile or dioxane provides compounds of formula 10.5 and 10.6.

EXAMPLES

Referring to the examples that follow, compounds of the preferred embodiments were synthesized using the methods described herein, or other methods, which are known in the art.

The compounds and/or intermediates were characterized by high performance liquid chromatography (HPLC) using a Waters Millenium chromatography system with a 2695 Separation Module (Milford, Mass.). The analytical columns were reversed phase Phenomenex Luna C18-5µ, 4.6×50 mm, from Alltech (Deerfield, Ill.). A gradient elution was used (flow 2.5 mL/min), typically starting with 5% acetonitrile/95% water and progressing to 100% acetonitrile over a period of 10 range 200-1500; cone Voltage 20 V; column temperature 40° C.) or a Hewlett Packard System (Series 1100 HPLC; Column: Eclipse XDB-C18, 2.1×50 mm; gradient: 5-95% acetonitrile in water with 0.05% TFA over a 4 min period; flow rate 0.8 mL/min; molecular weight range 150-850; cone Voltage 50 V; column temperature 30° C.). All masses were reported as those of the protonated parent ions.

GCMS analysis is performed on a Hewlett Packard instrument (HP6890 Series gas chromatograph with a Mass Selective Detector 5973; injector volume: 1 µL; initial column temperature: 50° C.; final column temperature: 250° C.; ramp time: 20 minutes; gas flow rate: 1 mL/min; column: 5% phenyl methyl siloxane, Model No. HP 190915-443, dimensions: 30.0 m×25 m×0.25 m).

Nuclear magnetic resonance (NMR) analysis was performed on some of the compounds with a Varian 300 MHz NMR (Palo Alto, Calif.). The spectral reference was either TMS or the known chemical shift of the solvent. Some compound samples were run at elevated temperatures (e.g., 75° C.) to promote increased sample solubility.

The purity of some of the compounds is assessed by elemental analysis (Desert Analytics, Tucson, Ariz.).

Melting points are determined on a Laboratory Devices Mel-Temp apparatus (Holliston, Mass.).

Preparative separations are carried out using a Flash 40 chromatography system and KP-Sil, 60A (Biotage, Charlottesville, Va.), or by flash column chromatography using silica gel (230-400 mesh) packing material, or by HPLC using a Waters 2767 Sample Manager, C-18 reversed phase column, 30×50 mm, flow 75 mL/min. Typical solvents employed for the Flash 40 Biotage system and flash column chromatography are dichloromethane, methanol, ethyl acetate, hexane, acetone, aqueous ammonia (or ammonium hydroxide), and triethyl amine. Typical solvents employed for the reverse phase HPLC are varying concentrations of acetonitrile and water with 0.1% trifluoroacetic acid.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

The examples below as well as throughout the application, the following abbreviations have the following meanings. If not defined, the terms have their generally accepted meanings.

Abbreviations

ACN Acetonitrile
BINAP 2,2'-bis(diphenylphosphino)-1,1'-binapthyl
DCM Dichloromethane
DIEA diisopropylethylamine
DIPEA N,N-diisopropylethylamine
DME 1,2-dimethoxyethane
DMF N,N-dimethylformamide
DMSO dimethyl sulfoxide
DPPF 1,1'-bis(diphenylphosphino)ferrocene
EtOAc ethyl acetate
EtOH ethanol
HATU 2-(7-Aza-1H-benzotriazole-1-yl)-1,1,3,3-tetramethyluronium hexafluorophosphate
HPLC high performance liquid chromatography
MCPBA meta-chloroperoxybenzoic acid
MeOH methanol
NBS N-bromosuccinimide
NMP N-methyl-2-pyrrolidone
RT room temperature
THF tetrahydrofuran Compounds of Formula I Example 1

Synthesis of 4-[2-(2-Chloro-benzylamino)-benzooxazol-6-yloxy]-pyridine-2-carboxylic acid methylamide (Table 2, Compound 8)

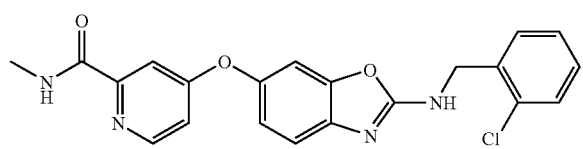

Step 1. Synthesis of 2-Mercapto-benzooxazol-6-ol

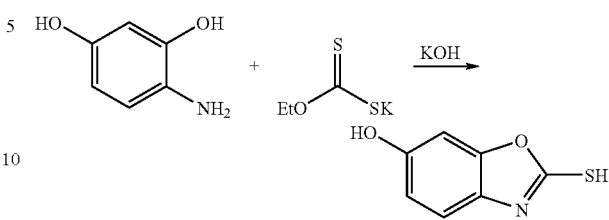

To a solution of 4-aminoresorcinol (1 eq) and ethylxanthic acid (3 eq) in ethanol was added potassium hydroxide (2.1 eq). The mixture was refluxed for two hours then diluted with water and acidified using 1N HCl to a pH of 4. The product was extracted into ethyl acetate then concentrated. The resulting solid was triturated with dichloromethane to give pure product with a 90% yield. MH+=168.1.

Step 2. Synthesis of 2-Chloro-benzooxazol-6-ol

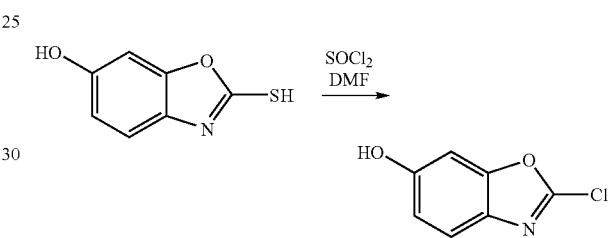

2-Mercapto-benzoxazol-6-ol (1 eq) was dissolved in thionyl chloride (10 eq). DMF (0.6 eq) was slowly added to this solution at room temperature. The mixture was heated to 80° C. and refluxed for 15 minutes. The reaction mixture was cooled to room temperature and the solvent was removed. The resulting solid was azeotroped three times with xylenes. The solid was dissolved in a 10% solution of THF in ethyl acetate and washed once with a saturated aqueous solution of sodium bicarbonate. The organic layer was dried with anhydrous sodium sulfate, filtered, and the solvent removed. The solid was triturated with acetonitrile to yield pure product with a 68% yield. MH+=170.0.

Step 3. Synthesis of 2-(2-Chloro-benzylamino)-benzooxazol-6-ol

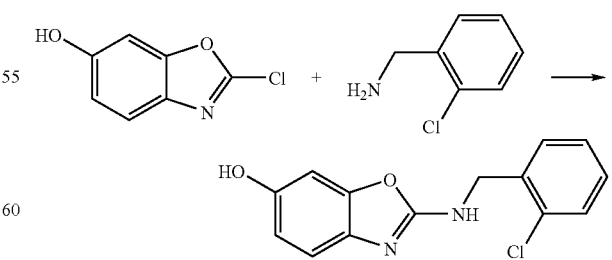

2-Chloro-benzooxazol-6-ol (1 eq) and 2-chloro-benzylamine (2 eq) was dissolved in NMP. Using a Personal Chemistry microwave system, the mixture was reacted at 180° C. for six minutes. The crude reaction mixture was diluted with ethyl acetate and washed once with brine and once with 1N HCl, or washed twice with brine, depending on the amine used. The organic layer was dried with anhydrous sodium sulfate, filtered and concentrated. This material was purified by silica gel column using hexane and ethyl acetate. MH+=275.1.

Step 4. Synthesis of 4-[2-(2-Chloro-benzylamino)-benzoxazol-6-yloxy]-pyridine-2-carboxylic acid methylamide

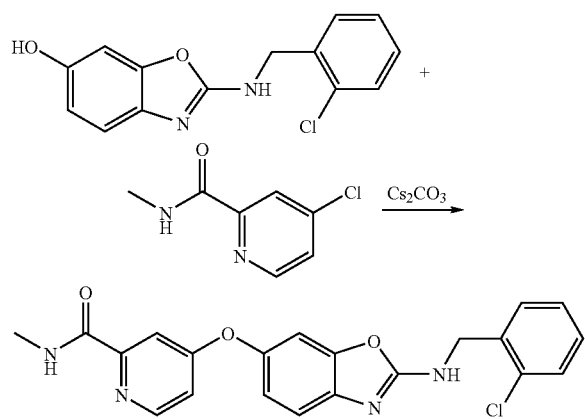

To a solution of 2-(2-chloro-benzylamino)-benzooxazol-6-ol (1 eq) in DMSO was added the 4-chloro-pyridine-2-carboxylic acid methylamide (1 eq). This was allowed to stir for 15 minutes at room temperature at which point cesium carbonate (1.2 eq) was added. The solution was heated in a Personal Chemistry microwave reactor at 150° C. for a total of 30 minutes. The crude reaction mixture was diluted with ethyl acetate, washed three times with brine, dried over anhydrous sodium sulfate, filtered and concentrated. The crude product was then purified by reverse phase preparatory HPLC to give the pure product 8. MH+=409.1.

Compounds 9, 11, 12, 18, 19, 20, 26, 27, 28, and 40 in Table 2, below, were synthesized following similar procedures in Example 1.

Example 2

4-[2-((1S,2R)-2-Hydroxy-indan-1-ylamino)-benzoxazol-6-yloxy]-pyridine-2-carboxylic acid methylamide (Table 2, Compound 50)

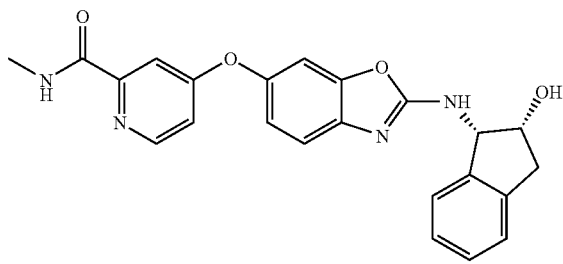

Step 1. Synthesis of 2-(methylthio)benzo[d]oxazol-6-ol

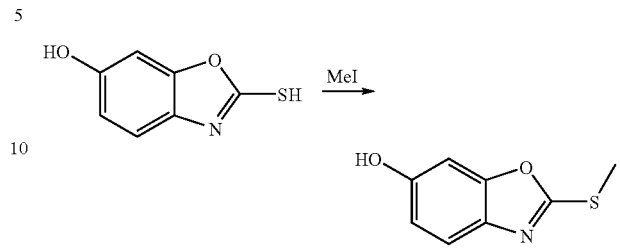

To a solution of the 2-mercaptobenzo[d]oxazol-6-ol (1.55 g, 9.28 mmol, 1.0 eq) in 20 mL of methylene chloride was added triethylamine (1.87 g, 18.56 mmol, 2.0 eq) and methyl iodide (1.77 g, 13.92 mmol, 1.5 eq) at room temperature. The reaction mixture was stirred at rt for 3 hours. The mixture was diluted with 100 mL of methylene chloride. The resulting mixture was washed with water (10 mL), brine (10 mL), then dried over MgSO4, filtered, and evaporated under reduced pressure to give crude product, which was purified by silica gel column eluted with ethyl acetate and hexane to give the titled compound. MH+=182.

Step 2. Synthesis of 4-(2-(methylthio)benzo[d]oxazol-6-yloxy)-N-methylpyridine-2-carboxamide

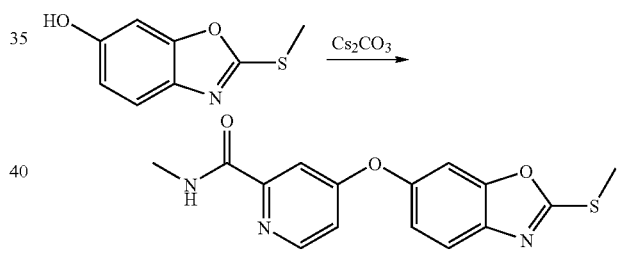

To a solution of 2-(methylthio)benzo[d]oxazol-6-ol (8.5 g, 46.7 mmol, 1 eq) in 80 mL of N,N-dimethylformamide was added 4-chloro-N-methylpyridine-2-carboxamide (16.0 g, 93.4 mmol, 2.0 eq) and cesium carbonate (45.7 g, 140.1 mmol, 3.0 eq). The reaction mixture was stirred at 75° C. for 6 hours. After the mixture was cooled to room temperature, the mixture was added 120 mL of water. After filtration, the solid was purified by silica gel column eluted with ethyl acetate and hexane to give the titled compound. MH+=316.

Step 3. Synthesis of 4-(2-(methylsulfinyl)benzo[d]oxazol-6-yloxy)-N-methylpyridine-2-carboxamide

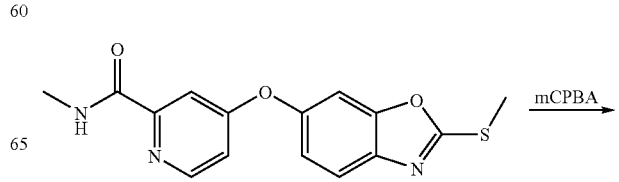

-continued

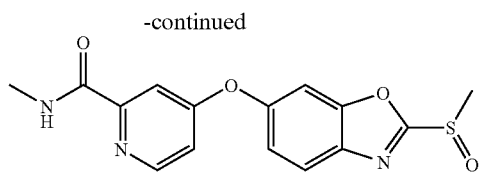

To a solution of the 4-(2-(methylthio)benzo[d]oxazol-6-yloxy)-N-methylpyridine-2-carboxamide (1.26 g, 4.0 mmol, 1.0 eq) in 40 mL of methylene chloride was added 3-chloroperoxybenzoic acid (70%, 989 mg, 4.4 mmol, 1.1 eq). The reaction mixture was stirred at room temperature for 5 hours and then was diluted with 200 mL of methylene chloride. The resulting mixture was washed with aqueous sodium bicarbonate and brine then dried over MgSO$_4$, filtered, and evaporated under reduced pressure to give crude product, which was used to next step without further purification. MH+=332.

Step 4. 4-[2-((1S,2R)-2-Hydroxy-indan-1-ylamino)-benzooxazol-6-yloxy]-pyridine-2-carboxylic acid methylamide

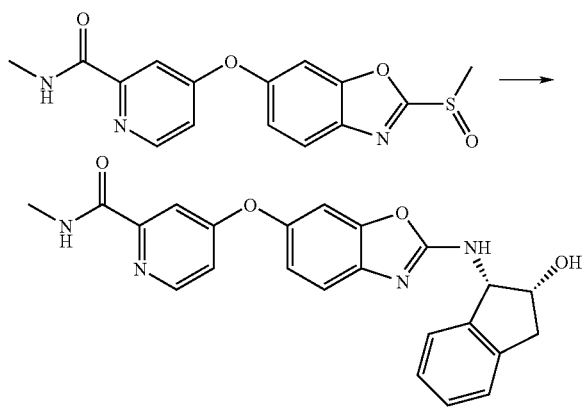

A solution of 4-(2-(methylsulfinyl)benzo[d]oxazol-6-yloxy)-N-methylpyridine-2-carboxamide (17 mg, 0.05 mmol, 1.0 eq) and (1S,2R)-1-amino-2,3-dihydro-1H-inden-2-ol (30 mg, 0.2 mml, 4.0 eq) in 1 mL of N,N-dimethylacetamide was heated in the microwave at 90° C. for 600 seconds. The crude product was purified by reverse phase prep HPLC to give the title compound. MH==417.0.

Compounds 45, 46, and 47, in Table 2, below, were synthesized following the similar procedures as in Example 2 varying the temperature to 140° C. Compounds 42, 57, 59, and 94 in Table 2, below, were synthesized following the similar procedures as in Example 2 varying the temperature to 120° C.

Example 3

Synthesis of 1-{[6-(2-Methylcarbamoyl-pyridin-4-yloxy)-benzooxazol-2-ylamino]methyl}-cyclohexanecarboxylic acid ethyl ester (Table 2, Compound 75)

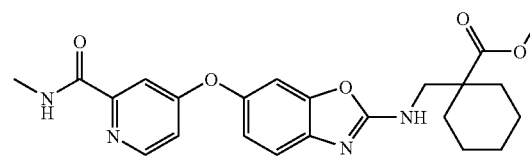

Step 1. Synthesis of 1-Cyano-cyclohexanecarboxylic acid ethyl ester

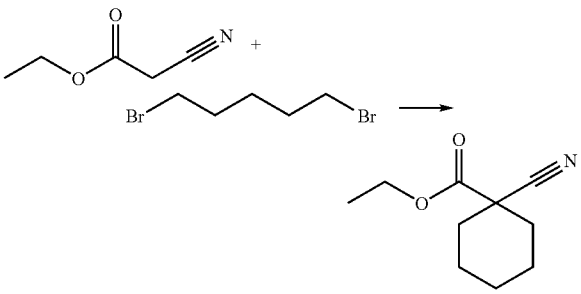

To a solution of cyanoacetate (1 eq) in DMF at 0° C. was slowly added cesium carbonate (2.5 eq), followed by the slow addition of 1,5-dibromopentane. This mixture was allowed to stir for 30 minutes at 0° C. and at room temperature for two hours. The crude reaction mixture was diluted with ethyl acetate and washed three times with water, dried with anhydrous sodium sulfate, filtered, and concentrated. The compound was clean enough to continue without purification. 57% yield. $^1$H NMR (300 MHz, CDCl$_3$) δ 4.25 (q, 2H), 2.12-1.68 (m, 10H), 1.31 (t, 3H).

Step 2. Synthesis of 1-Aminomethyl-cyclohexanecarboxylic acid ethyl ester

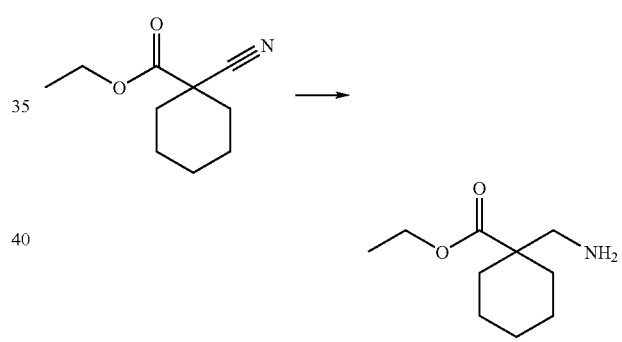

Excess Raney Nickel in an ethanol slurry was added to a solution of 1-cyano-cyclohexanecarboxylic acid ethyl ester in ethanol under a nitrogen atmosphere. The nitrogen atmosphere was replaced with excess hydrogen gas and the mixture was allowed to stir overnight. The reaction mixture was filtered through celite and the solvent was removed. The compound was clean enough to continue without purification. 80% yield. MH+=186.2.

Step 3. Synthesis of 1-{[6-(2-Methylcarbamoyl-pyridin-4-yloxy)-benzooxazol-2-ylamino]methyl}-cyclohexanecarboxylic acid ethyl ester

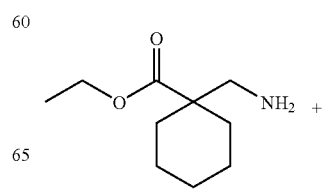

-continued

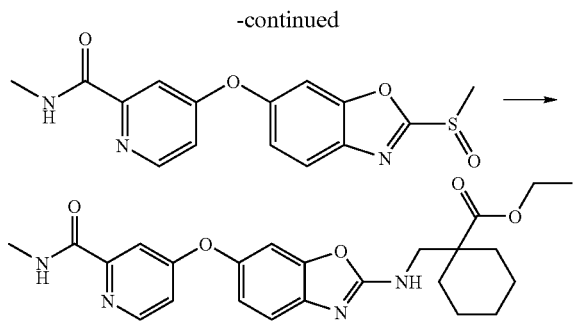

To a solution of 1-aminomethyl-cyclohexanecarboxylic acid ethyl ester in THF was added 4-(2-methanesulfinyl-benzooxazol-6-yloxy)-pyridine-2-carboxylic acid methylamide from Step 3 of Example 2. After reacting at room temperature for 2 hours the solvent was removed and the crude product was diluted with ethyl acetate and some dichloromethane, then washed three times with brine, dried with anhydrous sodium sulfate, filtered and concentrated. The final product was purified by reverse phase preparatory HPLC. MH+=453.1.

Example 4

Synthesis of 1-{[6-(2-Methylcarbamoyl-pyridin-4-yloxy)-benzooxazol-2-ylamino]-methyl}-cyclohexanecarboxylic acid (Table 2, Compound 93)

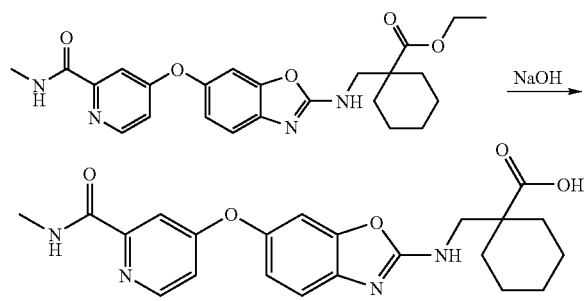

1-{[6-(2-Methylcarbamoyl-pyridin-4-yloxy)-benzooxazol-2-ylamino]methyl}-cyclohexanecarboxylic acid ethyl ester (1 eq) was dissolved in 3 M sodium hydroxide (20 eq); THF and methanol were added to homogenize the solution. The mixture was allowed to react at room temperature overnight. The solvents were removed. The crude product was brought to a pH of 4 with 1 N HCl, then to pH of 7 with saturated aqueous sodium bicarbonate. This solution was saturated with solid sodium chloride then extracted three times with ethyl acetate. The combined organic extracts were washed once with brine, dried with anhydrous sodium sulfate, filtered and concentrated. The product was purified by silica gel column in isopropanol and dichloromethane (50%) MH+=425.1.

Example 5

Synthesis Of 4-{2-[(1-Methylcarbamoyl-cyclohexylmethyl)-amino]-benzooxazol-6-yloxy}-pyridine-2-carboxylic acid methylamide (Table 2, Compound 112)

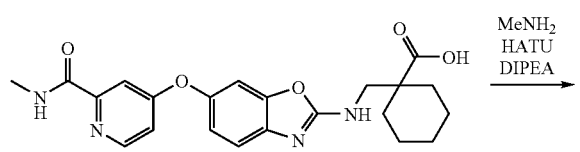

-continued

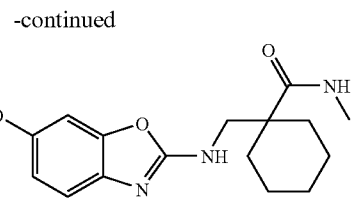

To a solution of 1-{[6-(2-methylcarbamoyl-pyridin-4-yloxy)-benzooxazol-2-ylamino]-methyl}-cyclohexanecarboxylic acid (1 eq) in DMF was added DIPEA (3 eq) and [dimethylamino-([1,2,3]triazolo[4,5-b]pyridin-3-yloxy)-methylene]-dimethyl-ammonium hexafluoro phosphate (1 eq). This was stirred at room temperature for 2 hours, then a 2 M solution of methylamine in THF (5 eq) was added and allowed to react overnight at 70° C. The mixture was diluted with ethyl acetate and washed twice with a saturated aqueous solution of ammonium chloride and once with brine, then dried with anhydrous sodium sulfate, filtered and concentrated, then purified by preparatory reverse phase HPLC. MH+=438.1.

Example 6

Synthesis of 4-{2-[3-(2-Piperidin-1-yl-ethyl)-phenylamino]-benzooxazol-6-yloxy}-pyridine-2-carboxylic acid methylamide (Table 2, Compound 44)

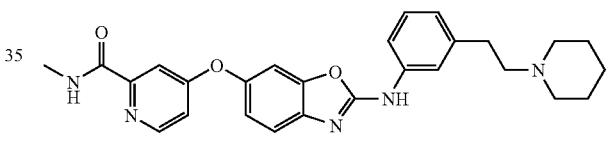

Step 1. Synthesis of Methanesulfonic acid 2-(3-nitro-phenyl)-ethyl ester

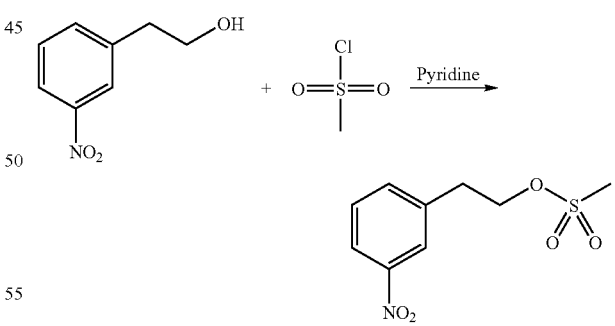

To a solution of 2-(3-nitro-phenyl)-ethanol (1 eq) in dichloromethane at 0° C. was added pyridine (4 eq) and methanesulfonyl chloride (2 eq). After stirring at 0° C. for one hour, then room temperature overnight, the mixture was diluted with dichloromethane and washed once with water, once with 1 N HCl, dried with anhydrous sodium sulfate, filtered and concentrated. The product was clean enough to be taken on to the next step without purification. MH+=246.0.

Step 2. Synthesis of 1-[2-(3-Nitro-phenyl)-ethyl]-piperidine

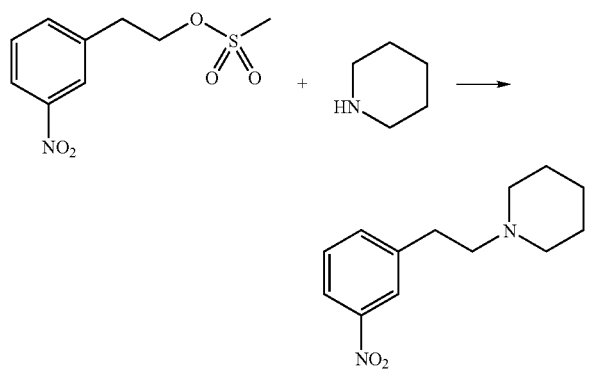

Methanesulfonic acid 2-(3-nitro-phenyl)-ethyl ester was dissolved in piperidine (20 eq) and THF and stirred at 60° C. for one hour. The solvent was removed. The crude product was diluted with ethyl acetate, washed three times with water, dried with anhydrous sodium sulfate, filtered and concentrated. The product was clean enough to carry forward without purification. 44% yield. MH+=235.1.

Step 3. Synthesis of 3-(2-Piperidin-1-yl-ethyl)-phenylamine

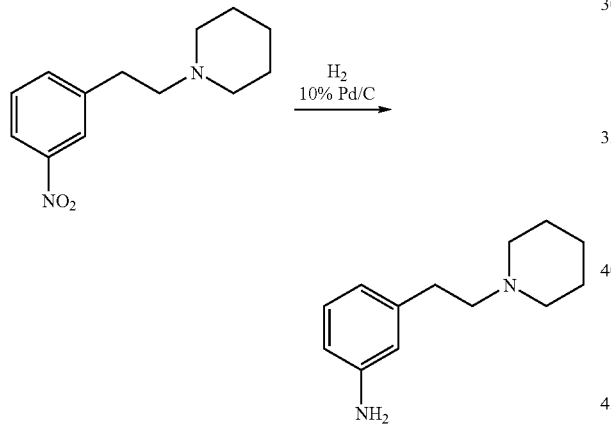

To a solution of 1-[2-(3-Nitro-phenyl)-ethyl]-piperidine in ethanol was added a catalytic amount 10% activated palladium on carbon and excess hydrogen gas. This mixture was allowed to stir overnight, then filtered and concentrated. The product was clean enough for the next reaction. 60% yield. MH+=205.1.

Step 4. Synthesis of 4-{2-[3-(2-Piperidin-1-yl-ethyl)-phenylamino]-benzooxazol-6-yloxy}-pyridine-2-carboxylic acid methylamide

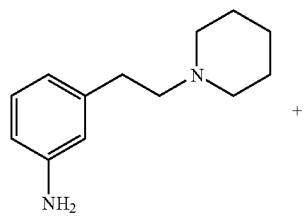

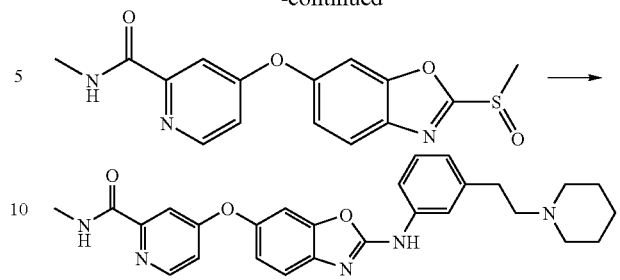

The 4-(2-methanesulfinyl-benzooxazol-6-yloxy)-pyridine-2-carboxylic acid methylamide from step 3 of Example 2 and 3-(2-piperidin-1-yl-ethyl)-phenylamine were dissolved in DMAC and heated in a CEM microwave reactor at 120° C. for 10 to 20 minutes. The crude reaction mixture was purified by preparatory reverse phase HPLC. MH+=472.2.

Example 7

4-{2-[3-(2-Morpholin-4-yl-ethyl)-phenylamino]-benzooxazol-6-yloxy}-pyridine-2-carboxylic acid methylamide (Table 2, Compound 74)

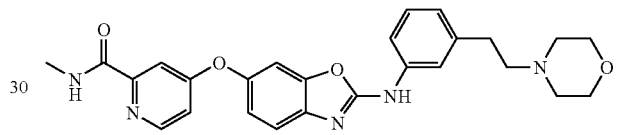

The compound Table 2, Entry 74 was synthesized following the similar procedure as in Example 6. MH+=474.2.

Example 8

Synthesis of 4-{2-[(2,3-Dihydro-benzo[1,4]dioxine-5-carbonyl)-amino]-benzooxazol-6-yloxy}-pyridine-2-carboxylic acid methylamide (Table 2, Compound 110)

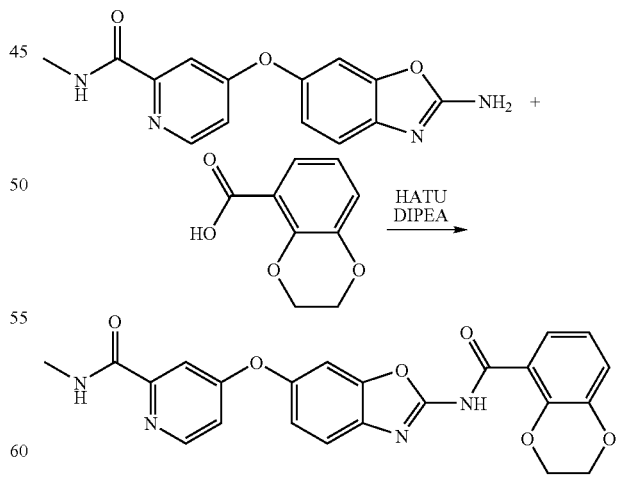

4-(2-Amino-benzooxazol-6-yloxy)-pyridine-2-carboxylic acid methylamide (1 eq) and 2,3-dihydro-1,4-benzodioxane-5-carboxylic acid (1 eq) were dissolved in DMF. To this solution were added DIPEA (3 eq) and [dimethylamino-([1,2,3]triazolo[4,5-b]pyridin-3-yloxy)-methylene]-dimethylammonium hexafluoro phosphate (1 eq). The mixture was stirred at 40° C. overnight, then diluted with ethyl acetate and washed once each with 1N HCl, saturated aqueous sodium bicarbonate, and brine, and finally dried with anhydrous sodium sulfate, filtered, and concentrated. This was purified by preparatory reverse phase HPLC. MH+=447.0.

Example 9

Synthesis of Cyclohexylmethyl-[6-(2-[1,3,4]oxadiazol-2-yl-pyridin-4-yloxy)-benzooxazol-2-yl]-amine (Table 2, Compound 81)

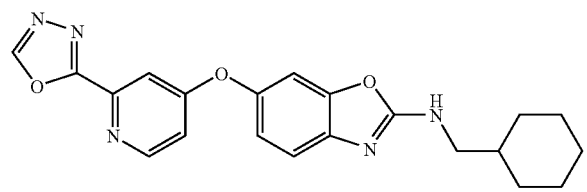

Step 1. Synthesis of 4-(2-(cyclohexylmethylamino) benzo[d]oxazol-6-yloxy)-N-methylpyridine-2-carboxamide

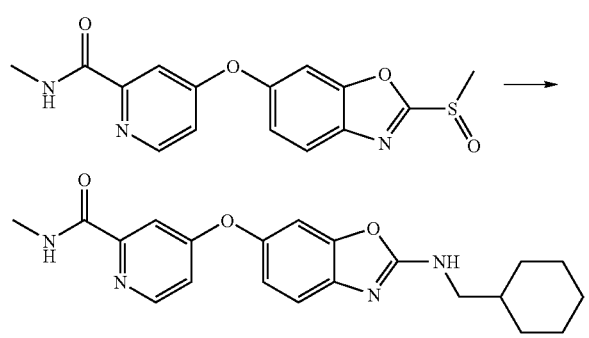

To a solution of 4-(2-(methylsulfinyl)benzo[d]oxazol-6-yloxy)-N-methylpyridine-2-carboxamide (1.40 g, 4.23 mmol, 1.0 eq) in 15 mL of THF was added cyclohexylmethanamine (955 mg, 8.46 mmol, 2.0 eq) at room temperature. The reaction mixture was stirred at that temperature for 2 hours. After the solvent was removed under reduced pressure, the residue was dissolved in 150 mL of ethyl acetate. The resulting mixture was washed with water (20 mL), brine (20 mL), then dried over MgSO$_4$, filtered, and evaporated under reduced pressure to give crude product, which was purified by silica gel column eluted with ethyl acetate and hexane to give the titled compound. MH$^+$=381.

Step 2. Synthesis of 4-[2-(Cyclohexylmethyl-amino)-benzooxazol-6-yloxy]-pyridine-2-carboxylic acid

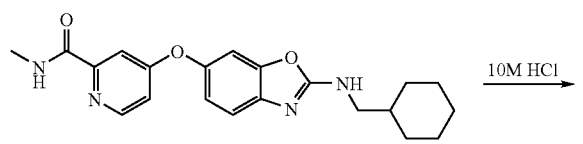

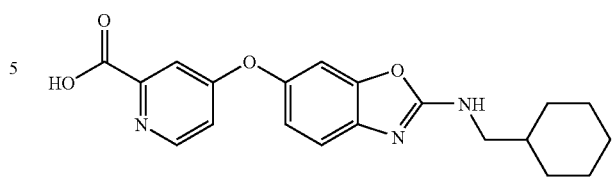

A solution of 4-(2-(cyclohexylmethylamino)benzo[d]oxazol-6-yloxy)-N-methylpyridine-2-carboxamide (300 mg, 0.79 mmol, 1.0 eq) in 10 mL of 10M aqueous hydrochloric acid solution was stirred at 100° C. for 24 hours. The reaction mixture was cooled to room temperature. Most of water was removed under reduced pressure. And then aqueous sodium bicarbonate was added to the mixture until pH>7.0. After filtration, the solid was washed with water and dried to give the titled compound. MH+=368.0.

Step 3. Synthesis of 4-(2-(cyclohexylmethylamino) benzo[d]oxazol-6-yloxy)pyridine-2-carbohydrazide

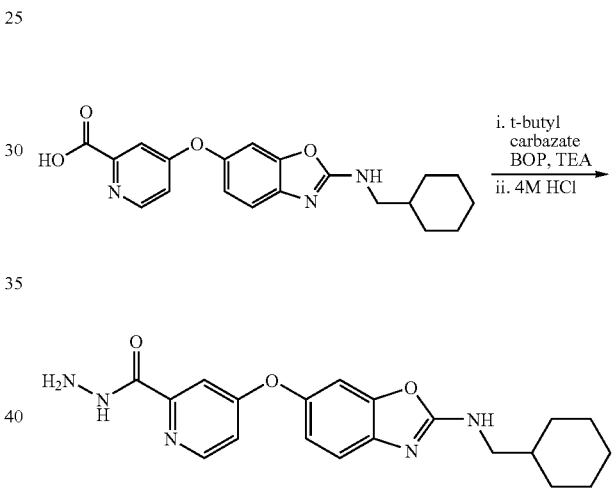

To a solution of the 4-[2-(Cyclohexylmethyl-amino)-benzooxazol-6-yloxy]-pyridine-2-carboxylic acid (110 mg, 0.30 mmol, 1.0 eq) in 2 mL of N,N-dimethylformamide was added benzotriazol-1-yloxytris(dimethylamino)-phosphonium hexafluorophosphate (199 mg, 0.45 mmol, 1.5 eq), tert-butyl carbazate (47 mg, 0.36 mmol, 1.2 eq) and triethyl amine (60 mg, 0.60 mmol, 2.0 eq) at room temperature. The reaction mixture was stirred at that temperature for 2 hours. Then the mixture was added 20 mL of water. After filtration, the solid was purified again by silica gel column eluted with ethyl acetate and hexane to give the Boc protected titled compound.

The Boc protected titled compound (54 mg, 0.112 mmol, 1.0 eq) was dissolved in 1 mL of methanol. And then the mixture was added 3 mL of 4M hydrogen chloride in dioxane. The reaction mixture was stirred at room temperature overnight. The solvents were removed to give the titled compound, which was used to next step without further purification. MH+=382.0.

Step 4. Synthesis of cyclohexylmethyl-[6-(2-[1,3,4] oxadiazol-2-yl-pyridin-4-yloxy)-benzo-oxazol-2-yl]-amine

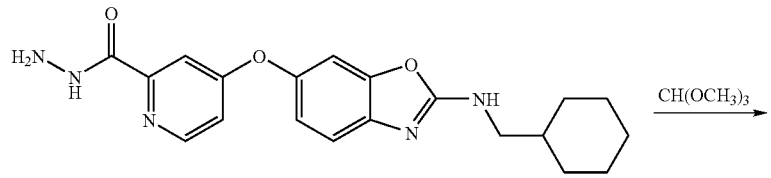

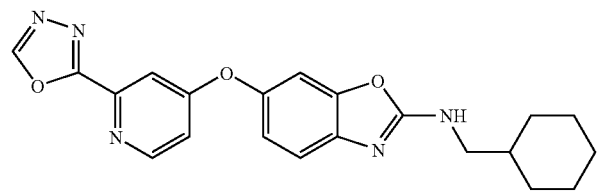

A solution of 4-(2-(cyclohexylmethylamino)benzo[d]oxazol-6-yloxy)pyridine-2-carbohydrazide (8 mg, 0.019 mmol, 1.0 eq) and 0.1 mL of 4 M hydrogen chloride in 1 mL trimethyl orthoformate was heated in the microwave at 120° C. for 1200 seconds. The crude product was purified by reverse phase prep HPLC to give the title compound. MH$^+$=392.0

Compound 81 was also isolated from the reaction. MH+=367.0.

Example 10

Synthesis of 4-[2-(Cyclohexylmethyl-amino)-benzooxazol-6-yloxy]-pyridine-2-carbonitrile (Table 2, Compound 82)

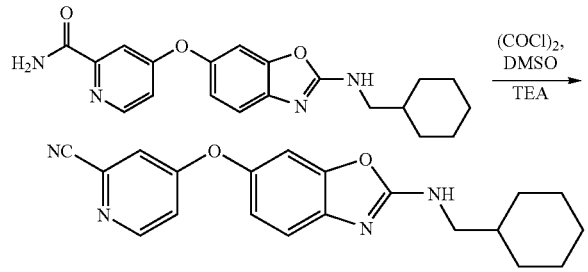

To a solution of the methylsulfoxide (32 mg, 0.41 mmol, 6.0 eq) in 1 mL of methylene chloride was added oxalyl chloride (2M, 0.135 mL, 0.27 mmol, 4.0 eq) at −78° C. After 15 minutes, the 4-(2-(cyclohexylmethylamino)benzo[d]oxazol-6-yloxy)pyridine-2-carboxamide (25 mg, 0.068 mmol, 1.0 eq) in 2 mL of methylene chloride was added to the reaction mixture. After being stirred at that temperature for 20 minutes, triethyl amine (83 mg, 0.83 mmol, 12 eq) was added to mixture. The reaction mixture was stirred at −78° C. for 2 hours, and then was quenched with aqueous ammonium chloride solution. The resulting mixture was extracted with ethyl acetate (2×20 mL). The combined organic layers were washed with water (5 mL), brine (5 mL), then dried over MgSO$_4$, filtered, and evaporated under reduced pressure to give crude product, which was purified by reverse phase prep HPLC to give the title compound. MH+=349.0.

Example 11

Synthesis of {4-[2-(Cyclohexylmethyl-amino)-benzooxazol-6-yloxy]-pyridin-2-yl}-methanol (Table 2, Compound 80)

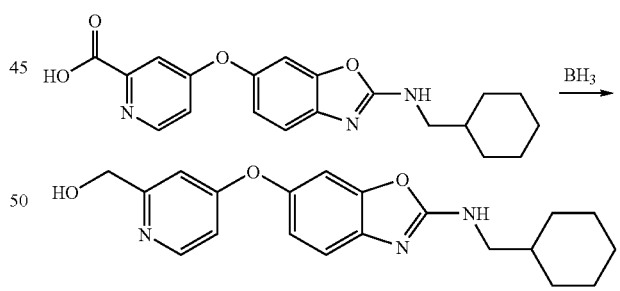

To a solution of the 4-(2-(cyclohexylmethylamino)benzo[d]oxazol-6-yloxy)pyridine-2-carboxylic acid (120 mg, 0.33 mmol, 1.0 eq) in 5 mL of THF was added borane-tetrahydrofuran complex (1M, 1 mL, 1 mmol) at 0° C. The reaction mixture was stirred at that temperature for 5 hours. The reaction was quenched with 1M hydrochloric acid. The resulting mixture was extracted with ethyl acetate (2×60 mL). The combined organic layers were washed with water (10 mL), brine (10 mL), then dried over MgSO$_4$, filtered, and evaporated under reduced pressure to give crude product, which was purified by silica gel column eluted with ethyl acetate and hexane to give the titled compound. MH+=354.0.

Example 12

Synthesis of Cyclohexylmethyl-{6-[2-(5-methyl-1H-imidazol-2-yl)-pyridin-4-yloxy]-benzooxazol-2-yl}-amine (Table 2, Compound 109)

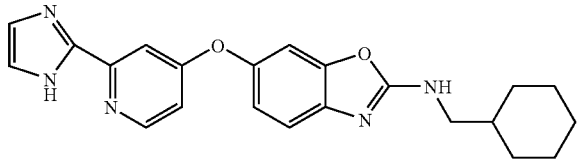

Step 1. Synthesis of 4-(2-(cyclohexylmethylamino)benzo[d]oxazol-6-yloxy)pyridine-2-carbaldehyde

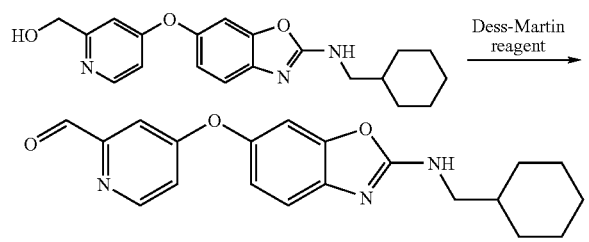

To a solution of the 4-(2-(cyclohexylmethylamino)benzo[d]oxazol-6-yloxy)pyridin-2-yl)methanol (20 mg, 0.057 mmol, 1.0 eq) in 2 mL of methylene chloride and 2 mL of THF was added Dess-Martin reagent (26 mg, 0.062 mmol, 1.1 eq) at room temperature. The reaction mixture was stirred at that temperature for 4 hours. Then the mixture was diluted with 50 mL of ethyl acetate. The resulting mixture was washed with aq sodium bicarbonate (5 mL), water (5 mL), brine (5 mL), then dried over MgSO$_4$, filtered, and evaporated under reduced pressure to give crude product, which was purified by preparative TLC sheet to give the titled compound. MH+=352.0.

Step 2. Synthesis of Cyclohexylmethyl-{6-[2-(5-methyl-1H-imidazol-2-yl)-pyridin-4-yloxy]-benzooxazol-2-yl}-amine

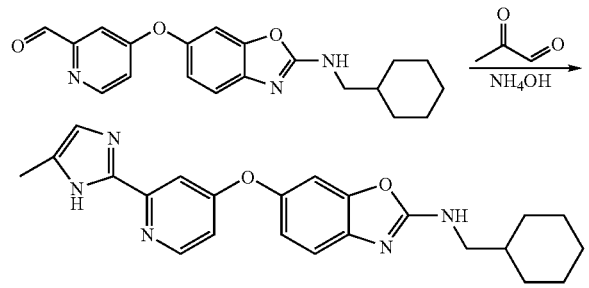

To a solution of the 4-(2-(cyclohexylmethylamino)benzo[d]oxazol-6-yloxy)pyridine-2-carbaldehyde (5 mg, 0.014 mmol, 1.0 eq) in 0.6 mL of methanol was added pyruvic aldehyde (40%, 0.1 mL) and 0.15 mL ammonium hydroxide at room temperature. The reaction mixture was stirred at that temperature for 2 hours. The crude product was purified by reverse phase prep HPLC to give the title compound. MH+=404.0.

Example 13

Synthesis of [6-(2-Aminomethyl-pyridin-4-yloxy)-benzooxazol-2-yl]-cyclohexylmethyl-amine (Table 2, Compound 111)

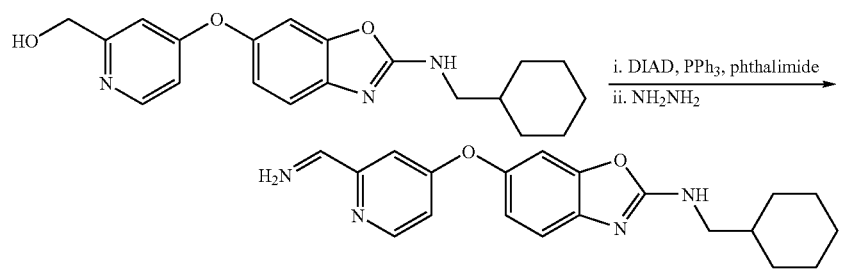

To a solution of the (4-(2-(cyclohexylmethylamino)benzo[d]oxazol-6-yloxy)pyridin-2-yl)methanol (20 mg, 0.057 mmol, 1.0 eq) in 2 mL of THF was added triphenyl phosphine (22 mg, 0.085 mmol, 1.5 eq), phthalimide (12.5 mg, 0.085 mmol, 1.5 eq) and diisopropyl azodicarboxylate (17 mg, 0.085 mmol, 1.5 eq) at room temperature. The reaction mixture was stirred at that temperature for 16 hours. Then the solvent was removed. The crude product was purified by preparative TLC sheet to give 2-((4-(2-(cyclohexylmethylamino)benzo[d]oxazol-6-yloxy)pyridin-2-yl)methyl)isoindoline-1,3-dione.

The 2-((4-(2-(cyclohexylmethylamino)benzo[d]oxazol-6-yloxy)pyridin-2-yl)methyl)-isoindoline-1,3-dione (6.2 mg, 0.013 mmol, 1 eq) was dissolved in 0.5 mL of ethanol. And then hydrazine monohydrate (6.4 mg, 0.13 mmol, 10 eq) was added to the reaction mixture. The mixture was stirred at room temperature for 3 hours. And then the solvents were removed. The crude product was purified by reverse phase prep HPLC to give the title compound. MH+=353.0.

Example 14

Synthesis of 4-{2-[1-(2,3-Dihydro-benzo[1,4]dioxin-5-yl)-ethylamino]-benzooxazol-6-yloxy}-pyridine-2-carboxylic acid methylamide (Table 2, Compound 125)

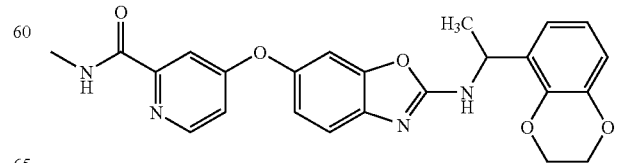

Step 1. Synthesis of C-(2,3-Dihydro-benzo[1,4]dioxin-5-yl)-methyleneamine

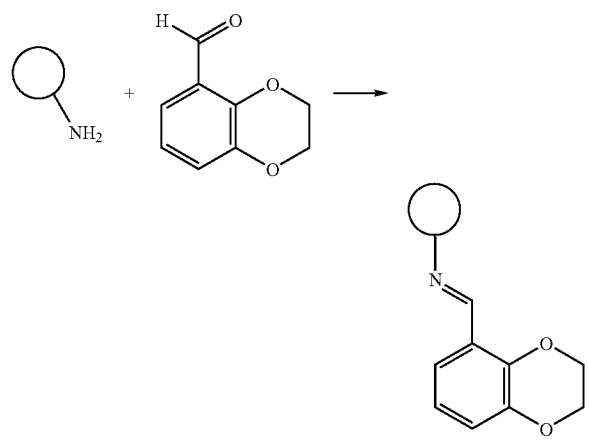

To a suspension of amine bound on a rink resin (1 eq) in trimethylorthoformate was added 2,3-dihydro-benzo[1,4]dioxine-5-carbaldehyde (2 eq). This mixture was shaken overnight, filtered and the solid dried.

Step 2. Synthesis of 1-(2,3-Dihydro-benzo[1,4]dioxin-5-yl)-ethylamine

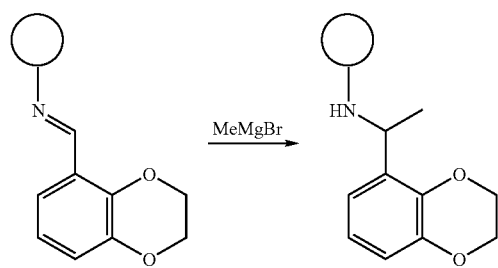

The dried resin to which the C-(2,3-dihydro-benzo[1,4]dioxin-5-yl)-methyleneamine (1 eq) was bound was suspended in dry toluene. Under a nitrogen atmosphere methyl magnesium bromide (150 eq) in a 3 M solution in ethyl ether was added. This mixture was shaken for 24 hours at 60° C. then filtered and washed with toluene, water, then methanol and dichloromethane alternately three times. The final wash was with methanol. The solid was dried under vacuum.

Step 3. Cleavage of 1-(2,3-Dihydro-benzo[1,4]dioxin-5-yl)-ethylamine from resin

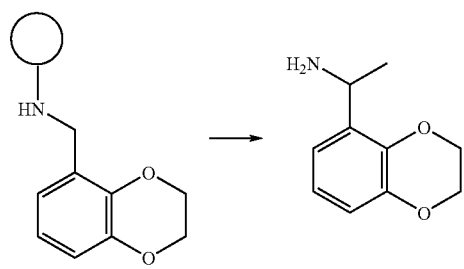

To the resin bound 1-(2,3-dihydro-benzo[1,4]dioxin-5-yl)-ethylamine suspended in dichloromethane was added trifluoroacetic acid (20% by volume). The mixture was shaken overnight then the mixture was made basic by the addition of 3 M sodium hydroxide. The solution was filtered to remove the resin, then diluted with dichloromethane and water. The water layer was extracted three times with dichloromethane. The combined organic extracts were washed once with brine, dried with anhydrous sodium sulfate, filtered and concentrated. The material recovered was clean enough to carry forward with no purification. MH+=180.1.

Step 4. Synthesis of 4-{2-[1-(2,3-Dihydro-benzo[1,4]dioxin-5-yl)-ethylamino]-benzooxazol-6-yloxy}-pyridine-2-carboxylic acid methylamide

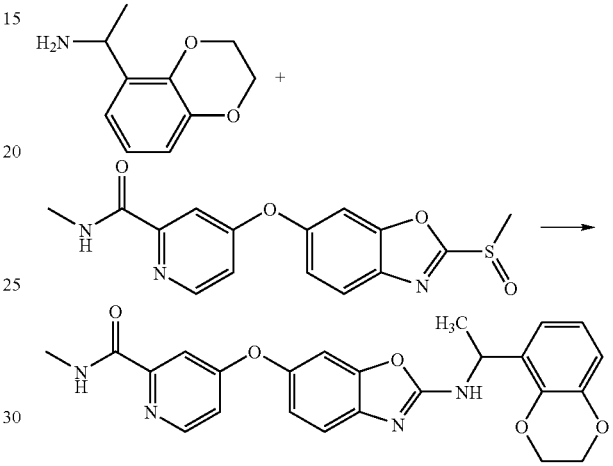

To a solution of 1-(2,3-dihydro-benzo[1,4]dioxin-5-yl)-ethylamine (3 eq) in THF was added 4-(2-methanesulfinyl-benzooxazol-6-yloxy)-pyridine-2-carboxylic acid methylamide (1 eq). This was stirred at room temperature for 8 hours, concentrated and the residue was purified by preparatory reverse phase HPLC. MH+=447.1.

Compounds 41, 42, 57, 59, 65, 90, 94, 113, and 122 in Table 2, below, were synthesized following the similar procedures as in Example 14.

Example 15

Scheme 8

Preparation of 4-[2-(Cyclohexylmethyl-amino)-benzothiazol-6-yloxy]-pyridine-2-carboxylic acid methylamide (Table 2, Compound 128)

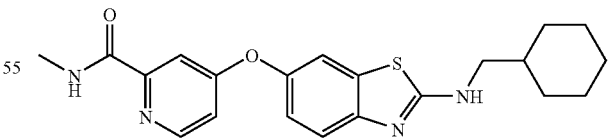

Step 1. Preparation of 2-Mercapto-benzothiazol-6-ol

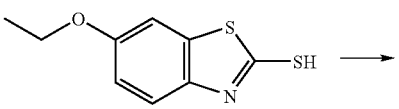

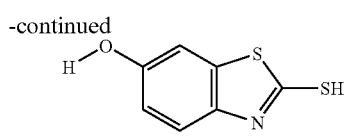

As per the U.S. Pat. No. 4,873,346, hereby incorporated by reference in its entirety—Substituted Benzothiazoles, Benzimidazoles and benzoxazoles; Anderson, David J.; The Upjohn Company, Kalamazoo, Mich.; Oct. 10, 1989. M+H=184.0

Step 2. Preparation of 2-Methylsulfanyl-benzothiazol-6-ol

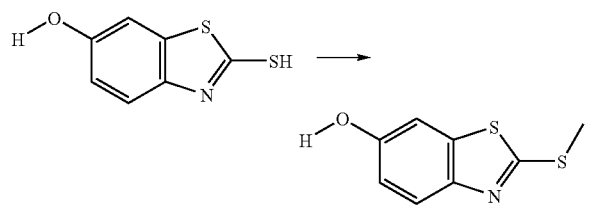

To the ice cooled solution of 2-mercapto-benzothiazol-6-ol from step 1 (3.80 g, 20.76 mmol, 1.0 eq) in DCM (40 mL, 0.5M) at 0° C., was added triethylamine (7.29 mL, 51.91 mmol, 2.5 eq) followed by iodomethane (1.93 mL, 31.14 mmol, 1.5 eq). The reaction was stirred from 0° C. to −10° C. for 3 hours. The solvent was removed in vacuo. Water (ca. 200 mL) was added and the aqueous layer was extracted with ethyl acetate (3×150 mL). The organic layer was dried over sodium sulfate, filtered, and evaporated in vacuo to yield 2-methylsulfanyl-benzothiazol-6-ol as light green powder (3.76 g, 92%). The crude product was used in the next step without purification. M+H=198.0

Step 3. Preparation of 4-(2-Methylsulfanyl-benzothiazol-6-yloxy)-pyridine-2-carboxylic acid methylamide

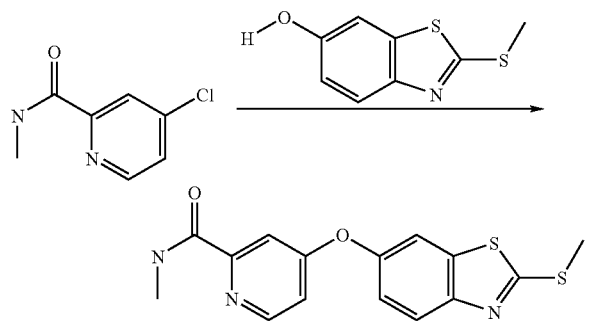

To the solution of 2-methylsulfanyl-benzothiazol-6-ol (3.76 g, 19.08 mmol, 1.0 eq) in DMF (25 mL), was added CsCO₃ (15.54 g, 47.70 mmol, 2.5 eq) at room temperature. After stirring for a while, 4-chloro-pyridine-2-carboxylic acid methylamide (4.86 g, 28.62 mmol, 1.5 eq) was added to the mixture and the mixture was stirred at 70° C. under reflux condenser overnight. After cooling the reaction mixture in ice bath, water (100 mL) was added and the aqueous layer was extracted with ethyl acetate (3×150 mL). The organic layer was dried over sodium sulfate, filtered, and evaporated in vacuo. The crude product was purified using 20 g of ISCO Silica Gel column (0%-50%-80%-100% ethyl acetate-hexane mixture over 45 min 40 mL/min run) to yield 4-(2-methylsulfanyl-benzothiazol-6-yloxy)-pyridine-2-carboxylic acid methylamide (3.88 g, 62%) as a white solid. M+H=332.1

Step 4. Preparation of 4-(2-Methanesulfinyl-benzothiazol-6-yloxy)-pyridine-2-carboxylic acid methylamide

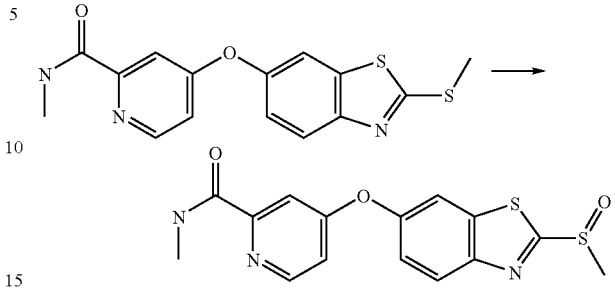

To the solution of 4-(2-methylsulfanyl-benzothiazol-6-yloxy)-pyridine-2-carboxylic acid methylamide from step 3 (3.88 g, 11.72 mmol, 1.0 eq) in DCM (20 mL) at 0° C., was added MCPBA (77%, 2.88 g, 1. eq). The mixture was stirred at this temperature for one hour. Saturated sodium bicarbonate solution (100 mL) was added. The aqueous layer was extracted with DCM (3×150 mL). The organic layer was dried over sodium sulfate, filtered, and evaporated in vacuo to yield 4-(2-methanesulfinyl-benzothiazol-6-yloxy)-pyridine-2-carboxylic acid methylamide as white powder in quantitative yields. The crude product was used in the next step without purification. M+H=348.0.

Step 5. Preparation of 4-[2-(Cyclohexylmethyl-amino)-benzothiazol-6-yloxy]-pyridine-2-carboxylic acid methylamide

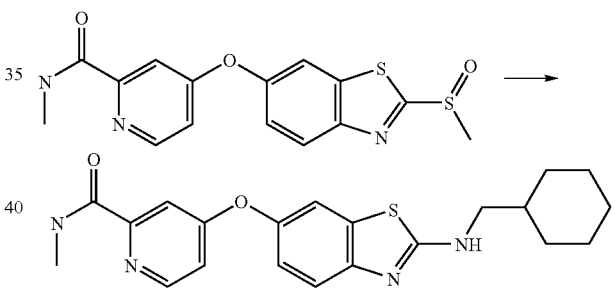

To the solution of 4-(2-methanesulfinyl-benzothiazol-6-yloxy)-pyridine-2-carboxylic acid methylamide (25 mg, 0.072 mmol, 1.0 eq) in DMF (500 μL), was added cyclohexylmethylamine (18.7 μL, 0.144 mmol, 2.0 eq) and reaction was stirred at 70° C. overnight. The neat reaction mixture was purified on reverse phase preparatory HPLC. Pure fractions were lyophilized as TFA salts. M+H=397.1

Example 16

Preparation of 4-(2-((1S,2S)-2-hydroxycyclohexylamino)benzo[d]thiazol-6-yloxy)-N-methylpicolinamide (Table 2, Compound 137)

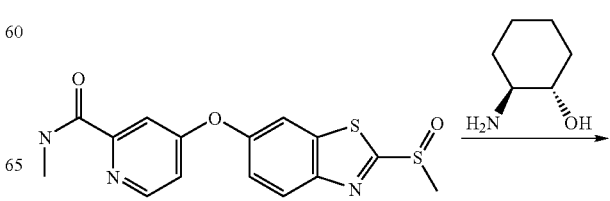

-continued

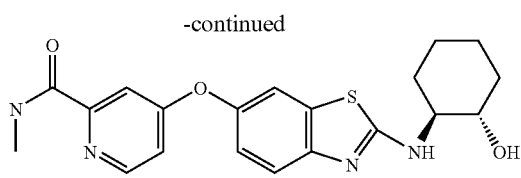

To the solution of 4-(2-methanesulfinyl-benzothiazol-6-yloxy)-pyridine-2-carboxylic acid methylamide (70 mg, 0.202 mmol, 1.0 eq) in DMA (600 µL), was added (1S,2S)-2-aminocyclohexanol hydrochloride (92 mg, 0.606 mmol, 3.0 eq) followed by diisopropylethylamine (0.21 mL, 1.21 mmol). The reaction was heated at 110° C. for 24-hours. The neat reaction mixture was purified on reverse phase preparatory HPLC. Pure fractions were lyophilized as TFA salts. M+H=398

Example 17

The compounds in the following Table 2 were made by the general procedures described above.

TABLE 2

| Compound | Structure | M + H; Rt (min) | Compound Name |
|---|---|---|---|
| 1 | 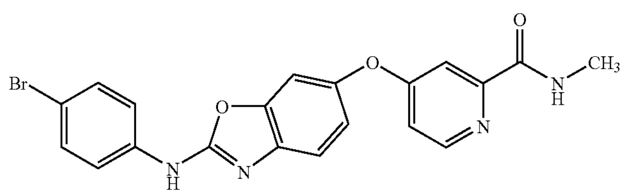 | 440.2; 5.1 | 4-[2-(4-Bromo-phenylamino)-benzooxazol-6-yloxy]-pyridine-2-carboxylic acid methylamide |
| 2 | 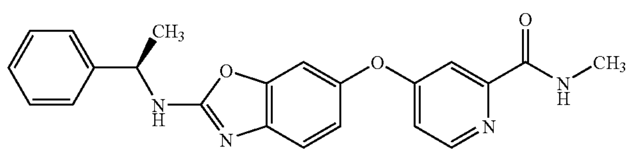 | 389.2 | 4-[2-((R)-1-Phenyl-ethylamino)-benzooxazol-6-yloxy]-pyridine-2-carboxylic acid methylamide |
| 3 | 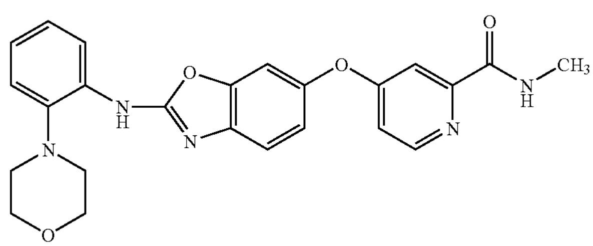 | 446.1; 2.74 | 4-[2-(2-Morpholin-4-yl-phenylamino)-benzooxazol-6-yloxy]-pyridine-2-carboxylic acid methylamide |
| 4 | 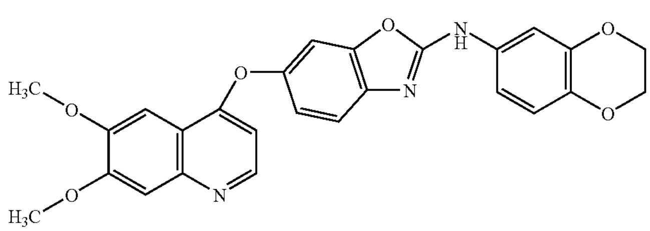 | 472.1; 2.46 | (2,3-Dihydro-benzo[1,4]dioxin-6-yl)-[6-(6,7-dimethoxy-quinolin-4-yloxy)-benzooxazol-2-yl]-amine |
| 5 | 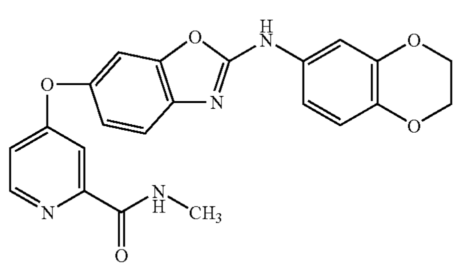 | 419.1; 2.53 | 4-[2-(2,3-Dihydro-benzo-[1,4]dioxin-6-ylamino)-benzooxazol-6-yloxy]-pyridine-2-carboxylic acid methylamide |

TABLE 2-continued

| Compound | Structure | M + H; Rt (min) | Compound Name |
|---|---|---|---|
| 6 | 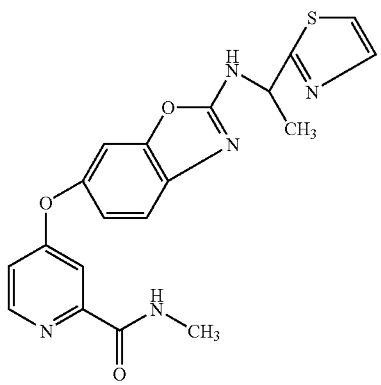 | 396.1; 2.07 | 4-[2-(1-Thiazol-2-yl-ethylamino)-benzooxazol-6-yloxy]-pyridine-2-carboxylic acid methylamide |
| 7 | 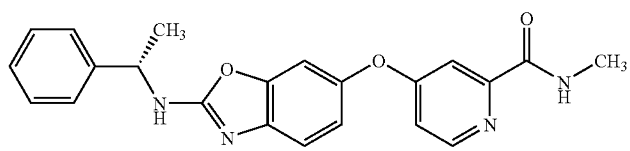 | 389.2; 2.48 | 4-[2-((S)-1-Phenyl-ethylamino)-benzooxazol-6-yloxy]-pyridine-2-carboxylic acid methylamide |
| 8 | 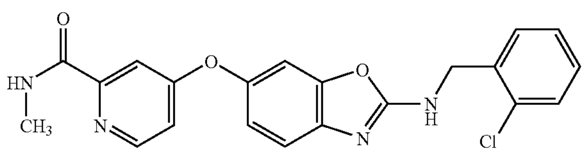 | 409.1; 2.62 | 4-[2-(2-Chloro-benzylamino)-benzooxazol-6-yloxy]-pyridine-2-carboxylic acid methylamide |
| 9 | 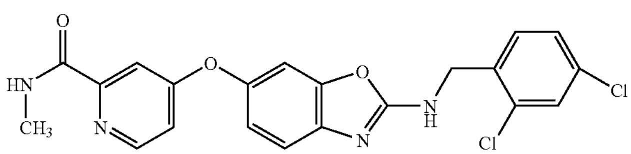 | 443.0; 2.92 | 4-[2-(2,4-Dichloro-benzylamino)-benzooxazol-6-yloxy]-pyridine-2-carboxylic acid methylamide |
| 10 | 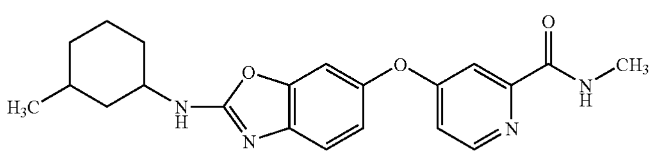 | 381.1; 2.53 | 4-[2-(3-Methyl-cyclohexyl-amino)-benzooxazol-6-yloxy]-pyridine-2-carboxylic amide methylamide |
| 11 | 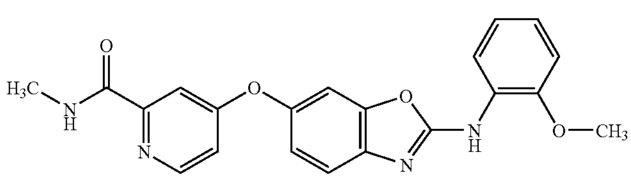 | 391.1; 2.77 | 4-[2-(2-Methoxy-phenylamino)-benzooxazol-6-yloxy]-pyridine-2-carboxylic acid methylamide |
| 12 | 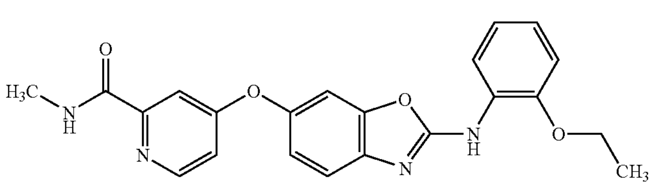 | 405.2; 2.98 | 4-[2-(2-Ethoxy-phenylamino)-benzooxazol-6-yloxy]-pyridine-2-carboxylic acid methylamide |

TABLE 2-continued

| Compound | Structure | M + H; Rt (min) | Compound Name |
|---|---|---|---|
| 13 | 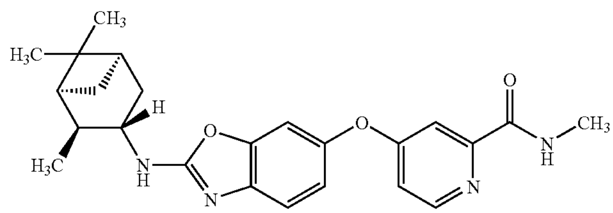 | 421.2; 2.98 | 4-[2-((1S,2S,3S,5R)-2,6,6-Trimethyl-bicyclo[3.1.1]hept-3-ylamino)-benzooxazol-6-yloxy]-pyridine-2-carboxylic acid methylamide |
| 14 | 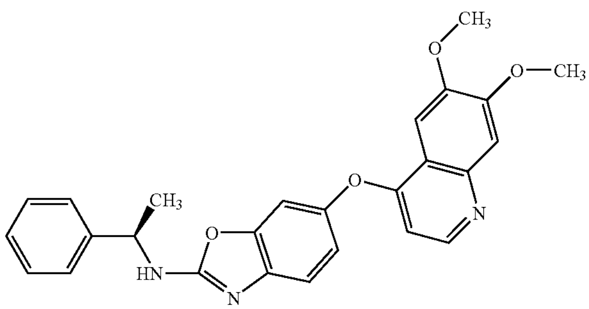 | 442.2; 2.50 | [6-(6,7-Dimethoxy-quinolin-4-yloxy)-benzooxazol-2-yl]-((R)-1-phenyl-ethyl)-amine |
| 15 | 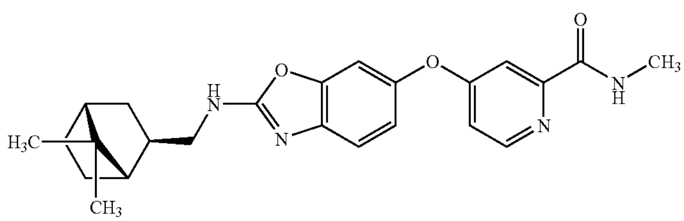 | 421.3; 2.96 | 4-{2-[((1S,2R,4R)-7,7-Dimethyl-bicyclo[2.2.1]hept-2-ylmethyl)-amino]-benzooxazol-6-yloxy}-pyridine-2-carboxylic acid methylamide |
| 16 | 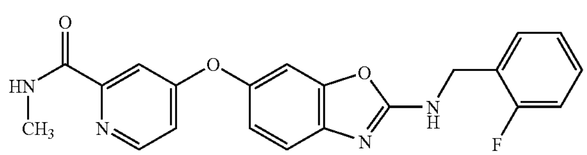 | 393.0; 2.46 | 4-[2-(2-Fluoro-benzylamino)-benzooxazol-6-yloxy]-pyridine-2-carboxylic acid methylamide |
| 17 | 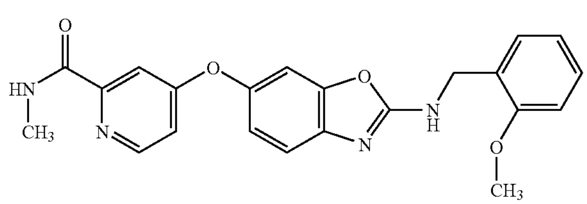 | 405.1; 2.44 | 4-[2-(2-Methoxy-benzylamino)-benzooxazol-6-yloxy]-pyridine-2-carboxylic acid methylamide |
| 18 | 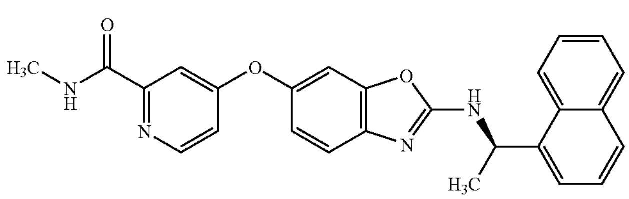 | 439.1; 2.83 | 4-[2-((R)-1-Naphthalen-1-yl-ethylamino)-benzooxazol-6-yloxy]-pyridine-2-carboxylic acid methylamide |
| 19 | 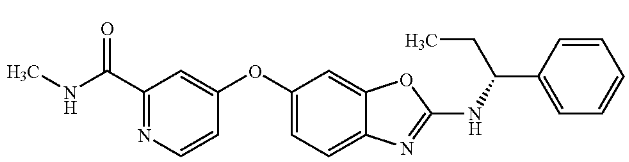 | 403.1; 2.62 | 4-[2-((R)-1-Phenyl-propyl-amino)-benzooxazol-6-yloxy]-pyridine-2-carboxylic acid methylamide |

TABLE 2-continued

| Compound | Structure | M + H; Rt (min) | Compound Name |
|---|---|---|---|
| 20 | 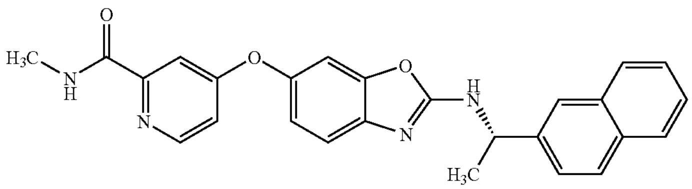 | 439.2; 2.83 | 4-[2-((S)-1-Naphthalen-2-yl-ethylamino)-benzooxazol-6-yloxy]-pyridine-2-carboxylic acid methylamide |
| 21 | 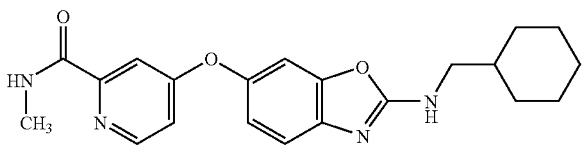 | 381.1; 2.55 | 4-[2-(Cyclohexylmethyl-amino)-benzooxazol-6-yloxy]-pyridine-2-carboxylic acid methylamide |
| 22 | 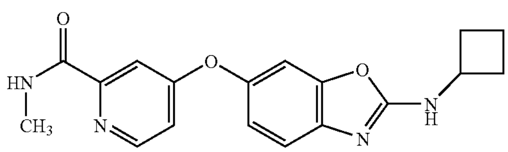 | 339.0; 2.09 | 4-(2-Cyclobutylamino-benzooxazol-6-yloxy)-pyridine-2-carboxylic acid methylamide |
| 23 | 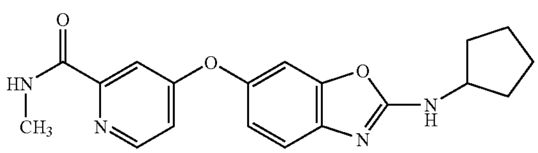 | 353.1; 2.18 | 4-(2-Cyclopentylamino-benzooxazol-6-yloxy)-pyridine-2-carboxylic acid methylamide |
| 24 | 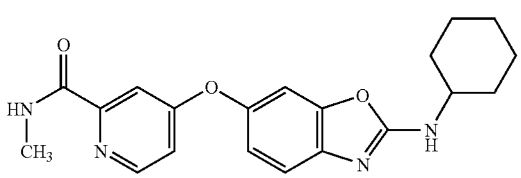 | 367.1; 2.33 | 4-(2-Cyclohexylamino-benzooxazol-6-yloxy)-pyridine-2-carboxylic acid methylamide |
| 25 | 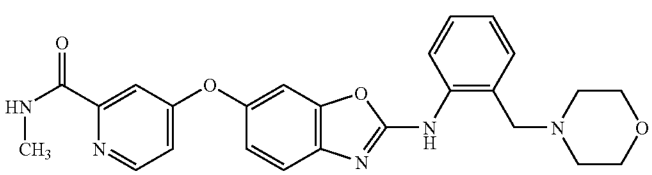 | 460.1; 2.02 | 4-[2-(2-Morpholin-4-ylmethyl-phenylamino)-benzooxazol-6-yloxy]-pyridine-2-carboxylic acid methylamide |
| 26 | 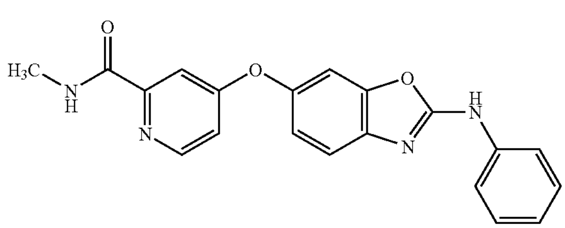 | 361.0; 2.61 | 4-(2-Phenylamino-benzooxazol-6-yloxy)-pyridine-2-carboxylic acid methylamide |
| 27 | 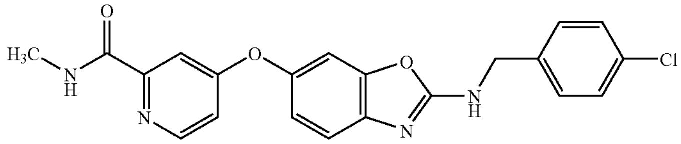 | 409.0; 2.61 | 4-[2-(4-Chloro-benzylamino)-benzooxazol-6-yloxy]-pyridine-2-carboxylic acid methylamide |

TABLE 2-continued

| Compound | Structure | M + H; Rt (min) | Compound Name |
|---|---|---|---|
| 28 | 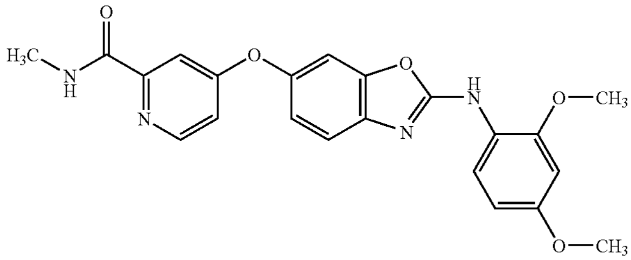 | 421.0; 2.57 | 4-[2-(2,4-Dimethoxy-phenyl-amino)-benzooxazol-6-yl-oxy]-pyridine-2-carboxylic acid methylamide |
| 29 | 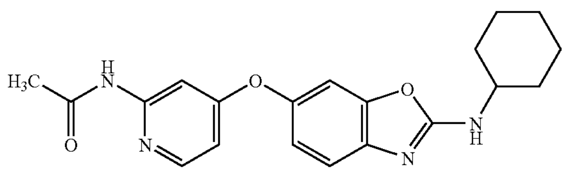 | 367.0; 2.11 | N-[4-(2-Cyclohexylamino-benzooxazol-6-yloxy)-pyridin-2-yl]-acetamide |
| 30 | 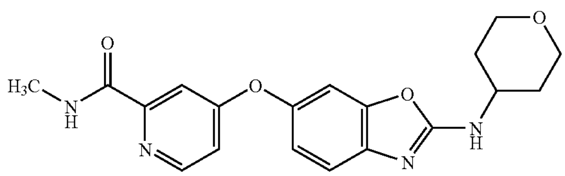 | 369.1; 1.90 | 4-[2-(Tetrahydro-pyran-4-yl-amino)-benzooxazol-6-yloxy]-pyridine-2-carboxylic acid methylamide |
| 31 | 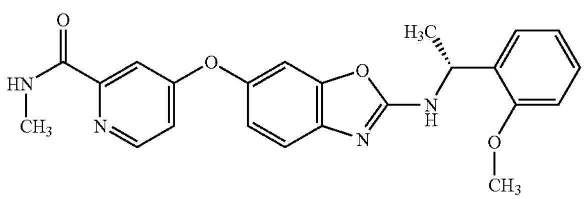 | 419.0; 2.55 | 4-{2-[(R)-1-(2-Methoxy-phenyl)-ethylamino]-benzooxazol-6-yloxy}-pyridine-2-carboxylic acid methylamide |
| 32 | 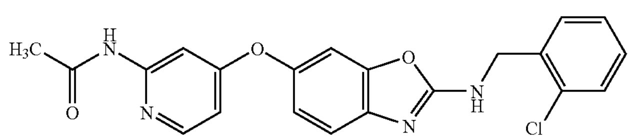 | 409.0; 2.31 | N-{4-[2-(2-Chloro-benzylamino)-benzooxazol-6-yloxy]-pyridin-2-yl}-acetamide |
| 33 | 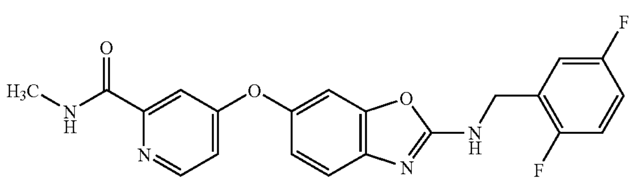 | 411.0; 2.53 | 4-[2-(2,5-Difluoro-benzylamino)-benzooxazol-6-yloxy]-pyridine-2-carboxylic acid methylamide |
| 34 | 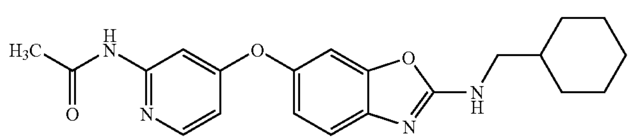 | 381.1; 2.33 | N-{4-[2-(Cyclohexylmethyl-amino)-benzooxazol-6-yloxy]-pyridin-2-yl}-acetamide |
| 35 | 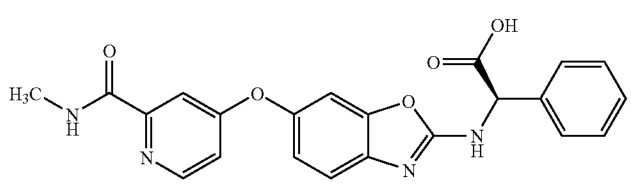 | 419.1; 2.26 | (R)-[6-(2-Methylcarbamoyl-pyridin-4-yloxy)-benzooxazol-2-ylamino]-phenyl-acetic acid |

TABLE 2-continued

| Compound | Structure | M + H; Rt (min) | Compound Name |
|---|---|---|---|
| 36 | 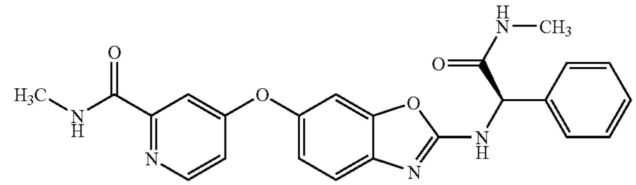 | 432.1; 2.16 | 4-{2-[((R)-Methylcarbamoyl-phenyl-methyl)-amino]-benzo-oxazol-6-yloxy}-pyridine-2-carboxylic acid methylamide |
| 37 | 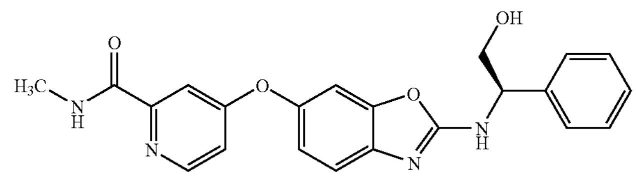 | 405.1; 2.07 | 4-[2-((R)-2-Hydroxy-1-phenyl-ethylamino)-benzooxazol-6-yloxy]-pyridine-2-carboxylic acid methylamide |
| 38 | 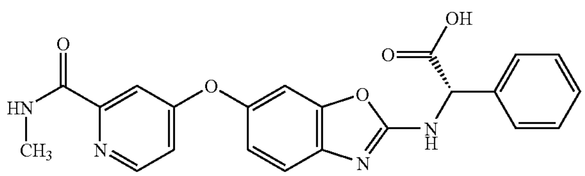 | 419.1; 2.26 | (S)-[6-(2-Methylcarbamoyl-pyridin-4-yloxy)-benzooxazol-2-ylamino]-phenyl-acetic acid |
| 39 | 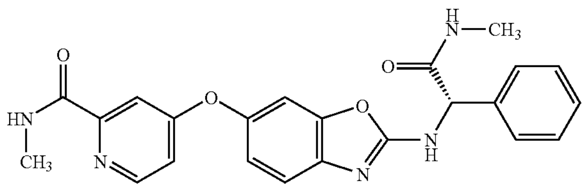 | 432.1; 2.16 | 4-{2-[((S)-Methylcarbamoyl-phenyl-methyl)-amino]-benzooxazol-6-yloxy}-pyridine-2-carboxylic acid methylamide |
| 40 | 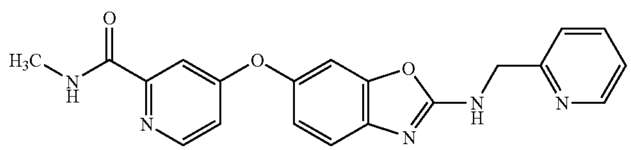 | 376.1; 1.76 | 4-{2-[(Pyridin-2-ylmethyl)-amino]-benzooxazol-6-yloxy}-pyridine-2-carboxylic acid methylamide |
| 41 | 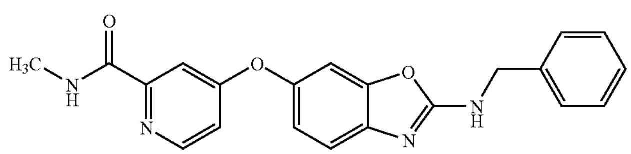 | 375.1; 2.38 | 4-(2-Benzylamino-benzooxazol-6-yloxy)-pyridine-2-carboxylic acid methylamide |
| 42 | 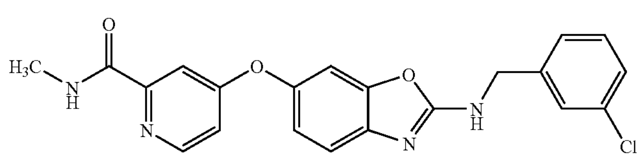 | 409.0; 2.62 | 4-[2-(3-Chloro-benzylamino)-benzooxazol-6-yloxy]-pyridine-2-carboxylic acid methylamide |
| 43 | 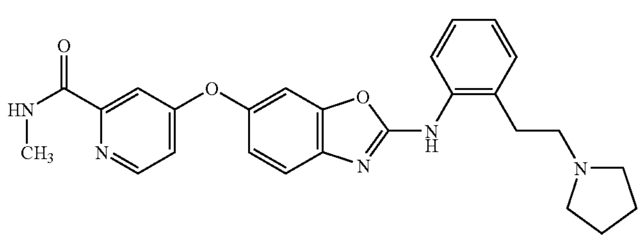 | 458.2; 2.13 | 4-{2-[2-(2-Pyrrolidin-1-yl-ethyl)-phenylamino]-benzooxazol-6-yloxy}-pyridine-2-carboxylic acid methylamide |

TABLE 2-continued

| Compound | Structure | M + H; Rt (min) | Compound Name |
|---|---|---|---|
| 44 | 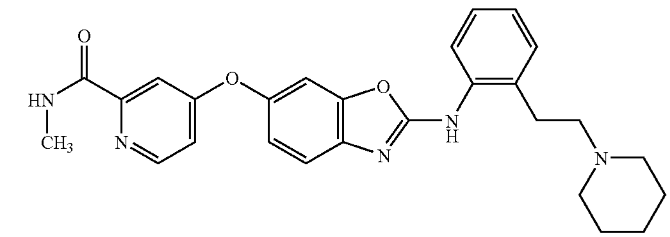 | 472.2; 2.16 | 4-{2-[2-(2-Piperidin-1-yl-ethyl)-phenylamino]-benzooxazol-6-yloxy}-pyridine-2-carboxylic acid methylamide |
| 45 | 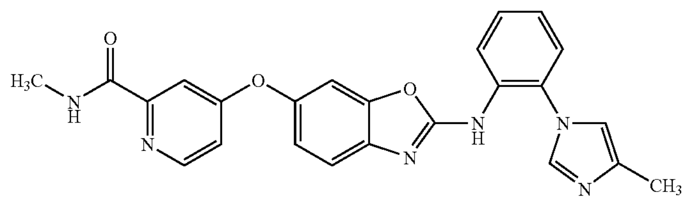 | 441.0; 2.11 | 4-{2-[2-(4-Methyl-imidazol-1-yl)-phenylamino]-benzooxazol-6-yloxy}-pyridine-2-carboxylic acid methylamide |
| 46 | 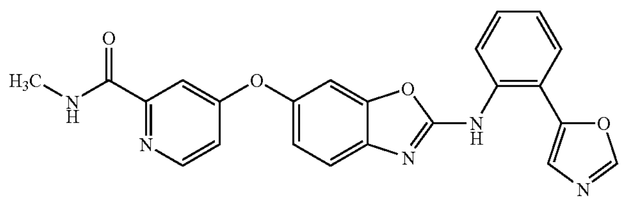 | 428.1; 2.42 | 4-[2-(2-Oxazol-5-yl-phenylamino)-benzooxazol-6-yloxy]-pyridine-2-carboxylic acid methylamide |
| 47 | 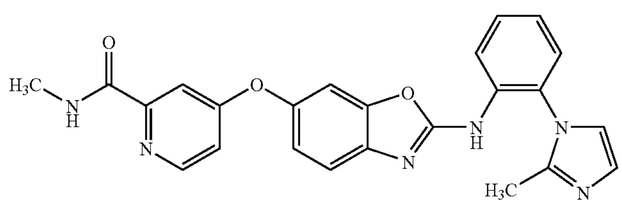 | 441.2; 2.29 | 4-{2-[2-(2-Methyl-imidazol-1-yl)-phenylamino]-benzooxazol-6-yloxy}-pyridine-2-carboxylic acid methylamide |
| 48 | 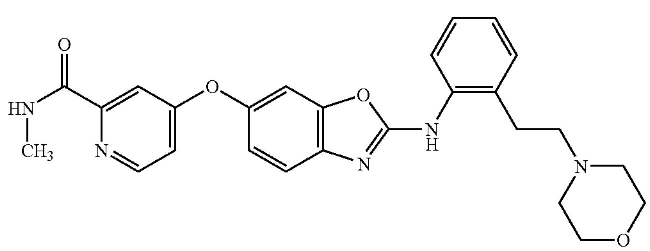 | 474.1; 2.09 | 4-{2-[2-(2-Morpholin-4-yl-ethyl)-phenylamino]-benzo-oxazol-6-yloxy}-pyridine-2-carboxylic acid methylamide |
| 49 | 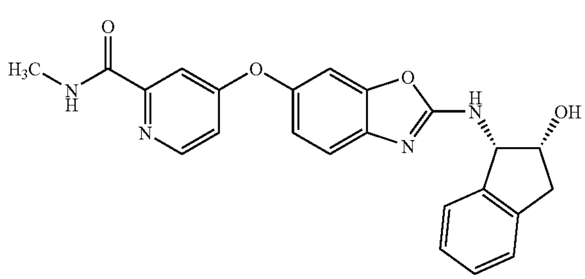 | 417.0; 2.05 | 4-[2-((1S,2R)-2-Hydroxy-indan-1-ylamino)-benzooxazol-6-yloxy]-pyridine-2-carboxylic acid methylamide |

TABLE 2-continued

| Compound | Structure | M + H; Rt (min) | Compound Name |
|---|---|---|---|
| 50 | 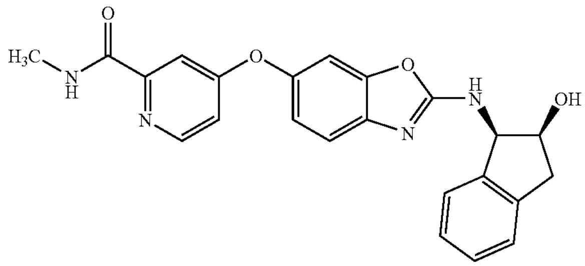 | 417.0; 2.05 | 4-[2-((1R,2S)-2-Hydroxy-indan-1-ylamino)-benzooxazol-6-yloxy]-pyridine-2-carboxylic acid methylamide |
| 51 | 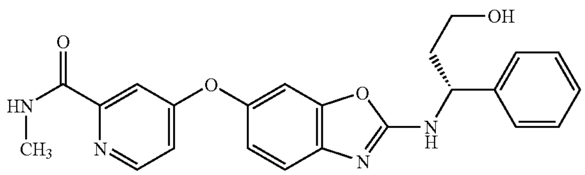 | 419.0; 2.18 | 4-[2-((R)-3-Hydroxy-1-phenyl-propylamino)-benzooxazol-6-yloxy]-pyridine-2-carboxylic acid methylamide |
| 52 | 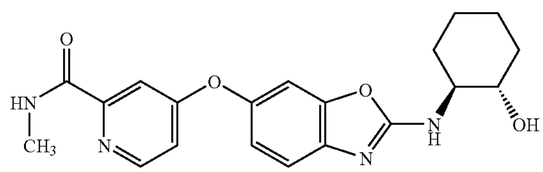 | 383.0; 1.94 | 4-[2-((1S,2S)-2-Hydroxy-cyclohexylamino)-benzooxazol-6-yloxy]-pyridine-2-carboxylic acid methylamide |
| 53 | 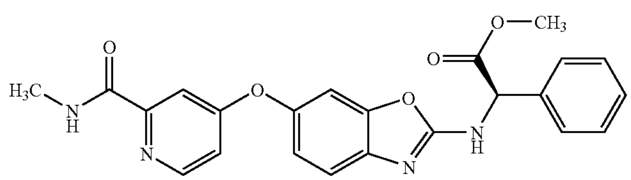 | 433.0; 2.51 | (R)-[6-(2-Methylcarbamoyl-pyridin-4-yloxy)-benzooxazol-2-ylamino]-phenyl-acetic acid methyl ester |
| 54 | 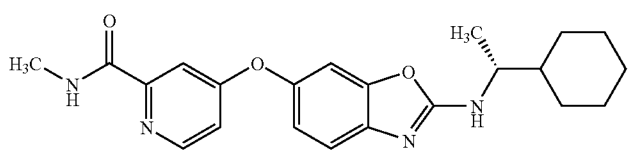 | 395.1; 2.68 | 4-[2-((R)-1-Cyclohexyl-ethylamino)-benzooxazol-6-yloxy]-pyridine-2-carboxylic acid methylamide |
| 55 | 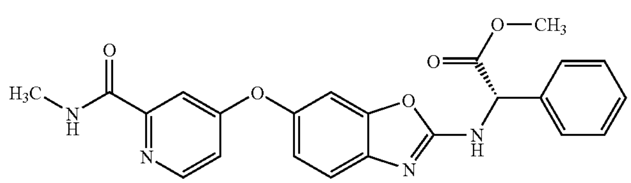 | 433.0; 2.53 | (S)-[6-(2-Methylcarbamoyl-pyridin-4-yloxy)-benzooxazol-2-ylamino]-phenyl-acetic acid methyl ester |
| 56 | 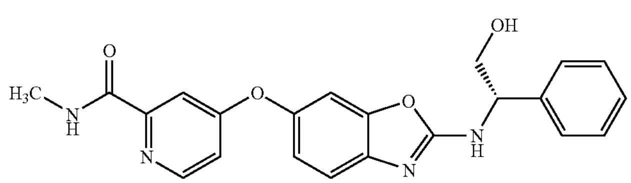 | 405.0; 2.01 | 4-[2-((S)-2-Hydroxy-1-phenyl-ethylamino)-benzooxazol-6-yloxy]-pyridine-2-carboxylic acid methylamide |
| 57 | 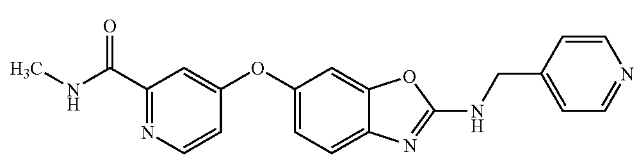 | 376.1; 1.72 | 4-{2-[(Pyridin-4-ylmethyl)-amino]-benzooxazol-6-yloxy}-pyridine-2-carboxylic acid methylamide |

TABLE 2-continued

| Compound | Structure | M + H; Rt (min) | Compound Name |
|---|---|---|---|
| 58 | 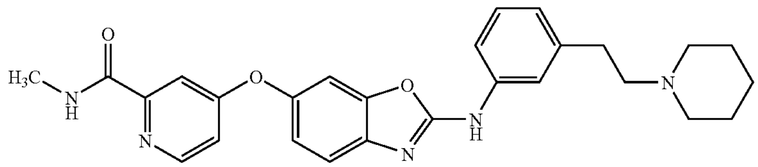 | 472.1; 2.16 | 4-{2-[3-(2-Piperidin-1-yl-ethyl)-phenylamino]-benzooxazol-6-yloxy}-pyridine-2-carboxylic acid methylamide |
| 59 | 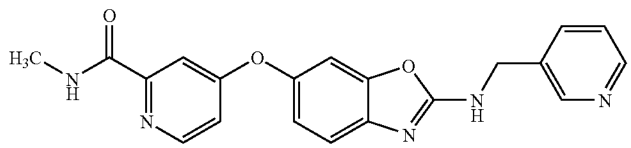 | 376.1; 1.76 | 4-{2-[(Pyridin-3-ylmethyl)-amino]-benzooxazol-6-yloxy}-pyridine-2-carboxylic acid methylamide |
| 60 | 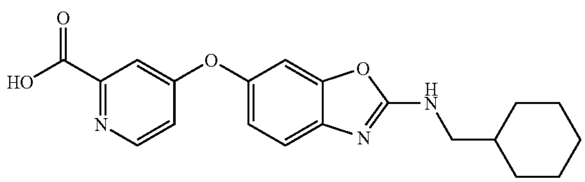 | 368.0; 2.13 | 4-[2-(Cyclohexylmethyl-amino)-benzooxazol-6-yloxy]-pyridine-2-carboxylic acid |
| 61 | 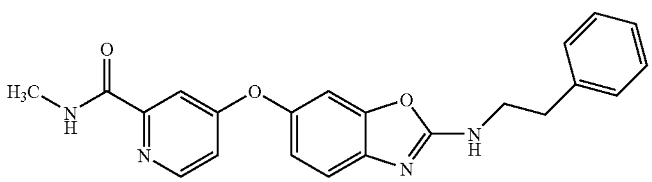 | 389.1; 2.40 | 4-(2-Phenethylamino-benzo-oxazol-6-yloxy)-pyridine-2-carboxylic acid methylamide |
| 62 | 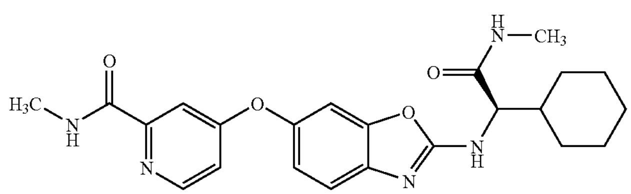 | 438.0; 2.33 | 4-{2-[((R)-Cyclohexyl-methylcarbamoyl-methyl)-amino]-benzooxazol-6-yloxy}-pyridine-2-carboxylic acid methylamide |
| 63 | 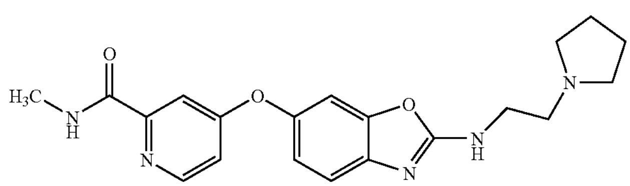 | 382.2; 1.74 | 4-[2-(2-Pyrrolidin-1-yl-ethylamino)-benzooxazol-6-yloxy]-pyridine-2-carboxylic acid methylamide |
| 64 | 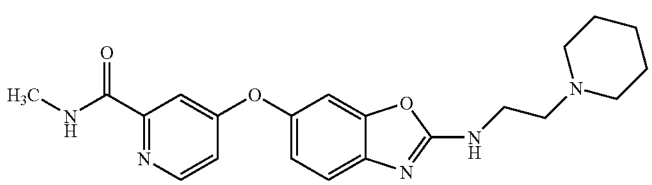 | 396.2; 1.83 | 4-[2-(2-Piperidin-1-yl-ethyl-amino)-benzooxazol-6-yloxy]-pyridine-2-carboxylic acid methylamide |
| 65 | 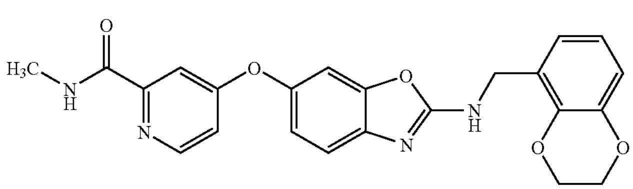 | 433.0; 2.40 | 4-{2-[2,3-Dihydro-benzo-[1,4]dioxin-5-ylmethyl)-amino]-benzooxazol-6-yloxy}-pyridine-2-carboxylic acid methylamide |

TABLE 2-continued

| Compound | Structure | M + H; Rt (min) | Compound Name |
|---|---|---|---|
| 66 | 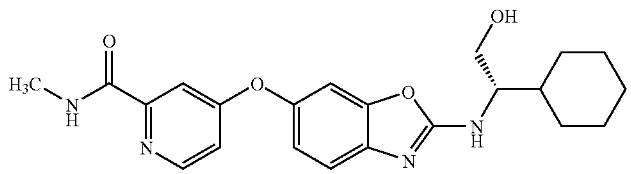 | 411.1; 2.31 | 4-[2-((S)-1-Cyclohexyl-2-hydroxy-ethylamino)-benzooxazol-6-yloxy]-pyridine-2-carboxylic acid methylamide |
| 67 | 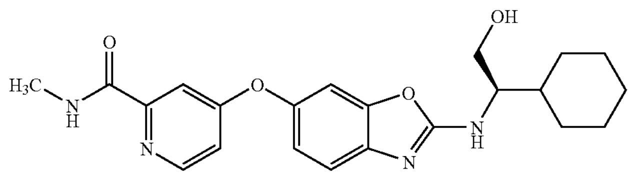 | 411.1; 2.33 | 4-[2-((R)-1-Cyclohexyl-2-hydroxy-ethylamino)-benzooxazol-6-yloxy]-pyridine-2-carboxylic acid methylamide |
| 68 | 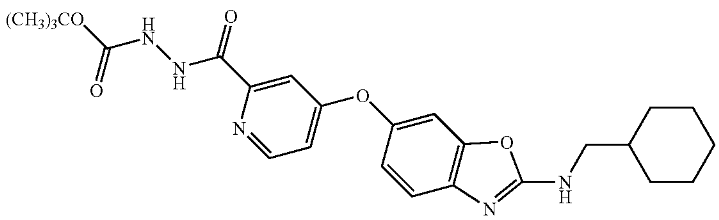 | 482.1; 2.92 | N'-{4-[2-(Cyclohexylmethyl-amino)-benzooxazol-6-yloxy]-pyridine-2-carbonyl}-hydrazinecarboxylic acid tert-butyl ester |
| 69 | 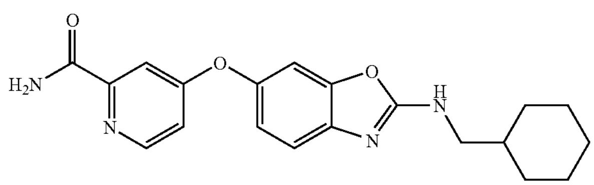 | 367.1; 2.46 | 4-[2-(Cyclohexylmethyl-amino)-benzooxazol-6-yloxy]-pyridine-2-carboxylic acid amide |
| 70 | 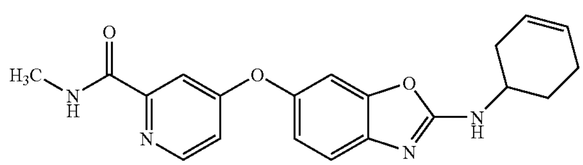 | 365.1; 2.29 | 4-[2-(Cyclohex-3-enylamino)-benzooxazol-6-yloxy]-pyridine-2-carboxylic acid methylamide |
| 71 | 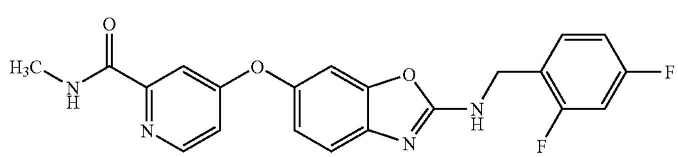 | 411.1; 2.53 | 4-[2-(2,4-Difluoro-benzylamino)-benzooxazol-6-yloxy]-pyridine-2-carboxylic acid methylamide |
| 72 | 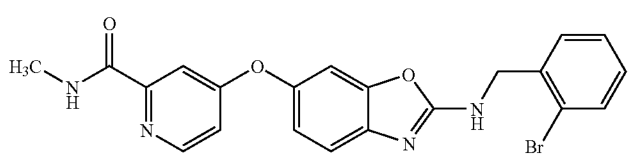 | 455.0; 2.66 | 4-[2-(2-Bromo-benzylamino)-benzooxazol-6-yloxy]-pyridine-2-carboxylic acid methylamide |
| 73 | 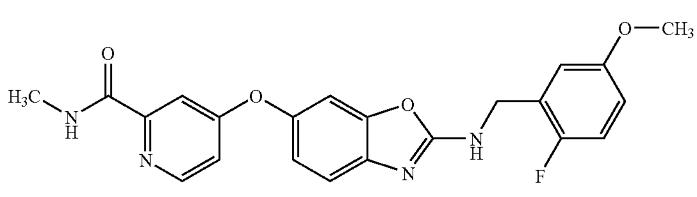 | 423.0; 2.48 | 4-[2-(2-Fluoro-5-methoxy-benzylamino)-benzooxazol-6-yloxy]-pyridine-2-carboxylic acid methylamide |

TABLE 2-continued

| Compound | Structure | M + H; Rt (min) | Compound Name |
|---|---|---|---|
| 74 | 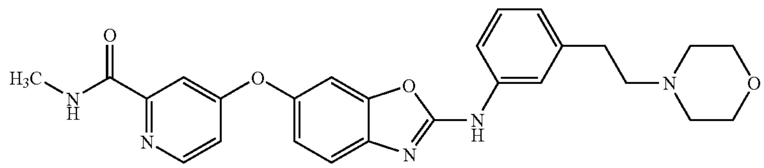 | 474.2; 2.03 | 4-{2-[3-(2-Morpholin-4-yl-ethyl)-phenylamino]-benzo-oxazol-6-yloxy}-pyridine-2-carboxylic acid methylamide |
| 75 | 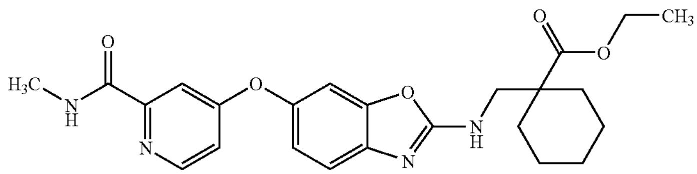 | 453.1; 2.79 | 1-{[6-(2-Methylcarbamoyl-pyridin-4-yloxy)-benzooxazol-2-ylamino]-methyl}-cyclohexane-carboxylic acid ethyl ester |
| 76 | 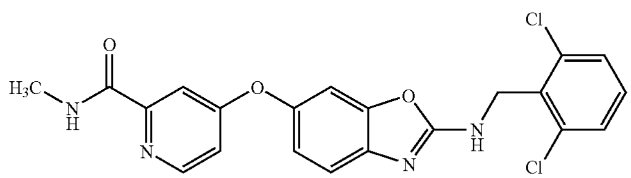 | 443.0; 2.72 | 4-[2-(2,6-Dichloro-benzylamino)-benzooxazol-6-yloxy]-pyridine-2-carboxylic acid methylamide |
| 77 | 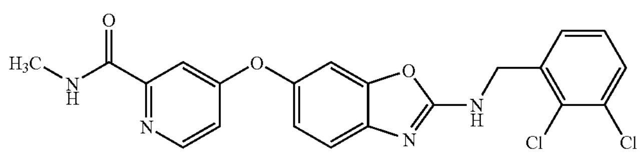 | 443.0; 2.83 | 4-[2-(2,3-Dichloro-benzylamino)-benzooxazol-6-yloxy]-pyridine-2-carboxylic acid methylamide |
| 78 | 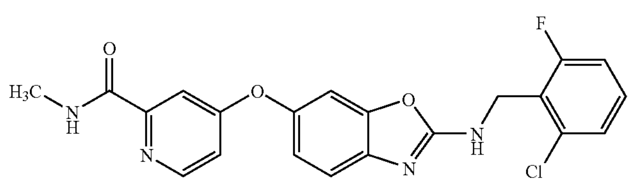 | 427.0; 2.59 | 4-[2-(2-Chloro-6-fluoro-benzylamino)-benzooxazol-6-yloxy]-pyridine-2-carboxylic acid methylamide |
| 79 | 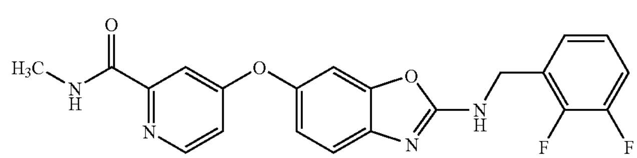 | 411.1; 2.53 | 4-[2-(2,3-Difluoro-benzylamino)-benzooxazol-6-yloxy]-pyridine-2-carboxylic acid methylamide |
| 80 | 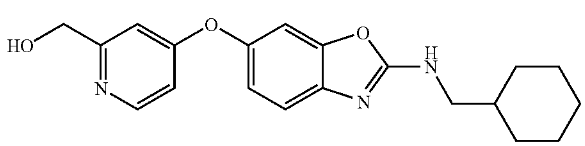 | 354.1; 2.22 | {4-[2-(Cyclohexylmethyl-amino)-benzooxazol-6-yloxy]-pyridin-2-yl}-methanol |
| 81 | 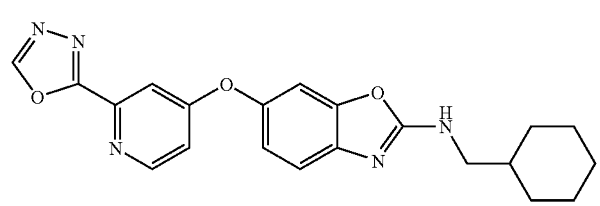 | 392.1; 2.59 | Cyclohexylmethyl-[6-(2-[1,3,4]oxadiazol-2-yl-pyridin-4-yloxy)-benzooxazol-2-yl]-amine |
| 82 | 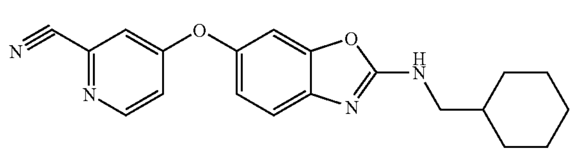 | 349.1; 2.93 | 4-[2-(Cyclohexylmethyl-amino)-benzooxazol-6-yloxy]-pyridine-2-carbonitrile |

TABLE 2-continued

| Compound | Structure | M + H; Rt (min) | Compound Name |
|---|---|---|---|
| 83 | 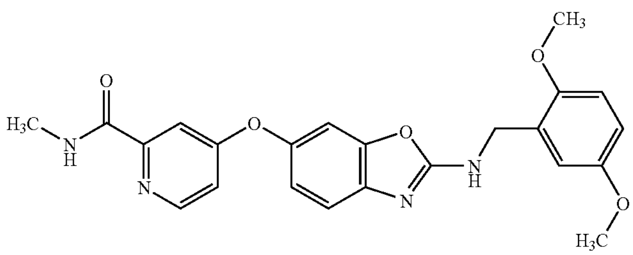 | 435.1; 2.46 | 4-[2-(2,5-Dimethoxy-benzyl-amino)-benzooxazol-6-yloxy]-pyridine-2-carboxylic acid methylamide |
| 84 | 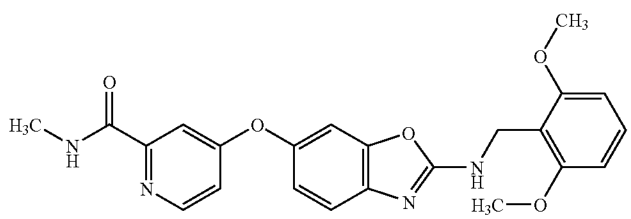 | 435.1; 2.44 | 4-[2-(2,6-Dimethoxy-benzyl-amino)-benzooxazol-6-yloxy]-pyridine-2-carboxylic acid methylamide |
| 85 | 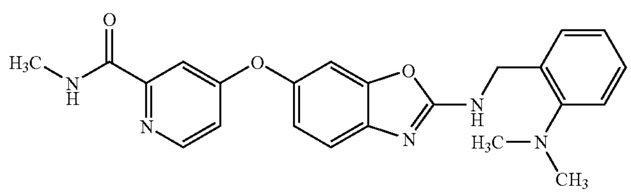 | 419.1; 2.55 | 4-[2-(2-Dimethylamino-benzylamino)-benzooxazol-6-yloxy]-pyridine-2-carboxylic acid methylamide |
| 86 | 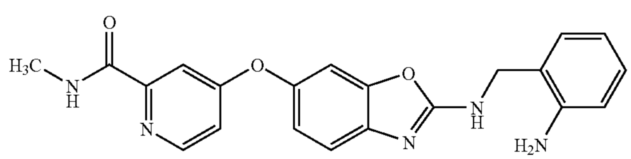 | 390.1; 1.98 | 4-[2-(2-Amino-benzylamino)-benzooxazol-6-yloxy]-pyridine-2-carboxylic acid methylamide |
| 87 | 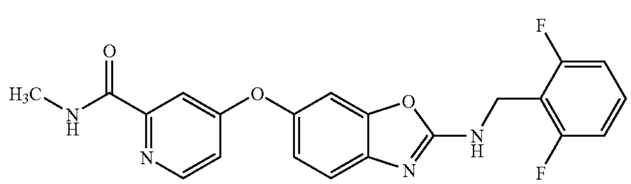 | 411.1; 2.48 | 4-[2-(2,6-Difluoro-benzylamino)-benzooxazol-6-yloxy]-pyridine-2-carboxylic acid methylamide |
| 88 | 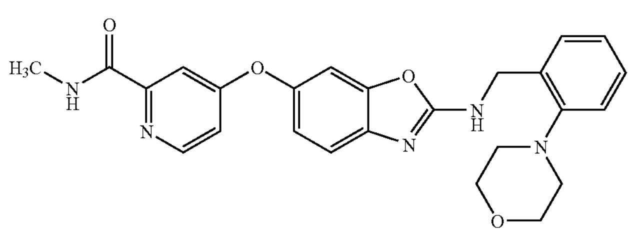 | 460.1; 2.40 | 4-[2-(2-Morpholin-4-yl-benzylamino)-benzooxazol-6-yloxy]-pyridine-2-carboxylic acid methylamide |
| 89 | 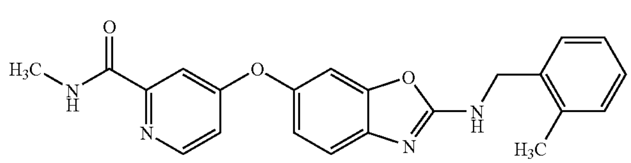 | 389.1; 2.53 | 4-[2-(2-Methyl-benzylamino)-benzooxazol-6-yloxy]-pyridine-2-carboxylic acid methylamide |

TABLE 2-continued

| Compound | Structure | M + H; Rt (min) | Compound Name |
|---|---|---|---|
| 90 | 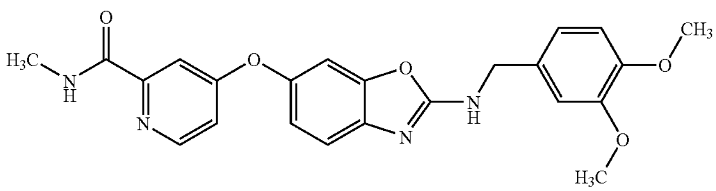 | 435.1; 2.29 | 4-[2-(3,4-Dimethoxy-benzyl-amino)-benzooxazol-6-yloxy]-pyridine-2-carboxylic acid methylamide |
| 91 | 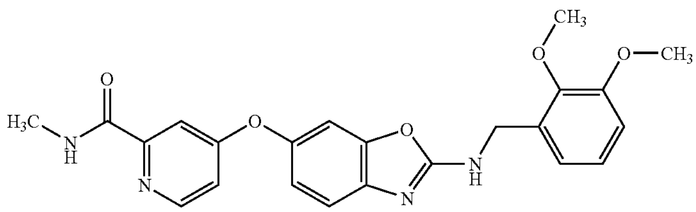 | 435.1; 2.42 | 4-[2-(2,3-Dimethoxy-benzyl-amino)-benzooxazol-6-yloxy]-pyridine-2-carboxylic acid methylamide |
| 92 | 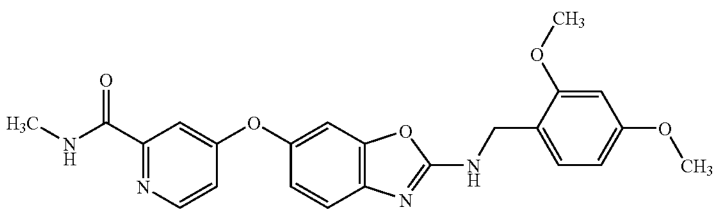 | 435.1; 2.44 | 4-[2-(2,4-Dimethoxy-benzyl-amino)-benzooxazol-6-yloxy]-pyridine-2-carboxylic acid methylamide |
| 93 | 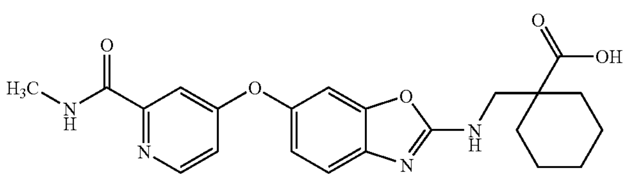 | 425.1; 2.29 | 1-{[6-(2-Methylcarbamoyl-pyridin-4-yloxy)-benzooxazol-2-ylamino]-methyl}-cyclohexane-carboxylic acid |
| 94 | 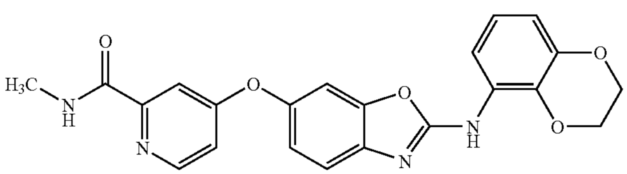 | 419.1; 2.62 | 4-[2-(2,3-Dihydro-benzo-[1,4]dioxin-5-ylamino)-benzooxazol-6-yloxy]-pyridine-2-carboxylic acid methylamide |
| 95 | 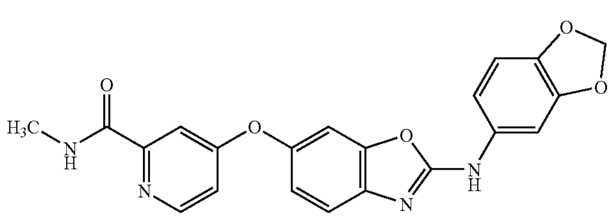 | 405.0; 2.57 | 4-[2-(Benzo[1,3]dioxol-5-yl-amino)-benzooxazol-6-yloxy]-pyridine-2-carboxylic acid methylamide |
| 96 | 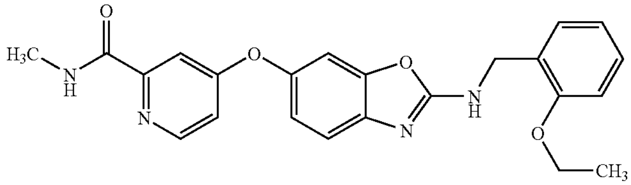 | 419.1; 2.62 | 4-[2-(2-Ethoxy-benzylamino)-benzooxazol-6-yloxy]-pyridine-2-carboxylic acid methylamide |

TABLE 2-continued

| Compound | Structure | M + H; Rt (min) | Compound Name |
|---|---|---|---|
| 97 | 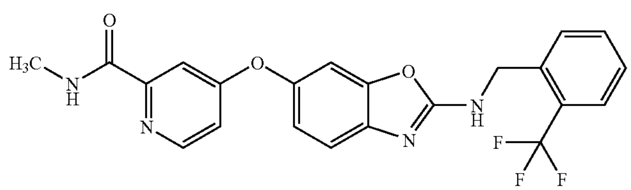 | 443.1; 2.77 | 4-[2-(2-Trifluoromethyl-benzylamino)-benzooxazol-6-yloxy]-pyridine-2-carboxylic acid methylamide |
| 98 | 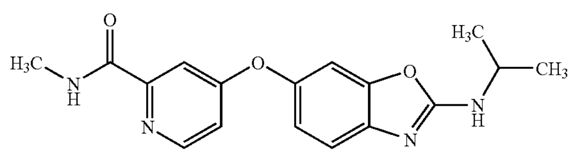 | 327.1; 1.94 | 4-(2-Isopropylamino-benzo-oxazol-6-yloxy)-pyridine-2-carboxylic acid methylamide |
| 99 | 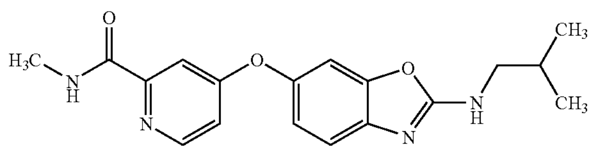 | 341.1; 2.18 | 4-(2-Isobutylamino-benzooxazol-6-yloxy)-pyridine-2-carboxylic acid methylamide |
| 100 | 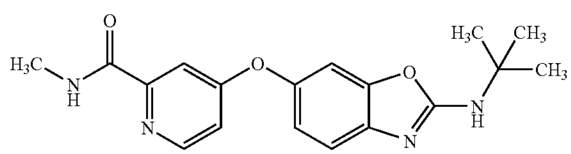 | 341.1; 2.24 | 4-(2-tert-Butylamino-benzo-oxazol-6-yloxy)-pyridine-2-carboxylic acid methylamide |
| 101 | 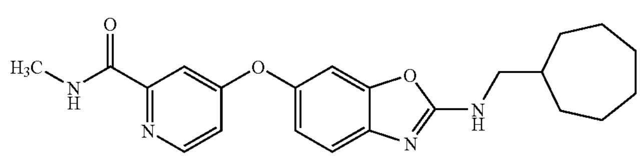 | 395.2; 2.74 | 4-[2-(Cycloheptylmethyl-amino)-benzooxazol-6-yloxy]-pyridine-2-carboxylic acid methylamide |
| 102 | 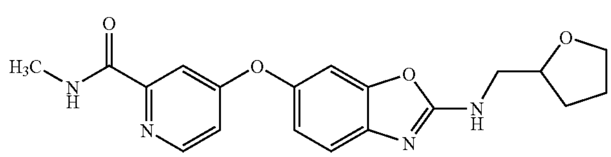 | 369.1; 1.98 | 4-{2-[(Tetrahydro-furan-2-ylmethyl)-amino]-benzooxazol-6-yloxy}-pyridine-2-carboxylic acid methylamide |
| 103 | 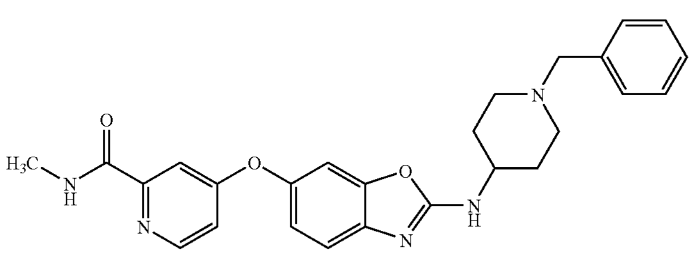 | 458.1; 2.05 | 4-[2-(1-Benzyl-piperidin-4-ylamino)-benzooxazol-6-yloxy]-pyridine-2-carboxylic acid methylamide |
| 104 | 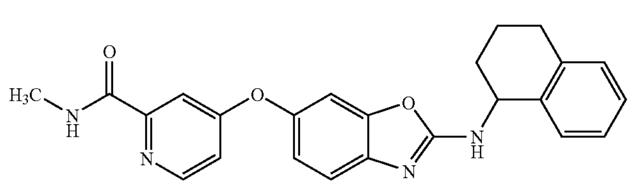 | 415.1; 2.70 | 4-[2-(1,2,3,4-Tetrahydro-naphthalen-1-ylamino)-benzooxazol-6-yloxy]-pyridine-2-carboxylic acid methylamide |

TABLE 2-continued

| Compound | Structure | M + H; Rt (min) | Compound Name |
|---|---|---|---|
| 105 | 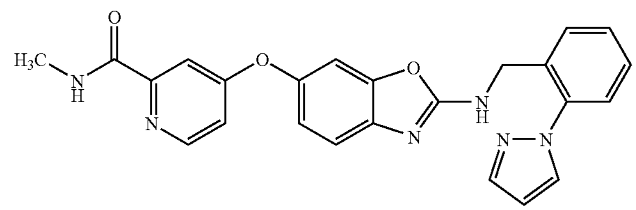 | 441.1; 2.40 | 4-[2-(2-Pyrazol-1-yl-benzyl-amino)-benzooxazol-6-yloxy]-pyridine-2-carboxylic acid methylamide |
| 106 | 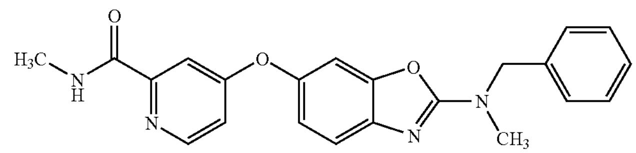 | 389.1; 2.66 | 4-[2-(Benzyl-methyl-amino)-benzooxazol-6-yloxy]-pyridine-2-carboxylic acid methylamide |
| 107 | 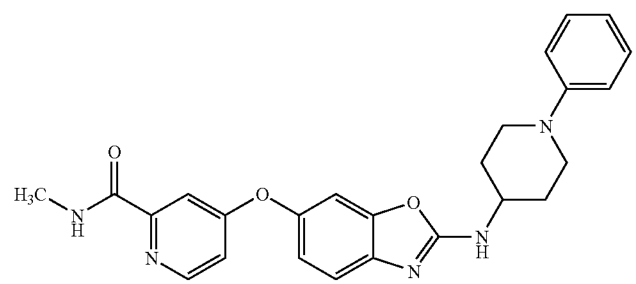 | 444.1; 2.02 | 4-[2-(1-Phenyl-piperidin-4-ylamino)-benzooxazol-6-yloxy]-pyridine-2-carboxylic acid methylamide |
| 108 | 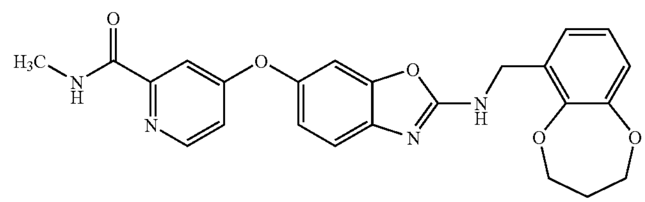 | 447.1; 2.42 | 4-{2-[3,4-Dihydro-2H-benzo[b][1,4]dioxepin-6-ylmethyl)-amino]-benzooxazol-6-yloxy}-pyridine-2-carboxylic acid methylamide |
| 109 | 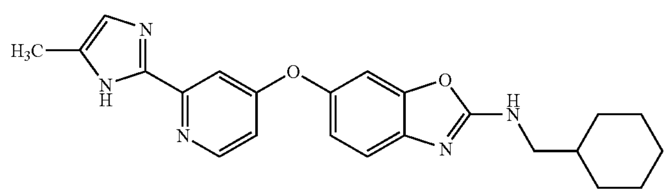 | 404.1; 2.38 | Cyclohexylmethyl-{6-[2-(5-methyl-1H-imidazol-2-yl)-pyridin-4-yloxy]-benzooxazol-2-yl}-amine |
| 110 | 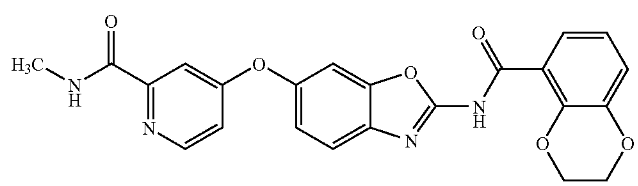 | 447.0; 2.42 | 4-{2-[(2,3-Dihydro-benzo-[1,4]dioxine-5-carbonyl)-amino]-benzooxazol-6-yloxy}-pyridine-2-carboxylic acid methylamide |
| 111 | 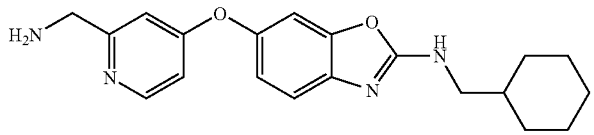 | 353.1; 2.18 | [6-(2-Aminomethyl-pyridin-4-yloxy)-benzooxazol-2-yl]-cyclohexylmethyl-amine |

TABLE 2-continued

| Compound | Structure | M + H; Rt (min) | Compound Name |
|---|---|---|---|
| 112 | 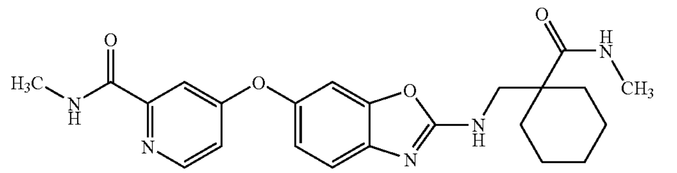 | 438.1; 2.16 | 4-{2-[(1-Methylcarbamoyl-cyclohexylmethyl)-amino]-benzooxazol-6-yloxy}-pyridine-2-carboxylic acid methylamide |
| 113 | 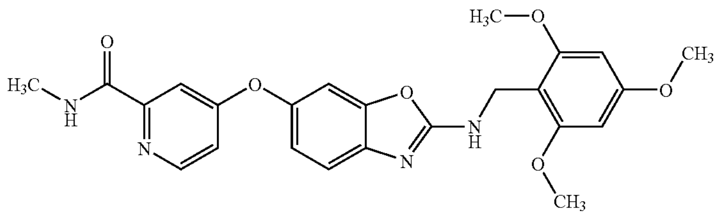 | 465.1; 2.46 | 4-[2-(2,4,6-Trimethoxy-benzylamino)-benzooxazol-6-yloxy]-pyridine-2-carboxylic acid methylamide |
| 114 | 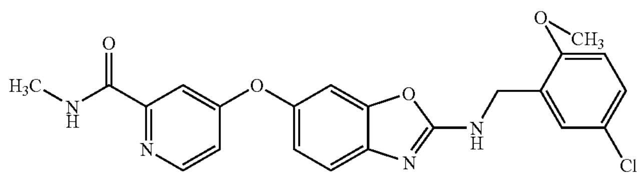 | 439.1; 2.68 | 4-[2-(5-Chloro-2-methoxy-benzylamino)-benzooxazol-6-yloxy]-pyridine-2-carboxylic acid methylamide |
| 115 | 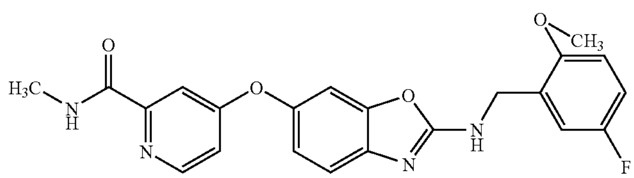 | 423.1; 2.53 | 4-[2-(5-Fluoro-2-methoxy-benzylamino)-benzooxazol-6-yloxy]-pyridine-2-carboxylic acid methylamide |
| 116 | 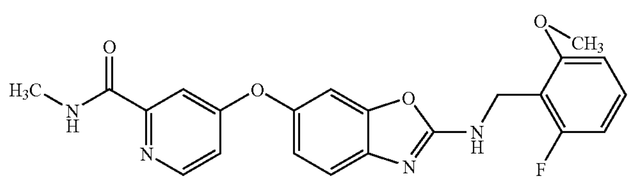 | 423.1; 2.48 | 4-[2-(2-Fluoro-6-methoxy-benzylamino)-benzooxazol-6-yloxy]-pyridine-2-carboxylic acid methylamide |
| 117 | 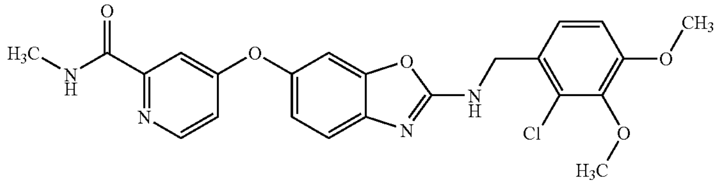 | 469.1; 2.57 | 4-[2-(2-Chloro-3,4-dimethoxy-benzylamino)-benzooxazol-6-yloxy]-pyridine-2-carboxylic acid methylamide |
| 118 | 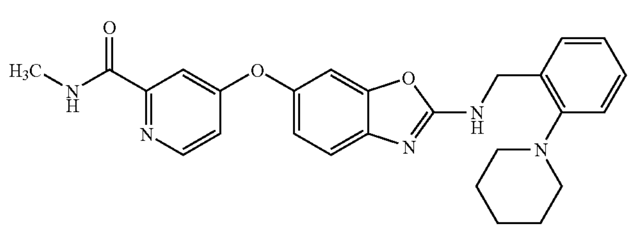 | 458.1; 2.20 | 4-[2-(2-Piperidin-1-yl-benzylamino)-benzooxazol-6-yloxy]-pyridine-2-carboxylic acid methylamide |
| 119 | 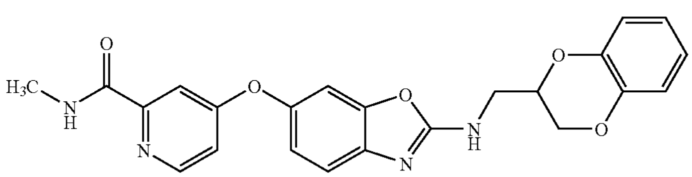 | 433.1; 2.55 | 4-{2-[(2,3-Dihydro-benzo-[1,4]dioxin-2-ylmethyl)-amino]-benzooxazol-6-yloxy}-pyridine-2-carboxylic acid methylamide |

TABLE 2-continued

| Compound | Structure | M + H; Rt (min) | Compound Name |
|---|---|---|---|
| 120 | 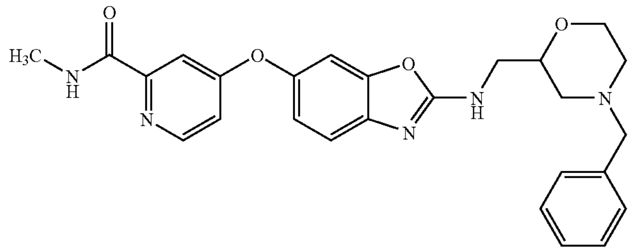 | 474.1; 2.01 | 4-{2-[(4-Benzyl-morpholin-2-ylmethyl)-amino]-benzooxazol-6-yloxy}-pyridine-2-carboxylic acid methylamide |
| 121 | 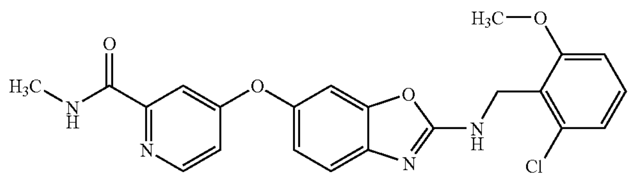 | 439.0; 2.63 | 4-[2-(2-Chloro-6-methoxy-benzylamino)-benzooxazol-6-yloxy]-pyridine-2-carboxylic acid methylamide |
| 122 | 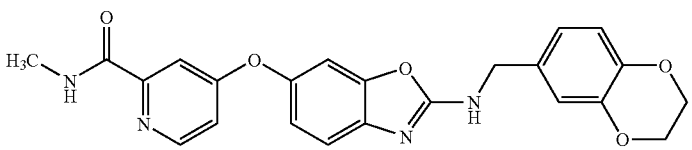 | 433.1; 2.37 | 4-{2-[(2,3-Dihydro-benzo-[1,4]dioxin-6-ylmethyl)-amino]-benzooxazol-6-yloxy}-pyridine-2-carboxylic acid methylamide |
| 123 | 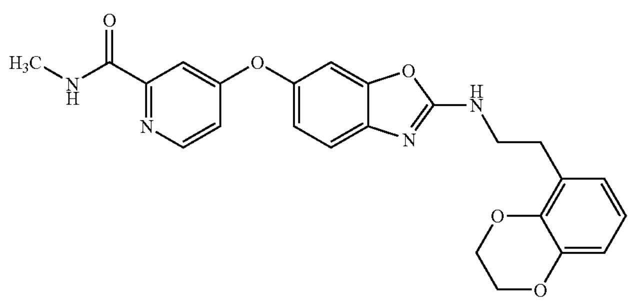 | 447.1; 2.44 | 4-{2-[2-(2,3-Dihydro-benzo-[1,4]dioxin-5-yl)-ethylamino]-benzooxazol-6-yloxy}-pyridine-2-carboxylic acid methylamide |
| 124 | 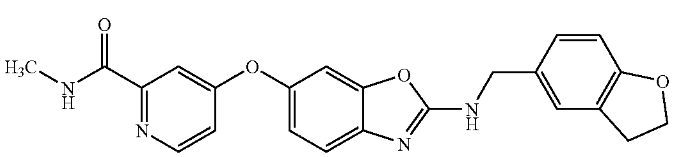 | 417.1; 2.37 | 4-{2-[(2,3-Dihydro-benzofuran-5-ylmethyl)-amino]-benzooxazol-6-yloxy}-pyridine-2-carboxylic acid methylamide |
| 125 | 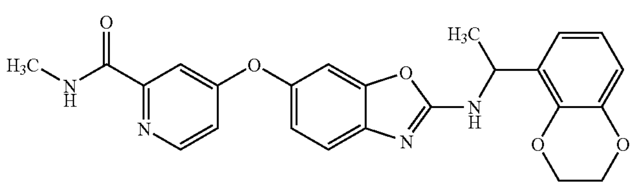 | 447.1; 2.50 | 4-{2-[1-(2,3-Dihydro-benzo-[1,4]dioxin-5-yl)-ethylamino]-benzooxazol-6-yloxy}-pyridine-2-carboxylic acid methylamide |
| 126 | 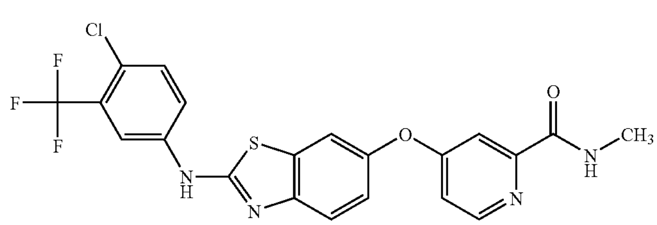 | 479.9; 5.1 | 4-[2-(4-Chloro-3-trifluoromethyl-phenylamino)-benzothiazol-6-yloxy]-pyridine-2-carboxylic acid methylamide |

TABLE 2-continued

| Compound | Structure | M + H; Rt (min) | Compound Name |
|---|---|---|---|
| 127 | 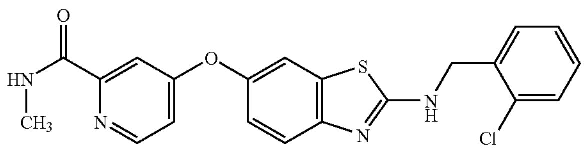 | 425.0; 2.57 | 4-[2-(2-Chloro-benzylamino)-benzothiazol-6-yloxy]-pyridine-2-carboxylic acid methylamide |
| 128 | 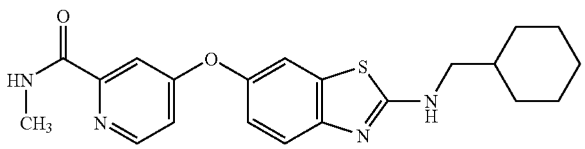 | 397.1; 2.48 | 4-[2-(Cyclohexylmethyl-amino)-benzothiazol-6-yloxy]-pyridine-2-carboxylic acid methylamide |
| 129 | 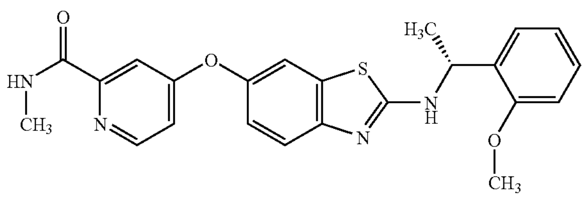 | 435.1; 2.48 | 4-{2-[(R)-1-(2-Methoxy-phenyl)-ethylamino]-benzothiazol-6-yloxy}-pyridine-2-carboxylic acid methylamide |
| 130 | 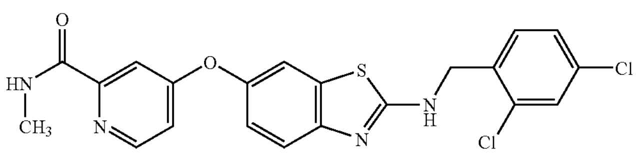 | 459.0; 2.88 | 4-[2-(2,4-Dichloro-benzylamino)-benzothiazol-6-yloxy]-pyridine-2-carboxylic acid methylamide |
| 131 | 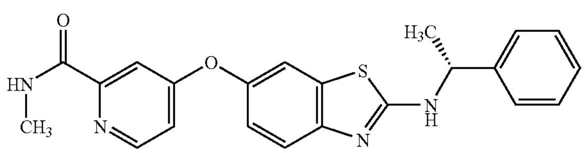 | 405.1; 2.42 | 4-[2-((R)-1-Phenyl-ethylamino)-benzothiazol-6-yloxy]-pyridine-2-carboxylic acid methylamide |
| 132 | 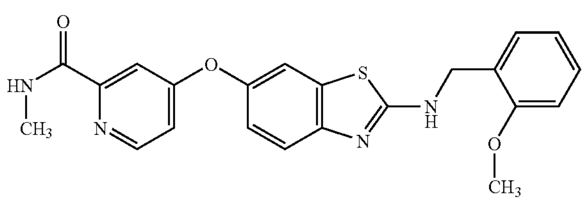 | 421.1; 2.37 | 4-[2-(2-Methoxy-benzylamino)-benzothiazol-6-yloxy]-pyridine-2-carboxylic acid methylamide |
| 133 | 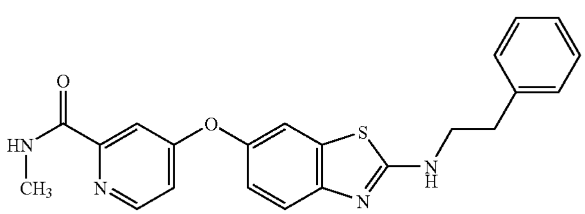 | 405.0; 2.35 | 4-(2-Phenethylamino-benzo-thiazol-6-yloxy)-pyridine-2-carboxylic acid methylamide |
| 134 | 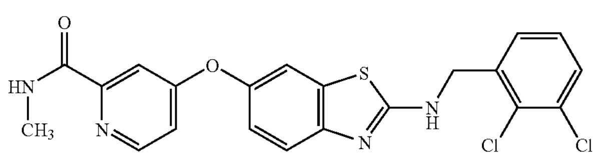 | 458.9; 2.81 | 4-[2-(2,3-Dichloro-benzylamino)-benzothiazol-6-yloxy]-pyridine-2-carboxylic acid methylamide |

TABLE 2-continued

| Compound | Structure | M + H; Rt (min) | Compound Name |
|---|---|---|---|
| 135 | 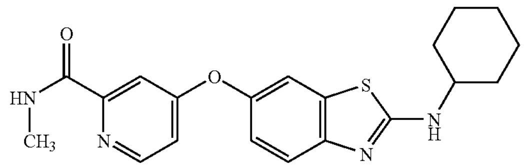 | 383.1; 2.27 | 4-(2-Cyclohexylamino)-benzothiazol-6-yloxy)-pyridine-2-carboxylic acid methylamide |
| 136 | 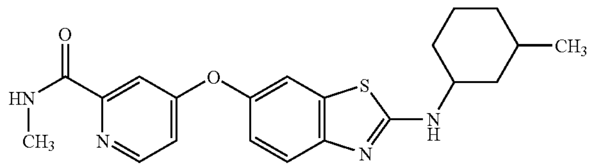 | 397.1; 2.46 | 4-[2-(3-Methyl-cyclohexyl-amino)-benzothiazol-6-yloxy]-pyridine-2-carboxylic acid methylamide |
| 137 | 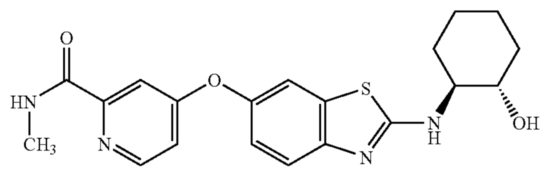 | 399.1; 1.94 | 4-[2-((1S,2S)-2-Hydroxy-cyclohexylamino)-benzothiazol-6-yloxy]-pyridine-2-carboxylic acid methylamide |
| 138 | 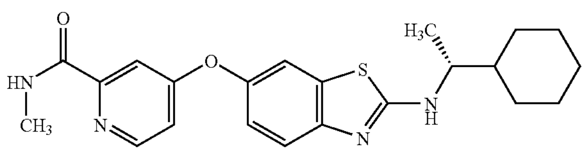 | 411.1; 2.59 | 4-[2-((R)-1-Cyclohexyl-ethylamino)-benothiazol-6-yloxy]-pyridine-2-carboxylic acid methylamide |
| 139 | 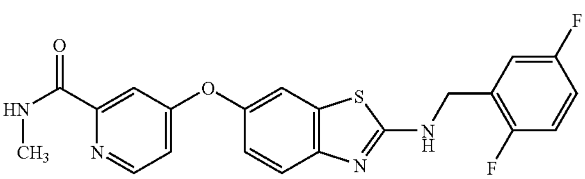 | 427.0; 2.53 | 4-[2-(2,5-Difluoro-benzylamino)-benzothiazol-6-yloxy]-pyridine-2-carboxylic acid methylamide |
| 140 | 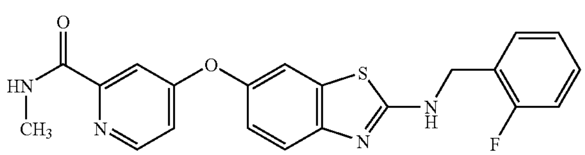 | 409.0; 2.40 | 4-[2-(2-Fluoro-benzylamino)-benzothiazol-6-yloxy]-pyridine-2-carboxylic acid methylamide |
| 141 | 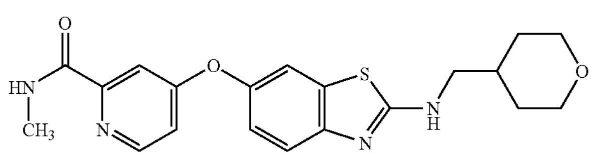 | 399.1; 1.94 | 4-{2-[(Tetrahydro-pyran-4-ylmethyl)-amino]-benzothiazol-6-yloxy}-pyridine-2-carboxylic acid methylamide |
| 142 | 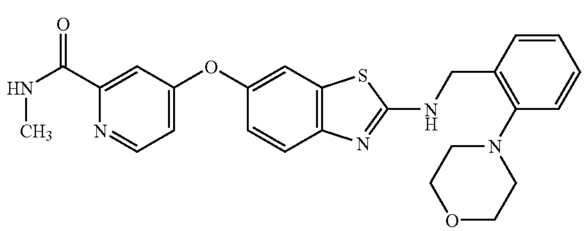 | 476.1; 2.38 | 4-[2-(2-Morpholin-4-yl-benzylamino)-benzothiazol-6-yloxy]-pyridine-2-carboxylic acid methylamide |

TABLE 2-continued

| Compound | Structure | M + H; Rt (min) | Compound Name |
|---|---|---|---|
| 143 | 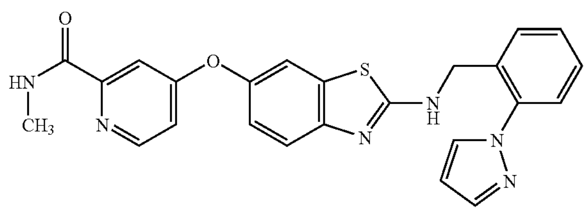 | 457.1; 2.33 | 4-[2-(2-Pyrazol-1-yl-benzyl-amino)-benzothiazol-6-yloxy]-pyridine-2-carboxylic acid methylamide |
| 144 | 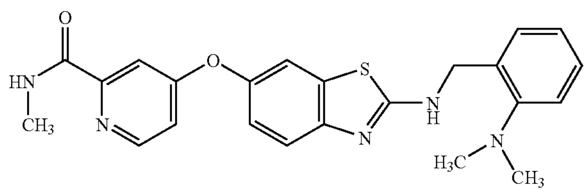 | 434.1; 2.05 | 4-[2-(2-Dimethylamino-benzylamino)-benzothiazol-6-yloxy]-pyridine-2-carboxylic acid methylamide |
| 145 | 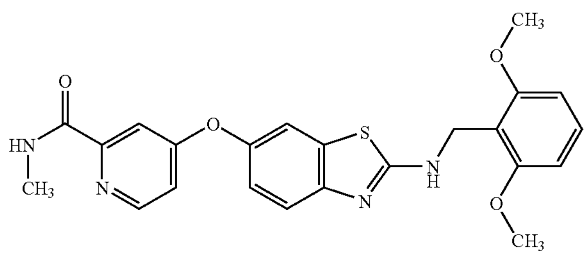 | 451.1; 2.38 | 4-[2-(2,6-Dimethoxy-benzyl-amino)-benzothiazol-6-yloxy]-pyridine-2-carboxylic acid methylamide |
| 146 | 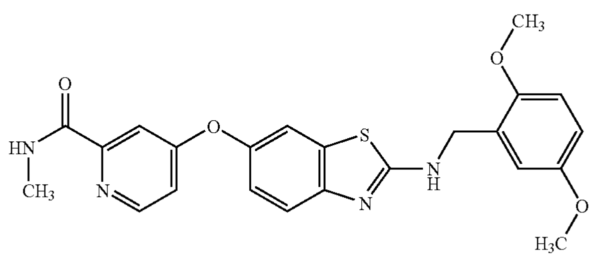 | 451.1; 2.39 | 4-[2-(2,5-Dimethoxy-benzyl-amino)-benzothiazol-6-yloxy]-pyridine-2-carboxylic acid methylamide |
| 147 | 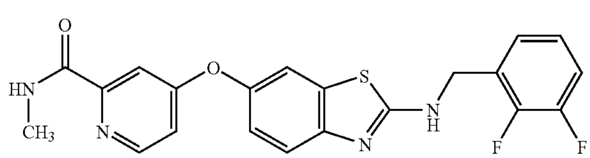 | 427.0; 2.53 | 4-[2-(2,3-Difluoro-benzylamino)-benzothiazol-6-yloxy]-pyridine-2-carboxylic acid methylamide |
| 148 | 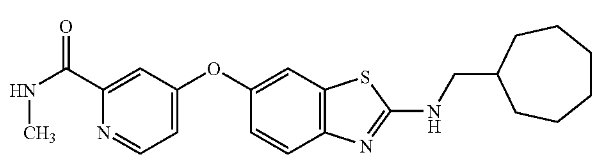 | 411.1; 2.62 | 4-[2-(Cycloheptylmethyl-amino)-benzothiazol-6-yloxy]-pyridine-2-carboxylic acid methylamide |
| 149 | 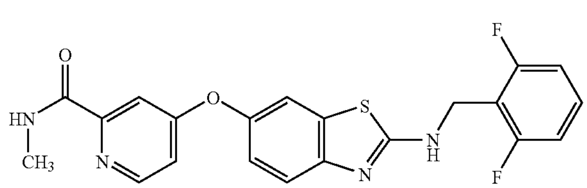 | 427.0; 2.46 | 4-[2-(2,6-Difluoro-benzylamino)-benzothiazol-6-yloxy]-pyridine-2-carboxylic acid methylamide |

TABLE 2-continued

| Compound | Structure | M + H; Rt (min) | Compound Name |
|---|---|---|---|
| 150 | 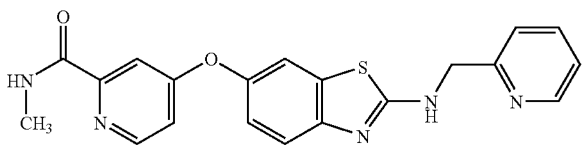 | 392.1; 1.83 | 4-{2-[(Pyridin-2-ylmethyl)-amino]-benzothiazol-6-yloxy}-pyridine-2-carboxylic acid methylamide |
| 151 | 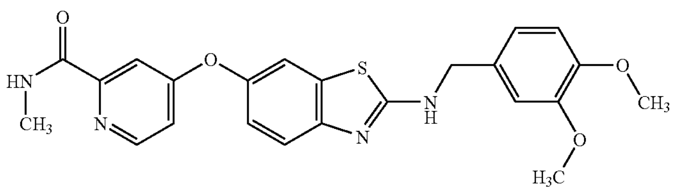 | 451.0; 2.22 | 4-[2-(3,4-Dimethoxy-benzyl-amino)-benzothiazol-6-yloxy]-pyridine-2-carboxylic acid methylamide |
| 152 | 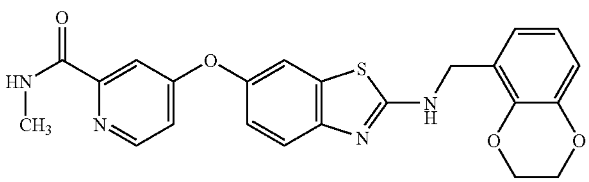 | 449.0; 2.35 | 4-{2-[(2,3-Dihydro-benzo-[1,4]dioxin-5-ylmethyl)-amino]-benzothiazol-6-yloxy}-pyridine-2-carboxylic acid methylamide |
| 153 | 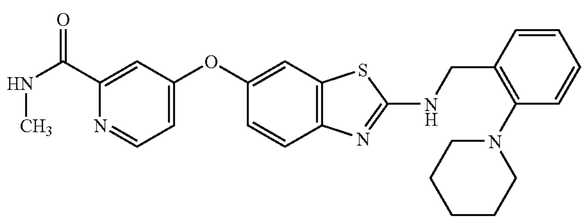 | 474.1; 2.31 | 4-[2-(2-Piperidin-1-yl-benzylamino)-benzothiazol-6-yloxy)-pyridine-2-carboxylic acid methylamide |
| 154 | 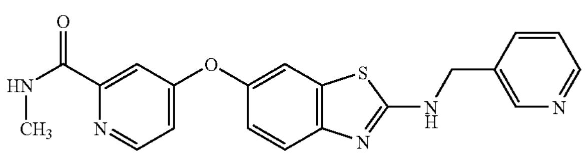 | 392.0; 1.78 | 4-{2-[(Pyridin-3-ylmethyl)-amino]-benzothiazol-6-yloxy}-pyridine-2-carboxylic acid methylamide |
| 155 | 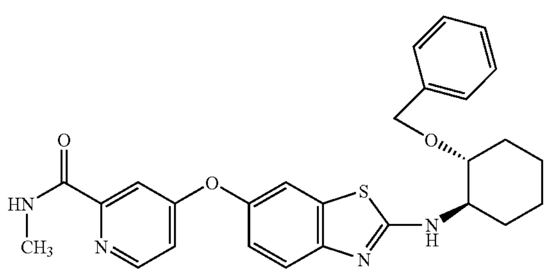 | 489.2; 2.57 | 4-[2-((1R,2R)-2-Benzyloxy-cyclohexylamino)-benzothiazol-6-yloxy]-pyridine-2-carboxylic acid methylamide |
| 156 | 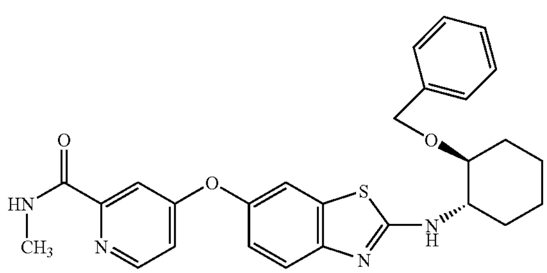 | 489.1; 2.57 | 4-[2-((1S,2S)-2-Benzyloxy-cyclohexylamino)-benzothiazol-6-yloxy]-pyridine-2-carboxylic acid methylamide |

TABLE 2-continued

| Compound | Structure | M + H; Rt (min) | Compound Name |
|---|---|---|---|
| 157 | 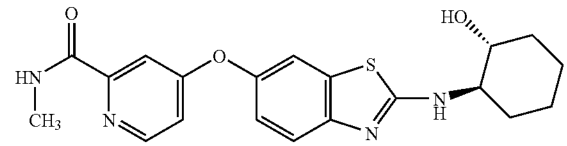 | 399.1; 1.94 | 4-[2-((1R,2R)-2-Hydroxy-cyclohexylamino)-benzothiazol-6-yloxy]-pyridine-2-carboxylic acid methylamide |
| 158 | 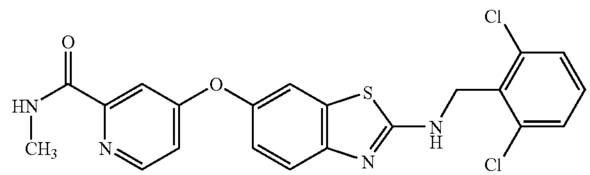 | 459.0; 2.68 | 4-[2-(2,6-Dichloro-benzylamino)-benzothiazol-6-yloxy]-pyridine-2-carboxylic acid methylamide |
| 159 | 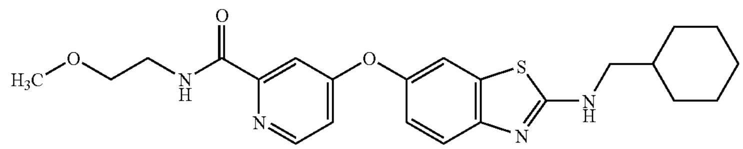 | 441.1; 2.59 | 4-(2-(cyclohexylmethyl-amino)benzothiazol-6-yloxy)-N-(2-methoxyethyl)-pyridine-2-carbamide |
| 160 | 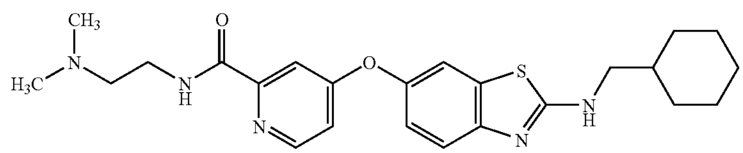 | 454.2; 2.26 | 4-(2-cyclohexylmethyl-amino)benzothiazol-6-yloxy)-N-(2-(dimethylamino)-ethyl)pyridine-2-carboxamide |
| 161 | 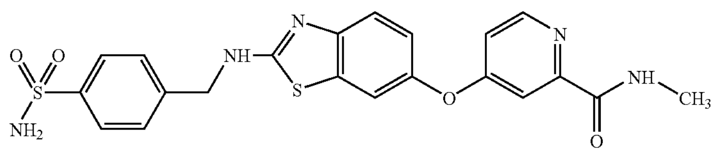 | 470.0; 2.00 | 4-[2-(4-Sulfonamide-benzyl-amino)-benzothiazol-6-yloxy]-pyridine-2-carboxylic acid methylamide |

Example 162

Preparation of 4-(2-((1R,2S)-2-hydroxy-2,3-dihydro-1H-inden-1-ylamino)benzo[d]thiazol-6-yloxy)-N-methylpicolinamide The subject compound was prepared according to the general Scheme below Step 1

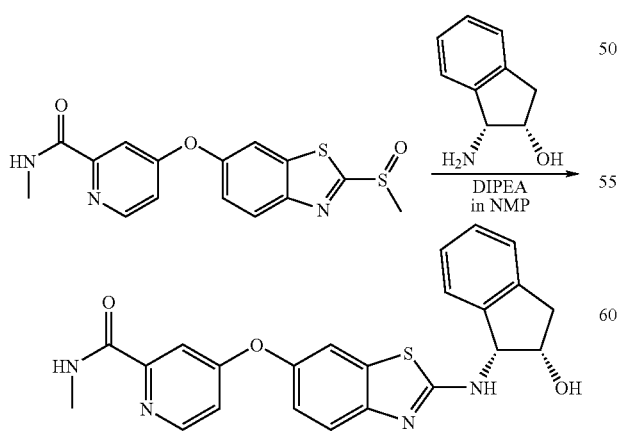

To the solution of N-methyl-4-(2-(methylsulfinyl)benzo[d]thiazol-6-yloxy)picolinamide (300 mg, 0.86 mmol) in 5 ml of NMP was added (1R,2S)-1-amino-2,3-dihydro-1H-inden-2-ol (597 mg, 4 mmol) and DIPEA (300 μL, 1.73 mmol). The reaction solution was stirred at 105° C. for 24 hours. The crude reaction solution was purified on prep HPLC and evaporated in vacuo to give 4-(2-((1R,2S)-2-hydroxy-2,3-dihydro-1H-inden-1-ylamino)benzo[d]thiazol-6-yloxy)-N-methylpicolinamide (347 mg, 0.63 mmol) as TFA salt. ES/MS m/z 433.1 (MH+).

Example 163

Preparation of 4-(2-((1R,2R)-2-acetamidocyclohexylamino)benzo[d]thiazol-6-yloxy)-N-methylpicolinamide The subject compound was prepared according to the general Scheme below:

Step 1

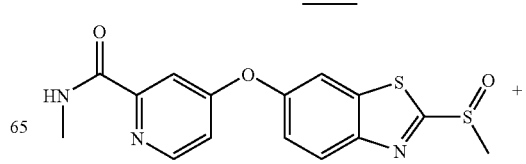

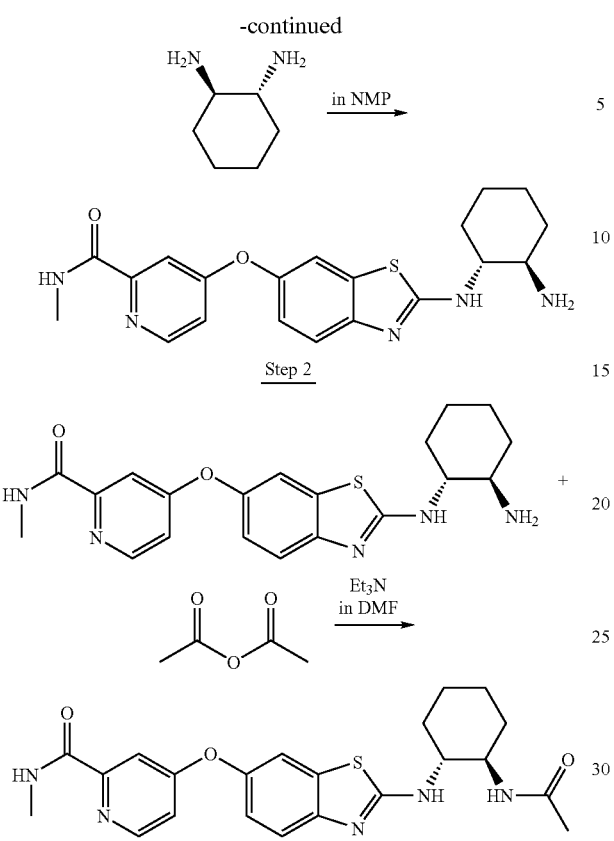

Step 1. Preparation of 4-(2-((1R,2R)-2-aminocyclo-hexylamino)benzo[d]thiazol-6-yloxy)-N-methylpicolinamide To the solution of N-methyl-4-(2-(methylsulfinyl)benzo[d]thiazol-6-yloxy)picolinamide (15 mg, 43 µmole) in 400 µL of NMP was added (1R,2R)-cyclohexane-1,2-diamine (17 mg, 150 µmole). The reaction solution was stirred at 105° C. for 24 hours. The crude reaction solution was purified on prep HPLC and evaporated in vacuo to give 4-(2-((1R,2R)-2-aminocyclohexylamino)benzo[d]thiazol-6-yloxy)-N-methylpicolinamide (12 mg, 30 µmole) as white powder. ES/MS m/z 398.1 (MH⁺).

Step 2. Preparation of 4-(2-((1R,2R)-2-acetamidocyclohexylamino)benzo[d]thiazol-6-yloxy)-N-methylpicolinamide To the solution of 4-(2-((1R,2R)-2-aminocyclohexylamino)benzo[d]thiazol-6-yloxy)-N-methylpicolinamide (9 mg, 22 µmole) and triethylamine (11 µL, 80 µmole) in 300 µL of DMF was added acetic anhydride (5 µL, 50 µmole). The reaction solution was stirred at room temperature for 1.5 hours. The crude reaction solution was purified on prep HPLC and evaporated in vacuo to give 4-(2-((1R,2R)-2-acetamidocyclohexylamino)benzo[d]thiazol-6-yloxy)-N-methylpicolinamide (5.1 mg, 12 µmole) as white powder. ES/MS m/z 440.2 (MH⁺).

Example 164

Preparation of (S)—N-methyl-4-(2-(1-(methylsulfonyl)piperidin-3-ylamino)benzo[d]thiazol-6-yloxy)picolinamide The subject compound was prepared according to the general Scheme below:

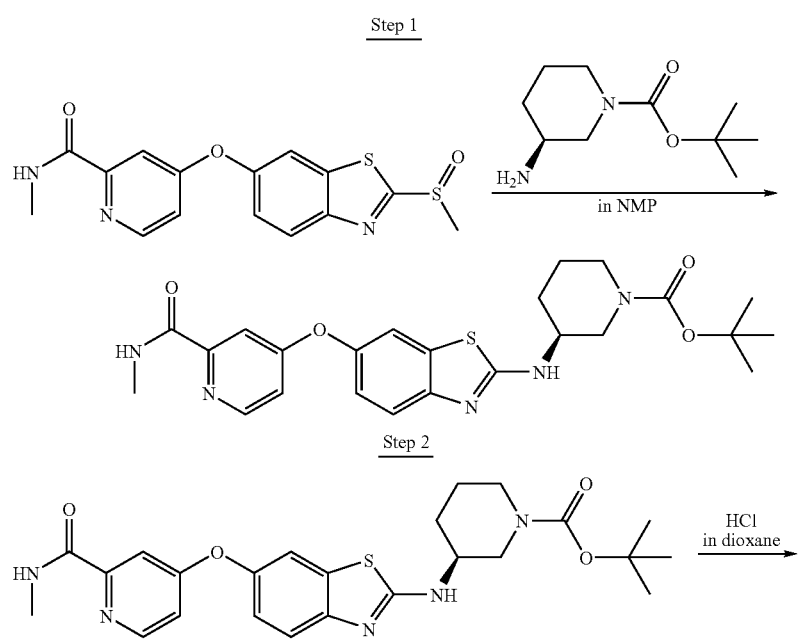

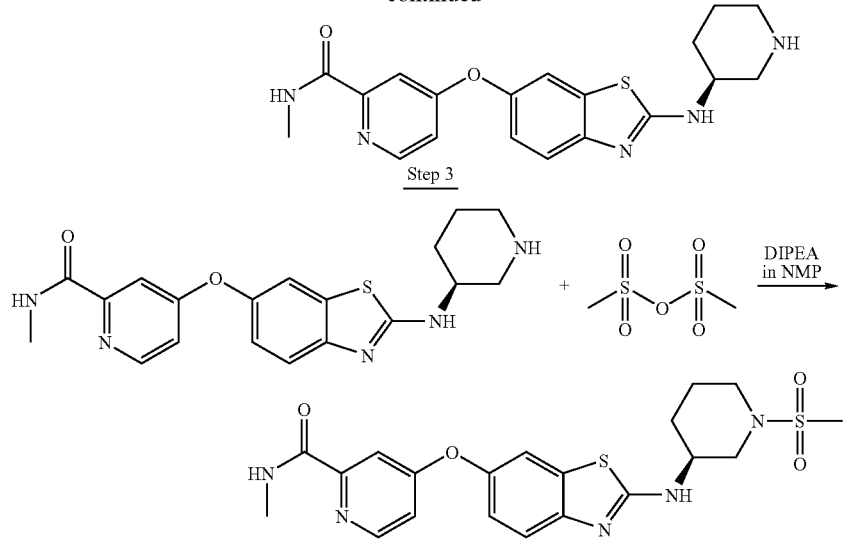

Step 1. Preparation of (S)-tert-butyl 3-(6-(2-(methylcarbamoyl)pyridin-4-yloxy)benzo[d]thiazol-2-ylamino)piperidine-1-carboxylate To the solution of N-methyl-4-(2-(methylsulfinyl)benzo[d]thiazol-6-yloxy)picolinamide (104 mg, 0.3 mmol) in 2 ml of NMP was added (S)-tert-butyl 3-aminopiperidine-1-carboxylate (240 mg, 1.2 mmol). The reaction solution was stirred at 105° C. for 5 days. The crude reaction solution was purified on prep HPLC and evaporated in vacuo to give (S)-tert-butyl 3-(6-(2-(methylcarbamoyl)pyridin-4-yloxy)benzo[d]thiazol-2-ylamino)piperidine-1-carboxylate (56 mg, 0.12 mmol) as white powder. ES/MS m/z 484.2 (MH$^+$).

Step 2. Preparation of (S)—N-methyl-4-(2-(piperidin-3-ylamino)benzo[d]thiazol-6-yloxy)picolinamide (S)-tert-butyl 3-(6-(2-(methylcarbamoyl)pyridin-4-yloxy)benzo[d]thiazol-2-ylamino)piperidine-1-carboxylate (56 mg, 0.12 mmol) was dissolved in 4 ml of 4M HCl in dioxane (16 mmol). The reaction solution was stirred at room temperature for 1 hour. The crude reaction solution was evaporated in vacuo to give (S)—N-methyl-4-(2-(piperidin-3-ylamino)benzo[d]thiazol-6-yloxy)picolinamide (46 mg, 0.12 mmol) as white solid. ES/MS m/z 384.0 (MH$^+$).

Step 3. Preparation of (S)—N-methyl-4-(2-(1-(methylsulfonyl)piperidin-3-ylamino)benzo[d]thiazol-6-yloxy)picolinamide To the solution of (S)—N-methyl-4-(2-(piperidin-3-ylamino)benzo[d]thiazol-6-yloxy)picolinamide hydrochloride (12.5 mg, 30 μmol) and DIPEA (28 μL, 160 μmol) in 300 μL of NMP was added methanesulfonic anhydride (17 mg, 100 μmol). The reaction solution was stirred at 105° C. for 46 hours. The crude reaction solution was purified on prep HPLC and evaporated in vacuo to give (S)—N-methyl-4-(2-(1-(methylsulfonyl)piperidin-3-ylamino)benzo[d]thiazol-6-yloxy)picolinamide (4.5 mg, 9.8 μmol) as white powder. ES/MS m/z 462.1 (MH$^+$).

Example 165

Preparation of (S)-4-(2-(1-acetylpiperidin-3-ylamino)benzo[d]thiazol-6-yloxy)-N-methylpicolinamide The subject compound was prepared according to the general Scheme below:

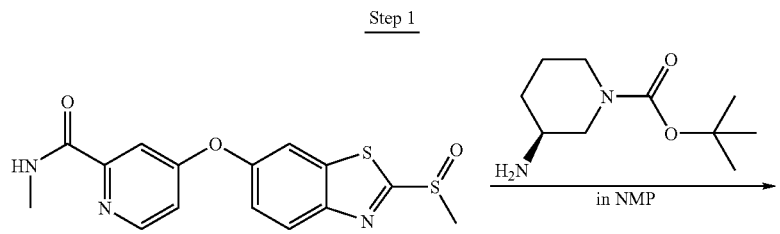

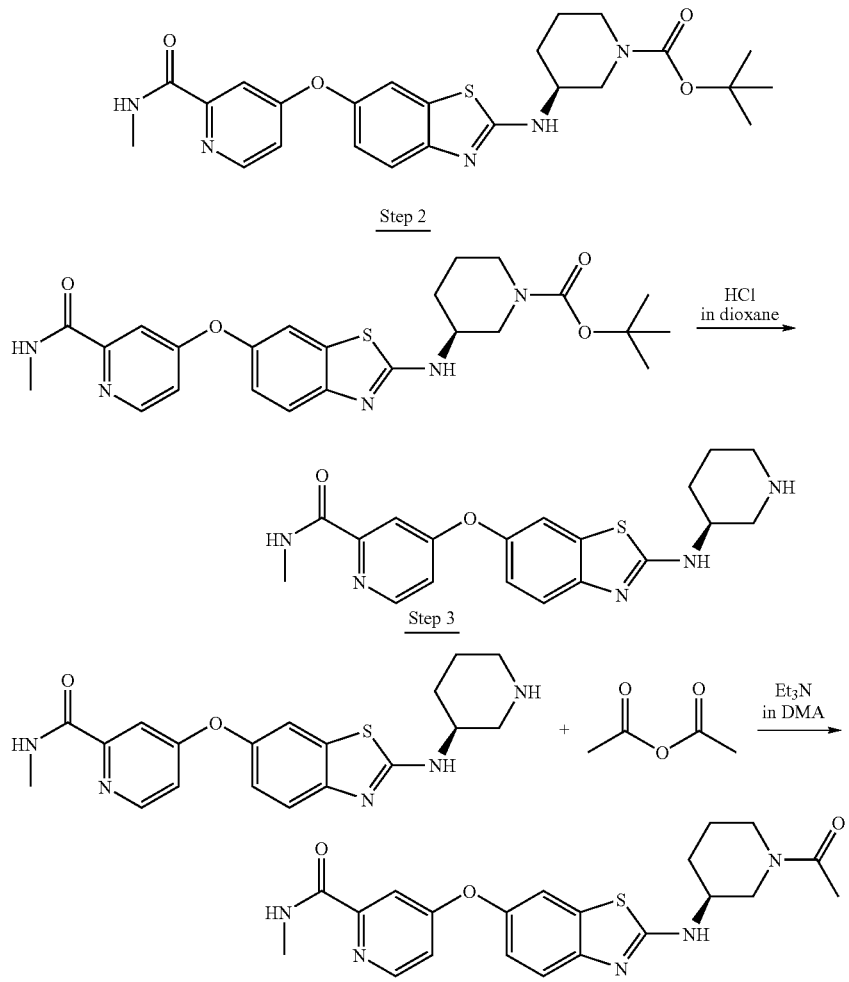

Step 1. Preparation of (S)-tert-butyl 3-(6-(2-(methyl-carbamoyl)pyridin-4-yloxy)benzo[d]thiazol-2-ylamino)piperidine-1-carboxylate To the solution of N-methyl-4-(2-(methylsulfinyl)benzo[d]thiazol-6-yloxy)picolinamide (104 mg, 0.3 mmol) in 2 ml of NMP was added (S)-tert-butyl 3-aminopiperidine-1-carboxylate (240 mg, 1.2 mmol). The reaction solution was stirred at 105° C. for 5 days. The crude reaction solution was purified on prep HPLC and evaporated in vacuo to give (S)-tert-butyl 3-(6-(2-(methylcarbamoyl)pyridin-4-yloxy)benzo[d]thiazol-2-ylamino)piperidine-1-carboxylate (56 mg, 0.12 mmol) as white powder. ES/MS m/z 484.2 (MH+).

Step 2. Preparation of (S)—N-methyl-4-(2-(piperidin-3-ylamino)benzo[d]thiazol-6-yloxy)picolinamide (S)-tert-butyl 3-(6-(2-(methylcarbamoyl)pyridin-4-yloxy)benzo[d]thiazol-2-ylamino)piperidine-1-carboxylate (56 mg, 0.12 mmol) was dissolved in 4 ml of 4M HCl in dioxane (16 mmol). The reaction solution was stirred at room temperature for 1 hour. The crude reaction solution was evaporated in vacuo to give (S)—N-methyl-4-(2-(piperidin-3-ylamino)benzo[d]thiazol-6-yloxy)picolinamide (46 mg, 0.12 mmol) as white solid. ES/MS m/z 384.0 (MH+).

Step 3. Preparation of (S)-4-(2-(1-acetylpiperidin-3-ylamino)benzo[d]thiazol-6-yloxy)-N-methylpicolinamide To the solution of (S)—N-methyl-4-(2-(piperidin-3-ylamino)benzo[d]thiazol-6-yloxy)picolinamide (13 mg, 30 μmol) and triethylamine (13 μL, 90 μmol) in 300 μL of DMA was added acetic anhydride (6 μl, 60 μmol). The reaction solution was stirred at room temperature for 1.5 hours. The crude reaction solution was purified on prep HPLC and evaporated in vacuo to give (S)-4-(2-(1-acetylpiperidin-3-ylamino)benzo[d]thiazol-6-yloxy)-N-methylpicolinamide (4.8 mg, 11 μmol) as white powder. ES/MS m/z 426.2 (MH+).

Example 166

Preparation of (S)-4-(2-(1-isobutyrylpiperidin-3-ylamino)benzo[d]thiazol-6-yloxy)-N-methylpicolinamide The subject compound was prepared according to the general Scheme below:

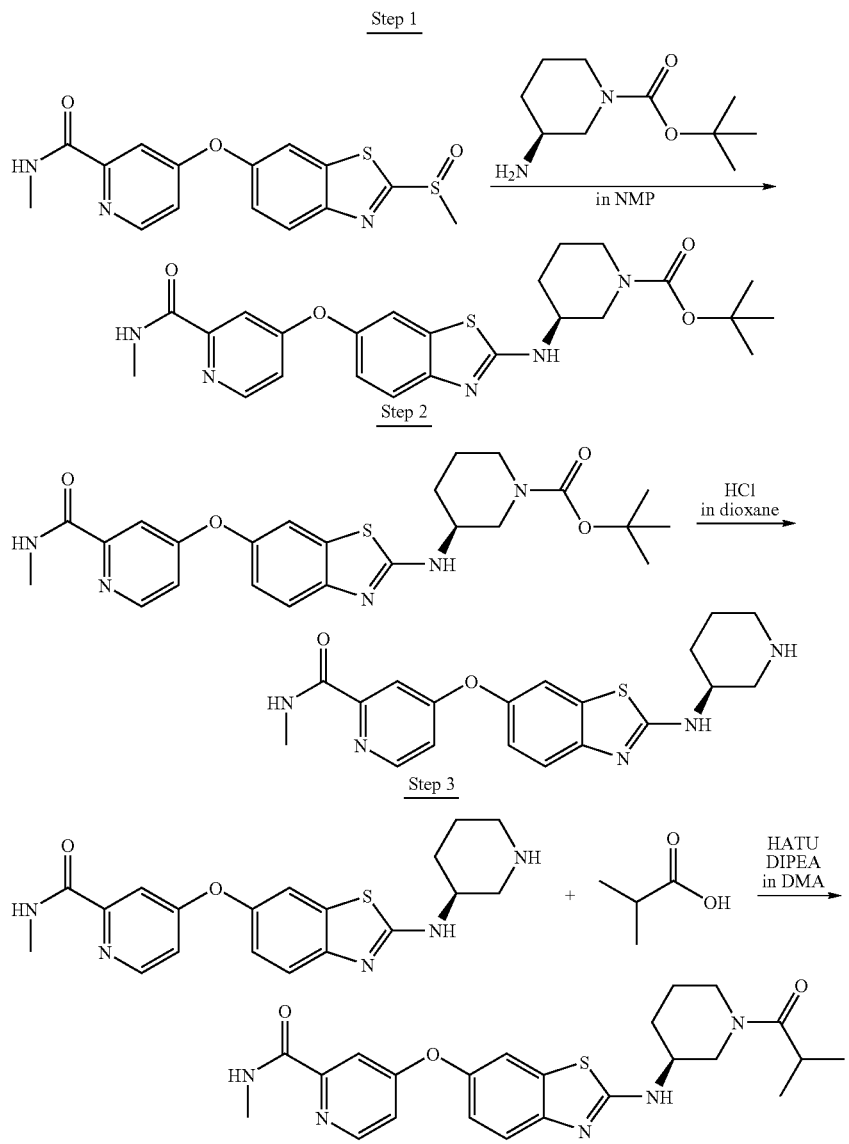

Step 1. Preparation of (S)-tert-butyl 3-(6-(2-(methyl-carbamoyl)pyridin-4-yloxy)benzo[d]thiazol-2-ylamino)piperidine-1-carboxylate To the solution of N-methyl-4-(2-(methylsulfinyl)benzo[d]thiazol-6-yloxy)picolinamide (104 mg, 0.3 mmol) in 2 ml of NMP was added (S)-tert-butyl 3-aminopiperidine-1-carboxylate (240 mg, 1.2 mmol). The reaction solution was stirred at 105° C. for 5 days. The crude reaction solution was purified on prep HPLC and evaporated in vacuo to give (S)-tert-butyl 3-(6-(2-(methylcarbamoyl)pyridin-4-yloxy)benzo[d]thiazol-2-ylamino)piperidine-1-carboxylate (56 mg, 0.12 mmol) as white powder. ES/MS m/z 484.2 (MH$^+$).

Step 2. Preparation of (S)—N-methyl-4-(2-(piperidin-3-ylamino)benzo[d]thiazol-6-yloxy)picolinamide (S)-tert-butyl 3-(6-(2-(methylcarbamoyl)pyridin-4-yloxy)benzo[d]thiazol-2-ylamino)piperidine-1-carboxylate (56 mg, 0.12 mmol) was dissolved in 4 ml of 4M HCl in dioxane (16 mmol). The reaction solution was stirred at room temperature for 1 hour. The crude reaction solution was evaporated in vacuo to give (S)—N-methyl-4-(2-(piperidin-3-ylamino)benzo[d]thiazol-6-yloxy)picolinamide (46 mg, 0.12 mmol) as white solid. ES/MS m/z 384.0 (MH$^+$).

Step 3. Preparation of (S)-4-(2-(1-isobutyrylpiperidin-3-ylamino)benzo[d]thiazol-6-yloxy)-N-methylpicolinamide To the reaction solution of isobutyric acid (4 µl, 40 µmol), HATU (15 mg, 40 µmol) and DIEA (14 µL, 80 µmol) in 400 µL of DMA was added (S)—N-methyl-4-(2-(piperidin-3-ylamino)benzo[d]thiazol-6-yloxy)picolinamide (13 mg, 30 µmol) and DIPEA (6 µL, 30 µmol). The reaction solution was stirred at room temperature for 16 hours. The crude reaction solution was purified on prep HPLC and evaporated in vacuo to give (S)-4-(2-(1-isobutyrylpiperidin-3-ylamino)benzo[d]thiazol-6-yloxy)-N-methylpicolinamide (6.8 mg, 15 µmol) as white powder. ES/MS m/z 454.2 (MH$^+$).

Example 167

Preparation of (S)-4-(2-(1-isobutyrylpiperidin-3-ylamino)benzo[d]thiazol-6-yloxy)-N-methylpicolinamide The subject compound was prepared according to the general Scheme below:

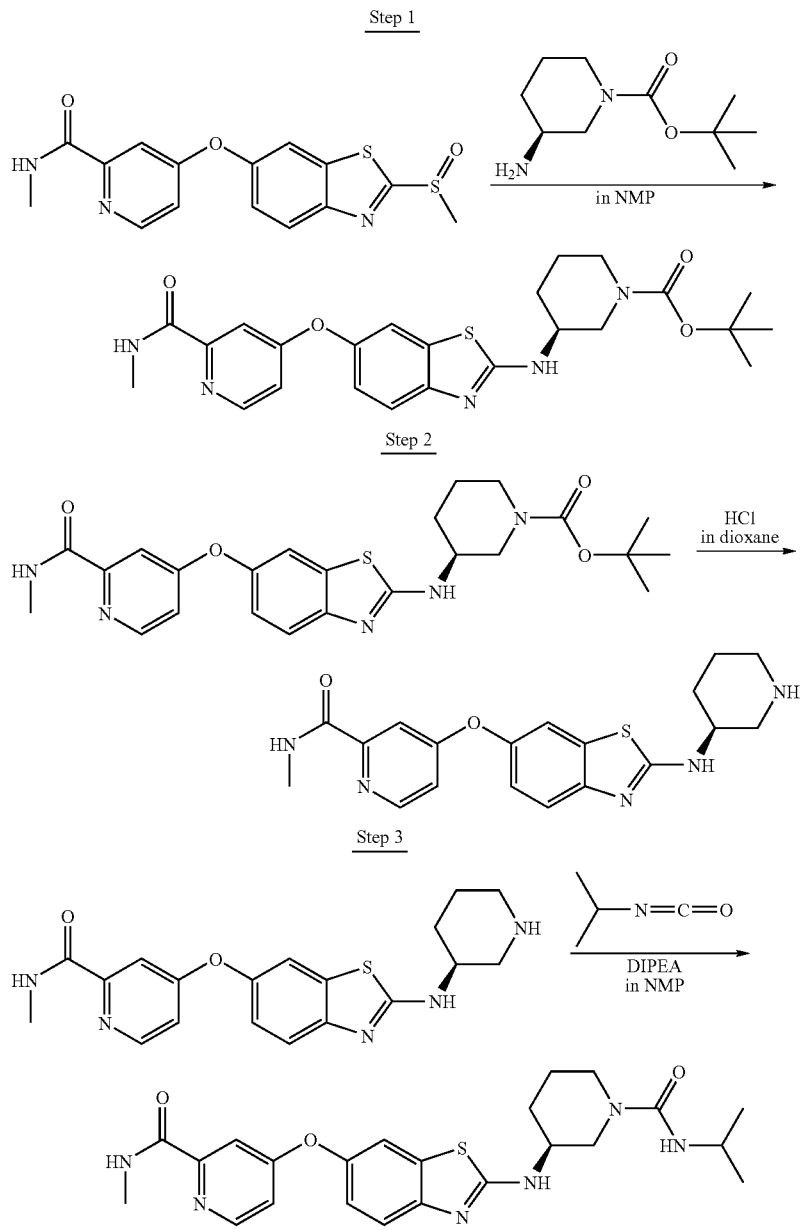

Step 1. Preparation of (S)-tert-butyl 3-(6-(2-(methylcarbamoyl)pyridin-4-yloxy)benzo[d]thiazol-2-ylamino)piperidine-1-carboxylate To the solution of N-methyl-4-(2-(methylsulfinyl)benzo[d]thiazol-6-yloxy)picolinamide (104 mg, 0.3 mmol) in 2 ml of NMP was added (S)-tert-butyl 3-aminopiperidine-1-carboxylate (240 mg, 1.2 mmol). The reaction solution was stirred at 105° C. for 5 days. The crude reaction solution was purified on prep HPLC and evaporated in vacuo to give (S)-tert-butyl 3-(6-(2-(methylcarbamoyl)pyridin-4-yloxy)benzo[d]thiazol-2-ylamino)piperidine-1-carboxylate (56 mg, 0.12 mmol) as white powder. ES/MS m/z 484.2 (MH$^+$).

Step 2. Preparation of (S)—N-methyl-4-(2-(piperidin-3-ylamino)benzo[d]thiazol-6-yloxy)picolinamide (S)-tert-butyl 3-(6-(2-(methylcarbamoyl)pyridin-4-yloxy)benzo[d]thiazol-2-ylamino)piperidine-1-carboxylate (56 mg, 0.12 mmol) was dissolved in 4 ml of 4M HCl in dioxane (16 mmol). The reaction solution was stirred at room temperature for 1 hour. The crude reaction solution was evaporated in vacuo to give (S)—N-methyl-4-(2-(piperidin-3-ylamino)benzo[d]thiazol-6-yloxy)picolinamide (46 mg, 0.12 mmol) as white solid. ES/MS m/z 384.0 (MH+).

Step 3. Preparation of (S)-4-(2-(1-(isopropylcarbamoyl)piperidin-3-ylamino)benzo[d]thiazol-6-yloxy)-N-methylpicolinamide To the solution of (S)—N-methyl-4-(2-(piperidin-3-ylamino)benzo[d]thiazol-6-yloxy)picolinamide (13 mg, 30 μmol) and DIPEA (17 μL, 100 μmol) in 300 μL of NMP was added 2-isocyanatopropane (5 μL, 50 μmol). The reaction solution was stirred at room temperature for 18 hours. The crude reaction solution was purified on prep HPLC and evaporated in vacuo to give (S)-4-(2-(1-(isopropylcarbamoyl)piperidin-3-ylamino)benzo[d]thiazol-6-yloxy)-N-methylpicolinamide (5.9 mg, 12 μmol) as white powder. ES/MS m/z 469.2 (MH+).

Example 168

Preparation of (R)-4-methyl-2-(6-(2-(1-methyl-1H-pyrazol-4-yl)pyridin-4-yloxy)benzo[d]thiazol-2-ylamino)pentan-1-ol The subject compound was prepared according to the general Scheme below:

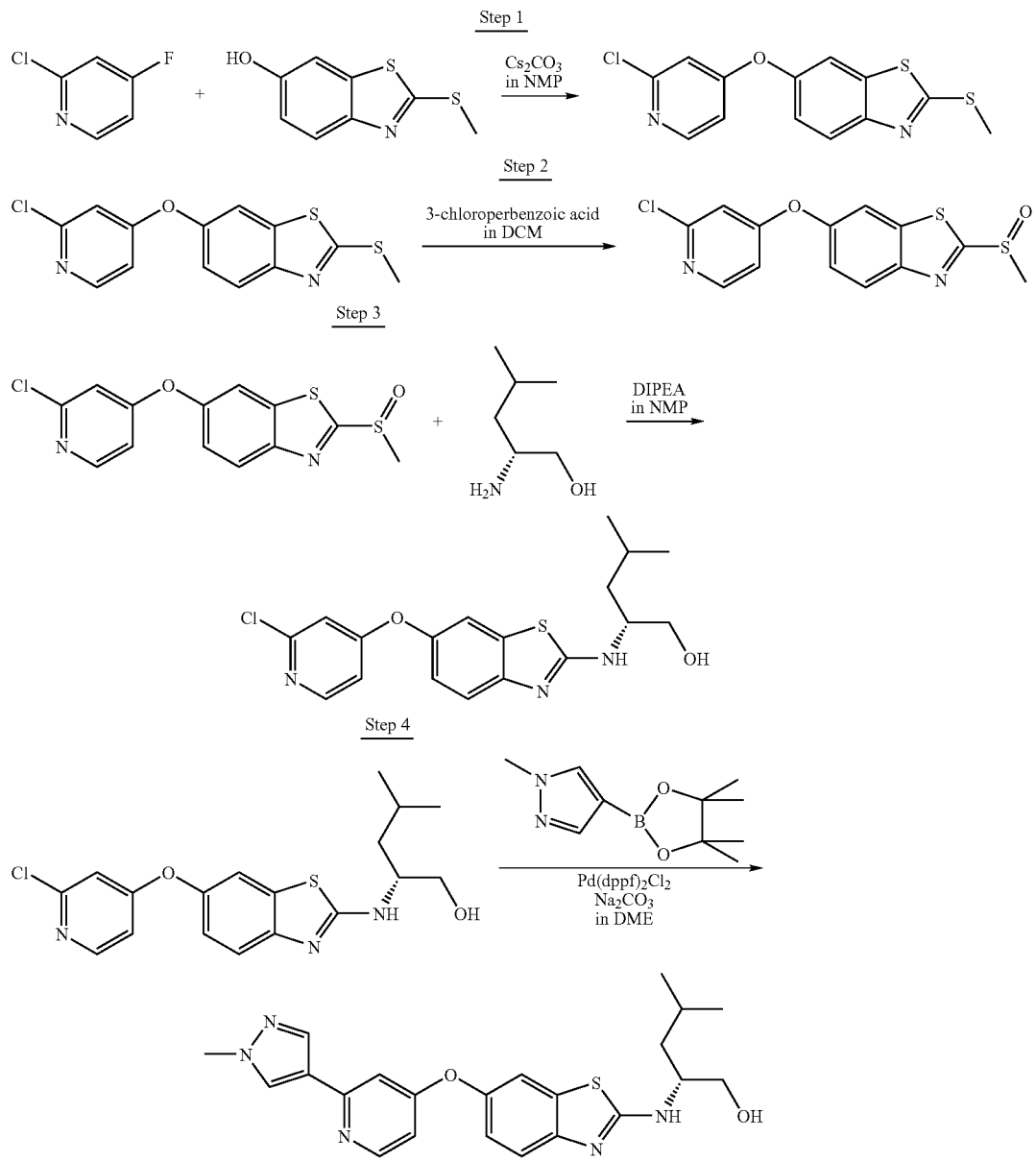

Step 1. Preparation of 6-(2-chloropyridin-4-yloxy)-2-(methylthio)benzo[d]thiazole To the mixture of 2-(methylthio)benzo[d]thiazol-6-ol (1 g, 5.08 mmol) and cesium carbonate (4.55 g, 14 mmol) in 15 ml of NMP was added 2-chloro-4-fluoropyridine (1.32 mg, 10 mmol). The reaction mixture was stirred at 55° C. for overnight. The reaction mixture was poured into 80 ml of aq. saturated NaHCO$_3$ and extracted with ethyl acetate (2×150 ml). The combined organic layers were washed with aq. 0.1M NaHSO$_4$ (60 ml), water (2×60 ml) and brine (60 ml), then dried over MgSO$_4$, filtered and evaporated in vacuo to give 6-(2-chloropyridin-4-yloxy)-2-(methylthio)benzo[d]thiazole (1.72 g) as brown oil that carried on to next step without purification. ES/MS m/z 308.9 (MH$^+$).

Step 2. Preparation of 6-(2-chloropyridin-4-yloxy)-2-(methylsulfinyl)benzo[d]thiazole To the solution of 6-(2-chloropyridin-4-yloxy)-2-(methylthio)benzo[d]thiazole (1.72 g, 5.08 mmol) in 32 ml of DCM was added 3-chloroperbenzoic acid (77%, 1.3 g, 5 mmol) portion-wise at 0° C. After being stirred at room temperature for 2 hours, the mixture was diluted with 80 ml of DCM. The resulting mixture was washed with aq. 0.2M Na$_2$S$_2$O$_3$ (25 ml), aq. saturated NaHCO$_3$ (25 ml), water (25 ml) and brine, then dried over Na$_2$SO$_4$, filtered and evaporated in vacuo to give a yellow brown solid (1.72 g). The residue was purified by flash column chromatography and evaporated in vacuo to give 6-(2-chloropyridin-4-yloxy)-2-(methylsulfinyl)benzo[d]thiazole (970 mg, 3 mmol) as ivory powder. ES/MS m/z 325.0 (MH$^+$).

Step 3. Preparation of (R)-2-(6-(2-chloropyridin-4-yloxy)benzo[d]thiazol-2-ylamino)-4-methylpentan-1-ol To the solution of 6-(2-chloropyridin-4-yloxy)-2-(methylsulfinyl)benzo[d]thiazole (26 mg, 80 μmol) in 400 μL of NMP was added (R)-2-amino-4-methylpentan-1-ol (33 μL, 250 μmol) and DIPEA (17 μL, 100 μmol). The reaction solution was stirred at 100° C. for 18 hours. The crude reaction solution was purified on prep HPLC and evaporated in vacuo to give (R)-2-(6-(2-chloropyridin-4-yloxy)benzo[d]thiazol-2-ylamino)-4-methylpentan-1-ol (12 mg, 31 μmol) as powder. ES/MS m/z 378.1 (MH$^+$).

Step 4. Preparation of (R)-4-methyl-2-(6-(2-(1-methyl-1H-pyrazol-4-yl)pyridin-4-yloxy)benzo[d]thiazol-2-ylamino)pentan-1-ol To the reaction mixture of (R)-2-(6-(2-chloropyridin-4-yloxy)benzo[d]thiazol-2-ylamino)-4-methylpentan-1-ol (12 mg, 31 μmol) in 400 μL of DME, 1-methyl-4-(4,4,5,5-tetramethyl-1,3,2-dioxaborolan-2-yl)-1H-pyrazole (21 mg, 100 μmol), Pd(dppf)$_2$Cl$_2$ (7 mg, 8 μmol) and aq. 2M Na$_2$CO$_3$ (100 μL, 200 μmol) were added. The reaction mixture was stirred at 90° C. for 24 hours. The reaction mixture filtered, purified on prep HPLC and evaporated in vacuo to give (R)-4-methyl-2-(6-(2-(1-methyl-1H-pyrazol-4-yl)pyridin-4-yloxy)benzo[d]thiazol-2-ylamino)pentan-1-ol as powder (4.2 mg). ES/MS m/z 424.1 (MH$^+$).

Example 169

Preparation of (S)—N-(1-(cyclopropylsulfonyl)piperidin-3-yl)-6-(2-(1-methyl-1H-pyrazol-4-yl)pyridin-4-yloxy)benzo[d]thiazol-2-amine The subject compound was prepared according to the general Scheme below:

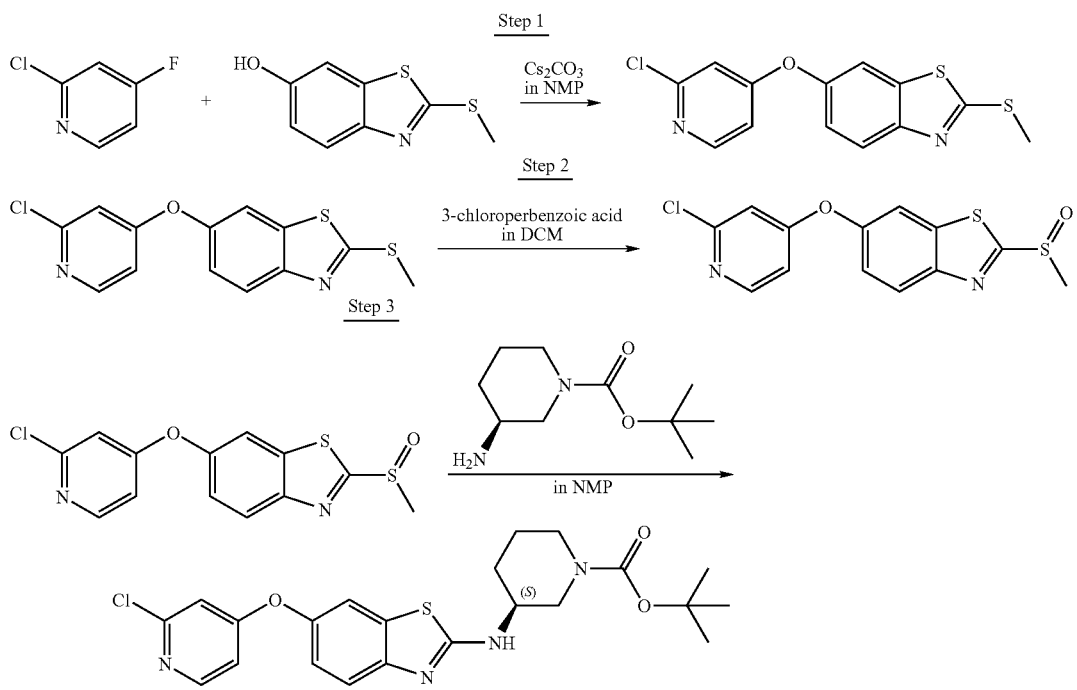

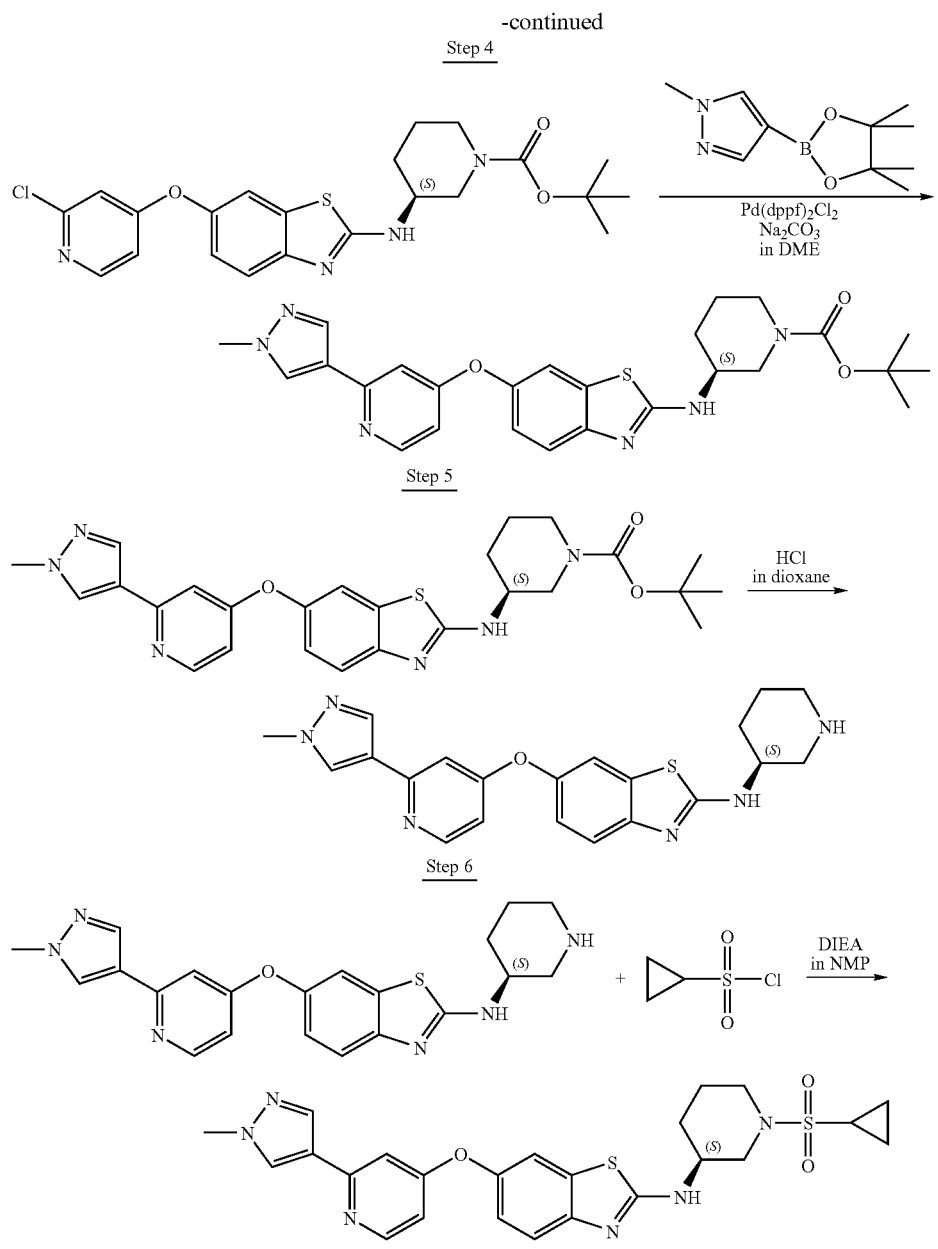

Step 1. Preparation of 6-(2-chloropyridin-4-yloxy)-2-(methylthio)benzo[d]thiazole To the mixture of 2-(methylthio)benzo[d]thiazol-6-ol (1 g, 5.08 mmol) and cesium carbonate (4.55 g, 14 mmol) in 15 ml of NMP was added 2-chloro-4-fluoropyridine (1.32 mg, 10 mmol). The reaction mixture was stirred at 55° C. for overnight. The reaction mixture was poured into 80 ml of aq. saturated NaHCO₃ and extracted with ethyl acetate (2×150 ml). The combined organic layers were washed with aq. 0.1M NaHSO₄ (60 ml), water (2×60 ml) and brine (60 ml), then dried over MgSO₄, filtered and evaporated in vacuo to give 6-(2-chloropyridin-4-yloxy)-2-(methylthio)benzo[d]thiazole (1.72 g) as brown oil that carried on to next step without purification. ES/MS m/z 308.9 (MH⁺).

Step 2. Preparation of 6-(2-chloropyridin-4-yloxy)-2-(methylsulfinyl)benzo[d]thiazole To the solution of 6-(2-chloropyridin-4-yloxy)-2-(methylthio)benzo[d]thiazole (1.72 g, 5.08 mmol) in 32 ml of DCM was added 3-chloroperbenzoic acid (77%, 1.3 g, 5 mmol) portion-wise at 0° C. After being stirred at room temperature for 2 hours, the mixture was diluted with 80 ml of DCM. The resulting mixture was washed with aq. 0.2M Na₂S₂O₃ (25 ml), aq. saturated NaHCO₃ (25 ml), water (25 ml) and brine, then dried over Na₂SO₄, filtered and evaporated in vacuo to give a yellow brown solid (1.72 g). The residue was purified by flash column chromatography and evaporated in vacuo to give 6-(2-chloropyridin-4-yloxy)-2-(methylsulfinyl)benzo[d]thiazole (970 mg, 3 mmol) as ivory powder. ES/MS m/z 325.0 (MH⁺).

Step 3. Preparation of (S)-tert-butyl 3-(6-(2-chloro-pyridin-4-yloxy)benzo[d]thiazol-2-ylamino)piperidine-1-carboxylate To the solution of 6-(2-chloropyridin-4-yloxy)-2-(methylsulfinyl)benzo[d]thiazole (100 mg, 0.31 mmol) in 1.6 ml of NMP was added (S)-tert-butyl 3-aminopiperidine-1-carboxylate (200 mg, 1 mmol) and DIPEA (70 µL, 0.4 mmol). The reaction solution was stirred at 95° C. for 5 days. The crude reaction solution was purified on prep HPLC and evaporated in vacuo to give (S)-tert-butyl 3-(6-(2-chloropyridin-4-yloxy)benzo[d]thiazol-2-ylamino)piperidine-1-carboxylate (160 mg) as TFA salt. ES/MS m/z 461.1 (MH+).

Step 4. Preparation of (S)-tert-butyl 3-(6-(2-(1-methyl-1H-pyrazol-4-yl)pyridin-4-yloxy)benzo[d]thiazol-2-ylamino)piperidine-1-carboxylate To the reaction mixture of (S)-tert-butyl 3-(6-(2-chloropyridin-4-yloxy)benzo[d]thiazol-2-ylamino)piperidine-1-carboxylate (68 mg, 148 µmol) in 1.2 m of DME, 1-methyl-4-(4,4,5,5-tetramethyl-1,3,2-dioxaborolan-2-yl)-1H-pyrazole (40 mg, 192 µmol), Pd(dppf)$_2$Cl$_2$ (18 mg, 22 µmol) and aq. 2M Na$_2$CO$_3$ (400 µL, 800 µmol) were added. The reaction mixture was stirred at 85° C. for 72 hours or until done by LC. The reaction mixture was poured into 40 ml of saturated NaHCO$_3$ solution and extracted with ethyl acetate (2×80 ml). The combined organic layers were washed with water (2×20 ml) and brine (20 ml), then dried over Na$_2$SO$_4$, filtered and evaporated in vacuo to give a brown glue (77 mg) that was purified on prep HPLC to give (S)-tert-butyl 3-(6-(2-(1-methyl-1H-pyrazol-4-yl)pyridin-4-yloxy)benzo[d]thiazol-2-ylamino)piperidine-1-carboxylate as powder (9.6 mg). ES/MS m/z 507.1 (MH+).

Step 5. Preparation of (S)—N-methyl-4-(2-(piperidin-3-ylamino)benzo[d]thiazol-6-yloxy)picolinamide (S)-tert-butyl 3-(6-(2-(1-methyl-1H-pyrazol-4-yl)pyridin-4-yloxy)benzo[d]thiazol-2-ylamino)piperidine-1-carboxylate (9.6 mg, 19 µmol) was dissolved in 1 ml of 4M HCl in dioxane (4 mmol). The reaction solution was stirred at room temperature for 1 hour. The crude reaction solution was evaporated in vacuo to give (S)-6-(2-(1-methyl-1H-pyrazol-4-yl)pyridin-4-yloxy)-N-(piperidin-3-yl)benzo[d]thiazol-2-amine (7.6 mg, 18 µmol) as white solid. ES/MS m/z 407.1 (MH+).

Step 6. Preparation of (S)—N-(1-(cyclopropylsulfonyl)piperidin-3-yl)-6-(2-(1-methyl-1H-pyrazol-4-yl)pyridin-4-yloxy)benzo[d]thiazol-2-amine To the solution of (S)-6-(2-(1-methyl-1H-pyrazol-4-yl)pyridin-4-yloxy)-N-(piperidin-3-yl)benzo[d]thiazol-2-amine (7.6 mg, 18 µmol) and DIPEA (35 µL, 200 µmol) in 400 µL of NMP was added cyclopropanesulfonyl chloride (10 mg, 98 µmol). The reaction solution was stirred at 55 for 16 hours. The crude reaction solution was purified on prep HPLC and evaporated in vacuo to give (S)—N-(1-(cyclopropylsulfonyl)piperidin-3-yl)-6-(2-(1-methyl-1H-pyrazol-4-yl)pyridin-4-yloxy)benzo[d]thiazol-2-amine (6.2 mg, 12 µmol) as white powder. ES/MS m/z 511.2 (MH+).

Example 170

Preparation of N-(cyclohexylmethyl)-6-(2-(ethylamino)pyridin-4-yloxy)benzo[d]thiazol-2-amine

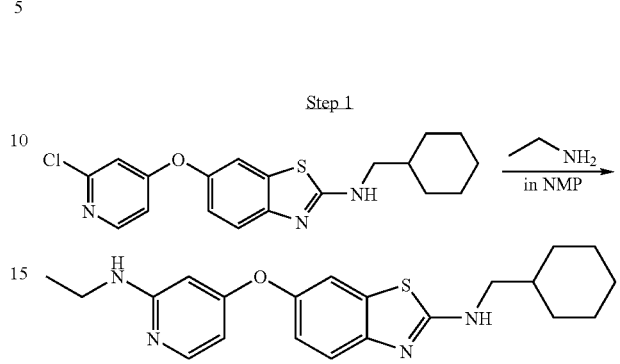

To the reaction solution of 6-(2-chloropyridin-4-yloxy)-N-(cyclohexylmethyl)benzo[d]thiazol-2-amine (12 mg, 0.03 mmol) in 400 µL of NMP was added DIPEA (9 µL, 0.05 mmol) and 70% ethylamine in water (200 µL, 2.51 mmol). The reaction mixture was stirred at 110° C. for 96 hours or until done by LC. The crude reaction mixture was filtered, purified on prep HPLC and evaporated in vacuo to give N-(cyclohexylmethyl)-6-(2-(ethylamino)pyridin-4-yloxy)benzo[d]thiazol-2-amine as TFA salt (1.8 mg). ES/MS m/z 383.1 (MH+).

Example 171

N-cyclopropyl-4-(2-((1R,2R)-2-hydroxycyclohexylamino)benzo[d]thiazol-6-yloxy)picolinamide The subject compound was prepared according to the general Scheme below:

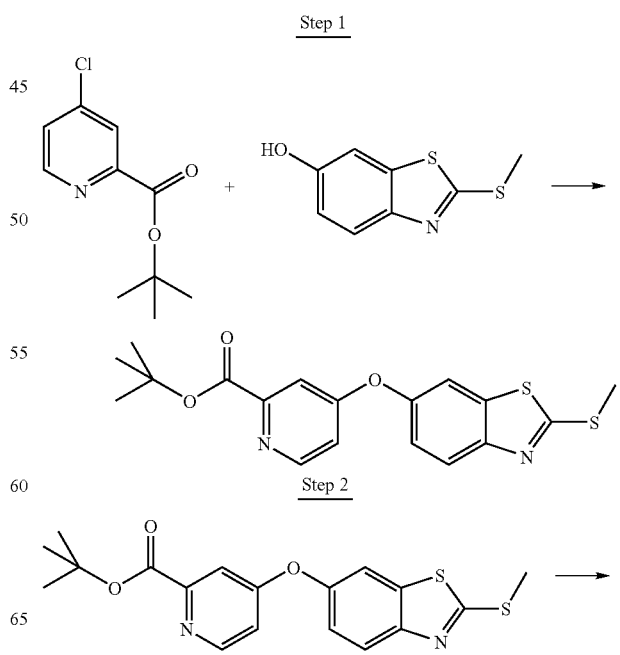

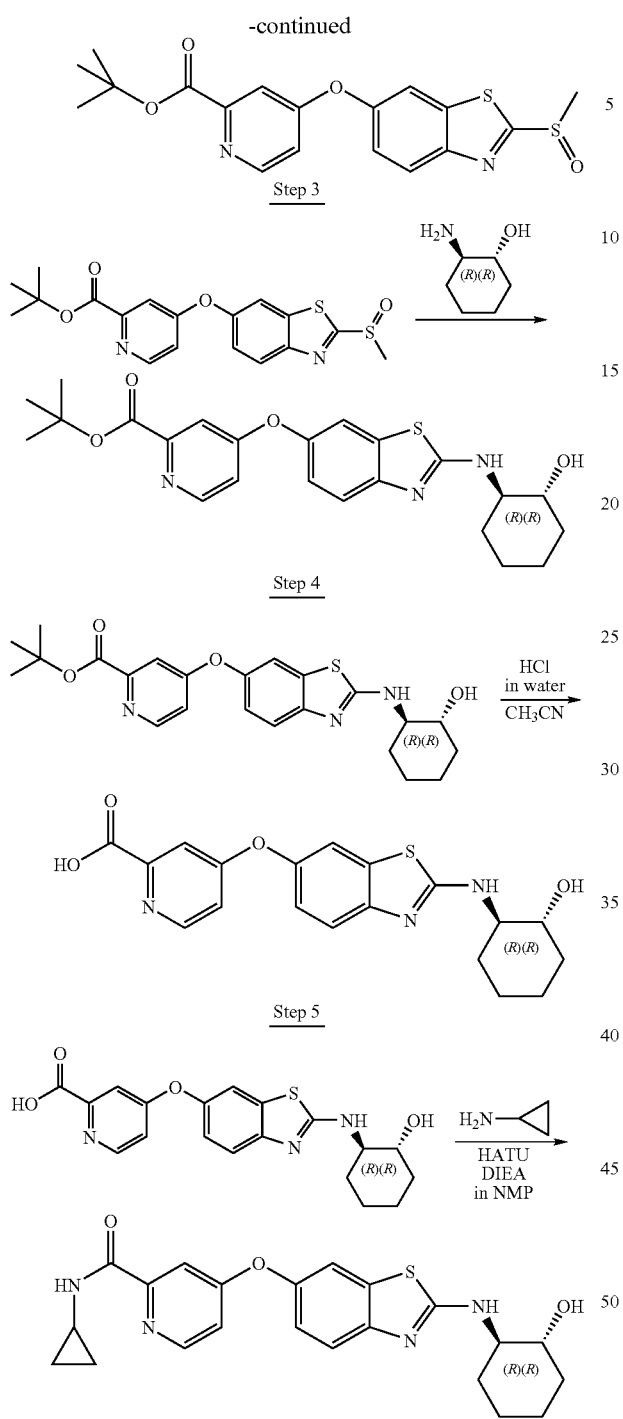

0%-50% mixture to give 5.84 g of the titled compound as brown powder (62%). MH+=375.

Step 2. Synthesis of tert-butyl 4-(2-(methylsulfinyl)benzo[d]thiazol-6-yloxy) picolinate To a solution of the tert-butyl 4-(2-(methylthio)benzo[d]thiazol-6-yloxy)picolinate (5.84 g, 15.61 mmol, 1.0 eq) in 25 mL of methylene chloride was added 3-chloroperoxybenzoic acid (77%, 3.84 g, 17.17 mmol, 1.1 eq). The reaction mixture was stirred at room temperature for 1.5 hours and then was diluted with 200 mL of methylene chloride. The resulting mixture was washed with aqueous sodium bicarbonate and brine then dried over MgSO$_4$, filtered, and evaporated under reduced pressure to give crude product, which was used to next step without further purification. MH+=391.0.

Step 3. Preparation of tert-butyl 4-(2-((1R,2R)-2 hydroxycyclohexylamino)-benzo[d]thiazol-6-yloxy) picolinate To the solution of tert-butyl 4-(2-(methylsulfinyl)benzo[d]thiazol-6-yloxy)picolinate (500 mg, 1.25 mmol) in 10 ml of NMP was added (1R,2R)-cyclohexane-1,2-diamine (581 mg, 3.84 mmol) and DIPEA (0.995 ml, 5.76 mmol). The reaction solution was stirred at 100° C. for 3 days. The crude reaction solution was purified on prep HPLC and evaporated in vacuo to give tert-butyl 4-(2-((1R,2R)-2-hydroxycyclohexylamino) benzo[d]thiazol-6-yloxy)picolinate (240 mg, 0.544 mmol) as white powder. ES/MS m/z 442.5 (MH$^+$).

Step 4. Preparation of 4-(2-((1R,2R)-2-hydroxycyclohexylamino)benzo[d]thiazol-6-yloxy)picolinic acid To the solution of tert-butyl 4-(2-((1R,2R)-2-hydroxycyclohexylamino)benzo[d]thiazol-6-yloxy)picolinate (250 mg, 0566 mmol) in 10 ml of acetonitrile was added 6 M of hydrochloric acid (1 ml, 6 mmol). The reaction solution was stirred at room temperature for 1 hour and then at 60° C. for 2 hours. The crude reaction solution was concentrated and re-dissolved with 10 ml of acetonitrile. The resulting solution was evaporated in vacuo to give light brown oily product 4-(2-((1R,2R)-2-hydroxycyclohexylamino)benzo[d]thiazol-6-yloxy)picolinic acid (215 mg, 0.56 mmol). ES/MS m/z 386.5 (MH$^+$).

Step 5. Preparation of N-cyclopropyl-4-(2-((1R,2R)-2-hydroxycyclohexylamino)-benzo[d]thiazol-6-yloxy)picolinamide To the reaction solution of 4-(2-((1R,2R)-2-hydroxycyclohexylamino)benzo[d]thiazol-6-yloxy)picolinic acid (5 mg, 39 μmol), HATU (15 mg, 39 μmol) and DIPEA (14 μL, 78 μmol) in 1 ml of NMP was added cyclopropylamine (7 ul mg, 30 μmol). The reaction solution was stirred at room temperature for 12 hours. The crude reaction solution was purified on prep HPLC and evaporated in vacuo to give N-cyclopropyl-4-(2-((1R,2R)-2-hydroxycyclohexylamino)benzo[d]thiazol-6-yloxy)picolinamide (1 mg, 2.3 μmol) as white powder. ES/MS m/z 425.2 (MH$^+$).

Example 172

Preparation of 4-(2-(cyclohexylmethoxy)benzo[d]thiazol-6-yloxy)-N-methylpicolinamide The subject compound was prepared according to the general Scheme below:

Step 1

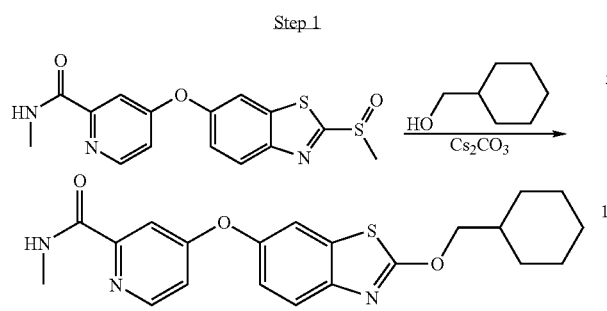

Step 1. Preparation of 4-(2-(cyclohexylmethoxy)benzo[d]thiazol-6-yloxy)-N-methylpicolinamide N-methyl-4-(2-(methylsulfinyl)benzo[d]thiazol-6-yloxy)picolinamide (15 mg, 43 μmol) was mixed with 500 μL of cyclohexylmethanol and cesium carbonate (42 mg, 0.13 mmol). The resulting reaction mixture was stirred at 90° C. for 12 hours. The crude reaction mixture was filtered and purified on prep HPLC and then evaporated in vacuo to give 4-(2-(cyclohexylmethoxy)benzo[d]thiazol-6-yloxy)-N-methylpicolinamide (7 mg, 17.6 μmol) as powder. ES/MS m/z 398.1 (MH+).

Example 173

Preparation of (1R,2R)-2-(6-(2-chloropyridin-4-yloxy)benzo[d]thiazol-2-ylamino)cyclohexanol The subject compound was prepared according to the general Scheme below:

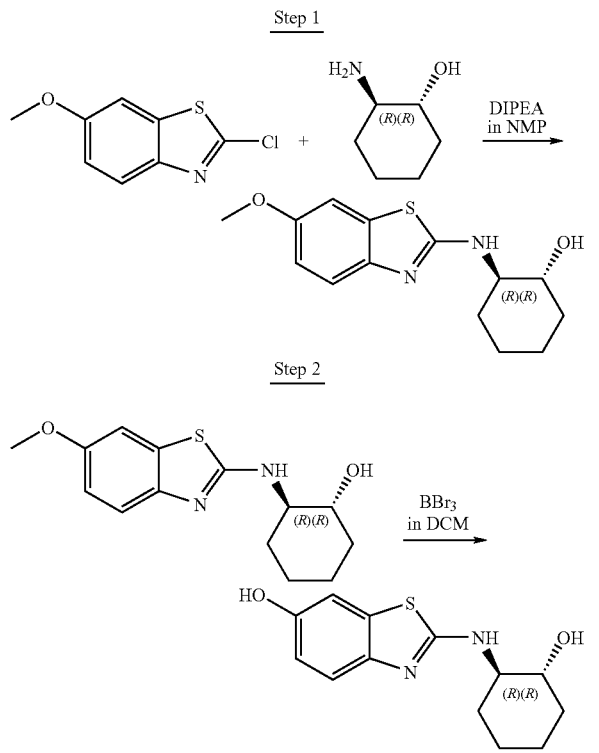

-continued
Step 3

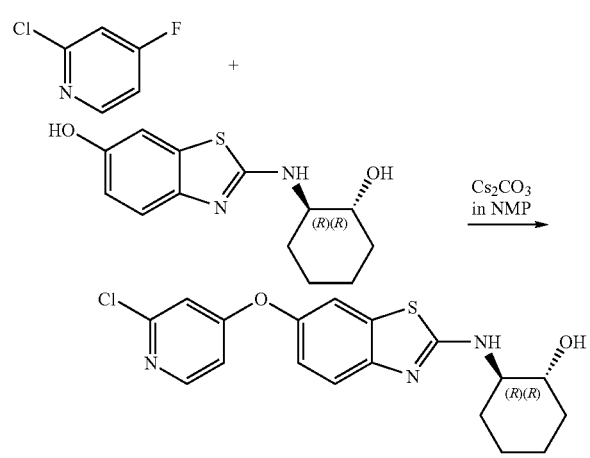

Step 1. Preparation of (1R,2R)-2-(6-methoxybenzo[d]thiazol-2-ylamino)cyclohexanol To the solution of 2-chloro-6-methoxybenzo[d]thiazole (1.0 g, 5 mmol) in 5.5 ml of NMP was added (1R,2R)-2-aminocyclohexanol hydrochloride (910 mg, 6 mmol) and DIPEA (2.44 ml, 14 mmol). The reaction solution was stirred at 115° C. for 96 hours. The crude reaction solution was purified by prep HPLC to give purified fractions that was combined and neutralized with solid NaHCO₃. The resulting solution was extracted with ethyl acetate (2×300 ml). The combined organic layers were washed with water (60 ml) and brine (60 ml), then dried over Na₂SO₄ and evaporated in vacuo to give (1R,2R)-2-(6-methoxybenzo[d]thiazol-2-ylamino)cyclohexanol (1.06 g, 3.81 mmol) as an ivory solid. ES/MS m/z 279.1 (MH+).

Step 2. Preparation of 2-((1R,2R)-2-hydroxycyclohexylamino)benzo[d]thiazol-6-ol To the solution of (1R,2R)-2-(6-methoxybenzo[d]thiazol-2-ylamino)cyclohexanol (1.06 g, 3.81 mmol) in 16 ml of DCM was added 1 M boron tribromide in DCM (8 ml, 8 mmol) slowly at 0° C. The reaction solution was stirred at room temperature for 2 hours. Removal of all solvent in vacuo, followed by quenching with water (ca. 30 ml) and diluted NaHCO₃ solution, and extraction of aqueous phase with ethyl acetate (3×100 ml) and drying of combined organic extracts over Na₂SO₄ and subsequent removal of ethyl acetate in vaccuo yielded the desired product (1.16 g) as pink solid. The residue was purified by flash column chromatography to give 2-((1R,2R)-2-hydroxycyclohexylamino)benzo[d]thiazol-6-ol (1.0 g, 3.78 mmol) as brown solid. ES/MS m/z 265.1 (MH+).

Step 3. Preparation of (1R,2R)-2-(6-(2-chloropyridin-4-yloxy)benzo[d]thiazol-2-ylamino)cyclohexanol To the mixture of 2-((1R,2R)-2-hydroxycyclohexylamino)benzo[d]thiazol-6-ol (265 mg, 1 mmol) and cesium carbonate (651 mg, 2 mmol) in 3 ml of NMP was added 2-chloro-4-fluoropyridine (263 mg, 2 mmol). The reaction mixture was stirred at 60° C. for 20 hours. The crude reaction mixture was filtered and then purified on prep HPLC to give (1R,2R)-2-

(6-(2-chloropyridin-4-yloxy)benzo[d]thiazol-2-ylamino)cyclohexanol as powder (341 mg, 0.9 mmol). ES/MS m/z 376.0 (MH+).

Example 174

Preparation of (1R,2R)-2-(6-(2-(1-methyl-1H-pyrazol-4-yl)pyridin-4-yloxy)benzo[d]thiazol-2-ylamino)cyclohexanol

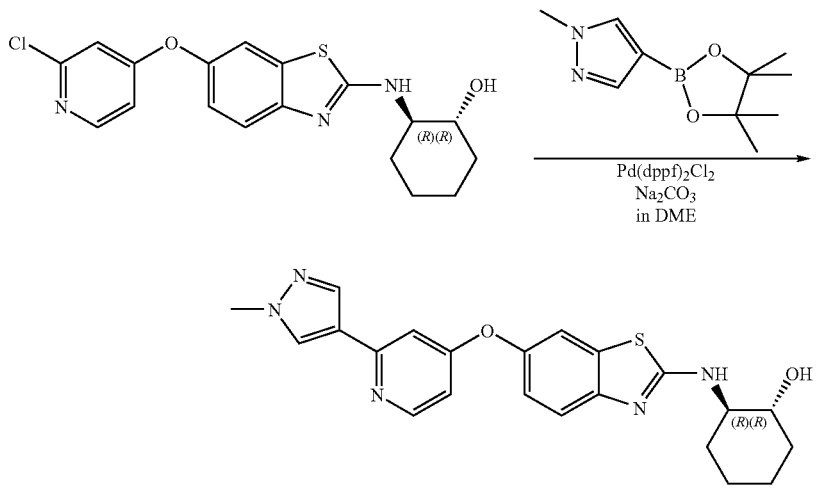

Step 4. Preparation of (1R,2R)-2-(6-(2-(1-methyl-1H-pyrazol-4-yl)pyridin-4-yloxy)benzo[d]thiazol-2-ylamino)cyclohexanol To the reaction mixture of (1R,2R)-2-(6-(2-chloropyridin-4-yloxy)benzo[d]thiazol-2-ylamino)cyclohexanol (20 mg, 40 μmol) in 400 μL of DME, 1-methyl-4-(4,4,5,5-tetramethyl-1,3,2-dioxaborolan-2-yl)-1H-pyrazole (21 mg, 100 μmol), Pd(dppf)$_2$Cl$_2$ (4 mg, 5 μmol) and 2M Na$_2$CO$_3$ (100 μL, 200 μmol) were added. The reaction mixture was stirred at 90° C. for 24 hours. The reaction mixture was poured into 10 ml of saturated NaHCO$_3$ solution and extracted with ethyl acetate (2×30 ml). The combined organic layers were washed with water (2×10 ml) and brine (20 ml), then dried over Na$_2$SO$_4$ and evaporated in vacuo to give a brown solid (65 mg) that was purified on prep HPLC to give (1R,2R)-2-(6-(2-(1-methyl-1H-pyrazol-4-yl)pyridin-4-yloxy)benzo[d]thiazol-2-ylamino)cyclohexanol as powder (6.4 mg). ES/MS m/z 422.2 (MH+).

Example 175

Preparation of (1R,2R)-2-(6-(2-(1-methyl-1H-imidazol-5-yl)pyridin-4-yloxy)benzo[d]thiazol-2-ylamino)cyclohexanol The subject compound was prepared according to the general Scheme below:

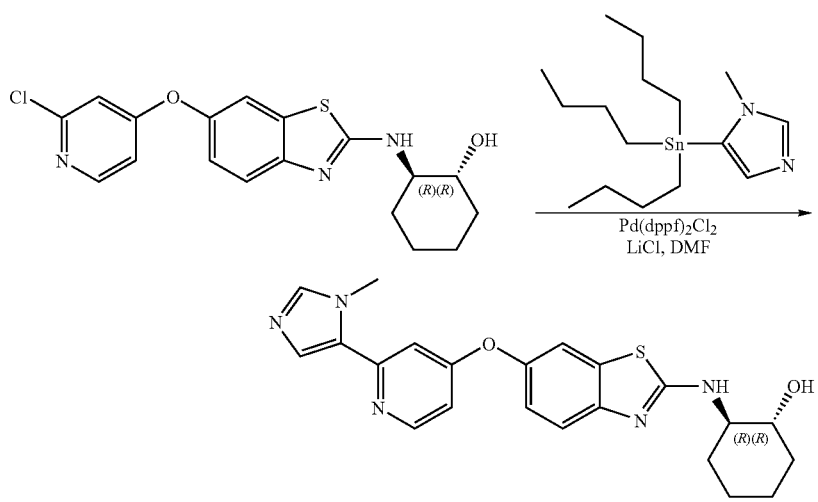

Preparation of (1R,2R)-2-(6-(2-(1-methyl-1H-imidazol-5-yl)pyridin-4-yloxy)benzo[d]thiazol-2-ylamino)cyclohexanol To the reaction mixture of (1R,2R)-2-(6-(2-chloropyridin-4-yloxy)benzo[d]thiazol-2-ylamino)cyclohexanol (11 mg, 0.029 mmol) in 0.5 ml of DMF was added Pd(dppf)$_2$Cl$_2$ (7.2 mg, 0.0088 mmol), LiCl (19 mg, 0.44 mmol) and then 1-methyl-5-(tributylstannyl)-1H-imidazole (44 mg, 0.117 mmol). The reaction solution was stirred at 105-110° C. for 18 hours or done by LC. The crude reaction mixture was filtered, purified on prep HPLC and lyophilized to give (1R,2R)-2-(6-(2-(1-methyl-1H-imidazol-5-yl)pyridin-4-yloxy)benzo[d]thiazol-2-ylamino)cyclohexanol as TFA salt (3.5 mg). ES/MS m/z 422.1 (MH$^+$).

Example 176

Preparation of (1R,2R)-2-(6-(2-(1-(2,2-difluoroethyl)-1H-pyrazol-4-yl)pyridin-4-yloxy)benzo[d]thiazol-2-ylamino)cyclohexanol The subject compound was prepared according to the general Scheme below:

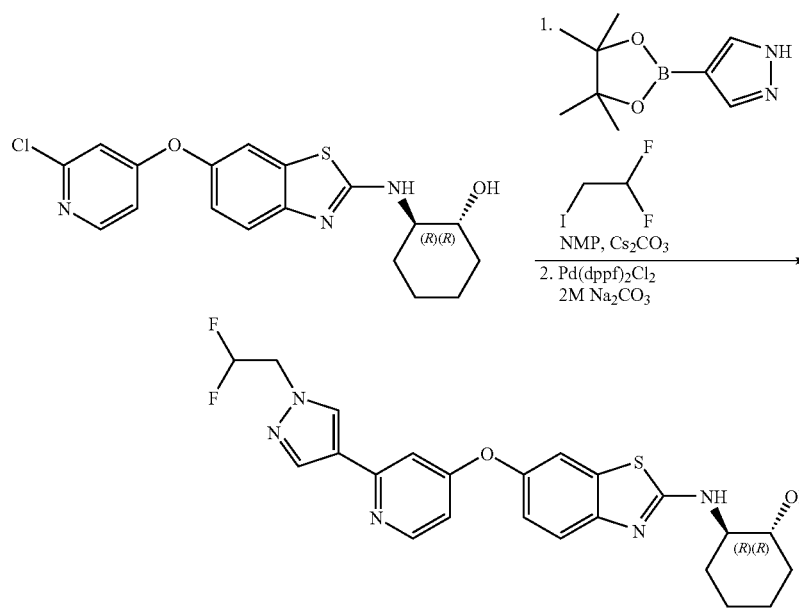

Preparation of (1R,2R)-2-(6-(2-(1-(2,2-difluoroethyl)-1H-pyrazol-4-yl)pyridin-4-yloxy)benzo[d]thiazol-2-ylamino)cyclohexanol To the reaction mixture of 4-(4,4,5,5-tetramethyl-1,3,2-dioxaborolan-2-yl)-1H-pyrazole (210 mg, 1.08 mmol) in 2.0 ml of NMP was added Cesium Carbonate (672 mg, 2.06 mmol). The reaction mixture was stirred for 5 minutes and then 1,1-difluoro-2-iodoethane (197 mg, 1.03 mmol) was added and stirred at RT for 40 hours. From the above crude reaction mixture remove (0.8 ml, 0.432 mol) and use. (The remaining 1.2 ml was stored in freezer). To the 0.8 ml reaction mixture add (1R,2R)-2-(6-(2-chloropyridin-4-yloxy)benzo[d]thiazol-2-ylamino)cyclohexanol (20 mg, 0.053 mmol), Pd(dppf)$_2$Cl$_2$ (15.2 mg, 0.019 mmol) and 2M Na$_2$CO$_3$ (0.150 ml, 0.3 mmol). The reaction mixture was microwaved at 140° C. for 720 seconds. The crude reaction mixture was filtered, purified on prep HPLC and lyophilized to give (1R,2R)-2-(6-(2-(1-(2,2-difluoroethyl)-1H-pyrazol-4-yl)pyridin-4-yloxy)benzo[d]thiazol-2-ylamino)cyclohexanol as TFA salt (4.6 mg). ES MS m/z 472.0 (MH$^+$).

Example 177

Preparation of (1R,2R)-2-(6-(2-(4-methyl-1H-imidazol-2-yl)pyridin-4-yloxy)benzo[d]thiazol-2-ylamino)cyclohexanol The subject compound was prepared according to the general Scheme below:

Step 1

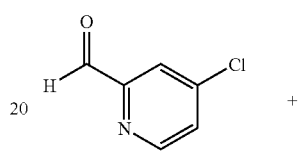

+

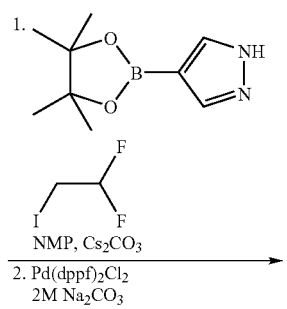

-continued

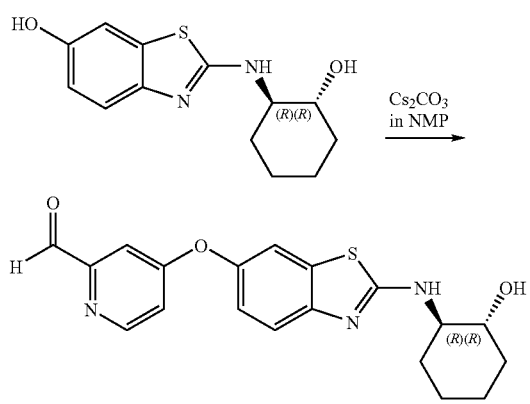

-continued

Step 2

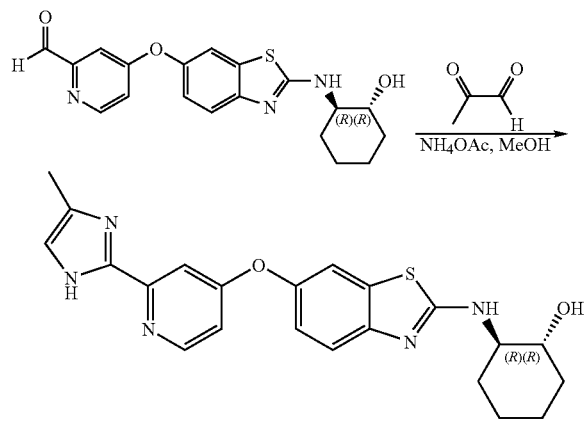

Step 1. Preparation of 4-(2-((1R,2R)-2-hydroxycyclohexylamino)benzo[d]thiazol-6-yloxy)picolinaldehyde To the reaction mixture of 2-((1R,2R)-2-hydroxycyclohexylamino)benzo[d]thiazol-6-ol (90 mg, 0.34 mmol) in 1.9 ml of NMP was added Cesium Carbonate (232 mg, 0.71 mmol) and 4-chloropicolinaldehyde (125 mg, 0.883 mmol). The reaction mixture was stirred at RT. for 10 minutes and then microwaved at 150° C. for 750 seconds. The crude reaction mixture was filtered, purified on prep HPLC and lyophilized to give 4-(2-((1R,2R)-2-hydroxycyclohexylamino)benzo[d]thiazol-6-yloxy)picolinaldehyde as TFA salt (88 mg). ES/MS m/z 388.1 (MH$^+$) as the hydrate (+18).

Step 2. Preparation of (1R,2R)-2-(6-(2-(4-methyl-1H-imidazol-2-yl)pyridin-4-yloxy)benzo[d]thiazol-2-ylamino)cyclohexanol To the reaction mixture of 4-(2-((1R,2R)-2-hydroxycyclohexylamino)benzo[d]thiazol-6-yloxy)picolinaldehyde (16 mg, 0.041 mmol) in 0.75 ml of MeOH was added ammonium acetate (32 mg, 0.41 mmol) and 2-oxopropanal 40% wt solution of in water (0.037 ml, 0.21 mmol). The reaction mixture was stirred at 70° C. for 2 hours. The crude reaction mixture was concentrated, re-dissolved in 0.8 ml DMF, filtered, purified on prep HPLC and lyophilized to give (1R,2R)-2-(6-(2-(4-methyl-1H-imidazol-2-yl)pyridin-4-yloxy)benzo[d]thiazol-2-ylamino)cyclohexanol as TFA salt (3.2 mg). ES/MS m/z 422.1 (MH$^+$).

Example 178

Preparation of (1R,2R)-2-(6-(3-bromopyridin-4-yloxy)benzo[d]thiazol-2-ylamino)cyclohexanol The subject compound was prepared according to the general Scheme below:

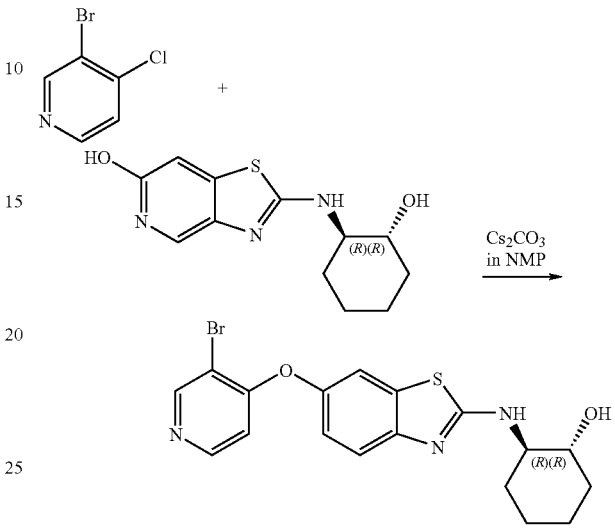

Preparation of (1R,2R)-2-(6-(3-bromopyridin-4-yloxy)benzo[d]thiazol-2-ylamino)cyclohexanol To the reaction mixture of 2-((1R,2R)-2-hydroxycyclohexylamino)benzo[d]thiazol-6-ol (12.5 mg, 0.047 mmol) in 0.4 ml of NMP was added Cesium Carbonate (39 mg, 0.118 mmol) and stirred at RT for 1-3 minutes. To this mixture was added 3-bromo-4-chloropyridine (18.2 mg, 0.094 mmol). The reaction mixture was stirred at 90° C. for 4 hours or until done by LC. The crude reaction mixture was filtered, purified on prep HPLC and lyophilized to (1R,2R)-2-(6-(3-bromopyridin-4-yloxy)benzo[d]thiazol-2-ylamino)cyclohexanol as TFA salt (9.2 mg). ES/MS m/z 420.1/422.0 (MH$^+$).

Example 179

Preparation of (1R,2R)-2-(6-(3-(1-methyl-1H-pyrazol-4-yl)pyridin-4-yloxy)benzo[d]thiazol-2-ylamino)cyclohexanol The subject compound was prepared according to the general Scheme below:

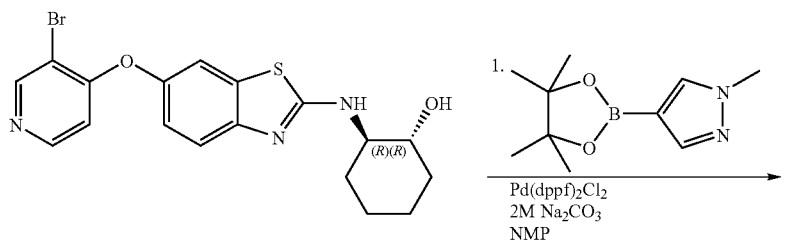

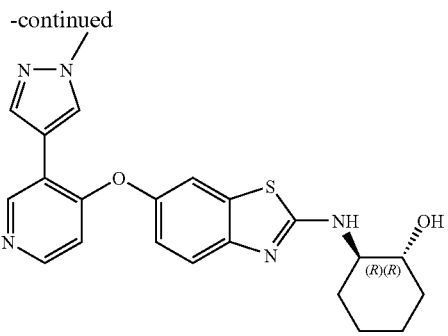

Preparation of (1R,2R)-2-(6-(3-(1-methyl-1H-pyrazol-4-yl)pyridin-4-yloxy)benzo[d]thiazol-2-ylamino)cyclohexanol To the reaction mixture of (1R,2R)-2-(6-(3-bromopyridin-4-yloxy)benzo[d]thiazol-2-ylamino)cyclohexanol (15 mg, 0.036 mmol) in 0.5 ml of NMP was added Pd(dppf)$_2$Cl$_2$ (8.8 mg, 0.0107 mmol), 1-methyl-4-(4,4,5,5-tetramethyl-1,3,2-dioxaborolan-2-yl)-1H-pyrazole (30 mg, 0.143 mmol) and 2M Na$_2$CO$_3$ (0.12 ml, 0.24 mmol). The reaction solution was stirred at 105-110° C. for 2 hours or until done by LC. The crude reaction mixture was filtered, purified on prep HPLC and lyophilized to give (1R,2R)-2-(6-(3-(1-methyl-1H-pyrazol-4-yl)pyridin-4-yloxy)benzo[d]thiazol-2-ylamino)cyclohexanol as TFA salt (5.5 mg). ES/MS m/z 422.1 (MH$^+$).

Example 180

Preparation of 4-(2-(cyclohexylmethylamino)benzo[d]thiazol-6-yloxy)picolinonitrile The subject compound was prepared according to the general Scheme below:

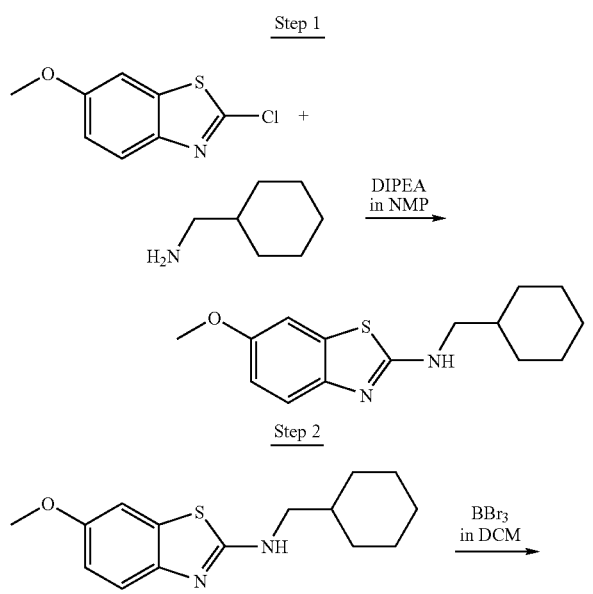

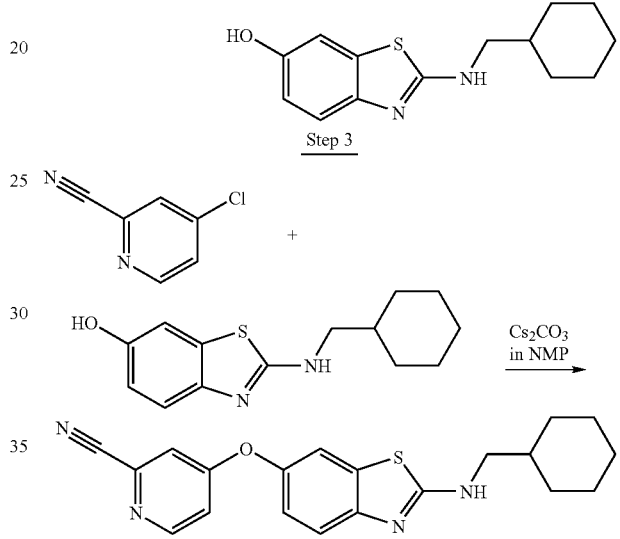

Step 1. Preparation of N-(cyclohexylmethyl)-6-methoxybenzo[d]thiazol-2-amine

To the solution of 2-chloro-6-methoxybenzo[d]thiazole (900 mg, 4.5 mmol) in 4.5 ml of NMP was added cyclohexylmethanamine (865 mg, 7.65 mmol) and DIPEA (1.57 ml, 9.0 mmol). The reaction solution was stirred at 105-110° C. for 66 hours. The reaction was worked up by adding 250 ml ethyl acetate and washed with 2×60 ml of saturated NaHCO$_3$, 3×60 ml water, 1×60 ml saturated NaCl, dried with sodium sulfate, filtered and concentrated in vacuo to give N-(cyclohexylmethyl)-6-methoxybenzo[d]thiazol-2-amine as solid (1.18 grams). ES/MS m/z 277.1 (MH$^+$).

Step 2. Preparation of 2-(cyclohexylmethylamino)benzo[d]thiazol-6-ol

To the solution of N-(cyclohexylmethyl)-6-methoxybenzo[d]thiazol-2-amine (1.40 g, 5.05 mmol) in 12 ml of DCM was added 1 M boron tribromide in DCM (10.6 ml, 10.6 mmol) slowly over about 3 minutes at 0° C. The reaction solution was stirred at 0° C. for 20 min and then at RT. for 2 hr. The reaction mixture was concentrated to a solid. To the residual solids add 200 ml of ethyl acetate and 50 ml of water and stir at RT. for 10 minutes. With stirring, carefully add excess solid NaHCO$_3$ until basic. Stir at RT. about 1 hour to dissolve the solids.

Remove the aqueous layer and extract with 100 ml of ethyl acetate. Combine organic layers and wash with 1×30 ml water, 1×25 ml saturated NaCl solution and dry with sodium sulfate. This mixture was filter through a silica gel plug (1.25 in.×3 in.) and flushed with ethyl acetate. The filtrate was concentrated under reduced pressure to give 2-(cyclohexylmethylamino)benzo[d]thiazol-6-ol as solid (1.32 grams). ES/MS m/z 263.1 (MH$^+$).

Step 3. Preparation of 4-(2-(cyclohexylmethylamino)benzo[d]thiazol-6-yloxy)picolinonitrile To the reaction mixture of 2-(cyclohexylmethylamino)benzo[d]thiazol-6-ol (18 mg, 0.068 mmol) in 0.4 ml of NMP was added Cesium Carbonate (56 mg, 0.171 mmol) and stirred at RT for 1-3 minutes. To this mixture was added 4-chloropicolinonitrile (19 mg, 0.136 mmol). The reaction mixture was stirred at 60° C. for 5 hours or until done by LC. The crude reaction mixture was filtered, purified on prep HPLC and lyophilized to give 4-(2-(cyclohexylmethylamino)benzo[d]thiazol-6-yloxy)picolinonitrile as TFA salt (9.8 mg). ES/MS m/z 365.1 (MH$^+$)

Example 181

Preparation of 6-(2-(1H-tetrazol-5-yl)pyridin-4-yloxy)-N-(cyclohexylmethyl)benzo[d]thiazol-2-amine The subject compound was prepared according to the general Scheme below:

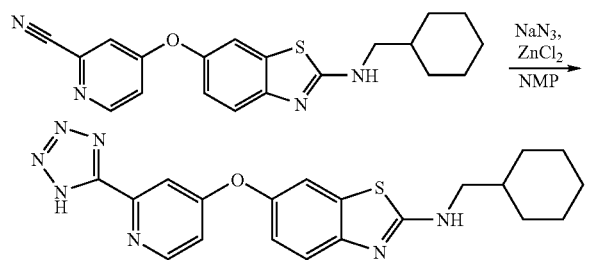

Preparation of 6-(2-(1H-tetrazol-5-yl)pyridin-4-yloxy)-N-(cyclohexylmethyl)benzo[d]thiazol-2-amine To the reaction mixture of 4-(2-(cyclohexylmethylamino)benzo[d]thiazol-6-yloxy)picolinonitrile (20 mg, 0.055 mmol) in 0.6 ml of NMP was added ZnCl$_2$ (37 mg, 0.274 mmol) and sodium azide (35.5 mg, 0.55 mmol). The reaction solution was microwaved at 170° C. for 800 seconds. The crude reaction mixture was filtered, purified on prep HPLC and lyophilized to give 6-(2-(1H-tetrazol-5-yl)pyridin-4-yloxy)-N-(cyclohexylmethyl)benzo[d]thiazol-2-amine as TFA salt (6.6 mg). ES/MS m/z 408.2 (MH$^+$).

Example 182

Preparation of 6-(quinolin-4-yloxy)-N-(2-(tetrahydro-2H-pyran-4-yl)ethyl)benzo[d]thiazol-2-amine The subject compound was prepared according to the general Scheme below:

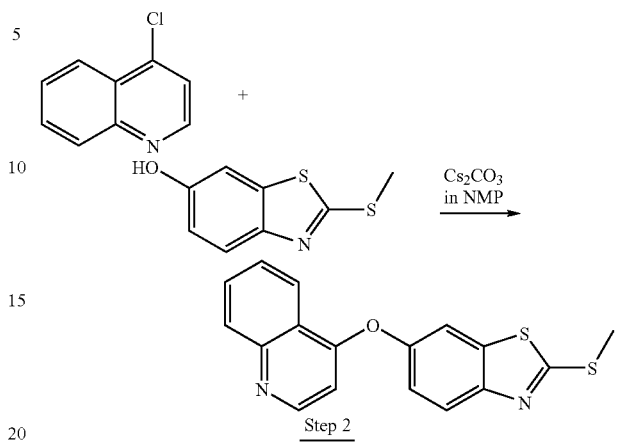

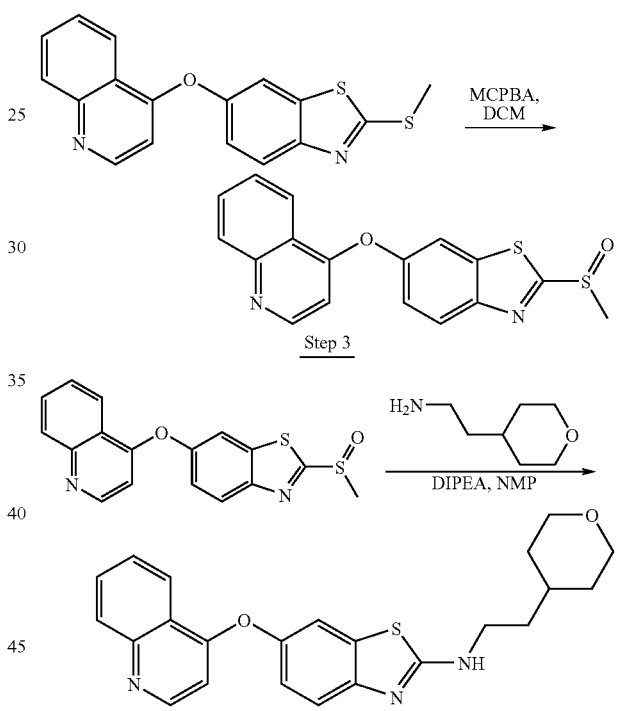

Step 1. Preparation of 2-(methylthio)-6-(quinolin-4-yloxy)benzo[d]thiazole

To the reaction mixture of 2-(methylthio)benzo[d]thiazol-6-ol (750 mg, 3.79 mmol) in 10 ml of NMP was added Cesium Carbonate (3.2 g, 9.5 mmol) and stirred at RT for 3 minutes. To this mixture was added 4-chloroquinoline (682 mg, 4.17 mmol). The reaction mixture was stirred at 110° C. for 24 hours. The reaction was worked up by adding 250 ml ethyl acetate and washed with 75 ml of saturated NaHCO$_3$, 2×60 ml water, 1×50 ml saturated NaCl, dried with sodium sulfate, filtered and concentrated in vacuo. The resulting solid residue was purified by silica gel column chromatography, eluted with (40% EtOAc: 60% Hexanes) and concentrated in vaccuo to give 2-(methylthio)-6-(quinolin-4-yloxy)benzo[d]thiazole as solid (980 mg). ES/MS m/z 325.1 (MH$^+$).

Step 2. Preparation of 2-(methylsulfinyl)-6-(quinolin-4-yloxy)benzo[d]thiazole The reaction mixture of 2-(methylthio)-6-(quinolin-4-yloxy)benzo[d]thiazole (460 mg, 1.415 mmol) was dissolved in 8 ml of DCM and cooled to −5° C. A solution was made of 77% MCPBA (333 mg, 1.486 mmol) and 6 ml of DCM. This solution was added to above cooled reaction mixture dropwise over 3-4 minutes. The reaction was stirred at −5° C. for 10 minutes, stirred at RT. for 90 minutes. The reaction followed by LC indicated 95% completed and stalled. A new solution was made of 77% MCPBA (25 mg, 0.1132 mmol) and 1 ml of DCM. This solution was added to above RT. reaction mixture dropwise. The reaction was stirred for 90 minutes more with LC indicating the reaction was complete. The reaction was worked up by adding 80 ml of DCM and 25 ml of a 10% sodium thiosulfate solution and stirred at RT. for 10 minutes. Aqueous layer was extracted and the DCM layer was washed with 25 ml of saturated NaHCO$_3$, 2×25 ml 5% NaHCO$_3$ solution, 1×25 ml water, 1×25 ml saturated NaCl, dried with sodium sulfate. About 1 gram of Silica gel was added and stirred for 10 minutes. The mixture was filtered and concentrated in vacuo to give 2-(methylsulfinyl)-6-(quinolin-4-yloxy)benzo[d]thiazole as solid (357 mg). ES/MS m/z 341.0 (MH$^+$).

Step 3. Preparation of 6-(quinolin-4-yloxy)-N-(2-(tetrahydro-2H-pyran-4-yl)ethyl)benzo[d]thiazol-2-amine To the reaction mixture of 2-(methylsulfinyl)-6-(quinolin-4-yloxy)benzo[d]thiazole (11.5 mg, 0.034 mmol) in 0.4 mL of NMP was added (DIPEA) diisopropylethylamine (15 uL, 0.084 mmol) and 2-(tetrahydro-2H-pyran-4-yl)ethanamine (17.4 mg, 0.134 mmol). The reaction mixture was stirred at 100° C. for 20 hours or until done by LC. The crude reaction mixture was filtered, purified on prep HPLC and lyophilized to give 6-(quinolin-4-yloxy)-N-(2-(tetrahydro-2H-pyran-4-yl)ethyl)benzo[d]thiazol-2-amine as TFA salt (5.1 mg). ES/MS m/z 406.1 (MH$^+$).

Example 183

Preparation of (1R,2R)-2-(6-(2-morpholinopyridin-4-yloxy)benzo[d]thiazol-2-ylamino)cyclohexanol

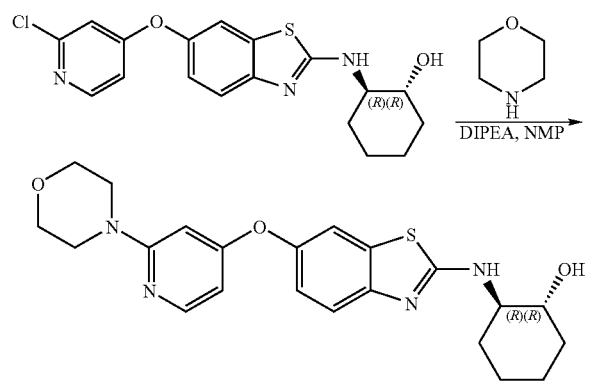

Preparation of (1R,2R)-2-(6-(2-morpholinopyridin-4-yloxy)benzo[d]thiazol-2-ylamino)cyclohexanol To the reaction mixture of (1R,2R)-2-(6-(2-chloropyridin-4-yloxy)benzo[d]thiazol-2-ylamino)cyclohexanol (14 mg, 0.037 mmol) in 0.4 ml of NMP was added (DIPEA) diisopropylethylamine (13 ul, 0.074 mmol) and morpholine (49 mg, 0.558 mmol). The reaction mixture was stirred at 110° C. for 48 hours or until done by LC. The crude reaction mixture was filtered, purified on prep HPLC and lyophilized to give (1R,2R)-2-(6-(2-morpholinopyridin-4-yloxy)benzo[d]thiazol-2-ylamino)cyclohexanol as TFA salt (3.7 mg). ES/MS m/z 427.1 (MH$^+$).

Example 184

(S)-6-(2-chloropyridin-4-yloxy)-N-(1-cyclohexylethyl)benzo[d]thiazol-2-amine

The subject compound was prepared according to the general Scheme below:

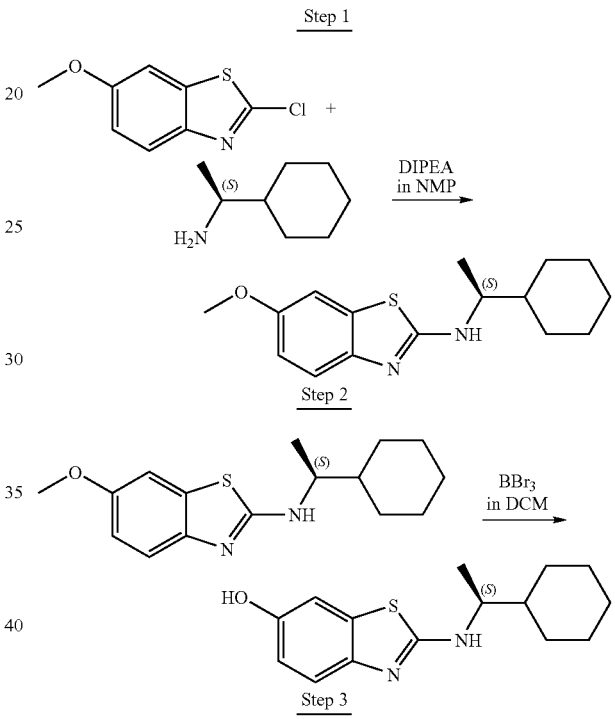

Step 1. Preparation of (S)—N-(1-cyclohexylethyl)-6-methoxybenzo[d]thiazol-2-amine To the solution of 2-chloro-6-methoxybenzo[d]thiazole (2.0 g, 10 mmol) in 10 ml of NMP was added (S)-1-cyclohexylethanamine (2.3 g, 18 mmol) and DIPEA (3.5 ml, 20 mmol). The reaction solution was stirred at 110° C. for 96 hr. The reaction was worked up by adding 170 ml ethyl acetate and washed with 1×60 ml of saturated NaHCO₃, 1×60 ml 5% NaHCO₃ solution, 1×60 ml water, 1×60 ml saturated NaCl, dried with sodium sulfate, filtered and concentrated in vacuo to give (S)—N-(1-cyclohexylethyl)-6-methoxybenzo[d]thiazol-2-amine as crude solid (3.39 grams). ES/MS m/z 291.1 (MH⁺).

Step 2. Preparation of (S)-2-(1-cyclohexylethylamino)benzo[d]thiazol-6-ol

To the solution of (S)—N-(1-cyclohexylethyl)-6-methoxybenzo[d]thiazol-2-amine (3.39 g, 10 mmol) in 30 ml of DCM was added 1 M boron tribromide in DCM (20 ml, 20 mmol) slowly at 0° C. The reaction solution was stirred at 0° C. then at RT for 2 hr. The reaction mixture was concentrated to a solid. To the residual solids add 400 ml of ethyl acetate and 90 ml of water and stir at RT. for 10 minutes. With stirring, carefully add excess solid NaHCO₃ until basic. Stir at RT about 1 hour to dissolve the solids. Remove the aqueous layer and extract with 100 ml of ethyl acetate. Combine organic layers and wash with 1×50 ml water, 1×50 ml saturated NaCl solution, dry with sodium sulfate, filter and concentrate under reduced pressure. The resulting solid was purified by silica gel column chromatography, eluted with (30% EtOAc: 70% Hexanes) and concentrated in vacuo to give (S)-2-(1-cyclohexylethylamino)benzo[d]thiazol-6-ol as solid (2.0 grams). ES/MS m/z 277.1 (MH⁺).

Step 3. Preparation of (S)-6-(2-chloropyridin-4-yloxy)-N-(1-cyclohexylethyl)benzo[d]thiazol-2-amine To the mixture (S)-2-(1-cyclohexylethylamino)benzo[d]thiazol-6-ol (270 mg, 0.974 mmol) and cesium carbonate (794 mg, 2.44 mmol) in 3.6 ml of NMP was added 2-chloro-4-fluoropyridine (254 mg, 1.95 mmol). The reaction mixture was stirred at 60° C. for 18 hours or until done by LC. The crude reaction mixture was filtered, purified on prep HPLC and lyophilized to give (S)-6-(2-chloropyridin-4-yloxy)-N-(1-cyclohexylethyl)benzo[d]thiazol-2-amine as TFA salt (298 mg). ES/MS m/z 388.1 (MH⁺).

Example 185

Preparation of (S)-6-(2,3'-bipyridin-4-yloxy)-N-(1-cyclohexylethyl)benzo[d]thiazol-2-amine To the reaction mixture of (S)-6-(2-chloropyridin-4-yloxy)-N-(1-cyclohexylethyl)benzo[d]thiazol-2-amine (15 mg, 0.039 mmol) in 0.6 ml of DME, 3-(4,4,5,5-tetramethyl-1,3,2-dioxaborolan-2-yl)pyridine (32 mg, 0.155 mmol), Pd(dppf)₂Cl₂ (7.9 mg, 0.0096 mmol) and 2M Na₂CO₃ (0.18 ml, 0.36 mmol) were added. The reaction solution was stirred at 100-105° C. for 90 minutes or until done by LC. The crude reaction mixture was concentrated to solid, re-dissolved in 0.8 ml DMF, filtered, purified on prep HPLC and lyophilized to give (S)-6-(2,3'-bipyridin-4-yloxy)-N-(1-cyclohexylethyl)benzo[d]thiazol-2-amine as TFA salt (5.2 mg). ES/MS m/z 431.2 (MH⁺)

Example 186

(S)—N-(1-cyclohexylethyl)-6-(2-(4-methyl-1H-imidazol-2-yl)pyridin-4-yloxy)benzo[d]thiazol-2-amine The subject compound was prepared according to the general Scheme below:

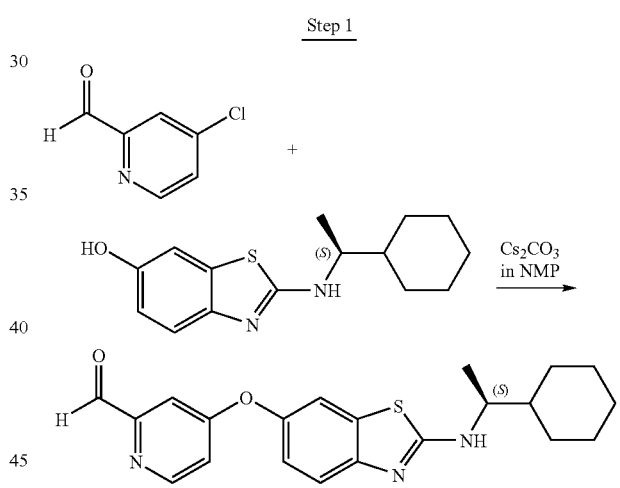

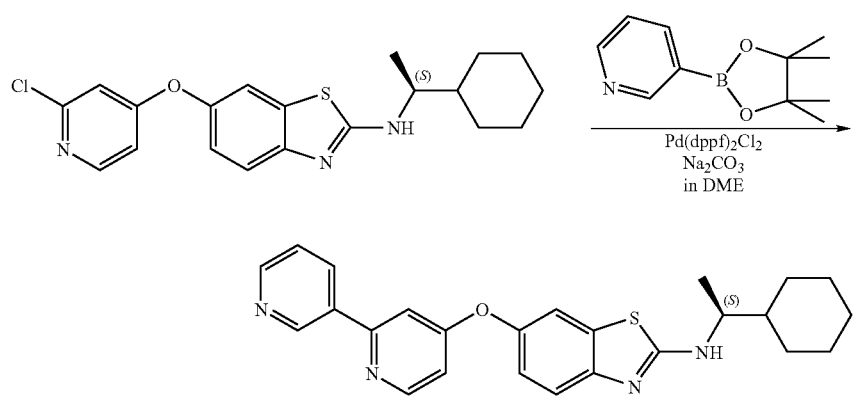

165

-continued
Step 2

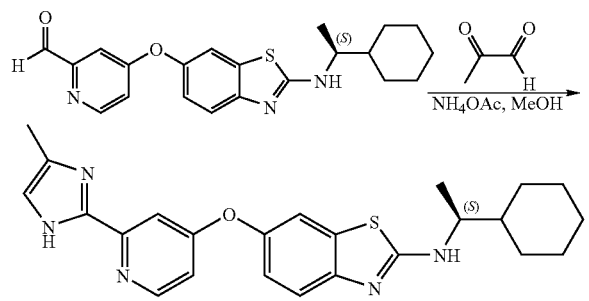

Step 1. Preparation of (S)-4-(2-(1-cyclohexylethylamino)benzo[d]thiazol-6-yloxy)picolinaldehyde To the reaction mixture of (S)-2-(1-cyclohexylethylamino) benzo[d]thiazol-6-ol (110 mg, 0.40 mmol) in 2.0 ml of NMP was added Cesium Carbonate (272 mg, 0.834 mmol) and 4-chloropicolinaldehyde (146 mg, 1.03 mmol). The reaction mixture was stirred at RT. for 20 minutes and then microwaved at 150° C. for 750 seconds. The crude reaction mixture was filtered, purified on prep HPLC and lyophilized to give (S)-4-(2-(1-cyclohexylethylamino)benzo[d]thiazol-6-yloxy) picolinaldehyde as TFA salt (105 mg). ES/MS m/z 400.2 (MH+) as the hydrate (+18).

Step 2. Preparation of (S)—N-(1-cyclohexylethyl)-6-(2-(4-methyl-1H-imidazol-2-yl)pyridin-4-yloxy) benzo[d]thiazol-2-amine To the reaction mixture of (S)-4-(2-(1-cyclohexylethylamino)benzo[d]thiazol-6-yloxy)picolinaldehyde (15 mg, 0.038 mmol) in 0.6 ml of methanol was added ammonium acetate (29 mg, 0.38 mmol) and 2-oxopropanal 40% wt solution of in water (0.034 ml, 0.19 mmol). The reaction mixture was stirred at 70° C. for 2 hours. The crude reaction mixture was concentrated to solid, re-dissolved in 0.8 ml DMF, filtered, purified on prep HPLC and lyophilized to give (S)—N-(1-cyclohexylethyl)-6-(2-(4-methyl-1H-imidazol-2-yl) pyridin-4-yloxy)benzo[d]thiazol-2-amine as TFA salt (6.5 mg). ES/MS m/z 434.2 (MH+).

166

Example 187

Preparation of (1R,2R)-2-(6-(2-(1H-imidazol-1-yl) pyridin-4-yloxy)benzo[d]thiazol-2-ylamino)cyclohexanol

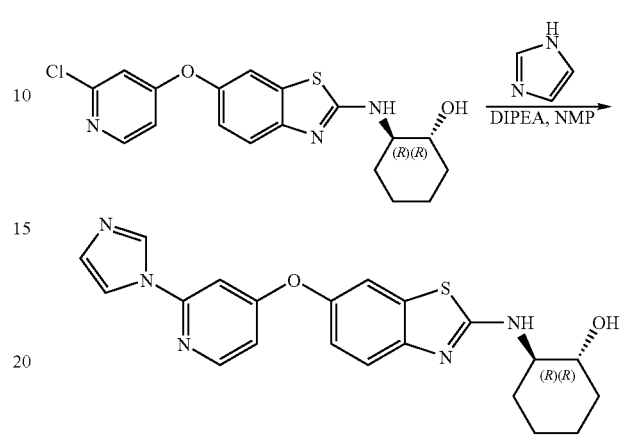

Preparation of (1R,2R)-2-(6-(2-(1H-imidazol-1-yl) pyridin-4-yloxy)benzo[d]thiazol-2-ylamino)cyclohexanol To the reaction mixture of (1R,2R)-2-(6-(2-chloropyridin-4-yloxy)benzo[d]thiazol-2-ylamino)cyclohexanol (12 mg, 0.032 mmol) in 0.55 ml of NMP was added (DIPEA) diisopropylethylamine (17 ul, 0.096 mmol) and 1H-imidazole (180 mg, 2.64 mmol). The reaction mixture was followed by LC, LCMS and microwaved as follows: (150° C. for 750 seconds, 230° C. for 750 seconds, 250° C. for 1000 seconds, again at 250° C. for 1000 seconds). The crude reaction mixture was filtered, purified on prep HPLC and lyophilized to give (1R,2R)-2-(6-(2-(1H-imidazol-1-yl)pyridin-4-yloxy) benzo[d]thiazol-2-ylamino)cyclohexanol as TFA salt (1.4 mg). ES/MS m/z 408.2 (MH+).

Example 188

Preparation of (1R,2R)-2-(6-(2-(1,2,3,6-tetrahydropyridin-4-yl)pyridin-4-yloxy)benzo[d]thiazol-2-ylamino)cyclohexanol Step 1

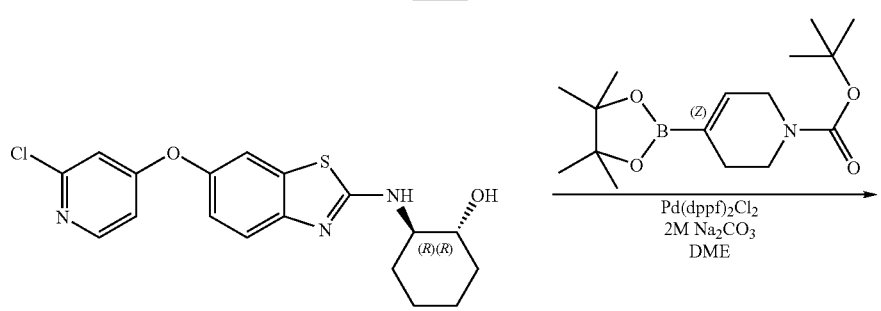

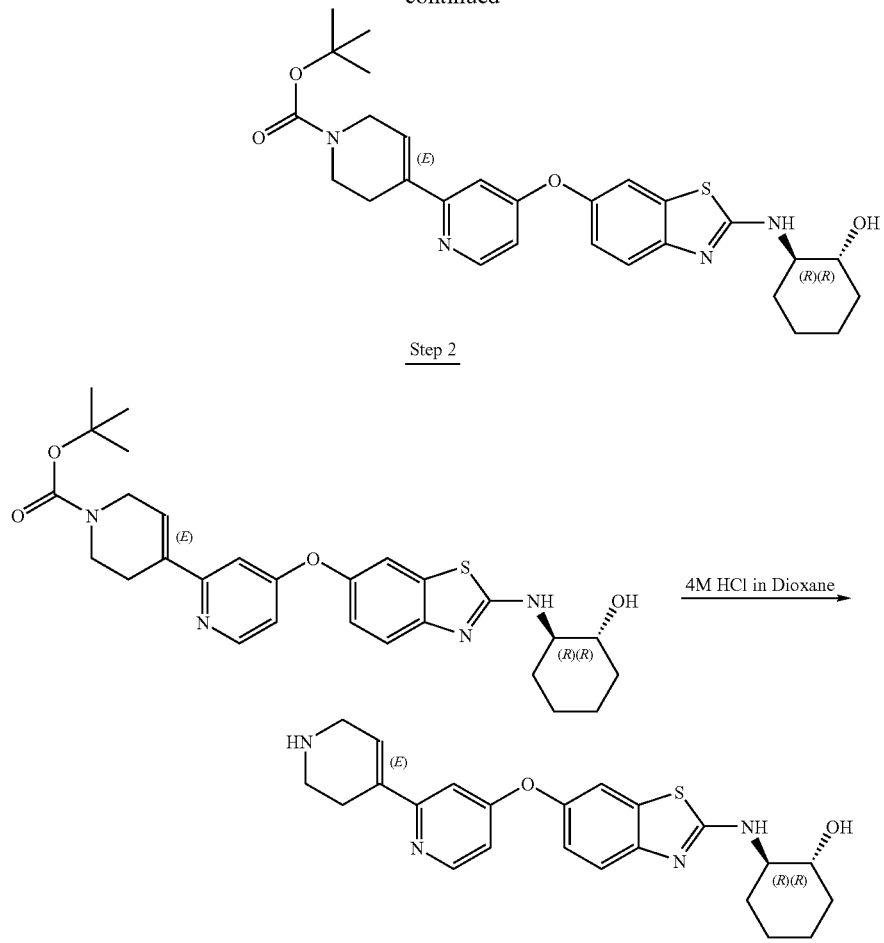

Step 2

Step 1. Preparation of tert-butyl 4-(4-(2-((1R,2R)-2-hydroxycyclohexylamino)benzo[d]thiazol-6-yloxy)pyridin-2-yl)-5,6-dihydropyridine-1(2H)-carboxylate To the reaction mixture of (1R,2R)-2-(6-(2-chloropyridin-4-yloxy)benzo[d]thiazol-2-ylamino)cyclohexanol (11 mg, 0.029 mmol) in 0.5 ml of DME, tert-butyl 4-(4,4,5,5-tetramethyl-1,3,2-dioxaborolan-2-yl)-5,6-dihydropyridine-1(2H)-carboxylate (36 mg, 0.117 mmol), Pd(dppf)$_2$Cl$_2$ (7.2 mg, 0.0088 mmol) and 2M Na$_2$CO$_3$ (0.125 ml, 0.25 mmol) were added. The reaction solution was stirred at 105-110° C. for 24 hours or until done by LC. The crude reaction mixture was concentrated to solid re-dissolved in 0.8 ml DMF, filtered, purified on prep HPLC and lyophilized to give tert-butyl 4-(4-(2-((1R,2R)-2-hydroxycyclohexylamino)benzo[d]thiazol-6-yloxy)pyridin-2-yl)-5,6-dihydropyridine-1(2H)-carboxylate as TFA salt (2.5 mg). ES/MS m/z 523.1 (MH$^+$).

Step 2. Preparation of (1R,2R)-2-(6-(2-(1,2,3,6-tetrahydropyridin-4-yl)pyridin-4-yloxy)benzo[d]thiazol-2-ylamino)cyclohexanol To the solid of tert-butyl 4-(4-(2-((1R,2R)-2-hydroxycyclohexylamino)benzo[d]thiazol-6-yloxy)pyridin-2-yl)-5,6-dihydropyridine-1(2H)-carboxylate (2.5 mg, 0.0039 mmol) was added 4M HCL in Dioxane (1 ml, 4.0 mmol). The reaction mixture was stirred at RT for 45 minutes. The crude reaction mixture was concentrated to solid and lyophilized to give (1R,2R)-2-(6-(2-(1,2,3,6-tetrahydropyridin-4-yl)pyridin-4-yloxy)benzo[d]thiazol-2-ylamino)cyclohexanol as HCl salt (1.4 mg). ES/MS m/z 423.1 (MH$^+$).

Example 189

Preparation of 4-(2-((1s,4s)-4-aminocyclohexylamino)benzo[d]thiazol-6-yloxy)-N-methylpicolinamide The subject compound was prepared according to the general Scheme below Step 1

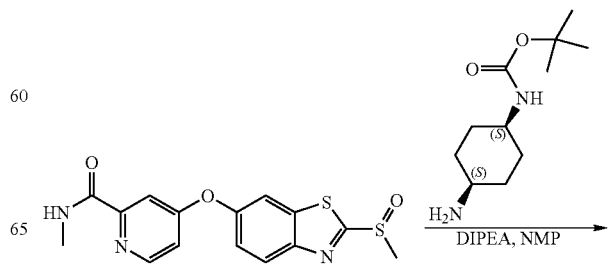

-continued

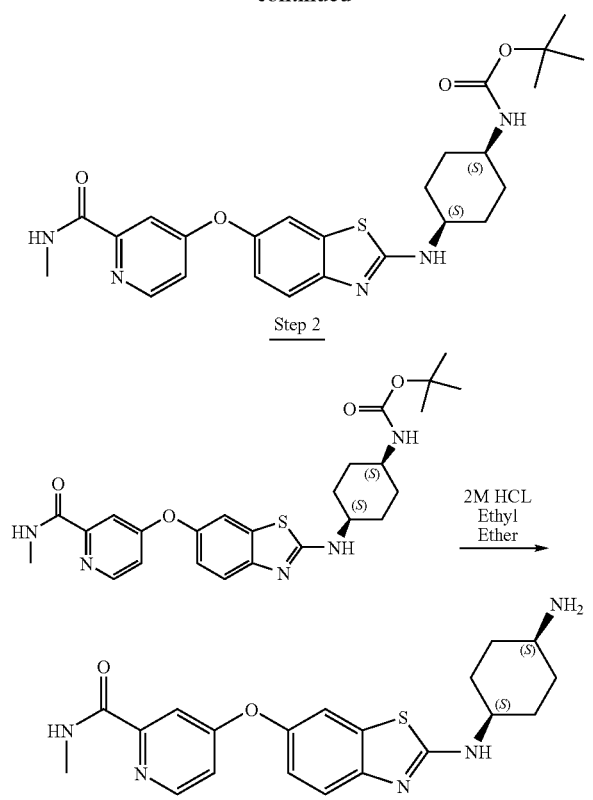

Step 1. Preparation of tert-butyl (1s, 4s)-4-(6-(2-(methylcarbamoyl)pyridin-4-yloxy)benzo[d]thiazol-2-ylamino)cyclohexylcarbamate To the reaction mixture of N-methyl-4-(2-(methylsulfinyl)benzo[d]thiazol-6-yloxy)picolinamide (15 mg, 0.043 mmol) in 0.4 ml of NMP was added tert-butyl (1s,4s)-4-aminocyclohexylcarbamate (47 mg, 0.215 mmol) and (DIPEA) diisopropylethylamine (22 ul, 0.129 mmol). The reaction mixture was stirred at 105-100° C. for 20 hr or until done by LC. The crude reaction solution was purified by prep HPLC and lyophilized to give tert-butyl (1s,4s)-4-(6-(2-(methylcarbamoyl)pyridin-4-yloxy)benzo[d]thiazol-2-ylamino)cyclohexylcarbamate (16 mg) as TFA salt. ES/MS m/z 498.2 (MH+).

Step 2. Preparation of 4-(2-((1s,4s)-4-aminocyclohexylamino)benzo[d]thiazol-6-yloxy)-N-methylpicolinamide To the solid of tert-butyl (1s,4s)-4-(6-(2-(methylcarbamoyl)pyridin-4-yloxy)benzo[d]thiazol-2-ylamino)cyclohexylcarbamate (16 mg, 0.032 mmol) was added 2M HCL in Ethyl Ether (2 ml, 4.0 mmol). The reaction mixture was stirred at RT for 60 minutes. The crude reaction mixture was concentrated to solid and lyophilized to give 4-(2-((1s,4s)-4-aminocyclohexylamino)benzo[d]thiazol-6-yloxy)-N-methylpicolinamide as HCl salt (12.0 mg). ES/MS m/z 398.1 (MH+).

Example 190

Preparation of 4-(2-((1s,4s)-4-acetamidocyclohexylamino)benzo[d]thiazol-6-yloxy)-N-methylpicolinamide The subject compound was prepared according to the general Scheme below

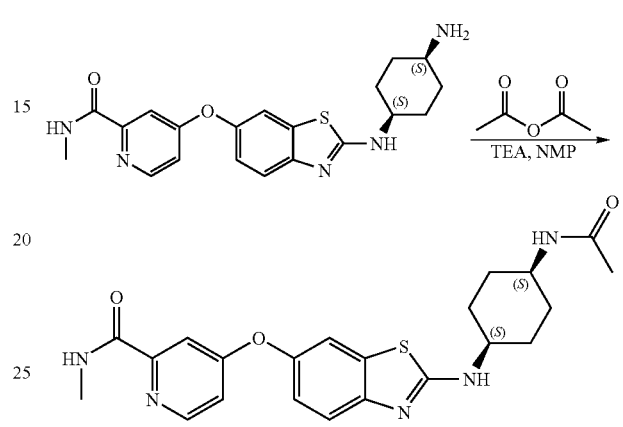

Preparation 4-(2-((1s,4s)-4-acetamidocyclohexylamino)benzo[d]thiazol-6-yloxy)-N-methylpicolinamide To the reaction mixture of 4-(2-((1s,4s)-4-aminocyclohexylamino)benzo[d]thiazol-6-yloxy)-N-methylpicolinamide (9.0 mg, 0.0226 mmol) in 0.6 ml of NMP was added (TEA) triethylamine (19 ul, 0.136 mmol) and then acetic anhydride (7.0 mg, 0.0678 mmol). The reaction mixture was stirred at RT. for 90 minutes. The crude reaction solution was purified by prep HPLC and lyophilized to give 4-(2-((1s,4s)-4-acetamidocyclohexylamino)benzo[d]thiazol-6-yloxy)-N-methylpicolinamide (8.7 mg) as TFA salt. ES/MS m/z 440.2 (MH+).

Example 191

Preparation of 4-(2-((1s,4s)-4-isobutyramidocyclohexylamino)benzo[d]thiazol-6-yloxy)-N-methylpicolinamide The subject compound was prepared according to the general Scheme below:

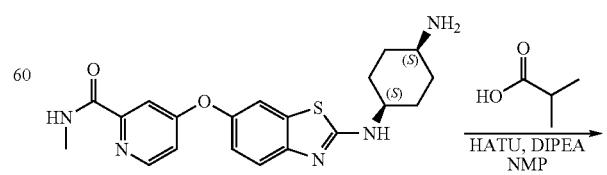

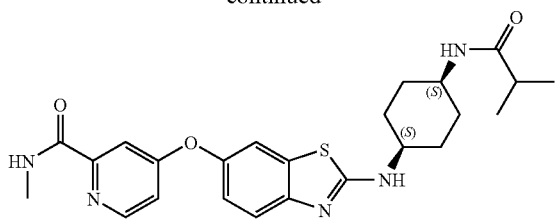

Preparation 4-(2-((1s,4s)-4-isobutyramidocyclohexylamino)benzo[d]thiazol-6-yloxy)-N-methylpicolinamide To the reaction mixture of isobutyric acid (4.4 mg, 0.050 mmol) in 0.3 ml of NMP was added HATU (17.1 mg, 0.045 mmol) and then (DIPEA) diisopropylethylamine (11 ul, 0.0625 mmol). The reaction mixture was stirred at RT. for 10-15 minutes. To the above reaction mixture was added a solution of 4-(2-((1s,4s)-4-aminocyclohexylamino)benzo[d]thiazol-6-yloxy)-N-methylpicolinamide (10 mg, 0.025 mmol) and (DIPEA) diisopropylethylamine (13 ul, 0.075 mmol) in 0.3 ml of NMP. The reaction solution was stirred at RT. for 18 hours. The crude reaction solution was purified by prep HPLC and lyophilized to give 4-(2-((1s,4s)-4-isobutyramidocyclohexylamino)benzo[d]thiazol-6-yloxy)-N-methylpicolinamide (4.0 mg) as TFA salt. ES/MS m/z 468.3 (MH+).

Example 192

Preparation of (1R,2R)-2-(6-(6-fluoroquinolin-4-yloxy)benzo[d]thiazol-2-ylamino)cyclohexanol The subject compound was prepared according to the general Scheme below:

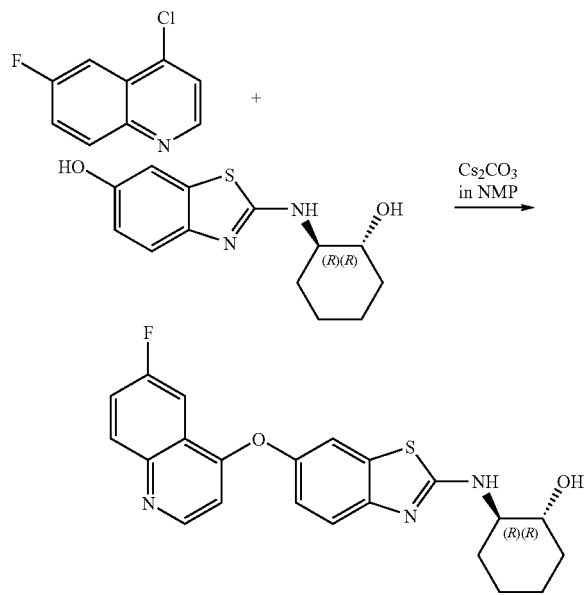

Preparation of (1R,2R)-2-(6-(6-fluoroquinolin-4-yloxy)benzo[d]thiazol-2-ylamino)cyclohexanol To the reaction mixture of 2-((1R,2R)-2-hydroxycyclohexylamino)benzo[d]thiazol-6-ol (15.1 mg, 0.057 mmol) in 0.4 ml of NMP was added Cesium Carbonate (47 mg, 0.143 mmol) and stirred at RT for 1-3 minutes. To this mixture was added 4-chloro-6-fluoroquinoline (21 mg, 0.114 mmol). The reaction mixture was stirred at 105-110° C. for 18 hours or until done by LC. The crude reaction mixture was filtered, purified on prep HPLC and lyophilized to give (1R,2R)-2-(6-(6-fluoroquinolin-4-yloxy)benzo[d]thiazol-2-ylamino)cyclohexanol as TFA salt (9.2 mg). ES/MS m/z 410.1 (MH+).

Example 193

4-(2-(cyclohexylmethylamino)-4-methylbenzo[d]thiazol-6-yloxy)-N-methylpicolinamide

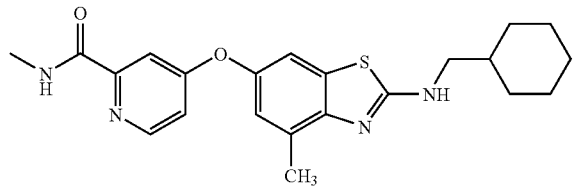

Step 1. Synthesis of 4-(4-amino-3-methylphenoxy)-N-methylpicolinamide

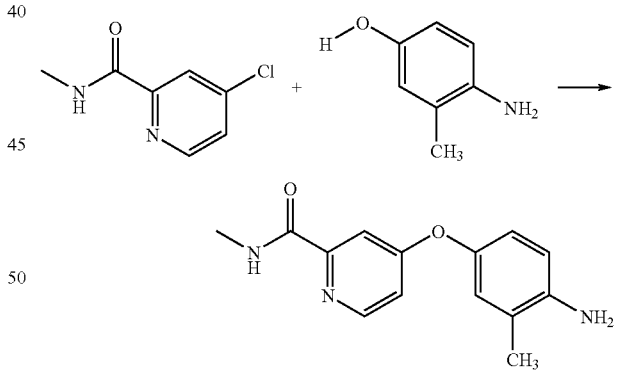

To the solution of 4-amino-m-cresol (125 mg, 1.01 mmol, 1.0 eq) in 1 mL of NMP was added 4-chloro-N-methylpicolinamide (189 mg, 1.11 mmol, 1.1 eq) and cesium carbonate (658 mg, 2.02 mmol, 2.0 eq) at room temperature. The reaction mixture was stirred at 75° C. for 12 hours, thereafter the mixture was diluted with water (ca. 50 mL) and aqueous layer extracted with ethyl acetate (ca. 50 mL×3). Combined organic layers were dried over sodium sulfate, filtered and condensed under reduced pressure to give sufficiently pure crude product which was carried to next step without further purification. LC/MS (m/z) [258.1] (MH+).

Step 2. Synthesis of 4-(2-amino-4-methylbenzo[d]thiazol-6-yloxy)-N-methylpicolinamide

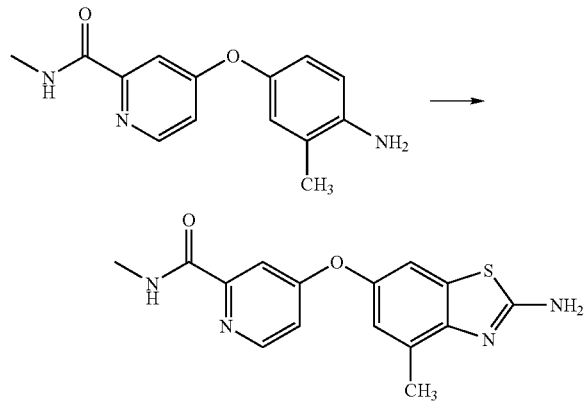

To the solution of 4-(4-amino-3-methylphenoxy)-N-methylpicolinamide (25 mg, 0.097 mmol, 1.0 eq) in 1 mL of cold acetic acid was added ammonium thiocyanate (11 mg, 0.145 mmol, 1.5 eq). After stirring for a few minutes, bromine (6 μL, 0.116 mmol, 1.2 eq) was injected dropwise and reaction stirred at room temperature for 3 hours. Thereafter, reaction was quenched with NaHCO₃ saturated solution (ca. 10 mL) and extracted with ethyl acetate (ca. 25 mL×3), combined organic extracts were dried over sodium sulfate and condensed under reduced pressure to give sufficiently pure crude product which was carried to next step without further purification. LC/MS (m/z) [315.1] (MH⁺).

Step 3. Synthesis of 4-(2-(cyclohexylmethylamino)-4-methylbenzo[d]thiazol-6-yloxy)methyl picolinamide

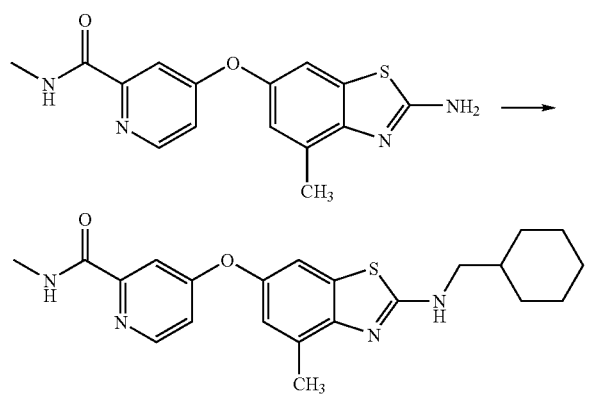

To the solution of 4-(2-amino-4-methylbenzo[d]thiazol-6-yloxy)-N-methylpicolinamide (30 mg, 0.095 mmol, 1.0 eq) in 1 mL of NMP was added bromomethyl cyclohexane (20 μL, 0.142 mmol, 1.5 eq) and potassium carbonate (40 mg, 0.285 mmol, 3.0 eq) at room temperature. The reaction mixture was stirred at 80° C. for 12 hours and thereafter purified via reverse phase HPLC. LC/MS (m/z) [411.1] (MH⁺)

Example 194

4-(4-chloro-2-(cyclohexylmethylamino)benzo[d]thiazol-6-yloxy)-N-methylpicolinamide

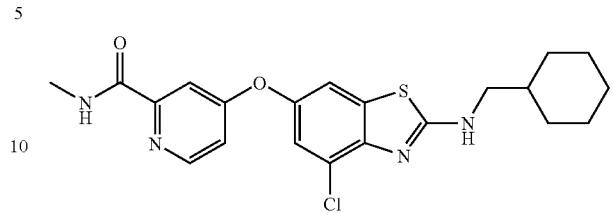

Step 1. Synthesis of 4-(4-amino-3-chlorophenoxy)-N-methylpicolinamide

Prepared following the procedure outlined in Step 1 of Example 1 LC/MS (m/z) [278.1] (MH⁺)

Step 2. Synthesis of 4-(2-amino-4-chlorobenzo[d]thiazol-6-yloxy)-N-methylpicolinamide Prepared following the procedure outlined in Step 2 of Example 1. LC/MS (m/z) [335.0] (MH⁺)

Step 3. Synthesis of 4-(4-chloro-2-(cyclohexylmethylamino)benzo[d]thiazol-6-yloxy)-N-methylpicolinamide

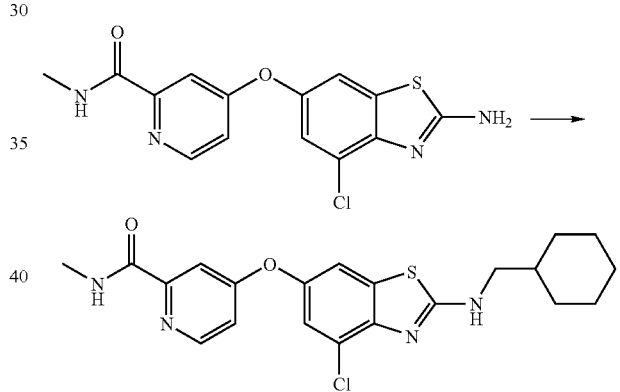

To the solution of 4-(2-amino-4-chlorobenzo[d]thiazol-6-yloxy)-N-methylpicolinamide (30 mg, 0.089 mmol, 1.0 eq) in 2 mL of NMP was added bromomethyl cyclohexane (18 μL, 0.134 mmol, 1.5 eq) and potassium carbonate (36 mg, 0.267 mmol, 3.0 eq) at room temperature. The reaction mixture was stirred at 80° C. for 2 hours and thereafter purified via reverse phase HPLC. LC/MS (m/z) [431.0] (MH+)

Example 195

4-(7-bromo-2-((1R,2R)-2-hydroxycyclohexylamino)benzo[d]thiazol-6-yloxy)-N-methylpicolinamide

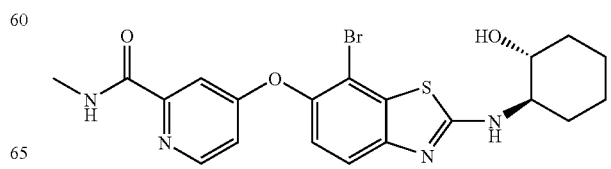

Step 1. Synthesis of 7-bromo-2-chloro-6-methoxybenzo[d]thiazole

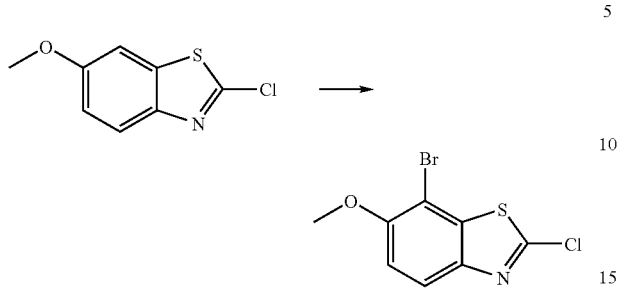

To the solution of 2-chloro-6-methoxy-benzothiazole (200 mg, 1.0 mmol, 1.0 eq) in 5 mL of NMP was added N-bromosuccinimide (213 mg, 1.20 mmol, 1.2 eq) at room temperature. The reaction mixture was stirred at 75° C. for >24 hours with subsequent addition of NBS in small batches for reaction progress, thereafter the mixture was diluted with water (ca. 100 mL) and aqueous layer extracted with ethyl acetate (ca. 150 mL×3). Combined organic layers were dried over sodium sulfate, filtered and condensed under reduced pressure. Purification on ISCO using gradient 0%-50% ethyl acetate-hexane gave 336 mg of product as off white fluffy powder in 60% yields structure of which was confirmed by H⁺NMR. LC/MS (m/z) [279.9] (MH⁺)

Step 2. Synthesis of (1R,2R)-2-(7-bromo-6-methoxybenzo[d]thiazol-2ylamino)cyclohexanol

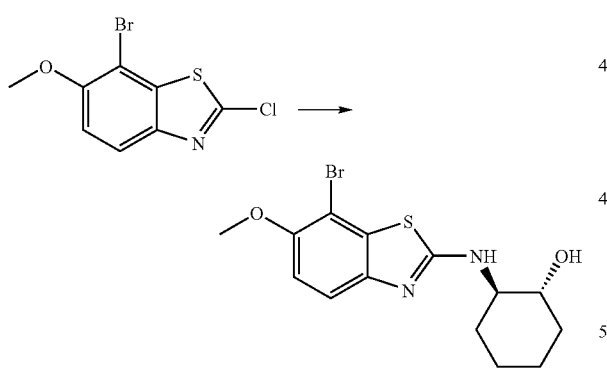

To the solution of 7-bromo-2-chloro-6-methoxybenzo[d]thiazole (150 mg, 0.539 mmol, 1.0 eq) in 1 mL of NMP was added (1R,2R)-2-aminocyclohexanol hydrochloride (0.123 mg, 0.809 mmol, 1.5 eq) and DIPEA (263 μL, 1.503 mmol, 2.8 eq) at room temperature. The reaction mixture was stirred at 125° C. for 12 hours, thereafter the mixture was diluted with saturated sodium bicarbonate solution (ca. 100 mL) and aqueous layer extracted with ethyl acetate (ca. 200 mL×3). Combined organic layers were dried over sodium sulfate, filtered and condensed under reduced pressure to give crude product as brown oil which was sufficiently pure and was carried to next step without further purification. LC/MS (m/z) [359.0] (MH⁺)

Step 3. Synthesis of 7-bromo-2-((1R,2R)-2-hydroxycyclohexylamino)-benzo[d]thiazol-6-ol

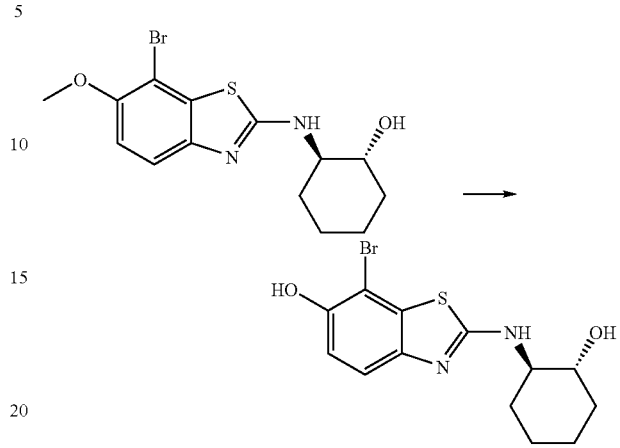

To the solution of (1R,2R)-2-(7-bromo-6-methoxybenzo[d]thiazol-2-ylamino) cyclohexanol (191 mg, 0.537 mmol, 1.0 eq) in 10 mL of DCM was added 1 M solution of boron tribromide (ca. 3.0 mL, 2.68 mmol, 5.0 eq) at room temperature. The reaction mixture was refluxed for 12 hours, thereafter the mixture was diluted with saturated sodium bicarbonate (ca. 100 mL) till PH=7 and aqueous layer extracted with ethyl acetate (ca. 150 mL×3). Combined organic layers were dried over sodium sulfate, filtered and condensed under reduced pressure to give sufficiently pure crude product which was carried to next step without further purification LC/MS (m/z) [345.0] (MH⁺).

Step 4. Synthesis of 4-(7-bromo-2-((1R,2R)-2-hydroxycyclohexylamino)benzo[d]thiazol-6-yloxy)-N-methylpicolinamide

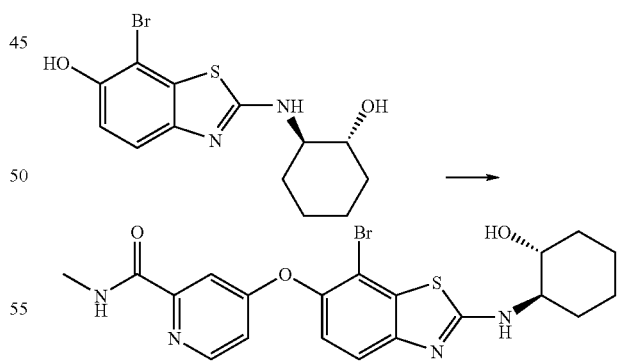

To the solution of 7-bromo-2-((1R,2R)-2-hydroxycyclohexylamino)benzo[d]thiazol-6-ol (50 mg, 0.145 mmol, 1.0 eq) in 1 mL of NMP was added 4-chloro-N-methylpicolinamide (29 mg, 0.174 mmol, 1.2 eq) and cesium carbonate (165 mg, 0.507 mmol, 3.5 eq) at room temperature. The reaction mixture was stirred at 80° C. for ca. 12 hours, thereafter the mixture was purified on the reverse phase HPLC. LC/MS (m/z) [479.0] (MH⁺)

Example 196

4-(2-((1R,2R)-2-hydroxycyclohexylamino)-7-methylbenzo[d]thiazol-6-yloxy)-N-methylpicolinamide

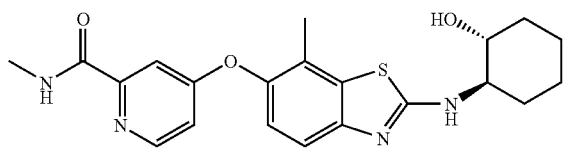

Step 1. Synthesis of 2-((1R,2R)-2-hydroxycyclohexylamino)-7-methylbenzo[d]thiazol-6-ol

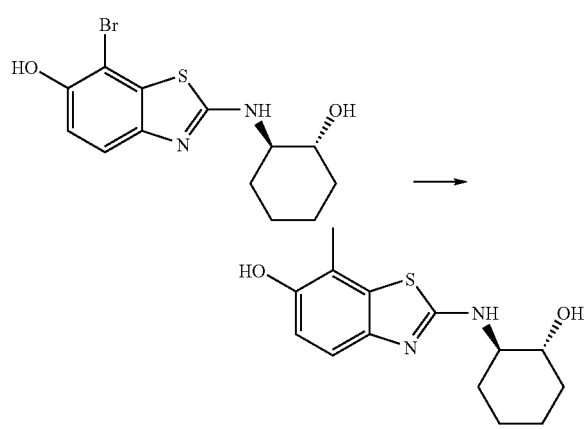

To the solution of 7-bromo-2-((1R,2R)-2-hydroxycyclohexylamino)benzo[d]thiazol-6-ol (117 mg, 0.34 mmol, 1.0 eq) in 1 mL DMF in a microwave vial was added trimethylboraxine (128 mg, 1.02 mmol, 3.0 eq), Pd(Cl$_2$)dPPf (27 mg, 0.034 mmol, 0.1 eq) and 1 mL of 2M Na$_2$CO$_3$ solution at room temperature. Thereafter, the reaction mixture was heated in the microwave at 120° C. for 15 minutes. The reaction was quenched with saturated NaHCO$_3$ solution (25 ml) and the aqueous phase extracted with ethyl acetate (50 mL×3), combined organic layers dried over Na$_2$SO$_4$, filtered and condensed under reduced pressure. Purification over ISCO using a gradient of 0%-18% methanol-DCM gave 17 mg of product as brownish powder in 17% yield. LC/MS (m/z) [279.1] (MH$^+$)

Step 2. Synthesis of 4-(2-((1R,2R)-2-hydroxycyclohexylamino)-7-methylbenzo-[d]thiazol-6-yloxy)-N-methylpicolinamide

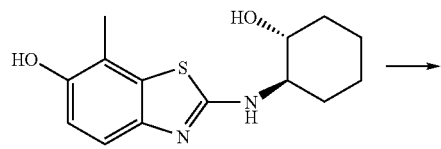

-continued

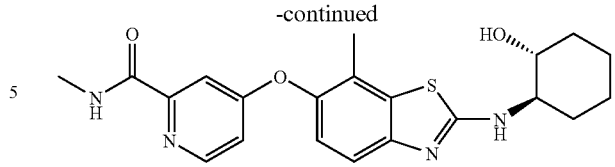

Prepared following the procedure in example 543 step 4. LC/MS (m/z) [413.1] (MH$^+$)

Example 197

4-(7-chloro-2-((1R,2R)-2-hydroxycyclohexylamino)benzo[d]thiazol-6-yloxy)-N-methylpicolinamide

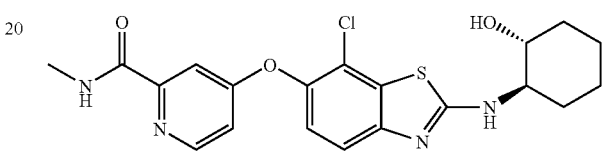

Step 1. Synthesis of 7-chloro-2-(methylthio)benzo[d]thiazol-6-ol

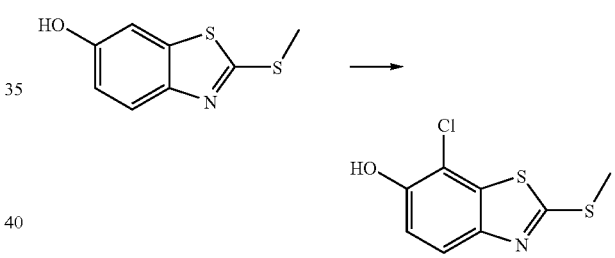

To the solution of 2-(methylthio)benzo[d]thiazol-6-ol (500 mg, 2.53 mmol, 1.0 eq) in 10 mL of NMP was added N-chlorosuccinimide (507 mg, 3.80 mmol, 1.5 eq) at room temperature. The reaction mixture was stirred at room temperature for 1 hour thereafter the mixture was diluted with saturated sodium bicarbonate solution (ca. 100 mL) and aqueous layer extracted with DCM (ca. 150 mL×3). Combined organic layers were dried over sodium sulfate, filtered and condensed under reduced pressure. Purification on ISCO using gradient 0%-100% ethyl acetate-hexane gave 283.39 mg of product in 48% yields structure of which was confirmed by H$^+$NMR. LC/MS (m/z) [232.0] (MH$^+$)

Step 2. Synthesis of 4-(7-chloro-2-(methylthio)benzo[d]thiazol-6-yloxy)-N methyl picolinamide

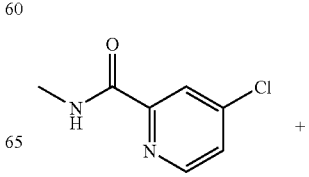 +

-continued

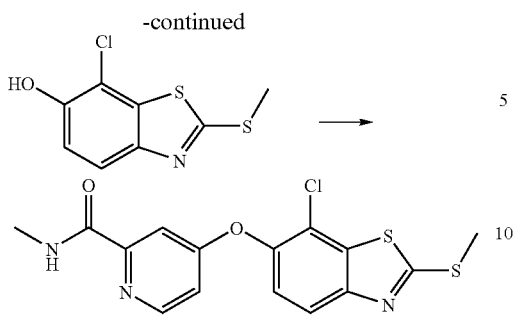

To the solution of 7-chloro-2-(methylthio)benzo[d]thiazol-6-ol (80 mg, 0.346 mmol, 1.0 eq) in 1 mL of NMP was added 4-chloro-N-methylpicolinamide (88 mg, 0.519 mmol, 1.5 eq) and cesium carbonate (281 mg, 0.865 mmol, 2.5 eq) at room temperature. The reaction mixture was stirred at 85° C. for >48 hours till ca. 75%-80% completion, thereafter the mixture was diluted with water (ca. 50 mL) and aqueous layer extracted with ethyl acetate (ca. 50 mL×3). Combined organic layers were dried over sodium sulfate, filtered and condensed under reduced pressure to give crude product which was purified on ISCO using gradient 0%-100% ethyl acetate-hexane mixture to give 64 mg of product in 50% yield. LC/MS (m/z) [366.0] (MH+)

Step 3. Synthesis of 4-(7-chloro-2-(methylsulfinyl) benzo[d]thiazol-6-yloxy)-N-methylpicolinamide

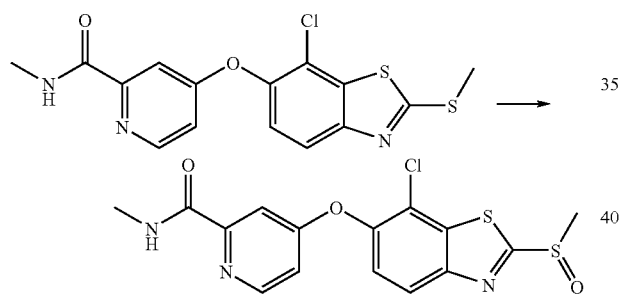

To the solution of 4-(7-chloro-2-(methylthio)benzo[d] thiazol-6-yloxy)-N-methylpicolinamide (64 mg, 0.175 mmol, 1.0 eq) in 5 mL of DCM was added MCPBA (33 mg, 0.192 mmol, 1.1 eq) at 0° C. and reaction stirred for 30-45 min. Thereafter, it was quenched with water (10 mL) and aqueous phase extracted with ethyl acetate (25 mL×5), combined organic layers dried over sodium sulfate, filtered and condensed under reduced pressure to yield crude product which was sufficiently pure and was carried to next step without further purification. LC/MS (m/z) [382.0] (MH+)

Step 4. Synthesis of 4-(7-chloro-2-((1R,2R)-2-hydroxycyclohexylamino)benzo[d]thiazol-6-yloxy)-N-methylpicolinamide

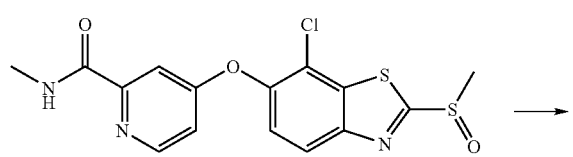

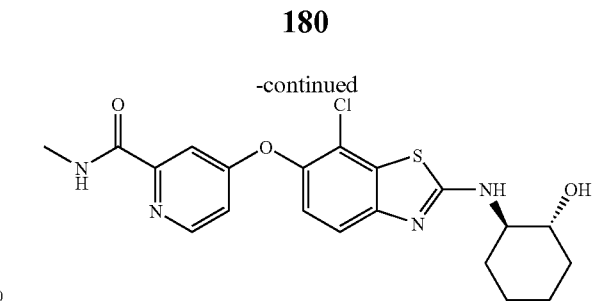

To the solution of 4-(7-chloro-2-(methylsulfinyl)benzo[d] thiazol-6-yloxy)-Nmethylpicolinamide (10 mg, 0.026 mmol, 1.0 eq) in NMP was added (1R,2R)-2-aminocyclohexanol hydrochloride (6 mg, 0.039 mmol, 1.5 eq) and DIPEA (13 µL, 0.078 mmol, 3.0 eq) and reaction mixture heated at 160° C. in microwave for 15 min. Thereafter, the product was purified via reverse phase HPLC. LC/MS (m/z) [433.1] (MH+)

Example 198

4-(2-(cyclohexylmethylamino)-5-fluorobenzo[d] thiazol-6-yloxy)-N-methylpicolinamide

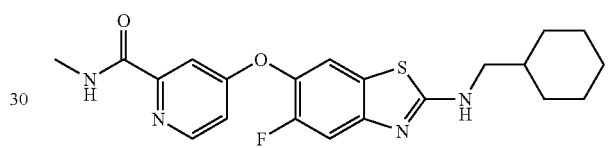

Step 1. Synthesis of 5-fluoro-6-methoxybenzo[d]thiazol-2-amine

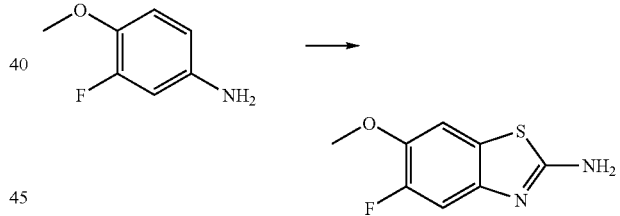

Reference used—"Synthesis and biological activity of α-[(6-chloro-5-fluoro-2 benzothiazolyl)amino]acetanilides". Pattan, S. R.; Narendra, Babu S. N.; Angadi, J. S. Dept. of Mechanical Chemistry, K.L.E.S's College of Pharmacy, Belg. Indian Drugs (2002), 39(10), 515-517.

To the solution of 3-fluoro-p-anisidine (1.00 g, 7.09 mmol, 1.0 eq) in 30 mL of cold acetic acid was added ammonium thiocyanate (1.07 g, 14.18 mmol, 2.0 eq). After stirring for a few minutes, bromine (437 µL, 8.50 mmol, 1.2 eq) in 6 mL acetic acid was injected slowly dropwise through addition funnel and reaction stirred at room temperature for 3 hours. Thereafter, acetic acid was removed under reduced pressure and NaHCO$_3$ saturated solution (100 mL) added to the residue which was extracted with ethyl acetate (125 mL×3), combined organic extracts were dried over sodium sulfate and condensed under reduced pressure to give crude which was sufficiently pure and was carried to next step without further purification.

NMR (H+) (DMSO) 1H (d) 7.51, 7.48, 2H (s) 7.34, 1H (d) 7.17, 7.13, 3H (s) 3.78.

LC/MS (m/z) [199.0] (MH+)

Step 2. Synthesis of N-(cyclohexylmethyl)-5-fluoro-6-methoxybenzo[d]thiazol-2-amine

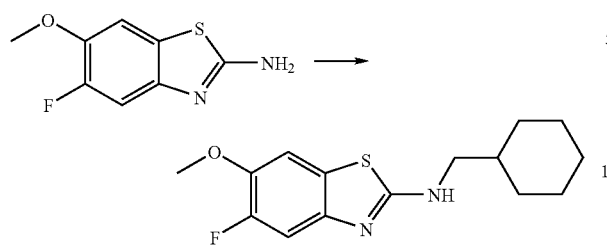

To the solution of 5-fluoro-6-methoxybenzo[d]thiazol-2-amine (350 mg, 1.76 mmol, 1.0 eq) in 2 mL of NMP was added bromomethyl cyclohexane (370 μL, 2.65 mmol, 1.5 eq) and potassium carbonate (366 mg, 2.65 mmol, 1.5 eq) at room temperature. The reaction mixture was stirred at 80° C. for 24 hours with subsequent addition of reagents till reaction completion and thereafter quenched with saturated sodium bicarbonate solution (100 mL) which was then extracted with ethyl acetate (125 mL×3), combined organic layers dried over sodium sulfate, filtered and condensed under reduced pressure. Purification of the crude over ISCO using slow gradient of 0%-50% ethyl acetate-hexane gave 310 mg of product in 60% yield. LC/MS (m/z) [295.1] (MH+)

Step 3. Synthesis of 2-(cyclohexylmethylamino)-5-fluorobenzo[d]thiazol-6-ol

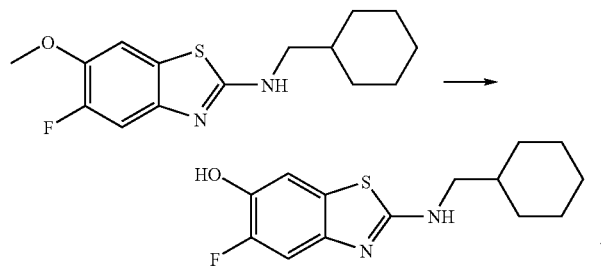

To the solution of N-(cyclohexylmethyl)-5-fluoro-6-methoxybenzo[d]thiazol-2-amine (114 mg, 0.387 mmol, 1.0 eq) in 10 mL of DCM was added 1M solution of boron tribromide (ca. 1.0 mL, 0.775 mmol, 2.0 eq) at room temperature. The reaction mixture was stirred for 2 hours, thereafter the mixture was diluted with saturated sodium bicarbonate solution (ca. 100 mL) till PH=7 and aqueous layer extracted with ethyl acetate (ca. 150 mL×3). Combined organic layers were dried over sodium sulfate, filtered and condensed under reduced pressure to give crude product which was sufficiently pure and was carried to next step without further purification. LC/MS (m/z) [281.1] (MH+)

Step 4. Synthesis of 4-(2-(cyclohexylmethylamino)-5-fluorobenzo[d]thiazol-6-yloxy)-N-methylpicolinamide

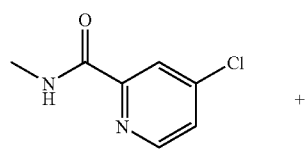 +

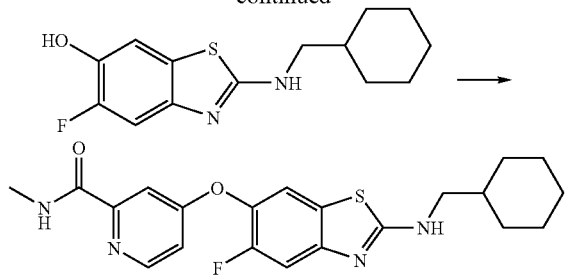

To the solution of 2-(cyclohexylmethylamino)-5-fluorobenzo[d]thiazol-6-ol (25 mg, 0.089 mmol, 1.0 eq) in 2 mL of NMP was added 4-chloro-N-methylpicolinamide (18 mg, 0.107 mmol, 1.2 eq) and cesium carbonate (86 mg, 0.267 mmol, 3.0 eq) at room temperature. The reaction mixture was stirred at 85° C. for 12 hours, thereafter the mixture was purified on reverse phase HPLC giving 1.6 mg of product as TFA salt in ca. 3.5% yield. LC/MS (m/z) [415.1] (MH+)

Example 199

N-methyl-4-(2-(4-((4-methylpiperazin-1-yl)methyl) benzylamino)benzo[d]thiazol-6-yloxy)picolinamide

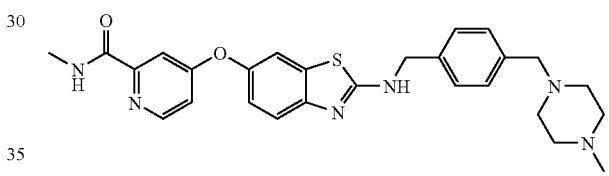

To the solution of N-methyl-4-(2-(methylsulfinyl)benzo[d]thiazol-6-yloxy)picolinamide (25 mg, 0.072 mmol, 1.0 eq) in 2 mL of NMP was added (4-((4-methylpiperazin-1-yl)methyl)phenyl)methanamine (23 mg, 0.108 mmol, 1.5 eq) and DIPEA (37 μL, 0.216 mmol, 3.0 eq) and reaction mixture heated at 80° C. in oil bath for 12 hours. Thereafter, the product was purified via reverse phase HPLC. LC/MS (m/z) [503.1] (MH+).

Example 200

N-methyl-4-(2-(2-(2-(4-methylpiperazin-1-yl) ethoxy)phenylamino)benzo[d]thiazol-6-yloxy)picolinamide

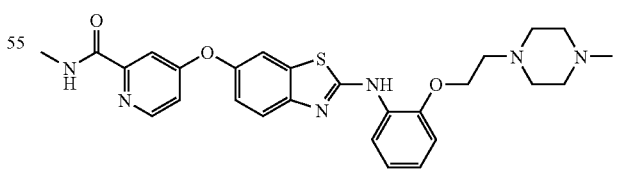

To the solution of N-methyl-4-(2-(methylsulfinyl)benzo[d]thiazol-6-yloxy)picolinamide (25 mg, 0.072 mmol, 1.0 eq) in 1 mL of IPA and 1 mL conc. HCl was added 2-(2-(4-methylpiperazin-1-yl)ethoxy) aniline (25 mg, 0.108 mmol, 1.5 eq) and reaction mixture heated at 80° C. in oil bath for 2 hours. Thereafter, the product was purified via reverse phase HPLC. This procedure was generalized for other analogues for which progress of the reaction was monitored by LC-MS and amount of aniline and reaction time adjusted as needed. LC/MS (m/z) [519.1] (MH+)

Example 201

4-(2-((1R,2R)-2-hydroxycyclohexylamino)benzo[d]oxazol-6-yloxy)-N-methylpicolinamide

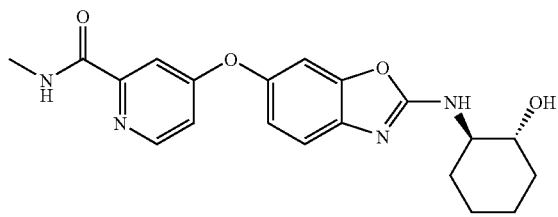

To the solution of N-methyl-4-(2-(methylsulfinyl)benzo[d]oxazol-6-yloxy)picolinamide (25 mg, 0.075 mmol, 1.0 eq) in 1 mL of NMP was added (1R,2R)-2-aminocyclohexanol hydrochloride (17 mg, 0.112 mmol, 1.5 eq) and DIPEA (40 µL, 0.225 mmol, 3.0 eq) and reaction mixture stirred at room temperature for 48 hours. Thereafter, the product was purified via reverse phase HPLC. LC/MS (m/z) [383.1] (MH+)

Intermediates

Synthesis of 4-chloro-N-methylpyridine-3-carboxamide

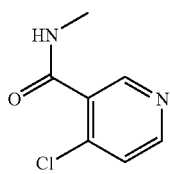

Step 1. To a suspension of 4-chloronicotinic acid (1.57 g, 10.0 mmol, 1.0 eq) in 25 mL of toluene was added thionyl chloride (1.8 mL, 25.0 mmol, 2.5 eq) at room temperature. The reaction mixture was stirred at 100° C. for 3 hours. The mixture was concentrated under reduced pressure, dissolved in 25 mL of toluene and concentrated again to give crude 4-chloronicotinoyl chloride hydrochloride salt, which was used in the next step without further purification.

Step 2. To a suspension of crude 4-chloronicotinoyl chloride hydrochloride in 25 mL of THF was added methylamine solution (2M in THF, 20 mL, 40 mmol, 4.0 eq) at 0° C. The reaction mixture was stirred at room temperature for 1 hour and concentrated under reduced pressure. The crude material was dissolved in ethylacetate (75 mL) and water/brine/saturated sodium bicarbonate solution (1/1/1, 75 mL). The separated aqueous layer was extracted with EtOAc. The combined organic layers were washed with water/brine/saturated sodium bicarbonate solution (1/1/1, 25 mL) and brine (25 mL) and dried over sodium sulfate. Removal of the solvent under reduced pressure afforded the title compound as orange solid (400 mg, 24%), which was used without further purification. MH+=171.0, Rt=0.55 min.

Synthesis of 4-chloro-N',N'-dimethylpyridine-2-carboxhydrazide

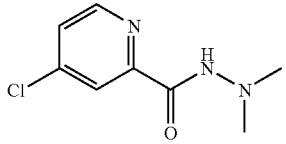

To a suspension of 4-chloropicolinoyl chloride hydrochloride (352 mg, 2.0 mmol, 1.0 eq) in 10 mL of THF were added N,N-dimethylhydrazine (120 mg, 2.0 mmol, 1.0 eq) and N,N-diisopropylethylamine (383 µL, 2.2 mmol, 1.1 eq) at room temperature. The reaction mixture was stirred for 15 min and diluted with water (25 mL) and EtOAc (50 mL). The separated organic layer was washed with brine (25 mL), saturated sodium bicarbonate solution (25 mL) and dried over sodium sulfate. Concentration under reduced pressure gave the title compound as colorless solid (223 mg, 56%), which was used without further purification. MH+=200, Rt=1.42 min.

Synthesis of 4-chloro-N-methylpicolinamide and 4-chloropicolinoyl chloride

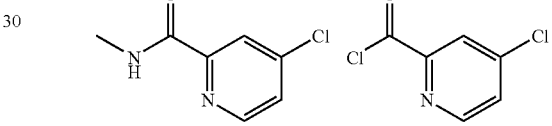

Prepared following the method described in "A Scaleable Synthesis of BAY 43-9006: A Potent Raf Kinase Inhibitor for the treatment of cancer". Donald Bankston, Jacques Dumas, Reina Natero, Bernd Riedl, Mary-Katherine Monahan, Robert Sibley; Bayer Research Center. Pharmaceutical Division. Organic Process Research and Development 2002 (6) 777-781.

Synthesis of (1R,2R)-2-aminocyclohexanol hydrochloride

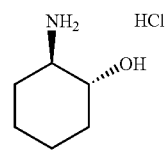

To an ice bath cooled solution of amine (1R,2R)-(−)-2-Benzyloxycyclohexylamine (20 g, 97.4 mmol) in dry MeOH (390 mL) was added 4.0 M HCl solution in dioxane (49 mL, 195 mmol) slowly via syringe. The ice bath was removed and resulting solution was sparged with $N_2$ for 10 min. 10% Pd/C (3 g, 28 mmol) was added to the solution and the reaction was purged with $H_2$ and maintained under a $H_2$ atmosphere. After 4 h, an additional 10 mL of 4.0 M HCl solution in dioxane was added[2] and the reaction was maintained under a $H_2$ atmosphere overnight. Upon completion (followed by LCMS), the reaction was filtered through a thin, tightly packed pad of Celite and the collected solids were washed successively with MeOH and EtOAc. The combined organic filtrates were evaporated and dried under vacuum gave (1R,2R)-2-aminocyclohexanol hydrochloride as a pale-colored solid, (13.8 g, 91 mmol, 93%). LCMS m/z 116.0 (MH⁺), t_R=0.37 min.

(1S,2S)-2-aminocyclohexanol hydrochloride was prepared in the same manner.

Example 202

4-chloro-N-isobutoxypicolinamide

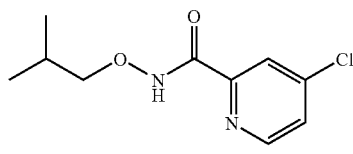

To a suspension of 4-chloropicolinoyl chloride hydrochloride (1.0 g, 5.68 mmol, 1.0 eq) in 25 ml of THF were added O-isobutylhydroxylamin hydrochloride (785 mg, 6.25 mmol, 1.1 eq) and N,N-diisopropylethylamine (2.97 ml, 17.0 mmol, 3.0 eq) at room temperature. The reaction mixture was stirred for 30 min and diluted with water (25 mL) and EtOAc (50 mL). The separated organic layer was washed with brine (25 mL), saturated sodium bicarbonate solution (2×25 mL) and dried over sodium sulfate. Concentration under reduced pressure gave the title compound as colorless solid (870 mg, 67%), which was used without further purification. ES/MS m/z 229.0 (MH⁺), Rt=2.61 min.

Example 203

4-(2-(cyclohexylmethylamino)benzo[d]thiazol-6-yloxy)-N-isobutoxypicolinamide

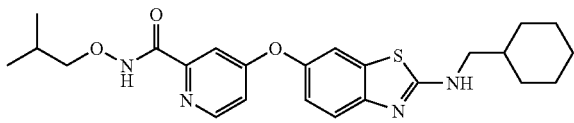

To the reaction mixture 2-(cyclohexylmethylamino)benzo[d]thiazol-6-ol (30 mg, 0.114 mmol)) and cesium carbonate (326 mg, 0.228 mmol) in 1.2 ml of DMF was added 4-chloro-N-isobutoxypicolinamide (40 mg, 0.171 mmol). The reaction mixture was stirred at rt for 10 min and then microwaved at 130° C. for 3×20 min. The crude reaction mixture was filtered, purified on preparative HPLC and lyophilized to give the title compound as its TFA salt as a white solid (15 mg, 23%). ES/MS m/z 455.1 (MH⁺), Rt=2.90 min.

Example 204

4-(2-((1R,2R)-2-hydroxycyclohexylamino)benzo[d]thiazol-6-yloxy)-N-isobutoxypicolinamide

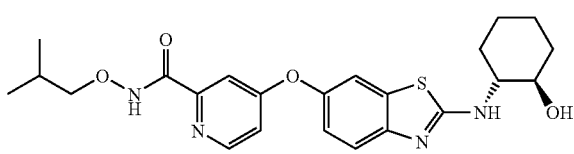

Prepared as in the preceding example. ES/MS m/z 457.0 (MH⁺), Rt=2.35 min.

Example 205

N-(cyclohexylmethyl)-6-(2-(4,5-dimethyl-1H-imidazol-2-yl)pyridin-4-yloxy)benzo[d]thiazol-2-amine The subject compound was prepared according to the general Scheme below:

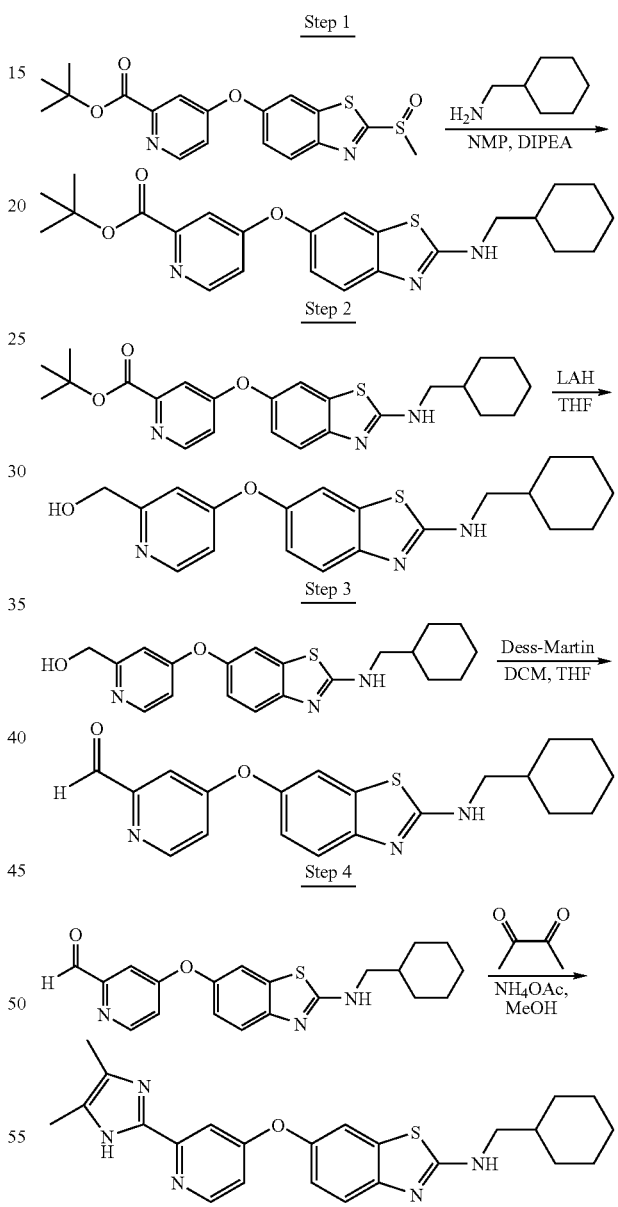

Step 1. Preparation of (1R,2R)-2-(6-methoxybenzo[d]thiazol-2-ylamino)cyclohexanol To the solution of tert-butyl 4-(2-(methylsulfinyl)benzo[d]thiazol-6-yloxy)picolinate (500 mg, 1.28 mmol) in 8.0 ml of NMP was added cyclohexylmethanamine (407 mg, 3.6 mmol) and DIPEA (0.887 ml, 5.12 mmol). The reaction solution was stirred at 110° C. for 12 hours or until done by LCMS. The crude reaction mixture was filtered, purified on prep HPLC and lyophilized to give tert-butyl 4-(2-(cyclohexylmethylamino)benzo[d]thiazol-6-yloxy)picolinate as TFA salt (420 mg). ES/MS m/z 440.2 (MH+).

Step 2. Preparation of (4-(2-(cyclohexylmethylamino)benzo[d]thiazol-6-yloxy)pyridin-2-yl)methanol To the solution of tert-butyl 4-(2-(cyclohexylmethylamino)benzo[d]thiazol-6-yloxy)picolinate (420 mg, 1.14 mmol) under argon in 50 ml of THF was added 1 M LAH solution in THF (3.41 ml, 3.41 mmol) slowly at room temperature. The reaction mixture was stirred at room temperature for 30 minutes. The crude reaction mixture was worked up by carefully adding methanol (5 ml), then 6M NaOH (5 ml), and water (5 ml) with stirring at room temperature. The aluminum salts were allowed to precipitate out. Ethyl acetate (200 ml) was added and the organic layer was decanted off from salts. The salts were washed again with ethyl acetate (100 ml) and decanted. The organic layers were combined and washed with brine (2×50 ml), dried with Na₂SO₄, filtered and concentrated. The resulting solid residue was purified by silica gel column chromatography, eluted with (5% methanol 95% DCM) and concentrated in vacuo to give (4-(2-(cyclohexylmethylamino)benzo[d]thiazol-6-yloxy)pyridin-2-yl) methanol as solid (157 mg). ES/MS m/z 370.2 (MH+).

Step 3. Preparation of 4-(2-(cyclohexylmethylamino) benzo[d]thiazol-6-yloxy)picolinaldehyde To the solution of (4-(2-(cyclohexylmethylamino)benzo [d]thiazol-6-yloxy)pyridin-2-yl)methanol (30 mg, 0.081 mmol) in 2 ml of THF and 2 ml of DCM was added Dess-Martin Periodinane (38 mg, 0.089 mmol). The reaction mixture was stirred at room temperature for 30 minutes. The crude reaction mixture diluted with ethyl acetate (60 ml), washed with saturated sodium bicarbonate (2×15 ml), brine (1×15 ml), dried with Na₂SO₄, filter and concentrated in vacuo to give 4-(2-(cyclohexylmethylamino)benzo[d]thiazol-6-yloxy)picolinaldehyde as solid (29 mg). ES/MS m/z 386.1 (MH+) as the hydrate (+18).

Step 4. Preparation of N-(cyclohexylmethyl)-6-(2-(4,5-dimethyl-1H-imidazol-2-yl)pyridin-4-yloxy)benzo[d]thiazol-2-amine To the solution of 4-(2-(cyclohexylmethylamino)benzo[d] thiazol-6-yloxy)picolinaldehyde (15 mg, 0.041 mmol) in 1.0 ml of methanol was added ammonium acetate (32 mg, 0.41 mmol) and biacetyl (14 mg, 0.163 mmol). The reaction mixture was stirred at 70° C. for 2 hours or until done by LCMS. The crude reaction mixture was concentrated to solid, re-dissolved in 0.8 ml NMP, filtered, purified on prep HPLC and lyophilized to give N-(cyclohexylmethyl)-6-(2-(4,5-dimethyl-1H-imidazol-2-yl)pyridin-4-yloxy)benzo[d]thiazol-2-amine as TFA salt (3.0 mg). ES/MS m/z 434.2 (MH+).

Example 206

N-(cyclohexylmethyl)-6-(2-(4-(trifluoromethyl)-1H-imidazol-2-yl)pyridin-4-yloxy)benzo[d]thiazol-2-amine The subject compound was prepared according to the general Scheme below

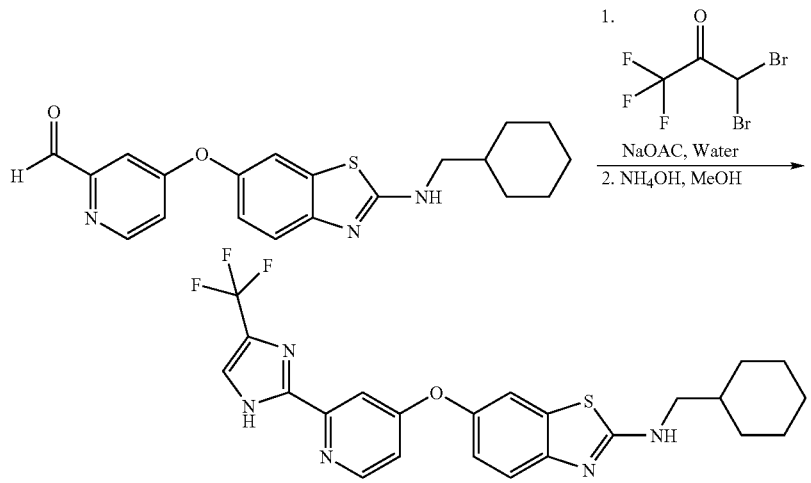

To the solution of sodium acetate (300 mg, 3.7 mmol) in 1.6 ml of water was added 3,3-dibromo-1,1,1-trifluoropropan-2-one (500 mg, 1.85 mmol). The reaction mixture was stirred at 100° C. for 1 hour. From the above crude reaction mixture remove approximately (0.5 ml, 0.46 mol), cool to room temperature. This crude mixture was added to a solution of 4-(2-(cyclohexylmethylamino)benzo[d]thiazol-6-yloxy)picolinaldehyde (15 mg, 0.041 mmol) in 2 ml of methanol. To the crude reaction mixture was added ammonium hydroxide (28%-30%) solution (0.5 ml, 4 mmol). The reaction mixture was stirred at room temperature for 18 hours or until done by LCMS. The crude reaction mixture was concentrated to solid, re-dissolved in 0.8 ml NMP, filtered, purified on prep HPLC and lyophilized to give N-(cyclohexylmethyl)-6-(2-(4-(trifluoromethyl)-1H-imidazol-2-yl)pyridin-4-yloxy)benzo[d] thiazol-2-amine as TFA salt (3.0 mg). ES/MS m/z 474.2 (MH+).

Example 207

(1R,2R)-2-(6-(6'-(pyrrolidin-1-yl)-2,3'-bipyridin-4-yloxy)benzo[d]thiazol-2-ylamino)cyclohexanol The subject compound was prepared according to the general Scheme below:

Step 1.

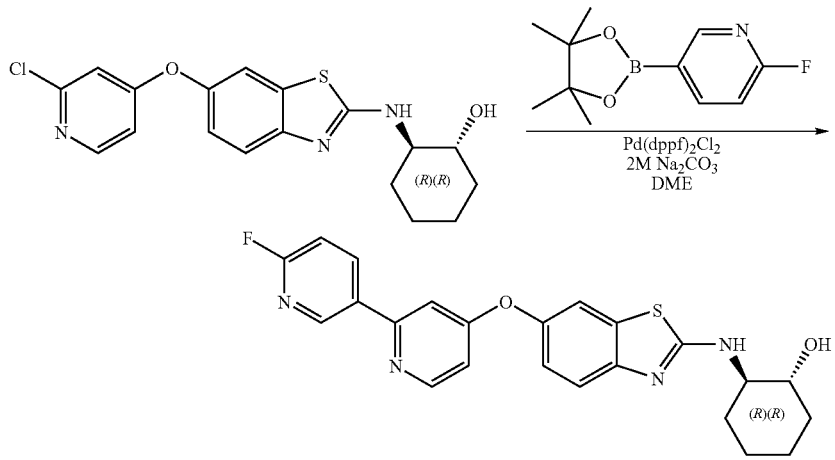

Step 2.

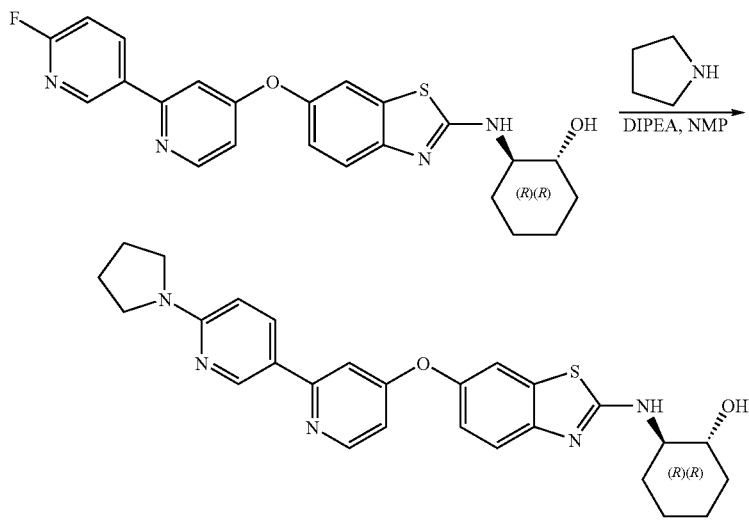

Step 1. Preparation of (1R,2R)-2-(6-(6'-fluoro-2,3'-bipyridin-4-yloxy)benzo[d]thiazol-2-ylamino)cyclohexanol To the reaction mixture of (1R,2R)-2-(6-(2-chloropyridin-4-yloxy)benzo[d]thiazol-2-ylamino)cyclohexanol (130 mg, 0.345 mmol) in 5.0 ml of DME, 2-fluoro-5-(4,4,5,5-tetramethyl-1,3,2-dioxaborolan-2-yl)pyridine (268 mg, 1.21 mmol), Pd(dppf)₂Cl₂ (56 mg, 0.069 mmol) and 2M Na₂CO₃ (1.05 ml, 2.1 mmol) were added. The reaction solution was stirred at 105° C. for 2 hours or until done by LC. The crude reaction mixture was concentrated to solid, re-dissolved in 3 ml of DMF, filtered, purified on prep HPLC and lyophilized to give (1R,2R)-2-(6-(6'-fluoro-2,3'-bipyridin-4-yloxy)benzo[d]thiazol-2-ylamino)cyclohexanol as TFA salt (149 mg). ES/MS m/z 437.1 (MH$^+$).

Step 2. Preparation of (1R,2R)-2-(6-(6'-(pyrrolidin-1-yl)-2,3'-bipyridin-4-yloxy)benzo[d]thiazol-2-ylamino)cyclohexanol To the reaction mixture of (1R,2R)-2-(6-(6'-fluoro-2,3'-bipyridin-4-yloxy)benzo[d]thiazol-2-ylamino)cyclohexanol (11 mg, 0.0252 mmol) in 0.4 ml of NMP was added (DIPEA) diisopropylethylamine (13 ul, 0.0756 mmol) and pyrrolidine (14.4 mg, 0.202 mmol). The reaction mixture was stirred at 105-110° C. for 20 hours or until done by LC. The crude reaction mixture was filtered, purified on prep HPLC and lyophilized to give (1R,2R)-2-(6-(6'-(pyrrolidin-1-yl)-2,3'-bipyridin-4-yloxy)benzo[d]thiazol-2-ylamino)cyclohexanol as TFA salt (2.3 mg). ES/MS m/z 488.1 (MH$^+$).

Example 208

(1R,2R)-2-(6-(2-(4-(pyrrolidin-1-ylmethyl)phenyl)pyridin-4-yloxy)benzo[d]thiazol-2-ylamino)cyclohexanol The subject compound was prepared according to the general Scheme below:

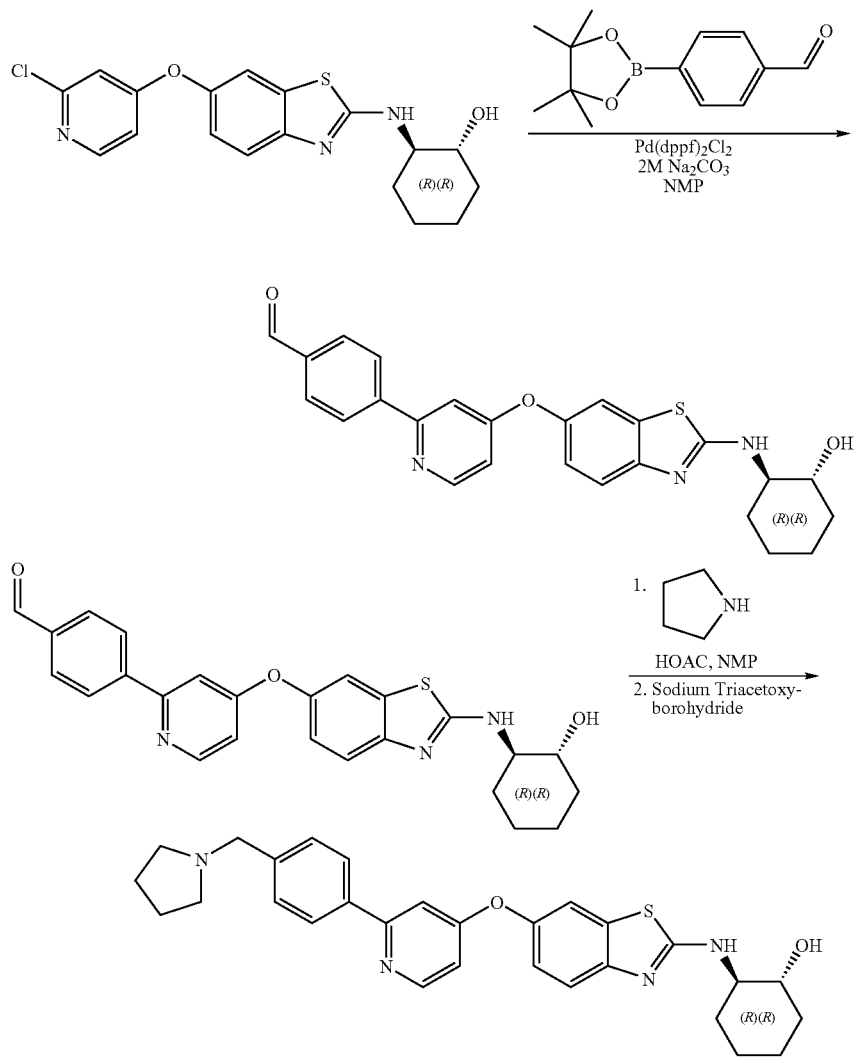

Step 1. Preparation of 4-(4-(2-((1R,2R)-2-hydroxy-cyclohexylamino)benzo[d]thiazol-6-yloxy)pyridin-2-yl)benzaldehyde To the reaction mixture of (1R,2R)-2-(6-(2-chloropyridin-4-yloxy)benzo[d]thiazol-2-ylamino)cyclohexanol (70 mg, 0.186 mmol) in 2.5 ml of NMP, 4-(4,4,5,5-tetramethyl-1,3,2-dioxaborolan-2-yl)benzaldehyde (130 mg, 0.558 mmol), Pd(dppf)$_2$Cl$_2$ (38 mg, 0.0465 mmol) and 2M Na$_2$CO$_3$ (0.56 ml, 1.12 mmol) were added. The reaction solution was stirred at 110° C. for 4 hours or until done by LC. The crude reaction mixture was filtered, purified on prep HPLC and lyophilized to give 4-(4-(2-((1R,2R)-2-hydroxycyclohexylamino)benzo[d]thiazol-6-yloxy)pyridin-2-yl)benzaldehyde as TFA salt (61 mg). ES/MS m/z 446.0 (MH$^+$).

Step 2. Preparation of (1R,2R)-2-(6-(2-(4-(pyrrolidin-1-ylmethyl)phenyl)pyridin-4-yloxy)benzo[d]thiazol-2-ylamino)cyclohexanol To the reaction mixture of 4-(4-(2-((1R,2R)-2-hydroxycyclohexylamino)benzo[d]thiazol-6-yloxy)pyridin-2-yl)benzaldehyde (12 mg, 0.027 mmol) in 0.6 ml of NMP was added in order pyrrolidine (19.2 mg, 0.27 mmol), excess acetic acid (0.060 ml, 1.0 mmol) and triethyl orthoformate (20 mg, 0.135 mmol). The reaction mixture was stirred at room temperature for 20 minutes. To this reaction mixture was added sodium triacetoxyborohydride (14.3 mg, 0.0675 mmol). The reaction mixture was stirred at room temperature for 18 hours. The crude reaction mixture was filtered, purified on prep HPLC and lyophilized to give (1R,2R)-2-(6-(2-(4-(pyrrolidin-1-ylmethyl)phenyl)pyridin-4-yloxy)benzo[d]thiazol-2-ylamino)cyclohexanol as TFA salt (2.8 mg). ES/MS m/z 501.2 (MH$^+$).

Example 209

(1R,2R)-2-(6-(2-(1-(2-(pyrrolidin-1-yl)ethyl)-1H-pyrazol-4-yl)pyridin-4-yloxy)benzo[d]thiazol-2-ylamino)cyclohexanol The subject compound was prepared according to the general Scheme below:

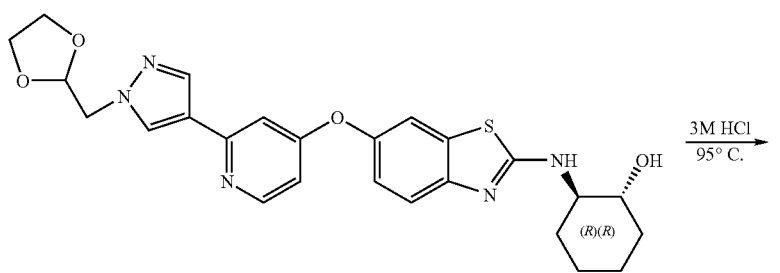

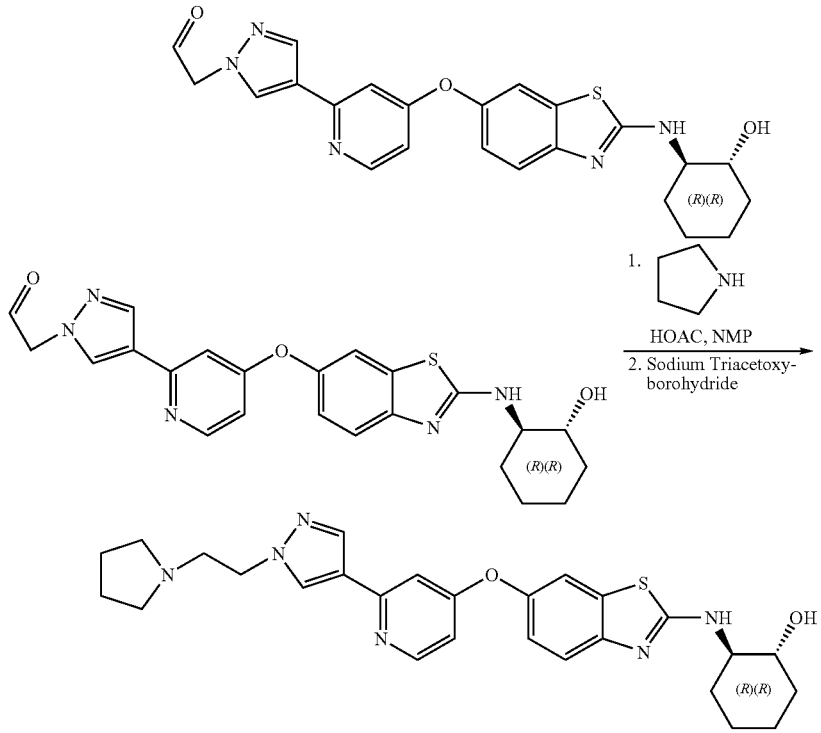

Step 1. Preparation of 2-(4-(4-(2-((1R,2R)-2-hydroxycyclohexylamino)benzo[d]thiazol-6-yloxy)pyridin-2-yl)-1H-pyrazol-1-yl)acetaldehyde To the reaction solid of (1R,2R)-2-(6-(2-(1-((1,3-dioxolan-2-yl)methyl)-1H-pyrazol-4-yl)pyridin-4-yloxy)benzo[d]thiazol-2-ylamino)cyclohexanol (195 mg, 0.395 mmol) was added 3M HCl (6.0 ml, 18 mmol). The reaction solution was stirred at 95° C. for 6 hours or until done by LC. The crude reaction mixture was lyophilized to solid and re-dissolved in 2 ml of water and 2 ml of NMP, purified on prep HPLC and lyophilized to give 2-(4-(4-(2-((1R,2R)-2-hydroxycyclohexylamino)benzo[d]thiazol-6-yloxy)pyridin-2-yl)-1H-pyrazol-1-yl)acetaldehyde as TFA salt (50 mg). ES/MS m/z 468.2 (MH+).

Step 2. Preparation of (1R,2R)-2-(6-(2-(1-(2-(pyrrolidin-1-yl)ethyl)-1H-pyrazol-4-yl)pyridin-4-yloxy)benzo[d]thiazol-2-ylamino)cyclohexanol To the reaction mixture of 2-(4-(4-(2-((1R,2R)-2-hydroxycyclohexylamino)benzo[d]thiazol-6-yloxy)pyridin-2-yl)-1H-pyrazol-1-yl)acetaldehyde (12.5 mg, 0.0267 mmol) in 0.5 ml of NMP was added pyrrolidine (19 mg, 0.267 mmol) and stirred for 10 minutes. To this reaction mixture was added excess acetic acid (0.070 ml, 1.16 mmol) and stirred for 20 minutes. To this reaction mixture was added sodium triacetoxyborohydride (13 mg, 0.0614 mmol). The reaction mixture was stirred at room temperature for 90 minutes. The crude reaction mixture was filtered, purified on prep HPLC and lyophilized to give (1R,2R)-2-(6-(2-(1-(2-(pyrrolidin-1-yl)ethyl)-1H-pyrazol-4-yl)pyridin-4-yloxy)benzo[d]thiazol-2-ylamino)cyclohexanol as TFA salt (1.4 mg). ES/MS m/z 505.2 (MH+).

Example 210

Preparation of N-(cyclohexylmethyl)-6-(pyridin-4-yloxy)benzo[d]thiazol-2-amine

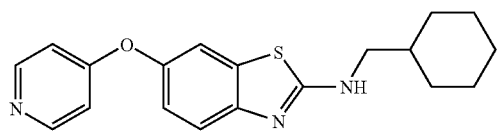

To the solution of N-(cyclohexylmethyl)-6-(pyridin-4-yloxy)benzo[d]thiazol-2-amine (20 mg, 0.076 mmol, 1.0 eq) in NMP at room temperature was added cesium carbonate (61 mg, 0.190 mmol, 2.5 eq), 4-chloropyridine HCl (12.5 mg, 0.083 mmol, 1.1 eq) and DIPEA (33 µL, 0.190 mmol, 2.5 eq) and reaction left stirring at 80° C. for 72 hours. Thereafter, the product was isolated by preparative HPLC and pure fraction lyophilized to give the title compound as TFA salt (1.4 mg). ES/MS m/z 340.1 (MH+).

Example 211

Preparation of 4-(2-((1R,2R)-2-hydroxycyclohexy-lamino)-1-oxo-benzo[d]thiazol-6-yloxy)-N-methylpicolinamide

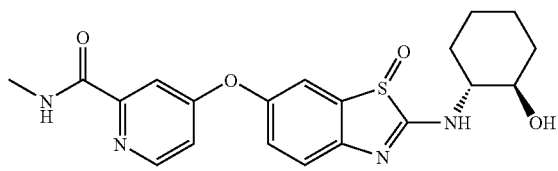

A solution of OXONE® (KHSO$_5$, 380 mg, mmol) in water (4 ml) was added dropwise to a solution of 4-(2-((1R,2R)-2-hydroxycyclohexylamino)benzo[d]thiazol-6-yloxy)-N-methylpicolinamide (25 mg, mmol) in methanol (4 ml) at rt. After stirring for 23 hours the suspension is diluted with water (50 ml) and extracted with ethyl acetate (2×10 ml). The combined organic layers were washed with brine, concentrated, and purified by prep HPLC to yield the title compound as white solid. Yield: 2.4 mg. ES/MS m/z 415.1 (MH$^+$), Rt=1.81 min.

Example 212

Preparation of (S)—N-(1-cyclohexylethyl)-6-(2-(1-ethyl-1H-pyrazol-4-yl)pyridin-4-yloxy)benzo[d]thiazol-2-amine

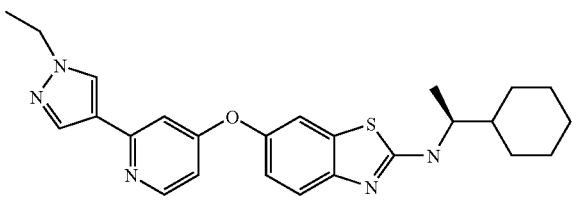

Following the procedure for Example 176 (Table 3). The reaction mixture was heated at 110° C. for 3 hours and purified by prep HPLC to give the title compound. Yield: 13 mg. ES/MS m/z 448.1 (MH$^+$), Rt=2.79 min.

Example 213

Preparation of (S)—N-(1-cyclohexylethyl)-6-(2-(1-(2-morpholinoethyl)-1H-pyrazol-4-yl)pyridin-4-yloxy)benzo[d]thiazol-2-amine

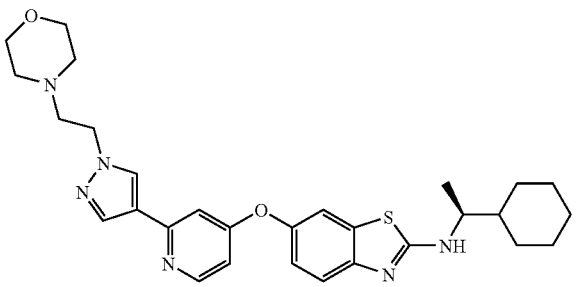

Following the procedure of Example 185 (Table 3), the crude material was firstly purified by prep HPLC and lyophilized. The residue was dissolved in ethyl acetate/saturated sodium bicarbonate solution (10 ml/10 ml). The separated organic layer was dried over sodium sulfate, concentrated in vacuo, and purified by prep TLC using dichloromethane/methanol (95:5). The purified product was dissolved in acetonitrile (3 ml) and 1N aqueous HCl (0.5 ml) and lyophilized to give the title compound as its HCl salt. Yield: 11 mg. ES/MS m/z 533.1 (MH$^+$), Rt=2.14 min.

Example 214

Preparation of (S)-6-(2-chloropyridin-4-yloxy)-N-(1-(ethylsulfonyl)piperidin-3-yl)benzo[d]thiazol-2-amine

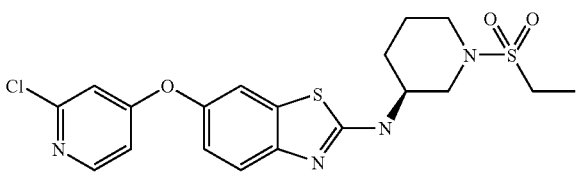

Step 1. Preparation of (S)-tert-butyl 3-(6-methoxybenzo[d]thiazol-2-ylamino)piperidine-1-carboxylate To the solution of 2-chloro-6-methoxybenzo[d]thiazole (2.6 g, 13 mmol) in 25 ml of NMP was added (S)-tert-butyl 3-(6-methoxybenzo[d]thiazol-2-ylamino)piperidine-1-carboxylate (5 g, 25 mmol) and DIPEA (2.6 ml, 15 mmol). The reaction solution was stirred at 100° C. for 7 days. The crude reaction solution was mixed with ethyl acetate (250 ml) and diluted aqueous sodium bicarbonate solution (80 ml) and the organic phase was separated. The separated organic layer was washed with water (2×60 ml) and brine (60 ml), then dried over sodium sulfate and evaporated in vacuo to give a brown oily product that was purified by flash chromatography over silica gel with ethyl acetate:hexane (35:65-50:50) to give (S)-tert-butyl 3-(6-methoxybenzo[d]thiazol-2-ylamino)piperidine-1-carboxylate (3.33 g, 9.16 mmol) as an ivory solid. ES/MS m/z 364.2 (MH$^+$). Rt=2.2 min.

Step 2. Preparation of (S)-6-methoxy-N-(piperidin-3-yl)benzo[d]thiazol-2-amine To a solution of (S)-tert-butyl 3-(6-methoxybenzo[d]thiazol-2-ylamino)piperidine-1-carboxylate (3.35 g, 9.22 mmol) in methanol/dioxane (3 ml/3 ml) was added slowly 4M HCl in dioxane (60 ml, 240 mmol) [Caution: gas development!]. The reaction mixture was stirred 2.5 hours at ambient temperature and concentrated in vacuo in order to remove methanol and half of dioaxane. The residue was suspended in diethylether (50 ml). The solids were filtered off, washed with diethylether (50 ml) and dried in vacuo to give (S)-6-methoxy-N-(piperidin-3-yl)benzo[d]thiazol-2-amine as its hydrochloride salt as white solid. Yield: 4.29 g. ES/MS m/z 264.1 (MH$^+$), Rt=1.62 min.

Step 3. Preparation of (S)—N-(1-(ethylsulfonyl)piperidin-3-yl)-6-methoxybenzo[d]thiazol-2-amine A mixture of (S)-6-methoxy-N-(piperidin-3-yl)benzo[d]thiazol-2-amine hydrochloride salt (2.0 g, 5.95 mmol), ethylsulfonyl chloride (1.13 ml, 11.91 mmol) and DIPEA (4.11 ml, 23.8 mmol) in NMP (25 ml) was heated at 55° C. for 16 hours 50 min. The reaction mixture was allowed to cool down to room temperature and diluted with water (150 ml) and ethyl acetate (150 ml). After stirring vigorously for 1 hour the separated organic layer was washed with water (3×100 ml), saturated sodium bicarbonate solution (3×100 ml), water (100 ml) and brine (100 ml) and dried over sodium sulfate. Concentration in vacuo and purification by flash chromatography over silica gel with ethyl acetate:hexane (20:80-100:0) provided (S)—N-(1-(ethylsulfonyl)piperidin-3-yl)-6-methoxybenzo[d]thiazol-2-amine as tan solid. Yield: 1.22 g. ES/MS m/z 356.0 (MH$^+$), Rt=2.12 min.

Step 4. Preparation of (S)-2-(1-(ethylsulfonyl)piperidin-3-ylamino)benzo[d]thiazol-6-ol A solution of (S)—N-(1-(ethylsulfonyl)piperidin-3-yl)-6-methoxybenzo[d]thiazol-2-amine (1.22 g, 3.43 mmol) in dichloromethane (25 ml) under nitrogen atmosphere was treated with boron tribromide (1M in dichloromethane, 7.5 ml) at 0° C. Stirring was continued for 10 min at 0° C. and for 135 min at ambient temperature. The reaction mixture was carefully diluted with water (50 ml), ethyl acetate (200 ml) and treated with solid sodium bicarbonate (until no further gas development was observed). The mixture was stirred until phases became clear. The separated organic phase was washed with saturated sodium bicarbonate solution (2×75 ml), water (75 ml), brine (75 ml) and dried over sodium sulfate. Concentration in vacuo afforded crude (S)-2-(1-(ethylsulfonyl)piperidin-3-ylamino)benzo[d]thiazol-6-ol which was used in the next step without further purification. Yield: 1.15 g. ES/MS m/z 342.0 (MH$^+$), Rt=1.86 min.

Step 5. Preparation of (S)-6-(2-chloropyridin-4-yloxy)-N-(1-(ethylsulfonyl)piperidin-3-yl)benzo[d]thiazol-2-amine To a mixture of (S)-2-(1-(ethylsulfonyl)piperidin-3-ylamino)benzo[d]thiazol-6-ol (1.15 g, 3.37 mmol) and cesium carbonate (2.20 g, 6.74 mmole) in 12 ml of NMP was added 2-chloro-4-fluoropyridine (532 mg, 4.05 mmol). The reaction mixture was stirred at 60° C. for 17 hours. The reaction mixture was diluted with water (100 ml) and ethyl acetate (100 ml). The separated organic layer was washed with water (3×50 ml), saturated sodium bicarbonate solution (3×50 ml), water (50 ml), brine (100 ml) and dried over sodium sulfate. Concentration in vacuo and purification by flash chromatography over silica gel with ethyl acetate:hexane (1:1 to 3:1) provided the title compound. Yield: 671 mg. ES/MS m/z 453.0 (MH$^+$), Rt=2.59 min.

Example 215

(1R,2R)-2-(6-(2-(3-methoxyprop-1-ynyl)pyridin-4-yloxy)benzo[d]thiazol-2-ylamino)cyclohexanol The subject compound was prepared according to the general Scheme below:

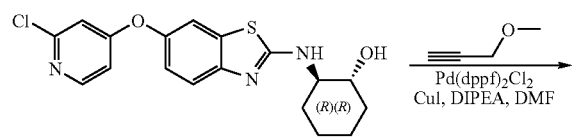

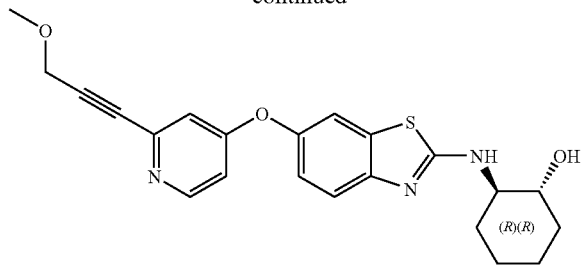

Preparation of (1R,2R)-2-(6-(2-(3-methoxyprop-1-ynyl)pyridin-4-yloxy)benzo[d]thiazol-2-ylamino)cyclohexanol To the reaction mixture of (1R,2R)-2-(6-(2-chloropyridin-4-yloxy)benzo[d]thiazol-2-ylamino)cyclohexanol (18.8 mg, 0.05 mmol) in 0.5 ml of DMF was added Pd(dppf)$_2$Cl$_2$ (8.2 mg, 0.01 mmol), CuI (4.3 mg, 0.0225 mmol), 3-methoxyprop-1-yne (15.8 mg, 0.225 mmol) and last add DIPEA (0.026 ml, 0.15 mmol). The reaction solution was stirred at 100° C. for 90 minutes or until done by LC. The crude reaction mixture was filtered, purified on prep HPLC and lyophilized to give (1R,2R)-2-(6-(2-(3-methoxyprop-1-ynyl)pyridin-4-yloxy)benzo[d]thiazol-2-ylamino)cyclohexanol as TFA salt (9.2 mg). ES/MS m/z 410.1 (MH$^+$).

Example 216

(1R,2R)-2-(6-(2-ethynylpyridin-4-yloxy)benzo[d]thiazol-2-ylamino)cyclohexanol The subject compound was prepared according to the general Scheme below:

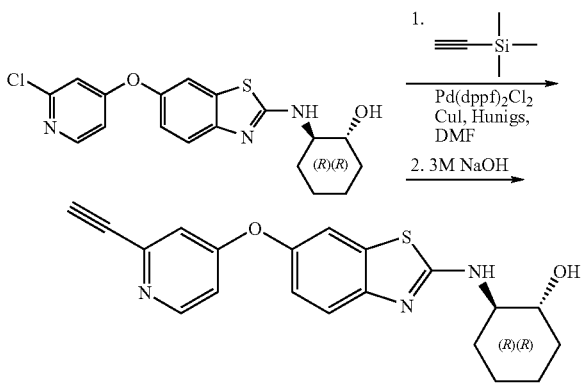

Preparation of (1R,2R)-2-(6-(2-ethynylpyridin-4-yloxy)benzo[d]thiazol-2-ylamino)cyclohexanol To the reaction mixture of (1R,2R)-2-(6-(2-chloropyridin-4-yloxy)benzo[d]thiazol-2-ylamino)cyclohexanol (16 mg, 0.043 mmol) in 0.5 ml of DMF was added Pd(dppf)$_2$Cl$_2$ (8.8 mg, 0.0108 mmol), CuI (4.5 mg, 0.024 mmol), ethynyltrimethylsilane (21.1 mg, 0.215 mmol) and last add DIPEA (0.023 ml, 0.129 mmol). The reaction solution was stirred at 100° C. for 90 minutes or until done by LC. To the crude reaction mixture a 3M NaOH solution (0.175 ml, 0.525 mmol) was added. The crude reaction mixture was stirred at room temperature for 30 minutes or until done by LC. The thick crude reaction mixture was neutralize with excess acetic acid (0.085, 1.41 mmol) and 0.5 ml DMF was added. The mixture was stirred for 5 minutes, filtered, purified on prep HPLC and lyophilized to give (1R,2R)-2-(6-(2-ethynylpyridin-4-yloxy)benzo[d]thiazol-2-ylamino)cyclohexanol as TFA salt (4.6 mg). ES/MS m/z 366.1 (MH$^+$).

Example 217

Preparation of (S)—N-(1-(ethylsulfonyl)piperidin-3-yl)-6-(2-(1-propyl-1H-pyrazol-4-yl)pyridin-4-yloxy)benzo[d]thiazol-2-amine

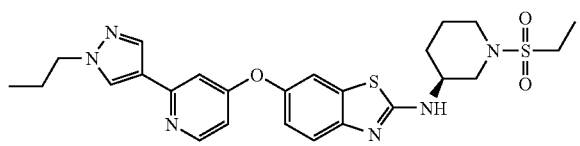

Following the procedure for Example 176. The reaction mixture was heated at 85° C. for 18 hours and at 90° C. for 24 hour. Purification by prep HPLC gave the title compound. Yield: 2.1 mg. ES/MS m/z 527.1 (MH$^+$), Rt=2.24 min.

Example 218

Preparation of (S)—N-(1-(ethylsulfonyl)piperidin-3-yl)-6-(2-(1-(2-fluoroethyl)-1H-pyrazol-4-yl)pyridin-4-yloxy)benzo[d]thiazol-2-amine

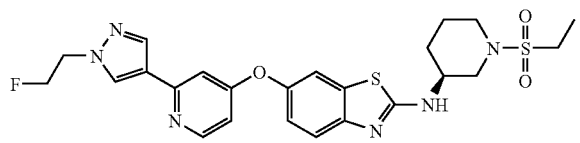

Following the procedure for Example 176. The reaction mixture was heated at 105° C. for 18 hours and purified by prep HPLC to give the title compound. Yield: 9.8 mg. ES/MS m/z 531.2 (MH$^+$), Rt=1.89 min.

Example 219

Preparation of (1R,2R)-2-(6-(pyridin-4-yloxy)benzo[d]thiazol-2-ylamino)cyclohexanol

To the reaction mixture of 2-((1R,2R)-2-hydroxycyclohexylamino)benzo[d]thiazol-6-ol (20 mg, 0.0755 mmole) in 0.5 ml of NMP was added cesium carbonate (62 mg, 0.189 mmol) and stirred at room temperature for 1-3 minutes. To this mixture was added additional cesium carbonate (98.5 mg, 0.302 mmol) and 4-chloropyridine hydrochloride (45.3 mg, 0.302 mmol). The reaction mixture was stirred at 105-110° C. for 48 hours or until done by LC. The crude reaction mixture was filtered, purified on prep HPLC and lyophilized to give (1R,2R)-2-(6-(pyridin-4-yloxy)benzo[d]thiazol-2-ylamino)cyclohexanol as TFA salt (1.1 mg). ES/MS m/z 342.1 (MH$^+$).

Compounds 1-381 in Table 3 and 1-102, 104-106, and 112-119 in Table 4 were made according to the examples above, and in particular according to the example noted in the Ex Prep (Example Preparation) column. Compounds 103 and 107-111 can be made according to the examples above.

TABLE 3

| Cmpd | Ex Prep | Structure | Name | (M + H)+, Rt (min.) |
|---|---|---|---|---|
| 1 | 199 | 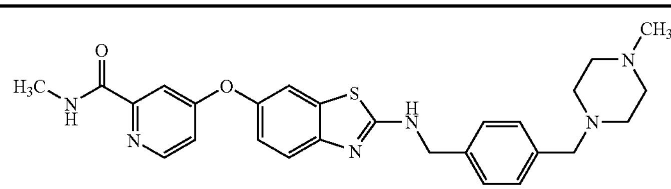 | N-methyl-4-(2-(4-((4-methylpiperazin-1-yl)methyl)benzylamino)benzo[d]thiazol-6-yloxy)picolinamide | 503, 1.89 |
| 2 | 199 | 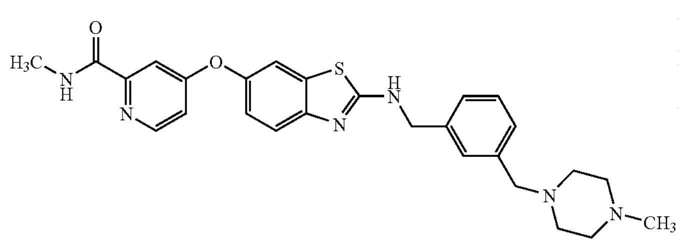 | N-methyl-4-(2-(3-((4-methylpiperazin-1-yl)methyl)benzylamino)benzo[d]thiazol-6-yloxy)picolinamide | 503, 1.89 |
| 3 | 199 | 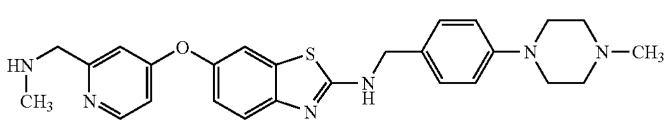 | N-methyl-4-(2-(4-(4-methylpiperazin-1-yl)benzylamino)benzo[d]thiazol-6-yloxy)picolinamide | 489, 1.98 |

TABLE 3-continued

| Cmpd | Ex Prep | Structure | Name | (M + H)+, Rt (min.) |
|---|---|---|---|---|
| 4 | 200 | 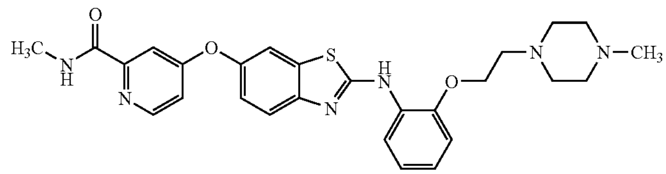 | N-methyl-4-(2-(2-(2-(4-methylpiperazin-1-yl)ethoxy)phenylamino)benzo[d]thiazol-6-yloxy)picolinamide | 519, 2.20 |
| 5 | 200 | 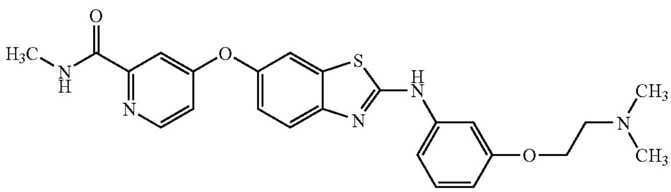 | 4-(2-(3-(2-(dimethylamino)ethoxy)phenylamino)benzo[d]thiazol-6-yloxy)-N-methylpicolinamide | 464, 2.18 |
| 6 | 200 | 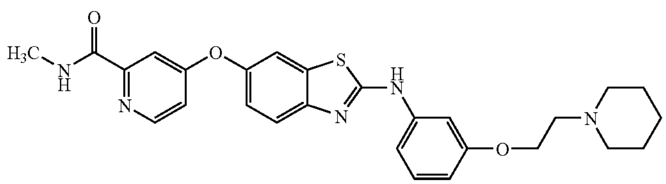 | N-methyl-4-(2-(3-(2-(piperidin-1-yl)ethoxy)phenylamino)benzo[d]thiazol-6-yloxy)picolinamide | 504, 2.29 |
| 7 | 201 | 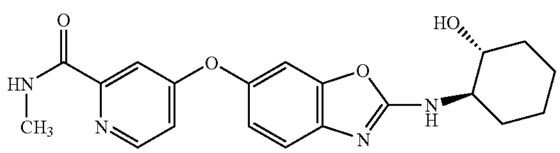 | 4-(2-((1R,2R)-2-hydroxycyclohexylamino)benzo[d]oxazol-6-yloxy)-N-methylpicolinamide | 383, 1.96 |
| 8 | 201 | 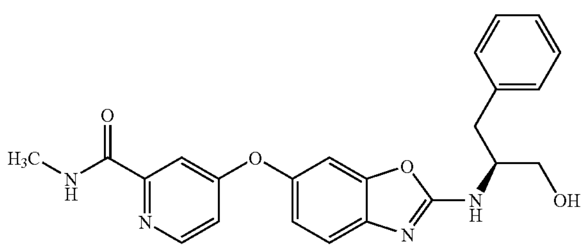 | (S)-4-(2-(1-hydroxy-3-phenylpropan-2-ylamino)benzo[d]oxazol-6-yloxy)-N-methylpicolinamide | 419, 2.22 |
| 9 | 201 | 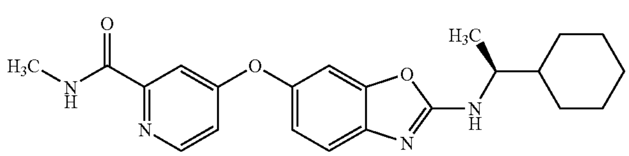 | (S)-4-(2-(1-cyclohexylethylamino)benzo[d]oxazol-6-yloxy)-N-methylpicolinamide | 395, 2.68 |
| 10 | 171 | 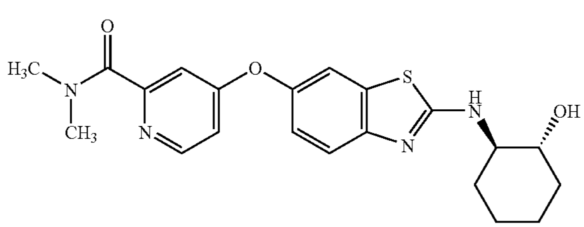 | 4-(2-((1R,2R)-2-hydroxycyclohexylamino)benzo[d]thiazol-6-yloxy)-N,N-dimethylpicolinamide | 413.1, 1.87 |

TABLE 3-continued

| Cmpd | Ex Prep | Structure | Name | (M + H)+, Rt (min.) |
|---|---|---|---|---|
| 11 | 171 | 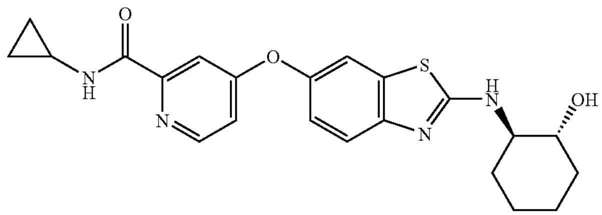 | N-cyclopropyl-4-(2-((1R,2R)-2-hydroxycyclohexylamino)benzo[d]thiazol-6-yloxy)picolinamide | 425.2, 2.13 |
| 12 | 171 | 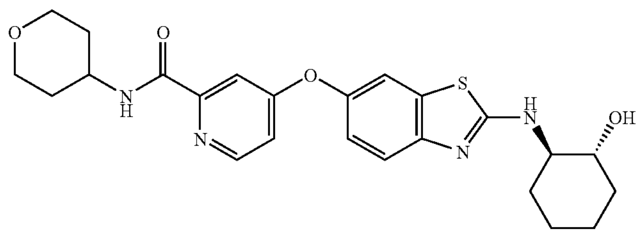 | 4-(2-((1R,2R)-2-hydroxycyclohexylamino)benzo[d]thiazol-6-yloxy)-N-(tetrahydro-2H-pyran-4-yl)picolinamide | 469.2, 2.09 |
| 13 | 171 | 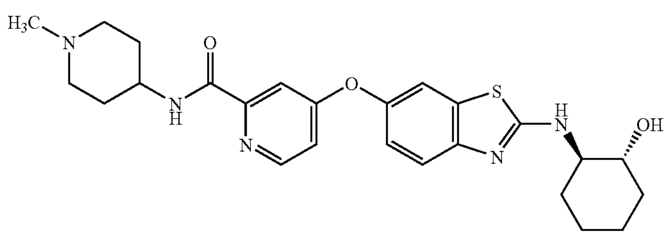 | 4-(2-((1R,2R)-2-hydroxycyclohexylamino)benzo[d]thiazol-6-yloxy)-N-(1-methylpiperidin-4-yl)picolinamide | 482.2, 1.85 |
| 14 | 171 | 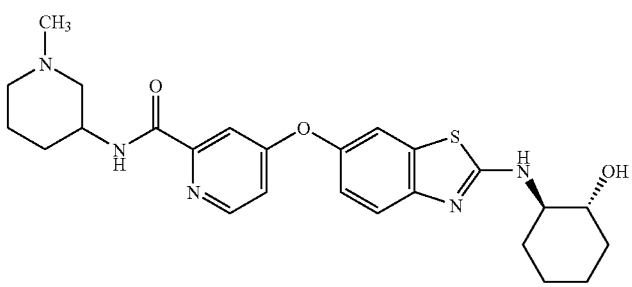 | 4-(2-((1R,2R)-2-hydroxycyclohexylamino)benzo[d]thiazol-6-yloxy)-N-(1-methylpiperidin-3-yl)picolinamide | 482.2, 1.87 |
| 15 | 171 | 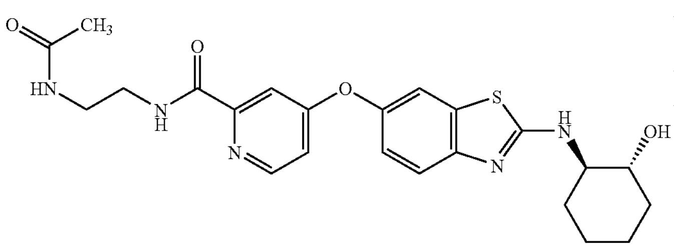 | N-(2-acetamidoethyl)-4-(2-((1R,2R)-2-hydroxycyclohexylamino)benzo[d]thiazol-6-yloxy)picolinamide | 470.2, 1.86 |
| 16 | 171 | 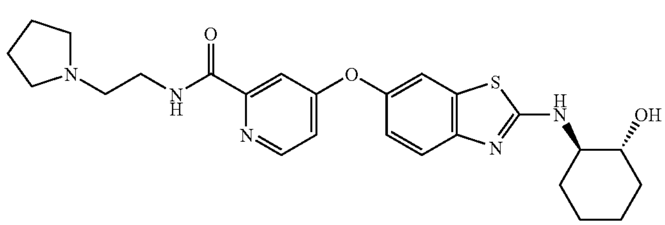 | 4-(2-((1R,2R)-2-hydroxycyclohexylamino)benzo[d]thiazol-6-yloxy)-N-(2-(pyrrolidin-1-yl)ethyl)picolinamide | 482.2, 1.84 |

TABLE 3-continued

| Cmpd | Ex Prep | Structure | Name | (M + H)+, Rt (min.) |
|---|---|---|---|---|
| 17 | 171 | 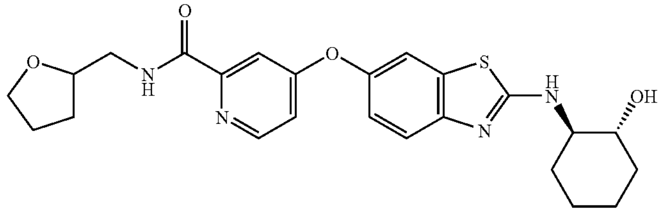 | 4-(2-((1R,2R)-2-hydroxycyclohexylamino)benzo[d]thiazol-6-yloxy)-N-((tetrahydrofuran-2-yl)methyl)picolinamide | 469.2, 2.16 |
| 18 | 171 | 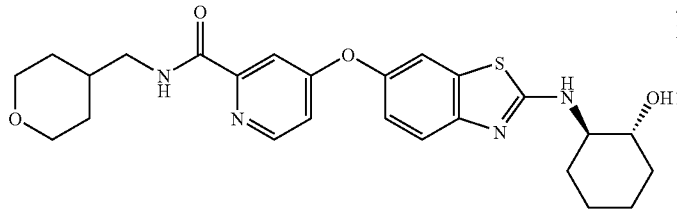 | 4-(2-((1R,2R)-2-hydroxycyclohexylamino)benzo[d]thiazol-6-yloxy)-N-((tetrahydro-2H-pyran-4-yl)methyl)picolinamide | 483.2, 2.12 |
| 19 | 171 | 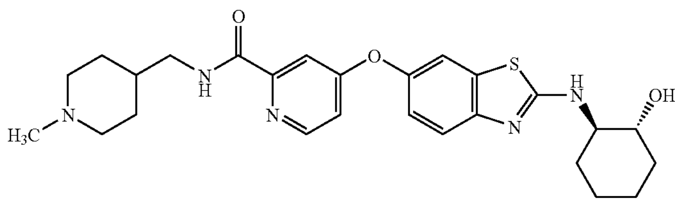 | 4-(2-((1R,2R)-2-hydroxycyclohexylamino)benzo[d]thiazol-6-yloxy)-N-((1-methylpiperidin-4-yl)methyl)picolinamide | 496.2, 1.84 |
| 20 | 171 | 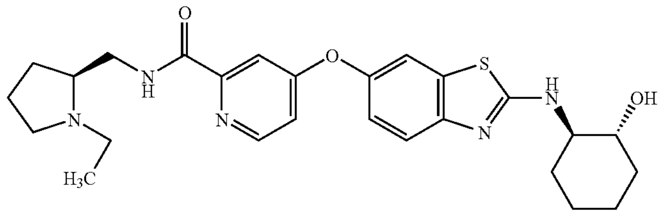 | N-(((S)-1-ethylpyrrolidin-2-yl)methyl)-4-(2-((1R,2R)-2-hydroxycyclohexylamino)benzo[d]thiazol-6-yloxy)picolinamide | 496.2, 1.88 |
| 21 | 200 | 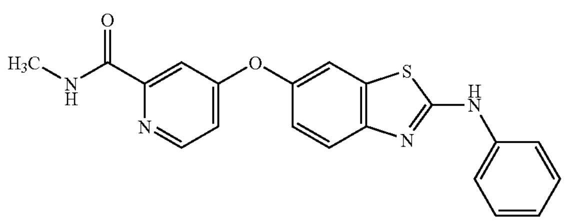 | N-methyl-4-(2-(phenylamino)benzo[d]thiazol-6-yloxy)picolinamide | 377.1, 2.70 |
| 22 | 200 | 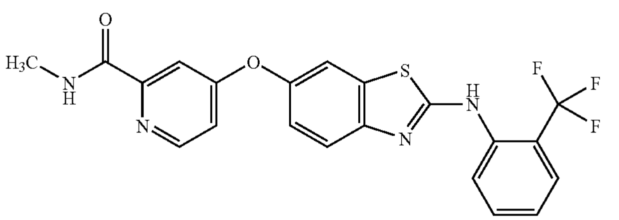 | N-methyl-4-(2-(2-(trifluoromethyl)phenylamino)benzo[d]thiazol-6-yloxy)picolinamide | 445.1, 2.84 |
| 23 | 200 | 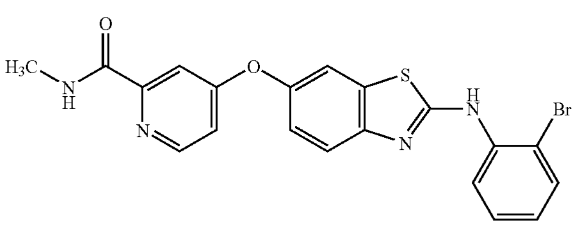 | 4-(2-(2-bromophenylamino)benzo[d]thiazol-6-yloxy)-N-methylpicolinamide | 4.55.0/ 457.0, 2.88 |

TABLE 3-continued

| Cmpd | Ex Prep | Structure | Name | (M + H)+, Rt (min.) |
|---|---|---|---|---|
| 24 | 200 | 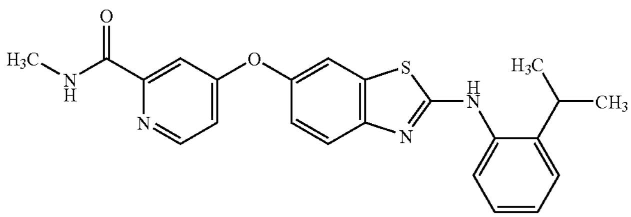 | 4-(2-(2-isopropylphenylamino)benzo[d]thiazol-6-yloxy)-N-methylpicolinamide | 419.2, 2.82 |
| 25 | 200 | 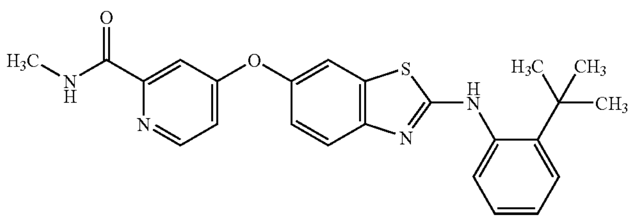 | 4-(2-(2-tert-butylphenylamino)benzo[d]thiazol-6-yloxy)-N-methylpicolinamide | 433.2, 2.87 |
| 26 | 200 | 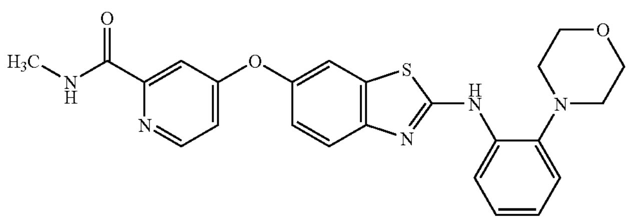 | N-methyl-4-(2-(2-morpholinophenylamino)benzo[d]thiazol-6-yloxy)picolinamide | 462.1, 2.70 |
| 27 | 200 | 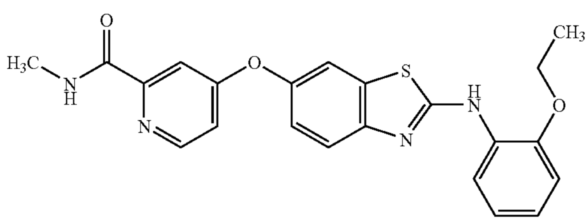 | 4-(2-(2-ethoxyphenylamino)benzo[d]thiazol-6-yloxy)-N-methylpicolinamide | 421.1, 2.92 |
| 28 | 200 | 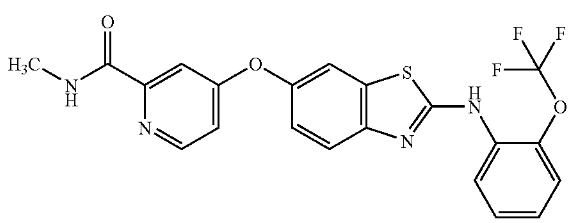 | N-methyl-4-(2-(2-(trifluoromethoxy)phenylamino)benzo[d]thiazol-6-yloxy)picolinamide | 461.1, 3.15 |
| 29 | 200 | 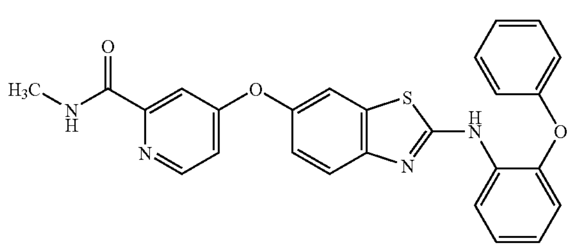 | N-methyl-4-(2-(2-phenoxyphenylamino)benzo[d]thiazol-6-yloxy)picolinamide | 469.1, 3.29 |

TABLE 3-continued

| Cmpd | Ex Prep | Structure | Name | (M + H)+, Rt (min.) |
|---|---|---|---|---|
| 30 | 200 | 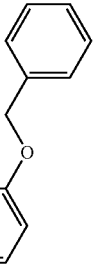 | 4-(2-(2-(benzyloxy)phenylamino)benzo[d]thiazol-6-yloxy)-N-methylpicolinamide | 483.2, 3.19 |
| 31 | 200 | 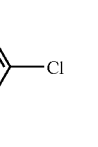 | 4-(2-(3-chlorophenylamino)benzo[d]thiazol-6-yloxy)-N-methylpicolinamide | 411.1, 3.09 |
| 32 | 200 | 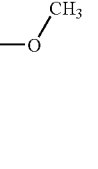 | 4-(2-(3-methoxyphenylamino)benzo[d]thiazol-6-yloxy)-N-methylpicolinamide | 407.1, 2.74 |
| 33 | 200 | 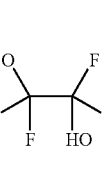 | N-methyl-4-(2-(3-(1,1,2,2-tetrafluoroethoxy)phenylamino)benzo[d]thiazol-6-yloxy)picolinamide | 493.1, 3.07 |
| 34 | 200 | 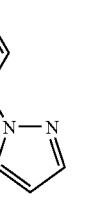 | 4-(2-(2-(1H-pyrazol-1-yl)phenylamino)benzo[d]thiazol-6-yloxy)-N-methylpicolinamide | 443.1, 2.85 |
| 35 | 200 | 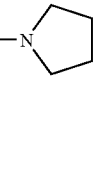 | N-methyl-4-(2-(3-(pyrrolidin-1-yl)phenylamino)benzo[d]thiazol-6-yloxy)picolinamide | 446.2, 2.63 |
| 36 | 200 | 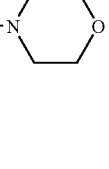 | N-methyl-4-(2-(3-morpholinophenylamino)benzo[d]thiazol-6-yloxy)picolinamide | 462.1, 2.42 |
| 37 | 200 | 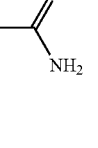 | 4-(2-(3-carbamoylphenylamino)benzo[d]thiazol-6-yloxy)-N-methylpicolinamide | 421.1, 2.38 |

TABLE 3-continued

| Cmpd | Ex Prep | Structure | Name | (M + H)+, Rt (min.) |
|---|---|---|---|---|
| 38 | 200 | 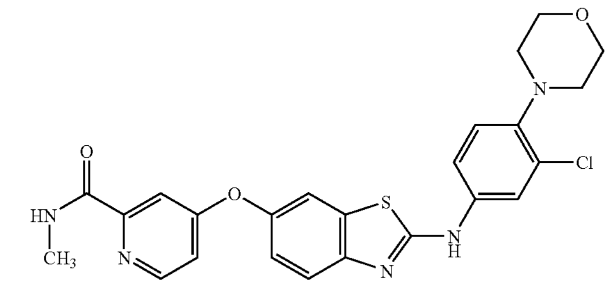 | 4-(2-(3-chloro-4-morpholinophenylamino)benzo[d]thiazol-6-yloxy)-N-methylpicolinamide | 496.1, 2.88 |
| 39 | 200 | 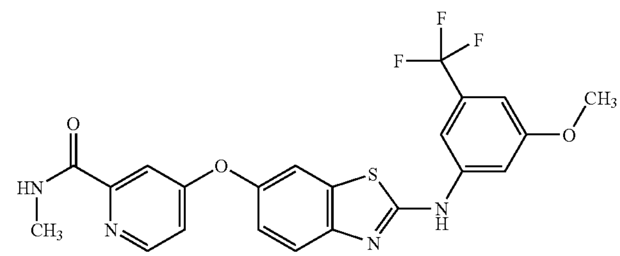 | 4-(2-(3-methoxy-5-(trifluoromethyl)phenylamino)benzo[d]thiazol-6-yloxy)-N-methylpicolinamide | 475.1, 3.25 |
| 40 | 200 | 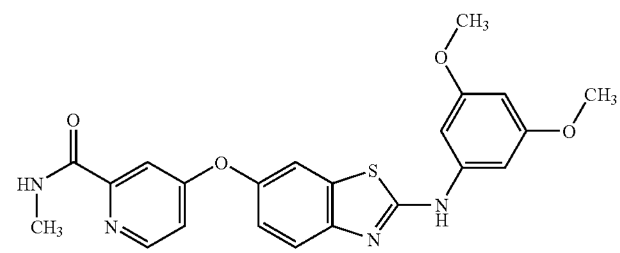 | 4-(2-(3,5-dimethoxyphenylamino)benzo[d]thiazol-6-yloxy)-N-methylpicolinamide | 437.1, 2.79 |
| 41 | 200 | 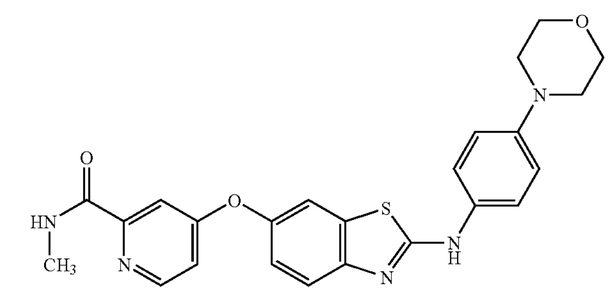 | N-methyl-4-(2-(4-morpholinophenylamino)benzo[d]thiazol-6-yloxy)picolinamide | 462.2, 2.20 |
| 42 | 162 | 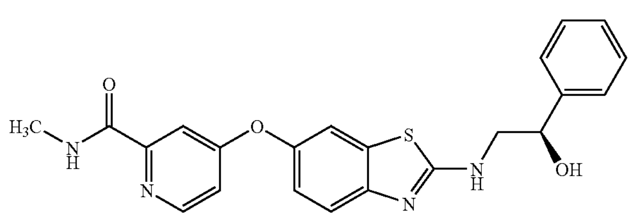 | (R)-4-(2-(2-hydroxy-2-phenylethylamino)benzo[d]thiazol-6-yloxy)-N-methylpicolinamide | 421.1, 2.13 |
| 43 | 162 | 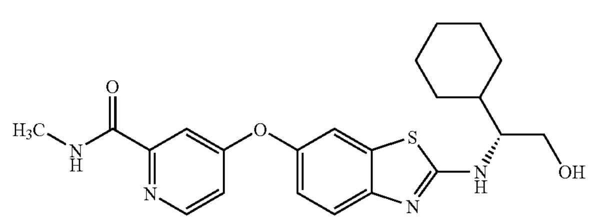 | (R)-4-(2-(1-cyclohexyl-2-hydroxyethylamino)benzo[d]thiazol-6-yloxyl)-N-methylpicolinamide | 427.2, 2.30 |

TABLE 3-continued

| Cmpd | Ex Prep | Structure | Name | (M + H)+, Rt (min.) |
|---|---|---|---|---|
| 44 | 162 | 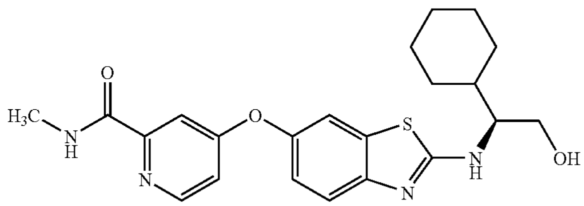 | (S)-4-(2-(1-cyclohexyl-2-hydroxyethylamino)benzo[d]thiazol-6-yloxyl)-N-methylpicolinamide | 427.2, 2.29 |
| 45 | 200 | 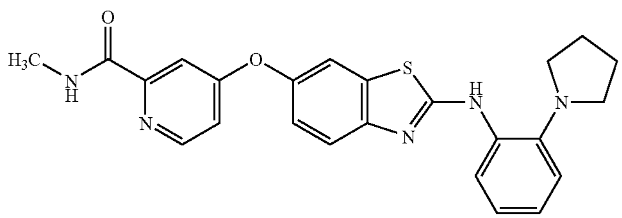 | N-methyl-4-(2-(2-(pyrrolidin-1-yl)phenylamino)benzo[d]thiazol-6-yloxy)picolinamide | 446.1, 2.24 |
| 46 | 200 | 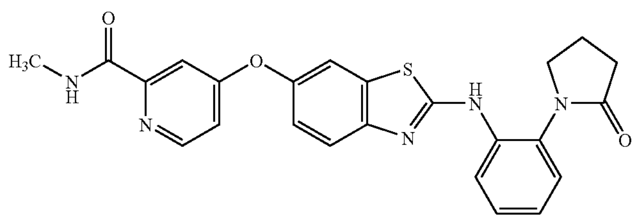 | N-methyl-4-(2-(2-(2-oxopyrrolidin-1-yl)phenylamino)benzo[d]thiazol-6-yloxy)picolinamide | 460.1, 2.35 |
| 47 | 171 | 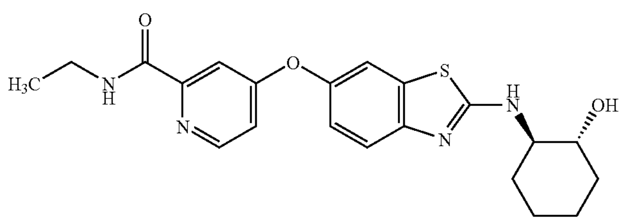 | N-ethyl-4-(2-((1R,2R)-2-hydroxycyclohexylamino)benzo[d]thiazol-6-yloxy)picolinamide | 413.2, 2.09 |
| 48 | 171 | 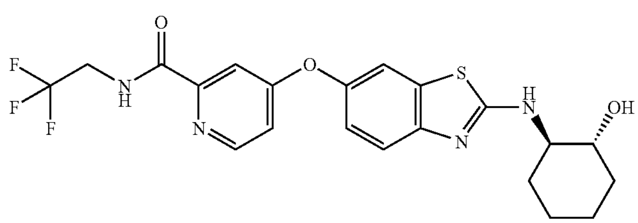 | 4-(2-((1R,2R)-2-hydroxycyclohexylamino)benzo[d]thiazol-6-yloxy)-N-(2,2,2-trifluoroethyl)picolinamide | 467.1, 2.37 |
| 49 | 171 | 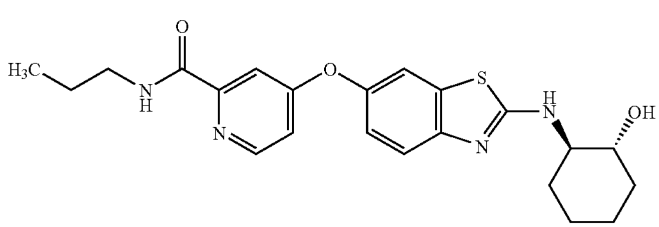 | 4-(2-((1R,2R)-2-hydroxycyclohexylamino)benzo[d]thiazol-6-yloxy)-N-propylpicolinamide | 427.1, 2.25 |
| 50 | 171 | 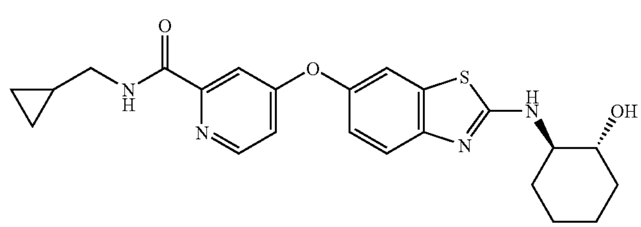 | N-(cyclopropylmethyl)-4-(2-((1R,2R)-2-hydroxycyclohexylamino)benzo[d]thiazol-6-yloxy)picolinamide | 439.2, 2.32 |

TABLE 3-continued

| Cmpd | Ex Prep | Structure | Name | (M + H)+, Rt (min.) |
|---|---|---|---|---|
| 51 | 171 | 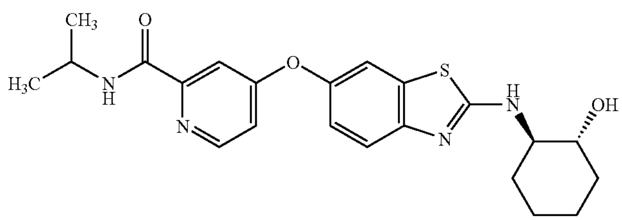 | 4-(2-((1R,2R)-2-hydroxycyclohexylamino)benzo[d]thiazol-6-yloxy)-N-isopropylpicolinamide | 427.2, 2.24 |
| 52 | 205 | 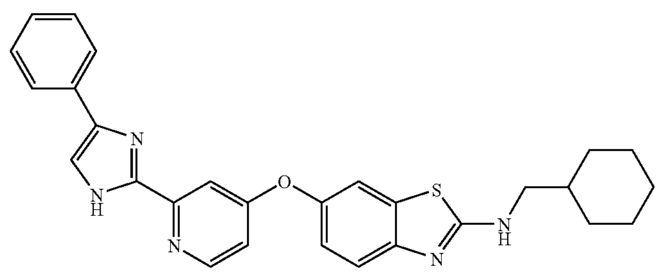 | N-(cyclohexylmethyl)-6-(2-(4-phenyl-1H-imidazol-2-yl)pyridin-4-yloxy)benzo[d]thiazol-2-amine | 482.2, 2.57 |
| 53 | 205 | 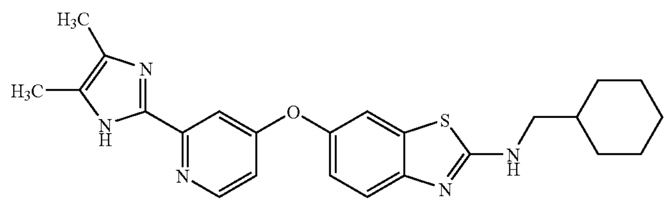 | N-(cyclohexylmethyl)-6-(2-(4,5-dimethyl-1H-imidazol-2-yl)pyridin-4-yloxy)benzo[d]thiazol-2-amine | 434.2, 2.33 |
| 54 | 206 | 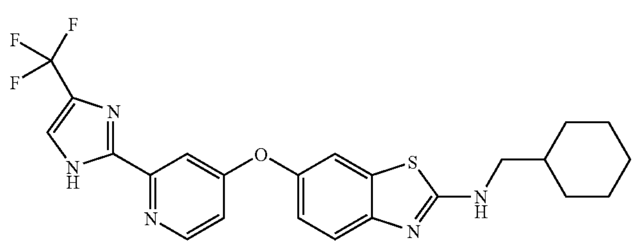 | N-(cyclohexylmethyl)-6-(2-(4-(trifluoromethyl)-1H-imidazol-2-yl)pyridin-4-yloxy)benzo[d]thiazol-2-amine | 474.2, 2.87 |
| 55 | 178 | 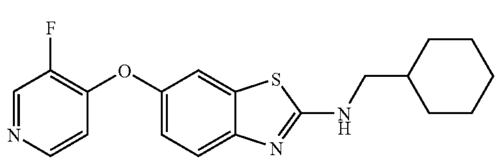 | N-(cyclohexylmethyl)-6-(3-fluoropyridin-4-yloxy)benzo[d]thiazol-2-amine | 358.1, 2.35 |
| 56 | 162 | 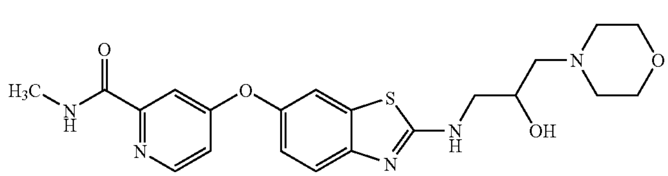 | 4-(2-(2-hydroxy-3-morpholinopropylamino)benzo[d]thiazol-6-yloxy)-N-methylpicolinamide | 444.2, 1.72 |
| 57 | 162 | 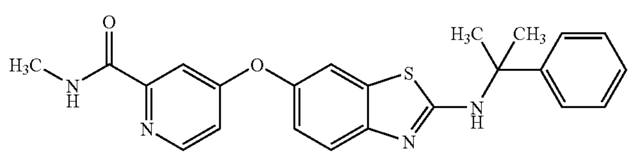 | N-methyl-4-(2-(2-phenylpropan-2-ylamino)benzo[d]thiazol-6-yloxy)picolinamide | 419.1, 2.51 |

TABLE 3-continued

| Cmpd | Ex Prep | Structure | Name | (M + H)+, Rt (min.) |
|---|---|---|---|---|
| 58 | 205 | 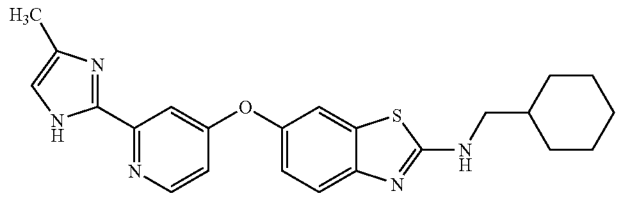 | N-(cyclohexylmethyl)-6-(2-(4-methyl-1H-imidazol-2-yl)pyridin-4-yloxy)benzo[d]thiazol-2-amine | 420.1, 2.26 |
| 59 | 162 | 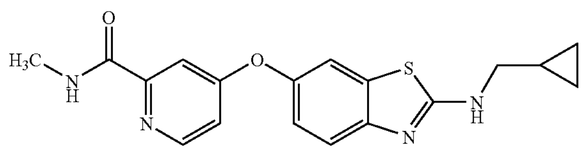 | 4-(2-(cyclopropylmethylamino)benzo[d]thiazol-6-yloxy)-N-methylpicolinamide | 355.1, 2.03 |
| 60 | 162 | 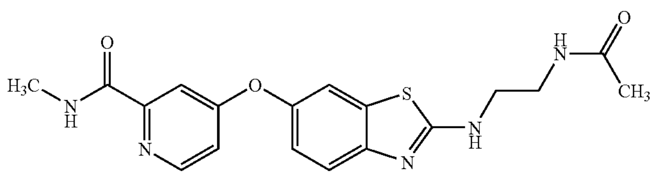 | 4-(2-(2-acetamidoethylamino)benzo[d]thiazol-6-yloxy)-N-methylpicolinamide | 386.1, 1.70 |
| 61 | 162 | 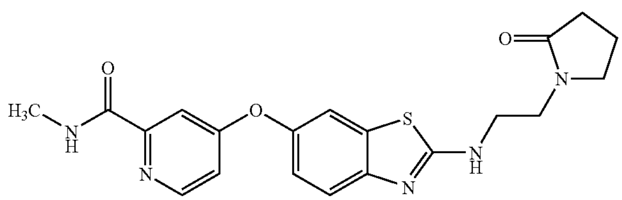 | N-methyl-4-(2-(2-(2-oxopyrrolidin-1-yl)ethylamino)benzo[d]thiazol-6-yloxy)picolinamide | 412.1, 1.82 |
| 62 | 162 | 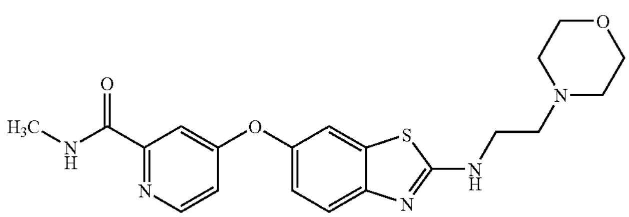 | N-methyl-4-(2-(2-morpholinoethylamino)benzo[d]thiazol-6-yloxy)picolinamide | 414.1, 1.79 |
| 63 | 162 | 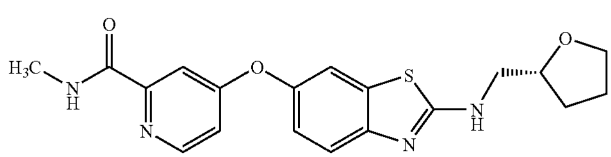 | (R)-N-methyl-4-(2-((tetrahydrofuran-2-yl)methylamino)benzo[d]thiazol-6-yloxy)picolinamide | 385.2, 1.93 |
| 64 | 162 | 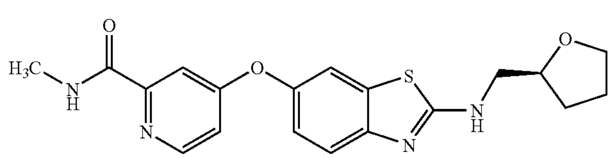 | (S)-N-methyl-4-(2-((tetrahydrofuran-2-yl)methylamino)benzo[d]thiazol-6-yloxy)picolinamide | 385.2, 1.95 |
| 65 | 162 | 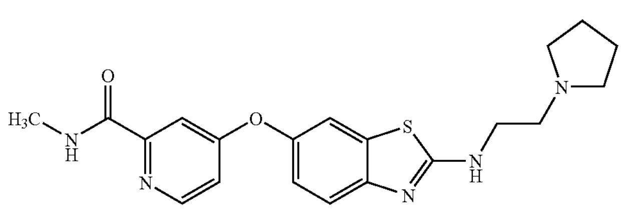 | N-methyl-4-(2-(2-(pyrrolidin-1-yl)ethylamino)benzo[d]thiazol-6-yloxy)picolinamide | 398.2, 1.83 |

TABLE 3-continued

| Cmpd | Ex Prep | Structure | Name | (M + H)+, Rt (min.) |
|---|---|---|---|---|
| 66 | 162 | 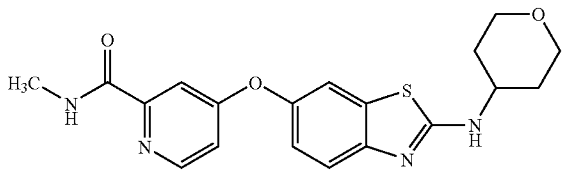 | N-methyl-4-(2-tetrahydro-2H-pyran-4-ylamino)benzo[d]thiazol-6-yloxy)picolinamide | 385.2, 1.88 |
| 67 | 162 | 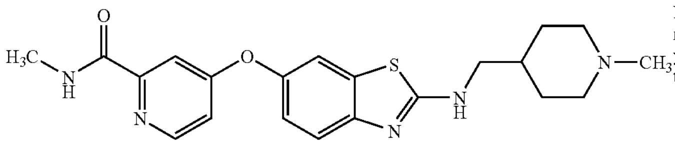 | N-methyl-4-(2-((1-methylpiperidin-4-yl)methylamino)benzo[d]thiazol-6-yloxy)picolinamide | 412.2, 1.70 |
| 68 | 162 | 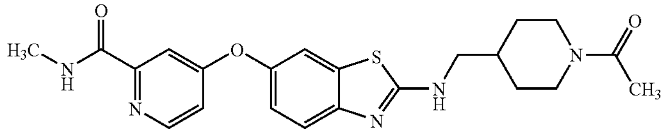 | 4-(2-((1-acetylpiperidin-4-yl)methylamino)benzo[d]thiazol-6-yloxyl)-N-methylpicolinamide | 440.2, 1.86 |
| 69 | 162 | 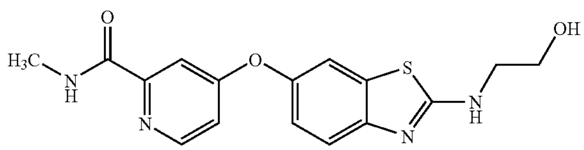 | 4-(2-(2-hydroxyethylamino)benzo[d]thiazol-6-yloxy)-N-methylpicolinamide | 345.1, 1.65 |
| 70 | 162 | 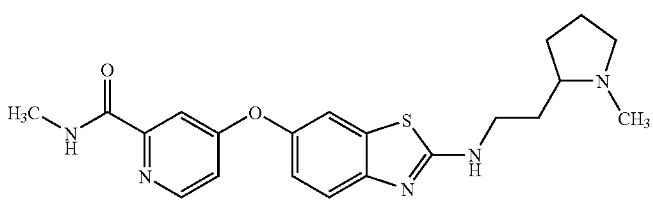 | N-methyl-4-(2-(2-(1-methypyrrolidin-2-yl)ethylamino)benzo[d]thiazol-6-yloxy)picolinamide | 412.2, 1.75 |
| 71 | 162 | 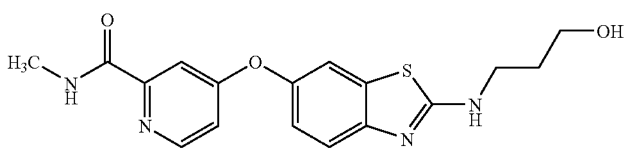 | 4-(2-(3-hydroxypropylamino)benzo[d]thiazol-6-yloxy)-N-methylpicolinamide | 359.1, 1.70 |
| 72 | 162 | 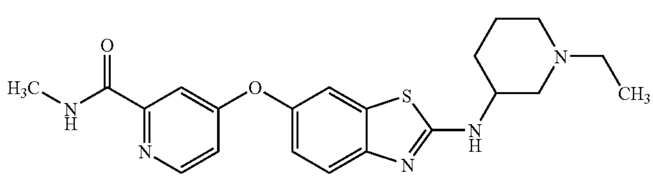 | 4-(2-(1-ethylpiperidin-3-ylamino)benzo[d]thiazol-6-yloxy)-N-methylpicolinamide | 412.2, 1.84 |
| 73 | 162 | 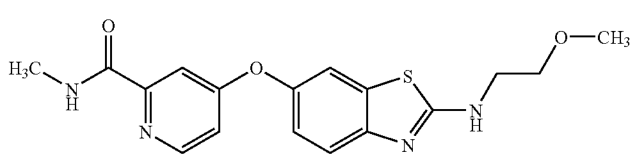 | 4-(2-(2-methoxyethylamino)benzo[d]thiazol-6-yloxy)-N-methylpicolinamide | 359.1, 1.83 |
| 74 | 162 | 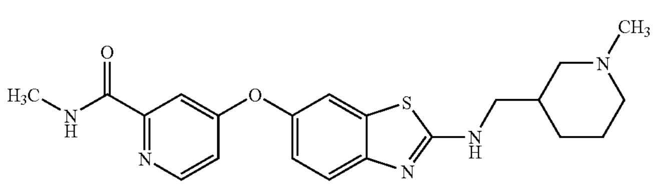 | N-methyl-4-(2-((1-methylpiperidin-3-yl)methylamino)benzo[d]thiazol-6-yloxy)picolinamide | 412.2, 1.75 |

TABLE 3-continued

| Cmpd | Ex Prep | Structure | Name | (M + H)+, Rt (min.) |
|---|---|---|---|---|
| 75 | 162 | 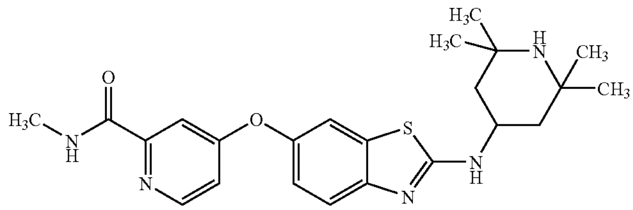 | N-methyl-4-(2-(2,2,6,6-tetramethylpiperidin-4-ylamino)benzo[d]thiazol-6-yloxy)picolinamide | 440.2, 1.89 |
| 76 | 162 | 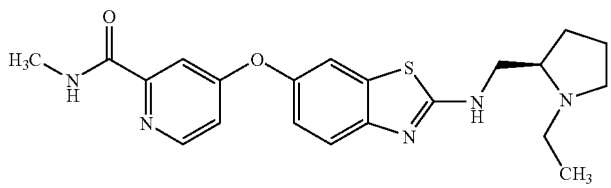 | (R)-4-(2-((1-ethylpyrrolidin-2-yl)methylamino)benzo[d]thiazol-6-yloxy)-N-methylpicolinamide | 412.2, 1.92 |
| 77 | 162 | 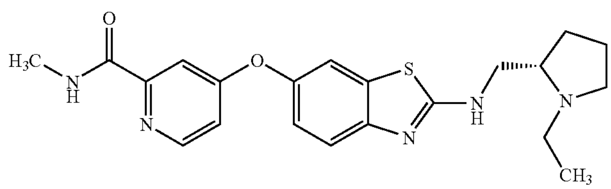 | (S)-4-(2-((1-ethylpyrrolidin-2-yl)methylamino)benzo[d]thiazol-6-yloxy)-N-methylpicolinamide | 412.2, 1.92 |
| 78 | 162 | 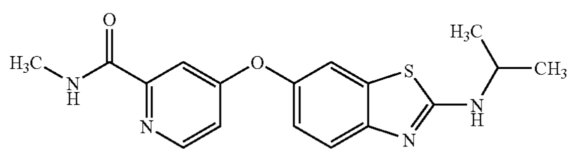 | 4-(2-(isopropylamino)benzo[d]thiazol-6-yloxy)-N-methylpicolinamide | 343.1, 1.92 |
| 79 | 162 | 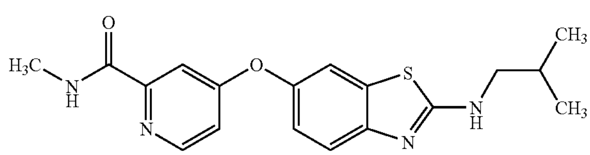 | 4-(2-(isobutylamino)benzo[d]thiazol-6-yloxy)-N-methylpicolinamide | 357.1, 2.10 |
| 80 | 162 | 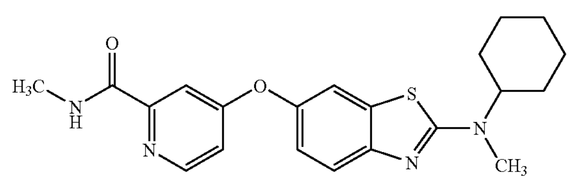 | 4-(2-(cyclohexyl(methyl)amino)benzo[d]thiazol-6-yloxy)-N-methylpicolinamide | 397.2, 2.49 |
| 81 | 162 | 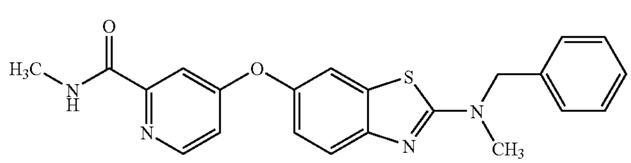 | 4-(2-(benzyl(methyl)amino)benzo[d]thiazol-6-yloxy)-N-methylpicolinamide | 405.1, 2.63 |
| 82 | 162 | 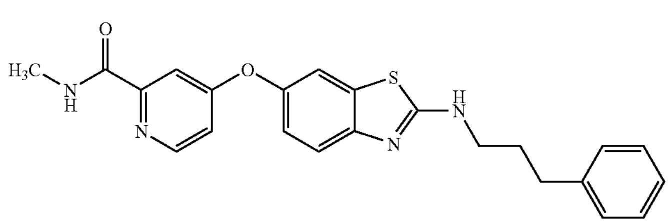 | N-methyl-4-(2-(3-phenylpropylamino)benzo[d]thiazol-6-yloxy)picolinamide | 419.2, 2.45 |

TABLE 3-continued

| Cmpd | Ex Prep | Structure | Name | (M + H)+, Rt (min.) |
|---|---|---|---|---|
| 83 | 162 | 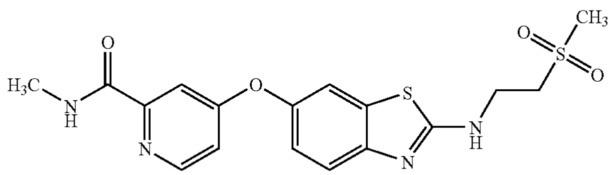 | N-methyl-4-(2-(2-(methylsulfonyl)ethylamino)benzo[d]thiazol-6-yloxy)picolinamide | 407.1, 1.85 |
| 84 | 162 | 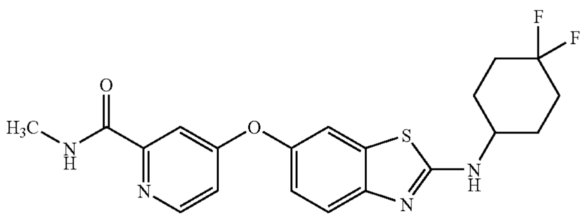 | 4-(2-(4,4-difluorocyclohexylamino)benzo[d]thiazol-6-yloxy)-N-methylpicolinamide | 419.2, 2.31 |
| 85 | 162 | 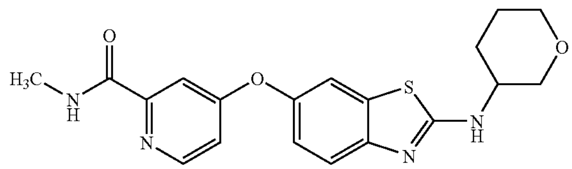 | N-methyl-4-(2-tetrahydro-2H-pyran-3-ylamino)benzo[d]thiazol-6-yloxy)picolinamide | 385.1, 1.95 |
| 86 | 162 | 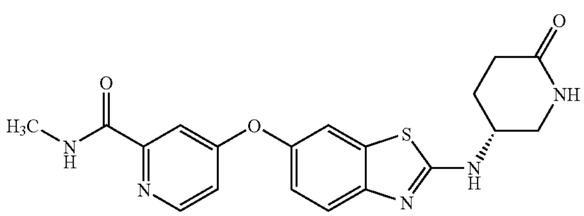 | (R)-N-methyl-4-(2-(6-oxopiperidin-3-ylamino)benzo[d]thiazol-6-yloxy)picolinamide | 398.1, 1.76 |
| 87 | 162 | 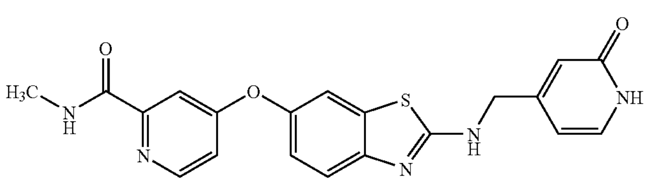 | N-methyl-4-(2-((2-oxo-1,2-dihydropyridin-4-yl)methylamino)benzo[d]thiazol-6-yloxy)picolinamide | 408.1, 1.79 |
| 88 | 162 | 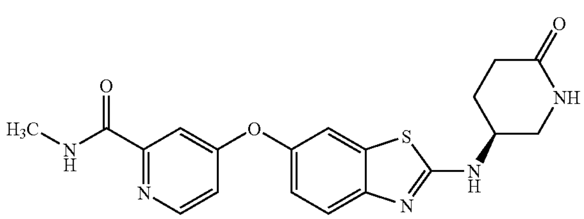 | (S)-N-methyl-4-(2-(6-oxopiperidin-3-ylamino)benzo[d]thiazol-6-yloxy)picolinamide | 398.1, 1.76 |
| 89 | 162 | 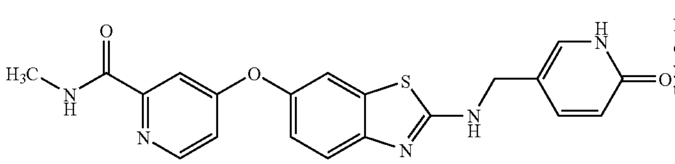 | N-methyl-4-(2-((6-oxo-1,6-dihydropyridin-3-yl)methylamino)benzo[d]thiazol-6-yloxy)picolinamide | 408.1, 1.77 |
| 90 | 162 | 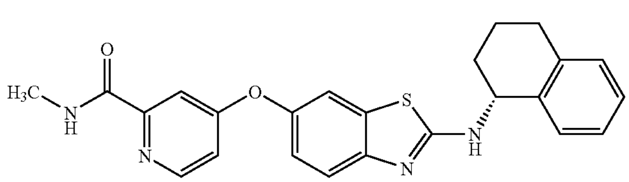 | (R)-N-methyl-4-(2-(1,2,3,4-tetrahydronaphthalen-1-ylamino)benzo[d]thiazol-6-yloxy)picolinamide | 431.2, 2.58 |

TABLE 3-continued

| Cmpd | Ex Prep | Structure | Name | (M + H)+, Rt (min.) |
|---|---|---|---|---|
| 91 | 162 | 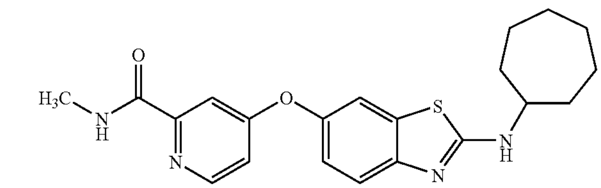 | 4-(2-(cycloheptylamino)benzo[d]thiazol-6-yloxy)-N-methylpicolinamide | 397.2, 2.41 |
| 92 | 162 | 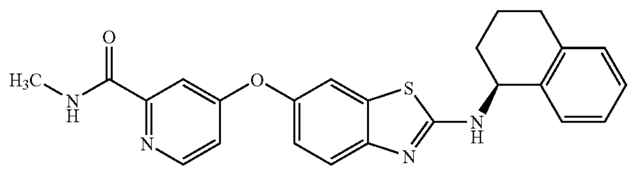 | (S)-N-methyl-4-(2-(1,2,3,4-tetrahydronaphthalen-1-ylamino)benzo[d]thiazol-6-yloxy)picolinamide | 431.2, 2.57 |
| 93 | 162 | 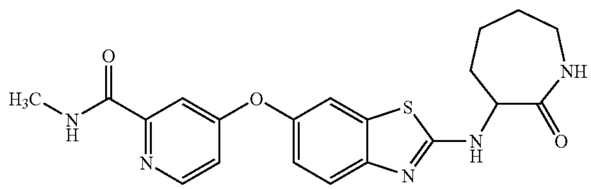 | N-methyl-4-(2-(2-oxoazepan-3-ylamino)benzo[d]thiazol-6-yloxy)picolinamide | 412.1, 1.95 |
| 94 | 162 | 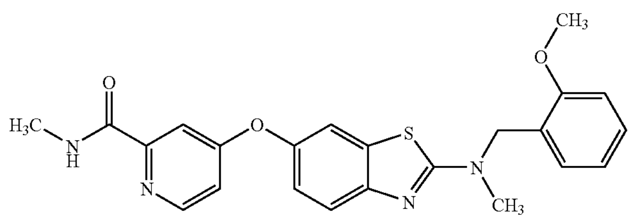 | 4-(2-((2-methoxybenzyl)(methyl)amino)benzo[d]thiazol-6-yloxy)-N-methylpicolinamide | 435.2, 2.56 |
| 95 | 162 | 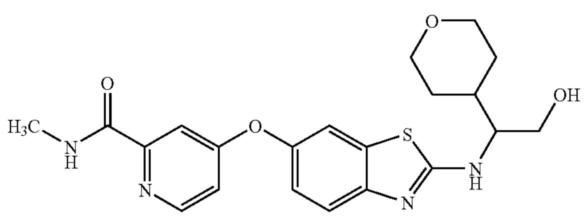 | 4-(2-(2-hydroxy-1-(tetrahydro-2H-pyran-4-yl)ethylamino)benzo[d]thiazol-6-yloxy)-N-methylpicolinamide | 429.2, 1.83 |
| 96 | 162 | 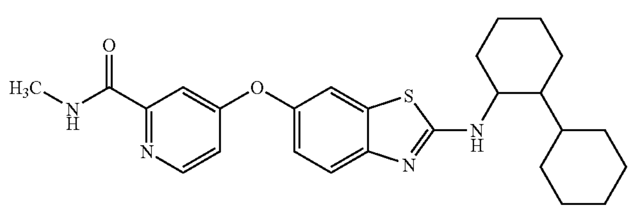 | 4-(2-(bi(cyclohexan)-2-ylamino)benzo[d]thiazol-6-yloxy)-N-methylpicolinamide | 465.2, 3.05 |
| 97 | 162 | 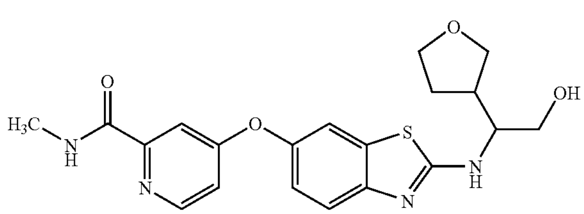 | 4-(2-(2-hydroxy-1-(tetrahydrofuran-3-yl)ethylamino)benzo[d]thiazol-6-yloxy)-N-methylpicolinamide | 415.1, 1.79 |

TABLE 3-continued

| Cmpd | Ex Prep | Structure | Name | (M + H)+, Rt (min.) |
|---|---|---|---|---|
| 98 | 189 | 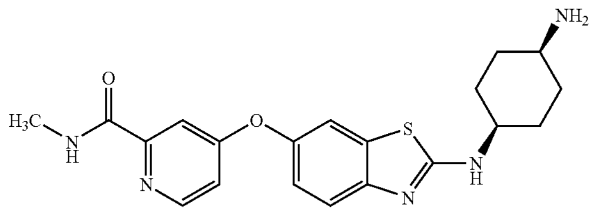 | 4-(2-((1s,4s)-4-aminocyclohexylamino)benzo[d]thiazol-6-yloxy)-N-methylpicolinamide | 398.1, 1.73 |
| 99 | 162 | 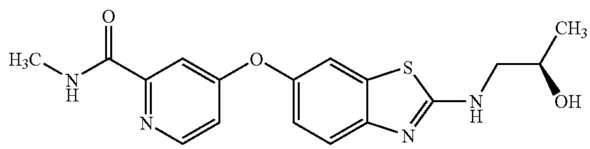 | (R)-4-(2-(2-hydroxypropylamino)benzo[d]thiazol-6-yloxy)-N-methylpicolinamide | 359.1, 1.75 |
| 100 | 162 | 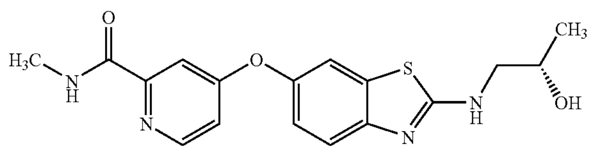 | (S)-4-(2-(2-hydroxypropylamino)benzo[d]thiazol-6-yloxy)-N-methylpicolinamide | 359.1, 1.74 |
| 101 | 162 | 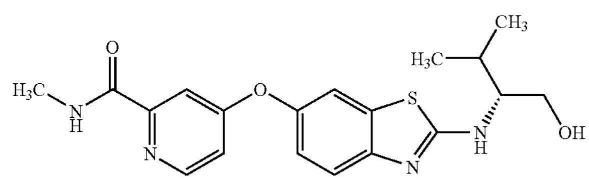 | (R)-4-(2-(1-hydroxy-3-methylbutan-2-ylamino)benzo[d]thiazol-6-yloxy)-N-methylpicolinamide | 387.2, 1.98 |
| 102 | 162 | 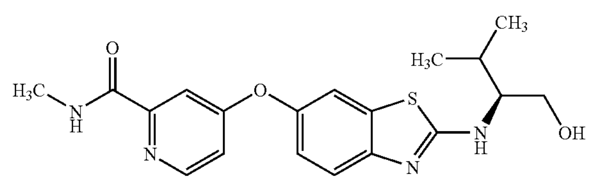 | (S)-4-(2-(1-hydroxy-3-methylbutan-2-ylamino)benzo[d]thiazol-6-yloxy)-N-methylpicolinamide | 387.2, 1.96 |
| 103 | 162 | 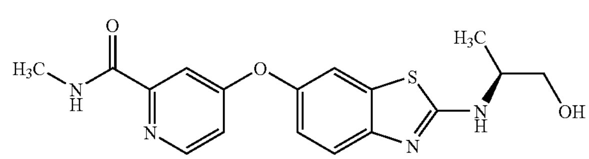 | (S)-4-(2-(1-hydroxypropan-2-ylamino)benzo[d]thiazol-6-yloxy)-N-methylpicolinamide | 359.1, 1.75 |
| 104 | 162 | 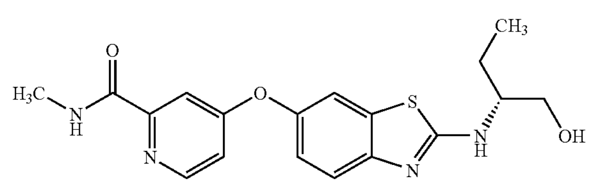 | (R)-4-(2-(1-hydroxybutan-2-ylamino)benzo[d]thiazol-6-yloxy)-N-methylpicolinamide | 373.1, 1.84 |
| 105 | 162 | 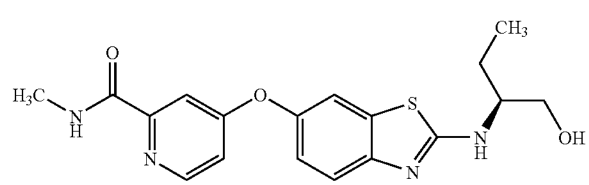 | (S)-4-(2-(1-hydroxybutan-2-ylamino)benzo[d]thiazol-6-yloxy)-N-methylpicolinamide | 373.1, 1.87 |

TABLE 3-continued

| Cmpd | Ex Prep | Structure | Name | (M + H)+, Rt (min.) |
|---|---|---|---|---|
| 106 | 162 | 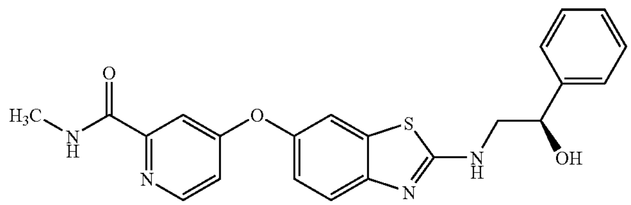 | (R)-4-(2-(2-hydroxy-2-phenylethylamino)benzo[d]thiazol-6-yloxy)-N-methylpicolinamide | 421.1, 2.13 |
| 107 | 162 | 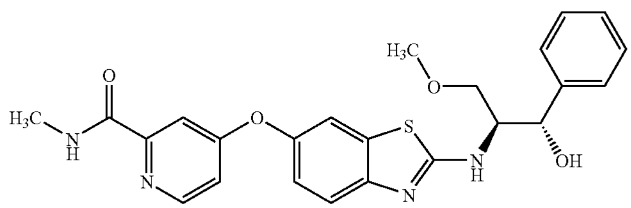 | 4-(2-((1S,2S)-1-hydroxy-3-methoxy-1-phenylpropan-2-ylamino)benzo[d]thiazol-6-yloxy)-N-methylpicolinamide | 465.2, 2.21 |
| 108 | 162 | 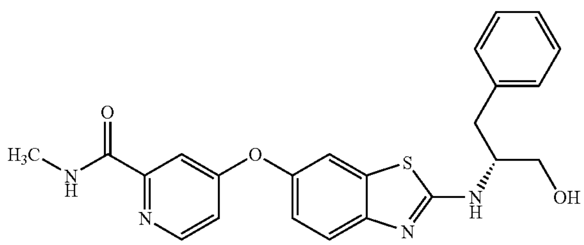 | (R)-4-(2-(1-hydroxy-3-phenylpropan-2-ylamino)benzo[d]thiazol-6-yloxy)-N-methylpicolinamide | 435.2, 2.17 |
| 109 | 162 | 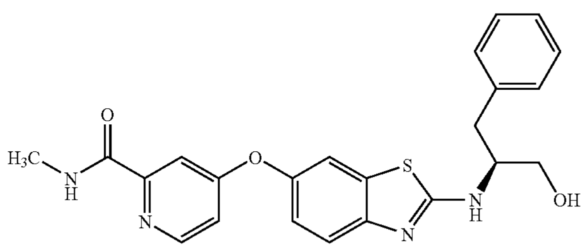 | (S)-4-(2-(1-hydroxy-3-phenylpropan-2-ylamino)benzo[d]thiazol-6-yloxy)-N-methylpicolinamide | 435.2, 2.18 |
| 110 | 162 | 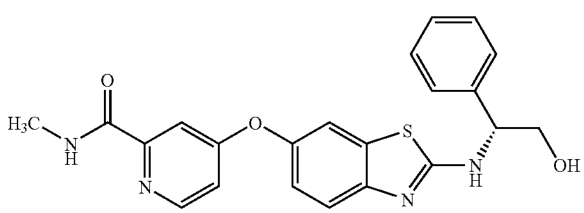 | (R)-4-(2-(2-hydroxy-1-phenylethylamino)benzo[d]thiazol-6-yloxy)-N-methylpicolinamide | 421.1, 2.15 |
| 111 | 162 | 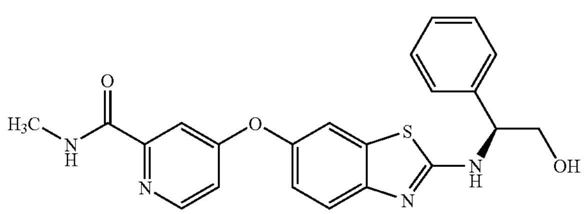 | (S)-4-(2-(2-hydroxy-1-phenylethylamino)benzo[d]thiazol-6-yloxy)-N-methylpicolinamide | 421.1, 2.16 |
| 112 | 162 | 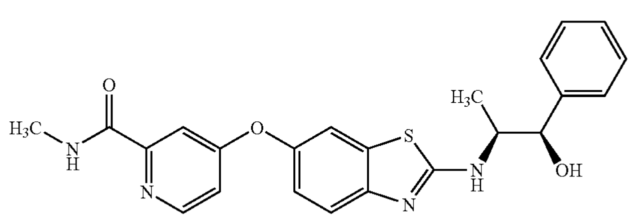 | 4-(2-((1R,2S)-1-hydroxy-1-phenylpropan-2-ylamino)benzo[d]thiazol-6-yloxy)-N-methylpicolinamide | 435.2, 2.20 |

TABLE 3-continued

| Cmpd | Ex Prep | Structure | Name | (M + H)+, Rt (min.) |
|---|---|---|---|---|
| 113 | 162 | 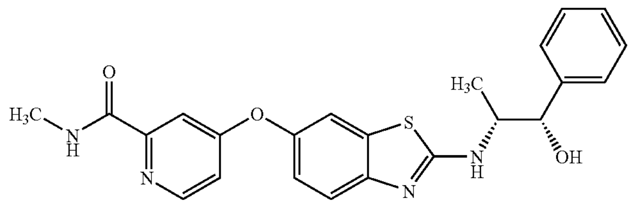 | 4-(2-((1S,2R)-1-hydroxy-1-phenylpropan-2-ylamino)benzo[d]thiazol-6-yloxy)-N-methylpicolinamide | 435.2, 2.19 |
| 114 | 162 | 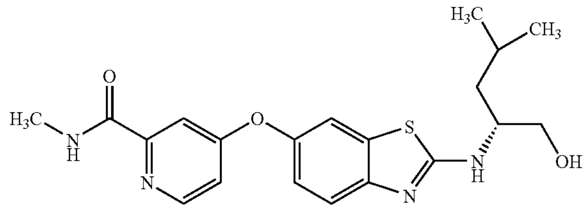 | (R)-4-(2-(1-hydroxy-4-methylpentan-2-ylamino)benzo[d]thiazol-6-yloxy)-N-methylpicolinamide | 401.2, 2.13 |
| 115 | 162 | 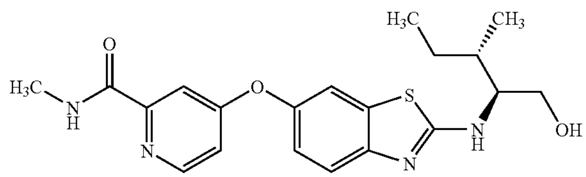 | 4-(2-((2S,3S)-1-hydroxy-3-methylpentan-2-ylamino)benzo[d]thiazol-6-yloxy)-N-methylpicolinamide | 401.2, 2.10 |
| 116 | 162 | 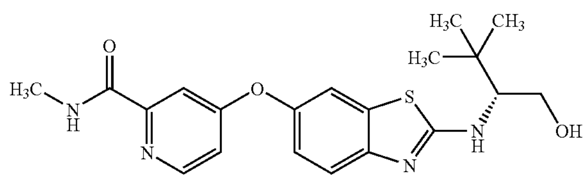 | (R)-4-(2-(1-hydroxy-3,3-dimethylbutan-2-ylamino)benzo[d]thiazol-6-yloxy)-N-methylpicolinamide | 401.2, 2.08 |
| 117 | 162 | 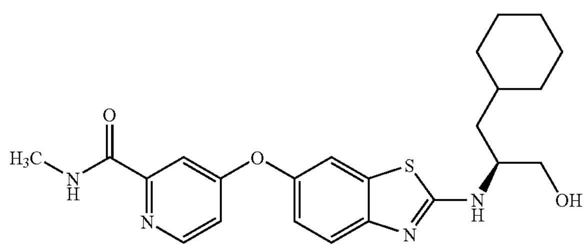 | (S)-4-(2-(1-cyclohexyl-3-hydroxypropan-2-ylamino)benzo[d]thiazol-6-yloxy)-N-methylpicolinamide | 441.2, 2.45 |
| 118 | 162 | 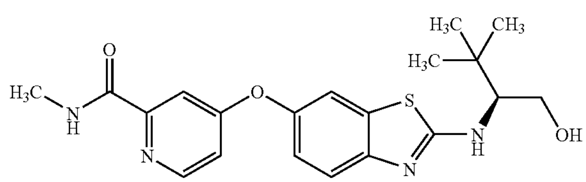 | (S)-4-(2-(1-hydroxy-3,3-dimethylbutan-2-ylamino)benzo[d]thiazol-6-yloxy)-N-methylpicolinamide | 401.2, 2.08 |
| 119 | 190 | 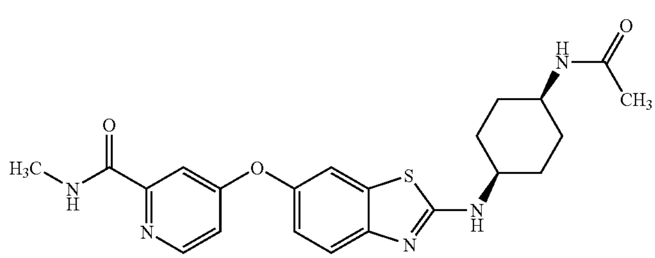 | 4-(2-((1s,4s)-4-acetamidocyclohexylamino)benzo[d]thiazol-6-yloxy)-N-methylpicolinamide | 440.2, 1.85 |

TABLE 3-continued

| Cmpd | Ex Prep | Structure | Name | (M + H)+, Rt (min.) |
|---|---|---|---|---|
| 120 | 190 | 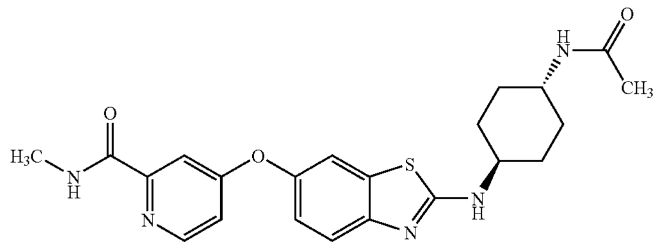 | 4-(2-((1r,4r)-4-acetamidocyclohexylamino)benzo[d]thiazol-6-yloxy)-N-methylpicolinamide | 440.2, 1.85 |
| 121 | 162 | 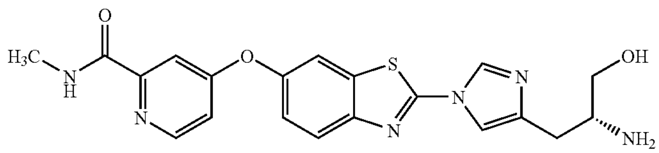 | (R)-4-(2-(4-(2-amino-3-hydroxypropyl)-1H-imidazol-1-yl)benzo[d]thiazol-6-yloxy)-N-methylpicolinamide | 425.2, 1.67 |
| 122 | 162 | 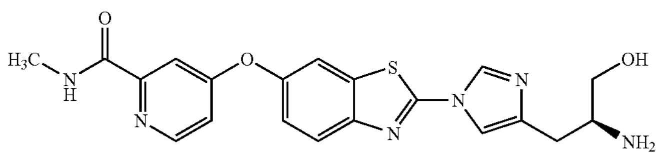 | (S)-4-(2-(4-(2-amino-3-hydroxypropyl)-1H-imidazol-1-yl)benzo[d]thiazol-6-yloxy)-N-methylpicolinamide | 425.2, 1.68 |
| 123 | 162 | 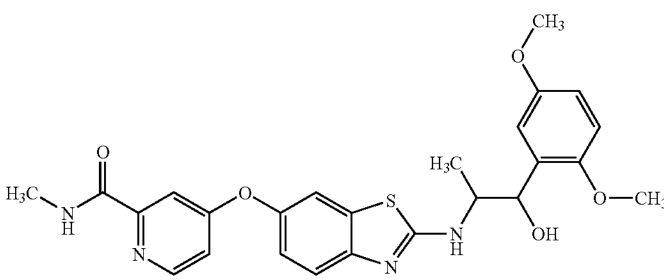 | 4-(2-(1-(2,5-dimethoxyphenyl)-1-hydroxypropan-2-ylamino)benzo[d]thiazol-6-yloxy)-N-picolinamide | 495.2, 2.29 |
| 124 | 162 | 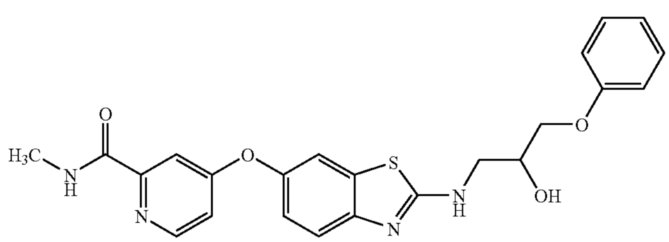 | 4-(2-(2-hydroxy-3-phenoxypropylamino)benzo[d]thiazol-6-yloxy)-N-methylpicolinamide | 451.1, 2.26 |
| 125 | 162 | 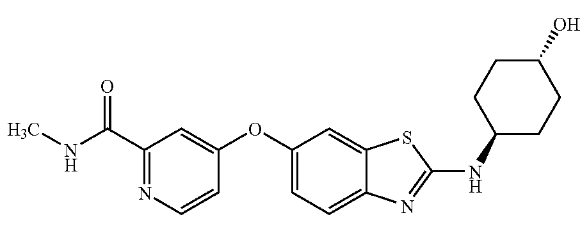 | 4-(2-((1r,4r)-4-hydroxycyclohexylamino)benzo[d]thiazol-6-yloxy)-N-methylpicolinamide | 399.1, 1.83 |
| 126 | 162 | 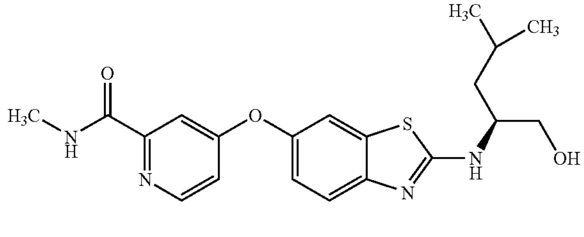 | (S)-4-(2-(1-hydroxy-4-methylpentan-2-ylamino)benzo[d]thiazol-6-yloxy)-N-methylpicolinamide | 401.1, 2.14 |

TABLE 3-continued

| Cmpd | Ex Prep | Structure | Name | (M + H)+, Rt (min.) |
|---|---|---|---|---|
| 127 | 162 | 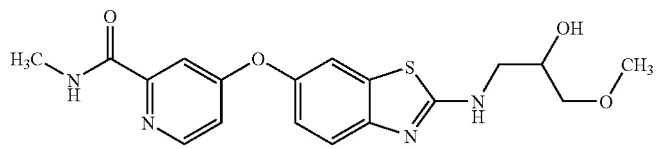 | 4-(2-(2-hydroxy-3-methoxypropylamino)benzo[d]thiazol-6-yloxy)-N-methylpicolinamide | 389.1, 1.77 |
| 128 | 162 | 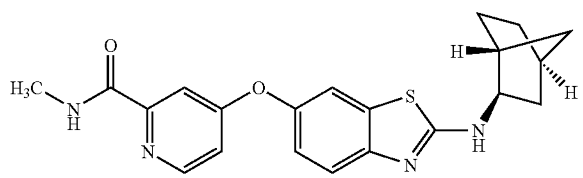 | 4-(2-((1R,2R,4S)-bicyclo[2.2.1]heptan-2-ylamino)benzo[d]thiazol-6-yloxy)-N-methylpicolinamide | 395.2, 2.36 |
| 129 | 162 | 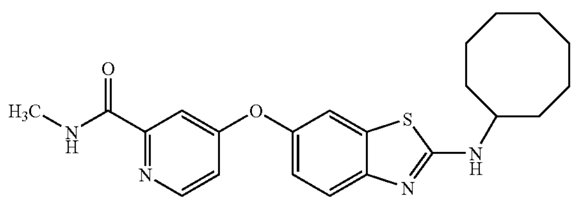 | 4-(2-(cyclooctylamino)benzo[d]thiazol-6-yloxy)-N-methylpicolinamide | 411.2, 2.60 |
| 130 | 162 | 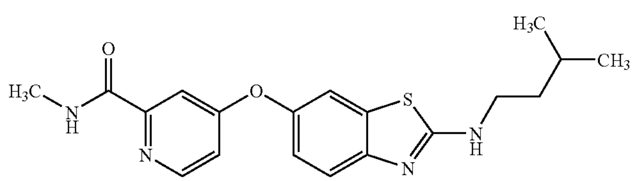 | 4-(2-(isopentylamino)benzo[d]thiazol-6-yloxy)-N-methylpicolinamide | 371.2, 2.31 |
| 131 | 162 | 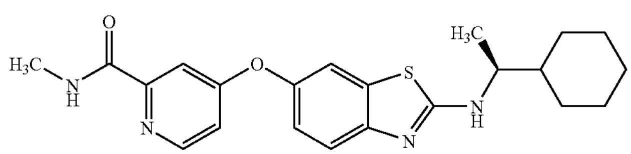 | (S)-4-(2-(1-cyclohexylethylamino)benzo[d]thiazol-6-yloxy)-N-methylpicolinamide | 411.2, 2.59 |
| 132 | 191 | 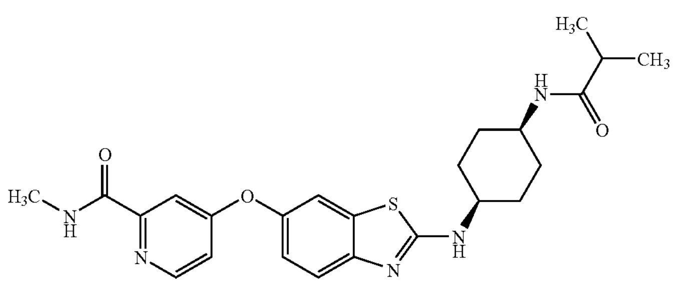 | 4-(2-((1s,4s)-4-isobutyramidocyclohexylamino)benzo[d]thiazol-6-yloxy)-N-methylpicolinamide | 468.3, 2.03 |
| 133 | 191 | 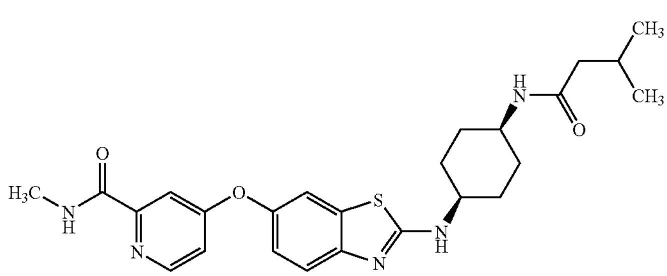 | N-methyl-4-(2-((1s,4s)-4-(3-methylbutanamido)cyclohexylamino)benzo[d]thiazol-6-yloxy)picolinamide | 482.2, 2.14 |

TABLE 3-continued

| Cmpd | Ex Prep | Structure | Name | (M + H)+, Rt (min.) |
|---|---|---|---|---|
| 134 | 191 | 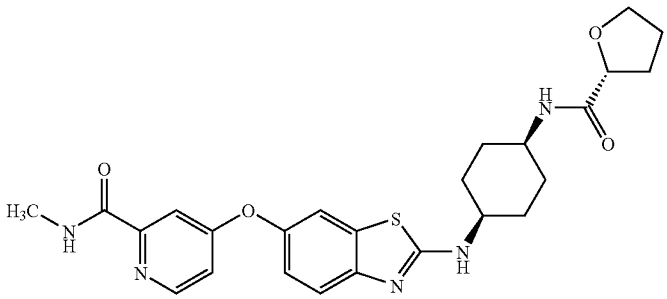 | N-methyl-4-(2-((1S,4s)-4-((R)-tetrahydrofuran-2-carboxamido)cyclohexylamino)benzo[d]thiazol-6-yloxy)picolinamide | 496.2, 2.01 |
| 135 | 191 | 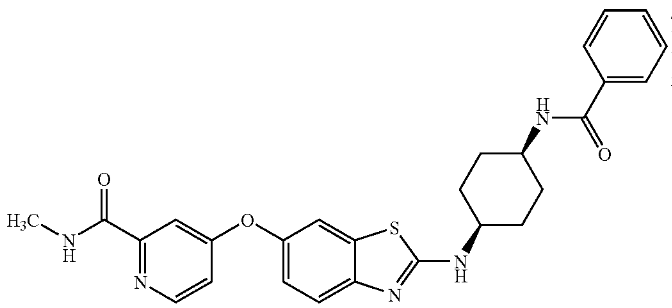 | 4-(2-((1s,4s)-4-benzamidocyclohexylamino)benzo[d]thiazol-6-yloxy)-N-methylpicolinamide | 502.2, 2.21 |
| 136 | 191 | 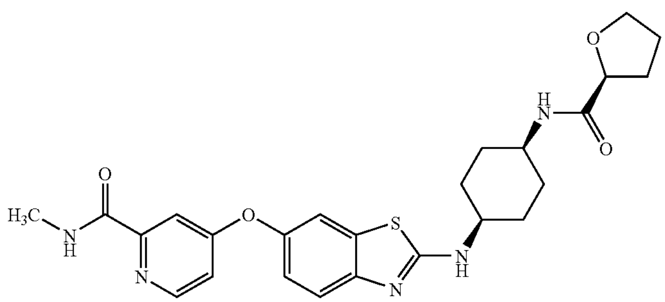 | N-methyl-4-(2-((1R,4s)-4-((S)-tetrahydrofuran-2-carboxamido)cyclohexylamino)benzo[d]thiazol-6-yloxy)picolinamide | 496.2, 2.01 |
| 137 | 191 | 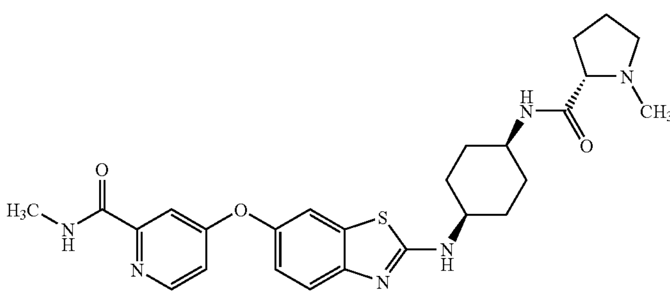 | N-methyl-4-(2-((1R,4s)-4-((S)-1-methylpyrrolidine-2-carboxamido)cyclohexylamino)benzo[d]thiazol-6-yloxy)picolinamide | 509.3, 1.83 |
| 138 | 162 | 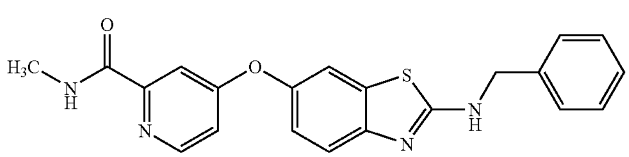 | 4-(2-(benzylamino)benzo[d]thiazol-6-yloxy)-N-methylpicolinamide | 391.1, 2.35 |
| 139 | 162 | 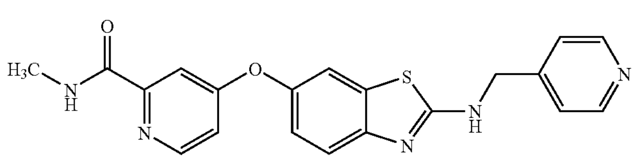 | N-methyl-4-(2-(pyridin-4-ylmethylamino)benzo[d]thiazol-6-yloxy)picolinamide | 392.1, 1.78 |

TABLE 3-continued

| Cmpd | Ex Prep | Structure | Name | (M + H)+, Rt (min.) |
|---|---|---|---|---|
| 140 | 162 | 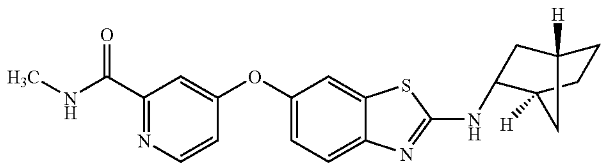 | 4-(2-((1S,4R)-bicyclo[2.2.1]heptan-2-ylamino)benzo[d]thiazol-6-yloxy)-N-methylpicolinamide | 395.2, 2.35 |
| 141 | 162 | 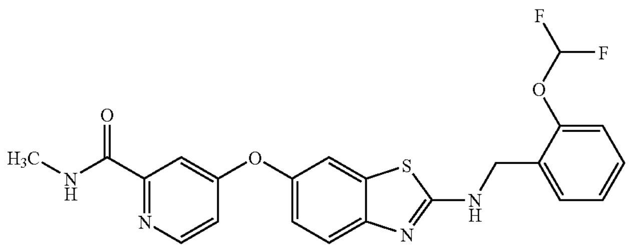 | 4-(2-(2-(difluoromethoxy)benzylamino)benzo[d]thiazol-6-yloxy)-N-methylpicolinamide | 457.1, 2.53 |
| 142 | 162 | 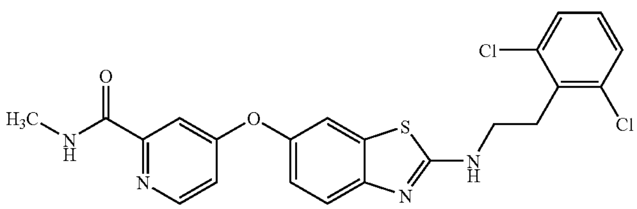 | 4-(2-(2,6-dichlorophenethylamino)benzo[d]thiazol-6-yloxy)-N-methylpicolinamide | 473.0, 2.68 |
| 143 | 162 | 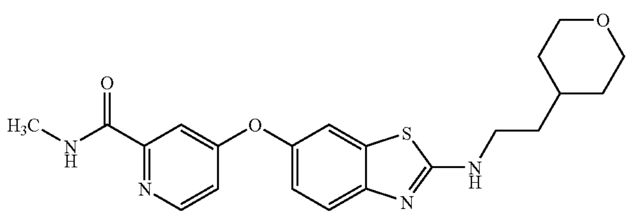 | N-methyl-4-(2-(2-(tetrahydro-2H-pyran-4-yl)ethylamino)benzo[d]thiazol-6-yloxy)picolinamide | 413.2, 2.02 |
| 144 | 162 | 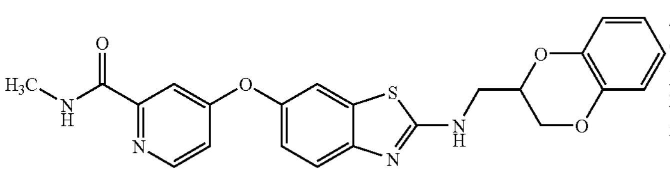 | 4-(2-((2,3-dihydrobenzo[b][1,4]dioxin-2-yl)methylamino)benzo[d]thiazol-6-yloxy)-N-methylpicolinamide | 449.1, 2.52 |
| 145 | 162 | 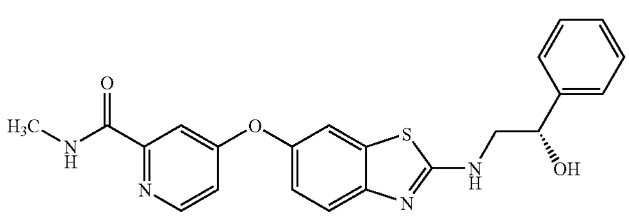 | (S)-4-(2-(2-hydroxy-2-phenylethylamino)benzo[d]thiazol-6-yloxy)-N-methylpicolinamide | 421.1, 2.13 |
| 146 | 162 | 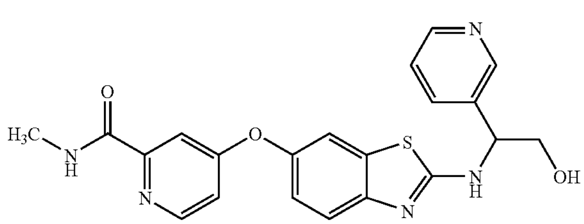 | 4-(2-(2-hydroxy-1-(pyridin-3-yl)ethylamino)benzo[d]thiazol-6-yloxy)-N-methylpicolinamide | 422.1, 1.75 |

TABLE 3-continued

| Cmpd | Ex Prep | Structure | Name | (M + H)+, Rt (min.) |
|---|---|---|---|---|
| 147 | 162 | 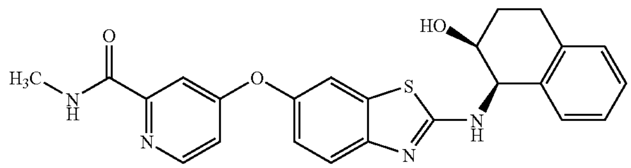 | 4-(2-((1R,2S)-2-hydroxy-1,2,3,4-tetrahydronaphthalen-1-ylamino)benzo[d]thiazol-6-yloxy)-N-methylpicolinamide | 447.2, 2.25 |
| 148 | 162 | 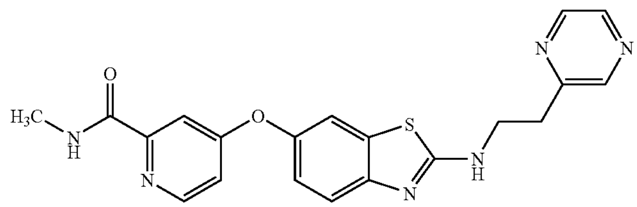 | N-methyl-4-(2-(2-(pyrazin-2-yl)ethylamino)benzo[d]thiazol-6-yloxy)picolinamide | 407.1, 1.85 |
| 149 | 162 | 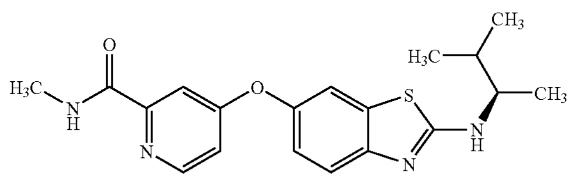 | (R)-N-methyl-4-(2-(3-methylbutan-2-ylamino)benzo[d]thiazol-6-yloxy)picolinamide | 371.2, 2.20 |
| 150 | 162 | 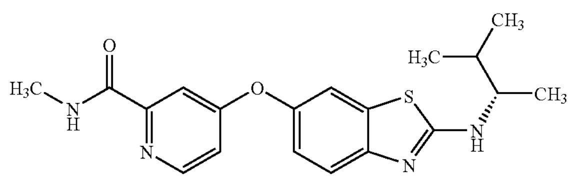 | (S)-N-methyl-4-(2-(3-methylbutan-2-ylamino)benzo[d]thiazol-6-yloxy)picolinamide | 371.2, 2.20 |
| 151 | 178 | 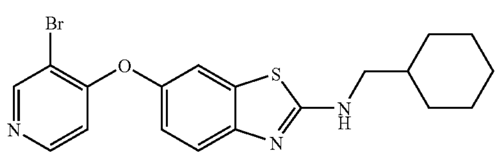 | 6-(3-bromopyridin-4-yloxy)-N-(cyclohexylmethyl)benzo[d]thiazol-2-amine | 418.1/ 420.1, 2.48 |
| 152 | 180 | 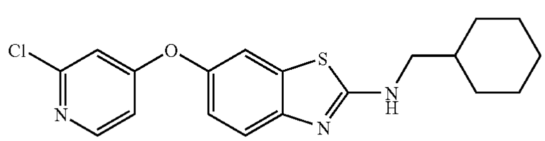 | 6-(2-chloropyridin-4-yloxy)-N-(cyclohexylmethyl)benzo[d]thiazol-2-amine | 374.1, 2.86 |
| 153 | 180 | 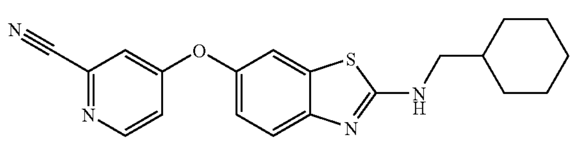 | 4-(2-(cyclohexylmethylamino)benzo[d]thiazol-6-yloxy)picolinamide | 365.1, 2.74 |
| 154 | 162 | 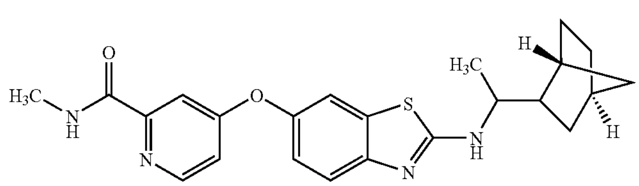 | 4-(2-(1-((1R,4S)-bicyclo[2.2.1]heptan-2-yl)ethylamino)benzo[d]thiazol-6-yloxy)-N-methylpicolinamide | 423.2, 2.31 |

TABLE 3-continued

| Cmpd | Ex Prep | Structure | Name | (M + H)+, Rt (min.) |
|---|---|---|---|---|
| 155 | 175 | 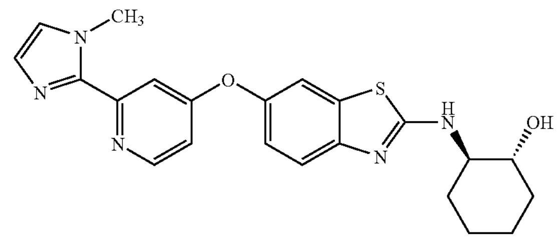 | (1R,2R)-2-(6-(2-(1-methyl-1H-imidazol-2-yl)pyridin-4-yloxy)benzo[d]thiazol-2-ylamino)cyclohexanol | 422.1, 1.83 |
| 156 | 175 | 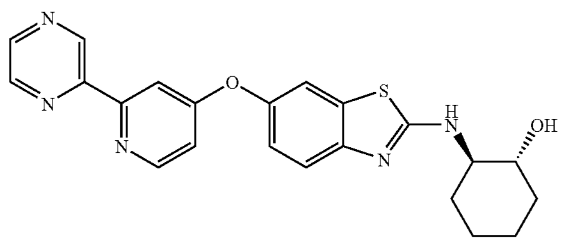 | (1R,2R)-2-(6-(2-(pyrazin-2-yl)pyridin-4-yloxy)benzo[d]thiazol-2-ylamino)cyclohexanol | 420.1, 1.91 |
| 157 | 175 | 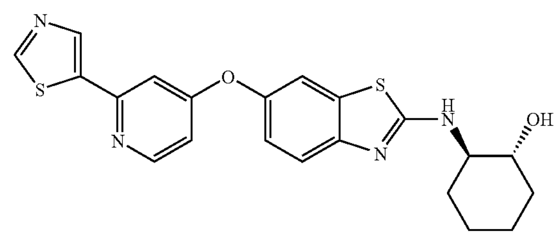 | (1R,2R)-2-(6-(2-(thiazol-5-yl)pyridin-4-yloxy)benzo[d]thiazol-2-ylamino)cyclohexanol | 425.0, 2.05 |
| 158 | 175 | 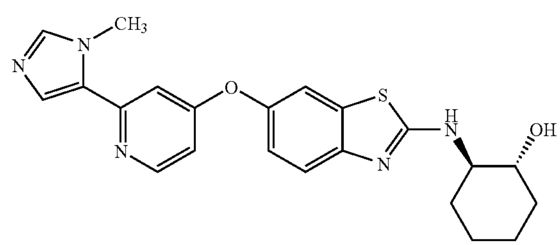 | (1R,2R)-2-(6-(2-(1-methyl-1H-imidazol-5-yl)pyridin-4-yloxy)benzo[d]thiazol-2-ylamino)cyclohexanol | 422.1, 1.84 |
| 159 | 175 | 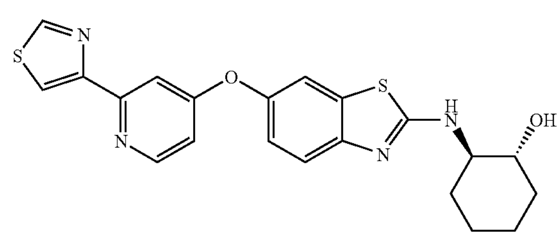 | (1R,2R)-2-(6-(2-(thiazol-4-yl)pyridin-4-yloxy)benzo[d]thiazol-2-ylamino)cyclohexanol | 425.0, 1.85 |
| 160 | 175 | 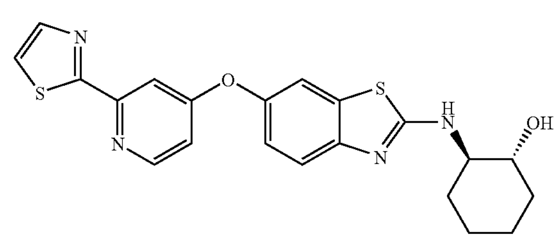 | (1R,2R)-2-(6-(2-(thiazol-2-yl)pyridin-4-yloxy)benzo[d]thiazol-2-ylamino)cyclohexanol | 425.0, 2.28 |

TABLE 3-continued

| Cmpd | Ex Prep | Structure | Name | (M + H)+, Rt (min.) |
|---|---|---|---|---|
| 161 | 188 | 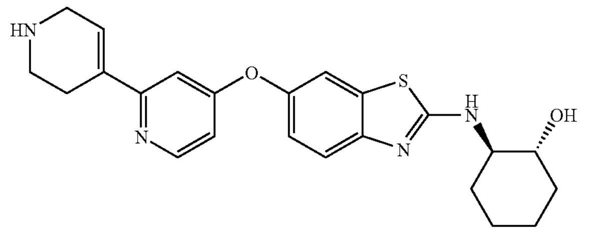 | (1R,2R)-2-(6-(2-(1,2,3,6-tetrahydropyridin-4-yl)pyridin-4-yloxy)benzo[d]thiazol-2-ylamino)cyclohexanol | 423.1, 1.38 |
| 162 | 177 | 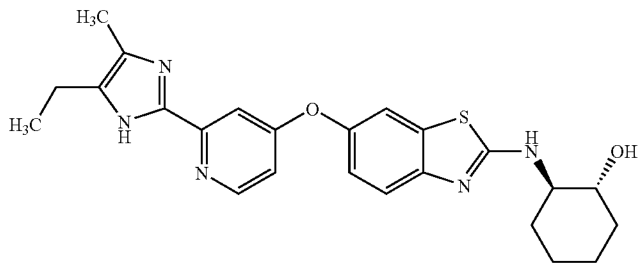 | (1R,2R)-2-(6-(2-(5-ethyl-4-methyl-1H-imidazol-2-yl)pyridin-4-yloxy)benzo[d]thiazol-2-ylamino)cyclohexanol | 450.1, 1.82 |
| 163 | 185 | 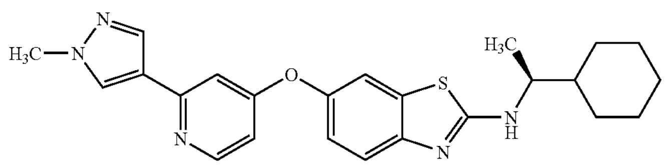 | (S)-N-(1-cyclohexylethyl)-6-(2-(1-methyl-1H-pyrazol-4-yl)pyridin-4-yloxy)benzo[d]thiazol-2-amine | 434.1, 2.31 |
| 164 | 174 | 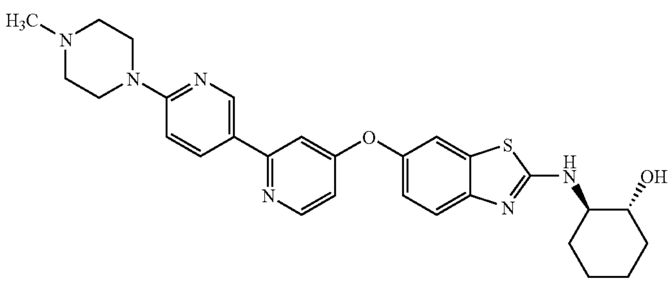 | (1R,2R)-2-(6-(6'-(4-methylpiperazin-1-yl)-2,3'-bipyridin-4-yloxy)benzo[d]thiazol-2-ylamino)cyclohexanol | 517.2, 1.75 |
| 165 | 174 | 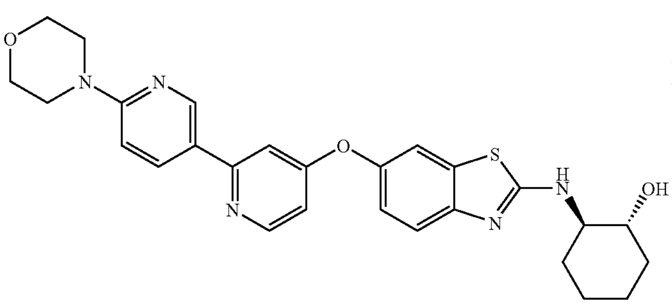 | (1R,2R)-2-(6-(6'-morpholino-2,3'-bipyridin-4-yloxy)benzo[d]thiazol-2-ylamino)cyclohexanol | 504.1, 1.93 |
| 166 | 174 | 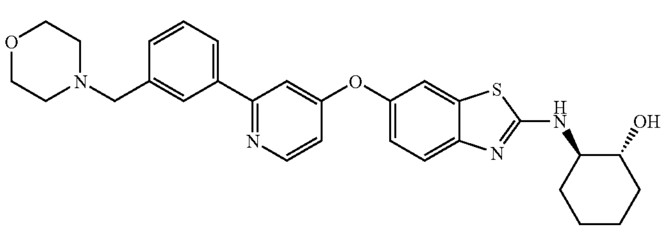 | (1R,2R)-2-(6-(2-(3-(morpholinomethyl)phenyl)pyridin-4-yloxy)benzo[d]thiazol-2-ylamino)cylcohexanol | 517.1, 1.78 |

TABLE 3-continued

| Cmpd | Ex Prep | Structure | Name | (M + H)+, Rt (min.) |
|---|---|---|---|---|
| 167 | 174 | 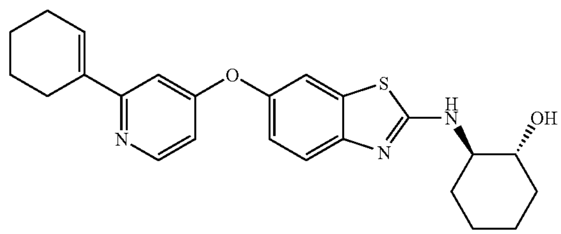 | (1R,2R)-2-(6-(2-cyclohexenylpyridin-4-yloxy)benzo[d]thiazol-2-ylamino)cyclohexanol | 422.1, 2.07 |
| 168 | 174 | 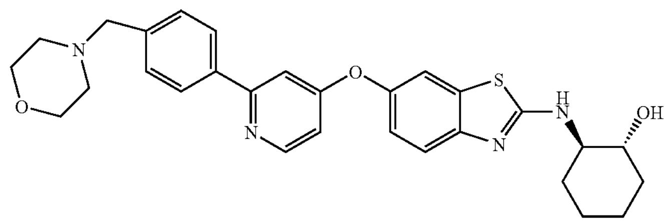 | (1R,2R)-2-(6-(2-(4-(morpholinomethyl)phenyl)pyridin-4-yloxy)benzo[d]thiazol-2-ylamino)cyclohexanol | 517.2, 1.76 |
| 169 | 174 | 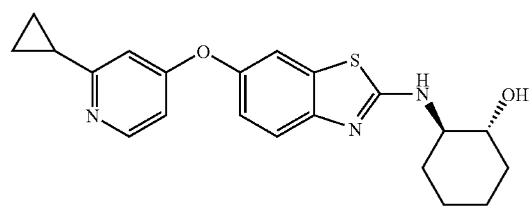 | (1R,2R)-2-(6-(2-cyclopropylpyridin-4-yloxy)benzo[d]thiazol-2-ylamino)cyclohexanol | 382.1, 1.84 |
| 170 | 174 | 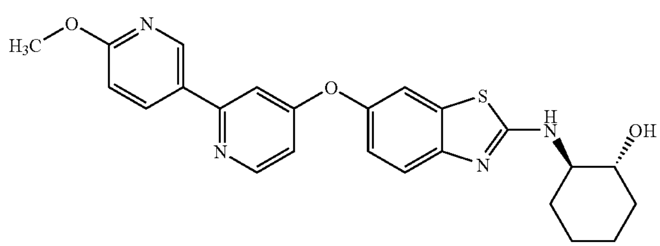 | (1R,2R)-2-(6-(6'-methoxy-2,3'-bipyridin-4-yloxy)benzo[d]thiazol-2-ylamino)cyclohexanol | 449.1, 1.98 |
| 171 | 174 | 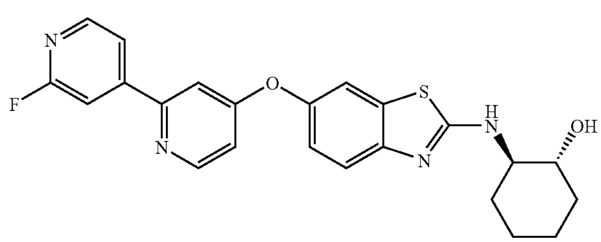 | (1R,2R)-2-(6-(2'-fluoro-2,4'-bipyridin-4-yloxy)benzo[d]thiazol-2-ylamino)cyclohexanol | 437.1, 2.22 |
| 172 | 174 | 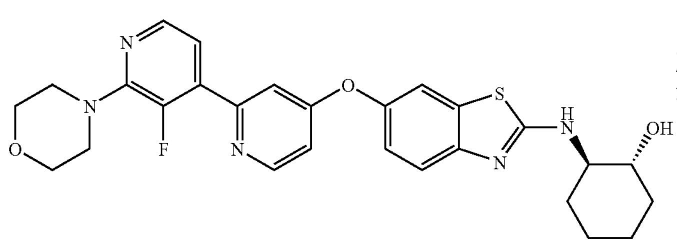 | (1R,2R)-2-(6-(3'-fluoro-2'-morpholino-2,4'-bipyridin-4-yloxy)benzo[d]thiazol-2-ylamino)cyclohexanol | 522.2, 2.17 |

TABLE 3-continued

| Cmpd | Ex Prep | Structure | Name | (M + H)+, Rt (min.) |
|---|---|---|---|---|
| 173 | 174 | 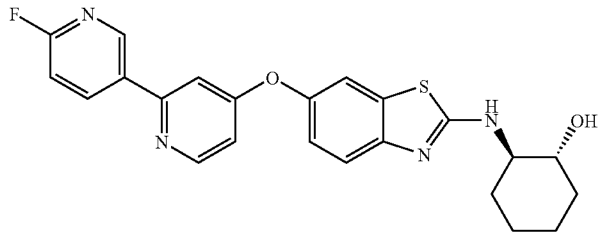 | (1R,2R)-2-(6-(6'-fluoro-2,3'-bipyridin-4-yloxy)benzo[d]thiazol-2-ylamino)cyclohexanol | 437.1, 2.04 |
| 174 | 183 | 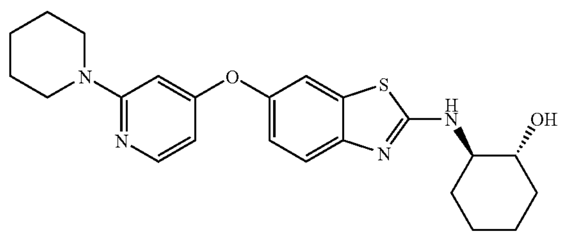 | (1R,2R)-2-(6-(2-(piperidin-1-yl)pyridin-4-yloxy)benzo[d]thiazol-2-ylamino)cyclohexanol | 425.1, 1.98 |
| 175 | 183 | 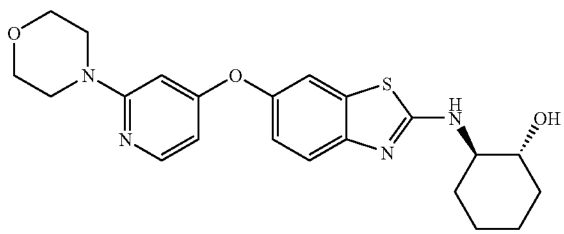 | (1R,2R)-2-(6-(2-morpholinopyridin-4-yloxy)benzo[d]thiazol-2-ylamino)cyclohexanol | 427.1, 1.80 |
| 176 | 183 | 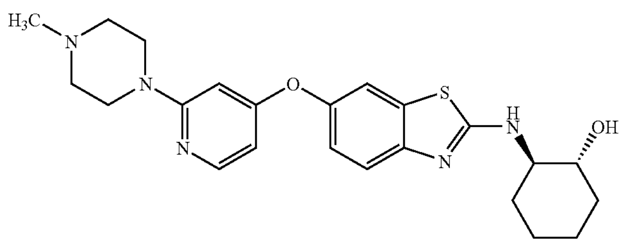 | (1R,2R)-2-(6-(2-(4-methylpiperazin-1-yl)pyridin-4-yloxy)benzo[d]thiazol-2-ylamino)cyclohexanol | 440.1, 1.66 |
| 177 | 183 | 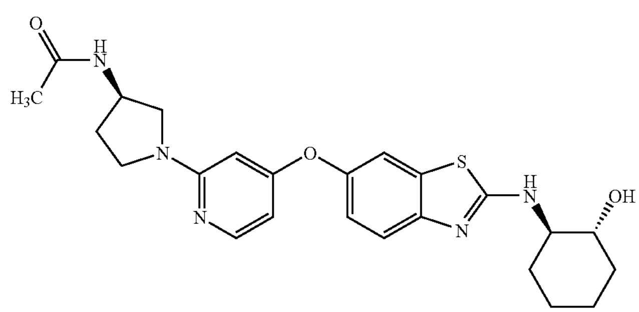 | N-((R)-1-(4-(2-((1R,2R)-2-hydroxycyclohexylamino)benzo[d]thiazol-6-yloxy)pyridin-2-yl)pyrrolidin-3-yl)acetamide | 468.1, 1.78 |
| 178 | 183 | Chiral | N-((S)-1-(4-(2-((1R,2R)-2-hydroxycyclohexylamino)benzo[d]thiazol-6-yloxy)pyridin-2-yl)pyrrolidin-3-yl)acetamide | 468.1, 1.77 |

TABLE 3-continued

| Cmpd | Ex Prep | Structure | | Name | (M + H)+, Rt (min.) |
|---|---|---|---|---|---|
| 179 | 183 | 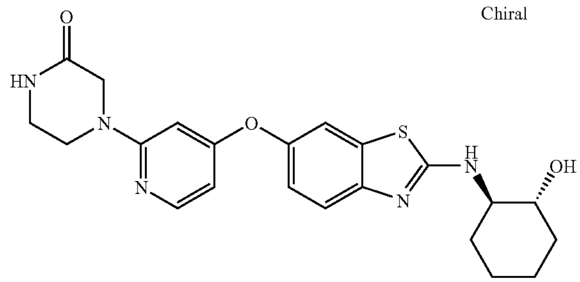 | Chiral | 4-(4-(2-((1R,2R)-2-hydroxycyclohexylamino)benzo[d]thiazol-6-yloxy)pyridin-2-yl)piperazin-2-one | 440.1, 1.70 |
| 180 | 175 | 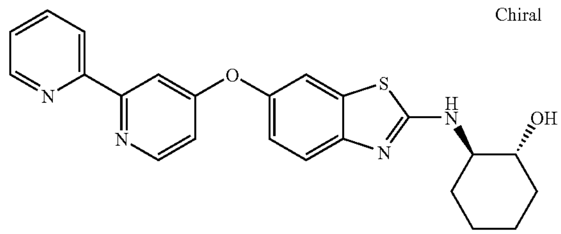 | Chiral | (1R,2R)-2-(6-(2,2'-bipyridin-4-yloxy)benzo[d]thiazol-2-ylamino)cyclohexanol | 419.0, 1.87 |
| 181 | 175 | 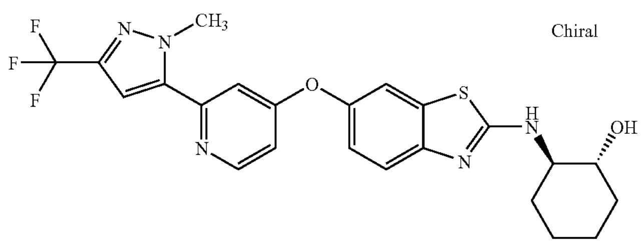 | Chiral | (1R,2R)-2-(6-(2-(1-methyl-3-(trifluoromethyl)-1H-pyrazol-5-yl)pyridin-4-yloxy)benzo[d]thiazol-2-ylamino)cyclohexanol | 490.1, 2.60 |
| 182 | 174 | 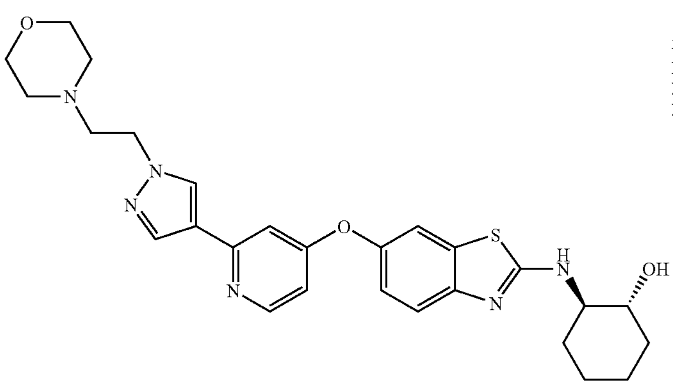 | | (1R,2R)-2-(6-(2-(1-(2-morpholinoethyl)-1H-pyrazol-4-yl)pyridin-4-yloxy)benzo[d]thiazol-2-ylamino)cyclohexanol | 521.1, 1.71 |
| 183 | 192 | 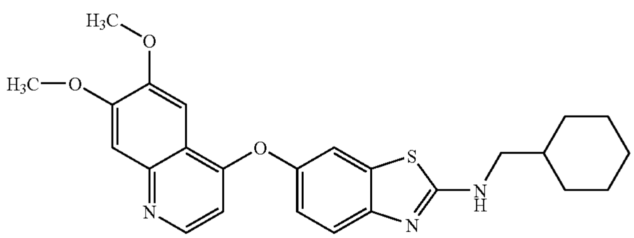 | | N-(cyclohexylmethyl)-6-(6,7-dimethoxyquinolin-4-yloxy)benzo[d]thiazol-2-amine | 450.1, 2.43 |

TABLE 3-continued

| Cmpd | Ex Prep | Structure | Name | (M + H)+, Rt (min.) |
|---|---|---|---|---|
| 184 | 192 | 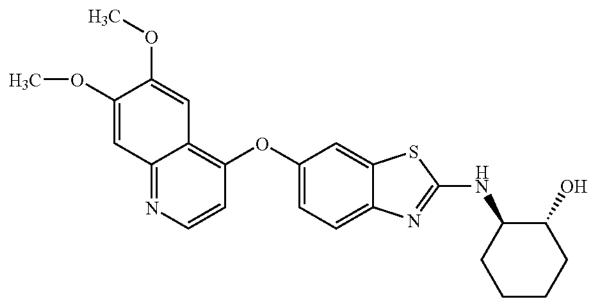 | (1R,2R)-2-(6-(6,7-dimethoxyquinolin-4-yloxy)benzo[d]thiazol-2-ylamino)cyclohexanol | 452.1, 2.00 |
| 185 | 176 | 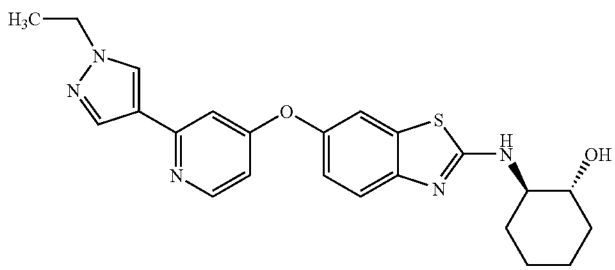 | (1R,2R)-2-(6-(2-(1-ethyl-1H-pyrazol-4-yl)pyridin-4-yloxy)benzo[d]thiazol-2-ylamino)cyclohexanol | 436.0, 1.89 |
| 186 | 176 | 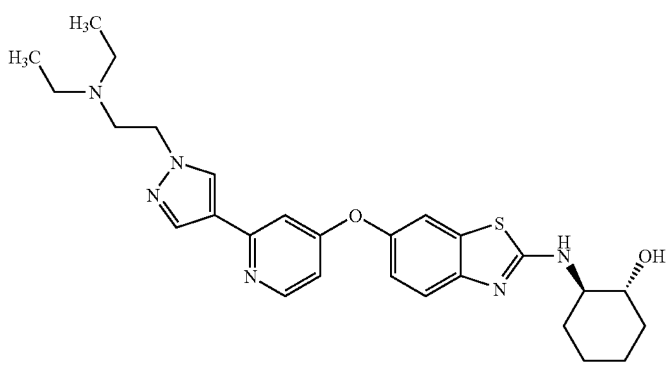 | (1R,2R)-2-(6-(2-(1-(2-(diethylamino)ethyl)-1H-pyrazol-4-yl)pyridin-4-yloxy)benzo[d]thiazol-2-ylamino)cyclohexanol | 507.1, 1.75 |
| 187 | 176 | 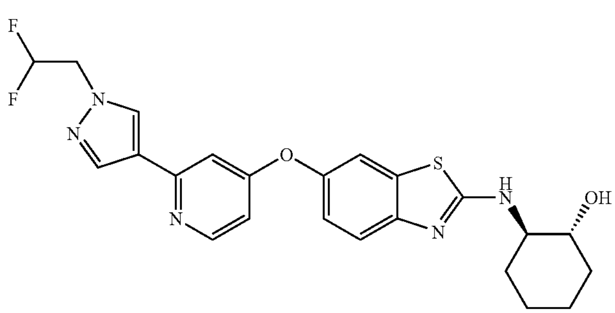 | (1R,2R)-2-(6-(2-(1-(2,2-difluoroethyl)-1H-pyrazol-4-yl)pyridin-4-yloxy)benzo[d]thiazol-2-ylamino)cyclohexanol | 472.0, 1.90 |
| 188 | 179 | 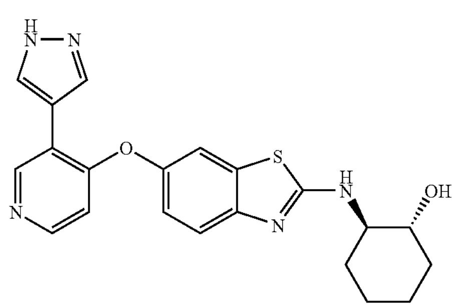 | (1R,2R)-2-(6-(3-(1H-pyrazol-4-yl)pyridin-4-yloxy)benzo[d]thiazol-2-ylamino)cyclohexanol | 408.1, 1.70 |

TABLE 3-continued

| Cmpd | Ex Prep | Structure | Name | (M + H)+, Rt (min.) |
|---|---|---|---|---|
| 189 | 179 | 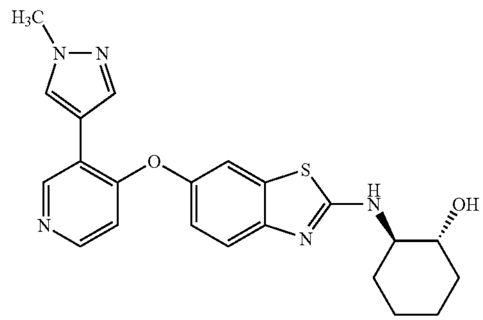 | (1R,2R)-2-(6-(3-(1-methyl-1H-pyrazol-4-yl)pyridin-4-yloxy)benzo[d]thiazol-2-ylamino)cyclohexanol | 422.1, 1.79 |
| 190 | 179 | 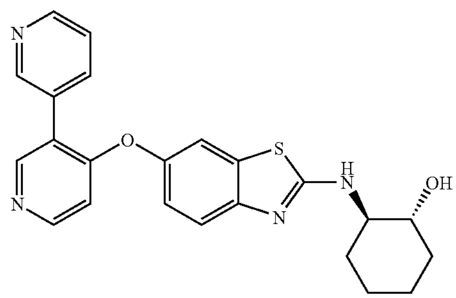 | (1R,2R)-2-(6-(3,3'-bipyridin-4-yloxy)benzo[d]thiazol-2-ylamino)cyclohexanol | 419.1, 1.66 |
| 191 | 179 | 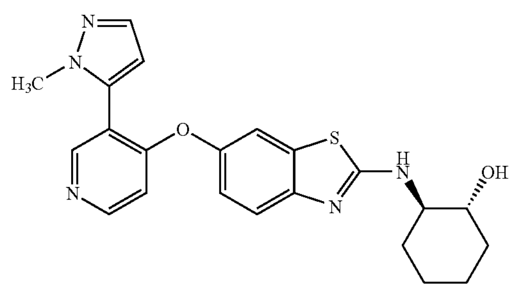 | (1R,2R)-2-(6-(3-(1-methyl-1H-pyrazol-5-yl)pyridin-4-yloxy)benzo[d]thiazol-2-ylamino)cyclohexanol | 422.1, 1.83 |
| 192 | 179 | 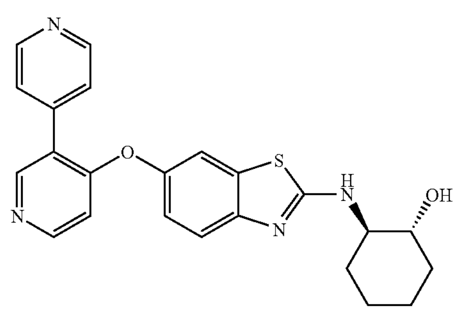 | (1R,2R)-2-(6-(3,4'-bipyridin-4-yloxy)benzo[d]thiazol-2-ylamino)cyclohexanol | 419.1, 1.61 |
| 193 | 179 | 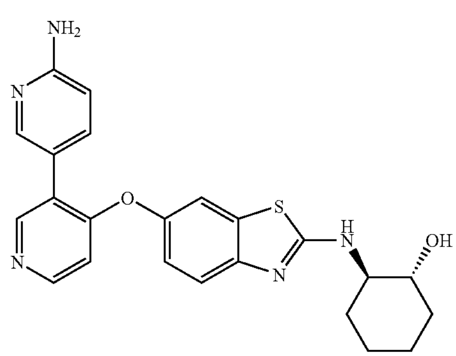 | (1R,2R)-2-(6-(6'-amino-3,3'-bipyridin-4-yloxy)benzo[d]thiazol-2-ylamino)cyclohexanol | 434.1, 1.60 |

TABLE 3-continued

| Cmpd | Ex Prep | Structure | Name | (M + H)+, Rt (min.) |
|---|---|---|---|---|
| 194 | 179 | 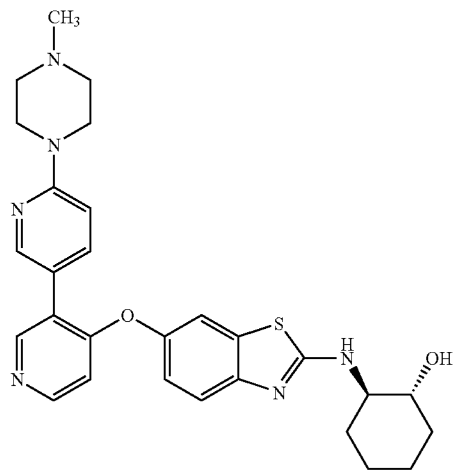 | (1R,2R)-2-(6-(6'-(4-methylpiperazin-1-yl)-3,3'-bipyridin-4-yloxy)benzo[d]thiazol-2-ylamino)cyclohexanol | 517.2, 1.64 |
| 195 | 179 | 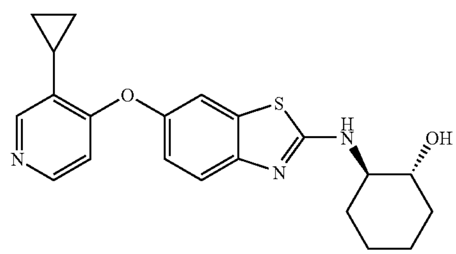 | (1R,2R)-2-(6-(3-cyclopropylpyridin-4-yloxy)benzo[d]thiazol-2-ylamino)cyclohexanol | 382.1, 1.97 |
| 196 | 174 | 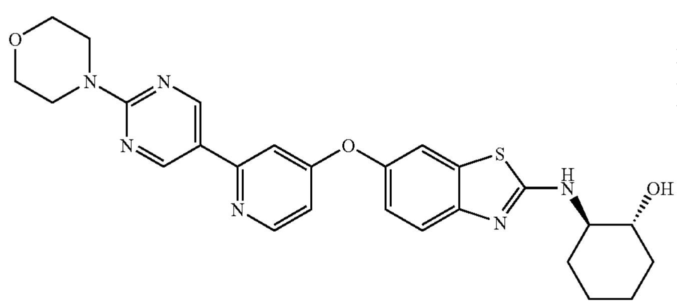 | (1R,2R)-2-(6-(2-(2-morpholinopyrimidin-5-yl)pyridin-4-yloxy)benzo[d]thiazol-2-ylamino)cyclohexanol | 505.1, 2.03 |
| 197 | 174 | 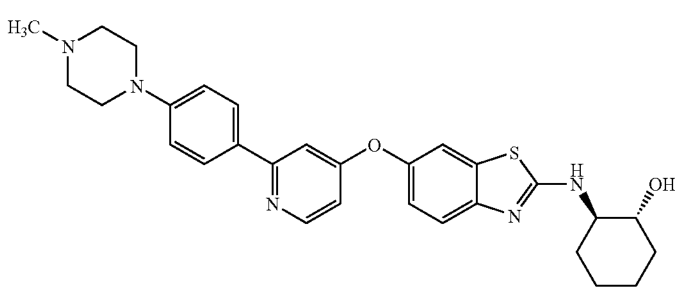 | (1R,2R)-2-(6-(2-(4-(4-methylpiperazin-1-yl)phenyl)pyridin-4-yloxy)benzo[d]thiazol-2-ylamino)cyclohexanol | 516.2, 1.85 |
| 198 | 185 | 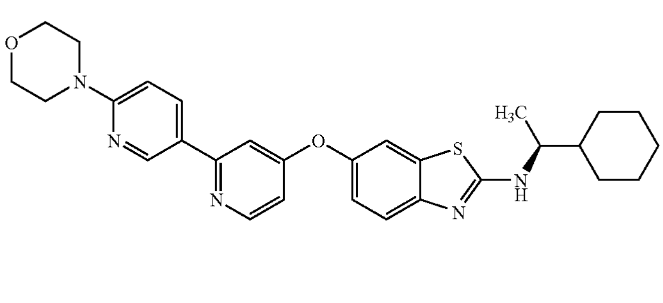 | (S)-N-(1-cyclohexylethyl)-6-(6'-morpholino-2,3'-bipyridin-4-yloxy)benzo[d]thiazol-2-amine | 516.1, 2.50 |

TABLE 3-continued

| Cmpd | Ex Prep | Structure | Name | (M + H)+, Rt (min.) |
|---|---|---|---|---|
| 199 | 185 | 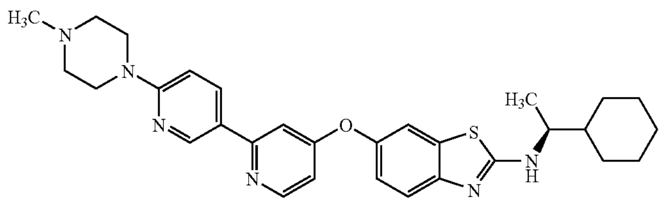 | (S)-N-(1-cyclohexylethyl)-6-(6'-(4-methylpiperazin-1-yl)-2,3'-bipyridin-4-yloxy)benzo[d]thiazol-2-amine | 529.2, 2.25 |
| 200 | 177 | Chiral | (1R,2R)-2-(6-(2-(4-(trifluoromethyl)-1H-imidazol-2-yl)pyridin-4-yloxy)benzo[d]thiazol-2-ylamino)cyclohexanol | 476.1, 2.35 |
| 201 | 181 | 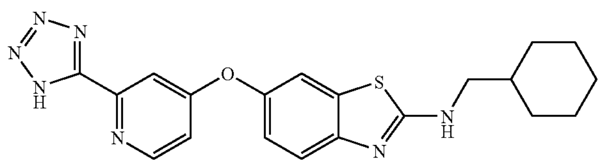 | 6-(2-(1H-tetrazol-5-yl)pyridin-4-yloxy)-N-(cyclohexylmethyl)benzo[d]thiazol-2-amine | 408.2, 2.35 |
| 202 | 192 | 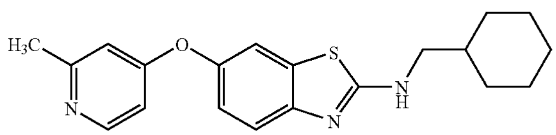 | N-(cyclohexylmethyl)-6-(2-methylpyridin-4-yloxy)benzo[d]thiazol-2-amine | 354.2, 2.19 |
| 203 | 192 | 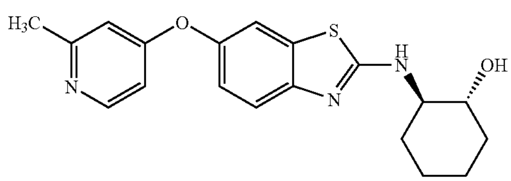 | (1R,2R)-2-(6-(2-methylpyridin-4-yloxy)benzo[d]thiazol-2-ylamino)cyclohexanol | 356.1, 1.73 |
| 204 | 192 | 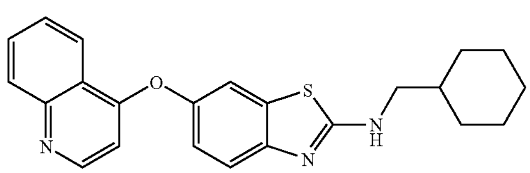 | N-(cyclohexylmethyl)-6-(quinolin-4-yloxy)benzo[d]thiazol-2-amine | 390.1, 2.38 |
| 205 | 192 | 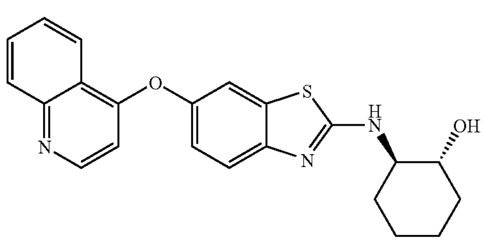 | (1R,2R)-2-(6-(quinolin-4-yloxy)benzo[d]thiazol-2-ylamino)cyclohexanol | 392.2, 1.93 |

TABLE 3-continued

| Cmpd | Ex Prep | Structure | Name | (M + H)+, Rt (min.) |
|---|---|---|---|---|
| 206 | 192 | 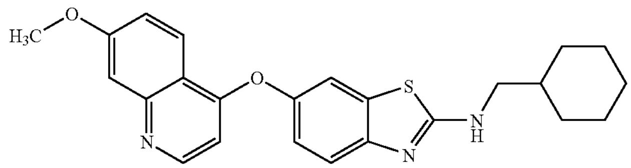 | N-(cyclohexylmethyl)-6-(7-methylquinolin-4-yloxy)benzo[d]thiazol-2-amine | 420.2, 2.49 |
| 207 | 192 | 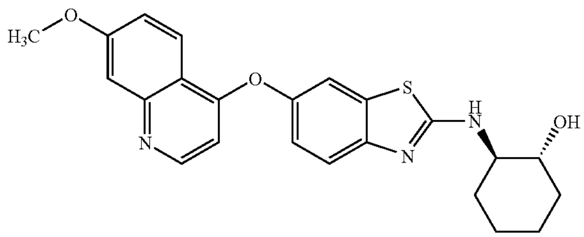 | (1R,2R)-2-(6-(7-methoxyquinolin-4-yloxy)benzo[d]thiazol-2-ylamino)cyclohexanol | 422.1, 2.03 |
| 208 | 192 | 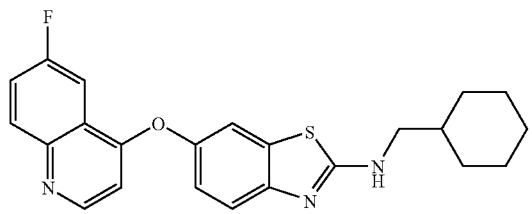 | N-(cyclohexylmethyl)-6-(6-fluoroquinolin-4-yloxy)benzo[d]thiazol-2-amine | 408.2, 2.45 |
| 209 | 192 | 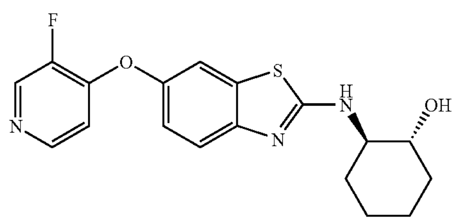 | (1R,2R)-2-(6-(3-fluoropyridin-4-yloxy)benzo[d]thiazol-2-ylamino)cyclohexanol | 360.1, 1.83 |
| 210 | 192 | 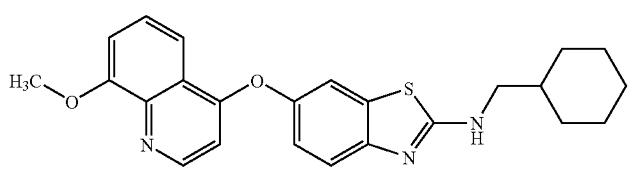 | N-(cyclohexylmethyl)-6-(8-methoxyquinolin-4-yloxy)benzo[d]thiazol-2-amine | 420.2, 2.46 |
| 211 | 192 | 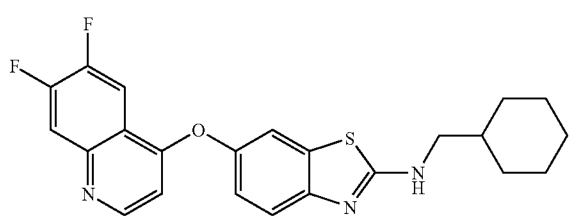 | N-(cyclohexylmethyl)-6-(6,7-difluoroquinolin-4-yloxy)benzo[d]thiazol-2-amine | 426.2, 2.61 |
| 212 | 192 | 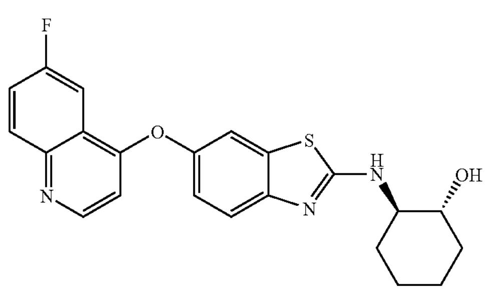 | (1R,2R)-2-(6-(6-fluoroquinolin-4-yloxy)benzo[d]thiazol-2-ylamino)cyclohexanol | 410.1, 1.98 |

TABLE 3-continued

| Cmpd | Ex Prep | Structure | Name | (M + H)+, Rt (min.) |
|---|---|---|---|---|
| 213 | 192 | 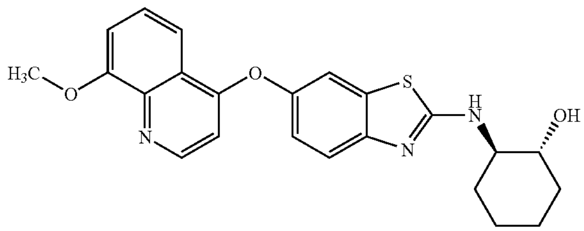 | (1R,2R)-2-(6-(8-methoxyquinolin-4-yloxy)benzo[d]thiazol-2-ylamino)cyclohexanol | 422.1, 1.96 |
| 214 | 192 | 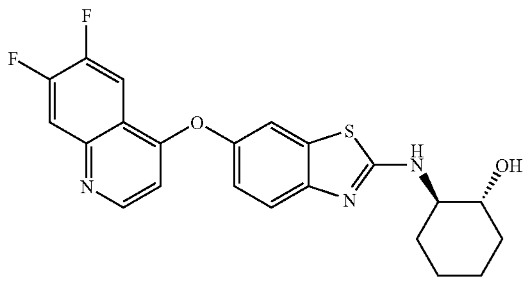 | (1R,2R)-2-(6-(6,7-difluoroquinolin-4-yloxy)benzo[d]thiazol-2-ylamino)cyclohexanol | 428.1, 2.08 |
| 215 | 192 | 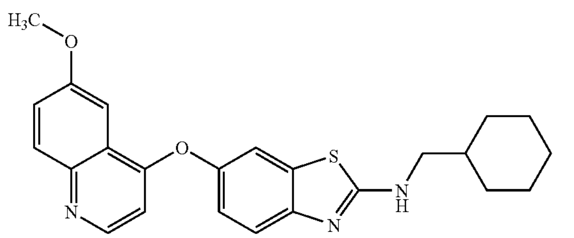 | N-(cyclohexylmethyl)-6-(6-methoxyquinolin-4-yloxy)benzo[d]thiazol-2-amine | 420.2, 2.47 |
| 216 | 192 | 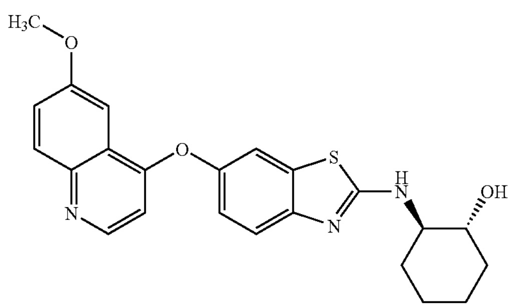 | (1R,2R)-2-(6-(6-methoxyquinolin-4-yloxy)benzo[d]thiazol-2-ylamino)cyclohexanol | 422.1, 1.98 |
| 217 | 162 | 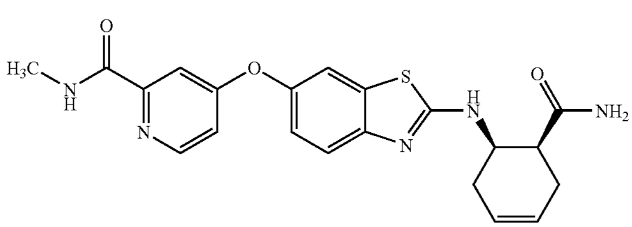 | 4-(2-((1R,6S)-6-carbamoylcyclohex-3-enylamino)benzo[d]thiazol-6-yloxy)-N-methylpicolinamide | 424.1, 1.86 |
| 218 | 162 | 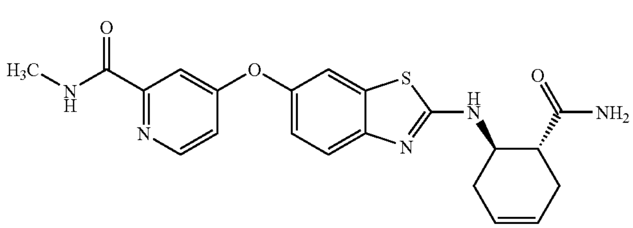 | 4-(2-((1R,6R)-6-carbamoylcyclohex-3-enylamino)benzo[d]thiazol-6-yloxy)-N-methylpicolinamide | 424.1, 1.90 |

TABLE 3-continued

| Cmpd | Ex Prep | Structure | Name | (M + H)+, Rt (min.) |
|---|---|---|---|---|
| 219 | 192 | 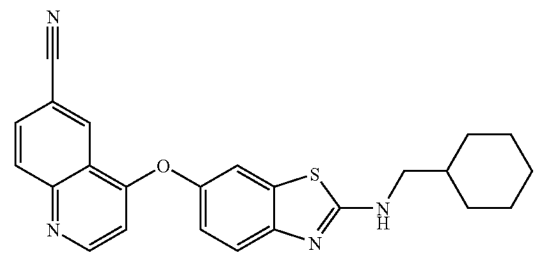 | 4-(2-(cyclohexylmethylamino)benzo[d]thiazol-6-yloxy)quinolin-6-carbonitrile | 415.1, 2.50 |
| 220 | 192 | 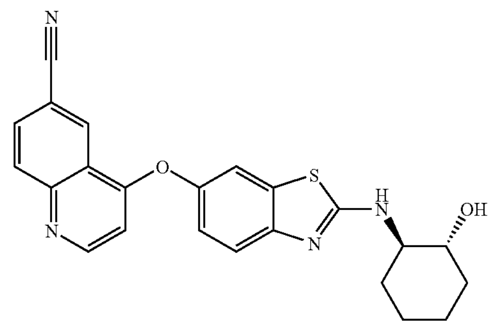 | 4-(2-((1R,2R)-2-hydroxycyclohexylamino)benzo[d]thiazol-6-yloxy)quinolin-6-carbonitrile | 417.1, 1.99 |
| 221 | 192 | 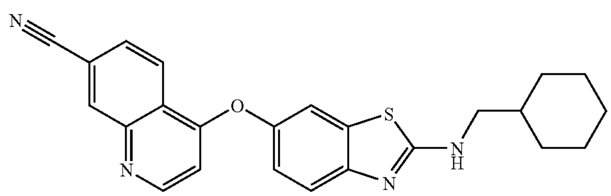 | 4-(2-cyclohexylamino)benzo[d]thiazol-6-yloxy)quinolin-7-carbonitrile | 415.1, 2.52 |
| 222 | 192 | 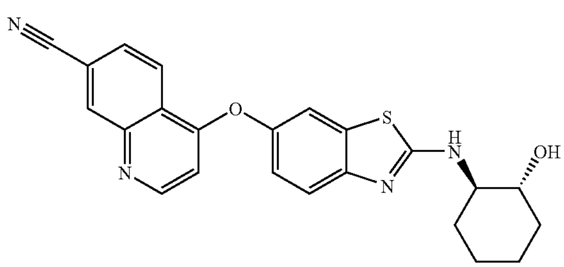 | 4-(2-((1R,2R)-2-hydroxycyclohexylamino)benzo[d]thiazol-6-yloxy)quinolin-7-carbonitrile | 417.1, 1.98 |
| 223 | 162 | 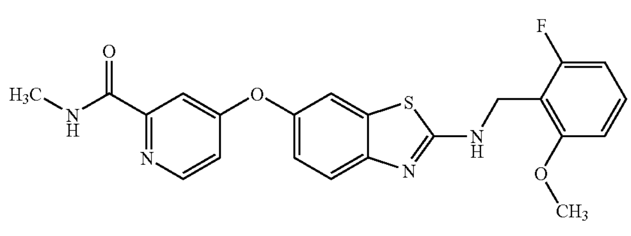 | 4-(2-(2-fluoro-6-methoxybenzylamino)benzo[d]thiazol-6-yloxy)-N-methylpicolinamide | 439.1, 2.40 |
| 224 | 178 | 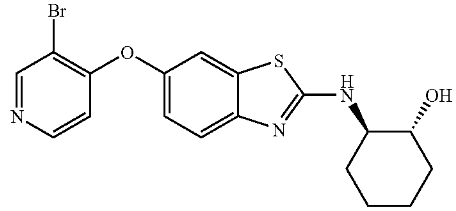 | (1R,2R)-2-(6-(3-bromopyridin-4-yloxy)benzo[d]thiazol-2-ylamino)cyclohexanol | 420.1/ 422.0, 1.81 |

TABLE 3-continued

| Cmpd | Ex Prep | Structure | Name | (M + H)+, Rt (min.) |
|---|---|---|---|---|
| 225 | 173 | 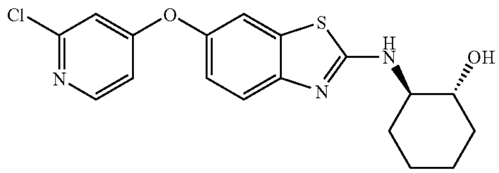 | (1R,2R)-2-(6-(2-chloropyridin-4-yloxy)benzo[d]thiazol-2-ylamino)cyclohexanol | 376.1, 2.13 |
| 226 | 173 | 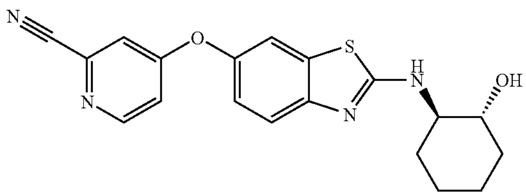 | 4-(2-((1R,2R)-2-hydroxycyclohexylamino)benzo[d]thiazol-6-yloxy)picolinotrile | 367.1, 2.03 |
| 227 | 192 | 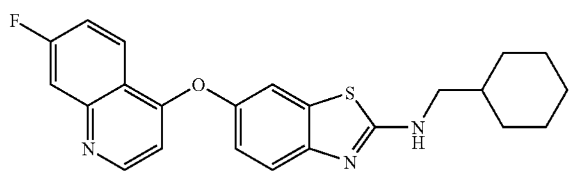 | N-(cyclohexylmethyl)-6-(7-fluoroquinolin-4-yloxy)benzo[d]thiazol-2-amine | 408.1, 2.44 |
| 228 | 192 | 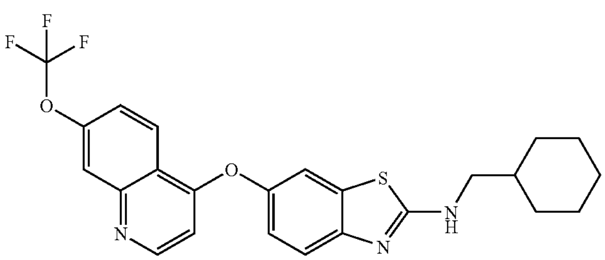 | N-(cyclohexylmethyl)-6-(7-(trifluoromethoxy)quinolin-4-yloxy)benzo[d]thiazol-2-amine | 474.1, 2.76 |
| 229 | 192 | 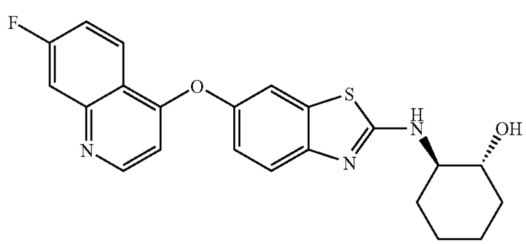 | (1R,2R)-2-(6-(7-fluoroquinolin-4-yloxy)benzo[d]thiazol-2-ylamino)cyclohexanol | 410.1, 1.95 |
| 230 | 192 | 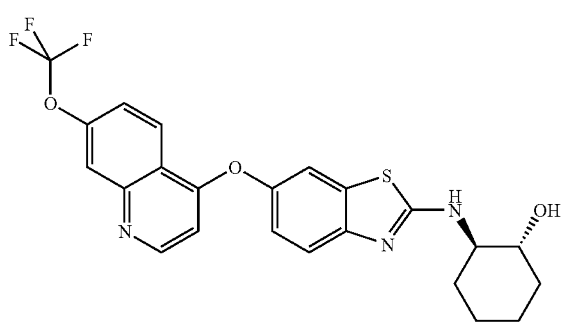 | (1R,2R)-2-(6-(7-(trifluoromethoxy)quinolin-4-yloxy)benzo[d]thiazol-2-ylamino)cyclohexanol | 476.1, 2.25 |

TABLE 3-continued

| Cmpd | Ex Prep | Structure | Name | (M + H)+, Rt (min.) |
|---|---|---|---|---|
| 231 | 177 | 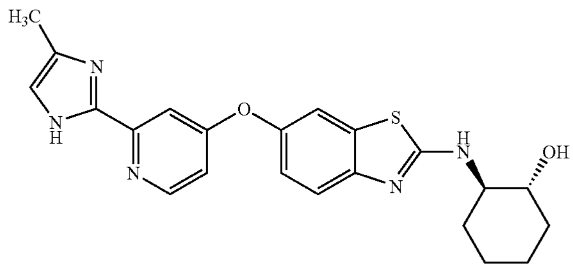 | (1R,2R)-2-(6-(2-(4-methyl-1H-imidazol-2-yl)pyridin-4-yloxy)benzo[d]thiazol-2-ylamino)cyclohexanol | 422.1, 1.88 |
| 232 | 177 | 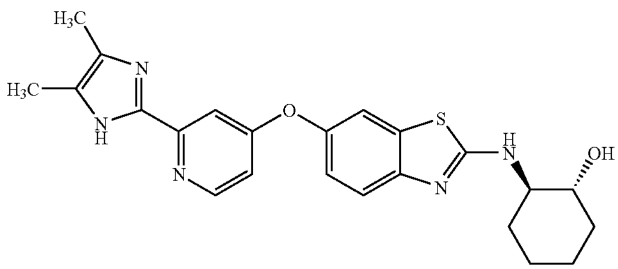 | (1R,2R)-2-(6-(2-(4,5-dimethyl-1H-imidazol-2-yl)pyridin-4-yloxy)benzo[d]thiazol-2-ylamino)cyclohexanol | 436.1, 1.93 |
| 233 | 182 | 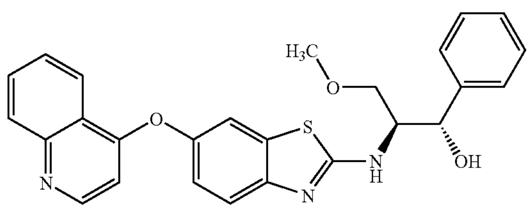 | (1S,2S)-3-methoxy-1-phenyl-2-(6-(quinolin-4-yloxy)benzo[d]thiazol-2-ylamino)propan-1-ol | 458.1, 2.18 |
| 234 | 182 | 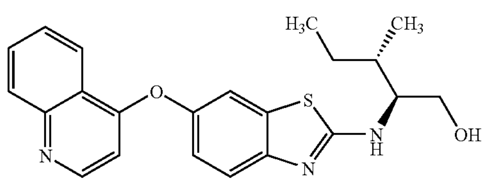 | (2S,3S)-3-methyl-2-(6-(quinolin-4-yloxy)benzo[d]thiazol-2-ylamino)pentan-1-ol | 394.2, 2.08 |
| 235 | 182 | 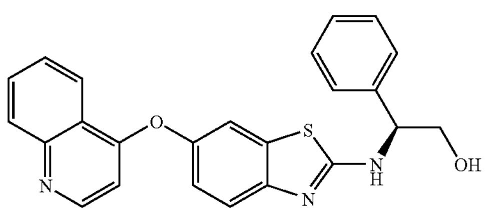 | (S)-2-phenyl-2-(6-(quinolin-4-yloxy)benzo[d]thiazol-2-ylamino)ethanol | 414.1, 2.11 |
| 236 | 182 | 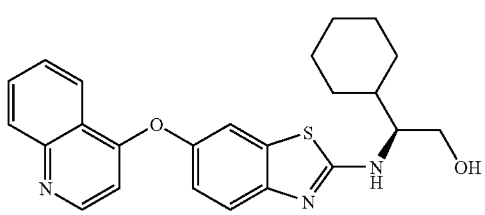 | (S)-2-cyclohexyl-2-(6-(quinolin-4-yloxy)benzo[d]thiazol-2-ylamino)ethanol | 420.2, 2.21 |

TABLE 3-continued

| Cmpd | Ex Prep | Structure | Name | (M + H)+, Rt (min.) |
|---|---|---|---|---|
| 237 | 182 | 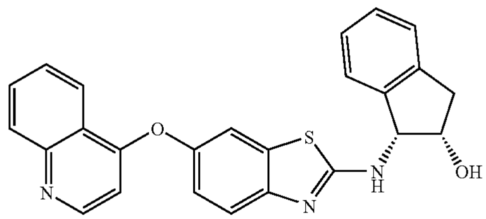 | (1R,2S)-1-(6-(quinolin-4-yloxy)benzo[d]thiazol-2-ylamino)-2,3-dihydro-1H-inden-2-ol | 426.1, 2.20 |
| 238 | 182 | 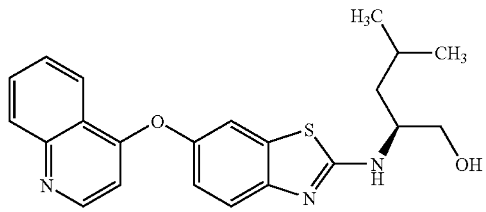 | (S)-4-methyl-2-(6-quinolin-4-yloxy)benzo[d]thiazol-2-ylamino)pentan-1-ol | 394.2, 2.09 |
| 239 | 182 | 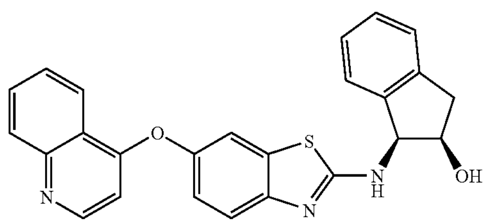 | (1S,2R)-1-(6-(quinolin-4-yloxy)benzo[d]thiazol-2-ylamino)-2,3-dihydro-1H-inden-2-ol | 426.1, 2.20 |
| 240 | 182 | 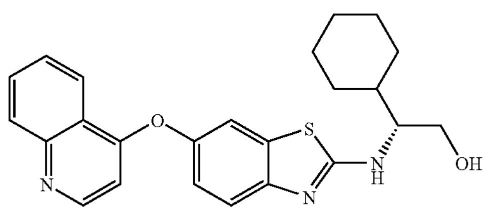 | (R)-2-cyclohexyl-2-(6-(quinolin-4-yloxy)benzo[d]thiazol-2-ylamino)ethanol | 420.2, 2.21 |
| 241 | 182 | 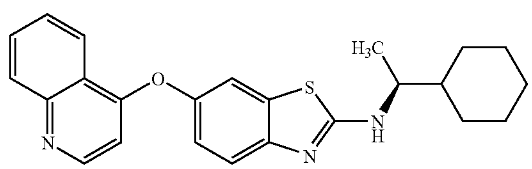 | (S)-N-(1-cyclohexylethyl)-6-(quinolin-4-yloxy)benzo[d]thiazol-2-amine | 404.1, 2.48 |
| 242 | 182 | 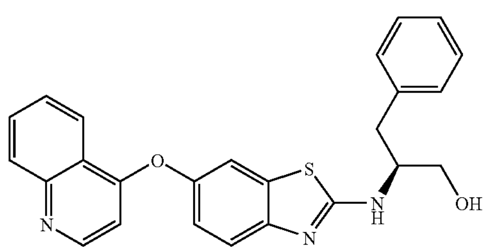 | (S)-3-phenyl-2-(6-(quinolin-4-yloxy)benzo[d]thiazol-2-ylamino)propan-1-ol | 428.0, 2.13 |
| 243 | 182 | 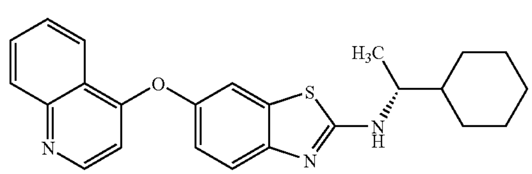 | (R)-N-(1-cyclohexylethyl)-6-(quinolin-4-yloxy)benzo[d]thiazol-2-amine | 404.1, 2.48 |

TABLE 3-continued

| Cmpd | Ex Prep | Structure | Name | (M + H)+, Rt (min.) |
|---|---|---|---|---|
| 244 | 182 | 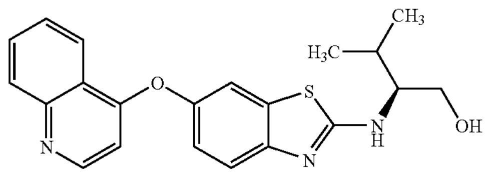 | (S)-3-methyl-2-(6-(quinolin-4-yloxy)benzo[d]thiazol-2-ylamino)butan-1-ol | 380.1, 1.95 |
| 245 | 182 | 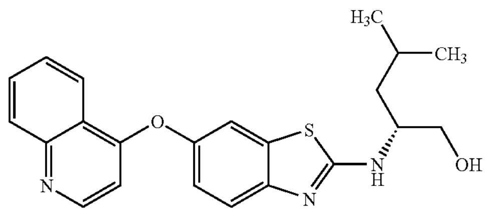 | (R)-4-methyl-2-(6-(quinolin-4-yloxy)benzo[d]thiazol-2-ylamino)pentan-1-ol | 394.2, 2.09 |
| 246 | 182 | 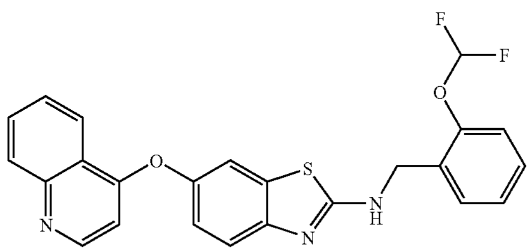 | N-(2-(difluoromethoxy)benzyl)-6-(quinolin-4-yloxy)benzo[d]thiazol-2-amine | 450.1, 2.47 |
| 247 | 182 | 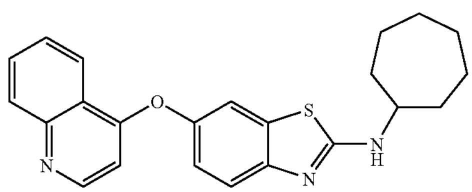 | N-cycloheptyl-6-(quinolin-4-yloxy)benzo[d]thiazol-2-amine | 390.1, 2.36 |
| 248 | 182 | 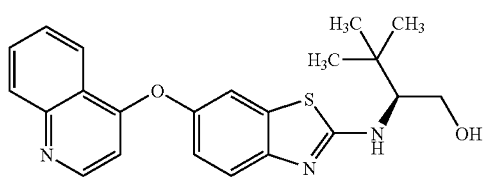 | (S)-3,3-dimethyl-2-(6-(quinolin-4-yloxy)benzo[d]thiazol-2-ylamino)butan-1-ol | 394.1, 2.05 |
| 249 | 182 | 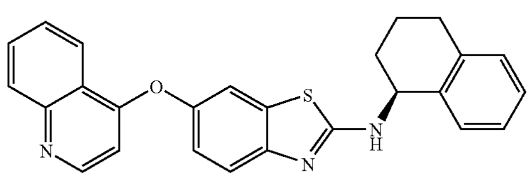 | (S)-6-(quinolin-4-yloxy)-N-(1,2,3,4-tetrahydronaphthalen-1-yl)benzo[d]thiazol-2-amine | 424.1, 2.54 |
| 250 | 182 | 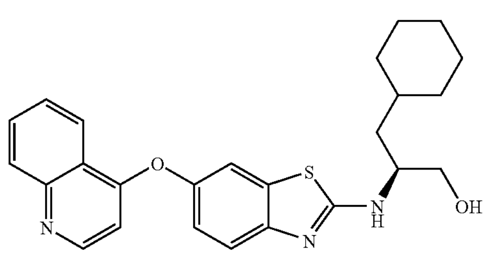 | (S)-3-cyclohexyl-2-(6-(quinolin-4-yloxy)benzo[d]thiazol-2-ylamino)propan-1-ol | 434.2, 2.37 |

TABLE 3-continued

| Cmpd | Ex Prep | Structure | Name | (M + H)+, Rt (min.) |
|---|---|---|---|---|
| 251 | 182 | 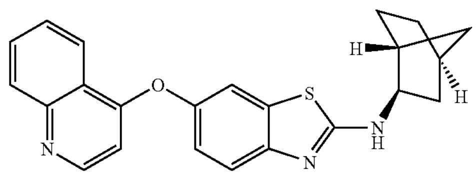 | N-((1R,2R,4S)-bicyclo[2.2.1]heptan-2-yl)-6-(quinolin-4-yloxy)benzo[d]thiazol-2-amine | 388.1, 2.29 |
| 252 | 182 | 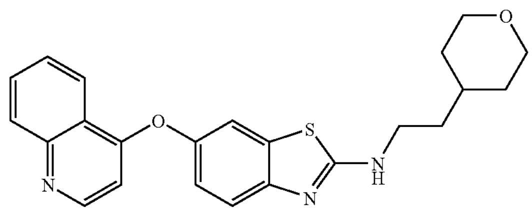 | 6-(quinolin-4-yloxy)-N-(2-(tetrahydro-2H-pyran-4-yl)ethyl)benzo[d]thiazol-2-amine | 406.1, 2.00 |
| 253 | 182 | 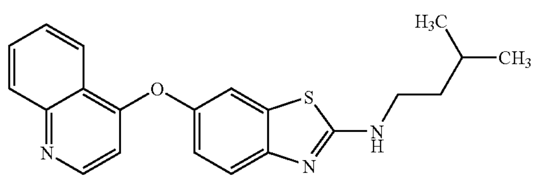 | N-isopentyl-6-(quinolin-4-yloxy)benzo[d]thiazol-2-amine | 364.1, 2.24 |
| 254 | 182 | 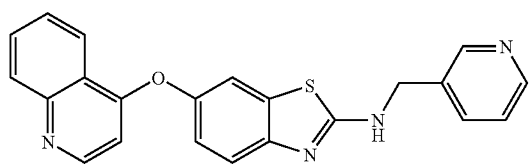 | N-(pyridin-3-ylmethyl)-6-(quinolin-4-yloxy)benzo[d]thiazol-2-amine | 385.1, 1.78 |
| 255 | 182 | 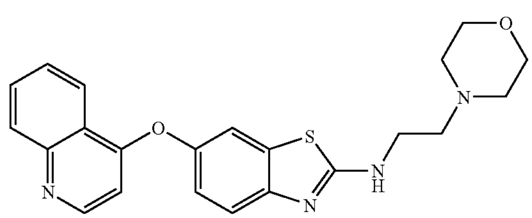 | N-(2-morpholinoethyl)-6-(quinolin-4-yloxy)benzo[d]thiazol-2-amine | 407.1, 1.77 |
| 256 | 182 | 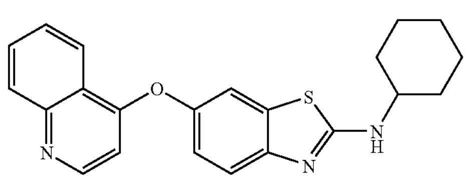 | N-cyclohexyl-6-(quinolin-4-yloxy)benzo[d]thiazol-2-amine | 376.1, 2.21 |
| 257 | 182 | 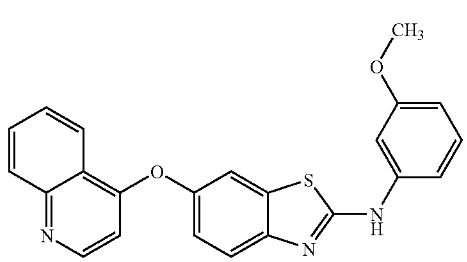 | N-(2-methoxybenzyl)-6-(quinolin-4-yloxy)benzo[d]thiazol-2-amine | 414.1, 2.29 |

TABLE 3-continued

| Cmpd | Ex Prep | Structure | Name | (M + H)+, Rt (min.) |
|---|---|---|---|---|
| 258 | 177 | 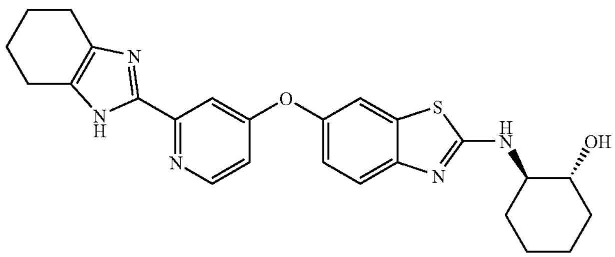 | (1R,2R)-2-(6-(2-(4,5,6,7-tetrahydro-1H-benzo[d]imidazol-2-yl)pyridin-4-yloxy)benzo[d]thiazol-2-ylamino)cyclohexanol | 462.2, 2.03 |
| 259 | 176 | 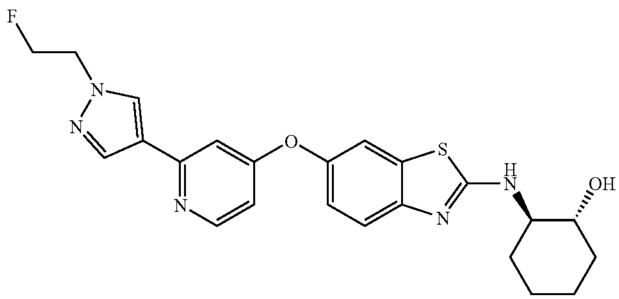 | (1R,2R)-2-(6-(2-(1-(2-fluoroethyl)-1H-pyrazol-4-yl)pyridin-4-yloxy)benzo[d]thiazol-2-ylamino)cyclohexanol | 454.2, 1.89 |
| 260 | 176 | 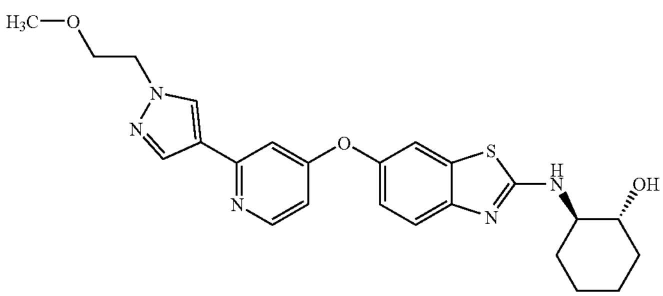 | (1R,2R)-2-(6-(2-(1-(2-methoxyethyl)-1H-pyrazol-4-yl)pyridin-4-yloxy)benzo[d]thiazol-2-ylamino)cyclohexanol | 466.2, 1.89 |
| 261 | 174 | 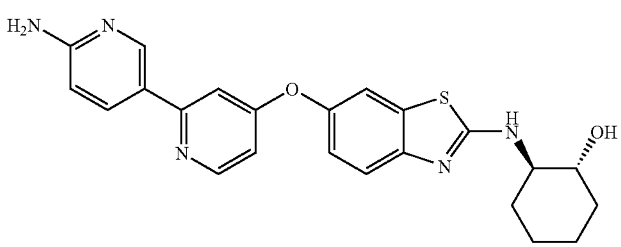 | (1R,2R)-2-(6-(6'-amino-2,3'-bipyridin-4-yloxy)benzo[d]thiazol-2-ylamino)cyclohexanol | 434.2, 1.78 |
| 262 | 187 | 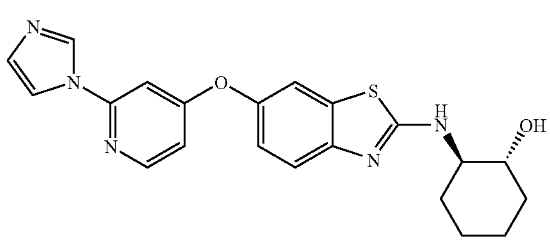 | (1R,2R)-2-(6-(2-(1H-imidazol-1-yl)pyridin-4-yloxy)benzo[d]thiazol-2-ylamino)cyclohexanol | 408.2, 1.85 |

TABLE 3-continued

| Cmpd | Ex Prep | Structure | Name | (M + H)+, Rt (min.) |
|---|---|---|---|---|
| 263 | 192 | 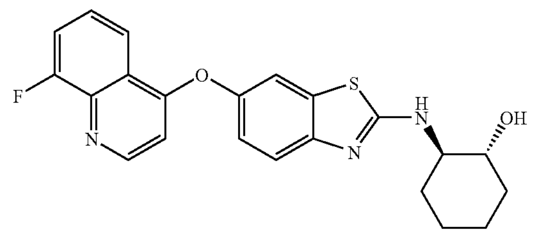 | (1R,2R)-2-(6-(8-fluoroquinolin-4-yloxy)benzo[d]thiazol-2-ylamino)cyclohexanol | 410.1, 1.95 |
| 264 | 184 | 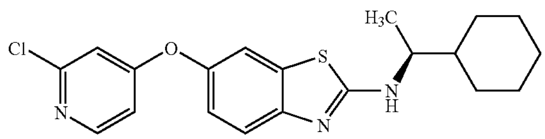 | (S)-6-(2-chloropyridin-4-yloxy)-N-(1-cyclohexylethyl)benzo[d]thiazol-2-amine | 388.1, 2.95 |
| 265 | 174 | 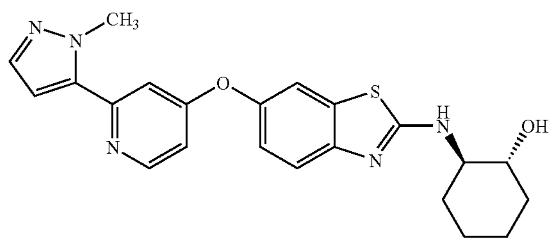 | (1R,2R)-2-(6-(2-(1-methyl-1H-pyrazol-5-yl)pyridin-4-yloxy)benzo[d]thiazol-2-ylamino)cyclohexanol | 422.1, 1.93 |
| 266 | 177 | 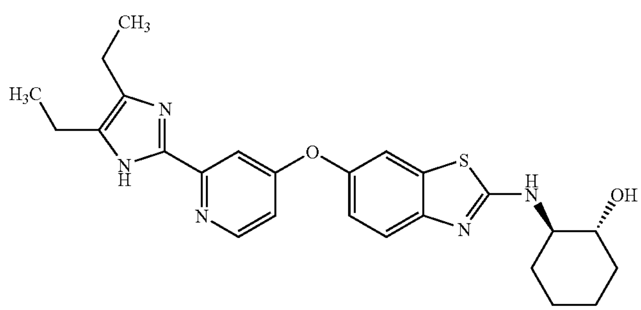 | (1R,2R)-2-(6-(2-(4,5-diethyl-1H-imidazol-2-yl)pyridin-4-yloxy)benzo[d]thiazol-2-ylamino)cyclohexanol | 464.2, 2.10 |
| 267 | 177 | 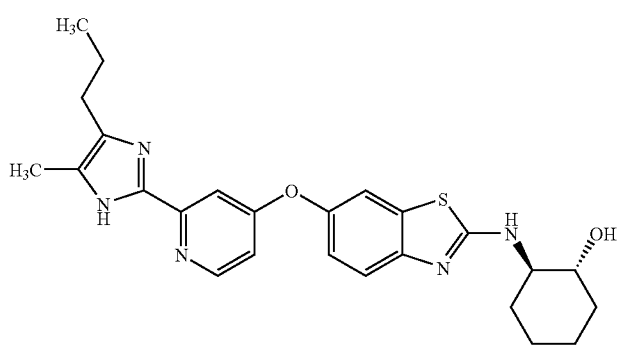 | (1R,2R)-2-(6-(2-(5-methyl-4-propyl-1H-imidazol-2-yl)pyridin-4-yloxy)benzo[d]thiazol-2-ylamino)cyclohexanol | 464.2, 2.10 |
| 268 | 186 | 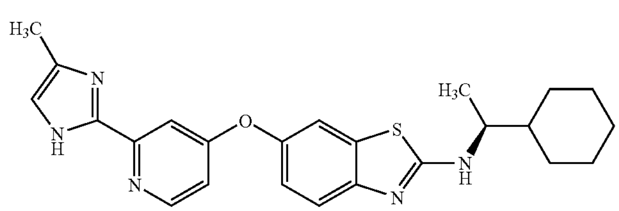 | (S)-N-(1-cyclohexylethyl)-6-(2-(4-methyl-1H-imidazol-2-yl)pyridin-4-yloxy)benzo[d]thiazol-2-amine | 434.2, 2.35 |

TABLE 3-continued

| Cmpd | Ex Prep | Structure | Name | (M + H)+, Rt (min.) |
|---|---|---|---|---|
| 269 | 186 | 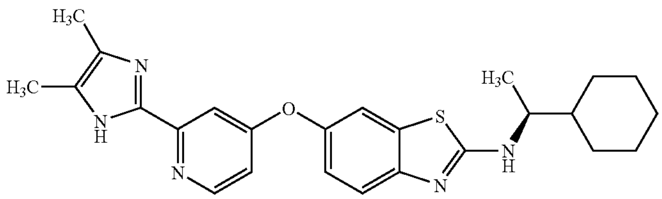 | (S)-N-(1-cyclohexylethyl)-6-(2-(4,5-dimethyl-1H-imidazol-2-yl)pyridin-4-yloxy)benzo[d]thiazol-2-amine | 448.2, 2.43 |
| 270 | 186 | 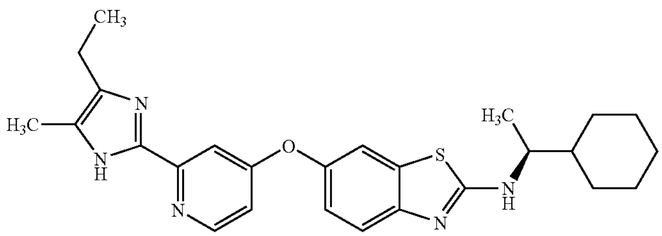 | (S)-N-(1-cyclohexylethyl)-6-(2-(4-ethyl-5-methyl-1H-imidazol-2-yl)pyridin-4-yloxy)benzo[d]thiazol-2-amine | 462.2, 2.49 |
| 271 | 186 | 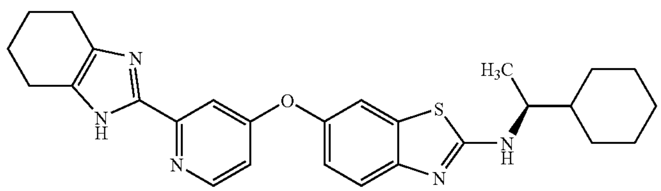 | (S)-N-(1-cyclohexylethyl)-6-(2-(4,5,6,7-tetrahydro-1H-benzo[d]imidazol-2-yl)pyridin-4-yloxy)benzo[d]thiazol-2-amine | 474.2, 2.54 |
| 272 | 186 | 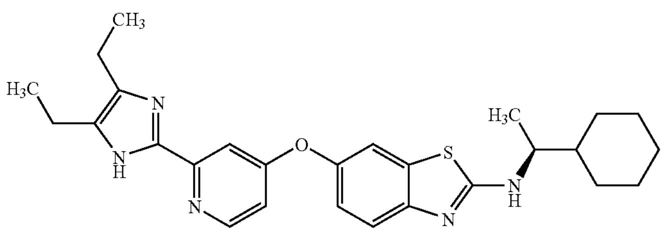 | (S)-N-(1-cyclohexylethyl)-6-(2-(4,5-diethyl-1H-imidazol-2-yl)pyridin-4-yloxy)benzo[d]thiazol-2-amine | 476.2, 2.62 |
| 273 | 185 | 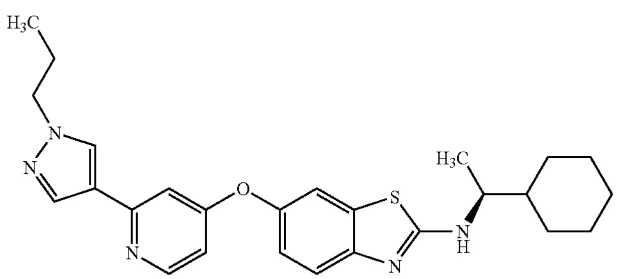 | (S)-N-(1-cyclohexylethyl)-6-(2-(1-propyl-1H-pyrazol-4-yl)pyridin-4-yloxy)benzo[d]thiazol-2-amine | 462.2, 2.53 |
| 274 | 185 | 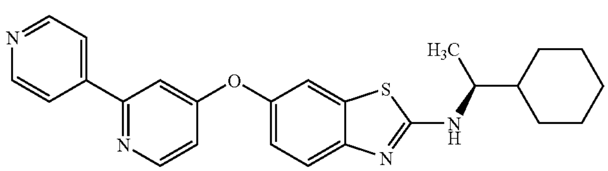 | (S)-6-(2,3'-bipyridin-4-yloxy)-N-(1-cyclohexylethyl)benzo[d]thiazol-2-amine | 431.2, 2.35 |
| 275 | 185 | 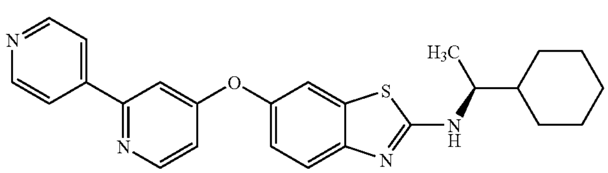 | (S)-6-(2,4'-bipyridin-4-yloxy)-N-(1-cyclohexylethyl)benzo[d]thiazol-2-amine | 431.2, 2.35 |

TABLE 3-continued

| Cmpd | Ex Prep | Structure | Name | (M + H)+, Rt (min.) |
|---|---|---|---|---|
| 276 | 185 | 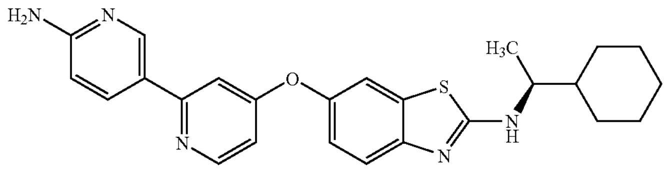 | (S)-6-(6'-amino-2,3'-bipyridin-4-yloxy)-N-(1-cyclohexylethyl)benzo[d]thiazol-2-amine | 446.1, 2.25 |
| 277 | 185 | 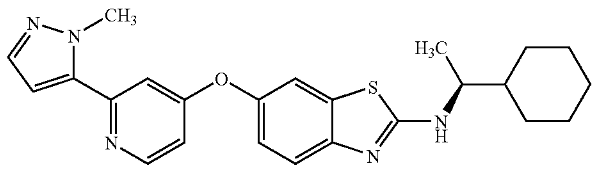 | (S)-N-(1-cyclohexylethyl)-6-(2-(1-methyl-1H-pyrazol-5-yl)pyridin-4-yloxy)benzo[d]thiazol-2-amine | 434.2, 2.58 |
| 278 | 185 | 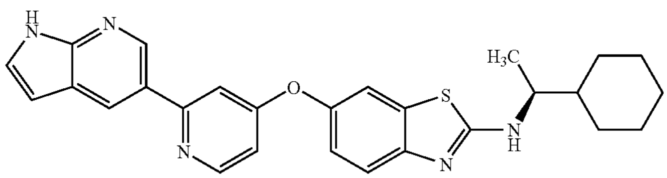 | (S)-6-(2-(1H-pyrrolo[2,3-b]pyridin-5-yl)pyridin-4-yloxy)-N-(1-cyclohexylethyl)benzo[d]thiazol-2-amine | 470.2, 2.46 |
| 279 | 185 | 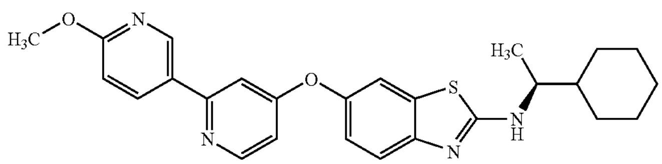 | (S)-N-(1-cyclohexylethyl)-6-(6'-methoxy-2,3'-bipyridin-4-yloxy)benzo[d]thiazol-2-amine | 461.2, 2.58 |
| 280 | 174 | 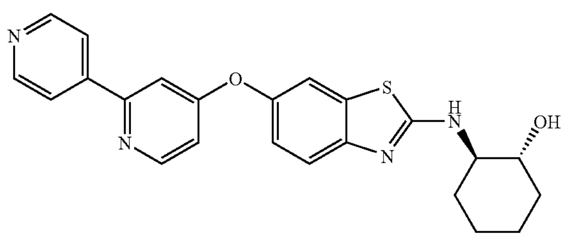 | (1R,2R)-2-(6-(2,4'-bipyridin-4-yloxy)benzo[d]thiazol-2-ylamino)cyclohexanol | 419.0, 1.68 |
| 281 | 174 | 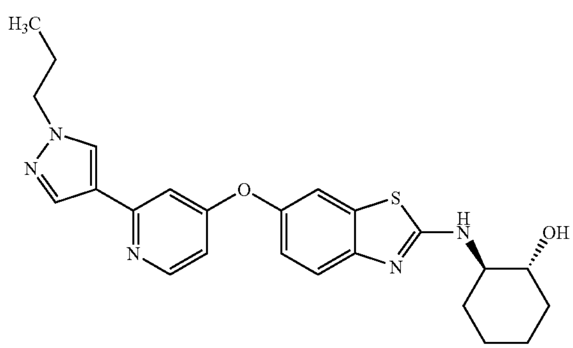 | (1R,2R)-2-(6-(2-(1-propyl-1H-pyrazol-4-yl)pyridin-4-yloxy)benzo[d]thiazol-2-ylamino)cyclohexanol | 450.0, 2.02 |
| 282 | 174 | 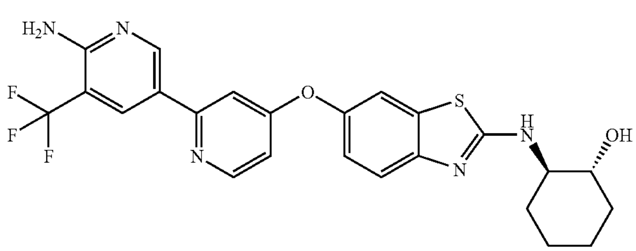 | (1R,2R)-2-(6-(6'-amino-5'-(trifluoromethyl)-2,3'-bipyridin-4-yloxy)benzo[d]thiazol-2-ylamino)cyclohexanol | 502.0, 2.02 |

TABLE 3-continued

| Cmpd | Ex Prep | Structure | Name | (M + H)+, Rt (min.) |
|---|---|---|---|---|
| 283 | 174 | 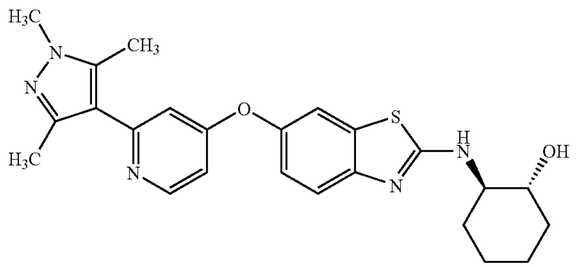 | (1R,2R)-2-(6-(2-(1,3,5-trimethyl-1H-pyrazol-4-yl)pyridin-4-yloxy)benzo[d]thiazol-2-ylamino)cyclohexanol | 450.0, 1.86 |
| 284 | 174 | 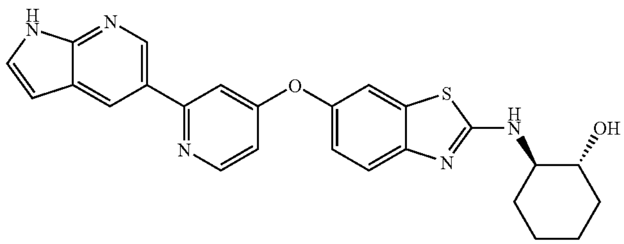 | (1R,2R)-2-(6-(2-(1H-pyrrolo[2,3-b]pyridin-5-yl)pyridin-4-yloxy)benzo[d]thiazol-2-ylamino)cyclohexanol | 458.0, 1.91 |
| 285 | 174 | 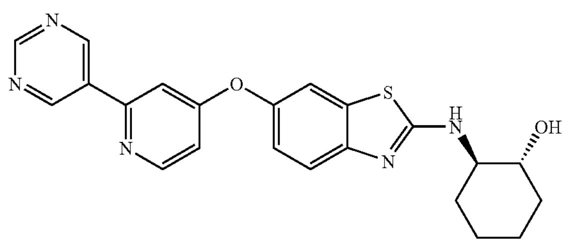 | (1R,2R)-2-(6-(2-(pyrimidin-5-yl)pyridin-4-yloxy)benzo[d]thiazol-2-ylamino)cyclohexanol | 420.1, 1.90 |
| 286 | 174 | 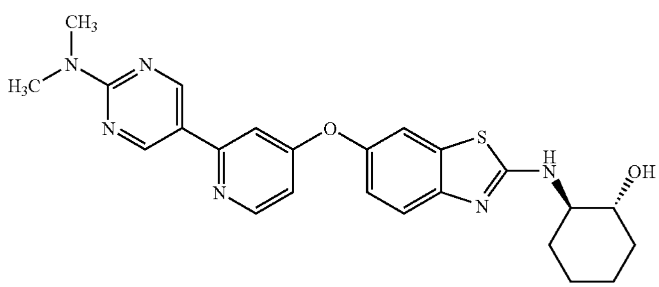 | (1R,2R)-2-(6-(2-(2-(dimethylamino)pyrimidin-5-yl)pyridin-4-yloxy)benzo[d]thiazol-2-ylamino)cyclohexanol | 463.1, 1.96 |
| 287 | 174 | 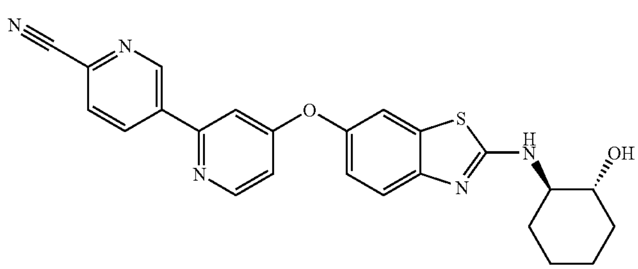 | 4-(2-((1R,2R)-2-hydroxycyclohexylamino)benzo[d]thiazol-6-yloxy)-2,3'-bipyridine-6'-carbonitrile | 444.0, 2.18 |
| 288 | 174 | 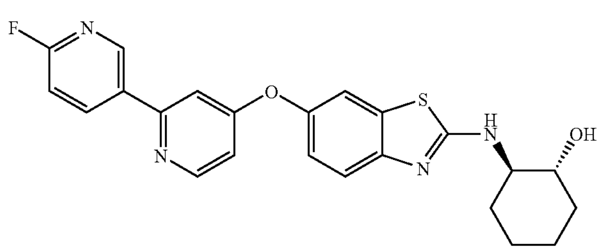 | (1R,2R)-2-(6-(2-(4-fluorophenyl)pyridin-4-yloxy)benzo[d]thiazol-2-ylamino)cyclohexanol | 436.0, 2.06 |

TABLE 3-continued

| Cmpd | Ex Prep | Name | (M + H)+, Rt (min.) |
|---|---|---|---|
| 289 | 195 | (S)-4-(2-(1-cyclohexylethylamino)benzo[d]thiazol-6-yloxy)-N',N'-dimethylpicolinohydrazide | 440.1, 2.33 |
| 290 | 162 | 4-(2-(2-cyclopropylethylamino)benzo[d]thiazol-6-yloxy)-N-methylpicolinamide | 369.0, 2.03 |
| 291 | 195 | 4-(2-((1R,2R)-2-hydroxycyclohexylamino)benzo[d]thiazol-6-yloxy)-N-methylnicotinamide | 399.1, 1.72 |
| 292 | 162 | 4-(2-((1S,2R)-2-aminocyclohexylamino)benzo[d]thiazol-6-yloxy)-N-methylpicolinamide | 398.1, 1.79 |
| 293 | 162 | 4-(2-(3-hydroxycyclohexylamino)benzo[d]thiazol-6-yloxy)-N-methylpicolinamide | 399.1, 1.76 |
| 294 | 162 | 4-(2-(3-aminocyclohexylamino)benzo[d]thiazol-6-yloxy)-N-methylpicolinamide | 398.1, 1.65 |
| 295 | 163 | 4-(2-((1S,2R)-2-acetamidocyclohexylamino)benzo[d]thiazol-6-yloxy)-N-methylpicolinamide | 440.2, 1.96 |
| 296 | 163 | 4-(2-(3-acetamidocyclohexylamino)benzo[d]thiazol-6-yloxy)-N-methylpicolinamide | 440.2, 1.87 |

TABLE 3-continued

| Cmpd | Ex Prep | Structure | Name | (M + H)+, Rt (min.) |
|---|---|---|---|---|
| 297 | 163 | 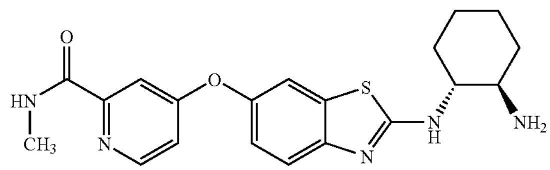 | 4-(2-((1R,2R)-2-aminocyclohexylamino)benzo[d]thiazol-6-yloxy)-N-methylpicolinamide | 398.2, 1.79 |
| 298 | 163 | 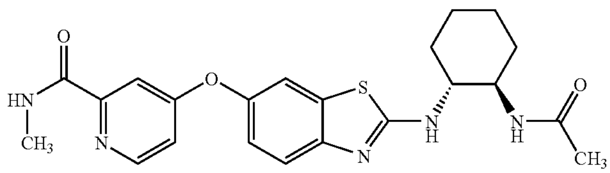 | 4-(2-((1R,2R)-2-acetamidocyclohexylamino)benzo[d]thiazol-6-yloxy)-N-methylpicolinamide | 440.2, 1.84 |
| 299 | 162 | 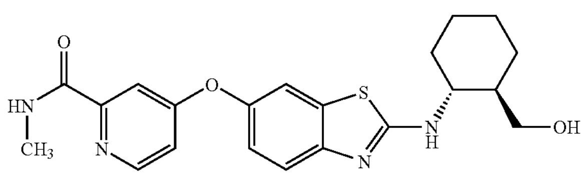 | 4-(2-((1R,2R)-2-(hydroxymethyl)cyclohexylamino)benzo[d]thiazol-6-yloxy)-N-methylpicolinamide | 413.1, 1.92 |
| 300 | 164 | 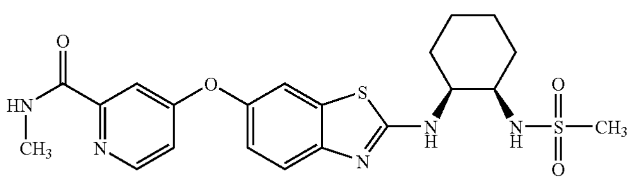 | N-methyl-4-(2-((1S,2R)-2-(methylsulfonamido)cyclohexylamino)benzo[d]thiazol-6-yloxy)picolinamide | 476.1, 2.05 |
| 301 | 167 | 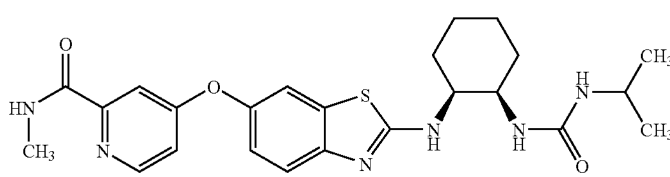 | 4-(2-((1S,2R)-2-(3-isopropylureido)cyclohexylamino)benzo[d]thiazol-6-yloxy)-N-methylpicolinamide | 483.2, 2.0 |
| 302 | 165 | 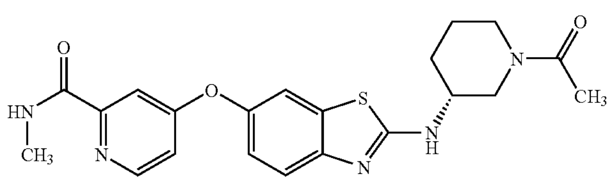 | (R)-4-(2-(1-acetylpiperidin-3-ylamino)benzo[d]thiazol-6-yloxy)-N-methylpicolinamide | 426.2, 1.91 |
| 303 | 165 | 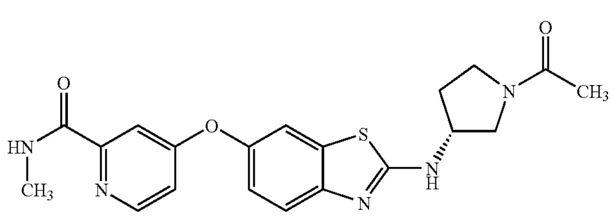 | (R)-4-(2-(1-acetylpyrrolidin-3-ylamino)benzo[d]thiazol-6-yloxy)-N-methylpicolinamide | 412.2, 1.84 |
| 304 | 165 | 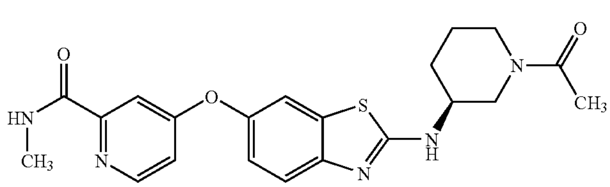 | (S)-4-(2-(1-acetylpiperidin-3-ylamino)benzo[d]thiazol-6-yloxy)-N-methylpicolinamide | 426.2, 1.91 |

TABLE 3-continued

| Cmpd | Ex Prep | Structure | Name | (M + H)+, Rt (min.) |
|---|---|---|---|---|
| 305 | 165 | 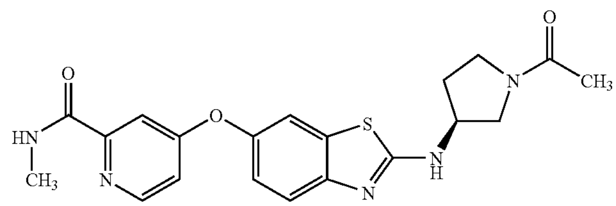 | (S)-4-(2-(1-acetylpyrrolidin-3-ylamino)benzo[d]thiazol-6-yloxy)-N-methylpicolinamide | 412.21, 1.84 |
| 306 | 165 | 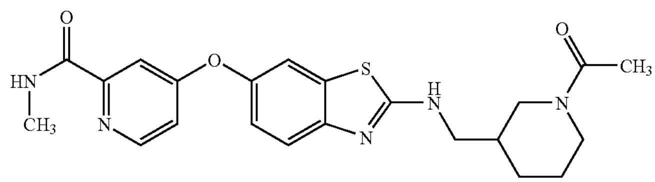 | 4-(2-((1-acetylpiperidin-3-yl)methylamino)benzo[d]thiazol-6-yloxy)-N-methylpicolinamide | 440.1, 2.04 |
| 307 | 165 | 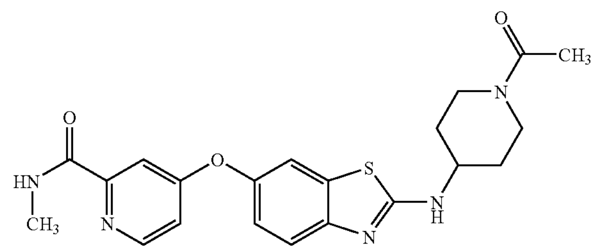 | 4-(2-(1-acetylpiperidin-4-ylamino)benzo[d]thiazol-6-yloxy)-N-methylpicolinamide | 426.2, 1.85 |
| 308 | 165 | 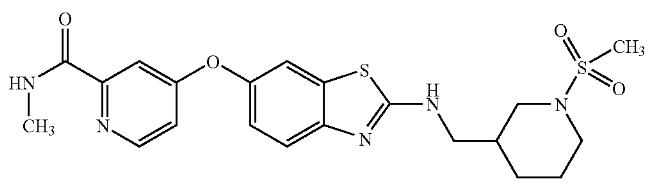 | N-methyl-3-(2-((1-(methylsulfonyl)piperidin-3-yl)methylamino)benzo[d]thiazol-6-yloxy)picolinamide | 476.1, 1.96 |
| 309 | 166 | 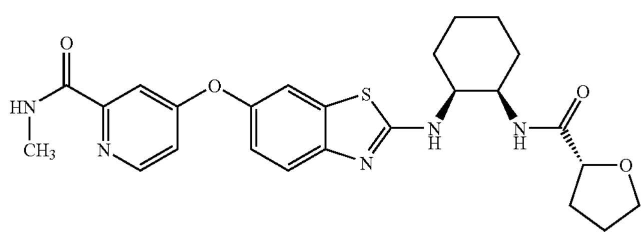 | N-methyl-4-(2-((1S,2R)-2-((R)-tetrahydrofuran-2-carboxamido)cyclohexylamino)benzo[d]thiazol-6-yloxy)picolinamide | 496.2, 2.13 |
| 310 | 166 | 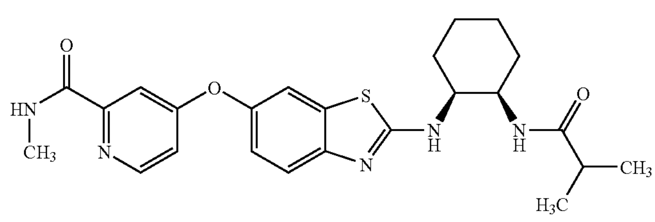 | 4-(2-((1S,2R)-2-isobutyramidocyclohexylamino)benzo[d]thiazol-6-yloxy)-N-methylpicolinamide | 468.2, 2.14 |
| 311 | 166 | 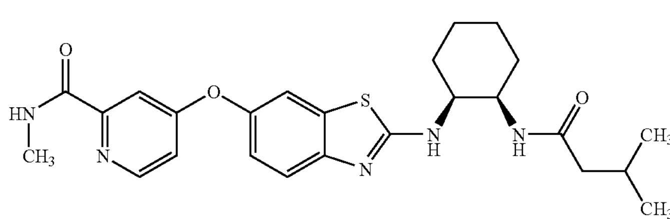 | N-methyl-4-(2-((1S,2R)-2-(3-methylbutanamido)cyclohexylamino)benzo[d]thiazol-6-yloxy)picolinamide | 482.2, 2.28 |

TABLE 3-continued

| Cmpd | Ex Prep | Structure | Name | (M + H)+, Rt (min.) |
|---|---|---|---|---|
| 312 | 166 | 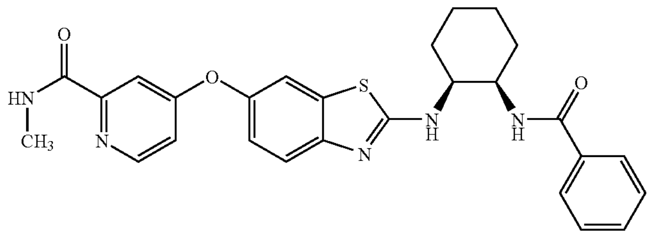 | 4-(2-((1S,2R)-2-benzamidocyclohexylamino)benzo[d]thiazol-6-yloxy)-N-methylpicolinamide | 502.2, 2.22 |
| 313 | 166 | 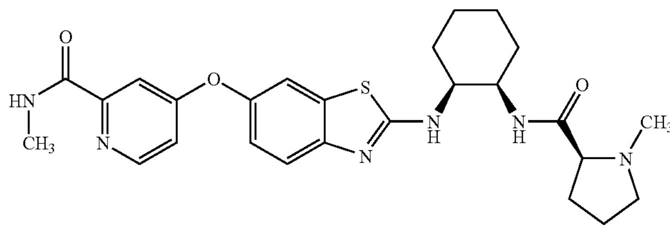 | N-methyl-4-(2-((1S,2R)-2-((S)-1-methylpyrrolidine-2-carboxamido)cyclohexylamino)benzo[d]thiazol-6-yloxy)picolinamide | 509.2, 1.82 |
| 314 | 162 | 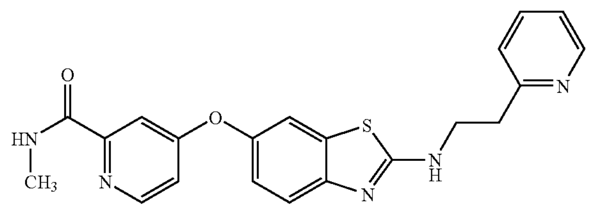 | N-methyl-4-(2-(2-(pyridin-2-yl)ethylamino)benzo[d]thiazol-6-yloxy)picolinamide | 406.1, 1.67 |
| 315 | 162 | 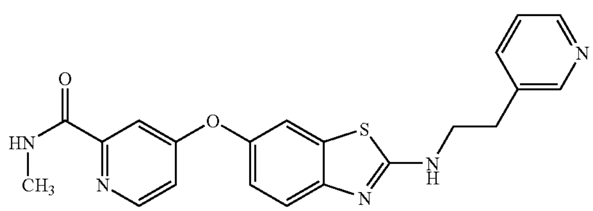 | N-methyl-4-(2-(2-(pyridin-3-yl)ethylamino)benzo[d]thiazol-6-yloxy)picolinamide | 406.1, 1.63 |
| 316 | 162 | 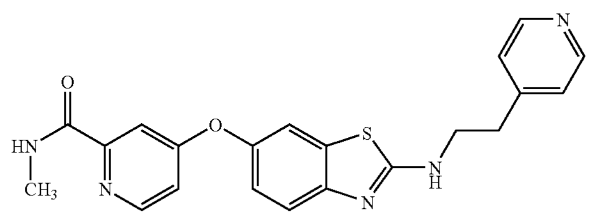 | N-methyl-4-(2-(2-(pyridin-4-yl)ethylamino)benzo[d]thiazol-6-yloxy)picolinamide | 406.1, 1.63 |
| 317 | 162 | 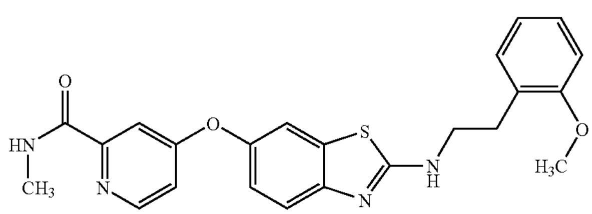 | 4-(2-(2-methoxyphenethylamino)benzo[d]thiazol-6-yloxy)-N-methylpicolinamide | 435.1, 2.29 |
| 318 | 162 | 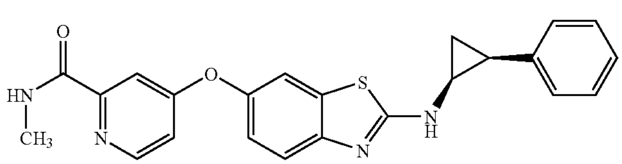 | N-methyl-4-(2-((1S,2S)-2-phenylcyclopropylamino)benzo[d]thiazol-6-yloxy)picolinamide | 417.1, 2.51 |

TABLE 3-continued

| Cmpd | Ex Prep | Structure | Name | (M + H)+, Rt (min.) |
|---|---|---|---|---|
| 319 | 162 | 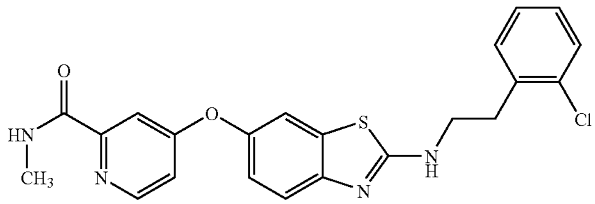 | 4-(2-(2-chlorophenethylamino)benzo[d]thiazol-6-yloxy)-N-methylpicolinamide | 439.1, 2.4 |
| 320 | 162 | 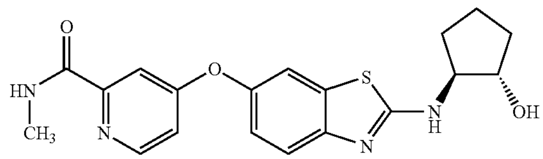 | 4-(2-((1S,2S)-2-hydroxycyclopentylamino)benzo[d]thiazol-6-yloxy)-N-methylpicolinamide | 385.1, 1.74 |
| 321 | 162 | 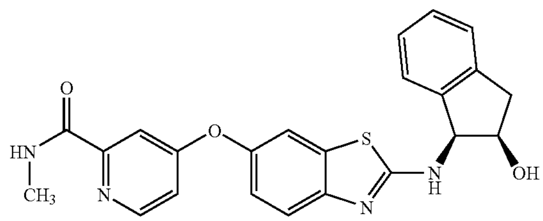 | 4-(2-((1S,2R)-2-hydroxy-2,3-dihydro-1H-inden-1-ylamino)benzo[d]thiazol-6-yloxy)-N-methylpicolinamide | 433.1, 2.08 |
| 322 | 162 | 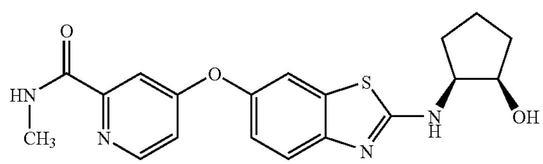 | 4-(2-((1S,2R)-2-hydroxycyclopentylamino)benzo[d]thiazol-6-yloxy)-N-methylpicolinamide | 385.1, 1.75 |
| 323 | 162 | 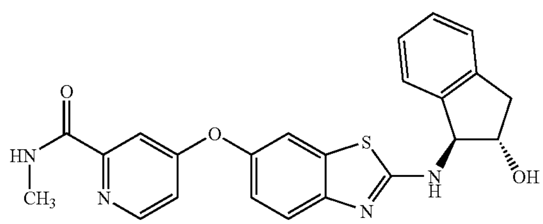 | 4-(2-((1R,2S)-2-hydroxy-2,3-dihydro-1H-inden-1-ylamino)benzo[d]thiazol-6-yloxy)-N-methylpicolinamide | 433.1, 2.08 |
| 324 | 162 | 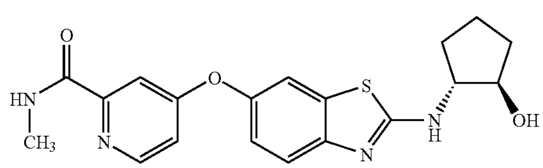 | 4-(2-((1R,2R)-2-hydroxycyclopentylamino)benzo[d]thiazol-6-yloxy)-N-methylpicolinamide | 385.1, 1.75 |
| 325 | 162 | 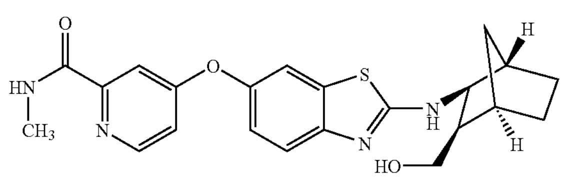 | 4-(2-((1S,3R,4R)-3-(hydroxymethyl)bicyclo[2.2.1]heptan-2-ylamino)benzo[d]thiazol-6-yloxy)-N-methylpicolinamide | 425.1, 1.92 |
| 326 | 164 | 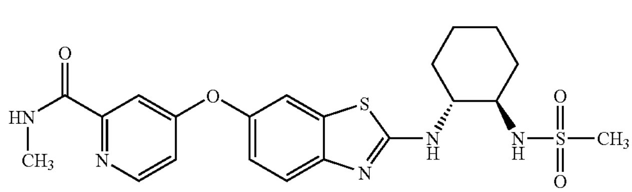 | N-methyl-4-(2-((1R,2R)-2-(methylsulfonamido)cyclohexylamino)benzo[d]thiazol-6-yloxy)picolinamide | 476.1, 1.87 |

TABLE 3-continued

| Cmpd | Ex Prep | Structure | Name | (M + H)+, Rt (min.) |
|---|---|---|---|---|
| 327 | 166 | 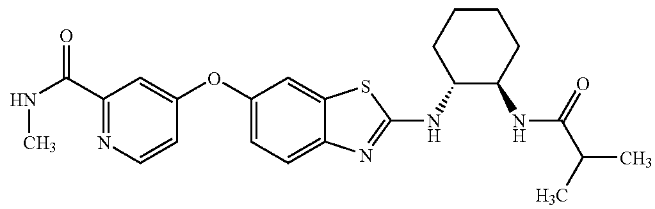 | 4-(2-((1R,2R)-2-isobutyramidocyclohexylamino)benzo[d]thiazol-6-ylxoy)-N-methylpicolinamide | 468.1, 2.02 |
| 328 | 162 | 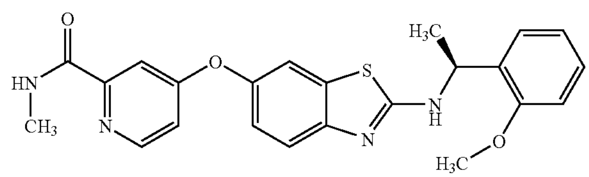 | (S)-4-(2-(1-(2-methoxyphenyl)ethylamino)benzo[d]thiazol-6-yloxy)-N-methylpicolinamide | 435.1, 2.32 |
| 329 | 162 | 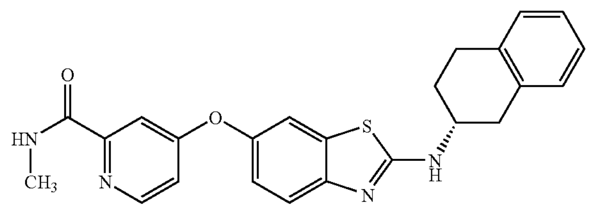 | (R)-N-methyl-4-(2-(1,2,3,4-tetrahydronaphthalen-2-ylamino)benzo[d]thiazol-6-yloxy)picolinamide | 431.1, 2.55 |
| 330 | 164 | 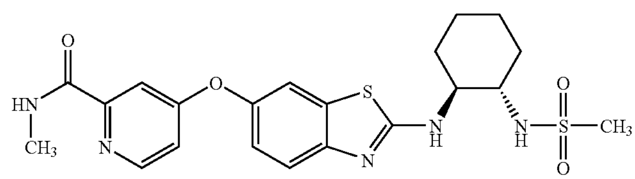 | N-methyl-4-(2-((1S,2S)-2-(methylsulfonamido)cyclohexylamino)benzo[d]thiazol-6-yloxy)picolinamide | 476.1, 1.87 |
| 331 | 164 | 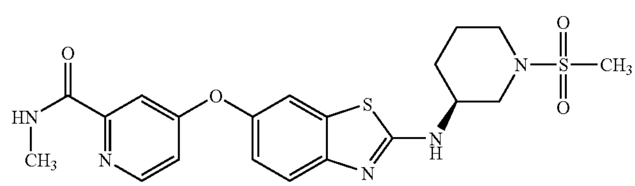 | (S)-N-methyl-4-(2-(1-(methylsulfonyl)piperidin-3-ylamino)benzo[d]thiazol-6-yloxy)picolinamide | 462.1, 1.90 |
| 332 | 162 | 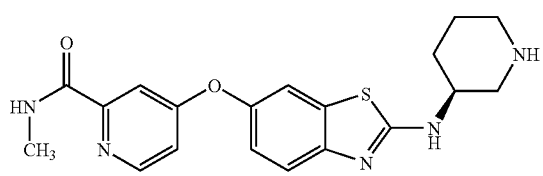 | (S)-N-methyl-4-(2-(piperidin-3-ylamino)benzo[d]thiazol-6-yloxy)picolinamide | 384.1, 1.65 |
| 333 | 167 | 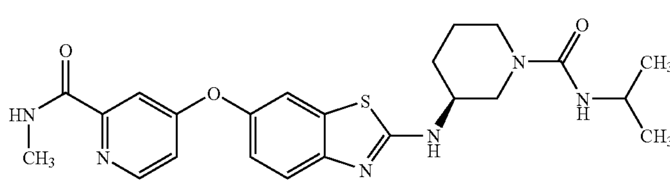 | (S)-4-(2-(1-(isopropylcarbamoyl)piperidin-3-ylamino)benzo[d]thiazol-6-yloxy)-N-methylpicolinamide | 469.2, 1.94 |
| 334 | 166 | 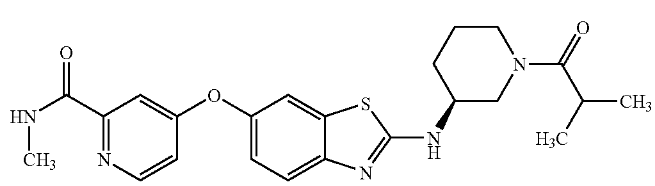 | (S)-4-(2-(1-isobutyrylpiperidin-3-ylamino)benzo[d]thiazol-6-yloxy)-N-methylpicolinamide | 454.2, 1.99 |

TABLE 3-continued

| Cmpd | Ex Prep | Structure | Name | (M + H)+, Rt (min.) |
|---|---|---|---|---|
| 335 | 166 | 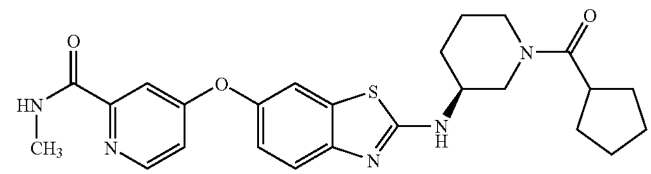 | (S)-4-(2-(1-(cyclopentanecarbonyl)piperidin-3-ylamino)benzo[d]thiazol-6-yloxy)-N-methylpicolinamide | 480.2, 2.2 |
| 336 | 166 | 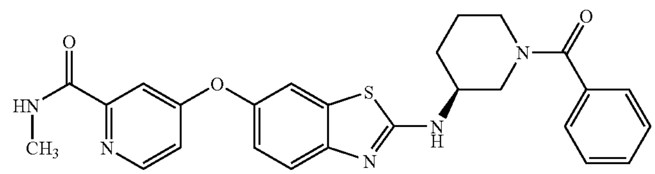 | (S)-4-(2-(1-benzoylpiperidin-3-ylamino)benzo[d]thiazol-6-yloxy)-N-methylpicolinamide | 488.2, 2.09 |
| 337 | 166 | 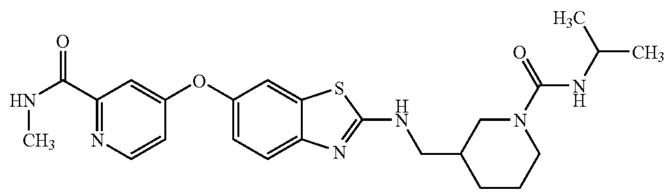 | 4-(2-((1-(isopropylcarbamoyl)piperidin-3-yl)methylamino)benzo[d]thiazol-6-yloxy)-N-methylpicolinamide | 483.2, 2.09 |
| 338 | 170 | 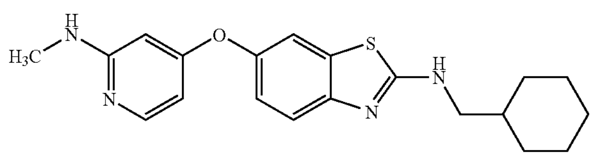 | N-(cyclohexylmethyl)-6-(2-(methylamino)pyridin-4-yloxy)benzo[d]thiazol-2-amine | 369.1, 2.09 |
| 339 | 170 | 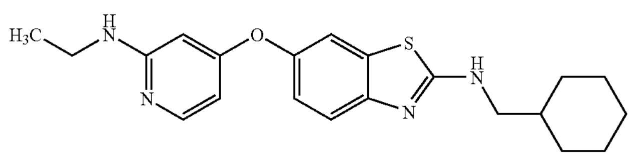 | N-(cyclohexylmethyl)-6-(2-(ethylamino)pyridin-4-yloxy)benzo[d]thiazol-2-amine | 383.1, 2.33 |
| 340 | 174 | 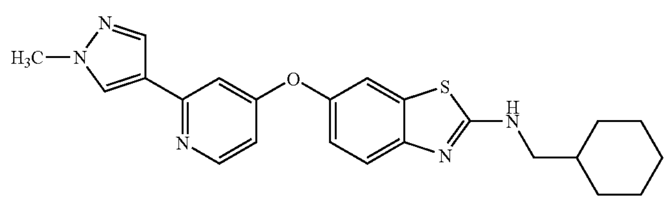 | N-(cyclohexylmethyl)-6-(2-(1-methyl-1H-pyrazol-4-yl)pyridin-4-yloxy)benzo[d]thiazol-2-amine | 420.2, 2.13 |
| 341 | 174 | 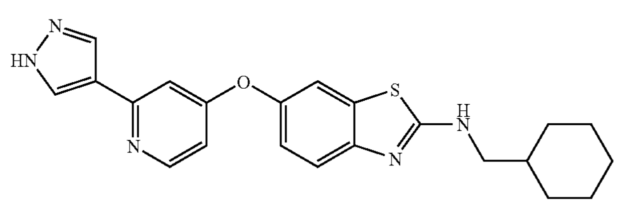 | 6-(2-(1H-pyrazol-4-yl)pyridin-4-yloxy)-N-(cyclohexylmethyl)benzo[d]thiazol-2-amine | 406.1, 2.12 |
| 342 | 175 | 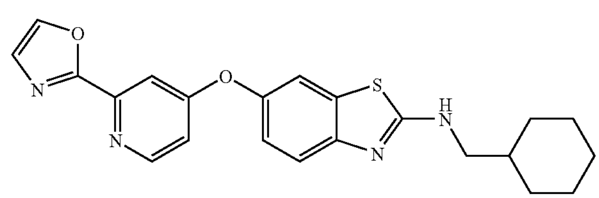 | N-(cyclohexylmethyl)-6-(2-(oxazol-2-yl)pyridin-4-yloxy)benzo[d]thiazol-2-amine | 407.1, 2.36 |

TABLE 3-continued

| Cmpd | Ex Prep | Structure | Name | (M + H)+, Rt (min.) |
|---|---|---|---|---|
| 343 | 170 | 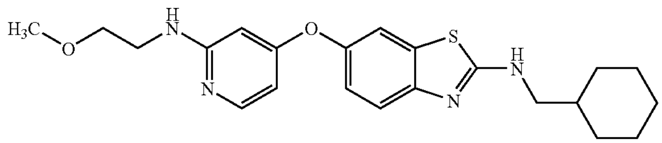 | N-(cyclohexylmethyl)-6-(2-(2-methoxyethylamino)pyridin-4-yloxy)benzo[d]thiazol-2-amine | 413.2, 2.16 |
| 344 | 174 | 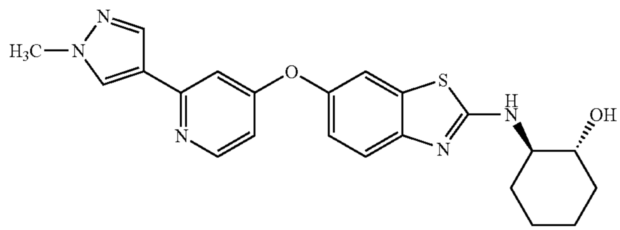 | (1R,2R)-2-(6-(2-(1-methyl-1H-pyrazol-4-yl)pyridin-4-yloxy)benzo[d]thiazol-2-ylamino)cyclohexanol | 422.2, 1.68 |
| 345 | 174 | 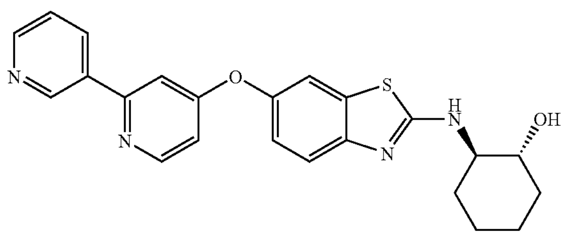 | (1R,2R)-2-(6-(2,3'-bipyridin-4-yloxy)benzo[d]thiazol-2-ylamino)cyclohexanol | 419.1, 1.69 |
| 346 | 174 | 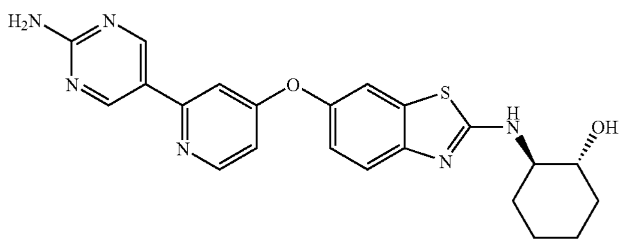 | (1R,2R)-2-(6-(2-(2-aminopyrimidin-5-yl)pyridin-4-yloxy)benzo[d]thiazol-2-ylamino)cyclohexanol | 435.2, 1.61 |
| 347 | 168 | 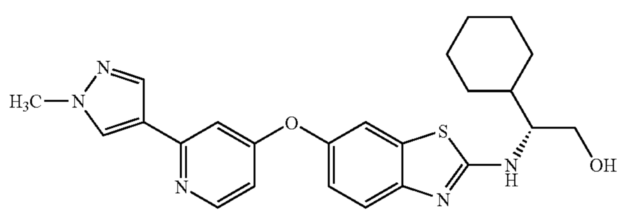 | (R)-2-cyclohexyl-2-(6-(2-(1-methyl-1H-pyrazol-4-yl)pyridin-4-yloxy)benzo[d]thiazol-2-ylamino)ethanol | 450.2, 1.96 |
| 348 | 168 | 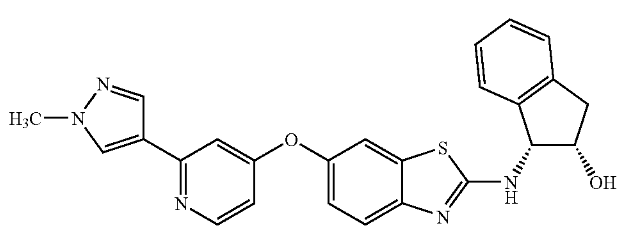 | (1R,2S)-1-(6-(2-(1-methyl-1H-pyrazol-4-yl)pyridin-4-yloxy)benzo[d]thiazol-2-ylamino)-2,3-dihydro-1H-inden-2-ol | 456.1, 1.94 |
| 349 | 168 | 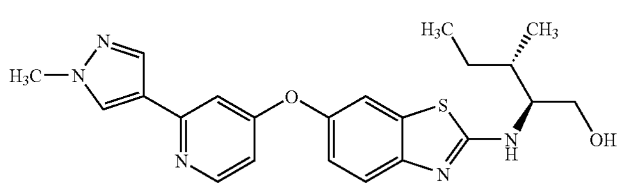 | (2S,3S)-3-methyl-2-(6-(2-(1-methyl-1H-pyrazol-4-yl)pyridin-4-yloxy)benzo[d]thiazol-2-ylamino)pentan-1-ol | 424.2, 1.83 |

TABLE 3-continued

| Cmpd | Ex Prep | Structure | Name | (M + H)+, Rt (min.) |
|---|---|---|---|---|
| 350 | 168 | 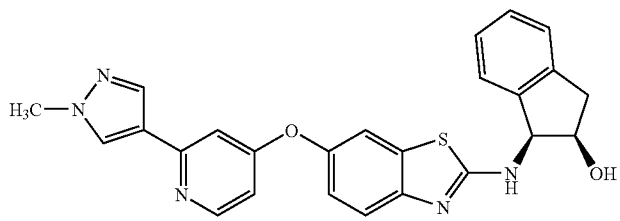 | (1S,2R)-1-(6-(2-(1-methyl-1H-pyrazol-4-yl)pyridin-4-yloxy)benzo[d]thiazol-2-ylamino)-2,3-dihydro-1H-inden-2-ol | 456.1, 1.95 |
| 351 | 168 | 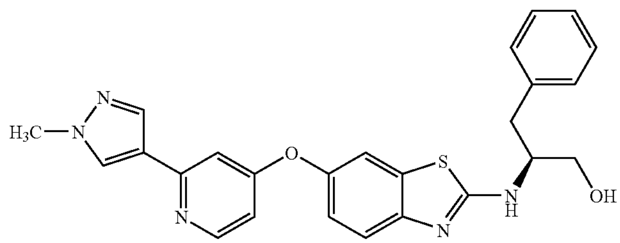 | (S)-2-(6-(2-(1-methyl-1H-pyrazol-4-yl)pyridin-4-yloxy)benzo[d]thiazol-2-ylamino)-3-phenylpropan-1-ol | 458.1, 1.89 |
| 352 | 168 | 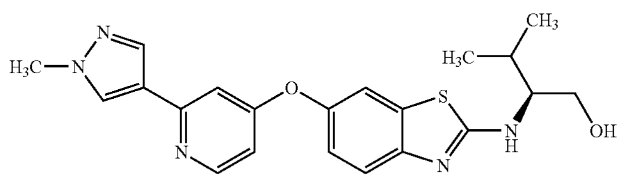 | (S)-3-methyl-2-(6-(2-(1-methyl-1H-pyrazol-4-yl)pyridin-4-yloxy)benzo[d]thiazol-2-ylamino)butan-1-ol | 410.1, 1.70 |
| 353 | 168 | 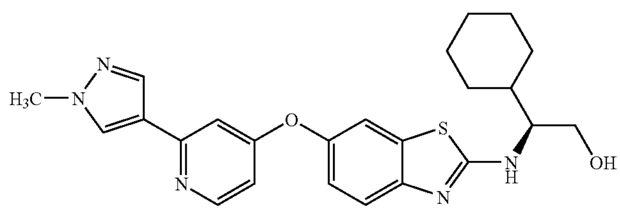 | (S)-2-cyclohexyl-2-(6-(2-(1-methyl-1H-pyrazol-4-yl)pyridin-4-yloxy)benzo[d]thiazol-2-ylamino)ethanol | 450.1, 1.97 |
| 354 | 168 | 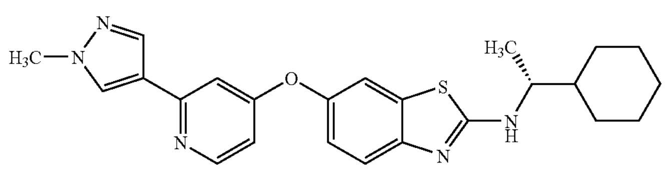 | (R)-N-(1-cyclohexylethyl)-6-(2-(1-methyl-1H-pyrazol-4-yl)pyridin-4-yloxy)benzo[d]thiazol-2-amine | 434.1, 2.21 |
| 355 | 168 | 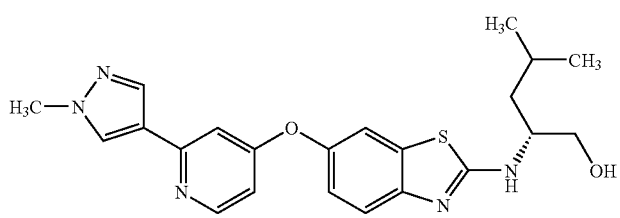 | (R)-4-methyl-2-(6-(2-(1-methyl-1H-pyrazol-4-yl)pyridin-4-yloxy)benzo[d]thiazol-2-ylamino)pentan-1-ol | 423.1, 1.85 |
| 356 | 168 | 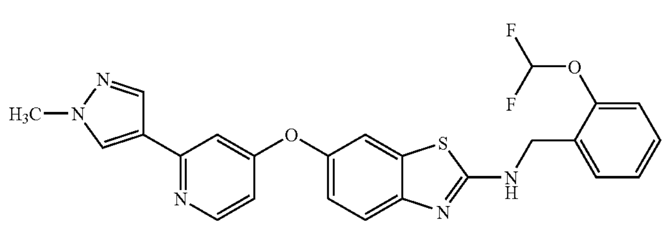 | N-(2-(difluoromethoxy)benzyl)-6-(2-(1-methyl-1H-pyrazol-4-yl)pyridin-4-yloxy)benzo[d]thiazol-2-amine | 480.1, 2.20 |

TABLE 3-continued

| Cmpd | Ex Prep | Structure | Name | (M + H)+, Rt (min.) |
|---|---|---|---|---|
| 357 | 168 | 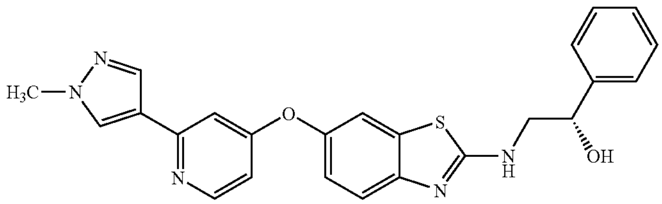 | (S)-2-(6-(2-(1-methyl-1H-pyrazol-4-yl)pyridin-4-yloxy)benzo[d]thiazol-2-ylamino)-1-phenylethanol | 444.1, 1.85 |
| 358 | 168 | 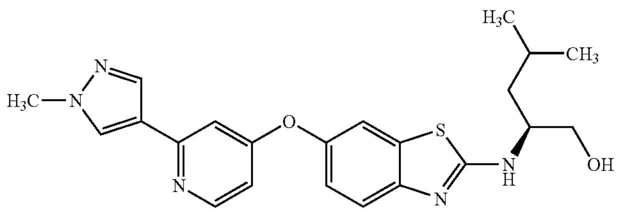 | (S)-4-methyl-2-(6-(2-(1-methyl-1H-pyrazol-4-yl)pyridin-4-yloxy)benzo[d]thiazol-2-ylamino)pentan-1-ol | 424.1, 1.85 |
| 359 | 174 | 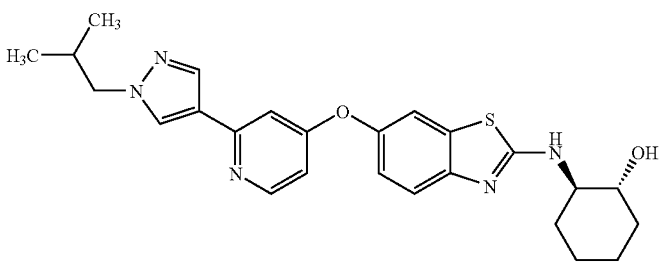 | (1R,2R)-2-(6-(2-(1-isobutyl-1H-pyrazol-4-yl)pyridin-4-yloxy)benzo[d]thiazol-2-ylamino)cyclohexanol | 464.4, 1.95 |
| 360 | 174 | 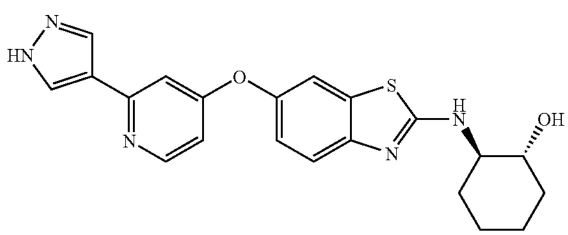 | (1R,2R)-2-(6-(1H-pyrazol-4-yl)pyridin-4-yloxy)benzo[d]thiazol-2-ylamino)cyclohexanol | 408.1, 1.63 |
| 361 | 168 | 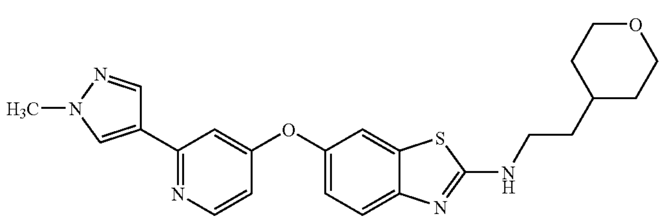 | 6-(2-(1-methyl-1H-pyrazol-4-yl)pyridin-4-yloxy)-N-(2-(tetrahydro-2H-pyran-4-yl)ethyl)benzo[d]thiazol-2-amine | 436.2, 1.74 |
| 362 | 168 | 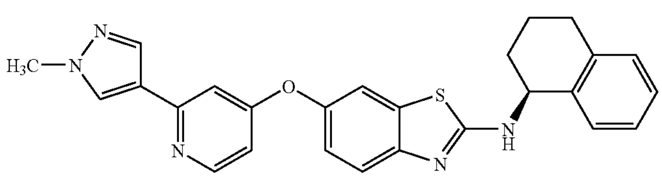 | (S)-6-(2-(1-methyl-1H-pyrazol-4-yl)pyridin-4-yloxy)-N-(1,2,3,4-tetrahydronaphthalen-1-yl)benzo[d]thiazol-2-amine | 454.2, 2.25 |
| 363 | 168 | 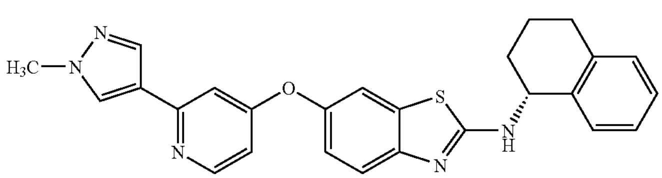 | (R)-6-(2-(1-methyl-1H-pyrazol-4-yl)pyridin-4-yloxy)-N-(1,2,3,4-tetrahydronaphthalen-1-yl)benzo[d]thiazol-2-amine | 454.2, 2.24 |

TABLE 3-continued

| Cmpd | Ex Prep | Structure | Name | (M + H)+, Rt (min.) |
|---|---|---|---|---|
| 364 | 168 | 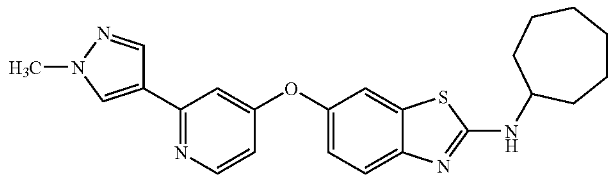 | N-cycloheptyl-6-(2-(1-methyl-1H-pyrazol-4-yl)pyridin-4-yloxy)benzo[d]thiazol-2-amine | 420.2, 2.08 |
| 365 | 168 | 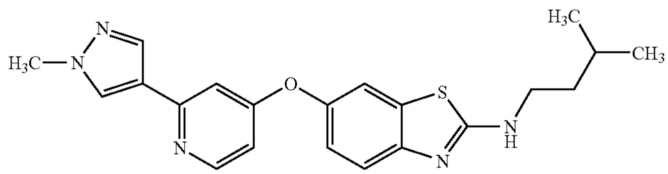 | N-isopentyl-6-(2-(1-methyl-1H-pyrazol-4-yl)pyridin-4-yloxy)benzo[d]thiazol-2-amine | 394.2, 1.98 |
| 366 | 168 | 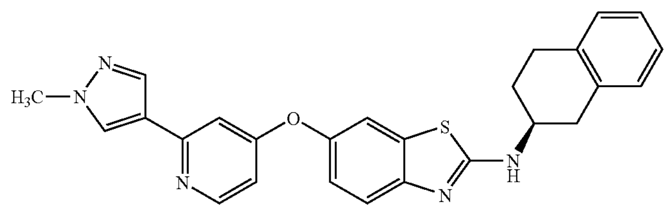 | (S)-6-(2-(1-methyl-1H-pyrazol-4-yl)pyridin-4-yloxy)-N-(1,2,3,4-tetrahydronaphthalen-2-yl)benzo[d]thiazol-2-amine | 454.2, 2.22 |
| 367 | 169 | 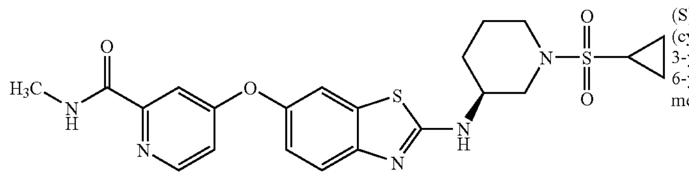 | (S)-4-(2-(1-(cyclopropylsulfonyl)piperidin-3-ylamino)benzo[d]thiazol-6-yloxy)-N-methylpicolinamide | 488.0, 2.17 |
| 368 | 170 | 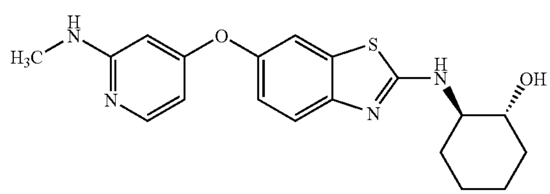 | (1R,2R)-2-(6-(2-(methylamino)pyridin-4-yloxy)benzo[d]thiazol-2-ylamino)cyclohexanol | 371.1, 1.79 |
| 369 | 170 | 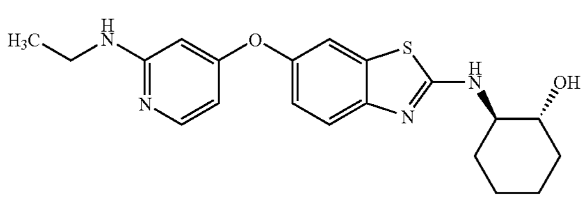 | (1R,2R)-2-(6-(2-(ethylamino)pyridin-4-yloxy)benzo[d]thiazol-2-ylamino)cyclohexanol | 385.1, 1.74 |
| 370 | 162 | 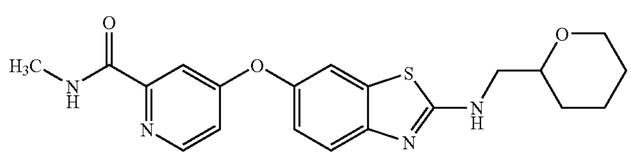 | N-methyl-4-(2-((tetrahydro-2H-pyran-2-yl)methylamino)benzo[d]thiazol-6-yloxy)picolinamide | 399.1, 2.16 |
| 371 | 175 | 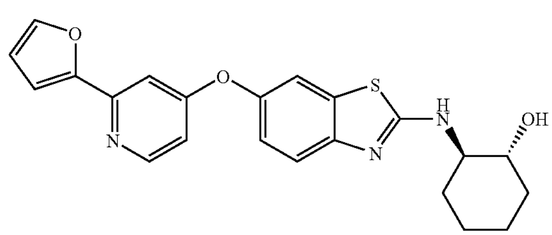 | (1R,2R)-2-(6-(2-furan-2-yl)pyridin-4-yloxy)benzo[d]thiazol-2-ylamino)cyclohexanol | 408.1, 1.94 |

TABLE 3-continued

| Cmpd | Ex Prep | Structure | Name | (M + H)+, Rt (min.) |
|---|---|---|---|---|
| 372 | 175 | 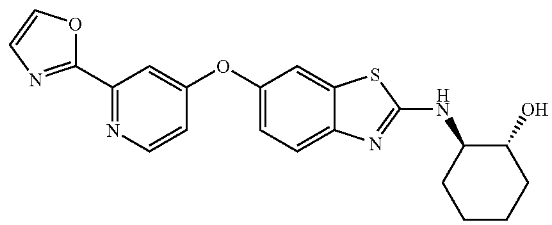 | (1R,2R)-2-(6-(2-oxazol-2-yl)pyridin-4-yloxy)benzo[d]thiazol-2-ylamino)cyclohexanol | 409.1, 1.98 |
| 373 | 169 | 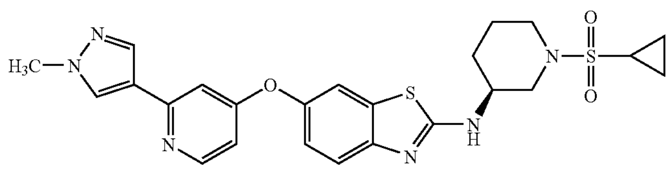 | (S)-N-(1-(cyclopropylsulfonyl)piperidin-3-yl)-6-(2-(1-methyl-1H-pyrazol-4-yl)pyridin-4-yloxy)benzo[d]thiazol-2-amine | 511.2, 2.0 |
| 374 | 193 | 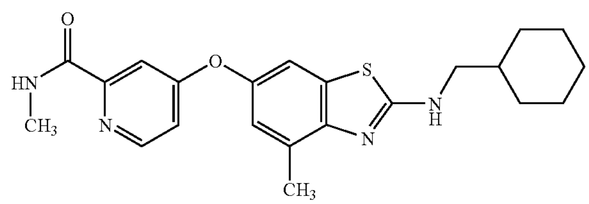 | 4-(2-(cyclohexylmethylamino)-4-methylbenzo[d]thiazol-6-yloxy)-N-methylpicolinamide | 411; 2.81 |
| 375 | 194 | 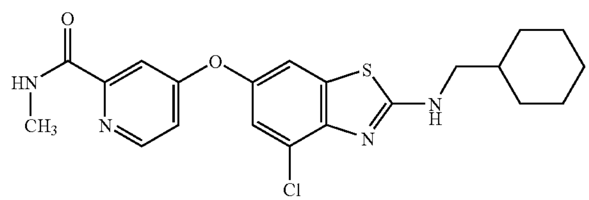 | 4-(4-chloro-2-(cyclohexylmethylamino)benzo[d]thiazol-6-yloxy)-N-methylpicolinamide | 431; 3.31 |
| 376 | 195 | 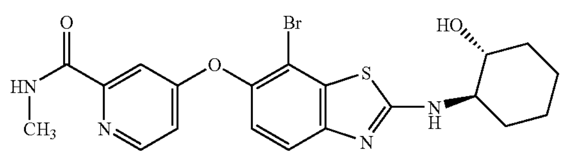 | 4-(7-bromo-2-((1R,2R)-2-hydroxycyclohexylamino)benzo[d]thiazol-6-yloxy)-N-methylpicolinamide | 479, 2.37 |
| 377 | 196 | 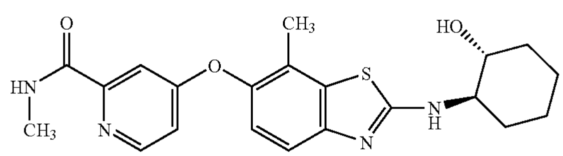 | 4-(2-((1R,2R)-2-hydroxycyclohexylamino)-7-methylbenzo[d]thiazol-6-yloxy)-N-methylpicolinamide | 413, 2.09 |
| 378 | 197 | 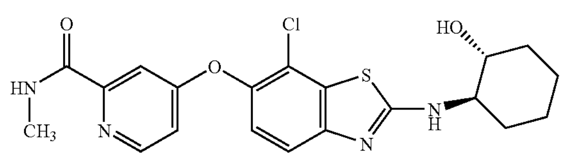 | 4-(7-chloro-2-((1R,2R)-2-hydroxycyclohexylamino)benzo[d]thiazol-6-yloxy)-N-methylpicolinamide | 433, 2.33 |
| 379 | 186 | 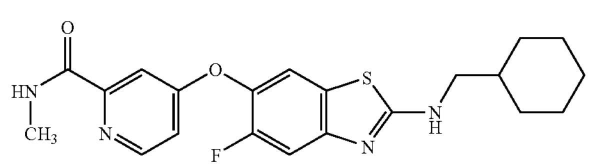 | 4-(2-(cyclohexylmethylamino)-5-fluorobenzo[d]thiazol-6-yloxy)-N-methylpicolinamide | 415, 2.81 |

TABLE 3-continued

| Cmpd | Ex Prep | Structure | Name | (M + H)+, Rt (min.) |
|---|---|---|---|---|
| 380 | 203 | 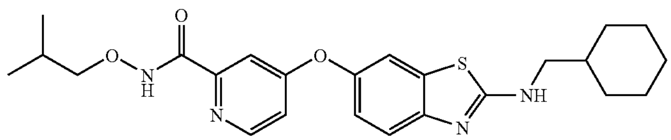 | 4-(2-(cyclohexylmethylamino)-benzo[d]thiazol-6-yloxy)-N-isobutoxypicolinamide | 455.1, 2.90 |
| 381 | 204 | 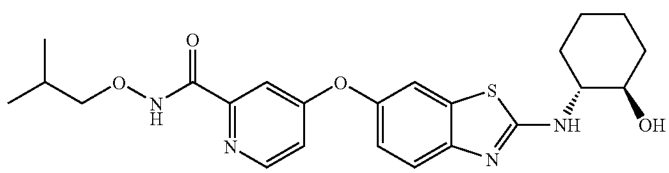 | 4-(2-((1R,2R)-2-hydroxycyclohexylamino)benzo[d]thiazol-6-yloxy)-N-isobutoxypicolinamide | 457.0, 2.35 |

TABLE 4

| Cmpd | Ex Prep | Structure | Name | (M + H)+, Rt (min.) |
|---|---|---|---|---|
| 1 | 168 | 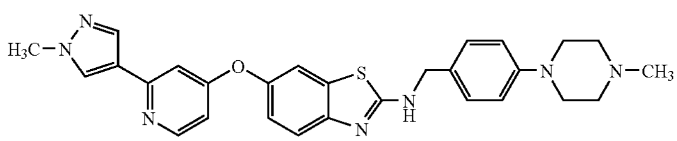 | 6-(2-(1-methyl-1H-pyrazol-4-yl)pyridin-4-yloxy)-N-(4-(4-methylpiperazin-1-yl)benzyl)benzo[d]thiazol-2-amine | 512.2, 1.79 |
| 2 | 199 | 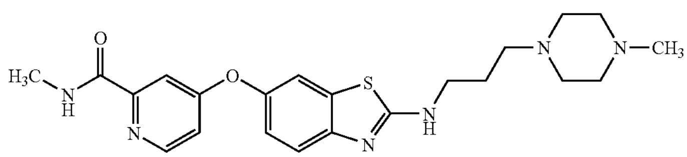 | N-methyl-4-(2-(3-(4-methylpiperazin-1-yl)propylamino)benzo[d]thiazol-6-yloxy)picolinamide | 441.0; 1.66 |
| 3 | 207 | Chiral | (1R,2R)-2-(6-(2'-morpholino-2,4'-bipyridin-4-yloxy)benzo[d]thiazol-2-ylamino)cyclohexanol | 504.1, 1.99 |
| 4 | 207 | Chiral | (1R,2R)-2-(6-(2'-(4-methylpiperazin-1-yl)-2,4'-bipyridin-4-yloxy)benzo[d]thiazol-2-ylamino)cyclohexanol | 517.2, 1.86 |
| 5 | 207 | Chiral | 1-(4-(2-((1R,2R)-2-hydroxycyclohexylamino)benzo[d]thiazol-6-yloxy)-2,4'-bipyridin-2'-yl)piperidin-4-ol | 518.2, 1.93 |

TABLE 4-continued

| Cmpd | Ex Prep | Structure | Name | (M + H)+, Rt (min.) |
|---|---|---|---|---|
| 6 | 207 | Chiral | (1R,2R)-2-(6-(2'-((R)-3-(dimethylamino)pyrrolidin-1-yl)-2,4'-bipyridin-4-yloxy)benzo[d]thiazol-2-ylamino)cyclohexanol | 531.2, 1.85 |
| 7 | 207 | Chiral | 4-(4-(2-((1R,2R)-2-hydroxycyclohexylamino)benzo[d]thiazol-6-yloxy)-2,4'-bipyridin-2'-yl)piperazin-2-one | 517.2, 1.89 |
| 8 | 207 | Chiral | (1R,2R)-2-(6-(2'-((S)-3-(dimethylamino)pyrrolidin-1-yl)-2,4'-bypyridin-4-yloxy)benzo[d]thiazol-2-ylamino)cyclohexanol | 531.2, 1.85 |
| 9 | 207 | Chiral | (1R,2R)-2-(6-(2'-(4-(dimethylamino)piperidin-1-yl)-2,4'-bipyridin-4-yloxy)benzo[d]thiazol-2-ylamino)cyclohexanol | 545.2, 1.87 |
| 10 | 207 | Chiral | (1R,2R)-2-(6-(2'-(pyrrolidin-1-yl)-2,4'-bipyridin-4-yloxy)benzo[d]thiazol-2-ylamino)cyclohexanol | 488.2, 2.05 |
| 11 | 207 | Chiral | (1R,2R)-2-(6-(2'-(4-fluoropiperidin-1-yl)-2,4'-bipyridin-4-yloxy)benzo[d]thiazol-2-ylamino)cyclohexanol | 520.2, 2.10 |

TABLE 4-continued

| Cmpd | Ex Prep | Structure | Name | (M + H)+, Rt (min.) |
|---|---|---|---|---|
| 12 | 207 | 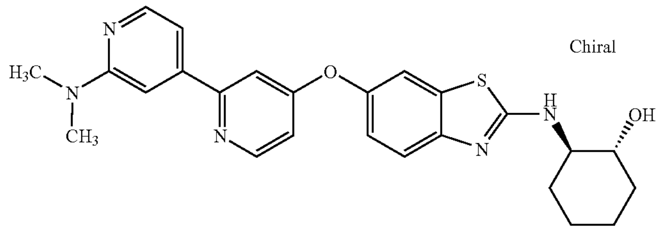 | (1R,2R)-2-(6-(2'-(dimethylamino)-2,4'-bipyridin-4-yloxy)benzo[d]thiazol-2-ylamino)cyclohexanol | 462.1, 1.95 |
| 13 | 207 | 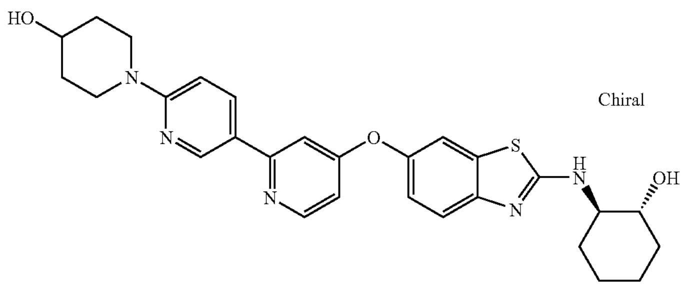 | 1-(4-(2-((1R,2R)-2-hydroxycyclohexylamino)benzo[d]thiazol-6-yloxy)-2,3'-bipyridin-6'-yl)piperidin-4-ol | 518.2, 1.88 |
| 14 | 207 | 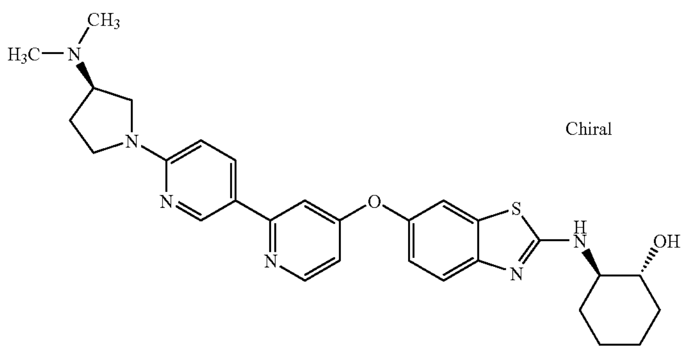 | (1R,2R)-2-(6-(6'-((R)-3-(dimethylamino)pyrrolidin-1-yl)-2,3'-bipyridin-4-yloxy)benzo[d]thiazol-2-ylamino)cyclohexanol | 531.2, 1.80 |
| 15 | 207 | 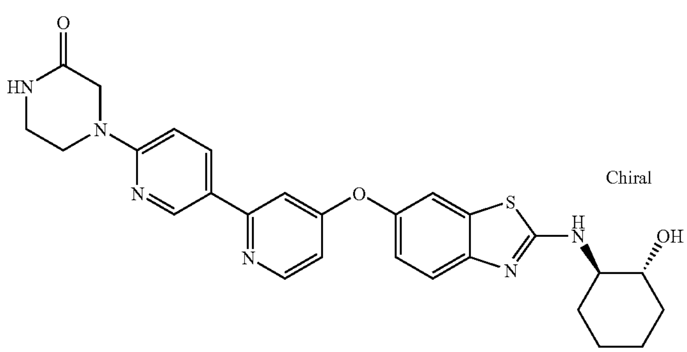 | 4-(4-(2-((1R,2R)-2-hydroxycyclohexylamino)benzo[d]thiazol-6-yloxy)-2,3'-bipyridin-6'-yl)piperazin-2-one | 517.2, 1.86 |
| 16 | 207 | 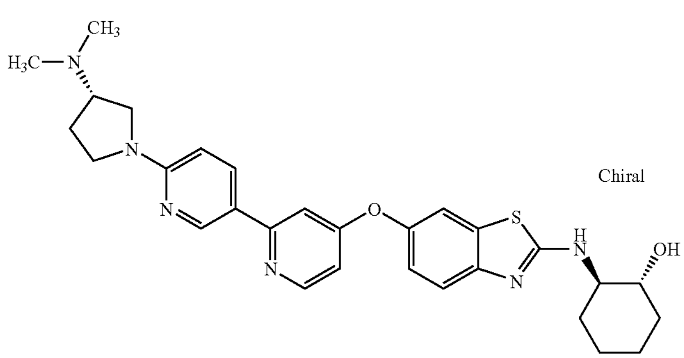 | (1R,2R)-2-(6-(6'-((S)-3-(dimethylamino)pyrrolidin-1-yl)-2,3'-bipyridin-4-yloxy)benzo[d]thiazol-2-ylamino)cyclohexanol | 531.2, 1.80 |

TABLE 4-continued

| Cmpd | Ex Prep | Structure | Name | (M + H)+, Rt (min.) |
|---|---|---|---|---|
| 17 | 207 | Chiral | (1R,2R)-2-(6-(6'-(4-(dimethylamino)piperidin-1-yl)-2,3'-bipyridin-4-yloxy)benzo[d]thiazol-2-ylamino)cyclohexanol | 545.2, 1.83 |
| 18 | 207 | Chiral | (1R,2R)-2-(6-(6'-(pyrrolidin-1-yl)-2,3'-bipyridin-4-yloxy)benzo[d]thiazol-2-ylamino)cyclohexanol | 488.1, 1.95 |
| 19 | 207 | Chiral | (1R,2R)-2-(6-(6'-(4-fluoropiperidin-1-yl)-2,3'-bipyridin-4-yloxy)benzo[d]thiazol-2-ylamino)cyclohexanol | 520.2, 2.10 |
| 20 | 207 | Chiral | (1R,2R)-2-(6-(6'-(dimethylamino)-2,3'-bipyridin-4-yloxy)benzo[d]thiazol-2-ylamino)cyclohexanol | 462.1, 1.88 |
| 21 | 207 | Chiral | (1R,2R)-2-(6-(6'-(piperidin-1-yl)-2,3'-bipyridin-4-yloxy)benzo[d]thiazol-2-ylamino)cyclohexanol | 502.2, 2.08 |

TABLE 4-continued

| Cmpd | Ex Prep | Structure | Name | (M + H)+, Rt (min.) |
|---|---|---|---|---|
| 22 | 207 | 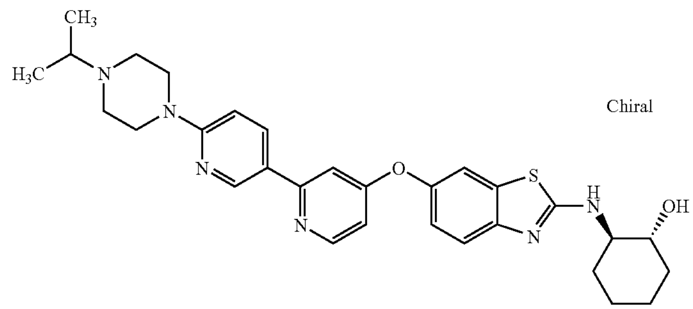 | (1R,2R)-2-(6-(6'-(4-isopropylpiperzin-1-yl)-2,3'-bipyridin-4-yloxy)benzo[d]thiazol-2-ylamino)cyclohexanol | 545.2, 1.87 |
| 23 | 210 | 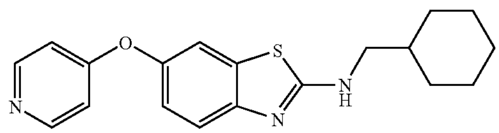 | N-(cyclohexylmethyl)-6-(pyridin-4-yloxy)benzo[d]thiazol-2-amine | 340.1, 2.11 |
| 24 | 169 | 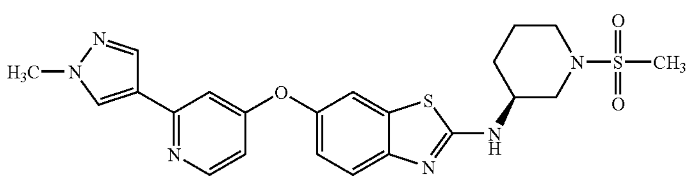 | (S)-6-(2-(1-methyl-1H-pyrazol-4-yl)pyridin-4-yloxy)-N-(1-(methylsulfonyl)piperidin-3-yl)benzo[d]thiazol-2-amine | 485.0, 1.91 |
| 25 | 169 | 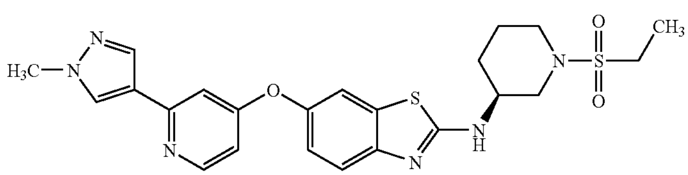 | (S)-N-(1-(ethylsulfonyl)piperidin-3-yl)-6-(2-(1-methyl-1H-pyrazol-4-yl)pyridin-4-yloxy)benzo[d]thiazol-2-amine | 499.0, 1.98 |
| 26 | 179 | 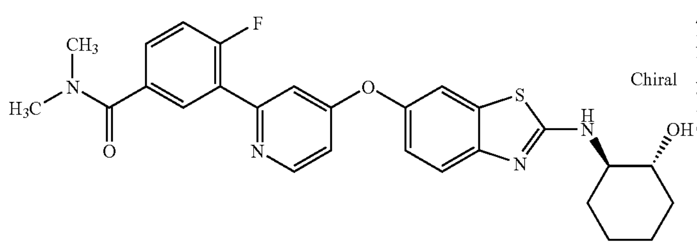 | 4-fluoro-3-(4-(2-((1R,2R)-2-hydroxycyclohexylamino)benzo[d]thiazol-6-yloxy)pyridin-2-yl)-N,N-dimethylbenzamide | 507.1, 1.95 |
| 27 | 179 | 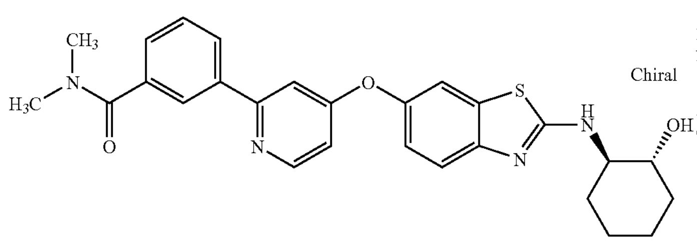 | 3-(4-(2-((1R,2R)-2-hydroxycyclohexylamino)benzo[d]thiazol-6-yloxy)pyridin-2-yl)-N,N-dimethylbenzamide | 489.1, 1.95 |

TABLE 4-continued

| Cmpd | Ex Prep | Structure | Name | (M + H)+, Rt (min.) |
|---|---|---|---|---|
| 28 | 179 | Chiral | (3-(4-(2-((1R,2R)-2-hydroxycyclohexylamino)benzo[d]thiazol-6-yloxy)pyridin-2-yl)phenyl)(pyrrolidin-1-yl)methanone | 515.2, 2.05 |
| 29 | 179 | Chiral | (3-(4-(2-((1R,2R)-2-hydroxycyclohexylamino)benzo[d]thiazol-6-yloxy)pyridin-2-yl)phenyl)(morpholino)methanone | 531.2, 1.95 |
| 30 | 179 | Chiral | (3-(4-(2-((1R,2R)-2-hydroxycyclohexylamino)benzo[d]thiazol-6-yloxy)pyridin-2-yl)phenyl(4-methylpiperazin-1-yl)methanone | 544.1, 1.72 |
| 31 | 179 | Chiral | (4-(2-((1R,2R)-2-hydroxycyclohexylamino)benzo[d]thiazol-6-yloxy)-2,3'-bipyridin-5'-yl)(morpholino)methanone | 532.1, 1.86 |
| 32 | 179 | Chiral | 4-(4-(2-((1R,2R)-2-hydroxycyclohexylamino)benzo[d]thiazol-6-yloxy)pyridin-2-yl)-N,N-dimethylbenzamide | 489.2, 1.95 |
| 33 | 179 | Chiral | (4-(4-(2-((1R,2R)-2-hydroxycyclohexylamino)benzo[d]thiazol-6-yloxy)pyridin-2-yl)phenyl)(pyrrolidin-1-yl)methanone | 515.2, 2.05 |

TABLE 4-continued

| Cmpd | Ex Prep | Structure | Name | (M + H)+, Rt (min.) |
|---|---|---|---|---|
| 34 | 179 | Chiral | (4-(4-(2-((1R,2R)-2-hydroxycyclohexylamino)benzo[d]thiazol-6-yloxy)pyridin-2-yl)phenyl)(morpholino)methanone | 531.2, 1.95 |
| 35 | 179 | Chiral | (4-(4-(2-((1R,2R)-2-hydroxycyclohexylamino)benzo[d]thiazol-6-yloxy)pyridin-2-yl)phenyl)(4-methylpiperazin-1-yl)methanone | 544.2, 1.80 |
| 36 | 179 | Chiral | 4-(4-(2-((1R,2R)-2-hydroxycyclohexylamino)benzo[d]thiazol-6-yloxy)pyridin-2-yl)-N-(2-hydroxyethyl)benzamide | 505.2, 1.84 |
| 37 | 179 | Chiral | 4-(4-(2-((1R,2R)-2-hydroxycyclohexylamino)benzo[d]thiazol-6-yloxy)pyridin-2-yl)benzamide | 461.1, 1.85 |
| 38 | 179 | Chiral | (1R,2R)-2-(6-(2-(2-(4-methylpiperazin-1-yl)pyrimidin-5-yl)pyridin-4-yloxy)benzo[d]thiazol-2-ylamino)cyclohexanol | 518.2, 1.81 |

TABLE 4-continued

| Cmpd | Ex Prep | Structure | Name | (M + H)+, Rt (min.) |
|---|---|---|---|---|
| 39 | 185 | Chiral | (1R,2R)-2-(6-(2-(1H-pyrazol-5-yl)pyridin-4-yloxy)benzo[d]thiazol-2-ylamino)cyclohexanol | 408.0, 1.78 |
| 40 | 185 | Chiral | 3-(4-(2-((1R,2R)-2-hydroxycyclohexylamino)benzo[d]thiazol-6-yloxy)pyridin-2-yl)-N-(2-hydroxyethyl)benzamide | 505.1, 1.86 |
| 41 | 177 | Chiral | (1R,2R)-2-(6-(2-(4-(4-methyl-1H-imidazol-2-yl)phenyl)pyridin-4-yloxy)benzo[d]thiazol-2-ylamino)cyclohexanol | 498.1, 1.89 |
| 42 | 177 | Chiral | (1R,2R)-2-(6-(2-(4-(4,5-dimethyl-1H-imidazol-2-yl)phenyl)pyridin-4-yloxy)benzo[d]thiazol-2-ylamino)cyclohexanol | 512.2, 1.93 |
| 43 | 180 | Chiral | (S)-4-(2-(1-cyclohexylethylamino)benzo[d]thiazol-6-yloxy)picolinamide | 379.1, 2.94 |

TABLE 4-continued

| Cmpd | Ex Prep | Structure | Name | (M + H)+, Rt (min.) |
|---|---|---|---|---|
| 44 | 177 | 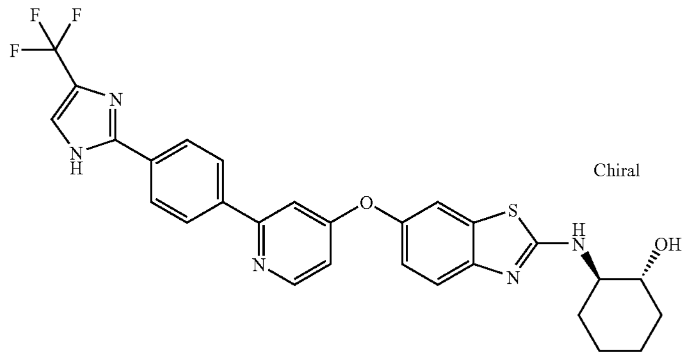 | (1R,2R)-2-(6-(2-(4-(4-(trifluoromethyl)-1H-imidazol-2-yl)phenyl)pyridin-4-yloxy)benzo[d]thiazol-2-ylamino)cyclohexanol | 552.1, 2.26 |
| 45 | 208 | 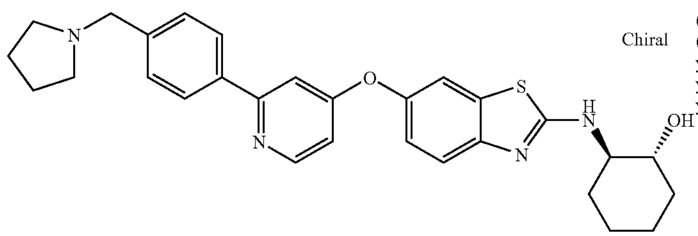 | (1R,2R)-2-(6-(2-(4-(pyrrolidin-1-ylmethyl)phenyl)pyridin-4-yloxy)benzo[d]thiazol-2-ylamino)cyclohexanol | 501.2, 1.85 |
| 46 | 208 | 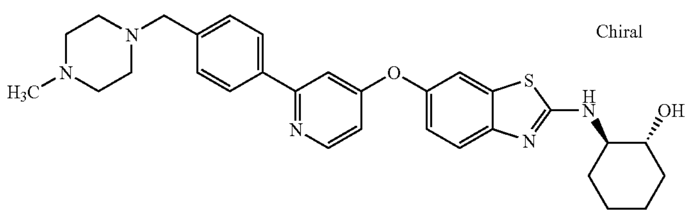 | (1R,2R)-2-(6-(2-(4-((4-methylpiperazin-1-yl)methyl)phenyl)pyridin-4-yloxy)benzo[d]thiazol-2-ylamino)cyclohexanol | 530.2, 1.82 |
| 47 | 211 | 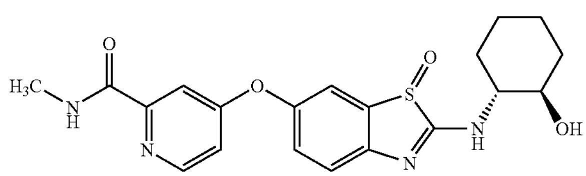 | 4-(2-(((1R,2R)-2-hydroxycyclohexylamino)-1-oxo-benzo[d]thiazol-6-yloxy)-N-methylpicolinamide | 415.1, 1.81 |
| 48 | 168 | 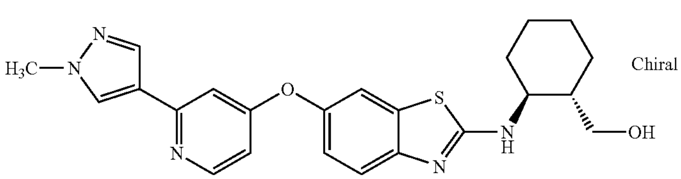 | ((1S,2S)-2-(6-(2-(1-methyl-1H-pyrazol-4-yl)pyridin-4-yloxy)benzo[d]thiazol-2-ylamino)cyclohexyl)methanol | 436.0, 1.90 |
| 49 | 179 | 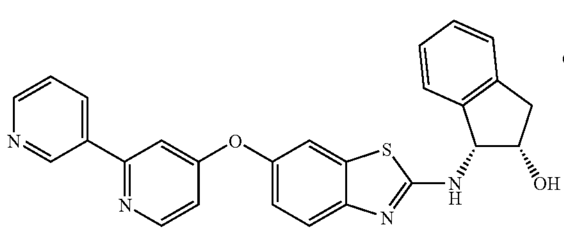 | (1R,2S)-1-(6-(2,3'-bipyridin-4-yloxy)benzo[d]thiazol-2-ylamino)-2,3-dihydro-1H-inden-2-ol | 453.0 2.09 |

TABLE 4-continued

| Cmpd | Ex Prep | Structure | Name | (M + H)+, Rt (min.) |
|---|---|---|---|---|
| 50 | 179 | 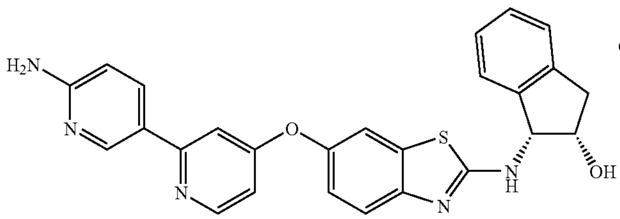 | (1R,2S)-1-(6-(6'-amino-2,3'-bipyridin-4-yloxy)benzo[d]thiazol-2-ylamino)-2,3-dihydro-1H-inden-2-ol | 468.0, 2.02 |
| 51 | 179 | 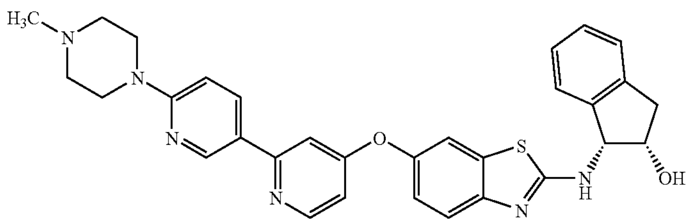 | (1R,2S)-1-(6-(6'-(4-methylpiperazin-1-yl)-2,3'-bipyridin-4-yloxy)benzo[d]thiazol-2-ylamino)-2,3-dihydro-1H-inden-2-ol | 551.1, 1.96 |
| 52 | 179 | 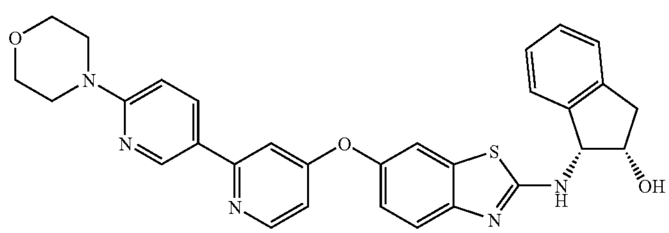 | (1R,2S)-1-(6-(6'-morpholino-2,3'-bipyridin-4-yloxy)benzo[d]thiazol-2-ylamino)-2,3-dihydro-1H-inden-2-ol | 538.1, 2.18 |
| 53 | 179 | 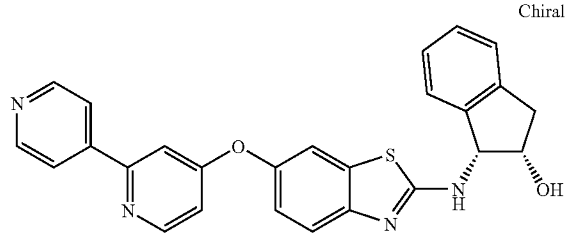 | (1R,2S)-1-(6-(2,4'-bipyridin-4-yloxy)benzo[d]thiazol-2-ylamino)-2,3-dihydro-1H-inden-2-ol | 453.1, 2.15 |
| 54 | 179 | 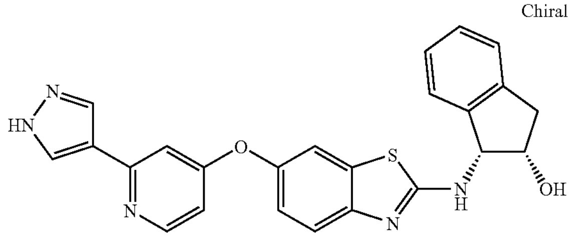 | (1R,2S)-1-(6-(2-(1H-pyrazol-4-yl)pyridin-4-yloxy)benzo[d]thiazol-2-ylamino)-2,3-dihydro-1H-inden-2-ol | 442.0, 2.01 |
| 55 | 179 | 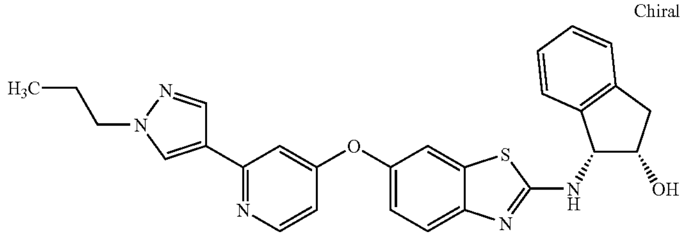 | (1R,2S)-1-(6-(2-(1-propyl-1H-pyrazol-4-yl)pyridin-4-yloxy)benzo[d]thiazol-2-ylamino)-2,3-dihydro-1H-inden-2-ol | 484.1, 2.25 |

TABLE 4-continued

| Cmpd | Ex Prep | Structure | Name | (M + H)+, Rt (min.) |
|---|---|---|---|---|
| 56 | 179 | 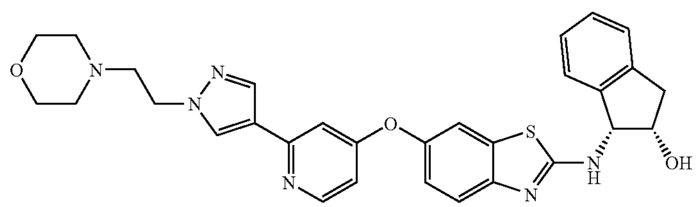 | Chiral (1R,2S)-1-(6-(2-(1-(2-morpholinoethyl)-1H-pyrazol-4-yl)pyridin-4-yloxy)benzo[d]thiazol-2-ylamino)-2,3-dihydro-1H-inden-2-ol | 555.1, 1.92 |
| 57 | 176 | 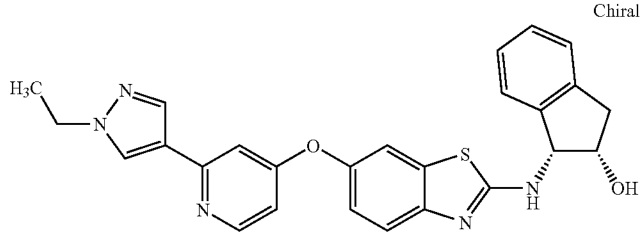 | Chiral (1R,2S)-1-(6-(2-(1-ethyl-1H-pyrazol-4-yl)pyridin-4-yloxy)benzo[d]thiazol-2-ylamino)-2,3-dihydro-1H-inden-2-ol | 470.0, 2.16 |
| 58 | 176 | 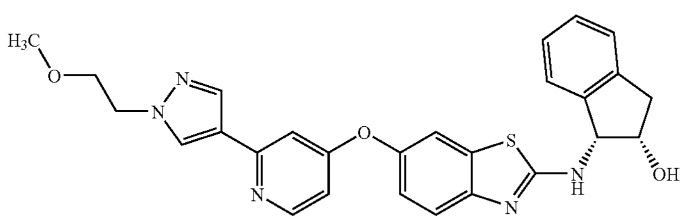 | Chiral (1R,2S)-1-(6-(2-(1-(2-methoxyethyl)-1H-pyrazol-4-yl)pyridin-4-yloxy)benzo[d]thiazol-2-ylamino)-2,3-dihydro-1H-inden-2-ol | 500.0, 2.12 |
| 59 | 176 | 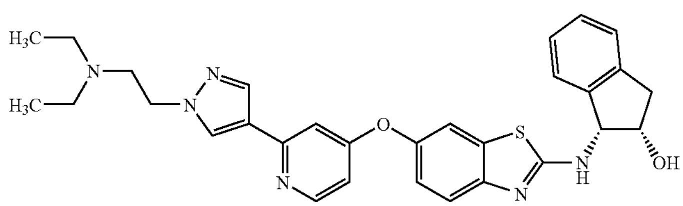 | (1R,2S)-1-(6-(2-(1-(2-(diethylamino)ethyl)-1H-pyrazol-4-yl)pyridin-4-yloxy)benzo[d]thiazol-2-ylamino)-2,3-dihydro-1H-inden-2-ol | 541.1, 1.97 |
| 60 | 179 | 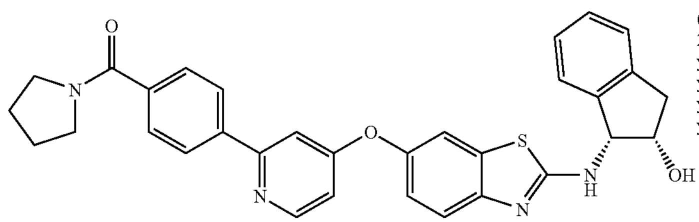 | (4-(4-(2-((1R,2S)-2-hydroxy-2,3-dihydro-1H-inden-1-ylamino)benzo[d]thiazol-6-yloxy)pyridin-2-yl)phenyl)(pyrrolidin-1-yl)methanone | 549.2, 2.25 |
| 61 | 212 | 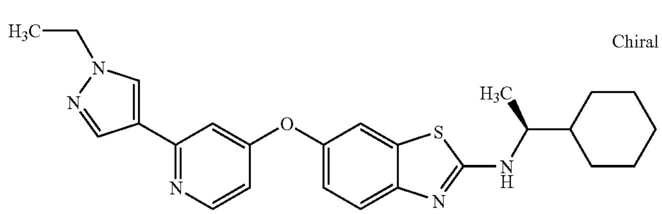 | Chiral (S)-N-(1-cyclohexylethyl)-6-(2-(1-ethyl-1H-pyrazol-4-yl)pyridin-4-yloxy)benzo[d]thiazol-2-amine | 448.1, 2.79 |

TABLE 4-continued

| Cmpd | Ex Prep | Structure | Name | (M + H)+, Rt (min.) |
|---|---|---|---|---|
| 62 | 212 | Chiral | (S)-N-(1-cyclohexylethyl)-6-(2-(1-(2,2-difluoroethyl)-1H-pyrazol-4-yl)pyridin-4-yloxy)benzo[d]thiazol-2-amine | 484.1, 2.44 |
| 63 | 212 | Chiral | (S)-N-(1-cyclohexylethyl)-6-(2-(1-(2-(diethylamino)ethyl)-1H-pyrazol-4-yl)pyridin-4-yloxy)benzo[d]thiazol-2-amine | 519.2, 2.18 |
| 64 | 212 | Chiral | (S)-N-(1-cyclohexylethyl)-6-(2-(1-(2-methoxyethyl)-1H-pyrazol-4-yl)pyridin-4-yloxy)benzo[d]thiazol-2-amine | 478.1, 2.37 |
| 65 | 212 | Chiral | (S)-N-(1-cyclohexylethyl)-6-(2-(1-(2-fluoroethyl)-1H-pyrazol-4-yl)pyridin-4-yloxy)benzo[d]thiazol-2-amine | 466.1, 2.38 |
| 66 | 213 | Chiral | (S)-N-(1-cyclohexylethyl)-6-(2-(1-(2-morpholinoethyl)-1H-pyrazol-4-yl)pyridin-4-yloxy)benzo[d]thiazol-2-amine | 533.1, 2.14 min |
| 67 | 176 | Chiral | (1R,2S)-1-(6-(2-(1-(2-fluoroethyl)-1H-pyrazol-4-yl)pyridin-4-yloxy)benzo[d]thiazol-2-ylamino)-2,3-dihydro-1H-inden-2-ol | 488.1, 2.17 |

TABLE 4-continued

| Cmpd | Ex Prep | Structure | Name | (M + H)+, Rt (min.) |
|---|---|---|---|---|
| 68 | 176 | Chiral | (1R,2S)-1-(6-(2-(1-(2,2-difluoroethyl)-1H-pyrazol-4-yl)pyridin-4-yloxy)benzo[d]thiazol-2-ylamino)-2,3-dihydro-1H-inden-2-ol | 506.1, 2.25 |
| 69 | 179 | Chiral | (1R,2S)-1-(6-(2'-(4-methylpiperazin-1-yl)-2,4'-bipyridin-4-yloxy)benzo[d]thiazol-2-ylamino)-2,3-dihydro-1H-inden-2-ol | 551.2, 2.09 |
| 70 | 207 | Chiral | (1R,2S)-1-(6-(6'-((S)-3-(dimethylamino)pyrrolidin-1-yl)-2,3'-bipyridin-4-yloxy)benzo[d]thiazol-2-ylamino)-2,3-dihydro-1H-inden-2-ol | 565.2, 2.02 |
| 71 | 179 | Chiral | 4-(4-(2-((1R,2R)-2-hydroxycyclohexylamino)benzo[d]thiazol-6-yloxy)pyridin-2-yl)pyridin-2(1H)-one | 435.1, 1.82 |
| 72 | 179 | Chiral | (1R,2R)-2-(6-(5'-fluoro-2,3'-bipyridin-4-yloxy)benzo[d]thiazol-2-ylamino)cyclhexanol | 437.1, 2.07 |

TABLE 4-continued

| Cmpd | Ex Prep | Structure | Name | (M + H)+, Rt (min.) |
|---|---|---|---|---|
| 73 | 179 | 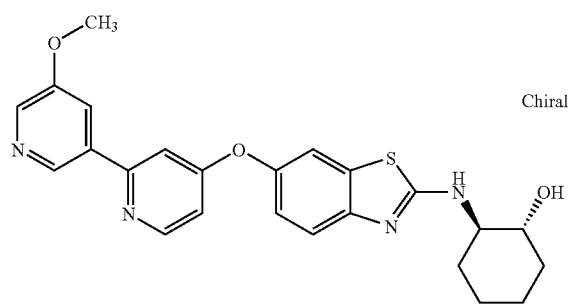 Chiral | (1R,2R)-2-(6-(5'-methoxy-2,3'-bipyridin-4-yloxy)benzo[d]thiazol-2-ylamino)cyclohexanol | 449.1, 2.00 |
| 74 | 179 | 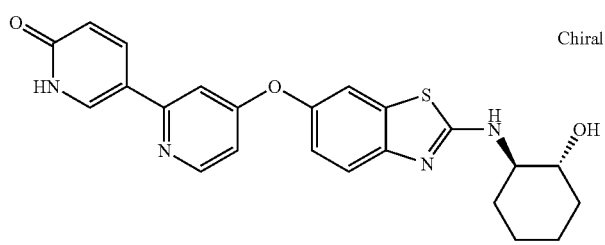 Chiral | 5-(4-(2-((1R,2R)-2-hydroxycyclohexylamino)benzo[d]thiazol-6-yloxy)pyridin-2-yl)pyridin-2(1H)-one | 435.1, 1.77 |
| 75 | 173 | 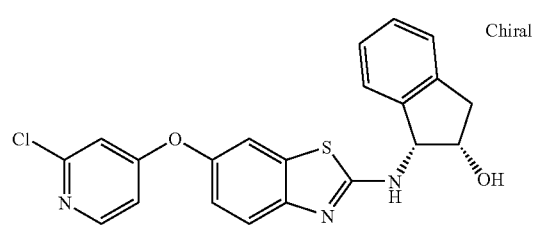 Chiral | (1R,2S)-1-(6-(2-chloropyridin-4-yloxy)benzo[d]thiazol-2-ylamino)-2,3-dihydro-1H-inden-2-ol | 410.0, 2.63 |
| 76 | 176 | 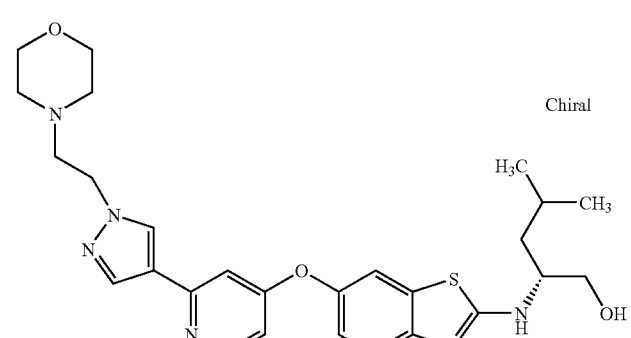 Chiral | (R)-4-methyl-2-(6-(2-(1-(2-morpholinoethyl)-1H-pyrazol-4-yl)pyridin-4-yloxy)benzo[d]thiazol-2-ylamino)pentan-1-ol | 523.1, 1.84 |
| 77 | 176 | 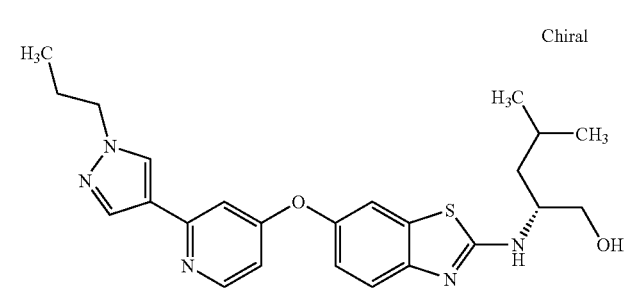 Chiral | (R)-4-methyl-2-(6-(2-(1-propyl-1H-pyrazol-4-yl)pyridin-4-yloxy)benzo[d]thiazol-2-ylamino)pentan-1-ol | 452.1, 2.31 |

TABLE 4-continued

| Cmpd | Ex Prep | Structure | Name | (M + H)+, Rt (min.) |
|---|---|---|---|---|
| 78 | 176 | Chiral | (R)-4-methyl-2-(6-(6'-(4-methylpiperazin-1-yl)-2,3'-bipyridin-4-yloxy)benzo[d]thiazol-2-ylamino)pentan-1-ol | 519.1, 1.85 |
| 79 | 176 | Chiral | (R)-2-(6-(6'-amino-2,3'-bipyridin-4-yloxy)benzo[d]thiazol-2-ylamino)-4-methylpentan-1-ol | 436.0, 1.94 |
| 80 | 176 | Chiral | (R)-2-(6-(2-(1-(2-(diethylamino)ethyl)-1H-pyrazol-4-yl)pyridin-4-yloxy)benzo[d]thiazol-2-ylamino)-4-methylpentan-1-ol | 509.1; 1.89 |
| 81 | 176 | Chiral | (R)-2-(6-(2-(1-(2,2-difluoroethyl)-1H-pyrazol-4-yl)pyridin-4-yloxy)benzo[d]thiazol-2-ylamino)-4-methylpentan-1-ol | 474.0, 2.07 |
| 82 | 176 | Chiral | (R)-2-(6-(2-(1-(2-methoxyethyl)-1H-pyrazol-4-yl)pyridin-4-yloxy)benzo[d]thiazol-2-ylamino)-4-methylpentan-1-ol | 468.1, 2.00 |

… TABLE 4-continued

| Cmpd | Ex Prep | Structure | Name | (M + H)+, Rt (min.) |
|---|---|---|---|---|
| 83 | 176 | Chiral | (R)-2-(6-(2-(1-ethyl-1H-pyrazol-4-yl)pyridin-4-yloxy)benzo[d]thiazol-2-ylamino)-4-methylpentan-1-ol | 438.1, 2.13 |
| 84 | 176 | Chiral | (R)-2-(6-(2-(1-(2-fluoroethyl)-1H-pyrazol-4-yl)pyridin-4-yloxy)benzo[d]thiazol-2-ylamino)-4-methylpentan-1-ol | 456.3, 2.11 |
| 85 | 16 | Chiral | 4-(2-(((1S,2R)-2-hydroxycyclohexylamino)benzo[d]thiazol-6-yloxy)-N-methylpicolinamide; 4-(2-(((1R,2S)-2-hydroxycyclohexylamino)benzo[d]thiazol-6-yloxy)-N-methylpicolinamide | 399.1, 2.07 |
| 86 | 177 | Chiral | (R)-2-(6-(2-(4-ethyl-5-methyl-1H-imidazol-2-yl)pyridin-4-yloxy)benzo[d]thiazol-2-ylamino)-4-methylpentan-1-ol | 452.1, 2.18 |
| 87 | 209 | Chiral | (1R,2R)-2-(6-(2-(1-(2-(4-methylpiperazin-1-yl)ethyl)-1H-pyrazol-4-yl)pyridin-4-yloxy)benzo[d]thiazol-2-ylamino)cyclohexanol | 534.3, 1.78 |
| 88 | 209 | Chiral | (1R,2R)-2-(6-(2-(1-(2-(dimethylamino)ethyl)-1H-pyrazol-4-yl)pyridin-4-yloxy)benzo[d]thiazol-2-ylamino)cyclohexanol | 479.2, 1.77 |

TABLE 4-continued

| Cmpd | Ex Prep | Structure | | Name | (M + H)+, Rt (min.) |
|---|---|---|---|---|---|
| 89 | 209 | 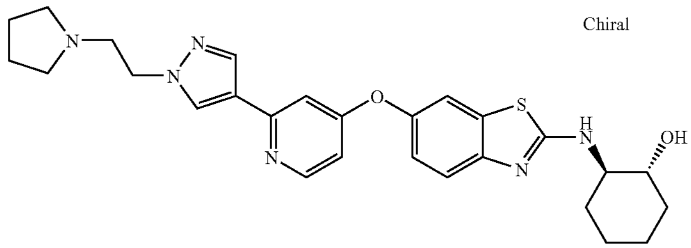 | Chiral | (1R,2R)-2-(6-(2-(1-(2-(pyrrolidin-1-yl)ethyl)-1H-pyrazol-4-yl)pyridin-4-yloxy)benzo[d]thiazol-2-ylamino)cyclohexanol | 505.2, 1.80 |
| 90 | 209 | 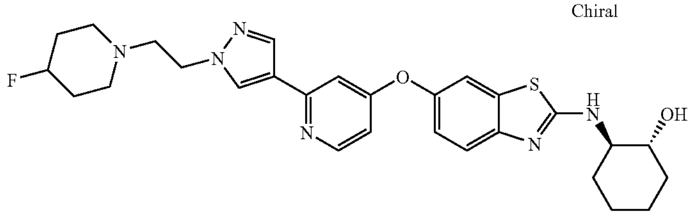 | Chiral | (1R,2R)-2-(6-(2-(1-(2-(4-fluoropiperidin-1-yl)ethyl)-1H-pyrazol-4-yl)pyridin-4-yloxy)benzo[d]thiazol-2-ylamino)cyclohexanol | 537.2, 1.83 |
| 91 | 209 | 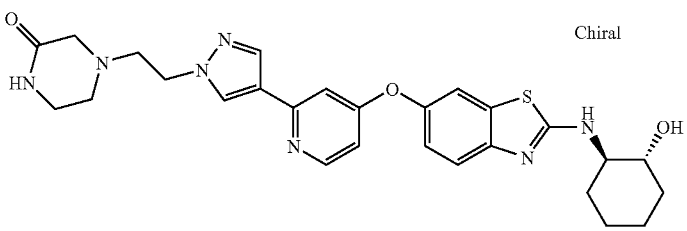 | Chiral | 4-(2-(4-(4-(2-((1R,2R)-2-hydroxycyclohexylamino)benzo[d]thiazol-6-yloxy)pyridin-2-yl)-1H-pyrazol-1-yl)ethyl)piperazin-2-one | 534.2, 1.73 |
| 92 | 179 | 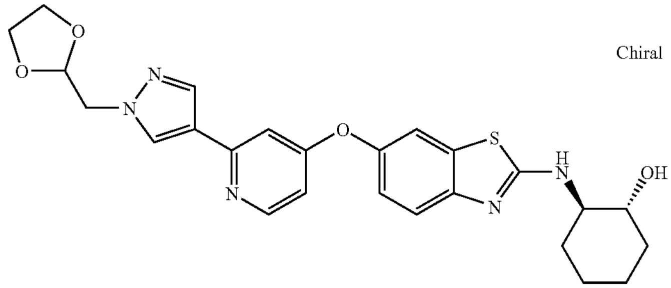 | Chiral | (1R,2R)-2-(6-(2-(1-((1,3-dioxolan-2-yl)methyl)-1H-pyrazol-4-yl)pyridin-4-yloxy)benzo[d]thiazol-2-ylamino)cyclohexanol | 494.2, 1.92 |
| 93 | 214 | 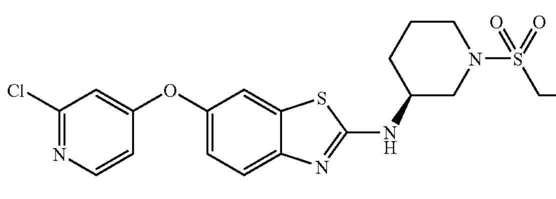 | Chiral | (S)-6-(2-chloropyridin-4-yloxy)-N-(1-(ethylsulfonyl)piperidin-3-yl)benzo[d]thiazol-2-amine | 453.0, 2.59 |
| 94 | 217 | 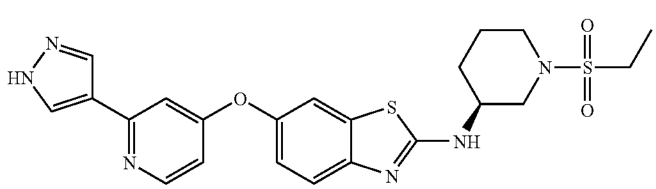 | | (S)-6-(2-(1H-pyrazol-4-yl)pyridin-4-yloxy)-N-(1-(ethylsulfonyl)piperidin-3-yl)benzo[d]thiazol-2-amine | 485.1; 1.73 |

TABLE 4-continued

| Cmpd | Ex Prep | Structure | Name | (M + H)+, Rt (min.) |
|---|---|---|---|---|
| 95 | 217 | 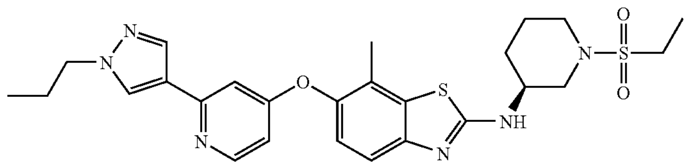 | (S)-N-(1-(ethylsulfonyl)piperidin-3-yl)-6-(2-(1-propyl-1H-pyrazol-4-yl)pyridin-4-yloxy)benzo[d]thiazol-2-amine | 527.1; 2.24 |
| 96 | 217 | 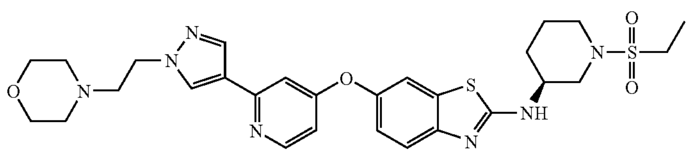 | (S)-N-(1-(ethylsulfonyl)piperidin-3-yl)-6-(2-(1-(2-morpholinoethyl)-1H-pyrazol-4-yl)pyridin-4-yl)pyridin-4-yloxy)benzo[d]thiazol-2-amine | 598.3; 1.67 |
| 97 | 218 | 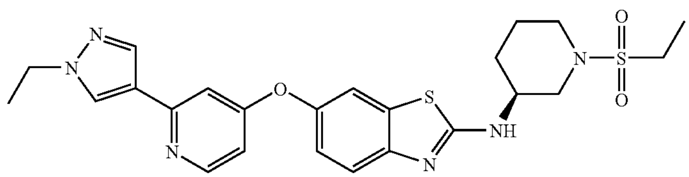 | (S)-6-(2-(1-ethyl-1H-pyrazol-4-yl)pyridin-4-yloxy)-N-(1-(ethylsulfonyl)piperidin-3-yl)benzo[d]thiazol-2-amine | 513.2; 1.89 |
| 98 | 218 | 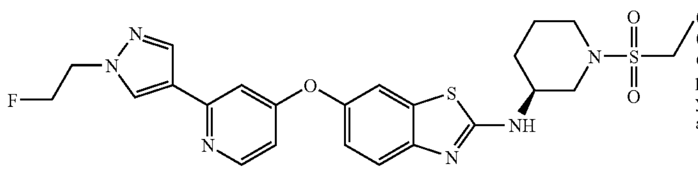 | (S)-N-(1-(ethylsulfonyl)piperidin-3-yl)-6-(2-(1-(2-fluoroethyl)-1H-pyrazol-4-yl)pyridin-4-yloxy)benzo[d]thiazol-2-amine | 531.2, 1.87 |
| 99 | 218 | 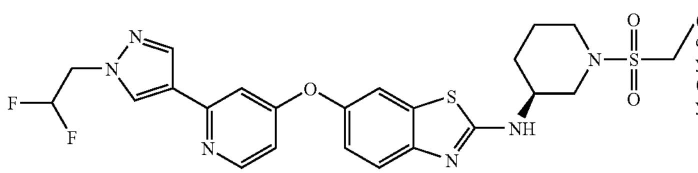 | (S)-6-(2-(1-(2,2-difluoroethyl)-1H-pyrazol-4-yl)pyridin-4-yloxy)-N-(1-(ethylsulfonyl)piperidin-3-yl)benzo[d]thiazol-2-amine | 549.2; 1.93 |
| 100 | 218 | 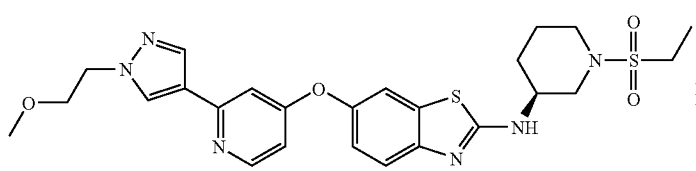 | (S)-N-(1-(ethylsulfonyl)piperidin-3-yl)-6-(2-(1-(2-methoxyethyl)-1H-pyrazol-4-yl)pyridin-4-yloxy)benzo[d]thiazol-2-amine | 543.2; 2.10 |
| 101 | 218 | 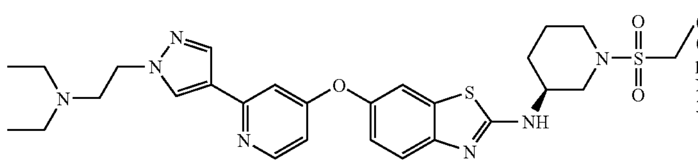 | (S)-6-(2-(1-(2-(diethylamino)ethyl)-1H-pyrazol-4-yl)pyridin-4-yloxy)-N-(1-ethylsulfonyl)piperidin-3-yl)benzo[d]thiazol-2-amine | 589.2, 1.94 |
| 102 | 177 | 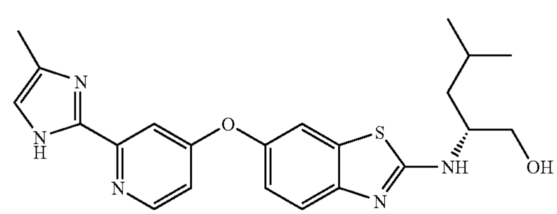 | (R)-4-methyl-2-(6-(2-(4-methyl-1H-imidazol-2-yl)pyridin-4-yloxy)benzo[d]thiazol-2-ylamino)pentan-1-ol | 424.2; 2.03 |

TABLE 4-continued

| Cmpd | Ex Prep | Structure | Name | (M + H)+, Rt (min.) |
|---|---|---|---|---|
| 103 | | 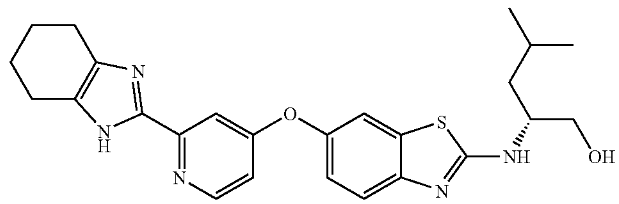 | (R)-4-methyl-2-(6-(2-(4,5,6,7-tetrahydro-1H-benzo[d]imidazol-2-yl)pyridin-4-yloxy)benzo[d]thiazol-2-ylamino)pentan-1-ol | |
| 104 | 219 | 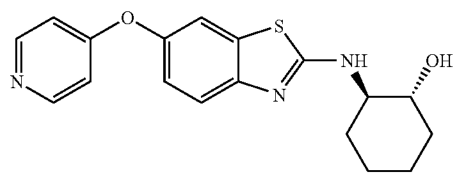 | (1R,2R)-2-(6-(pyridin-4-yloxy)benzo[d]thiazol-2-ylamino)cyclohexanol | 342.1; 1.74 |
| 105 | 207 | 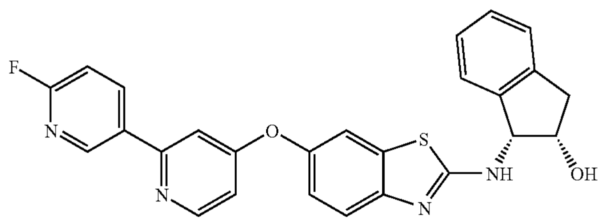 | (1R,2S)-1-(6-(6'-fluoro-2,3'-bipyridin-4-yloxy)benzo[d]thiazol-2-ylamino)-2,3-dihydro-1H-inden-2-ol | 471.1; 2.32 |
| 106 | 207 | 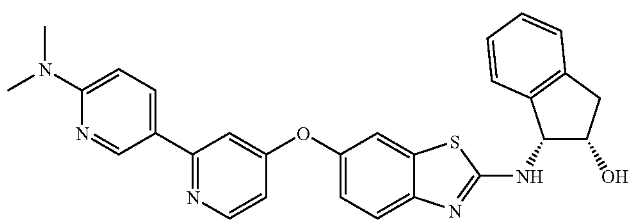 | (1R,2S)-1-(6-(6'-(dimethylamino)-2,3'-bipyridin-4-yloxy)benzo[d]thiazol-2-ylamino)-2,3-dihydro-1H-inden-2-ol | 496.1; 2.11 |
| 107 | | 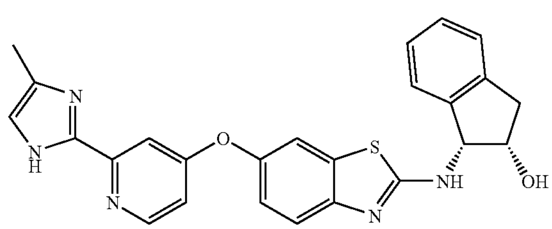 | (1R,2S)-1-(6-(2-(4-methyl-1H-imidazol-2-yl)pyridin-4-yloxy)benzo[d]thiazol-2-ylamino)-2,3-dihydro-1H-inden-2-ol | |
| 108 | | 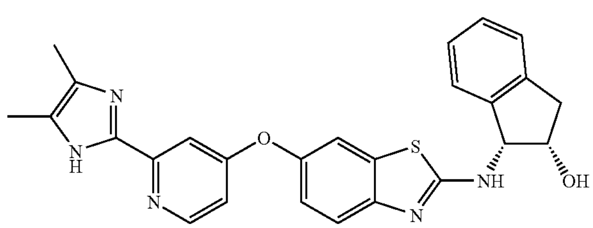 | (1R,2S)-1-(6-(2-(4,5-dimethyl-1H-imidazol-2-yl)pyridin-4-yloxy)benzo[d]thiazol-2-ylamino)-2,3-dihydro-1H-inden-2-ol | |
| 109 | | 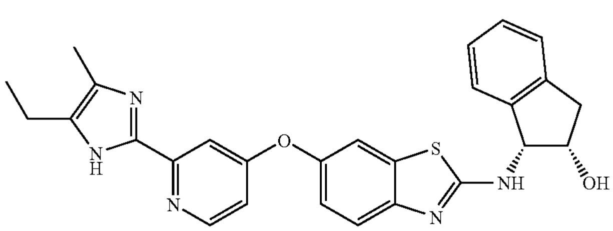 | (1R,2S)-1-(6-(2-(5-ethyl-4-methyl-1H-imidazol-2-yl)pyridin-4-yloxy)benzo[d]thiazol-2-ylamino)-2,3-dihydro-1H-inden-2-ol | |

TABLE 4-continued

| Cmpd | Ex Prep | Structure | Name | (M + H)+, Rt (min.) |
|---|---|---|---|---|
| 110 | | 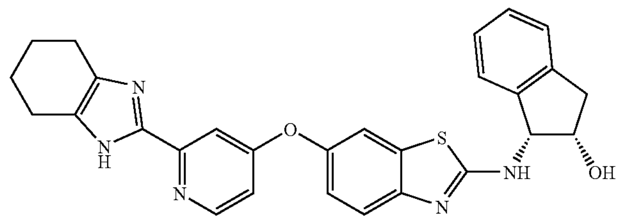 | (1R,2S)-1-(6-(2-(4,5,6,7-tetrahydro-1H-benzo[d]imidazol-2-yl)pyridin-4-yloxy)benzo[d]thiazol-2-ylamino)-2,3-dihydro-1H-inden-2-ol | |
| 111 | | 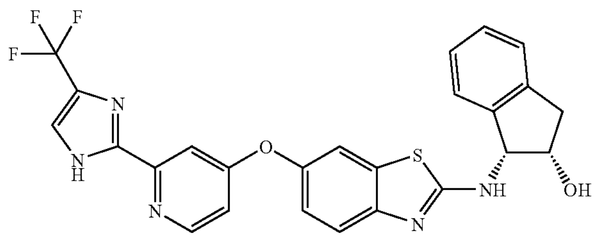 | (1R,2S)-1-(6-(2-(4-(trifluoromethyl)-1H-imidazol-2-yl)pyridin-4-yloxy)benzo[d]thiazol-2-ylamino)-2,3-dihydro-1H-inden-2-ol | |
| 112 | 216 | 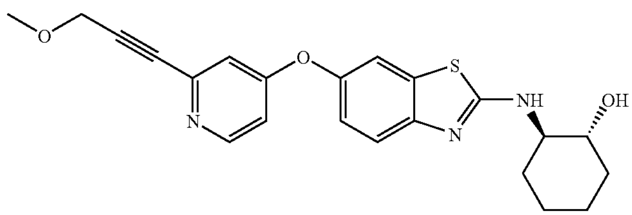 | (1R,2R)-2-(6-(2-(3-methoxyprop-1-ynyl)pyridin-4-yloxy)benzo[d]thiazol-2-ylamino)cyclohexanol | 410.1; 1.96 |
| 113 | 216 | 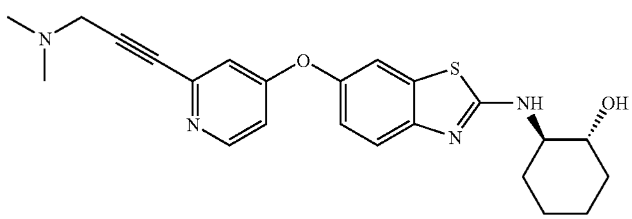 | (1R,2R)-2-(6-(2-(3-(dimethylamino)prop-1-ynyl)pyridin-4-yloxy)benzo[d]thiazol-2-ylamino)cyclohexanol | 423.2; 1.80 |
| 114 | 216 | 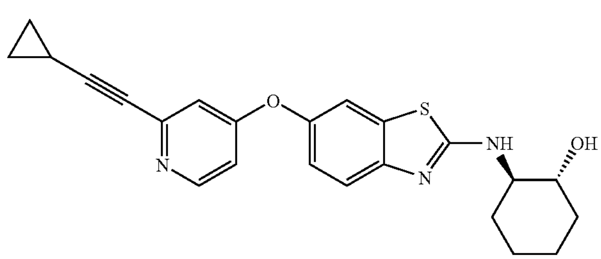 | (1R,2R)-2-(6-(2-(cyclopropylethynyl)pyridin-4-yloxy)benzo[d]thiazol-2-ylamino)cyclohexanol | 406.2; 2.04 |
| 115 | 215 | 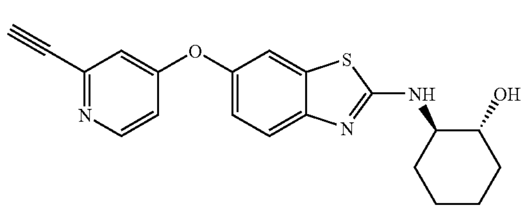 | (1R,2R)-2-(6-(2-ethynylpyridin-4-yloxy)benzo[d]thiazol-2-ylamino)cyclohexanol | 366.1; 1.91 |

TABLE 4-continued

| Cmpd | Ex Prep | Structure | Name | (M + H)+, Rt (min.) |
|---|---|---|---|---|
| 116 | 216 | 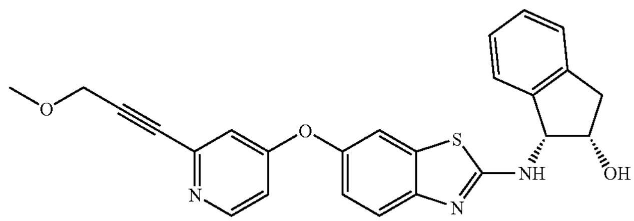 | (1R,2S)-1-(6-(2-(3-methoxyprop-1-ynyl)pyridin-4-yloxy)benzo[d]thiazol-2-ylamino)-2,3-dihydro-1H-inden-2-ol | 444.1; 2.26 |
| 117 | 216 | 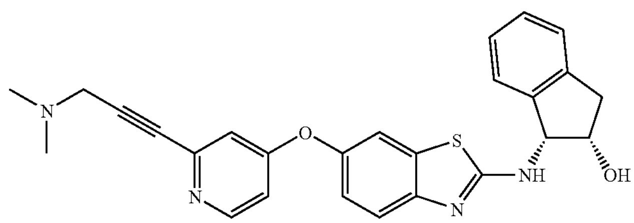 | (1R,2S)-1-(6-(2-(3-(dimethylamino)prop-1-ynyl)pyridin-4-yloxy)benzo[d]thiazol-2-ylamino)-2,3-dihydro-1H-inden-2-ol | 457.1; 2.05 |
| 118 | 216 | 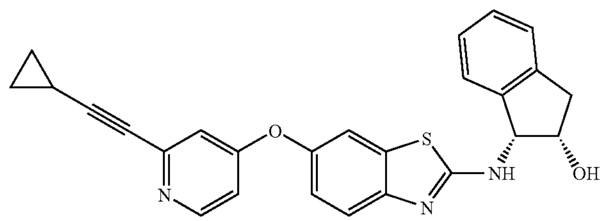 | (1R,2S)-1-(6-(2-(cyclopropylethynyl)pyridin-4-yloxy)benzo[d]thiazol-2-ylamino)-2,3-dihydro-1H-inden-2-ol | 440.0; 2.35 |
| 119 | 215 | 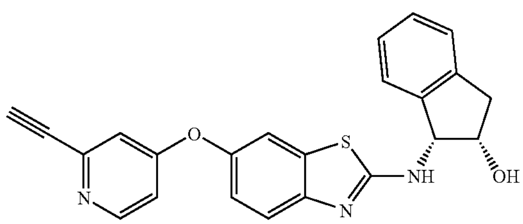 | (1R,2S)-1-(6-(2-ethynylpyridin-4-yloxy)benzo[d]thiazol-2-ylamino)-2,3-dihydro-1H-inden-2-ol | 400.1; 2.20 |

Each of the compounds listed in Table 2 were shown to have activity with respect to inhibition of CSF-1R with an $IC_{50}$ of less than about 10 μM. Many of the compounds exhibited activity with an $IC_{50}$ of less than about 1 μM, or less than about 0.1 μM, or less than about 0.01 μM with respect to CSF-1R inhibition. The compounds of Tables 3 and 4 were found to have an activity of less than 1 μM. As such, each of the compounds of Tables 2, 3, and 4 is preferred individually and as a member of a group.

In addition to CSF-1R inhibitory activity, many of the compounds of Tables 2, 3, and 4 were also screened for Raf inhibition (according to biochemical screens described in U.S. Ser. No. 10/405,945, which is entirely incorporated by reference), as well as other kinases, and shown to inhibit CSF-1R significantly greater (between about 2 and about 1,000 fold greater) than Raf and other kinases screened. More particularly, many of the compounds screened had activity greater about 1 μM with respect to Raf inhibition, whereas many of the same compounds exhibited activities with respect to CSF-1R at less than about 0.1 μM. As such, many of the compounds of Tables 2, 3, and 4 are potent and selective inhibitors of CSF-1R.

BIOLOGICAL EXAMPLES

Biological Example 1

In Vitro Kinase Assays for Colony Stimulating Factor-1 Receptor (CSF-1R)

The kinase activity of various protein tyrosine kinases can be measured by providing ATP and a suitable peptide or protein tyrosine-containing substrate, and assaying the transfer of phosphate moiety to the tyrosine residue. Recombinant protein corresponding to the cytoplasmic domain of the human CSF-1R was purchased from Invitrogen Corporation, Carlsbad, Calif. U.S.A. (#PV3249). For each assay, test compounds were serially diluted, starting at 25 μM with 3 fold dilutions, in DMSO in 384 well plates then mixed with an appropriate kinase reaction buffer consisting of 50 mM Hepes, 5 mM $MgCl_2$, 10 mM $MnCl_2$, 0.1% BSA, pH 7.5, 1.0 mM dithiothreitol, 0.01% Tween 80 plus 1 μM ATP. Kinase protein and an appropriate biotinylated peptide substrate at 50 nM were added to give a final volume of 20 μL, reactions were incubated for 2 hours at room temperature and stopped by the addition of 10 μL of 45 mM EDTA, 50 mM Hepes pH 7.5. Added to the stopped reaction mix was 30 μL of PT66 Alphascreen beads (Perkin Elmer, Boston, Mass., U.S.A.). The reaction was incubated overnight and read on the Envision (Perkin Elmer). Phosphorylated peptide product was measured with the AlphaScreen system (Perkin Elmer) using acceptor beads coated with anti-phosphotyrosine antibody PT66 and donor beads coated with streptavidin that emit a fluorescent signal at the 520-620 nM emission wave length if in close proximity. The concentration of each compound for 50% inhibition ($IC_{50}$) was calculated by non-linear regression using XL Fit data analysis software.

CSF-1R kinase was assayed in 50 mM Hepes pH 7.0, 5 mM $MgCl_2$, 10 mM $MnCl_2$, 1 mM DTT, 1 mg/ml BSA, 1.0 μM ATP, and 0.05 μM biotin-GGGGRPRAATF-$NH_2$ (SEQ ID NO:2) peptide substrate. CSF-1R kinase was added at final concentration of 4 nM.

Biological Example 2

In Vitro Inhibition of CSF-1R Receptor Tyrosine Phosphorylation

To test the inhibition of CSF-1R receptor tyrosine phosphorylation, HEK293H purchased from Invitrogen Cat. #11631017 cells transfected with the full-length human CSF-1R receptor cloned in house into mammalian episomal transfection vector were incubated for 1 h with serial dilutions of compounds starting at 10 μM with 3 fold dilutions and then stimulated for 8 min with 50 ng/ml MCSF. After the supernatant was removed, the cells were lysed on ice with lysis buffer (150 mM NaCl, 20 mM Tris, pH 7.5, 1 mM EDTA, 1 mM EGTA, 1% Triton X-100 and NaF, protease and phosphatase inhibitors) and then shaken for 15-20 min at 4° C. The lysate was then transferred to total CSF-1R antibody coated 96-well plates that had already been blocked with 3% Blocker A from Mesoscale discovery (MSD) for 2 hours and washed afterwards. Lysates were incubated overnight at 4° C. and the plates were then washed 4× with MSD Tris Wash Buffer. The SULFO-TAG anti-pTyr antibody from MSD was diluted to 20 nM final in 1% Blocker A (MSD) solution and added to the washed plates and incubated for 1.5-2 h before addition of read buffer (MSD). The plates were read on the Sector 6000 instrument (MSD). Raw data was imported in Abase and $EC_{50}$s calculated with XL-fit data analysis software.

Biological Example 3

CSF-1R Inhibitors in MNFS-60 Pk/Pd Model

Five million MNFS-60 cells were implanted in HBSS/matrigel solution s.q. in the right flank. Approximately 3 weeks following tumor cell injection tumors were measured and selected mice were randomized (n=3 except for the vehicle group, where n=6) into groups based on their tumor size.

Compounds that inhibited M-CSF mediated proliferation in MNFS-60 cells and phosphorylation of CSF-1R with $EC_{50}$s<100 nM were tested in the MNFS-60 syngeneic tumor model (5×$10^6$ where implanted subcutaneously in matrigel and grown 3-4 weeks until they reached approximately 150 $mm^2$). A single 100 mg/kg dose of representative compounds disclosed herein was administered to MNFS-60 tumored animals; plasma and tumor samples were harvested at various time points after dosing starting at 1 h up to 24 h.

Several of the compounds disclosed herein were shown to inhibit Tyr723 phosphorylation of CSF-1R in tumor lysates at ≧50% compared to vehicle control 4 hrs after dosing as determined by Western Blot.

Additionally, several of the compounds disclosed herein were tested in a rapid onset severe arthritis mouse model (Terato, K. et al., *Journal of Immunology* 148:2103-2108; 1992) and treatment started on day three after injection of the anti-collagen antibody cocktail followed by LPS stimulation. Throughout the 12 days of treatment with CSF-1R inhibitors, the extent of swelling in the paws and bone resorption severity was scored. Significant attenuation of the swelling was not observed in the treated compared to control group; however, there was a trend toward improvement of bone resorption severity. There are no reports to date that CSF-1R inhibitors are effective in this arthritis model. The only successful reduction of disease progression was reported for inhibition by CSF-1R signaling with an Anti-MCSF antibody in a less severe, slower onset arthritis mouse model (Campbell et al *J. Leukoc. Biol.* 68: 144-150; 2000).

Biological Example 4

Inhibition of Raf Kinase Signaling in an In Vitro Biochemical Assay

The inhibitory effect of compounds on Raf was determined using the following biotinylated assay. The Raf kinase activity was measured by providing ATP, a recombinant kinase inactive MEK substrate and assaying the transfer of phosphate moiety to the MEK residue. Recombinant full length MEK with an inactivating K97R ATP binding site mutation (rendering kinase inactive) was expressed in *E. coli* and labelled with biotin post purification. The MEK cDNA was subcloned with an N-terminal $(His)_6$ tag and expressed in *E. coli* and the recombinant MEK substrate was purified from *E. coli* lysate by nickel affinity chromatography followed by anion exchange. The final MEK substrate preparation was biotinylated (Pierce EZ-Link Sulfo-NHS-LC-Biotin) and concentrated to 11.25 μM. Recombinant Raf (including c-Raf and mutant B-Raf isoforms) was obtained by purification from sf9 insect cells infected with the corresponding human Raf recombinant expression vectors. The recombinant Raf isoforms were purified via a Glu antibody interaction or by Metal Ion Chromatography.

For each assay, the compound was serially diluted, starting at 25 μM with 3-fold dilutions, in DMSO and then mixed with various Raf isoforms (0.50 nM each). The kinase inactive biotin-MEK substrate (50 nM) was added in reaction buffer plus ATP (1 μM). The reaction buffer contained 30 mM Tris-$HCL_2$ pH 7.5, 10 mM $MgCl_2$, 2 mM DTT, 4 mM EDTA, 25 mM beta-glycerophosphate, 5 mM $MnCl_2$, and 0.01% BSA/PBS. Reactions were subsequently incubated for 2 hours at room temperature and stopped by the addition of 0.5 M EDTA. Stopped reaction mixture was transferred to a neutradavin-coated plate (Pierce) and incubated for 1 hour. Phosphorylated product was measured with the DELFIA time-resolved fluorescence system (Wallac), using a rabbit anti-p-MEK (Cell Signaling) as the primary antibody and europium labeled anti-rabbit as the secondary antibody. Time resolved fluorescence can be read on a Wallac 1232 DELFIA fluorometer. The concentration of the compound for 50% inhibition ($IC_{50}$) was calculated by non-linear regression using XL Fit data analysis software.

Biological Example 5

Inhibition of cKIT and PDGFRb Kinase Signaling in an In Vitro Biochemical Assay

The IC50 values for the inhibition of RTKs were determined in the alphascreen format measuring the inhibition by compound of phosphate transfer to a substrate by the respective enzyme. Briefly, the respective RTK domain purchased as human recombinant protein (cKIT Upstate #14-559, PDG-FRb Invitrogen #P3082) were incubated with serial dilutions of compound in the presence of substrate and ATP concentrations within 3 times the Km of the enzyme.

The kinase domain of cKIT was assayed in 50 mM Hepes, pH=7.5, 5 mM MgCl2, 10 mM MnCl2, 1 mM DTT, 0.1% BSA with 0.06 uM biotinylated peptide substrate (GGLFD-DPSYVNVQNL-NH2)(SEQ ID NO: 1) and 15 uM ATP (ATP KM apparent=15 uM). The kinase domain of PDGFRβ was assayed in 50 mM Hepes, pH=7.5, 20 mM MgCl2, 1 mM DTT, 0.1% BSA with 0.1 uM biotinylated peptide substrate (GGLFDDPSYVNVQNL-NH2)(SEQ ID NO: 1) and 10 uM ATP (ATP KM apparent=25 uM). Reactions were incubated at room temperature for 3 to 4 hr and stopped with buffer (20 mM EDTA, 0.01% Tween-20 for both PDGFRb and cKIT). Alphascreen PY20 beads were added to the stopped cKIT reactions and PY20 Ab/Protein A Alphascreen beads were added to the PDGFRβ stopped reactions. Both reactions were incubated overnight and read on the Alphascreen reader. The concentration of compound for 50% inhibition (IC50) was calculated employing non-linear regression using XL-Fit data analysis software. As a control compound, staurosporine is run in every assay and a Z'>0.5 is required to validate results.

Biological Example 6

Cell Viability Assay in MCSF Dependent MNFS60 Cells

Cell viability was assessed by Cell Titer Glo, Promega. MNFS60 (murine AML cells) were seeded in TC treated 96-well plates at a density of 5,000 cells per well in RPMI-1640, 10% FBS, and 1% Penicillin Streptomycin prior to addition of compound. Test compounds were serially diluted (3 fold) in DMSO to 500× the final concentration. For each concentration of test compound, 2 µl (500×) aliquots of compound or 100% DMSO (control) were diluted in 500 µl of culture medium that contained 2× final concentration of growth factor MCSF for 2× concentration and then diluted 1× on the cells. Final concentration of MCSF is 10 ng/ml. Cells were incubated for 72 hrs at 37° C., 5% $CO_2$. After the incubation 100 µl Cell Titer Glo is added to each well to determine viable cells. The assay was performed according to the manufacturer's instruction (Promega Corporation, Madison, Wis. USA). Each experimental condition was performed in triplicate. Raw data was imported in Abase and $EC_{50}$s calculated with XL-fit data analysis software. Relative light units of wells that contained cells without MCSF in the media and as a consequence didn't grow were defined as 100% inhibited.

Biological Example 7

Tumor Induced Osteolysis Model

Tumor-induced osteolysis (TIO) models have been shown to recapitulate gross bone destruction seen in cancer patients with osteolytic tumor metastasis and have been reported extensively in both the bisphosphonate literature and in conjunction with the testing of novel anti-osteolytic agents. Results from these studies correlate well with human clinical activity (Kim S-J et al., 2005, Canc. Res., 65(9): 3707; Corey, E et al., 2003, Clin. Canc. Res., 9:295; Alvarez, E. et al., 2003, Clin. Canc. Res., 9: 5705). The procedure includes injection of tumor cells directly into the proximal tibia. Once the cells are established, they proliferate and secrete factors that potentiate osteoclast activity, resulting in trabecular and cortical bone resorption. Animals are treated with anti-resorptive agents following tumor cell implantation and bone destruction is measured in a number of ways at the end of the study.

The tumor cell lines utilized in this protocol are of human origin and represent tumor lines that have been previously modified such that they now express the enzyme Luciferase in order to track tumor cells in the animal using the Xenogen system. The strength of the light signal also gives an indication of approximately how many tumor cells are located at a particular site.

Mice are injected subcutaneously with either 2.5 mg/kg flunixin meglumine 30 minutes prior to cell inoculation to provide post-procedural analgesia. The mice are then be anesthetized by isoflurane inhalation (ketamine/xylazine injection may be used if isoflurane is not available). Anesthetized animals are placed in the supine position and following tumor cell aspiration into a 50 or 100 µl micro-syringe fitted with a 26- or 27-gauge needle, the needle will be inserted through the cortex of the anterior tuberosity of the right tibia with a rotating "drill-like" movement to minimize the chance for cortical fracture. Successful passage of the needle through the cortex and into the marrow is indicated by loss of resistance against the forward movement of the needle. Once the bone cortex is traversed, 10-20 µl of cell suspension (6×10^5 MDA-MB-231Luc breast carcinoma or 3×10^5 PC-3MLuc prostate carcinoma cells) will be injected into the tibia bone marrow. Animals will be observed to ensure uneventful recovery (warming pad or lamp) until they have recovered from anesthesia.

Progression of tumor growth in the bone can be divided into five stages (Stages 0-4). The stages are defined as follows and can be monitored by comparison to the uninjected (left) leg of the mouse:

Stage 0: normal, no sign of any change in the bone.
Stage 1: Equivocal or minimal lesion; cortex/architecture normal.
Stage 2: Definite lesion; minimal cortex/architecture disruption.
Stage 3: Large lesion; cortex/architecture disruption.
Stage 4: Gross destruction; no preservation of architecture, "late stage". Animals reaching this stage will be taken off the study and euthanized.

Photon imaging of the legs are used to assess the tumor growth at the injection and remote sites during study using the Xenogen system to quantitate tumor cells in the tibia and confirm lack of leakage into other areas. Radiograms of the legs are taken up to once a week through the end of the study using Faxitron X-ray Unit to assess cortical bone destruction at the injection site. While using more invasive cell lines such as the PC-3M-Luc, we monitor bone damage one to two weeks after injection and weekly thereafter. For cell lines that form lesions at a slower rate, such as the MDA-MB-231Luc, which does not manifest bone damage until 4-5 weeks post-implantation, first radiographic images are taken approximately 4 weeks after animals have been intratibially implanted with cells to establish baseline controls and then once a week to measure bone damage starting at a time point when lesions begin to develop based on model development pilot studies. For example, in mice injected with MDA-MB-231Luc, an image would be taken approximately 4 weeks post-implantation, with weekly images thereafter.

Animals may be dosed with small molecules, monoclonal antibodies, or proteins once or twice daily, by any standard routes.

The endpoint of this study is the time point at which the majority of untreated (negative control) animals have reached late stage disease (Stage 4) and have been euthanized. At that point, the remaining animals in the study are euthanized, regardless of the stage of their tumors. Studies last approximately 5-10 weeks depending on the cell line. After the final x-ray is taken, blood is drawn from the animals by cardiac puncture (for assaying serum bone markers; see below). Endpoint x-ray images are then distributed to 5 volunteers who score each image according to the scoring system detailed above. Scores for each mouse are averaged and expressed as mean osteolytic score or percent of animals with severe osteolysis (animals with scores greater than 2).

Biological Example 8

Mouse Trap5b Assay (IDS Inc., Fountain Hills, Ariz.)

This assay is a solid phase immunofixed enzyme activity assay for the determination of osteoclast-derived tartrate-resistant acid phosphatase 5b in mouse serum samples. Trap5b is expressed by bone resorbing osteoclasts and secreted into the circulation. Thus, serum Trap5b is considered to be a useful marker of osteoclast activity, number and bone resorption.

The mouse Trap5b assay uses a polyclonal antibody prepared using recombinant mouse Trap5b as antigen. In the test, the antibody is incubated in anti-rabbit IgG-coated microtiter wells. After washing, standard, controls and diluted serum samples are incubated in the wells, and bound Trap5b activity is determined with a chromogenic substrate to develop color. The reaction is stopped and the absorbance of the reaction mixture read in a microtiter plate reader at 405 nm. Color intensity is directly proportional to the amount and activity of Trap5b present in the sample. By plotting the mean absorbance for each standard on the ordinate against concentration on the abscissa, values for unknown samples can be read from the standard curve and expressed in U/L Trap5b. Analytical sensitivity of the assay is 0.1 U/L and inter- and intra-assay variation are below 10%. Trap5b levels were found to correlate well with mean osteolytic score (assessed by x-ray).

While a number of preferred embodiments of the invention and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

The percent inhibition activities of the compounds of Tables 2, 3, and 4 when tested at about 1 µM in the indicated assay as described in the Biological Examples are shown respectively in Tables 5, 6, and 7. It is contemplated that compounds having 0% inhibition at 1 µM will exhibit inhibitory activities at a higher concentration. An "N/D" means that the compound was not tested in the particular assay.

TABLE 5

Activities of the compounds of Table 2

| Cmpd | PDGFRβ | CSF-1R | cKit | M-NFS-60 CP | pCSF1R |
|---|---|---|---|---|---|
| 1 | N/D | 99 | N/D | 21 | N/D |
| 2 | N/D | 100 | N/D | 63 | 80 |
| 3 | N/D | 96 | N/D | 0 | N/D |
| 4 | N/D | 100 | N/D | 100 | 91 |
| 5 | N/D | 99 | N/D | 100 | 93 |
| 6 | N/D | 85 | N/D | N/D | N/D |
| 7 | N/D | 94 | N/D | 17 | 21 |
| 8 | N/D | 99 | N/D | 60 | 92 |
| 9 | N/D | 99 | N/D | 58 | 75 |
| 10 | 35 | 99 | N/D | 62 | 79 |
| 11 | 96 | 99 | N/D | 26 | N/D |
| 12 | 12 | 99 | N/D | 30 | N/D |
| 13 | 65 | 99 | N/D | 76 | 75 |
| 14 | 85 | 99 | N/D | 56 | 71 |
| 15 | 88 | 100 | N/D | 97 | 92 |
| 16 | 20 | 99 | N/D | 25 | 81 |
| 17 | 10 | 100 | 85 | 81 | 94 |
| 18 | 35 | 100 | N/D | 91 | 74 |
| 19 | 2 | 100 | N/D | 36 | N/D |
| 20 | 0 | 15 | N/D | N/D | N/D |
| 21 | 0 | 99 | N/D | 55 | 65 |
| 22 | 0 | 21 | N/D | N/D | N/D |
| 23 | 0 | 50 | N/D | N/D | N/D |
| 24 | 20 | 99 | N/D | 12 | N/D |
| 25 | 7 | 98 | N/D | 42 | 35 |
| 26 | 100 | 98 | N/D | 24 | N/D |
| 27 | 28 | 99 | N/D | 97 | 96 |
| 28 | 98 | 99 | N/D | 98 | 88 |
| 29 | 51 | 99 | N/D | 0 | N/D |
| 30 | 14 | 25 | N/D | N/D | N/D |
| 31 | N/D | 100 | 18 | 57 | 79 |
| 32 | 22 | 100 | N/D | 70 | 93 |
| 33 | 35 | 98 | N/D | 35 | 83 |
| 34 | 89 | 99 | N/D | 68 | 65 |
| 35 | 9 | 19 | N/D | N/D | N/D |
| 36 | 6 | 78 | 0 | N/D | N/D |
| 37 | 16 | 79 | N/D | N/D | N/D |
| 38 | 14 | 34 | N/D | N/D | N/D |
| 39 | 10 | 67 | N/D | N/D | N/D |
| 40 | 6 | 99 | N/D | 0 | N/D |
| 41 | 30 | 100 | N/D | 100 | 94 |
| 42 | 12 | 99 | N/D | 100 | 97 |
| 43 | 15 | 26 | N/D | N/D | N/D |
| 44 | 15 | 37 | N/D | N/D | N/D |
| 45 | 14 | 11 | N/D | N/D | N/D |
| 46 | 15 | 94 | N/D | 1 | N/D |
| 47 | 12 | 13 | N/D | N/D | N/D |
| 48 | 0 | 84 | N/D | 0 | N/D |
| 49 | 25 | 55 | 63 | N/D | N/D |
| 50 | 8 | 56 | 59 | N/D | N/D |
| 51 | 2 | 95 | 40 | N/D | N/D |
| 52 | 50 | 100 | 12 | 56 | 71 |
| 53 | 0 | 95 | 21 | N/D | N/D |
| 54 | 7 | 100 | 17 | 64 | 60 |
| 55 | 11 | 97 | 21 | N/D | N/D |
| 56 | 0 | 66 | 55 | N/D | N/D |
| 57 | 3 | 97 | 35 | 35 | N/D |
| 58 | 85 | 98 | 48 | 30 | N/D |
| 59 | 0 | 97 | 21 | N/D | N/D |
| 60 | 2 | 92 | 6 | N/D | N/D |
| 61 | 0 | 94 | 74 | 35 | N/D |
| 62 | 5 | 19 | 7 | N/D | N/D |
| 63 | 3 | 45 | 6 | N/D | N/D |
| 64 | 21 | 77 | 0 | N/D | N/D |
| 65 | 38 | 99 | 98 | 100 | 97 |
| 66 | 37 | 100 | 55 | 18 | 37 |
| 67 | 1 | 97 | 8 | 10 | 0 |
| 68 | 3 | 99 | 6 | 18 | N/D |
| 69 | 0 | 100 | 0 | 0 | N/D |
| 70 | 0 | 99 | 0 | 0 | N/D |
| 71 | 0 | 100 | 27 | 11 | N/D |
| 72 | 0 | 100 | 65 | 48 | N/D |
| 73 | 2 | 100 | 21 | 0 | N/D |
| 74 | 31 | 100 | 34 | 14 | N/D |
| 75 | 0 | 99 | 7 | 0 | N/D |
| 76 | 0 | 98 | 9 | 0 | N/D |
| 77 | 15 | 100 | 92 | 79 | 94 |
| 78 | 0 | 87 | 9 | N/D | N/D |
| 79 | 0 | 100 | 31 | 57 | 94 |
| 80 | 0 | 87 | 7 | N/D | N/D |

TABLE 5-continued

Activities of the compounds of Table 2

| Cmpd | PDGFRβ | CSF-1R | cKit | M-NFS-60 CP | pCSF1R |
|---|---|---|---|---|---|
| 81 | 0 | 54 | 16 | N/D | N/D |
| 82 | 0 | 46 | 9 | N/D | N/D |
| 83 | 0 | 99 | 12 | 26 | N/D |
| 84 | 0 | 99 | 12 | 32 | 44 |
| 85 | N/D | 99 | 79 | 100 | 98 |
| 87 | N/D | 99 | 42 | 21 | N/D |
| 88 | N/D | 100 | 98 | 100 | 96 |
| 90 | N/D | 99 | 22 | 18 | N/D |
| 91 | N/D | 99 | 93 | 87 | 97 |
| 92 | N/D | 99 | 98 | 17 | N/D |
| 94 | N/D | 99 | 14 | 28 | N/D |
| 95 | 8 | 98 | 40 | N/D | N/D |
| 96 | 3 | 99 | 33 | 75 | 89 |
| 97 | 5 | 99 | 99 | 67 | 84 |
| 98 | 0 | 26 | 7 | N/D | N/D |
| 99 | 9 | 63 | 12 | N/D | N/D |
| 100 | 9 | 99 | 10 | N/D | N/D |
| 101 | 91 | 99 | 85 | 85 | 91 |
| 102 | 0 | 83 | 14 | N/D | N/D |
| 103 | 14 | 60 | 8 | N/D | N/D |
| 104 | 10 | 99 | 18 | 47 | 63 |
| 105 | 8 | 99 | 22 | 49 | 70 |
| 106 | 0 | 99 | 2 | N/D | N/D |
| 107 | 0 | 67 | 8 | N/D | N/D |
| 108 | 40 | 99 | 100 | 100 | 98 |
| 109 | 75 | 100 | 53 | 81 | 90 |
| 110 | 8 | 85 | 16 | N/D | N/D |
| 111 | 2 | 25 | 15 | N/D | N/D |
| 112 | 5 | 28 | 0 | N/D | N/D |
| 113 | 17 | 97 | 7 | 19 | N/D |
| 114 | 15 | 100 | 92 | 36 | N/D |
| 115 | 18 | 99 | 88 | 21 | N/D |
| 116 | 18 | 100 | 100 | 10 | N/D |
| 117 | 0 | 100 | 96 | 61 | 88 |
| 118 | 49 | 100 | 95 | 83 | 69 |
| 119 | 32 | 99 | 18 | 13 | N/D |
| 120 | 0 | 75 | 5 | N/D | N/D |
| 121 | 30 | 100 | 9 | 17 | N/D |
| 122 | 0 | 100 | 53 | 19 | N/D |
| 123 | 2 | 99 | 15 | 0 | N/D |
| 124 | 0 | 99 | 32 | 51 | 94 |
| 125 | 0 | 100 | 35 | 44 | 45 |
| 126 | 99 | 68 | 83 | N/D | N/D |
| 127 | 20 | 100 | 81 | 95 | 95 |
| 128 | 83 | 100 | 90 | 95 | 95 |
| 129 | 34 | 99 | 92 | 94 | 92 |
| 130 | 25 | 99 | 87 | 72 | 85 |
| 131 | 55 | 99 | 96 | 100 | 98 |
| 132 | 58 | 99 | 98 | 100 | 98 |
| 133 | 3 | 99 | 53 | 45 | 92 |
| 134 | 0 | 98 | 98 | 93 | 93 |
| 135 | 20 | 100 | 68 | 96 | 91 |
| 136 | 84 | 100 | 88 | 100 | 97 |
| 137 | 98 | 100 | 45 | 100 | 98 |
| 138 | 93 | 99 | 93 | 100 | 88 |
| 139 | 0 | 100 | 21 | 48 | 94 |
| 140 | 0 | 100 | 92 | 52 | 90 |
| 141 | 0 | 100 | 1 | 22 | N/D |
| 142 | 97 | 99 | 98 | 100 | 88 |
| 143 | 4 | 99 | 33 | 97 | 91 |
| 144 | 100 | 99 | 100 | 100 | N/D |
| 145 | 25 | 99 | 34 | 100 | 98 |
| 146 | 3 | 99 | 5 | 56 | 86 |
| 147 | 0 | 98 | 90 | 90 | 97 |
| 148 | 100 | 99 | 99 | 100 | 98 |
| 149 | 0 | 99 | 4 | 67 | 92 |
| 150 | 1 | 99 | 34 | 49 | 87 |
| 151 | 0 | 99 | 5 | 26 | N/D |
| 152 | 82 | 99 | 100 | 100 | 98 |
| 153 | 91 | 97 | 0 | 63 | N/D |
| 154 | 18 | 99 | 17 | 48 | 93 |
| 155 | 8 | 87 | 0 | N/D | N/D |
| 156 | 41 | 100 | 27 | 63 | 16 |
| 157 | 20 | 100 | 20 | 100 | 99 |
| 158 | 2 | 99 | 11 | 1 | N/D |
| 159 | 1 | 99 | 12 | 17 | N/D |
| 160 | 18 | 99 | 13 | 30 | N/D |
| 161 | 94 | 100 | 0 | 38 | N/D |

TABLE 6

Activities of the compounds of Table 3

| Cmpd | PDGFRβ | CSF-1R | cKit | M-NFS-60 CP | pCSF1R |
|---|---|---|---|---|---|
| 1 | 7 | 100 | 36 | 34 | N/D |
| 2 | 18 | 100 | 64 | N/D | N/D |
| 3 | 0 | 100 | 14 | 89 | 72 |
| 4 | 14 | 99 | 0 | 15 | N/D |
| 5 | 29 | 100 | 0 | 76 | 79 |
| 6 | 29 | 100 | 61 | 65 | 74 |
| 7 | 9 | 100 | 12 | 35 | N/D |
| 8 | 31 | 95 | 99 | 0 | N/D |
| 9 | 84 | 100 | 14 | 2 | N/D |
| 10 | 9 | 67 | 0 | N/D | N/D |
| 11 | 60 | 100 | 0 | 69 | 92 |
| 12 | 1 | 95 | 0 | N/D | N/D |
| 13 | 0 | 93 | 9 | N/D | N/D |
| 14 | 0 | 96 | 3 | N/D | N/D |
| 15 | 7 | 99 | 15 | 4 | N/D |
| 16 | 9 | 99 | 12 | 30 | N/D |
| 17 | 12 | 99 | 19 | 23 | N/D |
| 18 | 23 | 99 | 80 | 22 | N/D |
| 19 | 0 | 96 | 8 | 23 | N/D |
| 20 | 0 | 76 | 0 | N/D | N/D |
| 21 | 7 | 100 | 64 | 11 | N/D |
| 22 | 21 | 100 | 6 | 36 | N/D |
| 23 | 20 | 57 | 48 | 34 | N/D |
| 24 | 8 | 100 | 40 | 65 | 80 |
| 25 | 33 | 99 | 65 | 13 | N/D |
| 26 | 8 | 100 | 18 | 37 | N/D |
| 27 | 13 | 100 | 38 | 71 | 95 |
| 28 | 6 | 100 | 20 | 53 | 83 |
| 29 | 12 | 100 | 64 | 48 | 72 |
| 30 | 12 | 100 | 25 | 28 | N/D |
| 31 | 20 | 100 | 50 | 57 | 84 |
| 32 | 11 | 100 | 45 | 65 | 93 |
| 33 | 2 | 100 | 18 | 54 | 66 |
| 34 | 0 | 100 | 21 | 43 | 62 |
| 35 | 24 | 100 | 59 | 56 | 57 |
| 36 | 24 | 100 | 73 | 85 | 80 |
| 37 | 0 | 55 | 19 | N/D | N/D |
| 38 | 21 | 99 | 99 | N/D | N/D |
| 39 | 5 | 100 | 60 | 76 | 61 |
| 40 | 18 | 100 | 92 | 90 | 92 |
| 41 | 0 | 94 | 52 | N/D | N/D |
| 42 | 6 | 100 | 4 | 44 | 87 |
| 43 | 18 | 100 | 8 | 100 | 98 |
| 44 | 98 | 100 | 87 | 100 | 99 |
| 45 | 11 | 99 | 35 | 58 | 66 |
| 46 | 30 | 55 | 46 | N/D | N/D |
| 47 | 4 | 100 | 0 | 55 | 83 |
| 48 | 16 | 99 | 14 | 26 |  |
| 49 | 12 | 100 | 21 | 33 | 77 |
| 50 | 14 | 99 | 13 | 18 | N/D |
| 51 | 0 | 95 | 10 | N/D | N/D |
| 52 | 47 | 100 | 61 | 47 | N/D |
| 53 | 96 | 100 | 100 | 100 | N/D |
| 54 | 65 | 100 | 40 | 39 | N/D |
| 55 | 46 | 100 | 40 | 42 | 53 |
| 56 | 8 | 96 | 20 | 13 | N/D |
| 57 | 19 | 95 | 38 | N/D | N/D |
| 58 | 93 | 100 | 96 | 100 | N/D |
| 59 | 0 | 98 | 12 | 5 | 28 |
| 60 | 4 | 69 | 0 | N/D | N/D |
| 61 | 12 | 95 | 3 | N/D | N/D |
| 62 | 0 | 99 | 14 | 3 | 56 |

TABLE 6-continued

Activities of the compounds of Table 3

| Cmpd | PDGFRβ | CSF-1R | cKit | M-NFS-60 CP | pCSF1R |
|---|---|---|---|---|---|
| 63 | 7 | 100 | 1 | 28 | 44 |
| 64 | 0 | 100 | 1 | 16 | 49 |
| 65 | 0 | 87 | 1 | N/D | N/D |
| 66 | 0 | 89 | 13 | N/D | N/D |
| 67 | 0 | 55 | 7 | N/D | N/D |
| 68 | 0 | 96 | 17 | 19 | 54 |
| 69 | 0 | 90 | 6 | N/D | N/D |
| 70 | 5 | 94 | 16 | N/D | N/D |
| 71 | 1 | 75 | 13 | N/D | N/D |
| 72 | 0 | 95 | 8 | N/D | N/D |
| 73 | 5 | 96 | 13 | N/D | N/D |
| 74 | 4 | 79 | 3 | N/D | N/D |
| 75 | 2 | 76 | 11 | N/D | N/D |
| 76 | 0 | 64 | 5 | N/D | N/D |
| 77 | 2 | 88 | 7 | N/D | N/D |
| 78 | 8 | 88 | 11 | N/D | N/D |
| 79 | 0 | 99 | 6 | 22 | 34 |
| 80 | 14 | 99 | 0 | 8 | 19 |
| 81 | 6 | 100 | 71 | 9 | 18 |
| 82 | 0 | 100 | 31 | 50 | 92 |
| 83 | 3 | 100 | 8 | 28 | 62 |
| 84 | 14 | 100 | 45 | 80 | 90 |
| 85 | 0 | 99 | 8 | 24 | 46 |
| 86 | 32 | 63 | 15 | N/D | N/D |
| 87 | 5 | 99 | 30 | 20 | 6 |
| 88 | 1 | 67 | 12 | N/D | N/D |
| 89 | 2 | 100 | 15 | 15 | 65 |
| 90 | 42 | 100 | 64 | 97 | 96 |
| 91 | 83 | 100 | 86 | 100 | 96 |
| 92 | 25 | 100 | 97 | 100 | 97 |
| 93 | 0 | 100 | 12 | 23 | 47 |
| 94 | 9 | 100 | 90 | 17 | 38 |
| 95 | 2 | 100 | 0 | 60 | 65 |
| 96 | 0 | 70 | 29 | N/D | N/D |
| 97 | 0 | 100 | 7 | 50 | 59 |
| 98 | 0 | 60 | 6 | N/D | N/D |
| 99 | 0 | 86 | 0 | N/D | N/D |
| 100 | 6 | 81 | 0 | N/D | N/D |
| 101 | 0 | 99 | 5 | 20 | N/D |
| 102 | 9 | 100 | 0 | 75 | 88 |
| 103 | 7 | 95 | 0 | N/D | N/D |
| 104 | 0 | 86 | 0 | N/D | N/D |
| 105 | 6 | 100 | 7 | 31 | N/D |
| 107 | 99 | 100 | 19 | 100 | 96 |
| 108 | 4 | 100 | 10 | 70 | 94 |
| 109 | 16 | 100 | 13 | 67 | N/D |
| 110 | 0 | 98 | 0 | 34 | N/D |
| 111 | 71 | 100 | 76 | 100 | 98 |
| 112 | 5 | 100 | 8 | 46 | 90 |
| 113 | 0 | 97 | 6 | 14 | N/D |
| 114 | 0 | 100 | 4 | 86 | 97 |
| 115 | 55 | 100 | 18 | 97 | 82 |
| 116 | 0 | 100 | 21 | 41 | N/D |
| 117 | 48 | 100 | 70 | 63 | 92 |
| 118 | 25 | 100 | 18 | 71 | 67 |
| 119 | 0 | 94 | 1 | N/D | N/D |
| 120 | 0 | 65 | 0 | N/D | N/D |
| 121 | 0 | 61 | 4 | N/D | N/D |
| 122 | 0 | 67 | 0 | N/D | N/D |
| 123 | 0 | 62 | 1 | N/D | N/D |
| 124 | 10 | 99 | 0 | 18 | N/D |
| 125 | 9 | 99 | 2 | 17 | N/D |
| 126 | 83 | 100 | 36 | 100 | 97 |
| 127 | 0 | 95 | 0 | N/D | N/D |
| 128 | 20 | 100 | 29 | 82 | 88 |
| 129 | 99 | 100 | 99 | N/D | N/D |
| 130 | 70 | 100 | 90 | 79 | N/D |
| 131 | 23 | 100 | 35 | 98 | 96 |
| 132 | 30 | 80 | 18 | N/D | N/D |
| 133 | 14 | 67 | 19 | N/D | N/D |
| 134 | 13 | 53 | 11 | N/D | N/D |
| 135 | 11 | 75 | 21 | N/D | N/D |
| 136 | 0 | 86 | 3 | N/D | N/D |
| 137 | 2 | 71 | 8 | N/D | N/D |
| 138 | 37 | 100 | 100 | 105 | N/D |
| 139 | 19 | 100 | 24 | 46 | 88 |
| 140 | 100 | 100 | 27 | 25 | N/D |
| 141 | 80 | 100 | 100 | 100 | 99 |
| 142 | 84 | 100 | 100 | 97 | 96 |
| 143 | 22 | 100 | 63 | 80 | 90 |
| 144 | 12 | 100 | 38 | 41 | N/D |
| 145 | 33 | 100 | 39 | 58 | 86 |
| 146 | 8 | 100 | 24 | 32 | N/D |
| 147 | 100 | 100 | 93 | 100 | 97 |
| 148 | 2 | 96 | 23 | 1 | N/D |
| 149 | 21 | 100 | 29 | 48 | N/D |
| 150 | 2 | 100 | 24 | 22 | N/D |
| 151 | 38 | 100 | 46 | 43 | N/D |
| 152 | 21 | 97 | 25 | 13 | N/D |
| 153 | 23 | 97 | 17 | 15 | N/D |
| 154 | 95 | 100 | 96 | 86 | 83 |
| 155 | 18 | 99 | 34 | 0 | N/D |
| 156 | 3 | 100 | 36 | 33 | N/D |
| 157 | 17 | 100 | 43 | 42 | N/D |
| 158 | 1 | 99 | 27 | 0 | N/D |
| 159 | 23 | 100 | 29 | 98 | 96 |
| 160 | 19 | 100 | 95 | 30 | N/D |
| 161 | 26 | 54 | 20 | N/D | N/D |
| 162 | 30 | 100 | 20 | 100 | 99 |
| 163 | 39 | 100 | 32 | 100 | 99 |
| 164 | 87 | 100 | 79 | 100 | 100 |
| 165 | 83 | 100 | 83 | 100 | 98 |
| 166 | 0 | 100 | 13 | 49 | 78 |
| 167 | 0 | 100 | 16 | 24 | N/D |
| 168 | 43 | 100 | 40 | 100 | 99 |
| 169 | 0 | 75 | 12 | N/D | N/D |
| 170 | 23 | 100 | 28 | 100 | 96 |
| 171 | 18 | 100 | 25 | 96 | 95 |
| 172 | 18 | 100 | 22 | 100 | 97 |
| 173 | 8 | 100 | 18 | 52 | 81 |
| 174 | 3 | 86 | 18 | N/D | N/D |
| 175 | 1 | 100 | 11 | 17 | N/D |
| 176 | 0 | 63 | 12 | N/D | N/D |
| 177 | 0 | 67 | 15 | N/D | N/D |
| 178 | −3 | 82 | 17 | N/D | N/D |
| 179 | 16 | 98 | 10 | 27 | N/D |
| 180 | 12 | 100 | 23 | 96 | 93 |
| 181 | 17 | 72 | 27 | N/D | N/D |
| 182 | 4 | 100 | 16 | 100 | 98 |
| 183 | 99 | 100 | 100 | 100 | 98 |
| 184 | 84 | 100 | 45 | 100 | 95 |
| 185 | 29 | 100 | 32 | 100 | 94 |
| 186 | 14 | 100 | 13 | 100 | 99 |
| 187 | 25 | 100 | 32 | 100 | 98 |
| 188 | 35 | 100 | 55 | 38 | N/D |
| 189 | 23 | 100 | 31 | 26 | N/D |
| 190 | 19 | 98 | 22 | 5 | N/D |
| 191 | 15 | 45 | 19 | N/D | N/D |
| 192 | 22 | 99 | 56 | 14 | N/D |
| 193 | 15 | 95 | 27 | 0 | N/D |
| 194 | 16 | 77 | 20 | N/D | N/D |
| 195 | 25 | 81 | 90 | N/D | N/D |
| 196 | 23 | 100 | 29 | 100 | 98 |
| 197 | 89 | 100 | 93 | 100 | 98 |
| 198 | 39 | 100 | 48 | 100 | 94 |
| 199 | 81 | 100 | 61 | 100 | 97 |
| 200 | 19 | 100 | 29 | 69 | 83 |
| 201 | 22 | 52 | 17 | N/D | N/D |
| 202 | 19 | 100 | 32 | 17 | N/D |
| 203 | 15 | 98 | 22 | 20 | N/D |
| 204 | 74 | 100 | 92 | 85 | N/D |
| 205 | 39 | 100 | 24 | 96 | 93 |
| 206 | 98 | 100 | 100 | 100 | N/D |
| 207 | 72 | 100 | 36 | 100 | 98 |
| 208 | 80 | 100 | 99 | 83 | N/D |
| 209 | 1 | 100 | 17 | 36 | N/D |
| 210 | 26 | 100 | 19 | 26 | N/D |
| 211 | 50 | 100 | 85 | 23 | N/D |
| 212 | 28 | 100 | 37 | 97 | 94 |
| 213 | 0 | 100 | 30 | 34 | N/D |

TABLE 6-continued

Activities of the compounds of Table 3

| Cmpd | PDGFRβ | CSF-1R | cKit | M-NFS-60 CP | pCSF1R |
|---|---|---|---|---|---|
| 214 | 13 | 100 | 30 | 60 | 76 |
| 215 | 80 | 100 | 100 | 86 | N/D |
| 216 | 45 | 100 | 59 | 98 | 93 |
| 217 | 23 | 99 | 16 | 0 | N/D |
| 218 | 23 | 100 | 28 | 16 | N/D |
| 219 | 85 | 100 | 97 | 53 | N/D |
| 220 | 65 | 100 | 48 | 84 | 91 |
| 221 | 88 | 100 | 97 | 52 | N/D |
| 222 | 69 | 100 | 52 | 91 | 68 |
| 223 | 28 | 100 | 54 | 100 | 97 |
| 224 | 0 | 100 | 26 | 33 | N/D |
| 225 | 0 | 90 | 21 | N/D | N/D |
| 226 | 0 | 80 | 20 | N/D | N/D |
| 227 | 47 | 100 | 100 | 65 | N/D |
| 228 | 26 | 100 | 70 | 32 | N/D |
| 229 | 30 | 100 | 21 | 80 | 92 |
| 230 | 14 | 100 | 6 | 58 | 65 |
| 231 | 49 | 100 | 9 | 100 | 99 |
| 232 | 64 | 100 | 34 | 100 | 99 |
| 233 | 84 | 100 | 85 | 59 | N/D |
| 234 | 56 | 100 | 64 | 78 | N/D |
| 235 | 81 | 100 | 100 | 100 | N/D |
| 236 | 97 | 100 | 100 | 100 | N/D |
| 237 | 13 | 100 | 24 | 100 | 94 |
| 238 | 90 | 100 | 100 | 100 | N/D |
| 239 | 25 | 100 | 100 | 90 | N/D |
| 240 | 16 | 100 | 21 | 66 | 71 |
| 241 | 23 | 100 | 25 | 51 | 65 |
| 242 | 35 | 100 | 97 | 51 | N/D |
| 243 | 69 | 100 | 100 | 76 | N/D |
| 244 | 35 | 100 | 25 | 67 | 85 |
| 245 | 21 | 100 | 16 | 53 | 81 |
| 246 | 82 | 100 | 100 | 100 | N/D |
| 247 | 80 | 100 | 100 | 100 | N/D |
| 248 | 41 | 100 | 33 | 51 | 39 |
| 249 | 0 | 100 | 69 | 100 | N/D |
| 250 | 0 | 97 | 98 | 20 | N/D |
| 251 | 28 | 100 | 56 | 80 | 74 |
| 252 | 6 | 100 | 100 | 81 | N/D |
| 253 | 6 | 100 | 100 | 86 | N/D |
| 254 | 0 | 100 | 98 | 100 | N/D |
| 255 | 8 | 100 | 92 | 69 | N/D |
| 256 | 3 | 100 | 71 | 87 | 87 |
| 257 | 11 | 100 | 100 | 100 | N/D |
| 258 | 62 | 100 | 44 | 100 | 99 |
| 259 | 6 | 100 | 24 | 100 | 98 |
| 260 | 0 | 100 | 25 | 100 | 98 |
| 261 | 30 | 100 | 25 | 100 | 98 |
| 262 | 3 | 100 | 20 | 46 | 48 |
| 263 | 0 | 99 | 12 | 22 | 24 |
| 264 | 4 | 97 | 25 | 3 | N/D |
| 265 | 12 | 100 | 9 | 32 | N/D |
| 266 | 21 | 100 | 18 | 100 | 94 |
| 267 | 26 | 100 | 16 | 100 | 96 |
| 268 | 29 | 100 | 25 | 84 | 87 |
| 269 | 13 | 100 | 18 | 75 | 85 |
| 270 | 11 | 98 | 21 | 50 | 74 |
| 271 | 24 | 98 | 46 | 54 | 55 |
| 272 | 7 | 98 | 24 | 38 | N/D |
| 273 | 14 | 100 | 41 | 95 | 88 |
| 274 | 12 | 100 | 28 | 76 | 82 |
| 275 | 16 | 100 | 45 | 89 | 94 |
| 276 | 26 | 100 | 39 | 100 | 97 |
| 277 | 5 | 100 | 26 | 24 | N/D |
| 278 | 12 | 100 | 38 | 82 | 75 |
| 279 | 7 | 100 | 30 | 60 | 59 |
| 280 | 22 | 100 | 11 | 100 | 65 |
| 281 | 36 | 100 | 22 | 100 | 96 |
| 282 | 7 | 99 | 23 | 22 | N/D |
| 283 | 20 | 99 | 38 | 0 | N/D |
| 284 | 53 | 100 | 61 | 100 | N/D |
| 285 | 8 | 99 | 33 | 0 | N/D |
| 286 | 0 | 100 | 23 | 71 | 94 |
| 287 | 20 | 100 | 57 | 35 | N/D |
| 288 | 24 | 100 | 78 | 70 | N/D |
| 289 | 2 | 99 | 28 | 0 | N/D |
| 290 | 15 | 100 | 10 | 2 | N/D |
| 291 | 0 | 48 | 4 | N/D | N/D |
| 292 | 0 | 95 | 3 | N/D | N/D |
| 293 | 0 | 100 | 22 | 67 | 82 |
| 294 | 0 | 87 | 1 | N/D | N/D |
| 295 | 0 | 85 | 5 | N/D | N/D |
| 296 | 9 | 97 | 1 | N/D | N/D |
| 297 | 9 | 98 | 0 | 42 | 90 |
| 298 | 0 | 98 | 13 | 41 | N/D |
| 299 | 57 | 100 | 32 | 94 | 95 |
| 300 | 0 | 99 | 2 | 14 | N/D |
| 301 | 7 | 55 | 0 | N/D | N/D |
| 302 | 0 | 68 | 20 | N/D | N/D |
| 303 | 12 | 74 | 24 | N/D | N/D |
| 304 | 18 | 100 | 9 | 23 | N/D |
| 305 | 7 | 87 | 15 | N/D | N/D |
| 306 | 0 | 99 | 6 | 48 | N/D |
| 307 | 6 | 90 | 15 | N/D | N/D |
| 308 | 27 | 100 | 51 | 54 | 81 |
| 309 | 13 | 74 | 6 | N/D | N/D |
| 310 | 13 | 15 | 13 | N/D | N/D |
| 311 | 88 | 93 | 22 | N/D | N/D |
| 312 | 14 | 76 | 0 | N/D | N/D |
| 313 | 2 | 52 | 23 | N/D | N/D |
| 314 | 12 | 99 | 13 | 20 | N/D |
| 315 | 0 | 98 | 17 | 27 | N/D |
| 316 | 12 | 99 | 8 | 41 | 98 |
| 317 | 12 | 100 | 70 | 50 | 95 |
| 318 | 13 | 100 | 47 | 24 | 78 |
| 319 | 24 | 100 | 93 | 61 | 91 |
| 320 | 20 | 100 | 16 | 25 | N/D |
| 321 | 41 | 100 | 52 | 82 | 97 |
| 322 | 11 | 99 | 18 | 21 | N/D |
| 323 | 24 | 100 | 25 | 100 | 98 |
| 324 | 19 | 99 | 21 | 15 | N/D |
| 325 | 43 | 100 | 27 | 66 | N/D |
| 326 | 7 | 65 | 44 | 33 | 81 |
| 327 | 0 | 47 | 6 | N/D | N/D |
| 328 | 0 | 100 | 14 | 63 | 80 |
| 329 | 17 | 100 | 59 | 84 | 92 |
| 330 | 8 | 99 | 41 | 58 | 50 |
| 331 | 10 | 100 | 41 | 68 | 79 |
| 332 | 10 | 48 | 38 | N/D | N/D |
| 333 | 6 | 86 | 21 | N/D | N/D |
| 334 | 15 | 100 | 20 | 67 | 71 |
| 335 | 0 | 100 | 21 | 57 | 50 |
| 336 | 14 | 94 | 23 | 17 | N/D |
| 337 | 0 | 95 | 14 | 19 | N/D |
| 338 | 52 | 100 | 51 | 44 | N/D |
| 339 | 69 | 100 | 66 | 66 | 84 |
| 340 | 98 | 100 | 100 | 100 | 96 |
| 341 | 88 | 100 | 99 | 99 | 96 |
| 342 | 61 | 100 | 84 | 75 | 87 |
| 343 | 28 | 100 | 59 | 57 | N/D |
| 344 | 65 | 100 | 45 | 100 | 95 |
| 345 | 13 | 100 | 19 | 97 | 93 |
| 346 | 0 | 100 | 13 | 67 | 84 |
| 347 | 58 | 100 | 37 | 100 | 99 |
| 348 | 55 | 100 | 47 | 100 | 90 |
| 349 | 73 | 100 | 77 | 100 | N/D |
| 350 | 91 | 100 | 100 | 100 | N/D |
| 351 | 79 | 100 | 98 | 100 | N/D |
| 352 | 74 | 100 | 45 | 100 | 97 |
| 353 | 100 | 100 | 100 | 100 | N/D |
| 354 | 98 | 100 | 100 | 100 | N/D |
| 355 | 27 | 100 | 27 | 100 | 99 |
| 356 | 99 | 100 | 100 | 100 | N/D |
| 357 | 44 | 100 | 91 | 100 | N/D |
| 358 | 99 | 100 | 100 | 100 | N/D |
| 359 | 19 | 100 | 31 | 95 | 93 |
| 360 | 16 | 100 | 29 | 100 | 98 |
| 361 | 75 | 100 | 100 | N/D | N/D |
| 362 | 92 | 100 | 99 | 100 | 100 |
| 363 | 99 | 100 | 100 | N/D | N/D |

TABLE 6-continued

Activities of the compounds of Table 3

| Cmpd | PDGFRβ | CSF-1R | cKit | M-NFS-60 CP | pCSF1R |
|---|---|---|---|---|---|
| 364 | 100 | 100 | 100 | N/D | N/D |
| 365 | 79 | 100 | 100 | 100 | 97 |
| 366 | 26 | 100 | 94 | 100 | 98 |
| 367 | 7 | 100 | 13 | 81 | 89 |
| 368 | 8 | 100 | 24 | 12 | N/D |
| 369 | 12 | 100 | 26 | 44 | N/D |
| 370 | 34 | 100 | 64 | 60 | 81 |
| 371 | 9 | 100 | 29 | 69 | 79 |
| 372 | 8 | 100 | 21 | 75 | 88 |
| 373 | 0 | 101 | 51 | 100 | 91 |
| 374 | 41 | 99 | 98 | 3 | N/D |
| 375 | 38 | 100 | 97 | 19 | N/D |
| 376 | 28 | 100 | 72 | 87 | 77 |
| 377 | 49 | 100 | 75 | 93 | N/D |
| 378 | 43 | 100 | 62 | 90 | 87 |
| 379 | 36 | 77 | 16 | N/D | N/D |
| 380 | 49 | 100 | 53 | 79 | 94 |
| 381 | 20 | 100 | 30 | 100 | 99 |

TABLE 7

Activities of the compounds of Table 4

| Cmpd | PDGFRβ | CSF-1R | cKit | M-NFS-60 CP | pCSF1R |
|---|---|---|---|---|---|
| 1 | 13 | 100 | 73 | 50 | 47 |
| 2 | 8 | 80 | 14 | N/D | N/D |
| 3 | 1 | 100 | 15 | 67 | 85 |
| 4 | 0 | 100 | 29 | 92 | 94 |
| 5 | 8 | 100 | 18 | 91 | 92 |
| 6 | 26 | 100 | 26 | 100 | 99 |
| 7 | 5 | 100 | 23 | 54 | N/D |
| 8 | 35 | 100 | 25 | 100 | 98 |
| 9 | 45 | 100 | 15 | 100 | 98 |
| 10 | 9 | 100 | 6 | 76 | 83 |
| 11 | 4 | 100 | 8 | 38 | N/D |
| 12 | 6 | 100 | 14 | 100 | 95 |
| 13 | 45 | 100 | 73 | N/D | N/D |
| 14 | 85 | 100 | 71 | N/D | N/D |
| 15 | 60 | 100 | 59 | 100 | 99 |
| 16 | 59 | 100 | 41 | 100 | 100 |
| 17 | 72 | 100 | 61 | 100 | 100 |
| 18 | 28 | 100 | 45 | 100 | 100 |
| 19 | 19 | 100 | 33 | 100 | 100 |
| 20 | 12 | 100 | 30 | 100 | 99 |
| 21 | 22 | 100 | 32 | N/D | N/D |
| 22 | 90 | 100 | 89 | N/D | N/D |
| 23 | 0 | 100 | 29 | 7 | N/D |
| 24 | 0 | 100 | 26 | 100 | 100 |
| 25 | 1 | 100 | 33 | 100 | 86 |
| 26 | 0 | 100 | 29 | 33 | N/D |
| 27 | 0 | 100 | 67 | N/D | N/D |
| 28 | 0 | 100 | 98 | N/D | N/D |
| 29 | 0 | 100 | 65 | 73 | 90 |
| 30 | 0 | 100 | 18 | 73 | 93 |
| 31 | 0 | 96 | 26 | N/D | N/D |
| 32 | 0 | 100 | 71 | N/D | N/D |
| 33 | 0 | 100 | 65 | 100 | 98 |
| 34 | 1 | 100 | 90 | N/D | N/D |
| 35 | 90 | 100 | 46 | 100 | 98 |
| 36 | 26 | 100 | 45 | 5 | N/D |
| 37 | 24 | 100 | 88 | N/D | N/D |
| 38 | 16 | 100 | 27 | 100 | 99 |
| 39 | 9 | 100 | 98 | N/D | N/D |
| 40 | 0 | 100 | 27 | 83 | 96 |
| 41 | 19 | 100 | 66 | 100 | 97 |
| 42 | 28 | 100 | 28 | 100 | 99 |
| 43 | 0 | 95 | 14 | N/D | N/D |
| 44 | 24 | 100 | 45 | 94 | 53 |
| 45 | 44 | 100 | 53 | 100 | 99 |
| 46 | 42 | 100 | 24 | 100 | 99 |
| 47 | 31 | 100 | 55 | 58 | 79 |

TABLE 7-continued

Activities of the compounds of Table 4

| Cmpd | PDGFRβ | CSF-1R | cKit | M-NFS-60 CP | pCSF1R |
|---|---|---|---|---|---|
| 48 | 98 | 100 | 79 | 100 | 100 |
| 49 | 1 | 100 | 11 | 100 | 99 |
| 50 | 14 | 100 | 10 | 100 | 99 |
| 51 | 78 | 100 | 36 | 100 | 100 |
| 52 | 42 | 100 | 27 | 100 | 100 |
| 53 | 14 | 100 | 12 | 100 | 99 |
| 54 | 1 | 100 | 11 | 100 | 99 |
| 55 | 2 | 100 | 11 | 100 | 95 |
| 56 | 11 | 100 | 13 | 100 | 99 |
| 57 | 11 | 100 | 15 | 100 | 99 |
| 58 | 0 | 100 | 11 | 100 | 95 |
| 59 | 27 | 100 | 25 | 100 | 99 |
| 60 | 0 | 100 | 9 | 100 | 99 |
| 61 | 23 | 100 | 3 | 100 | 98 |
| 62 | 27 | 100 | 5 | 97 | 97 |
| 63 | 21 | 100 | 10 | 100 | 99 |
| 64 | 16 | 100 | 7 | 91 | 96 |
| 65 | 21 | 100 | 6 | 100 | 98 |
| 66 | 28 | 100 | 12 | 100 | 99 |
| 67 | 42 | 100 | 97 | 100 | 98 |
| 68 | 100 | 100 | 57 | 100 | 99 |
| 69 | 28 | 100 | 12 | 100 | 99 |
| 70 | 86 | 100 | 26 | 100 | 100 |
| 71 | 25 | 100 | 5 | 73 | 95 |
| 72 | 20 | 100 | 6 | 65 | 95 |
| 73 | 20 | 100 | 3 | 56 | 96 |
| 74 | 22 | 100 | 0 | 60 | 97 |
| 75 | 10 | 99 | 0 | 0 | N/D |
| 76 | 15 | 100 | 8 | 95 | 96 |
| 77 | 25 | 100 | 6 | 100 | 99 |
| 78 | 71 | 100 | 7 | 100 | 100 |
| 79 | 28 | 100 | 2 | 99 | 99 |
| 80 | 25 | 100 | 0 | 46 | N/D |
| 81 | 18 | 100 | 4 | 87 | 97 |
| 82 | 24 | 100 | 2 | 92 | 99 |
| 83 | 36 | 100 | 7 | 100 | 99 |
| 84 | 30 | 100 | 11 | 100 | 97 |
| 85 | 53 | 100 | 13 | 100 | 53 |
| 86 | 25 | 99 | 22 | 85 | 60 |
| 87 | N/D | 100 | 19 | N/D | N/D |
| 88 | N/D | 100 | 14 | N/D | N/D |
| 89 | N/D | 100 | 18 | N/D | N/D |
| 90 | N/D | 100 | 18 | N/D | N/D |
| 91 | N/D | 100 | 17 | N/D | N/D |
| 92 | N/D | 100 | 15 | N/D | N/D |
| 93 | N/D | 99 | 5 | N/D | N/D |
| 94 | N/D | 100 | 12 | N/D | N/D |
| 95 | N/D | 100 | 42 | N/D | N/D |
| 96 | N/D | 100 | 7 | N/D | N/D |
| 97 | N/D | 100 | 14 | N/D | N/D |
| 98 | N/D | 100 | 8 | N/D | N/D |
| 99 | N/D | 100 | 0 | N/D | N/D |
| 100 | N/D | 100 | 5 | N/D | N/D |
| 101 | N/D | 100 | 10 | N/D | N/D |
| 102 | N/D | 100 | 18 | N/D | N/D |
| 103 | N/D | N/D | N/D | N/D | N/D |
| 104 | N/D | 100 | 4 | N/D | N/D |
| 105 | N/D | 100 | 10 | N/D | N/D |
| 106 | N/D | 100 | 17 | N/D | N/D |
| 107 | N/D | N/D | N/D | N/D | N/D |
| 108 | N/D | N/D | N/D | N/D | N/D |
| 109 | N/D | N/D | N/D | N/D | N/D |
| 110 | N/D | N/D | N/D | N/D | N/D |
| 111 | N/D | N/D | N/D | N/D | N/D |
| 112 | N/D | 100 | 11 | N/D | N/D |
| 113 | N/D | 92 | 10 | N/D | N/D |
| 114 | N/D | 100 | 6 | N/D | N/D |
| 115 | N/D | 95 | 12 | N/D | N/D |
| 116 | N/D | 100 | 13 | N/D | N/D |
| 117 | N/D | 100 | 11 | N/D | N/D |
| 118 | N/D | 100 | 11 | N/D | N/D |
| 119 | N/D | 95 | 16 | N/D | N/D |

The following references are cited in the specification.

Sherr, C. J., et al., *The c-fms proto-oncogene product is related to the receptor for the mononuclear phagocyte growth factor, CSF* 1. Cell, 1985. 41(3): p. 665-676.

Roussel, M. F., et al., *Transforming potential of the c-fms proto-oncogene (CSF-1 receptor)*. 1987. 326(6104): p. 549-552.

Lee, P. S., et al., *The Cbl protooncoprotein stimulates CSF-1 receptor multiubiquitination and endocytosis, and attenuates macrophage proliferation*. Embo J, 1999. 18(13): p. 3616-28.

Inaba, T., et al., *Expression of M-CSF receptor encoded by c-fms on smooth muscle cells derived from arteriosclerotic lesion*. J Biol Chem, 1992. 267(8): p. 5693-9.

Baker, A. H., et al., *Expression of the colony-stimulating factor 1 receptor in B lymphocytes*. Oncogene, 1993. 8(2): p. 371-8.

Sawada, M., et al., *Activation and proliferation of the isolated microglia by colony stimulating factor-1 and possible involvement of protein kinase C*. Brain Res, 1990. 509(1): p. 119-24.

Stanley, E. R., et al., *Biology and action of colony-stimulating factor-1*. Mol Reprod Dev, 1997. 46(1): p. 4-10.

Bourette, R. P. and L. R. Rohrschneider, *Early events in M-CSF receptor signaling*. Growth Factors, 2000, 17(3): p. 155-66.

Pollard, J. W., *Role of colony-stimulating factor-1 in reproduction and development*. Mol Reprod Dev, 1997. 46(1): p. 54-60; discussion 60-1.

Dai, X. M., et al., *Targeted disruption of the mouse colony-stimulating factor 1 receptor gene results in osteopetrosis, mononuclear phagocyte deficiency, increased primitive progenitor cell frequencies, and reproductive defects*. Blood, 2002. 99(1): p. 111-20.

Scholl, S. M., et al., *Anti-colony-stimulating factor-1 antibody staining in primary breast adenocarcinomas correlates with marked inflammatory cell infiltrates and prognosis*. J Natl Cancer Inst, 1994. 86(2): p. 120-6.

Kacinski, B. M., *CSF-1 and its receptor in breast carcinomas and neoplasms of the female reproductive tract*. Mol Reprod Dev, 1997. 46(1): p. 71-4.

Ngan, H. Y., et al., *Proto-oncogenes and p53 protein expression in normal cervical stratified squamous epithelium and cervical intra-epithelial neoplasia*. Eur J Cancer, 1999. 35(10): p. 1546-50.

Kirma, N., et al., *Elevated expression of the oncogene c-fms and its ligand, the macrophage colony-stimulating factor-1, in cervical cancer and the role of transforming growth factor-beta1 in inducing c-fms expression*. Cancer Res, 2007. 67(5): p. 1918-26.

Ridge, S. A., et al., *FMS mutations in myelodysplastic, leukemic, and normal subjects*. Proc Natl Acad Sci USA, 1990. 87(4): p. 1377-80.

Abu-Duhier, F. M., et al., *Mutational analysis of class III receptor tyrosine kinases (C-KIT, C-FMS, FLT3) in idiopathic myelofibrosis*. Br J Haematol, 2003. 120(3): p. 464-70.

Yang, D. H., et al., *The relationship between point mutation and abnormal expression of c-fms oncogene in hepatocellular carcinoma*. Hepatobiliary Pancreat Dis Int, 2004. 3(1): p. 86-9.

West, R. B., et al., *A landscape effect in tenosynovial giant-cell tumor from activation of CSF1 expression by a translocation in a minority of tumor cells*. Proc Natl Acad Sci USA, 2006. 103(3): p. 690-5.

Tanaka, S., et al., *Macrophage colony-stimulating factor is indispensable for both proliferation and differentiation of osteoclast progenitors*. J Clin Invest, 1993. 91(1): p. 257-63.

Choueiri, M. B., et al., *The central role of osteoblasts in the metastasis of prostate cancer*. Cancer Metastasis Rev, 2006. 25(4): p. 601-9.

Vessella, R. L. and E. Corey, *Targeting factors involved in bone remodeling as treatment strategies in prostate cancer bone metastasis*. Clin Cancer Res, 2006. 12(20 Pt 2): p. 6285s-6290s.

Bingle, L., N. J. Brown, and C. E. Lewis, *The role of tumour-associated macrophages in tumour progression: implications for new anticancer therapies*. J Pathol, 2002. 196(3): p. 254-65.

Pollard, J. W., *Tumour-educated macrophages promote tumour progression and metastasis*. Nat Rev Cancer, 2004. 4(1): p. 71-8.

Zins, K., et al., *Colon Cancer Cell-Derived Tumor Necrosis Factor-{alpha} Mediates the Tumor Growth-Promoting Response in Macrophages by Up-regulating the Colony-Stimulating Factor-1 Pathway*10.1158/0008-5472. CAN-06-2295. Cancer Res, 2007. 67(3): p. 1038-1045.

Paulus, P., et al., *Colony-Stimulating Factor-1 Antibody Reverses Chemoresistance in Human MCF-7 Breast Cancer Xenografts*10.1158/0008-5472. CAN-05-3523. Cancer Res, 2006. 66(8): p. 4349-4356.

Balkwill, F., K. A. Charles, and A. Mantovani, *Smoldering and polarized inflammation in the initiation and promotion of malignant disease*. Cancer Cell, 2005. 7(3): p. 211-7.

Mantovani, A., et al., *The chemokine system in diverse forms of macrophage activation and polarization*. Trends Immunol, 2004. 25(12): p. 677-86.

Balkwill, F., *TNF-alpha in promotion and progression of cancer*. Cancer Metastasis Rev, 2006. 25(3): p. 409-16.

Cohen, M. S., et al., *Structural bioinformatics-based design of selective, irreversible kinase inhibitors*. Science, 2005. 308(5726): p. 1318-21.

Rabello, D., et al., *CSF1 gene associated with aggressive periodontitis in the Japanese population*. Biochem Biophys Res Commun, 2006. 347(3): p. 791-6.

da Costa, C. E., et al., *Presence of osteoclast-like multinucleated giant cells in the bone and nonostotic lesions of Langerhans cell histiocytosis*. J Exp Med, 2005. 201(5): p. 687-93.

Cenci, S., et al., *M-CSF neutralization and egr-1 deficiency prevent ovariectomy-induced bone loss*. J Clin Invest, 2000. 105(9): p. 1279-87.

Roggia, C., et al., *Role of TNF-alpha producing T-cells in bone loss induced by estrogen deficiency*. Minerva Med, 2004. 95(2): p. 125-32.

Kitaura, H., et al., *M-CSF mediates TNF-induced inflammatory osteolysis*. J Clin Invest, 2005. 115(12): p. 3418-27.

Daroszewska, A. and S. H. Ralston, *Mechanisms of disease: genetics of Paget's disease of bone and related disorders*. Nat Clin Pract Rheumatol, 2006. 2(5): p. 270-7.

Lester, J. E., et al., *Current management of treatment-induced bone loss in women with breast cancer treated in the United Kingdom*. Br J Cancer, 2006. 94(1): p. 30-5.

Lester, J., et al., *The causes and treatment of bone loss associated with carcinoma of the breast*. Cancer Treat Rev, 2005. 31(2): p. 115-42.

Stoch, S. A., et al., *Bone loss in men with prostate cancer treated with gonadotropin-releasing hormone agonists*. J Clin Endocrinol Metab, 2001. 86(6): p. 2787-91.

Drees, P., et al., *Mechanisms of disease: Molecular insights into aseptic loosening of orthopedic implants.* Nat Clin Pract Rheumatol, 2007. 3(3): p. 165-71.

Guzman-Clark, J. R., et al., *Barriers in the management of glucocorticoid-induced osteoporosis.* Arthritis Rheum, 2007. 57(1): p. 140-6.

Feldstein, A. C., et al., *Practice patterns in patients at risk for glucocorticoid-induced osteoporosis.* Osteoporos Int, 2005. 16(12): p. 2168-74.

*interleukin-1, interleukin-6, and nitric oxide production by microglial cells.* J Biol Chem, 1998. 273(33): p. 20967-71.

Murphy, G. M., Jr., et al., *Expression of macrophage colony-stimulating factor receptor is increased in the AbetaPP (V717F) transgenic mouse model of Alzheimer's disease.* Am J Pathol, 2000. 157(3): p. 895-904.

Kaku, M., et al., *Amyloid beta protein deposition and neuron loss in osteopetrotic (op/op) mice.* Brain Res Brain Res Protoc, 2003. 12(2): p. 104-8.

```
                        SEQUENCE LISTING

<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Leu Phe Asp Asp Pro Ser Tyr Val Asn Val Gln Asn Leu
  1               5                  10                  15

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Gly Gly Arg Pro Arg Ala Ala Thr Phe
  1               5                  10
```

Ritchlin, C. T., et al., *Mechanisms of TNF-alpha-and RANKL-mediated osteoclastogenesis and bone resorption in psoriatic arthritis.* J Clin Invest, 2003. 111(6): p. 821-31.

Campbell, I. K., et al., *The colony-stimulating factors and collagen-induced arthritis: exacerbation of disease by M-CSF and G-CSF and requirement for endogenous M-CSF.* J Leukoc Biol, 2000. 68(1): p. 144-50.

Saitoh, T., et al., *Clinical significance of increased plasma concentration of macrophage colony-stimulating factor in patients with angina pectoris.* J Am Coll Cardiol, 2000. 35(3): p. 655-65.

Ikonomidis, I., et al., *Increased circulating C-reactive protein and macrophage-colony stimulating factor are complementary predictors of long-term outcome in patients with chronic coronary artery disease.* Eur Heart J, 2005. 26(16): p. 1618-24.

Murayama, T., et al., *Intraperitoneal administration of anti-c-fms monoclonal antibody prevents initial events of atherogenesis but does not reduce the size of advanced lesions in apolipoprotein E-deficient mice.* Circulation, 1999. 99(13): p. 1740-6.

Hao, A. J., S. T. Dheen, and E. A. Ling, *Expression of macrophage colony-stimulating factor and its receptor in microglia activation is linked to teratogen-induced neuronal damage.* Neuroscience, 2002. 112(4): p. 889-900.

Murphy, G. M., Jr., L. Yang, and B. Cordell, *Macrophage colony-stimulating factor augments beta-amyloid-induced*

What is claimed is:

1. A compound, stereoisomer, tautomer, oxide, or ester, of Formula (I) or a pharmaceutically acceptable salt thereof

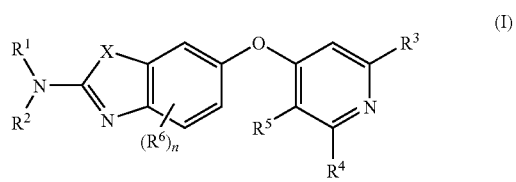

(I)

wherein X is O, S, or S(O);

$R^1$ and $R^2$ are independently selected from the group consisting of hydrogen, alkyl, substituted alkyl, acyl, cycloalkyl, substituted cycloalkyl, cycloalkenyl, substituted cycloalkenyl, aryl, substituted aryl, heterocyclyl, substituted heterocyclyl, heteroaryl, and substituted heteroaryl; or $R^1$ and $R^2$ are taken together to form a group selected from heterocyclyl, substituted heterocyclyl, heteroaryl, or substituted heteroaryl;

$R^3$ is selected from the group consisting of halo, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclyl, substituted heterocyclyl, amino, substituted amino, acyl, acylamino, alkoxy, substituted alkoxy, carboxyl, carboxyl ester, substituted sulfonyl, aminosulfonyl, and aminocarbonyl;

each $R^6$ is independently alkyl, substituted alkyl, alkoxy, substituted alkoxy, amino, substituted amino, or halo;

n is 0, 1, or 2; and when X is O, $R^4$ is hydrogen, substituted alkyl, alkenyl, substituted alkenyl, alkynyl, or substituted alkynyl, and $R^5$ is hydrogen, alkyl, substituted alkyl, alkenyl, substituted alkenyl, alkynyl, substituted alkynyl, aminocarbonyl, halo, heteroaryl, substituted heteroaryl, cycloalkyl, or substituted cycloalkyl, or $R^4$ and $R^5$ are taken together to form a group selected from heterocyclyl, substituted heterocyclyl, cycloalkyl, substituted cycloalkyl, aryl, substituted aryl, heteroaryl, and substituted heteroaryl; and when X is S or S(O), $R^4$ is hydrogen, substituted alkyl, alkenyl, substituted alkenyl, alkynyl, or substituted alkynyl, and $R^5$ is hydrogen, alkyl, substituted alkyl, alkenyl, substituted alkenyl, alkynyl, substituted alkynyl, aminocarbonyl, halo, heteroaryl, substituted heteroaryl, cycloalkyl, or substituted cycloalkyl.

2. A compound of claim 1, wherein X is O.

3. A compound of claim 1, wherein X is S.

4. A compound of claim 1, wherein $R^2$ is hydrogen or methyl.

5. A compound of claim 1, wherein $R^1$ is alkyl substituted with 0, 1, 2, or 3 substituents independently selected from halo, hydroxy, haloalkyl, alkoxy, haloalkoxy, aryloxy, aminocarbonyl, carboxyl ester, carboxyl, and substituted sulfonyl.

6. A compound of claim 1, wherein $R^1$ is $LR^{1a}$ wherein L is a covalent bond, alkylidene, or substituted alkylidene, and $R^{1a}$ selected from cycloalkyl, cycloalkenyl, aryl, heterocyclyl, and heteroaryl, wherein each $R^{1a}$ is substituted or unsubstituted.

7. A compound of claim 6, wherein $R^{1a}$ is selected from phenyl, furan-2-yl, furan-3-yl, tetrahydropyran-2-yl, tetrahydropyran-3-yl, tetrahydropyran-4-yl, cyclopropyl, cyclobutyl, cyclopentyl, cyclohexyl, cycloheptyl, cyclooctyl, cyclohexenyl, pyrid-2-yl, pyrid-3-yl, pyrid-4-yl, 2,3-dihydrobenzofuran, 2,3-dihydrobenzo[b][1,4]dioxine, 3,4-dihydro-2H-benzo[b][1,4]dioxepine, pyrazinyl, pyrrolidinyl, piperidinyl, piperidinone, pyrrolidinone, pyridin-2(1H)-one, morpholino, napthyl, bicyclo[3.1.1]heptane, bicyclo[2.2.1]heptane, 1,2,3,4-tetrahydronaphthalene, 2,3-dihydro-1H-indene, and azepan-2-one, wherein each $R^{1a}$ is substituted or unsubstituted.

8. A compound of claim 7, wherein L is a covalent bond.

9. A compound of claim 6, wherein L is alkylidene substituted with 0, 1, 2, or, 3 substituents independently selected from alkyl, substituted alkyl, hydroxy, alkoxy, haloalkoxy, aminocarbonyl, carboxyl ester, and carboxyl.

10. A compound of claim 1, wherein $R^1$ is

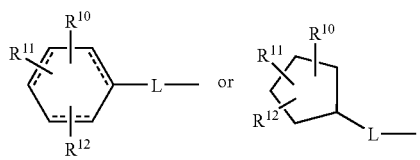

wherein the dashed lines are saturated bonds or unsaturated bonds;

wherein L is a covalent bond, alkylidene, or substituted alkylidene; and $R^{10}$, $R^{11}$, and $R^{12}$ are independently selected from the group consisting of hydrogen, halo, hydroxy, alkyl, substituted alkyl, alkoxy, substituted alkoxy, amino, substituted amino, cycloalkyl, substituted cycloalkyl, heterocyclyl, substituted heterocyclyl, aryl, substituted aryl, heteroaryl, and substituted heteroaryl; or $R^{11}$ is taken together with $R^{12}$ to form a group selected from the group consisting of aryl, substituted aryl, heterocyclyl, substituted heterocyclyl, heteroaryl, and substituted heteroaryl.

11. A compound of claim 10, wherein the dashed lines are saturated bonds, thereby forming cyclohexyl group.

12. A compound of claim 10, wherein L is a covalent bond.

13. A compound of claim 10, wherein L is methylene or substituted methylene.

14. A compound of claim 13, wherein L is substituted with alkyl, substituted alkyl, carboxyl, aminocarbonyl, and carboxyl ester.

15. A compound of claim 10, wherein $R^{10}$, $R^{11}$, and $R^{12}$ are independently selected from the group consisting of hydrogen, halo, hydroxyl, alkyl, substituted alkyl, and alkoxy.

16. A compound of claim 10, wherein at least one of $R^{10}$, $R^{11}$, and $R^{12}$ is hydroxy.

17. A compound of claim 10, wherein $R^{11}$ is taken together with $R^{12}$ to form aryl or substituted aryl.

18. A compound of claim 1, wherein $R^1$ is alkyl or substituted alkyl.

19. A compound of claim 18, wherein $R^1$ is substituted alkyl, wherein the substituent of $R^1$ is selected from the group consisting of alkyl, aryl, substituted aryl, cycloalkyl, substituted cycloalkyl, heterocyclyl, substituted heterocyclyl, heteroaryl, and substituted heteroaryl.

20. A compound of claim 19, wherein $R^1$ is substituted alkyl, wherein the substituent of $R^1$ is cycloalkyl or substituted cycloalkyl.

21. A compound of claim 1, wherein $R^1$ is selected from the group consisting of cycloalkyl, substituted cycloalkyl, cycloalkenyl, substituted cycloalkenyl, heterocyclyl, substituted heterocyclyl, heteroaryl, and substituted heteroaryl.

22. A compound of claim 21, wherein $R^1$ is selected from the group consisting of cycloalkyl, substituted cycloalkyl, heterocyclyl, and substituted heterocyclyl.

23. A compound of claim 1, wherein $R^3$ is acylamino or aminocarbonyl.

24. A compound of claim 23, wherein $R^3$ is —C(O)NH-$LR^{3a}$, wherein L is a covalent bond, alkylidene, or substituted alkylidene, and $R^{3a}$ is selected from the group consisting of alkyl, haloalkyl, amino, acylamino, (carboxyl ester)amino, hydroxy, alkoxy, substituted alkoxy, cycloalkyl, substituted cycloalkyl, heterocyclyl, and substituted heterocyclyl.

25. A compound of claim 24, wherein $R^3$ is —C(O)NHCH$_3$.

26. A compound of claim 1, wherein $R^3$ is carboxyl, substituted alkyl, carbonitrile, heteroaryl, or substituted heteroaryl.

27. A compound of claim 1, wherein $R^3$ is substituted alkyl, aryl, substituted aryl, heteroaryl, substituted heteroaryl, heterocyclyl, substituted heterocyclyl, cycloalkyl, substituted cycloalkyl, cycloalkenyl, or substituted cycloalkenyl.

28. A compound of claim 1, wherein $R^3$ is selected from the group consisting of pyrazol-1-yl, pyrazol-3-yl, pyrazol-4-yl, pyridine-2-yl, pyridine-3-yl, pyridine-4-yl, pyrimidin-4-yl, pyrimidin-3-yl, pyrimidin-2-yl, thiazoyl, tetrazolyl, imidazol-1-yl, imidazol-2-yl, imidazol-3-yl, pyrazinyl, phenyl, tetrahydropyridine, 1H-pyrrolo[2,3-b]pyridine, furanyl, oxazole, oxadiazole, cyclopropyl, cyclohexyl, cyclohexenyl, piperidinyl, morpholino, tetrahydro-1H-benzo[d]imidazole, pyrrolidinyl, piperazinyl, and piperazin-2-one, wherein each $R^3$ is substituted or unsubstituted.

29. A compound of claim 1, wherein $R^4$ is hydrogen.

30. A compound of claim 1, wherein $R^5$ is hydrogen.

31. A compound of claim 1 wherein n is, 0, $R^4$ and $R^5$ are hydrogen, and $R^3$ is selected from the group consisting of halo, substituted alkyl, carbonitrile, aryl, substituted aryl, heteroaryl, substituted heteroaryl, heterocyclyl, substituted heterocyclyl, amino, substituted amino, acyl, acylamino, alkoxy, substituted alkoxy, carboxyl, carboxyl ester, substituted sulfonyl, aminosulfonyl, and aminocarbonyl.

32. A compound of claim 1, wherein $R^4$ and $R^5$ are taken together to form an aryl or substituted aryl group.

33. A compound, stereoisomer, or tautomer of claim 1 having Formula (IIa) or (IIb) or a pharmaceutically acceptable salt thereof:

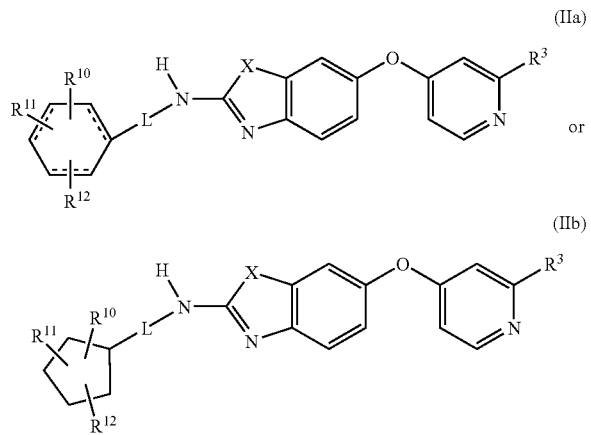

wherein X is O or S;
the dashed lines are saturated bonds or unsaturated bonds;
L is a covalent bond or is alkylidene or substituted alkylidene;
$R^{10}$, $R^{11}$, and $R^{12}$ are independently selected from the group consisting of hydrogen, halo, hydroxy, alkyl, substituted alkyl, alkoxy, substituted alkoxy, amino, substituted amino, cycloalkyl, substituted cycloalkyl, heterocyclyl, substituted heterocyclyl, aryl, substituted aryl, heteroaryl, and substituted heteroaryl; or $R^{11}$ is taken together with $R^{12}$ to form a group selected from the group consisting of aryl, substituted aryl, heterocyclyl, substituted heterocyclyl, heteroaryl, and substituted heteroaryl; and
$R^3$ is selected from the group consisting of halogen, substituted alkyl, carbonitrile, aryl, substituted aryl, heteroaryl, substituted heteroaryl, heterocyclyl, substituted heterocyclyl, amino, substituted amino, acyl, acylamino, alkoxy, substituted alkoxy, carboxyl, carboxyl ester, substituted sulfonyl, aminosulfonyl, and aminocarbonyl.

34. A compound of claim 33 wherein the dashed lines are saturated bonds, thereby forming cyclohexyl group.

35. A compound of claim 33, wherein X is O.

36. A compound of claim 33, wherein X is S.

37. A compound of claim 33, wherein L is a covalent bond.

38. A compound of claim 33, wherein L is methylene or substituted methylene.

39. A compound of claim 33, wherein L is substituted with alkyl, substituted alkyl, carboxyl, aminocarbonyl, or carboxyl ester.

40. A compound of claim 33, wherein $R^{10}$, $R^{11}$, and $R^{12}$ are independently selected from the group consisting of hydrogen, halo, hydroxyl, alkyl, substituted alkyl, and alkoxy.

41. A compound of claim 40, wherein at least one of $R^{10}$, $R^{11}$, and $R^{12}$ is hydroxy.

42. A compound of claim 33, wherein $R^{11}$ is taken together with $R^{12}$ to form aryl or substituted aryl.

43. A compound of claim 33, wherein $R^3$ is acylamino or aminocarbonyl.

44. A compound of claim 43, wherein $R^3$ is —C(O)NHCH$_3$.

45. A compound of claim 33, wherein $R^3$ carboxyl, substituted alkyl, carbonitrile, heteroaryl, or substituted heteroaryl.

46. A compound, stereoisomer, tautomer of claim 1 having Formula (IIIa) or a pharmaceutically acceptable salt thereof:

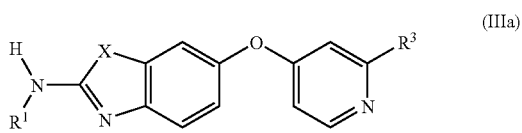

wherein X is O or S;
$R^1$ is alkyl or alkyl substituted with a substituent selected from the group consisting of aryl, cycloalkyl, heterocyclyl, substituted heterocyclyl, heteroaryl, and substituted heteroaryl; and
$R^3$ is selected from the group consisting of halogen, substituted alkyl, carbonitrile, aryl, substituted aryl, heteroaryl, substituted heteroaryl, heterocyclyl, substituted heterocyclyl, amino, substituted amino, acyl, acylamino, alkoxy, substituted alkoxy, carboxyl, carboxyl ester, substituted sulfonyl, aminosulfonyl, and aminocarbonyl.

47. A compound of claim 46, wherein X is O.

48. A compound of claim 46, wherein X is S.

49. A compound of claim 46, wherein $R^1$ is alkyl substituted with cycloalkyl.

50. A compound of claim 46, wherein $R^3$ is acylamino or aminocarbonyl.

51. A compound of claim 50, wherein $R^3$ is —C(O)NHCH$_3$.

52. A compound of claim 46, wherein $R^3$ is carboxyl, substituted alkyl, carbonitrile, heteroaryl, or substituted heteroaryl.

53. A compound, stereoisomer, or tautomer of claim 1 having Formula (IIIb) or a pharmaceutically acceptable salt thereof:

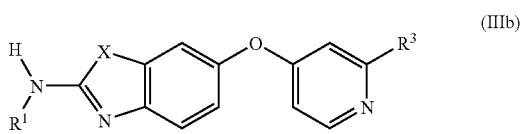

wherein X is O or S;
$R^1$ is selected from the group consisting of acyl, cycloalkyl, substituted cycloalkyl, cycloalkenyl, substituted cycloalkenyl, heterocyclyl, substituted heterocyclyl, heteroaryl, and substituted heteroaryl; and $R^3$ is selected from the group consisting of halogen, substituted alkyl, carbonitrile, aryl, substituted aryl, heteroaryl, substituted heteroaryl, heterocyclyl, substituted heterocyclyl, amino, substituted amino, acyl, acylamino, alkoxy, substituted alkoxy, carboxyl, carboxyl ester, substituted sulfonyl, aminosulfonyl, and aminocarbonyl.

54. A compound of claim 53, wherein X is O.
55. A compound of claim 53, wherein X is S.
56. A compound of claim 53, wherein $R^1$ is selected from the group consisting of cycloalkyl, substituted cycloalkyl, heterocyclyl, and substituted heterocyclyl.
57. A compound of claim 53, wherein $R^3$ is acylamino or aminocarbonyl.
58. A compound of claim 57, wherein $R^3$ is —C(O)NHCH$_3$.
59. A compound of claim 53, wherein $R^3$ is carboxyl, substituted alkyl, carbonitrile, heteroaryl, or substituted heteroaryl.
60. A compound, stereoisomer, tautomer, oxide, or ester of Formula (V) or a pharmaceutically acceptable salt thereof:

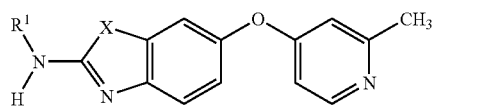

(V)

wherein X is O or S;
$R^1$ is -L$R^9$ or alkyl substituted with, 0, 1, 2, or, 3 substituents independently selected from halo, hydroxy, haloalkyl, alkoxy, haloalkoxy, aryloxy, aminocarbonyl, carboxyl ester, carboxy, and substituted sulfonyl;
L is a covalent bond, alkylidene, or substituted alkylidene; and
$R^9$ is selected from the group consisting of cycloalkyl, substituted cycloalkyl, tetrahydropyranyl, morpholino, and pyridyl.

61. A compound of claim 60, wherein X is S.
62. A compound of claim 60, wherein L is a covalent bond or is alkylidene.
63. A compound of claim 60, wherein $R^9$ is cyclohexyl or substituted cyclohexyl.
64. A compound of claim 1 or 60 or a stereoisomer, tautomer, oxide, ester, or pharmaceutically acceptable salt thereof selected from the group consisting of N-methyl-4-(2-(4-((4-methylpiperazin-1-yl)methyl)benzylamino)benzo[d]thiazol-6-yloxy)picolinamide; N-methyl-4-(2-(3-((4-methylpiperazin-1-yl)methyl)benzylamino)benzo[d]thiazol-6-yloxy)picolinamide; N-methyl-4-(2-(4-(4-methylpiperazin-1-yl)benzylamino)benzo[d]thiazol-6-yloxy)picolinamide; N-methyl-4-(2-(2-(4-methylpiperazin-1-yl)ethoxy)phenylamino)benzo[d]thiazol-6-yloxy)picolinamide; 4-(2-(3-(2-(dimethylamino)ethoxy)phenylamino)benzo[d]thiazol-6-yloxy)-N-methylpicolinamide; N -methyl-4-(2-(3-(2-(piperidin-1-yl)ethoxy)phenylamino)benzo[d]thiazol-6-yloxy)picolinamide; 4-(2-((1R,2R)-2-hydroxycyclohexylamino)benzo[d]oxazol-6-yloxy)-N-methylpicolinamide; (S)-4-(2-(1-hydroxy-3-phenylpropan-2-ylamino)benzo[d]oxazol-6-yloxy)-N-methylpicoinamide; (S) -4-(2-(1-cyclohexylethylamino)benzo[d]oxazol-6-yloxy)-N-methylpicoinamide; 4-(2-((1R,2R)-2-hydroxycyclohexylamino)benzo[d]thiazol-6-yloxy)-N,N-dimethylpicolinamide; N-cyclopropyl -4-(2-((1R,2R)-2-hydroxycyclohexylamino)benzo[d]thiazol-6-yloxy)picolinamide; 4-(2-((1R,2R)-2-hydroxycyclohexylamino)benzo[d]thiazol-6-yloxy)-N-(tetrahydro-2H-pyran-4-yl)picolinamide; 4-(2-((1R,2R)-2-hydroxycyclohexylamino)benzo[d]thiazol-6-yloxy)-N-(1-methylpiperidin-4-yl)picolinamide; 4-(2-((1R,2R)-2-hydroxycyclohexylamino)benzo[d]thiazol-6-yloxy)-N-(1-methylpiperidin-3-yl)picolinamide; N-(2-acetamidoethyl)-4-(2-((1R,2R)-2-hydroxycyclohexylamino)benzo[d]thiazol-6-yloxy)picolinamide; 4-(2-((1R,2R)-2-hydroxycyclohexylamino)benzo[d]thiazol-6-yloxy)-N-(2-(pyrrolidin-1-yl )ethyl)picolinamide; 4-(2-((1R,2R)-2-hydroxycyclohexylamino)benzo[d]thiazol-6-yloxy)-N-((tetrahydrofuran-2-yl)methyl)picolinamide; 4-(2-((1R,2R)-2-hydroxycyclohexylamino)benzo[d]thiazol-6-yloxy)-N -((tetrahydro-2H-pyran-4-yl)methyl)picolinamide; 4-(2-((1R,2R)-2-hydroxycyclohexylamino)benzo[d]thiazol-6-yloxy)-N-((1-methylpiperidin-4-yl)methyl)picolinamide; N—(((S)-1-ethylpyrrolidin-2-yl)methyl)-4-(2-((1R,2R)-2-hydroxycyclohexylamino)benzo[d]thiazol-6-yloxy)picolinamide; N-methyl-4-(2-(phenylamino)benzo[d]thiazol-6-yloxy)picolinamide; N-methyl-4-(2-(2-(trifluoromethyl)phenylamino)benzo[d]thiazol-6-yloxy)picolinamide; 4-(2-(2-bromophenylamino)benzo[d]thiazol-6-yloxy)-N-methylpicolinamide; 4-(2-(2-isopropylphenylamino)benzo[d]thiazol-6-yloxy)-N-methylpicolinamide; 4-(2-(2-tert-butylphenylamino)benzo[d]thiazol-6-yloxy)-N-methylpicolinamide; N-methyl-4-(2-(2-morpholinophenylamino)benzo[d]thiazol-6-yloxy)picolinamide; 4-(2-(2-ethoxyphenylamino)benzo[d]thiazol-6-yloxy)-N-methylpicolinamide; N-methyl-4-(2-(2-(trifluoromethoxy)phenylamino)benzo[d]thiazol-6-yloxy)picolinamide; N-methyl-4-(2-(2-phenoxyphenylamino)benzo[d]thiazol-6-yloxy)picolinamide; 4-(2-(2-(benzyloxy)phenylamino)benzo[d]thiazol-6-yloxy)-N-methylpicolinamide; 4-(2-(3-chlorophenylamino)benzo[d]thiazol-6-yloxy)-N-methylpicolinamide; 4-(2-(3-methoxyphenylamino)benzo[d]thiazol-6-yloxy)-N-methylpicolinamide; N-methyl-4-(2-(3-(1,1,2,2-tetrafluoroethoxy)phenylamino)benzo[d]thiazol-6-yloxy)picolinamide; 4-(2-(2-(1H -pyrazol-1-yl)phenylamino)benzo[d]thiazol-6-yloxy)-N-methylpicolinamide; N-methyl-4-(2-(3-(pyrrolidin-1-yl)phenylamino)benzo[d]thiazol-6-yloxy)picolinamide; N-methyl-4-(2-(3-morpholinophenylamino)benzo[d]thiazol-6-yloxy)picolinamide; 4-(2-(3-carbamoylphenylamino)benzo[d]thiazol-6-yloxy)-N-methylpicolinamide; 4-(2-(3-chloro-4-morpholinophenylamino)benzo[d]thiazol-6-yloxy)-N-methylpicolinamide; 4-(2-(3-methoxy-5-(trifluoromethyl)phenylamino)benzo[d]thiazol-6-yloxy)-N-methylpicolinamide; 4-(2-(3,5-dimethoxyphenylamino)benzo[d]thiazol-6-yloxy)-N-methylpicolinamide; N-methyl-4-(2-(4-morpholinophenylamino)benzo[d]thiazol-6-yloxy)picolinamide; (R)-4-(2-(2-hydroxy-2-phenylethylamino)benzo[d]thiazol-6-yloxy)-N-methylpicolinamide; (R)-4-(2-(1-cyclohexyl-2-hydroxyethylamino)benzo[d]thiazol-6-yloxy)-N-methylpicolinamide; (S)-4-(2-(1-cyclohexyl-2-hydroxyethylamino)benzo[d]thiazol-6-yloxy)-N-methylpicolinamide; N-methyl-4-(2-(2-(pyrrolidin-1- yl)phenylamino)benzo[d]thiazol-6-yloxy)picolinamide; N-methyl-4-(2-(2-(2-oxopyrrolidin-1-yl)phenylamino)benzo[d]thiazol-6-yloxy)picolinamide; N-ethyl-4-(2-((1R,2R)-2-hydroxycyclohexylamino)benzo[d]thiazol-6-yloxy)picolinamide; 4-(2-((1R,2R)-2-hydroxycyclohexylamino)benzo[d]thiazol-6-yloxy)-N-(2,2,2-trifluoroethyl)picolinamide; 4-(2-((1R,2R)-2-hydroxycyclohexylamino)benzo[d]thiazol-6-yloxy)-N-propylpicolinamide; N-(cyclopropylmethyl)-4-(2-((1R,2R)-2-hydroxycyclohexylamino)benzo[d]thiazol-6-yloxy)picolinamide; 4-(2-((1R,2R)-2-hydroxycyclohexylamino)benzo[d]thiazol-6-yloxy)-N-isopropylpicolinamide; N-(cyclohexylmethyl)-6-(2-(4-phenyl-1H-imidazol-2-yl)pyridin-4-yloxy) benzo[d]thiazol-2-amine; N-(cyclohexylmethyl)-6-(2-(4,5-dimethyl-1H-imidazol-2-yl)pyridin-4-yloxy)benzo[d]thiazol-2-amine; N-(cyclohexylmethyl)-6-(2-(4-(trifluoromethyl)-1H-imidazol-2-yl)pyridin-4-yloxy)benzo[d]thiazol-2-amine; 4-(2-(2-hydroxy-3-morpholinopropylamino)benzo[d]thiazol-6-yloxy)-N-methylpicolinamide; N-methyl-4-(2-(2-phenylpropan-2-ylamino)benzo[d]thiazol-6-yloxy)picolinamide; N-(cyclohexylmethyl)-6-(2-(4-methyl-1H-imidazol-2-yl)pyridin-4-yloxy)benzo[d]thiazol-2-amine; 4-(2-(cyclopropylmethylamino)benzo[d]thiazol-6-yloxy)-N-methylpicolinamide; 4-(2-(2-acetamidoethylamino)benzo[d]thiazol-6-yloxy)-N-methylpicolinamide; N-methyl-4-(2-(2-(2-oxopyrrolidin-1-yl)ethylamino)benzo[d]thiazol-6-yloxy)picolinamide; N-methyl-4-(2-(2-morpholinoethylamino)benzo[d]thiazol-6-yloxy)picolinamide; (R)—N-methyl-4-(2-((tetrahydrofuran-2-yl)methylamino)benzo[d]thiazol-6-yloxy)picolinamide; (S)—N-methyl-4-(2-((tetrahydrofuran-2-yl)methylamino)benzo[d]thiazol-6-yloxy)picolinamide; N-methyl-4-(2-(2-(pyrrolidin-1-yl)ethylamino)benzo[d]thiazol-6-yloxy)picolinamide; N-methyl-4-(2-(tetrahydro-2H-pyran-4-ylamino)benzo[d]thiazol-6-yloxy)picolinamide; N-methyl-4-(2-((1-metliyipiperidin-4-yl)methylamino)benzo[d]thiazol-6-yloxy)picolinamide; 4-(2-((1-acetylpiperidin-4-yl)methylamino)benzo[d]thiazol-6-yloxy)-N-methylpicolinamide; 4-(2-(2-hydroxyethylamino)benzo[d]thiazol-6-yloxy)-N-methylpicolinamide; N-methyl-4-(2-(2-(1-methylpyrrolidin-2-yl)ethylamino)benzo[d]thiazol-6-yloxy)picolinamide; 4-(2-(3-hydroxypropylamino)benzo[d]thiazol-6-yloxy)-N-methylpicolinamide; 4-(2-(1-ethylpiperidin-3-ylamino)benzo[d]thiazol-6-yloxy)-N-methylpicolinamide; 4-(2-(2-methoxyethylamino)benzo[d]thiazol-6-yloxy)-N-methylpicolinamide; N-methyl-4-(2-((1-methylpiperidin-3-yl)methylamino)benzo[d]thiazol-6-yloxy)picolinamide; N-methyl-4-(2-(2,2,6,6-tetramethylpiperidin-4-ylamino)benzo[d]thiazol-6-yloxy)picolinamide; (R)-4-(2-((1-ethylpyrrolidin-2-yl)methylamino)benzo[d]thiazol-6-yloxy)-N-methylpicolinamide; (S)-4-(2-((1-ethylpyrrolidin-2-yl)methylamino)benzo[d]thiazol-6-yloxy)-N-methylpicolinamide; 4-(2-(isopropylamino)benzo[d]thiazol-6-yloxy)-N-methylpicolinamide; 4-(2-(isobutylamino)benzor[d]thiazol-6-yloxy)-N-methylpicolinamide; 4-(2-(cyclohexyl(methyl)amino)benzo[d]thiazol-6-yloxy)-N-methylpicolinamide; 4-(2-(benzyl(methyl)amino)benzo[d]thiazol-6-yloxy)-N-methylpicolinamide; N-methyl-4-(2-(3-phenylpropylamino)benzo[d]thiazol-6-yloxy)picolinamide; N-methyl-4-(2-(2-(methylsulfonyl)ethylamino)benzo[d]thiazol-6-yloxy)picolinamide; 4-(2-(4,4-difluorocyclohexylamino)benzo[d]thiazol-6-yloxy)-N-methylpicolinamide; N-methyl-4-(2-(tetrahydro-2H-pyran-3-ylamino)benzo[d]thiazol-6-yloxy)picolinamide; (R)—N-methyl-4-(2-(6-oxopiperidin-3-ylamino)benzo[d]thiazol-6-yloxy)picolinamide; N-methyl-4-(2-((2-oxo-1,2-dihydropyridin-4-yl)methylamino)benzo[d]thiazol-6-yloxy)picolinamide; (S)—N-methyl-4-(2-(6-oxopiperidin-3-ylamino)benzo[d]thiazol-6-yloxy)picolinamide; N-methyl-4-(2-((6-oxo-1,6-dihydropyridin-3-yl)methylamino)benzo[d]thiazol-6-yloxy)picolinamide; (R)—N-methyl-4-(2-(1,2,3,4-tetrahydronaphthalen-1-ylamino)benzo[d]thiazol-6-yloxy)picolinamide; 4-(2-(cycloheptylamino)benzo[d]thiazol-6-yloxy)-N-methylpicolinamide; (S)—N-methyl-4-(2-(1,2,3,4-tetrahydronaphthalen-1-ylamino)benzo[d]thiazol-6-yloxy)picolinamide; N-methyl-4-(2-(2-oxoazepan-3-ylamino)benzo[d]thiazol-6-yloxy)picolinamide; 4-(2-((2-methoxybenzyl)(methyl)amino)benzo[d]thiazol-6-yloxy)-N-methylpicolinamide; 4-(2-(2-hydroxy-1-(tetrahydro-2H-pyran-4-yl)ethylamino)benzo[d]thiazol-6-yloxy-N-methylpicolinamide; 4-(2-(bi(cyclohexan)-2-ylamino)benzo[d]thiazol-6-yloxy)-N-methylpicolinamide; 4-(2-(2-hydroxy-1-(tetrahydrofuran-3-yl)ethylamino)benzo[d]thiazol-6-yloxy)-N-methylpicolinamide; 4-(2-((1S,4S)-4-aminocyclohexylamino)benzo[d]thiazol-6-yloxy)-N-methylpicolinamide; (R)-4-(2-(2-hydroxypropylamino)benzo[d]thiazol-6-yloxy)-N-methylpicolinamide; (S)-4-(2-(2-hydroxypropylamino)benzo[d]thiazol-6-yloxy)-N-methylpicolinamide; (R)-4-(2-(1-hydroxy-3-methylbutan-2-ylamino)benzo[d]thiazol-6-yloxy)-N-methylpicolinamide; (S)-4-(2-(1-hydroxy-3-methylbutan-2-ylamino)benzo[d]thiazol-6-yloxy)-N-methylpicolinamide; (S)-4-(2-(1-hydroxypropan-2-ylamino)benzo[d]thiazol-6-yloxy)-N-methylpicolinamide; (R)-4-(2-(1-hydroxybutan-2-ylamino)benzo[d]thiazol-6-yloxy)-N-methylpicolinamide; (S)-4-(2-(1-hydroxybutan-2-ylamino)benzo[d]thiazol-6-yloxy)-N-methylpicolinamide; (R)-4-(2-(2-hydroxy-2-phenylethylamino)benzo[d]thiazol-6-yloxy)-N-methylpicolinamide; 4-(2-((1S,2S)-1-hydroxy-3-methoxy-1-phenylpropan-2-ylamino)benzo[d]thiazol-6-yloxy)-N-methylpicolinamide; (R)-4-(2-(1-hydroxy-3-phenylpropan-2-ylamino)benzo[d]thiazol-6-yloxy)-N-methylpicolinamide; (S)-4-(2-(1-hydroxy-3-phenylpropan-2-ylamino)benzo[d]thiazol-6-yloxy)-N-methylpicolinamide; (R)-4-(2-(2-hydroxy-1-phenylethylamino)benzo[d]thiazol-6-yloxy)-N-methylpicolinamide; (S)-4-(2-(2-hydroxy-1-phenylethylamino)benzo[d]thiazol-6-yloxy)-N-methylpicolinamide; 4-(2-((1R,2S)-1-hydroxy-1-phenylpropan-2-ylamino)benzo[d]thiazol-6-yloxy)-N-methylpicolinamide; 4-(2-((1S,2R)-1-hydroxy-1-phenylpropan-2-ylamino)benzo[d]thiazol-6-yloxy)-N-methylpicolinamide; (R)-4-(2-(1-hydroxy-4-methylpentan-2-ylamino)benzo[d]thiazol-6-yloxy)-N-methylpicolinamide; 4-(2-((2S,3S)-1-hydroxy-3-methylpentan-2-ylamino)benzo[d]thiazol-6-yloxy)-N-methylpicolinamide; (R)-4-(2-(1-hydroxy-3,3-dimethylbutan-2-ylamino)benzo[d]thiazol-6-yloxy)-N-methylpicolinamide; (S)-4-(2-(1-cyclohexyl-3-hydroxypropan-2-ylamino)benzo[d]thiazol-6-yloxy)-N-methylpicolinamide; (S)-4-(2-(1-hydroxy-3,3-dimethylbutan-2-ylamino)benzo[d]thiazol-6-yloxy)-N-methylpicolinamide; 4-(2-((1S,4S)-4- acetamidocyclohexylamino)benzo[d]thiazol-6-yloxy)-N-methylpicolinamide; 4-(2-((1R,4R)-4-acetamidocyclohexylamino)benzo[d]thiazol-6-yloxy)-N-methylpicolinamide; (R)-4-(2-(4-(2-amino-3-hydroxypropyl)-1H-imidazol-1-yl)benzo[d]thiazol-6-yloxy)-N-methylpicolinamide; (S)-4-(2-(4-(2-amino-3-hydroxypropyl)-1H-imidazol-1-yl)benzo[d]thiazol-6-yloxy)-N-methylpicolinamide; 4-(2-(1-(2,5-dimethoxyphenyl)-1-hydroxypropan-2-ylamino)benzo[d]thiazol-6-yloxy)-N-methylpicolinamide; 4-(2-(2-hydroxy-3-phenoxypropylamino)benzo[d]thiazol-6-yloxy)-N-methylpicolinamide; 4-(2-((1R,4R)-4-hydroxycyclohexylamino)benzo[d]thiazol-6-yloxy)-N-methylpicolinamide; (S)-4-(2-(1-hydroxy-4-methylpentan-2-ylamino)benzo[d]thiazol-6-yloxy)-N-methylpicolinamide; 4-(2-(2-hydroxy-3-methoxypropylamino)benzo[d]thiazol-6-yloxy)-N-methylpicolinamide; 4-(2-(((1R,2R,4S)-bicyclo[2.2.1]heptan-2-ylamino)benzo[d]thiazol-6-yloxy)-N-methylpicolinamide; 4-(2-(cyclooctylamino)benzo[d]thiazol-6-yloxy)-N-methylpicolinamide; 4-(2-(isopentylamino)benzo[d]thiazol-6-yloxy)-N-methylpicolinamide; (S)-4-(2-(1-cyclohexylethylamino)benzo[d]thiazol-6-yloxy)-N-methylpicolinamide; 4-(2-((1S,4S)-4-isobutyramidocyclohexylamino)benzo[d]thiazol-6-yloxy)-N-methylpicolinamide; N-methyl-4-(2-((1S,4S)-4-(3-methylbutanamido)cyclohexylamino)benzo[d]thiazol-6-yloxy)picolinamide; N-methyl-4-(2-((1S,4S)-4-((R)-tetrahydrofuran-2-carboxamido)cyclohexylamino)benzo[d]thiazol-6-yloxy)picolinamide; 4-(2-((1S,4S)-4-benzamidocyclohexylamino)benzo[d]thiazol-6-yloxy)-N-methylpicolinamide; N-methyl-4-(2-((1R,4S)-4-((S)-tetrahydrofuran-2-carboxamido)cyclohexylamino)benzo[d]thiazol-6-yloxy)picolinamide; N-methyl-4-(2-((1R,4S)-4-((S)-1-methylpyrrolidine-2-carboxamido)cyclohexylamino)benzo[d]thiazol-6-yloxy)picolinamide; 4-(2-(benzylamino)benzo[d]thiazol-6-yloxy)-N-methylpicolinamide; N-methyl-4-(2-(pyridin-4-ylmethylamino)benzo[d]thiazol-6-yloxy)picolinamide; 4-(2-((1S,4R)-bicyclo[2.2.1]heptan-2-ylamino)benzo[d]thiazol-6-yloxy)-N-methylpicolinamide; 4-(2-(2-(difluoromethoxy)benzylamino)benzo[d]thiazol-6-yloxy)-N-methylpicolinamide; 4-(2-(2,6-dichlorophenethylamino)benzo[d]thiazol-6-yloxy)-N-methylpicolinamide; N-methyl-4-(2-(2-(tetrahydro-2H-pyran-4-yl)ethylamino)benzo[d]thiazol-6-yloxy)picolinamide; 4-(2-((2,3-dihydrobenzo[b][1.4]dioxin-2-yl)methylamino)benzo[d]thiazol-6-yloxy)-N-methylpicolinamide; (S)-4-(2-(2-hydroxy-2-phenylethylamino)benzo[d]thiazol-6-yloxy)-N-methylpicolinamide; 4-(2-(2-hydroxy-1-(pyridin-3-yl)ethylamino)benzo[d]thiazol-6-yloxy)-N-methylpicolinamide; 4-(2-((1R,2S)-2-hydroxy-1.2,3,4-tetrahydronaphthalen-1-ylamino)benzo[d]thiazol-6-yloxy)-N-methylpicolinamide; N-methyl-4-(2-(2-(pyrazin-2-yl)ethylamino)benzo[d]thiazol-6-yloxy)picolinamide; (R)—N-methyl-4-(2-(3-methylbutan-2-ylamino)benzo[d]thiazol-6-yloxy)picolinamide; (S)—N-methyl-4-(2-(3-methylbutan-2-ylamino)benzo[d]thiazol-6-yloxy)picolinamide; 6-(3-bromopyridin-4-yloxy)-N-(cyclohexylmethyl)benzo[d]thiazol-2-amine; 6-(2-chloropyridin-4-yloxy)-N-(cyclohexylmethyl)benzo[d]thiazol-2-amine; 4-(2-(cyclohexylmethylamino)benzo[d]thiazol-6-yloxy)picolinonitrile; 4-(2-(1-((1R,4S)-bicyclo[2.2.1]heptan-2-yl)ethylamino)benzo[d]thiazol-6-yloxy)-N-methylpicolinamide; (1R,2R)-2-(6-(2-(1-methyl-1H-imidazol-2-yl)pyridin-4-yloxy)benzo[d]thiazol-2-ylamino)cyclohexanol; (1R,2R)-2-(6-(2-(pyrazin-2-yl)pyridin-4-yloxy)benzo[d]thiazol-2-ylamino)cyclohexanol; (1R,2R)-2-(6-(2-(thiazol-5-yl)pyridin-4-yloxy)benzo[d]thiazol-2-ylamino)cyclohexanol; (1R,2R)-2-(6-(2-(1-methyl-1H-imidazol-5-yl)pyridin-4-yloxy)benzo[d]thiazol-2-ylamino)cyclohexanol; (1R,2R)-2-(6-(2-(thiazol-4-yl)pyridin-4-yloxy)benzo[d]thiazol-2-ylamino)cyclohexanol; (1R,2R)-2-(6-(2-(thiazol-2-yl)pyridin-4-yloxy)benzo[d]thiazol-2-ylamino)cyclohexanol; (1R,2R)-2-(6-(2-(1,2,3,6-tetrahydropyridin-4-yl)pyridin-4-yloxy)benzo[d]thiazol-2-ylamino)cyclohexanol; (1R,2R)-2-(6-(2-(5-ethyl-4-methyl-1H-imidazol-2-yl)pyridin-4-yloxy)benzo[d]thiazol-2-ylamino)cyclohexanol; (S)—N-(1-cyclohexylethyl)-6-(2-(1-methyl-1H-pyrazol-4-yl)pyridin-4-yloxy)benzo[d]thiazol-2-amine; (1R,2R)-2-(6-(6'-(4-methylpiperazin-1-yl)-2,3'-bipyridin-4-yloxy)benzo[d]thiazol-2-ylamino)cyclohexanol; (1R,2R)-2-(6-(6'-morpholino-2,3'-bipyridin-4-yloxy)benzo[d]thiazol-2-ylamino)cyclohexanol; (1R,2R)-2-(6-(2-(3-(morpholinomethyl)phenyl)pyridin-4-yloxy)benzo[d]thiazol-2-ylamino)cyclohexanol; (1R,2R)-2-(6-(2-cyclohexenylpyridin-4-yloxy)benzo[d]thiazol-2-ylamino)cyclohexanol; (1R,2R)-2-(6-(2-(4-(morpholinomethyl)phenyl)pyridin-4-yloxy)benzo[d]thiazol-2-ylamino)cyclohexanol; (1R,2R)-2-(6-(2-cyclopropylpyridin-4-yloxy)benzo[d]thiazol-2-ylamino)cyclohexanol; (1R,2R)-2-(6-(6'-methoxy-2,3'-bipyridin-4-yloxy)benzo[d]thiazol-2-ylamino)cyclohexanol; (1R,2R)-2-(6-(2'-fluoro-2,4'-bipyridin-4-yloxy)benzo[d]thiazol-2-ylamino)cyclohexanol; (1R,2R)-2-(6-(3'-fluoro-2'-morpholino-2,4'-bipyridin-4-yloxy)benzo[d]thiazol-2-ylamino)cyclohexanol; (1R,2R)-2-(6-(6'-fluoro-2,3'-bipyridin-4-yloxy)benzo[d]thiazol-2-ylamino)cyclohexanol; (1R,2R)-2-(6-(2-(piperidin-1-yl)pyridin-4-yloxy)benzo[d]thiazol-2-ylamino)cyclohexanol; (1R,2R)-2-(6-(2-morpholinopyridin-4-yloxy)benzo[d]thiazol-2-ylamino)cyclohexanol; (1R,2R)-2-(6-(2-(4-methylpiperazin-1-yl)pyridin-4-yloxy)benzo[d]thiazol-2-ylamino)cyclohexanol; N—((R)-1-(4-(2-((1R,2R)-2-hydroxycyclohexylamino)benzo[d]thiazol-6-yloxy)pyridin-2-yl)pyrrolidin-3-yl)acetamide; N—((S)-1-(4-(2-((1R,2R)-2-hydroxycyclohexylamino)benzo[d]thiazol-6-yloxy)pyridin-2-yl)pyrrolidin-3-yl)acetamide; 4-(4-(2-((1R,2R)-2-hydroxycyclohexylamino)benzo[d]thiazol-6-yloxy)pyridin-2-yl)piperazin-2-one; (1R,2R)-2-(6-(2,2'-bipyridin-4-yloxy)benzo[d]thiazol-2-ylamino)cyclohexanol; (1R,2R)-2-(6-(2-(1-methyl-3-(trifluoromethyl)-1H-pyrazol-5-yl)pyridin-4-yloxy)benzo[d]thiazol-2-ylamino)cyclohexanol; (1R,2R)-2-(6-(2-(1-(2-morpholinoethyl)-1H-pyrazol-4-yl)pyridin-4-yloxy)benzo[d]thiazol-2-ylamino)cyclohexanol; (1R,2R)-2-(6-(2-(1-ethyl-1H-pyrazol-4-yl)pyridin-4-yloxy)benzo[d]thiazol-2-ylamino)cyclohexanol; (1R,2R)-2-(6-(2-(1-(2-(diethylamino)ethyl)-1H-pyrazol-4-yl)pyridin-4-yloxy)benzo[d]thiazol-2-ylamino)cyclohexanol; (1R,2R)-2-(6-(2-(1-(2,2-difluoroethyl)-1H-pyrazol-4-yl)pyridin-4-yloxy)benzo[d]thiazol, 2-ylamino)cyclohexanol; (1R,2R)-2-(6-(2-(2-morpholinopyrimidin-5-yl)pyridin-4-yloxy)benzo[d]thiazol-2-ylamino)cyclohexanol; (1R,2R)-2-(6-(2-(4-(4-methylpiperazin-1-yl)phenyl)pyridin-4-yloxy)

benzo[d]thiazol-2-ylamino)cyclohexanol; (S)—N-(1-cyclohexylethyl)-6-(6'-morpholino-2,3'-bipyridin-4-yloxy)benzo[d]thiazol-2-amine; (S)—N-(1-cyclohexylethyl)-6-(6'-(4-methylpiperazin-1-yl)-2,3'-bipyridin-4-yloxy)benzo[d]thiazol-2-amine; (1R,2R)-2-(6-(2-(4-(trifluoromethyl)-1H-imidazol-2-yl)pyridin-4-yloxy)benzo[d]thiazol-2-ylamino)cyclohexanol; 6-(2-(1H-tetrazol-5-yl)pyridin-4-yloxy)-N-(cyclohexylmethyl)benzo[d]thiazol-2-amine; 4-(2-((1R,6S)-6-carbamoylcyclohex-3-enylamino)benzo[d]thiazol-6-yloxy)-N-methylpicolinamide; 4-(2-((1R,6R)-6-carbamoylcyclohex-3-enylamino)benzo[d]thiazol-6-yloxy)-N-methylpicoinamide; 4-(2-(2-fluoro-6-methoxybenzylamino)benzo[d]thiazol-6-yloxy)-N-methylpicolinamide; (1R,2R)-2-(6-(2-chloropyridin-4-yloxy)benzo[d]thiazol-2-ylamino)cyclohexanol; 4-(2-((1R,2R)-2-hydroxycyclohexylamino)benzo[d]thiazol-6-yloxy)picolinonitrile; (1R,2R)-2-(6-(2-(4-methyl-1H-imidazol-2-yl)pyridin-4-yloxy)benzo[d]thiazol-2-ylamino)cyclohexanol; (1R,2R)-2-(6-(2-(4,5-dimethyl-1H-imidazol-2-yl)pyridin-4-yloxy)benzo[d]thiazol-2-ylamino)cyclohexanol; (1R,2R)-2-(6-(2-(4,5,6,7-tetrahydro-1H-benzo[d]imidazol-2-yl)pyridin-4-yloxy)benzo[d]thiazol-2-ylamino)cyclohexanol; (1R,2R)-2-(6-(2-(1-(2-fluoroethyl)-1H-pyrazol-4-yl)pyridin-4-yloxy)benzo[d]thiazol-2-ylamino)cyclohexanol; (1R,2R)-2-(6-(2-(1-(2-methoxyethyl)-1H-pyrazol-4-yl)pyridin-4-yloxy)benzo[d]thiazol-2-ylamino)cyclohexanol; (1R,2R)-2-(6-(6'-amino-2,3'-bipyridin-4-yloxy)benzo[d]thiazol-2-ylamino)cyclohexanol; (1R,2R)-2-(6-(2-(1H-imidazol-1-yl)pyridin-4-yloxy)benzo[d]thiazol-2-ylamino)cyclohexanol; (S)-6-(2-chloropyridin-4-yloxy)-N-(1-cyclohexylethyl)benzo[d]thiazol-2-amine; (1R,2R)-2-(6-(2-(1-methyl-1H-pyrazol-5-yl)pyridin-4-yloxy)benzo[d]thiazol-2-ylamino)cyclohexanol; (1R,2R)-2-(6-(2-(4,5-diethyl-1H-imidazol-2-yl)pyridin-4-yloxy)benzo[d]thiazol-2-ylamino)cyclohexanol; (1R,2R)-2-(6-(2-(5-methyl-4-propyl-1H-imidazol-2-yl)pyridin-4-yloxy)benzo[d]thiazol-2-ylamino)cyclohexanol; (S)—N-(1-cyclohexylethyl)-6-(2-(4-methyl-1H-imidazol-2-yl)pyridin-4-yloxy)benzo[d]thiazol-2-amine; (S)—N-(1-cyclohexylethyl)-6-(2-(4,5-dimethyl-1H-imidazol-2-yl)pyridin-4-yloxy)benzo[d]thiazol-2-amine; (S)—N-(1-cyclohexylethyl)-6-(2-(4-ethyl-5-methyl-1H-imidazol-2-yl)pyridin-4-yloxy)benzo[d]thiazol-2-amine; (S)—N-(1-cyclohexylethyl)-6-(2-(4,5,6,7-tetrahydro-1H-benzo[d]imidazol-2-yl)pyridin-4-yloxy)benzo[d]thiazol-2-amine; (S)—N-(1-cyclohexylethyl)-6-(2-(4,5-diethyl-1H-imidazol-2-yl)pyridin-4-yloxy)benzo[d]thiazol-2-amine; (S)—N-(1-cyclohexylethyl)-6-(2-(1-propyl-1H-pyrazol-4-yl)pyridin-4-yloxy)benzo[d]thiazol-2-amine; (S)-6-(2,3'-bipyridin-4-yloxy)-N-(1-cyclohexylethyl)benzo[d]thiazol-2-amine; (S)-6-(2,4'-bipyridin-4-yloxy)-N-(1-cyclohexylethyl)benzo[d]thiazol-2-amine; (S)-6-(6'-amino-2,3'-bipyridin-4-yloxy)-N-(1-cyclohexylethyl)benzo[d]thiazol-2-amine; (S)—N-(1-cyclohexylethyl)-6-(2-(1-methyl-1H-pyrazol-5-yl)pyridin-4-yloxy)benzo[d]thiazol-2-amine; (S)-6-(2-(1H-pyrrolo[2,3-b]pyridin-5-yl)pyridin-4-yloxy)-N-(1-cyclohexylethyl)benzo[d]thiazol-2-amine; (S)—N-(1-cyclohexylethyl)-6-(6'-methoxy-2,3'-bipyridin-4-yloxy)benzo[d]thiazol-2-amine; (1R,2R)-2-(6-(2,4'-bipyridin-4-yloxy)benzo[d]thiazol-2-ylamino)cyclohexanol; (1R,2R)-2-(6-(2-(1-propyl-1H-pyrazol-4-yl)pyridin-4-yloxy)benzo[d]thiazol-2-ylamino)cyclohexanol; (1R,2R)-2-(6-(6'-amino-5'-(trifluoromethyl)-2,3'-bipyridin-4-yloxy)benzo[d]thiazol-2-ylamino')cyclohexanol; (1R,2R)-2-(6-(2-(1,3,5-trimethyl-1H-pyrazol-4-yl)pyridin-4-yloxy)benzo[d]thiazol-2-ylamino)cyclohexanol; (1R,2R)-2-(6-(2-(1H-pyrrolo[2,3-b]pyridin-5-yl)pyridin-4-yloxy)benzo[d]thiazol-2-ylamino)cyclohexanol; (1R,2R)-2-(6-(2-(pyrimidin-5-yl)pyridin-4-yloxy)benzo[d]thiazol-2-ylamino)cyclohexanol; (1R,2R)-2-(6-(2-(2-(dimethylamino)pyrimidin-5-yl)pyridin-4-yloxy)benzo[d]thiazol-2-ylamino)cyclohexanol; 4-(2-((1R,2R)-2-hydroxycyclohexylamino)benzo[d]thiazol-6-yloxy)-2,3'-bipyridine-6'-carbonitrile; (1R,2R)-2-(6-(2-(4-fluorophenyl)pyridin-4-yloxy)benzo[d]thiazol-2-ylamino)cyclohexanol; (S)-4-42-(1-cyclohexylethylamino)benzo[d]thiazol-6-yloxy)-N',N'-dimethylpicolinohydrazide; 4-(2-(2-cyclopropylethylamino)benzo[d]thiazol-6-yloxy)-N-methylpicolinamide; 4-(2-((1S,2R)-2-aminocyclohexylamino)benzo[d]thiazol-6-yloxy)-N-methylpicolinamide; 4-(2-(3-hydroxycyclohexylamino)benzo[d]thiazol-6-yloxy)-N-methylpicolinamide; 4-(2-(3-aminocyclohexylamino)benzo[d]thiazol-6-yloxy)-N-methylpicolinamide; 4-(2-((1S,2R)-2-acetamidocyclohexylamino)benzo[d]thiazol-6-yloxy)-N-methylpicolinamide; 4-(2-(3-acetamidocyclohexylamino)benzo[d]thiazol-6-yloxy)-N-methylpicolinamide; 4-(2-((1R,2R)-2-aminocyclohexylamino)benzo[d]thiazol-6-yloxy)-N-methylpicolinamide; 4-(2-((1R,2R)-2-acetamidocyclohexylamino)benzo[d]thiazol-6-yloxy)-N-methylpicolinamide; 4-(2-((1R,2R)-2-(hydroxymethyl)cyclohexylamino)benzo[d]thiazol-6-yloxy)-N-methylpicolinamide; N-methyl-4-(2-((1S,2R)-2-(methylsulfonamido)cyclohexylamino)benzo[d]thiazol-6-yloxy)picolinamide; 4-(2-((1S,2R)-2-(3-isopropylureido)cyclohexylamino)benzo[d]thiazol-6-yloxy)-N-methylpicolinamide; (R)-4-(2-(1-acetylpiperidin-3-ylamino)benzo[d]thiazol-6-yloxy)-N-methylpicolinamide; (R)-4-(2-(1-acetylpyrrolidin-3-ylamino)benzo[d]thiazol-6-yloxy)-N-methylpicolinamide; (S)-4-(2-(1-acetylpiperidin-3-ylamino)benzo[d]thiazol-6-yloxy-N-methylpicolinamide; (S)-4-(2-(1-acetylpyrrolidin-3-ylamino)benzo[d]thiazol-6-yloxy-N-methylpicolinamide; 4-(2-((1-acetylpiperidin-3-yl)methylamino)benzo[d]thiazol-6-yloxy)-N-methylpicolinamide; 4-(2-(1-acetylpiperidin-4-ylamino)benzo[d]thiazol-6-yloxy)-N-methylpicolinamide; N-methyl-4-(2-((1-(methylsulfonyl)piperidin-3-yl)methylaminomenzo[d]thiazol-6-yloxy)picolinamide; N-methyl-4-(2-((1S,2R)-2-((R)-tetrahydrofuran-2-carboxamido)cyclohexylamino)benzo[d]thiazol-6-yloxy)picolinamide; 4-(2-((1S,2R)-2-isobutyramidocyclohexylamino)benzo[d]thiazol-6-yloxy)-N-methylpicolinamide; N-methyl-4-(2-((1S,2R)-2-(3-methylbutanamido)cyclohexylamino)benzo[d]thiazol-6-yloxy)picolinamide; 4-(2-((1S,2R)-2-benzamidocyclohexylamino)benzo[d]thiazol-6-yloxy)-N-methylpicolinamide; N-methyl-4-(2-((1S,2R)-2-((S)-1-methylpyrrolidine-2-carboxamido)cyclohexylamino)benzo[d]thiazol-6-yloxy)picolinamide; N-methyl-4-(2-(2-(pyridin-2-yl)ethylamino)benzo[d]thiazol-6-yloxy)picolinamide; N-methyl-4-(2-(2-(pyridin-3-yl)ethylamino)benzo[d]thiazol-6-yloxy)picolinamide; N-methyl-4-(2-(2-(pyridin-4-yl)ethylamino)benzo[d]thiazol-6-yloxy)picolinamide; 4-(2-(2-methoxyphenethylamino)benzo[d]thiazol-6-yloxy)-N-methylpicolinamide; N-methyl-4-(2-((1S,2S)-2-phenylcyclopropylamino)benzo[d]thiazol-6-yloxy)picolinamide; 4-(2-(2-chlorophenethylamino)benzo[d]thiazol-6-yloxy)-N-methylpicolinamide; 4-(2-((1S,2S)-2-hydroxycyclopentylamino)benzo[d]thiazol-6-yloxy)-N-methylpicolinamide; 4-(2-((1S,2R)-2-hydroxy-2,3-dihydro-1H-inden-1-ylamino)benzo[d]thiazol-6-yloxy)-N-methylpicolinamide; 4-(2-((1S,2R)-2-hydroxycyclopentylamino)benzo[d]thiazol-6-yloxy)-N-methylpicolinamide; 4-(2-((1R,2S)-2-hydroxy-2,3-dihydro-1H-inden-1-ylamino)benzo[d]thiazol-6-yloxy)-N-methylpicolinamide; 4-(2-((1R,2R)-2-hydroxycyclopentylamino)benzo[d]thiazol-6-yloxy)-N-methylpicolinamide; 4-(2-((1S,3R,4R)-3-(hydroxymethyl)bicyclo[2.2.1]heptan-2-ylamino)benzo[d]thiazol-6-yloxy)-N-methylpicolinamide; N-methyl-4-(2-((1R,2R)-2-(methylsulfonamido)cyclohexylamino)benzo[d]thiazol-6-yloxy)picolinamide; 4-(2-((1R,2R)-2-isobutyramidocyclohexylamino)benzo[d]thiazol-6-yloxy)-N-methylpicolinamide; (S)-4-(2-(1-(2-methoxyphenyl)ethylamino)benzo[d]thiazol-6-yloxy)-N-methylpicolinamide; (R)—N-methyl-4-(2-(1,2,3,4-tetrahydronaphthalen-2-ylamino)benzo[d]thiazol-6-yloxy)picolinamide; N-methyl-4-(2-((1S,2S)-2-(methylsulfonamido)cyclohexylamino)benzo[d]thiazol-6-yloxy)picolinamide; (S)—N-methyl-4-(2-(1-(methylsulfonyl)piperidin-3-ylamino)benzo[d]thiazol-6-yloxy)picolinamide; (S)—N-methyl-4-(2-(piperidin-3-ylamino)benzo[d]thiazol-6-yloxy)picolinamide; (S)-4-(2-(1-(isopropylcarbamoyl)piperidin-3-ylamino)benzo[d]thiazol-6-yloxy)-N-methylpicolinamide; (S)-4-(2-(1-isobutyrylpiperidin-3-ylamino)benzo[d]thiazol-6-yloxy)-N-methylpicolinamide; (S)-4-(2-(1-(cyclopentanecarbonyl)piperidin-3-ylamino)benzo[d]thiazol-6-yloxy)-N-methylpicolinamide; (S)-4-(2-(1-benzoylpiperidin-3-ylamino)benzo[d]thiazol-6-yloxy)-N-methylpicolinamide; 4-(2-((1-(isopropylcarbamoyl)piperidin-3-yl)methylamino)benzo[d]thiazol-6-yloxy)-N-methylpicolinamide; N-(cyclohexylmethyl)-6-(2-(methylamino)pyridin-4-yloxy)benzo[d]thiazol-2-amine; N-(cyclohexylmethyl)-6-(2-(ethylamino)pyridin-4-yloxy)benzo[d]thiazol-2-amine; N-(cyclohexylmethyl)-6-(2-(1-methyl-1H-pyrazol-4-yl)pyridin-4-yloxy)benzo[d]thiazol-2-amine; 6-(2-(1H-pyrazol-4-yl)pyridin-4-yloxy)-N-(cyclohexylmethyl)benzo[d]thiazol-2-amine; N-(cyclohexylmethyl)-6-(2-(oxazol-2-yl)pyridin-4-yloxy)benzo[d]thiazol-2-amine; N-(cyclohexylmethyl)-6-(2-(2-methoxyethylamino)pyridin-4-yloxy)benzo[d]thiazol-2-amine; (1R,2R)-2-(6-(2-(1-methyl-1H-pyrazol-4-yl)pyridin-4-yloxy)benzo[d]thiazol-2-ylamino)cyclohexanol; (1R,2R)-2-(6-(2,3'-bipyridin-4-yloxy)benzo[d]thiazol-2-ylamino)cyclohexanol; (1R,2R)-2-(6-(2-(2-aminopyrimidin-5-yl)pyridin-4-yloxy)benzo[d]thiazol-2-ylamino)cyclohexanol; (R)-2-cyclohexyl-2-(6-(2-(1-methyl-1H-pyrazol-4-yl)pyridin-4-yloxy)benzo[d]thiazol-2-ylamino)ethanol; (1R,2S)-1-(6-(2-(1-methyl-1H-pyrazol-4-yl)pyridin-4-yloxy)benzo[d]thiazol-2-ylamino)-2,3-dihydro-1H-inden-2-ol; (2S,3S)-3-methyl-2-(6-(2-(1-methyl-1H-pyrazol-4-yl)pyridin-4-yloxy)benzo[d]thiazol-2-ylamino)pentan-1-ol; (1S,2R)-1-(6-(2-(1-methyl-1H-pyrazol-4-yl)pyridin-4-yloxy)benzo[d]thiazol-2-ylamino)-2,3-dihydro-1H-inden-2-ol; (S)-2-(6-(2-(1H-pyrazol-4-yl)pyridin-4-yloxy)benzo[d]thiazol-2-ylamino)-3-phenylpropan-1-ol; (S)-3-methyl-2-(6-(2-(1-methyl-1H-pyrazol-4-yl)pyridin-4-yloxy)benzo[d]thiazol-2-ylamino)butan-1-ol; (S)-2-cyclohexyl-2-(6-(2-(1-methyl-1H-pyrazol-4-yl)pyridin-4-yloxy)benzo[d]thiazol-2-ylamino)ethanol; (R)—N-(1-cyclohexylethyl)-6-(2-(1-methyl-1H-pyrazol-4-yl)pyridin-4-yloxy)benzo[d]thiazol-2-amine; (R)-4-methyl-2-(6-(2-(1-methyl-1H-pyrazol-4-yl)pyridin-4-yloxy)benzo[d]thiazol-2-ylamino)pentan-1-ol; N-(2-(difluoromethoxy)benzyl)-6-(2-(1-methyl-1H-pyrazol-4-yl)pyridin-4-yloxy)benzo[d]thiazol-2-amine; (S)-2-(6-(2-(1-methyl-1H-pyrazol-4-yl)pyridin-4-yloxy)benzo[d]thiazol-2-ylamino)-1-phenylethanol; (S)-4-methyl-2-(6-(2-(1-methyl-1H-pyrazol-4-yl)pyridin-4-yloxy)benzo[d]thiazol-2-ylamino)pentan-1-ol; (1R,2R)-2-(6-(2-(1-isobutyl-1H-pyrazol-4-yl)pyridin-4-yloxy)benzo[d]thiazol-2-ylamino)cyclohexanol; (1R,2R)-2-(6-(2-(1H-pyrazol-4-yl)pyridin-4-yloxy)benzo[d]thiazol-2-ylamino)cyclohexanol; 6-(2-(1-methyl-1H-pyrazol-4-yl)pyridin-4-yloxy)-N-(2-(tetrahydro-2H-pyran-4-yl)ethyl)benzo[d]thiazol-2-amine; (S)-6-(2-(1-methyl-1H-pyrazol-4-yl)pyridin-4-yloxy)-N-(1,2,3,4-tetrahydronaphthalen-1-yl)benzo[d]thiazol-2-amine; (R)-6-(2-(1-methyl-1H-pyrazol-4-yl)pyridin-4-yloxy)-N-(1,2,3,4-tetrahydronaphthalen-1-yl)benzo[d]thiazol-2-amine; N-cycloheptyl-6-(2-(1-methyl-1H-pyrazol-4-yl)pyridin-4-yloxy)benzo[d]thiazol-2-amine; N-isopentyl-6-(2-(1-methyl-1H-pyrazol-4-yl)pyridin-4-yloxy)benzo[d]thiazol-2-amine; (S)-6-(2-(1-methyl-1H-pyrazol-4-yl)pyridin-4-yloxy)-N-(1,2,3,4-tetrahydronaphthalen-2-yl)benzo[d]thiazol-2-amine; (S)-4-(2-(1-(cyclopropylsulfonyl)piperidin-3-ylamino)benzo[d]thiazol-6-yloxy)-N-methylpicolinamide; (1R,2R)-2-(6-(2-(methylamino)pyridin-4-yloxy)benzo[d]thiazol-2-ylamino)cyclohexanol; (1R,2R)-2-(6-(2-(ethylamino)pyridin-4-yloxy)benzo[d]thiazol-2-ylamino)cyclohexanol; N-methyl-4-(2-((tetrahydro-2H-pyran-2-yl)methylamino)benzo[d]thiazol-6-yloxy)picolinamide; (1R,2R)-2-(6-(2-(furan-2-yl)pyridin-4-yloxy)benzo[d]thiazol-2-ylamino)cyclohexanol; (1R,2R)-2-(6-(2-(oxazol-2-yl)pyridin-4-yloxy)benzo[d]thiazol-2-ylamino)cyclohexanol; (S)—N-(1-(cyclopropylsulfonyl)piperidin-3-yl)-6-(2-(1-methyl-1H-pyrazol-4-yl)pyridin-4-yloxy)benzo[d]thiazol-2-amine; 4-(2-(cyclohexylmethylamino)-4-methylbenzo[d]thiazol-6-yloxy)-N-methylpicolinamide; 4-(4-chloro-2-(cyclohexylmethylamino)benzo[d]thiazol-6-yloxy)-N-methylpicolinamide; 4-(7-bromo-2-((1R,2R)-2-hydroxycyclohexylamino)benzo[d]thiazol-6-yloxy)-N-methylpicolinamide; 4-(2-((1R,2R)-2-hydroxycyclohexylamino)-7-methylbenzo[d]thiazol-6-yloxy)-N-methylpicolinamide; 4-(7-chloro-2-((1R,2R)-2-hydroxycyclohexylamino)benzo[d]thiazol-6-yloxy)-N-methylpicolinamide; 4-(2-(cyclohexylmethylamino)-5-fluorobenzo[d]thiazol-6-yloxy)-N-methylpicolinamide; 4-(2-(cyclohexylmethylamino)benzo[d]thiazol-6-yloxy)-N-isobutoxypicolinamide; 4-(2-((1R,2R)-2-hydroxycyclohexylamino)benzo[d]thiazol-6-yloxy)-N-isobutoxypicolinamide; 6-(2-(1-methyl-1H-pyrazol-4-yl)pyridin-4-yloxy)-N-(4-(4-methylpiperazin-1-yl)benzyl)benzo[d]thiazol-2-amine; N-methyl-4-(2-(3-(4-methylpiperazin-1-yl)propylamino)benzo[d]thiazol-6-yloxy)picolinamide; (1R,2R)-2-(6-(2'-morpholino-2,4'-bipyridin-4-yloxy)benzo[d]thiazol-2-ylamino)cyclohexanol; (1R,2R)-2-(6-(2'-(4-methylpiperazin-1-yl)-2,4'-bipyridin-4-yloxy)benzo[d]thiazol-2-ylamino)

cyclohexanol; 1-(4-(2-((1R,2R)-2-hydroxycyclohexylamino)benzo[d]thiazol-6-yloxy)-2,4'-bipyridin-2'-yl)piperidin-4-ol; (1R,2R)-2-(6-(2'-((R)-3-(dimethylamino)pyrrolidin-1-yl)-2,4'-bipyridin-4-yloxy)benzo[d]thiazol-2-ylamino)cyclohexanol; 4-(4-(2-((1R,2R)-2-hydroxycyclohexylamino)benzo[d]thiazol-6-yloxy)-2,4'-bipyridin-2'-yl)piperazin-2-one; (1R,2R)-2-(6-(2'-((S)-3-(dimethylamino)pyrrolidin-1-yl)-2,4'-bipyridin-4-yloxy)benzo[d]thiazol-2-ylamino)cyclohexanol; (1R,2R)-2-(6-(2'-(4-(dimethylamino)piperidin-1-yl)-2,4'-bipyridin-4-yloxy)benzo[d]thiazol-2-ylamino)cyclohexanol; (1R,2R)-2-(6-(2'-(pyrrolidin-1-yl)-2,4'-bipyridin-4-yloxy)benzo[d]thiazol-2-ylamino)cyclohexanol; (1R,2R)-2-(6-(2'-(4-fluoropiperidin-1-yl)-2,4'-bipyridin-4-yloxy)benzo[d]thiazol-2-ylamino)cyclohexanol; (1R,2R)-2-(6-(2'-(dimethylamino)-2,4'-bipyridin-4-yloxy)benzo[d]thiazol-2-ylamino)cyclohexanol 1-(4-(2-((1R,2R)-2-hydroxycyclohexylamino)benzo[d]thiazol-6-yloxy)-2,3'-bipyridin-6'-yl)piperidin-4-ol; (1R,2R)-2-(6-(6'-((R)-3-(dimethylamino)pyrrolidin-1-yl)-2,3'-bipyridin-4-yloxy)benzo[d]thiazol-2-ylamino)cyclohexanol; 4-(4-(2-((1R,2R)-2-hydroxycyclohexylamino)benzo[d]thiazol-6-yloxy)-2,3'-bipyridin-6'-yl)piperazin-2-one; (1R,2R)-2-(6-(6'-((S)-3-(dimethylamino)pyrrolidin-1-yl)-2,3'-bipyridin-4-yloxy)benzo[d]thiazol-2-ylamino)cyclohexanol; (1R,2R)-2-(6-(6'-(4-(dimethylamino)piperidin-1-yl)-2,3'-bipyridin-4-yloxy)benzo[d]thiazol-2-ylamino)cyclohexanol; (1R,2R)-2-(6-(6'-(pyrrolidin-1-yl)-2,3'-bipyridin-4-yloxy)benzo[d]thiazol-2-ylamino)cyclohexanol; (1R,2R)-2-(6-(6'-(4-fluoropiperidin-1-yl)-2,3'-bipyridin-4-yloxy)benzo[d]thiazol-2-ylamino)cyclohexanol; (1R,2R)-2-(6-(6'-(dimethylamino)-2,3'-bipyridin-4-yloxy)benzo[d]thiazol-2-ylamino)cyclohexanol; (1R,2R)-2-(6-(6'-(piperidin-1-yl)-2,3'-bipyridin-4-yloxy)benzo[d]thiazol-2-ylamino)cyclohexanol; (1R,2R)-2-(6-(6'-(4-isopropylpiperazin-1-yl)-2,3'-bipyridin-4-yloxy)benzo[d]thiazol-2-ylamino)cyclohexanol; (S)-6-(2-(1-methyl-1H-pyrazol-4-yl)pyridin-4-yloxy)-N-(1-(methylsulfonyl)piperidin-3-yl)benzo[d]thiazol-2-amine; (S)—N-(1-(ethylsulfonyl)piperidin-3-yl)-6-(2-(1-methyl-1H-pyrazol-4-yl)pyridin-4-yloxy)benzo[d]thiazol-2-amine; 4-fluoro-3-(4-(2-((1R,2R)-2-hydroxycyclohexylamino)benzo[d]thiazol-6-yloxy)pyridin-2-yl)-N,N-dimethylbenzamide; 3-(4-(2-((1R,2R)-2-hydroxycyclohexylamino)benzo[d]thiazol-6-yloxy)pyridin-2-yl)-N,N-dimethylbenzamide; (3-(4-(2-((1R,2R)-2-hydroxycyclohexylamino)benzo[d]thiazol-6-yloxy)pyridin-2-yl)phenyl)(pyrrolidin-1-yl)methanone; (3-(4-(2-((1R,2R)-2-hydroxycyclohexylamino)benzo[d]thiazol-6-yloxy)pyridin-2-yl)phenyl)(morpholino)methanone; (3-(4-(2-((1R,2R)-2-hydroxycyclohexylamino)benzo[d]thiazol-6-yloxy)pyridin-2-yl)phenyl)(4-methylpiperazin-1-yl)methanone; (4-(2-((1R,2R)-2-hydroxycyclohexylamino)benzo[d]thiazol-6-yloxy)-2,3'-bipyridin-5'-yl)(morpholino)methanone; 4-(4-(2-((1R,2R)-2-hydroxycyclohexylamino)benzo[d]thiazol-6-yloxy)pyridin-2-yl)-N,N-dimethylbenzamide; (4-(4-(2-((1R,2R)-2-hydroxycyclohexylamino)benzo[d]thiazol-6-yloxy)pyridin-2-yl)phenyl)(pyrrolidin-1-yl)methanone; (4-(4-(2-((1R,2R)-2-hydroxycyclohexylamino)benzo[d]thiazol-6-yloxy)pyridin-2-yl)phenyl)(morpholino)methanone; (4-(4-(2-((1R,2R)-2-hydroxycyclohexylamino)benzo[d]thiazol-6-yloxy)pyridin-2-yl)phenyl)(4-methylpiperazin-1-yl)methanone; 4-(4-(2-((1R,2R)-2-hydroxycyclohexylamino)benzo[d]thiazol-6-yloxy)pyridin-2-yl)-N-(2-hydroxyethyl)benzamide; 4-(4-(2-((1R,2R)-2-hydroxycyclohexylamino)benzo[d]thiazol-6-yloxy)pyridin-2-yl)benzamide; (1R,2R)-2-(6-(2-(4-methylpiperazin-1-yl)pyrimidin-5-yl)pyridin-4-yloxy)benzo[d]thiazol-2-ylamino)cyclohexanol; (1R,2R)-2-(6-(2-(1H-pyrazol-5-yl)pyridin-4-yloxy)benzo[d]thiazol-2-ylamino)cyclohexanol; 3-(4-(2-((1R,2R)-2-hydroxycyclohexylamino)benzo[d]thiazol-6-yloxy)pyridin-2-yl)-N-(2-hydroxyethyl)benzamide; (1R,2R)-2-(6-(2-(4-(4-methyl-1H-imidazol-2-yl)phenyl)pyridin-4-yloxy)benzo[d]thiazol-2-ylamino)cyclohexanol; (1R,2R)-2-(6-(2-(4-(4,5-dimethyl-1H-imidazol-2-yl)phenyl)pyridin-4-yloxy)benzo[d]thiazol-2-ylamino)cyclohexanol; (S)-4-(2-(1-cyclohexylethylamino)benzo[d]thiazol-6-yloxy)picolinonitrile; (1R,2R)-2-(6-(2-(4-(4-(trifluoromethyl)-1H-imidazol-2-yl)phenyl)pyridin-4-yloxy)benzo[d]thiazol-2-ylamino)cyclohexanol; (1R,2R)-2-(6-(2-(4-(pyrrolidin-1-ylmethyl)phenyl)pyridin-4-yloxy)benzo[d]thiazol-2-ylamino)cyclohexanol; (1R,2R)-2-(6-(2-(4-((4-methylpiperazin-1-yl)methyl)phenyl)pyridin-4-yloxy)benzo[d]thiazol-2-ylamino)cyclohexanol; 4-(2-((1R,2R)-2-hydroxycyclohexylamino)-1-oxo-benzo[d]thiazol-6-yloxy)-N-methylpicolinamide; ((1S,2S)-2-(6-(2-(1-methyl-1H-pyrazol-4-yl)pyridin-4-yloxy)benzo[d]thiazol-2-ylamino)cyclohexyl)methanol; (1R,2S)-1-(6-(2,3'-bipyridin-4-yloxy)benzo[d]thiazol-2-ylamino)-2,3-dihydro-1H-inden-2-ol; (1R,2S)-1-(6-(6'-amino-2,3'-bipyridin-4-yloxy)benzo[d]thiazol-2-ylamino)-2,3-dihydro-1H-inden-2-ol; (1R,2S)-1-(6-(6'-(4-methylpiperazin-1-yl)-2,3'-bipyridin-4-yloxy)benzo[d]thiazol-2-ylamino)-2,3-dihydro-1H-inden-2-ol; (1R,2S)-1-(6-(6'-morpholino-2,3'-bipyridin-4-yloxy)benzo[d]thiazol-2-ylamino)-2,3-dihydro-1H-inden-2-ol; (1R,2S)-1-(6-(2,4'-bipyridin-4-yloxy)benzo[d]thiazol-2-ylamino)-2,3-dihydro-1H-inden-2-ol; (1R,2S)-1-(6-(2-(1H-pyrazol-4-yl)pyridin-4-yloxy)benzo[d]thiazol-2-ylamino)-2,3-dihydro-1H-inden-2-ol; (1R,2S)-1-(6-(2-(1-propyl-1H-pyrazol-4-yl)pyridin-4-yloxy)benzo[d]thiazol-2-ylamino)-2,3-dihydro-1H-inden-2-ol; (1R,2S)-1-(6-(2-(1-(2-morpholinoethyl)-1H-pyrazol-4-yl)pyridin-4-yloxy)benzo[d]thiazol-2-ylamino)-2,3-dihydro-1H-inden-2-ol; (1R,2S)-1-(6-(2-(1-ethyl-1H-pyrazol-4-yl)pyridin-4-yloxy)benzo[d]thiazol-2-ylamino)-2,3-dihydro-1H-inden-2-ol; (1R,2S)-1-(6-(2-(1-(2-methoxyethyl)-1H-pyrazol-4-yl)pyridin-4-yloxy)benzo[d]thiazol-2-ylamino)-2,3- dihydro-1H-inden-2-ol; (1R,2S)-1-(6-(2-(1-(2-(diethylamino)ethyl)-1H-pyrazol-4-yl)pyridin-4-yloxy)benzo[d]thiazol-2-ylamino)-2,3-dihydro-1H-inden-2-ol; (4-(4-(2-((1R,2S)-2-hydroxy-2,3-dihydro-1H-inden-1-ylamino)benzo[d]thiazol-6-yloxy)pyridin-2-yl)phenyl)(pyrrolidin-1-yl)methanone; (S)—N-(1-cyclohexylethyl)-6-(2-(1-ethyl-1H-pyrazol-4-yl)pyridin-4-yloxy)benzo[d]thiazol-2-amine; (S)—N-(1-cyclohexylethyl)-6-(2-(1-(2,2-difluoroethyl)-1H-pyrazol-4-yl)pyridin-4-yloxy)benzo[d]thiazol-2-amine; (S)—N-(1-cyclohexylethyl)-6-(2-(1-(2-(diethylamino)ethyl)-1H-pyrazol-4-yl)pyridin-4-yloxy)benzo[d]thiazol-2-amine; (S)—N-(1-cyclohexylethyl)-6-(2-(1-(2-methoxyethyl)-1H-pyrazol-4-yl)pyridin-4-yloxy)benzo[d]thiazol-2-amine; (S)—N-(1-cyclohexylethyl)-6-(2-(1-(2-fluoroethyl)-1H-pyrazol-4-yl)pyridin-4-yloxy)benzo

[d]thiazol-2-amine; (S)—N-(1-cyclohexylethyl)-6-(2-(1-(2-morpholinoethyl)-1H-pyrazol-4-yl)pyridin-4-yloxy)benzo[d]thiazol-2-amine; (1R,2S)-1-(6-(2-(1-(2-fluoroethyl)-1H-pyrazol-4-yl)pyridin-4-yloxy)benzo[d]thiazol-2-ylamino)-2,3-dihydro-1H-inden-2-ol; (1R,2S)-1-(6-(2-(1-(2,2-difluoroethyl)-1H-pyrazol-4-yl)pyridin-4-yloxy)benzo[d]thiazol-2-ylamino)-2,3-dihydro-1H-inden-2-ol; (1R,2S)-1-(6-(2'-(4-methylpiperazin-1-yl)-2,4'-bipyridin-4-yloxy)benzo[d]thiazol-2-ylamino)-2,3-dihydro-1H-inden-2-ol; (1R,2S)-1-(6-(6'-((S)-3-(dimethylamino)pyrrolidin-1-yl)-2,3'-bipyridin-4-yloxy)benzo[d]thiazol-2-ylamino)-2,3-dihydro-1H-inden-2-ol; 4-(4-(2-((1R,2R)-2-hydroxycyclohexylamino)benzo[d]thiazol-6-yloxy)pyridin-2-yl)pyridin-2(1H)-one; (1R,2R)-2-(6-(5'-fluoro-2,3'-bipyridin-4-yloxy)benzo[d]thiazol-2-ylamino)cyclohexanol; (1R,2R)-2-(6-(5'-methoxy-2,3'-bipyridin-4-yloxy)benzo[d]thiazol-2-ylamino)cyclohexanol; 5-(4-(2-((1R,2R)-2-hydroxycyclohexylamino)benzo[d]thiazol-6-yloxy)pyridin-2-yl)pyridin-2(1H)-one; (1R,2S)-1-(6-(2-chloropyridin-4-yloxy)benzo[d]thiazol-2-ylamino)-2,3-dihydro-1H-inden-2-ol; (R)-4-methyl-2-(6-(2-(1-(2-morpholinoethyl)-1H-pyrazol-4-yl)pyridin-4-yloxy)benzo[d]thiazol-2-ylamino)pentan-1-ol; (R)-4-methyl-2-(6-(2-(1-propyl-1H-pyrazol-4-yl)pyridin-4-yloxy)benzo[d]thiazol-2-ylamino)pentan-1-ol; (R)-4-methyl-2-(6-(6'-(4-methylpiperazin-1-yl)-2,3'-bipyridin-4-yloxy)benzo[d]thiazol-2-ylamino)pentan-1-ol; (R)-2-(6-(6'-amino-2,3'-bipyridin-4-yloxy)benzo[d]thiazol-2-ylamino)-4-methylpentan-1-ol; (R)-2-(6-(2-(1-(2-(diethylamino)ethyl)-1H-pyrazol-4-yl)pyridin-4-yloxy)benzo[d]thiazol-2-ylamino)-4-methylpentan-1-ol; (R)-2-(6-(2-(1-(2,2-difluoroethyl)-1H-pyrazol-4-yl)pyridin-4-yloxy)benzo[d]thiazol-2-ylamino)-4-methylpentan-1-ol; (R)-2-(6-(2-(1-(2-methoxyethyl)-1H-pyrazol-4-yl)pyridin-4-yloxy)benzo[d]thiazol-2-ylamino)-4-methylpentan-1-ol; (R)-2-(6-(2-(1-ethyl-1H-pyrazol-4-yl)pyridin-4-yloxy)benzo[d]thiazol-2-ylamino)-4-methylpentan-1-ol; (R)-2-(6-(2-(1-(2-fluoroethyl)-1H-pyrazol-4-yl)pyridin-4-yloxy)benzo[d]thiazol-2-ylamino)-4-methylpentan-1-ol; 4-(2-((1S,2R)-2-hydroxycyclohexylamino)benzo[d]thiazol-6-yloxy)-N-methylpicolinamide; 4-(2-((1R,2S)-2-hydroxycyclohexylamino)benzo[d]thiazol-6-yloxy)-N-methylpicolinamide; (R)-2-(6-(2-(4-ethyl-5-methyl-1H-imidazol-2-yl)pyridin-4-yloxy)benzo[d]thiazol-2-ylamino)-4-methylpentan-1-ol; (1R,2R)-2-(6-(2-(1-(2-(4-methylpiperazin-1-yl)ethyl)-1H-pyrazol-4-yl)pyridin-4-yloxy)benzo[d]thiazol-2-ylamino)cyclohexanol; (1R,2R)-2-(6-(2-(1-(2-(dimethylamino)ethyl)-1H-pyrazol-4-yl)pyridin-4-yloxy)benzo[d]thiazol-2-ylamino)cyclohexanol; (1R,2R)-2-(6-(2-(1-(2-(pyrrolidin-1-yl)ethyl)-1H-pyrazol-4-yl)pyridin-4-yloxy)benzo[d]thiazol-2-ylamino)cyclohexanol; (1R,2R)-2-(6-(2-(1-(2-(4-fluoropiperidin-1-yl)ethyl)-1H-pyrazol-4-yl)pyridin-4-yloxy)benzo[d]thiazol-2-ylamino)cyclohexanol; 4-(2-(4-(4-(2-((1R,2R)-2-hydroxycyclohexylamino)benzo[d]thiazol-6-yloxy)pyridin-2-yl)-1H-pyrazol-1-yl)ethyl)piperazin-2-one; (1R,2R)-2-(6-(2-(1-((1,3-dioxolan-2-yl)methyl)-1H-pyrazol-4-yl)pyridin-4-yloxy)benzo[d]thiazol-2-ylamino)cyclohexanol; (S)-6-(2-chloropyridin-4-yloxy)-N-(1-(ethylsulfonyl)piperidin-3-yl)benzo[d]thiazol-2-amine; (S)-6-(2-(1H-pyrazol-4-yl)pyridin-4-yloxy)-N-(1-(ethylsulfonyl)piperidin-3-yl)benzo[d]thiazol-2-amine; (S)—N-(1-(ethylsulfonyl)piperidin-3-yl)-6-(2-(1-propyl-1H-pyrazol-4-yl)pyridin-4-yloxy)benzo[d]thiazol-2-amine; (S)—N-(1-(ethylsulfonyl)piperidin-3-yl)-6-(2-(1-(2-morpholinoethyl)-1H-pyrazol-4-yl)pyridin-4-yloxy)benzo[d]thiazol-2-amine; (S)-6-(2-(1-ethyl-1H-pyrazol-4-yl)pyridin-4-yloxy)-N-(1-(ethylsulfonyl)piperidin-3-yl)benzo[d]thiazol-2-amine; (S)—N-(1-(ethylsulfonyl)piperidin-3-yl)-6-(2-(1-(2-fluoroethyl)-1H-pyrazol-4-yl)pyridin-4-yloxy)benzo[d]thiazol-2-amine; (S)-6-(2-(1-(2,2-difluoroethyl)-1H-pyrazol-4-yl)pyridin-4-yloxy)-N-(1-(ethylsulfonyl)piperidin-3-yl)benzo[d]thiazol-2-amine; (S)—N-(1-(ethylsulfonyl)piperidin-3-yl)-6-(2-(1-(2-methoxyethyl)-1H-pyrazol-4-yl)pyridin-4-yloxy)benzo[d]thiazol-2-amine; (S)-6-(2-(1-(2-(diethylamino)ethyl)-1H-pyrazol-4-yl)pyridin-4-yloxy)-N-(1-(ethylsulfonyl)piperidin-3-yl)benzo[d]thiazol-2-amine; (R)-4-methyl-2-(6-(2-(4-methyl-1H-imidazol-2-yl)pyridin-4-yloxy)benzo[d]thiazol-2-ylamino)pentan-1-ol; (R)-4-methyl-2-(6-(2-(4,5,6,7-tetrahydro-1H-benzo[d]imidazol-2-yl)pyridin-4-yloxy)benzo[d]thiazol-2-ylamino)pentan-1-ol; (1R,2S)-1-(6-(6'-fluoro-2,3'-bipyridin-4-yloxy)benzo[d]thiazol-2-ylamino)-2,3-dihydro-1H-inden-2-ol; (1R,2S)-1-(6-(6'-(dimethylamino)-2,3'-bipyridin-4-yloxy)benzo[d]thiazol-2-ylamino)-2,3-dihydro-1H-inden-2-ol; (1R,2S)-1-(6-(2-(4-methyl-1H-imidazol-2-yl)pyridin-4-yloxy)benzo[d]thiazol-2-ylamino)-2,3-dihydro-1H-inden-2-ol; (1R,2S)-1-(6-(2-(4,5-dimethyl-1H-imidazol-2-yl)pyridin-4-yloxy)benzo[d]thiazol-2-ylamino)-2,3-dihydro-1H-inden-2-ol; (1R,2S)-1-(6-(2-(5-ethyl-4-methyl-1H-imidazol-2-yl)pyridin-4-yloxy)benzo[d]thiazol-2-ylamino)-2,3-dihydro-1H-inden-2-ol; (1R,2S)-1-(6-(2-(4,5,6,7-tetrahydro-1H-benzo[d]imidazol-2-yl)pyridin-4-yloxy)benzo[d]thiazol-2-ylamino)-2,3-dihydro-1H-inden-2-ol; (1R,2S)-1-(6-(2-(4-(trifluoromethyl)-1H-imidazol-2-yl)pyridin-4-yloxy)benzo[d]thiazol-2-ylamino)-2,3-dihydro-1H-inden-2-ol; (1R,2R)-2-(6-(2-(3-methoxyprop-1-ynyl)pyridin-4-yloxy)benzo[d]thiazol-2-ylamino)cyclohexanol; (1R,2R)-2-(6-(2-(3-(dimethylamino)prop-1-ynyl)pyridin-4-yloxy)benzo[d]thiazol-2-ylamino)cyclohexanol; (1R,2R)-2-(6-(2-(cyclopropylethynyl)pyridin-4-yloxy)benzo[d]thiazol-2-ylamino)cyclohexanol; (1R,2R)-2-(6-(2-ethynylpyridin-4-yloxy)benzo[d]thiazol-2-ylamino)cyclohexanol; (1R,2S)-1-(6-(2-(3-methoxyprop-1-ynyl)pyridin-4-yloxy)benzo[d]thiazol-2-ylamino)-2,3-dihydro-1H-inden-2-ol; (1R,2S)-1-(6-(2-(3-(dimethylamino)prop-1-ynyl)pyridin-4-yloxy)benzo[d]thiazol-2-ylamino)-2,3-dihydro-1H-inden-2-ol; (1R,2S)-1-(6-(2-(cyclopropylethynyl)pyridin-4-yloxy)benzo[d]thiazol-2-ylamino)-2,3-dihydro-1H-inden-2-ol; (1R,2S)-1-(6-(2-ethynylpyridin-4-yloxy)benzo[d]thiazol-2-ylamino)-2,3-dihydro-1H-inden-2-ol; N-(cyclohexylmethyl)-6-(2-methylpyridin-4-yloxy)benzo[d]thiazol-2-amine; and (1R,2R)-2-(6-(2-methylpyridin-4-yloxy)benzo[d]thiazol-2-ylamino)cyclohexanol.

65. The compound of claim 2 selected from the group consisting of 4-[2-(4-Bromo-phenylamino)-benzooxazol-6-yloxy]-pyridine-2-carboxylic acid methylamide, 4-[2-((R)-1-Phenyl-ethylamino)-benzooxazol-6-yloxy]-pyridine-2-carboxylic acid methylamide, 4-[2-(2-Morpholin-4-yl-phenylamino)-benzooxazol-6-yloxy]-pyridine-2-carboxylic acid methylamide, 4-[2-(2,3-Dihydro-benzo[1,4]dioxin-6-ylamino)-benzooxazol-6-yloxy]-pyridine-2-carboxylic acid methylamide, 4-[2-(1-Thiazol-2-yl-ethylamino)-benzooxazol-6-yloxy]-pyridine-2-carboxylic acid methylamide, 4-[2-((S)-1-Phenyl-ethylamino)-benzooxazol-6-yloxy]-pyridine-2-carboxylic acid methylamide, 4-[2-(2-Chloro-benzylamino)-benzooxazol-6-yloxy]-pyridine-2-carboxylic acid methylamide, 4-[2-(2,4-Dichloro-benzylamino)-benzooxazol-6-yloxy]-pyridine-2-carboxylic acid methylamide, 4-[2-(3-Methyl-cyclohexylamino)-benzooxazol-6-yloxy]-pyridine-2-carboxylic acid methylamide, 4-[2-(2-Methoxy-phenylamino)-benzooxazol-6-yloxy]-pyridine-2-carboxylic acid methylamide, 4-[2-(2-Ethoxy-phenylamino)-benzooxazol-6-yloxy]-pyridine-2-carboxylic acid methylamide, 4-[2-((1S,2S,3S,5R)-2,6,6-Tri-methyl-bicyclo[3.1.1]hept-3-ylamino)-benzooxazol-6-yloxy]-pyridine-2-carboxylic acid methylamide, 4-{2-[((1S,2R,4R)-7,7-Dimethyl-bicyclo[2.2.1]hept-2-ylmethyl)-amino]-benzooxazol-6-yloxy}-pyridine-2-carboxylic acid methylamide, 4-[2-(2-Fluoro-benzylamino)-benzooxazol-6-yloxy]-pyridine-2-carboxylic acid methylamide, 4-[2-(2-Methoxy-benzylamino)-benzooxazol-6-yloxy]-pyridine-2-carboxylic acid methylamide, 4-[2-((R)-1-Naphthalen-1-yl-ethylamino)-benzooxazol-6-yloxy]-pyridine-2-carboxylic acid methylamide, 4-[2-((R)-1-Phenyl-propyl-amino)-benzooxazol-6-yloxy]-pyridine-2-carboxylic acid methylamide, 4-[2-((S)-1-Naphthalen-2-yl-ethylamino)-benzooxazol-6-yloxy]-pyridine-2-carboxylic acid methylamide, 4-[2-(Cyclohexylmethyl-amino) -benzooxazol-6-yloxy]-pyridine-2-carboxylic acid methylamide, 4-(2-Cyclobutylamino-benzooxazol-6-yloxy)-pyridine-2-carboxylic acid methylamide, 4-(2-Cyclopentylamino -benzooxazol-6-yloxy)-pyridine-2-carboxylic acid methylamide, 4-(2-Cyclohexylamino-benzooxazol-6-yloxy)-pyridine-2-carboxylic acid methylamide, 4-[2-(2-Morpholin -4-ylm-ethyl-phenylamino)-benzooxazol-6-yloxy]-pyridine-2-carboxylic acid methylamide, 4-(2-Phenylamino-benzooxazol-6-yloxy)-pyridine-2-carboxylic acid methylamide, 4-[2-(4-Chloro-benzylamino)-benzooxazol-6-yloxy]-pyridine-2-carboxylic acid methylamide, 4-[2-(2,4-Dimethoxy-phenylamino)-benzooxazol-6-yloxy]-pyridine-2-carboxylic acid methyl-amide, N-[4-(2-Cyclohexylamino-benzooxazol-6-yloxy)-pyridin-2-yl]-acetamide, 4-[2-(Tetrahydro-pyran-4-ylamino)-benzooxazol-6-yloxy]-pyridine-2-carboxylic acid methylamide, 4-{2-[(R)-1-(2-Methoxy-phenyl)-ethylamino]-benzooxazol-6-yloxy}-pyridine-2-carboxylic acid methylamide, N-{4-[2-(2-Chloro-benzylamino)-benzooxazol-6-yloxy]-pyridin-2-yl}-acetamide, 4-[2-(2,5-Difluoro-benzylamino)-benzooxazol-6-yloxy]-pyridine-2-carboxylic acid methylamide, N-{4-[2-(Cyclohexylmethyl-amino)-benzooxazol-6-yloxy]-pyridin-2-yl }-acetamide, (R)-[6-(2-Methylcarbamoyl-pyridin-4-yloxy)-benzooxazol-2-ylamino]-phenyl-acetic acid, 4-{2-[((R)-Methylcarbamoyl-phenyl-methyl)-amino]-benzooxazol-6-yloxy}-pyridine-2-carboxylic acid methylamide, 4-[2-((R)-2-Hydroxy-1-phenyl-ethylamino)-benzooxazol-6-yloxy]-pyridine-2-carboxylic acid methylamide, (S)-[6-(2-Methylcarbamoyl-pyridin-4-yloxy)-benzooxazol-2-ylamino]-phenyl-acetic acid, 4-{2-[((S)-Methylcarbamoyl-phenyl-methyl)-amino]-benzooxazol-6-yloxy}-pyridine-2-carboxylic acid methylamide, 4-{2-[(Pyridin-2-ylmethyl)-amino]-benzooxazol-6-yloxy}-pyridine-2-carboxylic acid methylamide, 4-(2-Benzylamino-benzooxazol-6-yloxy) -pyridine-2-carboxylic acid methylamide, 4-[2-(3-Chloro-benzylamino)-benzooxazol-6-yloxy]-pyridine-2-carboxylic acid methylamide, 4-{2-[2-(2-Pyrrolidin-1-yl-ethyl)-phenylamino]-benzooxazol -6-yloxy}-pyridine-2-carboxylic acid methylamide, 4-{2-[2-(2-Piperidin-1-yl-ethyl)-phenylamino]-benzooxazol-6-yloxy}-pyridine-2-carboxylic acid methylamide, 4-{2-[(4-Methyl-imidazol-1-yl)-phenylamino]-benzooxazol-6-yloxy}-pyridine-2-carboxylic acid methylamide, 4-[2-(2-Oxazol-5-yl-phenylamino)-benzooxazol-6-yloxy]-pyridine-2-carboxylic acid methylamide, 4-{2-[2-(2-Methyl-imidazol-1-yl)-phenylamino]-benzooxazol-6-yloxy}-pyridine -2-carboxylic acid methylamide, 4-(2-Amino-benzooxazol-6-yloxy)-pyridine-2-carboxylicm acid methylamide, 4{2-[2-(2-Morpholin-4-yl-ethyl)-phenylamino]-benzooxazol-6-yloxy}-pyridine-2-carboxylic acid methylamide, 4-[2-((1S,2R)-2-Hydroxy-indan-1-ylamino)-benzooxazol-6-yloxy]-pyridine-2-carboxylic acid methylamide, 4-[2-((1R,2S)-2-Hydroxy-indan-1-ylamino)-benzooxazol-6-yloxy]-pyridine-2-carboxylic acid methylamide, 4-[2-((R)-3-Hydroxy-1-phenyl-propylamino)-benzooxazol-6-yloxy]-pyridine-2-carboxylic acid methylamide, 4-[2((1S,2S)-2-Hydroxy-cyclohexylamino)-benzooxazol-6-yloxy]-pyridine-2-carboxylic acid methylamide, (R) -[6-(2-Methylcarbamoyl-pyridin-4-yloxy)-benzooxazol-2-ylamino]-phenyl-acetic acid methyl ester, 4-[2-((R)-1-Cyclohexyl-ethylamino)-benzooxazol-6-yloxy]-pyridine-2-carboxylic acid methylamide, (S)-[6-(2-Methylcarbamoyl-pyridin-4-yloxy)-benzooxazol-2-ylamino]-phenyl-acetic acid methyl ester, 4-[2-((S)-2-Hydroxy-1-phenyl-ethylamino)-benzooxazol-6-yloxy]-pyridine-2-carboxylic acid methylamide, 4-{2-[(Pyridin-4-ylmethyl)-amino]-benzooxazol-6-yloxy}-pyridine-2-carboxylic acid methylamide, 4-{2-[3-(2-Piperidin-1-yl-ethyl)-phenylamino]-benzooxazol-6-yloxy}-pyridine-2-carboxylic acid methylamide, 4-{2-[(Pyridin-3-ylmethyl)-amino]-benzooxazol-6-yloxy}-pyridine-2-carboxylic acid methylamide, 4-[2-(Cyclohexyl-methyl-amino)-benzooxazol-6-yloxy]-pyridine-2-carboxylic acid, 4-(2-Phenethylamino-benzooxazol-6-yloxy)-pyridine-2-carboxylic acid methylamide, 4-{2-[((R)-Cyclohexyl-methylcarbamoyl-methyl)-amino]-benzooxazol-6-yloxy}-pyridine-2-carboxylic acid methylamide, 4-[2-(2-Pyrrolidin-1-yl-ethylamino)-benzooxazol-6-yloxy]-pyridine-2-carboxylic acid methylamide, 4-[2-(2-Piperidin-1-yl-ethylamino)-benzooxazol-6-yloxy]-pyridine-2-carboxylic acid methylamide, 4-{2-[(2,3-Dihydro-benzo[1,4]dioxin-5-ylmethyl)-amino]-benzooxazol-6-yloxy}-pyridine-2-carboxylic acid methylamide, 4-[2-((S)-1-Cyclohexyl-2-hydroxy-ethylamino)-benzooxazol-6-yloxy]-pyridine-2-carboxylic acid methylamide, 4-[2-((R)-1-Cyclohexyl-2-hydroxy-ethylamino)-benzooxazol-6-yloxy]-pyridine-2-carboxylic acid methylamide, N'-{4-[2-(Cyclohexylmethyl-amino)-benzooxazol-6-yloxy]-pyridine-2-carbonyl}-hydrazinecarboxylic acid tert-butyl ester, 4-[2-(Cyclohexylmethyl-amino)-benzooxazol-6-yloxy]-pyridine-2-carboxylic acid amide, 4-[2-(Cyclohex-3-enylamino)-benzooxazol-6-yloxy]-pyridine-2-carboxylic acid methylamide, 4-[2-(2,4-Difluoro-benzylamino)-benzooxazol-6-yloxy]-pyridine-2-carboxylic acid methylamide, 4-[2-(2-Bromo-benzylamino)-benzooxazol-6-yloxy]-pyridine-2-carboxylic acid methylamide, 4-[2-(2-Fluoro-5-methoxy-benzylamino)-benzooxazol-6-yloxy]-pyridine-2-carboxylic acid methylamide, 4-{2-[3-(2-Morpholin-4-yl-ethyl)-phenylamino]-benzooxazol-6-yloxy}-pyridine-2-carboxylic acid methylamide, 1-{[6-(2-Methylcarbamoyl-pyridin-4-yloxy)-benzooxazol-2-ylamino]-methyl}-cyclohexanecarboxylic acid ethyl ester, 4-[2-(2,6-Dichloro-benzylamino)-benzooxazol-6-yloxy]-pyridine-2-carboxylic acid methylamide, 4-[2-(2,3-Dichioro-benzylamino)-benzooxazol-6-yloxy]-pyridine-2-carboxylic acid methylamide, 4-[2-(2-Chloro-6-fluoro-benzylamino)-benzooxazol-6-yloxy]-pyridine-2-carboxylic acid methylamide, 4-[2-(2,3-Difluoro-benzylamino)-benzooxazol-6-yloxy]-pyridine-2-carboxylic acid methylamide, {4-[2-(Cyclohexylmethyl-amino)-benzooxazol-6-yloxy]-pyridin-2-yl}-methanol, Cyclohexylmethyl-[6-(2-[1,3,4]oxadiazol-2-yl-pyridin-4-yloxy)-benzooxazol-2-yl]-amine, 4-[2-(Cyclohexylmethylamino)-benzooxazol-6-yloxy]-pyridine-2-carbonitrile, 4-[2-(2,5-Dimethoxy-benzylamino)-benzooxazol-6-yloxy]-pyridine-2-carboxylic acid methylamide, 4-[2-(2,6-Dimethoxy-benzyl-amino)-benzooxazol-6-yloxy]-pyridine-2-carboxylic acid methylamide, 4-[2-(2-Dimethylamino-benzylamino)-benzooxazol-6-yloxy]-pyridine-2-carboxylic acid methylamide, 4-[2-(2-Amino-benzylamino)-benzooxazol-6-yloxy]-pyridine-2-carboxylic acid methylamide, 4-[2-(2,6-Difluoro-benzylamino)-benzooxazol-6-yloxy]-pyridine-2-carboxylic acid methylamide, 4-[2-(2-Morpholin-4-yl-benzylamino)-benzooxazol-6-yloxy]-pyridine-2-carboxylic acid methylamide, 4-[2-(2-Methyl-benzylamino)-benzooxazol-6-yloxy]-pyridine-2-carboxylic acid methylamide, 4-[2-(3,4-Dimethoxy-benzylamino)-benzooxazol-6-yloxy]-pyridine-2-carboxylic acid methylamide, 4-[2-(2,3-Dimethoxy-benzylamino)-benzooxazol-6-yloxy]-pyridine-2-carboxylic acid methylamide, 4-[2-(2,4-Dimethoxy-benzylamino)-benzooxazol-6-yloxy]-pyridine-2-carboxylic acid methylamide, 1-{[6-(2-Methylcarbamoyl-pyridin-4-yloxy)-benzooxazol-2-ylamino]-methyl}-cyclohexanecarboxylic acid, 4-[2-(2,3-Dihydro-benzo[1,4]dioxin-5-ylamino)-benzo-oxazol-6-yloxy]-pyridine-2-carboxylic acid methylamide, 4-[2-(Benzo[1,3]dioxol-5-ylamino)-benzooxazol-6-yloxy]-pyridine-2-carboxylic acid methylamide, 4-[2-(2-Ethoxy-benzylamino)-benzooxazol-6-yloxy]-pyridine-2-carboxylic acid methylamide, 4-[2-(2-Trifluoromethyl-benzyl-amino)-benzooxazol-6-yloxy]-pyridine-2-carboxylic acid methylamide, 4-(2-Isopropylamino-benzooxazol-6-yloxy)-pyridine-2-carboxylic acid methylamide, 4-(2-Isobutylamino-benzooxazol-6-yloxy)-pyridine-2-carboxylic acid methylamide, 4-(2-tert-Butylamino-benzo-oxazol-6-yloxy)-pyridine-2-carboxylic acid methylamide, 4-[2-(Cycloheptylmethyl-amino)-benzooxazol-6-yloxy]-pyridine-2-carboxylic acid methylamide, 4-{2-[(Tetrahydro-furan-2-yl-methyl)-amino]-benzooxazol-6-yloxy}-pyridine-2-carboxylic acid methylamide, 4-[2-(1-Benzyl-piperidin-4-ylamino)-benzooxazol-6-yloxy]-pyridine-2-carboxylic acid methylamide, 4-[2-(1,2,3,4-Tetrahydro-naphthalen-1-ylamino)-benzooxazol-6-yloxy]-pyridine-2-carboxylic acid methylamide, 4-[2-(2-Pyrazol-1-yl-benzylamino)-benzooxazol-6-yloxy]-pyridine-2-carboxylic acid methylamide, 4-[2-(Benzyl-methyl-amino)-benzooxazol-6-yloxy]-pyridine-2-carboxylic acid methylamide, 4-[2-(1-Phenyl-piperidin-4-ylamino)-benzooxazol-6-yloxy]-pyridine-2-carboxylic acid methylamide, 4-{2-[(3,4-Dihydro-2H-benzo[b][1,4]dioxepin-6-ylmethyl)-amino]-benzooxazol-6-yloxy}-pyridine-2-carboxylic acid methylamide, Cyclohexylmethyl-{6-[2-(5-methyl-1H-imidazol-2-yl)-pyridin-4-yloxy]-benzooxazol-2-yl}-amine, 4-{2-[(2,3-Dihydro-benzo[1,4]dioxine-5-carbonyl)-amino]-benzooxazol-6-yloxy}-pyridine-2-carboxylic acid methylamide, [6-(2-Aminomethyl-pyridin-4-yloxy)-benzooxazol-2-yl]-cyclohexylmethyl-amine, 4-{2-[(1-Methylcarbamoyl-cyclohexylmethyl)-amino]-benzooxazol-6-yloxy}-pyridine-2-carboxylic acid methylamide, 4-[2-(2,4,6-Trimethoxy-benzylamino)-benzooxazol-6-yloxy]-pyridine-2-carboxylic acid methylamide, 4-[2-(5-Chloro-2-methoxy-benzylamino)-benzooxazol-6-yloxy]-pyridine-2-carboxylic acid methylamide, 4-[2-(5-Fluoro-2-methoxy-benzylamino)-benzooxazol-6-yloxy]-pyridine-2-carboxylic acid methylamide, 4-[2-(2-Fluoro-6-methoxy-benzylamino)-benzooxazol-6-yloxy]-pyridine-2-carboxylic acid methylamide, 4-[2-(2-Chloro-3,4-dimethoxy-benzylamino)-benzooxazol-6-yloxy]-pyridine-2-carboxylic acid methylamide, 4-[2-(2-Piperidin-1-yl-benzylamino)-benzooxazol-6-yloxy]-pyridine-2-carboxylic acid methylamide, 4-{2-[(2,3-Dihydro-benzo[1,4]dioxin-2-ylmethyl)-amino]-benzooxazol-6-yloxy}-pyridine-2-carboxylic acid methylamide, 4-{2-[(4-Benzyl-morpholin-2-ylmethyl)-amino]-benzooxazol-6-yloxy}-pyridine-2-carboxylic acid methylamide, 4-[2-(2-Chloro-6-methoxy-benzylamino)-benzooxazol-6-yloxy]-pyridine-2-carboxylic acid methylamide, 4-{2-[(2,3-Dihydro-benzo[1,4]dioxin-6-ylmethyl)-amino]-benzooxazol-6-yloxy}-pyridine-2-carboxylic acid methylamide, 4-{2-[2-(2,3-Dihydro-benzo[1,4]dioxin-5-yl)-ethylamino]-benzooxazol-6-yloxy}-pyridine-2-carboxylic acid methylamide, 4-{2-[(2,3-Dihydro-benzofuran-5-ylmethyl)-amino]-benzooxazol-6-yloxy}-pyridine-2-carboxylic acid methylamide, and 4-{2-[1-(2,3-Dihydro-benzo[1,4]dioxin-5-yl)-ethylamino]-benzooxazol-6-yloxy}-pyridine-2-carboxylic acid methylamide;

or a pharmaceutically acceptable salt, tautomer, or stereoisomer thereof.

66. The compound of claim 3 selected from the group consisting of 4-[2-(4-Chloro-3-trifluoromethyl-phenylamino)-benzothiazol-6-yloxy]-pyridine-2-carboxylic acid methylamide, 4-[2-(2-Chloro-benzylamino)-benzothiazol-6-yloxy]-pyridine-2-carboxylic acid methylamide, 4-[2-(Cyclohexylmethyl-amino)-benzothiazol-6-yloxy]-pyridine-2-carboxylic acid methylamide, 4-{2-[(R)-1-(2-Methoxy-phenyl)-ethylamino]-benzothiazol-6-yl-oxy}-pyridine-2-carboxylic acid methylamide, 4-[2-(2,4-Dichloro-benzylamino)-benzothiazol-6-yloxy]-pyridine-2-carboxylic acid methylamide, 4-[2-((R)-1-Phenyl-ethylamino)-benzothiazol-6-yloxy]-pyridine-2-carboxylic acid methylamide, 4-[2-(2-Methoxy-benzylamino)-benzothiazol-6-yloxy]-pyridine-2-carboxylic acid methylamide, 4-(2-Phenethylamino-benzothiazol-6-yloxy)-pyridine-2-carboxylic acid methylamide, 4-[2-(2,3-Dichloro-benzylamino)-benzothiazol-6-yloxy]-pyridine-2-carboxylic acid methylamide, 4-(2-Cyclohexylamino-benzothiazol-6-yloxy)-pyridine-2-carboxylic acid methylamide, 4-[2-(3-Methyl-cyclohexylamino)-benzothiazol-6-yloxy]-pyridine-2-carboxylic acid methylamide, 4-[2-((1S,2S)-2-Hydroxy-cyclohexylamino)-benzothiazol-6-yloxy]-pyridine-2-carboxylic acid methylamide, 4-[2-((R)-1-Cyclohexyl-ethylamino)-benzothiazol-6-yloxy]-pyridine-2-carboxylic acid methylamide, 4-[2-(2,5-Difluoro-benzylamino)-benzothiazol-6-yloxy]-pyridine-2-carboxylic acid methylamide, 4-[2-(2-Fluoro-benzylamino)-benzothiazol-6-yloxy]-pyridine-2-carboxylic acid methylamide, 4-{2-[(Tetrahydro-pyran-4-ylmethyl)-amino]-benzothiazol-6-yloxy}-pyridine-2-carboxylic acid methylamide, 4-[2-(2-Morpholin-4-yl-benzylamino)-benzothiazol-6-yloxy]-pyridine-2-carboxylic acid methylamide, 4-[2-(2-Pyrazol-1-yl-benzylamino)-benzothiazol-6-yloxy]-pyridine-2-carboxylic acid methylamide, 4-[2-(2-Dimethylamino-benzylamino)-benzothiazol-6-yloxy]-pyridine-2-carboxylic acid methylamide, 4-[2-(2,6-Dimethoxy-benzylamino)-benzothiazol-6-yloxy]-pyridine-2-carboxylic acid methylamide, 4-[2-(2,5-Dimethoxy-benzylamino)-benzothiazol-6-yloxy]-pyridine-2-carboxylic acid methylamide, 4-[2-(2,3-Difluoro-benzylamino)-benzothiazol-6-yloxy]-pyridine-2-carboxylic acid methylamide, 4-[2-(Cycloheptylmethyl-amino)-benzothiazol-6-yloxy]-pyridine-2-carboxylic acid methylamide, 4-[2-(2,6-Difluoro-benzylamino)-benzothiazol-6-yloxy]-pyridine-2-carboxylic acid methylamide, 4-{2-[(Pyridin-2-ylmethyl)-amino]-benzothiazol-6-yloxy}-pyridine-2-carboxylic acid methylamide, 4-[2-(3,4-Dimethoxy-benzylamino)-benzothiazol-6-yloxy]-pyridine-2-carboxylic acid methylamide, 4-{2-[(2,3-Dihydro-benzo[1,4]dioxin-5-ylmethyl)-amino]-benzothiazol-6-yloxy}-pyridine-2-carboxylic acid methylamide, 4-[2-(2-Piperidin-1-yl-benzylamino)-benzothiazol-6-yloxy]-pyridine-2-carboxylic acid methylamide, 4-{2-[(Pyridin-3-ylmethyl)-amino]-benzothiazol-6-yloxy}-pyridine-2-carboxylic acid methylamide, 4-[2-((1R,2R)-2-Benzyloxy-cyclohexylamino)-benzothiazol-6-yloxy]-pyridine-2-carboxylic acid methylamide, 4-[2-((1S,2S)-2-Benzyloxy-cyclohexylamino)-benzothiazol-6-yloxy]-pyridine-2-carboxylic acid methylamide, 4-[2-((1R,2R)-2-Hydroxy-cyclohexylamino)-benzothiazol-6-yloxy]-pyridine-2-carboxylic acid methylamide, 4-[2-(2,6-Dichloro-benzylamino)-benzothiazol-6-yloxy]-pyridine-2-carboxylic acid methylamide, 4-(2-(cyclohexylmethylamino)benzothiazol-6-yloxy)-N-(2-methoxyethyl)pyridine-2-carboxamide, 4-(2-(cyclohexylmethylamino)benzothiazol-6-yloxy)-N-(2-(dimethylamino)ethyl)pyridine-2-carboxamide, and 4-[2-(4-Sulfonamido-benzylamino)-benzothiazol-6-yloxy]-pyridine-2-carboxylic acid methylamide;

or a stereoisomer, tautomer, or pharmaceutically acceptable salt thereof.

67. A pharmaceutical composition comprising an effective amount of a compound, stereoisomer, tautomer, oxide, ester, or pharmaceutically acceptable salt thereof of claim 1 or 60, and a pharmaceutically acceptable carrier.

68. A composition of claim 67, wherein said compound exhibits an $IC_{50}$ value with respect to CSF-1R inhibition of less than 1 μM.

69. A composition of claim 67, further comprising an additional agent.

70. A composition of claim 69, wherein said additional agent is a bisphosphonate.

71. A compound of claim 1 or 60, wherein said compound preferentially inhibits CSF-1R over Raf kinase.

72. A compound of claim 71, wherein said compound inhibits CSF-1R at greater than about 5-fold the activity with respect to $IC_{50}$ values than in Raf kinase.

73. A compound of claim 71, wherein said compound inhibits CSF-1R at greater than about 10-fold, about 20-fold, about 30-fold, or about 50-fold the activity with respect to $IC_{50}$ values than in Raf kinase.

74. A compound of claim 71, wherein said compound inhibits CSF-1R at greater than about 100-fold, about 250-fold, about 500-fold, about 750-fold, about 1000-fold, or about 2000-fold the activity with respect to $IC_{50}$ values than in Raf kinase.

75. A compound of claim 71, wherein said compound inhibits Raf kinase at greater than 1 μM.

76. A compound of claim, 1 or a pharmaceutically acceptable salt thereof that is

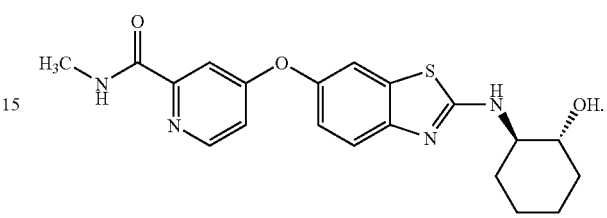

77. A compound of claim, 1 or a pharmaceutically acceptable salt thereof that is

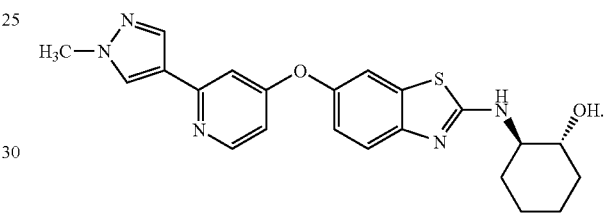

78. A pharmaceutical composition comprising an effective amount of a compound or pharmaceutically acceptable salt thereof of claims, 76 or, 77 and a pharmaceutically acceptable carrier.

* * * * *